(12) United States Patent
Moradei et al.

(10) Patent No.: US 8,598,168 B2
(45) Date of Patent: Dec. 3, 2013

(54) INHIBITORS OF HISTONE DEACETYLASE

(75) Inventors: Oscar Moradei, Kirkland (CA); Isabelle Paquin, Saint-Laurent (CA); Sylvie Frechette, Verdun (CA); Tammy Mallais, Kirkland (CA); Simon Roy, Roxboro (CA); Roger Machaalani, Laval (CA); Arkadii Vaisburg, Kirkland (CA); Jeffrey M Besterman, Baie d'Urfé (CA); Pierre Tessier, Hawkesbury (CA); David Smil, Montreal (CA); Silvana Leit, Kirkland (CA); Robert Déziel, Mount-Royal (CA)

(73) Assignee: MethylGene Inc., Montreal (CA)

( * ) Notice: Subject to any disclaimer, the term of this patent is extended or adjusted under 35 U.S.C. 154(b) by 455 days.

(21) Appl. No.: 11/696,880

(22) Filed: Apr. 5, 2007

(65) Prior Publication Data

US 2008/0132503 A1      Jun. 5, 2008

Related U.S. Application Data

(60) Provisional application No. 60/744,427, filed on Apr. 7, 2006, provisional application No. 60/886,019, filed on Jan. 22, 2007.

(51) Int. Cl.
  *A61K 31/535* (2006.01)
  *A61K 31/445* (2006.01)
  *A61K 31/44* (2006.01)
  *A61K 31/42* (2006.01)
  *A61K 31/415* (2006.01)
  *A61K 31/40* (2006.01)
  *A61K 31/28* (2006.01)

(52) U.S. Cl.
  USPC ............ 514/235.5; 514/231.5; 514/252.13; 514/253.11; 514/254.07; 514/311; 514/326; 514/343; 514/375; 514/394; 514/422; 514/438

(58) Field of Classification Search
  None
  See application file for complete search history.

(56) References Cited

U.S. PATENT DOCUMENTS

| | | | |
|---|---|---|---|
| 2,754,286 A | 7/1956 | Martin | |
| 3,576,869 A | 4/1971 | Schellenbaum et al. | |
| 4,994,479 A | 2/1991 | Mase et al. | |
| 5,137,918 A | 8/1992 | Weisershausen et al. | |
| 5,332,750 A | 7/1994 | Mederski et al. | |
| 5,366,878 A | 11/1994 | Pederson et al. | |
| 5,635,377 A | 6/1997 | Pederson et al. | |
| 5,652,355 A | 7/1997 | Metelev et al. | |
| 5,945,450 A | 8/1999 | Takenouchi et al. | |
| 6,034,251 A | 3/2000 | Aslanian et al. | |
| 6,174,905 B1 | 1/2001 | Suzuki et al. | |
| 6,376,515 B2 | 4/2002 | Zhu et al. | |
| 6,653,309 B1 | 11/2003 | Saunders et al. | |
| 6,777,217 B1 | 8/2004 | Schreiber et al. | |
| 2002/0061860 A1 | 5/2002 | Li et al. | |
| 2003/0096844 A1 | 5/2003 | Kozlowski et al. | |
| 2003/0232859 A1 | 12/2003 | Kozlowski et al. | |
| 2004/0010013 A1 | 1/2004 | Friary et al. | |
| 2004/0044051 A1 | 3/2004 | Kozlowski et al. | |
| 2004/0087798 A1 | 5/2004 | Yamada | |
| 2004/0106599 A1 | 6/2004 | Delorme et al. | |
| 2004/0132804 A1 | 7/2004 | Tong et al. | |
| 2004/0147569 A1 | 7/2004 | Suzuki et al. | |
| 2004/0186148 A1 | 9/2004 | Shankar et al. | |
| 2005/0096222 A1 | 5/2005 | Hidaka et al. | |
| 2006/0058298 A1 | 3/2006 | Delorme et al. | |
| 2007/0117824 A1* | 5/2007 | Berk et al. ............... 514/278 |

FOREIGN PATENT DOCUMENTS

| | | |
|---|---|---|
| CA | 2136288 | 11/1994 |
| CA | 2480356 | 10/2003 |
| CA | 2484065 | 11/2003 |
| CA | 2490579 | 1/2004 |
| DE | 14 70 097 A1 | 6/1969 |
| EP | 0 657 454 | 11/1994 |
| EP | 0 847 992 | 9/1997 |
| EP | 1 256 341 | 11/2002 |
| JP | 1996-258863 | 9/1996 |
| JP | 1999-269146 | 10/1999 |
| JP | 11269146 | 10/1999 |
| JP | 1999-302173 | 11/1999 |
| JP | 2003-137866 | 5/2003 |
| JP | 2003221380 | 8/2003 |
| WO | 98/42672 A1 | 10/1998 |
| WO | WO 98/45252 | 10/1998 |
| WO | WO 00/03704 | 1/2000 |
| WO | WO 01/16106 | 3/2001 |
| WO | WO 01/38322 | 5/2001 |
| WO | WO 01/60354 | 8/2001 |
| WO | WO 01/64643 A2 | 9/2001 |
| WO | WO 01/68585 | 9/2001 |
| WO | WO 01/70675 A2 | 9/2001 |
| WO | WO 02/069947 | 9/2002 |

(Continued)

OTHER PUBLICATIONS

Vippagunta et al (Adv Drug Deliv Rev 48:3-26, 2001).*
Stella et al (Prodrugs: Challenges and Rewards, Part 1, 2007).*
Raiford et al (J of Am Chem Soc 47:1454-1458, 1925).*
STN Report (Accession No. 1925:14261).*
STN Search Report (Accession No. 1968:50943) as evidence of Rakusan et al (Collection of Czechoslovak Chemical Communications 32(8):2882-2889, 1968).*
Suzuki et al., "Benzamide Analogs as Nuclear Receptor Agonists and Reinforcement Agents for Treatment of Cell Proliferation-, Hormone-, and Vitamin-related Diseases", JP 200256194, CA 133:247304, 2000.
Suzuki et al., "Benzamide Derivatives as Histone Deacetylase Inhibitors for Treating Tumors and Other Diseases", JP 11302173, CA 131:319669, 1999.
Suzuki et al., "Preparation of Cell Differentiation-Inducing N-Phenylbenzamides and Anticancers", JP 11269146, CA 131:257321, 1999.

(Continued)

*Primary Examiner* — Craig Ricci
(74) *Attorney, Agent, or Firm* — McDonnell Boehnen Hulbert & Berghoff LLP

(57) ABSTRACT

The invention relates to the inhibition of histone deacetylase. The invention provides compounds and methods for inhibiting histone deacetylase enzymatic activity. The invention also provides compositions and methods for treating cell proliferative diseases and conditions.

13 Claims, No Drawings

(56) References Cited

FOREIGN PATENT DOCUMENTS

| WO | WO 03/024448 A2 | 3/2003 | | |
|---|---|---|---|---|
| WO | WO 03/075929 | 9/2003 | | |
| WO | WO 03/076395 | 9/2003 | | |
| WO | WO 03/076400 | 9/2003 | | |
| WO | WO 03/076401 | 9/2003 | | |
| WO | WO 03/076421 | 9/2003 | | |
| WO | WO 03/076422 | 9/2003 | | |
| WO | WO 03/076430 | 9/2003 | | |
| WO | WO 03/076438 | 9/2003 | | |
| WO | WO 03/087057 | 10/2003 | | |
| WO | WO 03/092686 | 11/2003 | | |
| WO | 2004/005513 | 1/2004 | | |
| WO | WO 2004/058234 | 7/2004 | | |
| WO | WO 2004/069133 | 8/2004 | | |
| WO | WO 2004/069823 | 8/2004 | | |
| WO | WO 2004/071400 | 8/2004 | | |
| WO | WO 2005/030704 | * | 4/2005 | ............ C07C 237/40 |
| WO | WO 2005/030705 | * | 4/2005 | ............ C07C 237/40 |
| WO | WO 2006/122319 A | 11/2006 | | |

OTHER PUBLICATIONS

Cecil Textbook of Medicine, edited by Bennett, J.C., and Plum F., 20$^{th}$ Edition, vol. 1, 1004-1010, (1996).
Ragione, Fulvio Della et al., "Genes Modulated by Histone Acetylation as New Effectors of Butyrate Activity", FEBS Letters 499, 199-204, (2001).
Turner, W. W. et al., "Recent Advances in the Medicinal Chemistry of Antifungal Agents", Current Pharmaceutical Design, 2, 209-224 (1996).
Sugar, Alan M. et al., "Comparison of Three Methods of Antifunal Susceptibility Testing with the Proposed NCCLS Standard Broth Macrodilution Assay: Lack of Effect of Phenol Red", Diagn. Microbiol. Infect. Dis., 21, 129-133 (1995).
Snyder, JW et al., "Common Bacteria Whose Susceptibility to Antimicrobials is no Longer Predictable", J. Med. Liban, 48(4), 208-14 (2000).
Suzuki, et al., "Synthesis and Histone Deacetylase Inhibitory Activity of New Benzamide Derivatives," Journal of Medicinal Chemistry, American Chemical Society, Washington U.S., vol. 42, No. 15, 1999, pp. 3001-3003.
Database Crossfire Beilstein (Online) Beilstein Institut zur Föerderung der Chemischen Wissenschaftern, Frankfurt am Main, DE, N,N'-di (o-aminophenyl) terephthalamide, Database accession No. 5619310 XP-002229372, Third invention Abstract & Indian J. Chem. Sect. B., vol. 25, 1986, pp. 1146-1149.
Database Crossfire Beilstein (Online) Beilstein Institut zur Föerderung der Chemischen Wissenschaftern, Frankfurt am Main, DE, Database accession No. 3016237 XP-002229373, 4, 6-diamino-N, N'-bis-(2-amino-phenyl)-isophthalamide. Third invention abstract & Chem. Heterocycl. Compd. vol. 13, 1977, pp. 1029-1032.
Database Crossfire Beilstein (Online) Beilstein Institut zur Föerderung der Chemischen Wissenschaftern, Frankfurt am Main, DE, Database accession No. 3458834 XP-002229374, N, N'-bis-(2-amino-phenyl)-phthalamide. Third invention abstract & Justus Liebigs Ann. Chem., vol. 347, 1906, p. 116.
Picard et al., "Desymmetrization Reactions: A Convenient Synthesis of Aromatic Diamide Diamines" Synthesis, vol. 10, 2001, pp. 1471-1478.
Rabilloud G et al., "Réactions de condensation de l'o-phénylenediamine avec les benzoaxin-3, 1-ones-4 substituées en position 2", Bull. Soc. Chim. Fr., 1975, pp. 2682-2686.
Csordas, Adam, "On the Biological Role of Histone Acetylation," Biochem. J., vol. 265 (1990) pp. 23-38.
Taunton, Jack, et al. "A Mammalian Histone Deacetylase Related to the Yeast Transcriptional Regulator Rpd3p," Science, vol. 272 (1996) pp. 408-411.
Grozinger, Christina M., et al., "Three Proteins Define a Class of Human Histone Deacetylases Related to Yeast Hda1p," PNAS, vol. 96 (1999) pp. 4868-4873.
Kao, Hung-Ying, et al., "Isolation of a Novel Histone Deacetylase Reveals that Class I and Class II Deacetylases Promote SMRT-Mediated Repression," Genes & Development, vol. 14 (2000) pp. 55-66.
Van den Wyngaert, Ilse, et al. "Cloning and Characterization of Human Histone Deacetylase 8," FEBS Letters, vol. 478 (2000) pp. 77-83.
Zhou, Xianbo, et al., "Cloning and Characterization of a Histone Deacetylase, HDAC9," PNAS, vol. 98, No. 19, (2001) pp. 10572-10577.
Kao, Hung-Ying, et al., "Isolation and Characterization of Mammalian HDAC10, a Novel Histone Deaceylase," J. Biol. Chem., vol. 277, No. 1 (2002) pp. 187-193.
Gao, Lin, et al. "Cloning and Functional Characterization of HDAC11, a Novel Member of the Human Histone Deacetylase Family," J, Biol. Chem., vol. 277, No. 28 (2002) pp. 25748-25755.
Richon, Victoria M., et al. "A Class of Hybrid Polar Inducers of Transformed Cell Differentiation Inhibits Histone Deacetylases," PNAS, vol. 95 1998 pp. 3003-3007.
Yoshida, Minoru et al., "Reversible Arrest of Proliferation of Rat 3Y1 Fibroblasts in Both the G1 and G2 Phases by Trichostatin A," Experimental Cell Research, vol. 177 (1988) pp. 122-131.
Finnin, Michael S., et al., "Structures of a Histone Deacetylase Homologue Bound to the TSA and SAHA Inhibitors," Nature, vol. 401 (1999) pp. 188-193.
Yoshida, Minoru, et al., "Potent and Specific Inhibition of Mammalian Histone Deacetylase Both In Vivo and In Vitro by Trichostatin A," J. Biol. Chem., vol. 265, No. 28 (1990) pp. 17174-17179.
Ramchandani, Shyam, et al., "Inhibition of Tumorigenesis by a Cytosine-DNA, Methyltransferase, Antisense Oligodeoxynucleotide," PNAS, vol. 94 (1997) pp. 684-689.
Pon, Richard T., "Solid Phase Supports for Oligonucleotide Synthesis," Methods in Molecular Biology, vol. 20 (1993) pp. 465-496.
Alaimo, Robert J., "The Preparation and Characterization of 2-Amino-5,6-Dichloro and 2-Amino-6,7-Dichlorobenzothiazole," J. Het. Chem., vol. 8 (1971) pp. 309-310.
Zee-Cheng, Robert K. Y. et al., "Antileukemic Activity of Substituted Ureidothiazoles, Ureidothiadiazoles, and Related Compounds," J. Med. Chem., vol. 22, No. 1 (1979) pp. 28-32.
Taurins, Alfred et al., "Synthesis of Pyridyl- and Quinolyl-Substituted 2-Aminothiazoles," J. Het. Chem., vol. 7 (1970) pp. 1137-1141.
Rosowsky, Andre, et al., "5-Deaza-7-Desmethylene Analogues of 5,10-Methylene-5,6,7,8-Tetrahydrofolic Acid and Related Compounds: Synthesis and In Vitro Biological Activity," J. Het Chem., vol. 31 (1994) pp. 1241-1250.
Meyer, Thomas, et al., "A Derivative of Staurosporine (CGP 41 251) Shows Selectivity for Protein Kinase C Inhibition and In Vitro Anti-Proliferative as Well as In Vivo Anti-Tumor Activity," Int. J. Cancer, vol. 43 (1989) pp. 851-856.
Anderson, Malcolm, et al., "Imidazo[1,2-a]pyridines: A Potent and Selective Class of Cyclin-Dependent Kinase Inhibitors Identified Through Structure-Based Hybridisation," Bioorganic & Medical Chemistry Letters, vol. 13 (2003) pp. 3021-3026.
Zlatoidský, P. et al., "Synthesis of 4-(4-Guanidinobenzoyloxy)Benzamides and 1-(4-Guanidinobenzoyloxy)Benzoyloxy Acetamides as Trypsin Inhibitors," Eur. J. Med. Chem., vol. 31 (1996) pp. 895-899.
Zimmermann, Jürg, et al., "Phenylamino-Pyrimidine (PAP)—Derivates: A New Class of Potent and Highly Selective PDGF-Receptor Autophosphorylation Inhibitors," Bioorganic & Medicinal Chemistry Letters, vol. 6, No. 11 (1996) pp. 1221-1226.
Barvian, Mark, et al., "Pyrido[2,3-d]Pyrimidin-7-one Inhibitors of Cyclin-Dependent Kinases," J. Med. Chem., vol. 44 (2001), p. 1016.
Barvian, Mark, et al., "Pyrido[2,3-d]Pyrimidin-7-one Inhibitors of Cyclin-Dependent Kinases," J. Med. Chem., vol. 43, No. 24 (2000) pp. 4606-4616.
Piper, James R. et al., "Analogues of Methotrexate in Rheumatoid Arthritis. 2. Effects of 5-Deazaaminopterin, 5,10-Dideazaaminopterin, and Analogues on Type II Collagen-Induced Arthritis in Mice," J. Med. Chem., vol. 40, No. 3 (1997) pp. 377-381.
Grell, Wolfgang, et al., "Repaglinide and Related Hypoglycemic Benzoic Acid Derivatives," J. Med. Chem, vol. 41 (1998) pp. 5219-5246.

(56) References Cited

OTHER PUBLICATIONS

Geoffroy, Otto J, et al., "Chemoselective One-Pot Reductive Deamination of Aryl Amines," Tetrahedron Letters, vol. 42 (2001) pp. 5367-5369.

Boger, Dale L. et al., "Total Synthesis of Distamycin A and 2640 Analogues: A Solution-Phase Combinatorial Approach to the Discovery of New, Bioactive DNA Binding Agents and Development of a Rapid, High-Throughput Screen for Determining Relative DNA Binding Affinity or DNA Binding Sequence Selectivity," J. Am. Chem. Soc., vol. 122 (2000) pp. 6382-6394.

Matsuoka, Hiroharu, et al., "Antirheumatic Agents: Novel Methotrexate Derivatives Bearing a Benzoxazine or Benzothiazine Moiety," J. Med. Chem., vol. 40 (1997) pp. 105-111.

Hennequin, Laurent F., et al., "Novel 4-Anilinoquinazolines with C-7 Basic Side Chains: Design and Structure Activity Relationship of a Series of Potent, Orally Active, VEGF Receptor Tyrosine Kinase Inhibitors," J. Med. Chem., vol. 45 (2002) pp. 1300-1312.

Taylor, Edward C., "Novel 5-Desmethylene Analogues of 5,10-Dideaza-5,6,7,8-Tetrahydrofolic Acid as Potential Anticancer Agents," J. Org. Chem., Vol, 57 (1992) pp. 3218-3225.

Zhu, Zhijian, et al., "Synthesis of 2,6,7-Trichloro-1-(β-D-Ribofuranosyl)Naphtho[2,3-d]Imidazole: A Linear Dimensional Analogue of the Antiviral Agent TCRB," J. Org. Chem., vol. 63 (1998) pp. 977-983.

Charles et al, "Synthesis of substituted Benzamides, Benzimidazoles and Benzoxazines as potential Anthelmintic and Antimicrobial Agents", Archiv Der Pharmazie, 1982, 97-103, 315(2).

Perry et al., (1992) J. Org. Chem., 57:2883-2887; Database accession No. 5438997; XP002578745; Abstract.

Miletin et al., (2001) Molecules, 6:603-613; Database accession No. 8853038; XP002578746; Abstract.

Beer et al., (1996) J. Chem Soc., Dalton Trans., vol. 11, pp. 2341-2346; Database accession No. 7606264; XP002578749; Abstract.

\* cited by examiner

INHIBITORS OF HISTONE DEACETYLASE

This application claims the benefit of U.S. Provisional Application Ser. No. 60/744,427, filed Apr. 7, 2006 and U.S. Provisional Application Ser. No. 60/886,019, filed Jan. 22, 2007.

BACKGROUND OF THE INVENTION

1. Field of the Invention

This invention relates to the inhibition of histone deacetylase. More particularly, the invention relates to compounds and methods for inhibiting histone deacetylase enzymatic activity.

2. Summary of the Related Art

In eukaryotic cells, nuclear DNA associates with histones to form a compact complex called chromatin. The histones constitute a family of basic proteins which are generally highly conserved across eukaryotic species. The core histones, termed H2A, H2B, H3, and H4, associate to form a protein core. DNA winds around this protein core, with the basic amino acids of the histones interacting with the negatively charged phosphate groups of the DNA. Approximately 146 base pairs of DNA wrap around a histone core to make up a nucleosome particle, the repeating structural motif of chromatin.

Csordas, *Biochem. J.*, 286: 23-38 (1990) teaches that histones are subject to posttranslational acetylation of amino groups of N-terminal lysine residues, a reaction that is catalyzed by histone acetyl transferase (HAT1). Acetylation neutralizes the positive charge of the lysine side chain, and is thought to impact chromatin structure. Indeed, Taunton et al., *Science*, 272: 408-411 (1996), teaches that access of transcription factors to chromatin templates is enhanced by histone hyperacetylation. Taunton et al. further teaches that an enrichment in underacetylated histone H4 has been found in transcriptionally silent regions of the genome.

Histone acetylation is a reversible modification, with deacetylation being catalyzed by a family of enzymes termed histone deacetylases (HDACs). Grozinger et al., *Proc. Natl. Acad. Sci. USA*, 96: 4868-4873 (1999), teaches that HDACs are divided into two classes, the first represented by yeast Rpd3-like proteins, and the second represented by yeast Hda1-like proteins. Grozinger et al. also teaches that the human HDAC1, HDAC2, and HDAC3 proteins are members of the first class of HDACs, and discloses new proteins, named HDAC4, HDAC5, and HDAC6, which are members of the second class of HDACs. Kao et al., *Genes & Dev.*, 14: 55-66 (2000), discloses HDAC7, a new member of the second class of HDACs. More recently, Hu et al. J. Bio. Chem. 275:15254-13264 (2000) and Van den Wyngaert, *FEBS*, 478: 77-83 (2000) disclose HDAC8, a new member of the first class of HDACs. Histone deacetylases HDAC9-11 have also been described.

Richon et al., *Proc. Natl. Acad. Sci. USA*, 95: 3003-3007 (1998), discloses that HDAC activity is inhibited by trichostatin A (TSA), a natural product isolated from *Streptomyces hygroscopicus*, and by a synthetic compound, suberoylanilide hydroxamic acid (SAHA). Yoshida and Beppu, *Exper. Cell Res.*, 177: 122-131 (1988), teaches that TSA causes arrest of rat fibroblasts at the $G_1$ and $G_2$ phases of the cell cycle, implicating HDAC in cell cycle regulation. Indeed, Finnin et al., *Nature*, 401: 188-193 (1999), teaches that TSA and SAHA inhibit cell growth, induce terminal differentiation, and prevent the formation of tumors in mice. Suzuki et al., U.S. Pat. No. 6,174,905, EP 0847992, JP 258863/96, and Japanese Application No. 10138957, disclose benzamide derivatives that induce cell differentiation and inhibit HDAC. Delorme et al., WO 01/38322 and WO 01/70675, as well as Moradei et al., WO 05/030704 and WO 05/030705, disclose additional compounds that serve as HDAC inhibitors.

The molecular cloning of gene sequences encoding proteins with HDAC activity has established the existence of a set of discrete HDAC enzyme isoforms. Some isoforms have been shown to possess specific functions, for example, it has been shown that HDAC-6 is involved in modulation of microtubule activity. However, the role of the other individual HDAC enzymes has remained unclear.

These findings suggest that inhibition of HDAC activity represents a novel approach for intervening in cell cycle regulation and that HDAC inhibitors have great therapeutic potential in the treatment of cell proliferative diseases or conditions. It would thus be desirable to have new inhibitors of histone deacetylase.

BRIEF SUMMARY OF THE INVENTION

Ortho-amino benzamides are known HDAC inhibitors. Substitutions at the ortho- and meta-positions relative to the amino group are detrimental to the potency of the inhibitors; however, some small substituents such as —$CH_3$, —F, or —$OCH_3$ can be tolerated to a certain extent. We have found that o-amino benzamide HDAC inhibitors having a much bigger but flat aromatic and heteroaromatic substituents such as phenyl, furyl, thienyl and the like para to the amino moiety are not only well tolerated but cause significant increase in HDAC inhibitory activity.

Accordingly, the present invention provides new compounds and methods for treating cell proliferative diseases. The invention provides new inhibitors of histone deacetylase enzymatic activity.

In a first aspect, the invention provides compounds that are useful as inhibitors of histone deacetylase.

In a second aspect, the invention provides a composition comprising an inhibitor of histone deacetylase according to the invention or a pharmaceutically acceptable salt thereof and a pharmaceutically acceptable carrier, excipient, or diluent.

In a third aspect, the invention provides a method of inhibiting histone deacetylase in a cell, comprising contacting a cell in which inhibition of histone deacetylase is desired with an inhibitor of histone deacetylase of the invention.

The foregoing merely summarizes certain aspects of the invention and is not intended to be limiting in nature. These aspects and other aspects and embodiments are described more fully below. All publications (patent or other) are hereby incorporated by reference in their entirety; in the event of any conflict between these materials and the present specification, the present specification shall control.

DETAILED DESCRIPTION OF THE PREFERRED EMBODIMENTS

The invention provides compounds and methods for inhibiting histone deacetylase enzymatic activity. The invention also provides compositions and methods for treating cell proliferative diseases and conditions. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used (unless expressly stated otherwise):

As used herein, the terms "histone deacetylase" and "HDAC" are intended to refer to any one of a family of enzymes that remove acetyl groups from amino groups of lysine residues at the N-terminus of a protein, including but not limited to, a histone. Unless otherwise indicated by context, the term "histone" is meant to refer to any histone protein, including H1, H2A, H2B, H3, H4, and H5, from any species. Preferred histone deacetylases include class I and class II enzymes. Preferably the histone deacetylase is a human HDAC, including, but not limited to, HDAC-1, HDAC-2, HDAC-3, HDAC-4, HDAC-5, HDAC-6, HDAC-7, HDAC-8, HDAC-9, HDAC-10, and HDAC-11. In some other preferred embodiments, the histone deacetylase is derived from a protozoal or fungal source.

The terms "histone deacetylase inhibitor" and "inhibitor of histone deacetylase" are used to identify a compound having a structure as defined herein, which is capable of interacting with a histone deacetylase and inhibiting its enzymatic activity. "Inhibiting histone deacetylase enzymatic activity" means reducing the ability of a histone deacetylase to remove an acetyl group from a protein, including but not limited to, a histone. In some preferred embodiments, such reduction of histone deacetylase activity is at least about 50%, more preferably at least about 75%, and still more preferably at least about 90%. In other preferred embodiments, histone deacetylase activity is reduced by at least 95% and more preferably by at least 99%.

Preferably, such inhibition is specific, i.e., the histone deacetylase inhibitor reduces the ability of a histone deacetylase to remove an acetyl group from a protein, including but not limited to, a histone, at a concentration that is lower than the concentration of the inhibitor that is required to produce another, unrelated biological effect. Preferably, the concentration of the inhibitor required for histone deacetylase inhibitory activity is at least 2-fold lower, more preferably at least 5-fold lower, even more preferably at least 10-fold lower, and most preferably at least 20-fold lower than the concentration required to produce an unrelated biological effect.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B—, wherein a is 0 or 1. In such instances, when a is 0 the moiety is B— and when a is 1 the moiety is A-B—.

For simplicity, reference to a "$C_n$-$C_m$" heterocyclyl or "$C_n$-$C_m$" heteroaryl means a heterocyclyl or heteroaryl having from "n" to "m" annular atoms, where "n" and "m" are integers. Thus, for example, a $C_5$-$C_6$-heterocyclyl is a 5- or 6-membered ring having at least one heteroatom, and includes pyrrolidinyl ($C_5$) and piperidinyl ($C_6$); $C_6$heteroaryl includes, for example, pyridyl and pyrimidyl.

The term "hydrocarbyl" refers to a straight, branched, or cyclic alkyl, alkenyl, or alkynyl, each as defined herein. A "$C_0$" hydrocarbyl is used to refer to a covalent bond. Thus, "$C_0$-$C_3$-hydrocarbyl" includes a covalent bond, methyl, ethyl, ethenyl, ethynyl, propyl, propenyl, propynyl, and cyclopropyl.

The term "alkyl" as employed herein refers to straight and branched chain aliphatic groups having from 1 to 12 carbon atoms, preferably 1-8 carbon atoms, and more preferably 1-6 carbon atoms. Preferred alkyl groups include, without limitation, methyl, ethyl, propyl, isopropyl, butyl, isobutyl, sec-butyl, tert-butyl, pentyl, and hexyl. A "$C_0$" alkyl (as in "$C_0$-$C_3$-alkyl") is a covalent bond (like "$C_0$" hydrocarbyl).

The term "alkenyl" as used herein means an unsaturated straight or branched chain aliphatic group with one or more carbon-carbon double bonds, having from 2 to 12 carbon atoms, preferably 2-8 carbon atoms, and more preferably 2-6 carbon atoms. Preferred alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms, preferably 2-8 carbon atoms, and more preferably 2-6 carbon atoms. Preferred alkynyl groups include, without limitation, ethynyl, propynyl, butynyl, pentynyl, and hexynyl.

An "alkylene," "alkenylene," or "alkynylene" group is an alkyl, alkenyl, or alkynyl group, as defined hereinabove, that is positioned between and serves to connect two other chemical groups. Preferred alkylene groups include, without limitation, methylene, ethylene, propylene, and butylene. Preferred alkenylene groups include, without limitation, ethenylene, propenylene, and butenylene. Preferred alkynylene groups include, without limitation, ethynylene, propynylene, and butynylene.

The term "cycloalkyl" is intended to mean a saturated or unsaturated mono-, bi, tri- or poly-cyclic (fused and/or spiro) hydrocarbon group having about 3 to 15 carbons, preferably having 3 to 12 carbons, preferably 3 to 8 carbons, and more preferably 3 to 6 carbons. In certain preferred embodiments, the cycloalkyl group is fused to an aryl, heteroaryl or heterocyclic group. Preferred cycloalkyl groups include, without limitation, cyclopenten-2-enone, cyclopenten-2-enol, cyclohex-2-enone, cyclohex-2-enol, cyclopropyl, cyclobutyl, cyclopentyl, cyclopentenyl, cyclohexyl, cyclohexenyl, cycloheptyl, and cyclooctyl.

In certain preferred embodiments, the cycloalkyl group is a bridged cycloalkyl group, preferably a $C_5$-$C_{10}$ bridged bicyclic group. In certain preferred embodiments, the bridged cycloalkyl group is a $C_5$ bridged bicyclic group. In certain preferred embodiments, the bridged cycloalkyl group is a $C_6$ bridged bicyclic group. In certain preferred embodiments, the bridged cycloalkyl group is a $C_7$ bridged bicyclic group. In certain preferred embodiments, the bridged cycloalkyl group is a $C_8$ bridged bicyclic group. In certain preferred embodiments, the bridged cycloalkyl group is a $C_9$ bridged bicyclic. In certain preferred embodiments, the bridged cycloalkyl group has a bridge of 0, 1, 2 or 3 carbon atoms. A bridge of 0 carbon atoms is a bond, and equates to a cycloalkyl group fused to another ring structure. In certain preferred embodiments, the bridged cycloalkyl group has a bridge of 0, 1 or 3 carbon atoms. In certain preferred embodiments, the bridged cycloalkyl group has a bridge of 1 or 3 carbon atoms. In certain preferred embodiments, the bridged cycloalkyl group has a bridge of 1 carbon atom. In certain preferred embodiments, the bridged cycloalkyl group has a bridge of 2 carbon atoms. In certain preferred embodiments, the bridged cycloalkyl group has a bridge of 3 carbon atoms. If a bridged cycloalkyl group is described as "optionally substituted", it is intended to be optionally substituted on any position, including the bridge. The bridged cycloalkyl group is not limited to any particular stereochemistry.

The term "heteroalkyl" is intended to mean a saturated or unsaturated, straight or branched chain aliphatic group, wherein one or more carbon atoms in the chain are independently replaced by a heteroatom selected from the group consisting of O, S, and N.

The term "aryl" is intended to mean a mono-, bi-, tri- or polycyclic $C_6$-$C_{14}$ aromatic moiety, preferably comprising one to three aromatic rings. Preferably, the aryl group is a $C_6$-$C_{10}$ aryl group, more preferably a $C_6$ aryl group. Preferred aryl groups include, without limitation, phenyl, naphthyl, anthracenyl, and fluorenyl.

The terms "aralkyl" or "arylalkyl" are intended to mean a group comprising an aryl group covalently linked to an alkyl group. If an aralkyl group is described as "optionally substituted", it is intended that either or both of the aryl and alkyl moieties may independently be optionally substituted or unsubstituted. Preferably, the aralkyl group is ($C_1$-$C_6$)alk($C_6$-$C_{10}$)aryl, including, without limitation, benzyl, phenethyl, and naphthylmethyl. For simplicity, when written as "arylalkyl" this term, and terms related thereto, is intended to indicate the order of groups in a compound as "aryl-alkyl". Similarly, "alkyl-aryl" is intended to indicate the order of the groups in a compound as "alkyl-aryl".

The terms "heterocyclyl", "heterocyclic" or "heterocycle" are intended to mean a group which is a mono-, bi-, or polycyclic structure having from about 3 to about 14 atoms, wherein one or more atoms are independently selected from the group consisting of N, O, and S. The ring structure may be saturated, unsaturated or partially unsaturated. In certain preferred embodiments, the heterocyclic group is non-aromatic. In a bicyclic or polycyclic structure, one or more rings may be aromatic; for example one ring of a bicyclic heterocycle or one or two rings of a tricyclic heterocycle may be aromatic, as in indan and 9,10-dihydro anthracene. Preferred heterocyclic groups include, without limitation, epoxy, aziridinyl, tetrahydrofuryl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds where an annular O or S atom is adjacent to another O or S atom.

In certain preferred embodiments, the heterocyclic group is a bridged heterocyclic (or bridged heterocyclyl) group, preferably a $C_6$-$C_{10}$ bridged bicyclic group, wherein one or more carbon atoms are independently replaced by a heteroatom selected from the group consisting of N, O and S. In certain preferred embodiments, the bridged heterocyclic group is a $C_6$ bridged bicyclic group. In certain preferred embodiments, the bridged heterocyclic group is a $C_7$ bridged bicyclic group. In certain preferred embodiments, the bridged heterocyclic group is a $C_8$ bridged bicyclic group. In certain preferred embodiments, the bridged heterocyclic group is a $C_9$ bridged bicyclic. In certain preferred embodiments, the bridged heterocyclic group has a bridge of 0, 1, 2 or 3 carbon atoms. In certain preferred embodiments, the bridged heterocyclic group has a bridge of 0, 1 or 3 carbon atoms. A bridge of 0 carbon atoms is a bond, and equates to a heterocyclic group fused to another ring structure. In certain preferred embodiments, the bridged heterocyclic group has a bridge of 1 or 3 carbon atoms. In certain preferred embodiments, the bridged heterocyclic group has a bridge of 1 carbon atom. In certain preferred embodiments, the bridged heterocyclic group has a bridge of 2 carbon atoms. In certain preferred embodiments, the bridged heterocyclic group has a bridge of 3 carbon atoms. If a bridged heterocyclic group is described as "optionally substituted", it is intended to be optionally substituted on any position, including the bridge. The bridged heterocyclic group is not limited to any particular stereochemistry.

In certain preferred embodiments, the heterocyclic group is a heteroaryl group. As used herein, the term "heteroaryl" is intended to mean a mono-, bi, tri or polycyclic group having 5 to 14 ring atoms, preferably 5, 6, 9, or 10 ring atoms; having 6, 10, or 14 pi electrons shared in a cyclic array; and having, in addition to carbon atoms, between one or more heteroatoms selected from the group consisting of N, O, and S. For example, a heteroaryl group may be pyrimidyl, pyridyl, benzimidazolyl, thienyl, benzothiazolyl, benzofuryl and indolinyl. Preferred heteroaryl groups include, without limitation, thienyl, benzothienyl, furyl, benzofuryl, dibenzofuryl, pyrrolyl, imidazolyl, pyrazolyl, pyridyl, pyrazinyl, indolyl, quinolyl, isoquinolyl, quinoxalinyl, tetrazolyl, oxazolyl, thiazolyl, and isoxazolyl. As used herein, the term "thienyl" is the same as the term "thiophenyl".

A "heteroaralkyl" or "heteroarylalkyl" group comprises a heteroaryl group covalently linked to an alkyl group. If such a group is described as "optionally substituted", it is intended that, either or both the "alkyl" or "heteroaryl" moieties may independently be optionally substituted or unsubstituted. Preferred heteroalkyl groups comprise a $C_1$-$C_6$ alkyl group and a heteroaryl group having 5, 6, 9, or 10 ring atoms. Specifically excluded from the scope of this term are compounds having adjacent annular O and/or S atoms. Examples of preferred heteroaralkyl groups include pyridylmethyl, pyridylethyl, pyrrolylmethyl, pyrrolylethyl, imidazolylmethyl, imidazolylethyl, thiazolylmethyl, and thiazolylethyl.

An "arylene," "heteroarylene," or "heterocyclylene" group is an aryl, heteroaryl, or heterocyclyl group, as defined hereinabove, that is positioned between and serves to connect two other chemical groups.

Preferred heterocyclyls and heteroaryls include, but are not limited to, acridinyl, azocinyl, benzimidazolyl, benzofuryl, benzothiofuryl, benzothiophene, benzothiophenyl, benzoxazolyl, benzothiazolyl, benzotriazolyl, benzotetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furyl, furazanyl, imidazolidinyl, imidazolinyl, imidazolyl, 1H-indazolyl, indolenyl, indolinyl, indolizinyl, indolyl, 3H-indolyl, isobenzofuryl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridyl, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

As used herein, the term "pryidyl" is equivalent to the term "pyridinyl". Similarly, the term "pyrimidyl" is equivalent to the term "pyrimidinyl".

As employed herein, when a moiety (e.g., cycloalkyl, hydrocarbyl, aryl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—) nitro, halohydrocarbyl, hydrocarbyl, heterocycle, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, (b) $C_1$-$C_5$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ alkylsulfinyl, arylalkylsulfinyl, arylsulfinyl, $C_1$-$C_8$ alkylsulfonyl, arylalkylsulfonyl, arylsulfonyl, $C_0$-$C_6$ N-alkyl carbamoyl, $C_2$-$C_{15}$ N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, $C_5$-$C_{15}$ heteroaryl or any of these rings fused or spiro-fused to a cycloalkyl, heterocyclyl, aryl or heteroaryl, wherein each of the foregoing is further optionally substituted with one more moieties listed in (a), above; and (c) —$(CR^{32}R^{33})_s$—$NR^{30}R^{31}$, wherein s is an integer from 0 (in which case the nitrogen is directly bonded to the moiety that is substituted) to 6; $R^{32}$ and $R^{33}$ are each independently hydrogen, halo, hydroxyl, aryl, heteroaryl, cycloalkyl, heterocyclyl or $C_1$-$C_4$alkyl; and $R^{30}$ and $R^{31}$ are each independently hydrogen, cyano, oxo, hydroxyl, —$C_1$-$C_8$ alkyl, $C_1$-$C_8$ heteroalkyl, $C_1$-$C_8$ alkenyl, carboxamido, $C_1$-$C_3$ alkyl-carboxamido, carboxamido-$C_1$-$C_3$ alkyl, amidino, $C_2$-$C_8$hydroxyalkyl, $C_1$-$C_3$ alkylaryl, aryl-$C_1$-$C_3$ alkyl, $C_1$-$C_3$ alkylheteroaryl, heteroaryl-$C_1$-$C_3$ alkyl, $C_1$-$C_3$ alkylheterocyclyl, heterocyclyl-$C_1$-$C_3$ alkyl $C_1$-$C_3$ alkylcycloalkyl, cycloalkyl-$C_1$-$C_3$ alkyl, $C_2$-$C_8$ alkoxy, $C_2$-$C_8$ alkoxy-$C_1$-$C_4$alkyl, $C_1$-$C_8$ alkoxycarbonyl, aryloxycarbonyl, aryl-$C_1$-$C_3$ alkoxycarbonyl, heteroaryloxycarbonyl, heteroaryl-$C_1$-$C_3$ alkoxycarbonyl, $C_1$-$C_8$ acyl, $C_0$-$C_8$ alkyl-carbonyl, aryl-$C_0$-$C_8$ alkyl-carbonyl, heteroaryl-$C_0$-$C_8$ alkyl-carbonyl, cycloalkyl-$C_0$-$C_8$ alkyl-carbonyl, $C_0$-$C_8$ alkyl-NH-carbonyl, aryl-$C_0$-$C_8$ alkyl-NH-carbonyl, heteroaryl-$C_0$-$C_8$ alkyl-NH-carbonyl, cycloalkyl-$C_0$-$C_8$ alkyl-NH-carbonyl, $C_0$-$C_8$ alkyl-O-carbonyl, aryl-$C_0$-$C_8$ alkyl-O-carbonyl, heteroaryl-$C_0$-$C_8$ alkyl-O-carbonyl, cycloalkyl-$C_0$-$C_8$ alkyl-O-carbonyl, $C_1$-$C_8$ alkylsulfonyl, arylalkylsulfonyl, arylsulfonyl, heteroarylalkylsulfonyl, heteroarylsulfonyl, $C_1$-$C_8$ alkyl-NH-sulfonyl, arylalkyl-NH-sulfonyl, aryl-NH-sulfonyl, heteroarylalkyl-NH-sulfonyl, heteroaryl-NH-sulfonyl aroyl, aryl, cycloalkyl, heterocyclyl, heteroaryl, aryl-$C_1$-$C_3$ alkyl-, cycloalkyl-$C_1$-$C_3$ alkyl-, heterocyclyl-$C_1$-$C_3$ alkyl-, heteroaryl-$C_1$-$C_3$ alkyl-, or a protecting group, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents selected from the group consisting of (a) above, a protecting group, and ($X^{30}$—$Y^{31}$—), wherein said heterocyclyl may also be bridged (forming a bicyclic moiety with a methylene, ethylene or propylene bridge); wherein $X^{30}$ is selected from the group consisting of $C_1$-$C_8$alkyl, $C_2$-$C_8$alkenyl-, $C_2$-$C_8$alkynyl-, —$C_0$-$C_3$alkyl-$C_2$-$C_8$alkenyl-$C_0$-$C_3$alkyl, $C_0$-$C_3$alkyl-$C_2$-$C_8$alkynyl-$C_0$-$C_3$alkyl, $C_0$-$C_3$alkyl-O—$C_0$-$C_3$alkyl-, HO—$C_0$-$C_3$alkyl-, $C_0$-$C_4$alkyl-N($R^{30}$)—$C_0$-$C_3$alkyl-, N($R^{30}$)($R^{31}$)—$C_0$-$C_3$alkyl-, N($R^{30}$)($R^{31}$)—$C_0$-$C_3$alkenyl-, N($R^{30}$)($R^{31}$)—$C_0$-$C_3$alkynyl-, (N($R^{30}$)($R^{31}$))$_2$—C=N—, $C_0$-$C_3$alkyl-S(O)$_{0-2}$—$C_0$-$C_3$alkyl-, $CF_3$—$C_0$-$C_3$alkyl-, $C_1$-$C_8$heteroalkyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, N($R^{30}$)($R^{31}$)-heterocyclyl-$C_1$-$C_3$alkyl-, wherein the aryl, cycloalkyl, heteroaryl and heterocycyl are optionally substituted with from 1 to 3 substituents from (a); and $Y^{31}$ is selected from the group consisting of a direct bond, —O—, —N($R^{30}$)—, —C(O)—, —O—C(O)—, —C(O)—O—, —N($R^{30}$)—C(O)—, —C(O)—N($R^{30}$)—, —N($R^{30}$)—C(S)—, —C(S)—N($R^{30}$)—, —N($R^{30}$)—C(O)—N($R^{31}$)—, —N($R^{30}$)—C($NR^{30}$)—N($R^{31}$)—, —N($R^{30}$)—C($NR^{31}$)—, —C($NR^{31}$)—N($R^{30}$), —N($R^{30}$)—C(S)—N($R^{31}$)—, —N($R^{30}$)—C(O)—O—, —O—C(O)—N($R^{31}$)—, —N($R^{30}$)—C(S)—O—, —O—C(S)—N($R^{31}$)—, —S(O)$_{0-2}$—, —SO$_2$N($R^{31}$)—, —N($R^{31}$)—SO$_2$— and —N($R^{30}$)—SO$_2$N($R^{31}$)—.

As a non-limiting example, substituted phenyls include 2-fluorophenyl, 3,4-dichlorophenyl, 3-chloro-4-fluoro-phenyl, 2-fluoro-3-propylphenyl. As another non-limiting example, substituted n-octyls include 2,4-dimethyl-5-ethyloctyl and 3-cyclopentyl-octyl. Included within this definition are methylenes (—CH$_2$—) substituted with oxygen to form carbonyl —CO—.

When there are two optional substituents bonded to adjacent atoms of a ring structure, such as for example phenyl, thienyl, or pyridyl, the substituents, together with the atoms to which they are bonded, optionally form a 5- or 6-membered cycloalkyl or heterocycle having 1, 2, or 3 annular heteroatoms.

In a preferred embodiment, hydrocarbyl, heteroalkyl, heterocyclic and aryl groups are unsubstituted.

In other preferred embodiments, hydrocarbyl, heteroalkyl, heterocyclic and aryl groups are substituted with from 1 to 3 independently selected substituents.

Preferred substituents on alkyl groups include, but are not limited to, hydroxyl, halogen (e.g., a single halogen substituent or multiple halo substituents; in the latter case, groups such as $CF_3$ or an alkyl group bearing $Cl_3$), cyano, nitro, alkyl, cycloalkyl, alkenyl, cycloalkenyl, alkynyl, heterocycle, aryl, —OR$^u$, —SR$^u$, —S(=O)R$^y$, —S(=O)$_2$R$^y$, —P(=O)$_2$R$^y$, —S(=O)$_2$OR$^y$, —P(=O)$_2$OR$^y$, —NR$^v$R$^w$, —NR$^v$S(=O)$_2$R$^y$, —NR$^v$P(=O)$_2$R$^y$, —S(=O)$_2$NR$^v$R$^w$, —P(=O)$_2$NR$^v$R$^w$, —C(=O)OR$^y$, —C(=O)R$^u$, —C(=O)NR$^v$R$^w$, —OC(=O)R$^u$, —OC(=O)NR$^v$R$^w$, —NR$^v$C(=O)OR$^y$, —NR$^v$C(=O)NR$^v$R$^w$, —NR$^v$S(=O)$_2$NR$^v$R$^w$, —NR$^v$P(=O)$_2$NR$^v$R$^w$, —NR$^v$C(=O)R$^u$ or —NR$^v$P(=O)$_2$R$^y$, wherein R$^u$ is hydrogen, alkyl, cycloalkyl, alkenyl, cycloalkenyl, alkynyl, heterocycle or aryl; R$^v$, R$^w$ and R$^x$ are independently hydrogen, alkyl, cycloalkyl, heterocycle or aryl, or said R$^v$ and R$^w$ together with the N to which they are bonded optionally form a heterocycle; and R$^y$ is alkyl, cycloalkyl, alkenyl, cycloalkenyl, alkynyl, heterocycle or aryl. In the aforementioned exemplary substituents, groups such as alkyl, cycloalkyl, alkenyl, alkynyl, cycloalkenyl, heterocycle and aryl can themselves be optionally substituted.

Preferred substituents on alkenyl and alkynyl groups include, but are not limited to, alkyl or substituted alkyl, as well as those groups recited as preferred alkyl substituents.

Preferred substituents on cycloalkyl groups include, but are not limited to, nitro, cyano, alkyl or substituted alkyl, as well as those groups recited about as preferred alkyl substituents. Other preferred substituents include, but are not limited to, spiro-attached or fused cyclic substituents, preferably spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Preferred substituents on cycloalkenyl groups include, but are not limited to, nitro, cyano, alkyl or substituted alkyl, as well as those groups recited as preferred alkyl substituents. Other preferred substituents include, but are not limited to, spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Preferred substituents on aryl groups include, but are not limited to, nitro, cycloalkyl or substituted cycloalkyl, cycloalkenyl or substituted cycloalkenyl, cyano, alkyl or substituted alkyl, as well as those groups recited above as preferred alkyl substituents. Other preferred substituents include, but are not limited to, fused cyclic groups, especially fused cycloalkyl, fused cycloalkenyl, fused heterocycle, or fused aryl, where the aforementioned cycloalkyl, cylcoalkenyl, heterocycle and aryl substituents can themselves be optionally substituted. Still other preferred substituents on aryl groups (phenyl, as a non-limiting example) include, but are not limited to, haloalkyl and those groups recited as preferred alkyl substituents.

Preferred substituents on heterocylic groups include, but are not limited to, cycloalkyl, substituted cycloalkyl, cycloalkenyl, substituted cycloalkenyl, nitro, oxo (i.e., =O), cyano, alkyl, substituted alkyl, as well as those groups recited as preferred alkyl substituents. Other preferred substituents on heterocyclic groups include, but are not limited to, spiro-attached or fused cyclic substituents at any available point or points of attachment, more preferably spiro-attached cycloalkyl, spiro-attached cycloalkenyl, spiro-attached heterocycle (excluding heteroaryl), fused cycloalkyl, fused cycloakenyl, fused heterocycle and fused aryl, where the aforementioned cycloalkyl, cycloalkenyl, heterocycle and aryl substituents can themselves be optionally substituted.

In a preferred embodiment, a heterocyclic group is substituted on carbon, nitrogen and/or sulfur at one or more positions. Preferred substituents on nitrogen include, but are not limited to N-oxide, alkyl, aryl, aralkyl, alkylcarbonyl, alkylsulfonyl, arylcarbonyl, arylsulfonyl, alkoxycarbonyl, or aralkoxycarbonyl. Preferred substituents on sulfur include, but are not limited to, oxo and C$_{1-6}$alkyl. In certain preferred embodiments, nitrogen and sulfur heteroatoms may independently be optionally oxidized and nitrogen heteroatoms may independently be optionally quaternized.

Especially preferred substituents on alkyl groups include halogen and hydroxy.

Especially preferred substituents on ring groups, such as aryl, heteroaryl, cycloalkyl and heterocyclyl, include halogen, alkoxy and alkyl.

In addition, preferred substituents on cyclic moieties (i.e., cycloalkyl, heterocyclyl, aryl, heteroaryl) include 5-6 membered mono- and 9-14 membered bi-cyclic moieties fused to the parent cyclic moiety to form a bi- or tri-cyclic fused ring system. Substituents on cyclic moieties also include 5-6 membered mono- and 9-14 membered bi-cyclic moieties attached to the parent cyclic moiety by a covalent bond to form a bi- or tri-cyclic bi-ring system. For example, an optionally substituted phenyl includes, but is not limited to, the following:

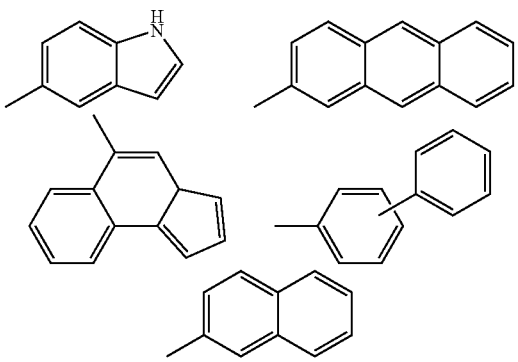

A "halohydrocarbyl" is a hydrocarbyl moiety in which from one to all hydrogens have been replaced with one or more halo. Similarly, "haloalkyl" is an alkyl moiety in which from one to all hydrogens have each been replaced with a halo.

The term "halogen" or "halo" as employed herein refers to chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., NH$_2$—CO—). The nitrogen atom of an acylamino or carbamoyl substituent is additionally substituted. The term "sulfonamido" refers to a sulfonamide substituent attached by either the sulfur or the nitrogen atom. The term "amino" is meant to include NH$_2$, alkylamino, di-alkylamino, arylamino, and cyclic amino groups. The term "ureido" as employed herein refers to a substituted or unsubstituted urea moiety.

The term "radical" as used herein means a chemical moiety comprising one or more unpaired electrons.

An "unsubstituted" moiety as defined above (e.g., unsubstituted cycloalkyl, unsubstituted heteroaryl, etc.) means that moiety as defined above that does not have any of the optional substituents for which the definition of the moiety (above) otherwise provides. Thus, for example, "unsubstituted aryl" does not include phenyl substituted with a halo.

Throughout the specification preferred embodiments of one or more chemical substituents are identified. Also preferred are combinations of preferred embodiments.

The term "protecting group" is intended to mean a group used in synthesis to temporarily mask the characteristic chemistry of a functional group because it interferes with another reaction. A good protecting group should be easy to put on, easy to remove and in high yielding reactions, and inert to the conditions of the reaction required. A protecting group or protective group is introduced into a molecule by chemical modification of a functional group in order to obtain chemoselectivity in a subsequent chemical reaction. One skilled in the art will recognize that during any of the processes for preparation of the compounds in the present invention, it may be necessary and/or desirable to protect sensitive or reactive groups on any of the molecules concerned. This may be achieved by means of conventional protecting groups, such as but not limited to Bn- (or —CH$_2$Ph), —CHPh$_2$, alloc (or CH$_2$=CH—CH$_2$—O—C(O)—), BOC-, -Cbz (or Z-), —F-moc, —C(O)—CF$_3$, N-Phthalimide, 1-Adoc-, TBDMS-, TBDPS-, TMS-, TIPS-, IPDMS-, —SiR$_3$, SEM-, t-Bu-, Tr-, THP- and Allyl-. These protecting groups may be removed at a convenient stage using methods known from the art.

Some compounds of the invention may have chiral centers and/or geometric isomeric centers (E- and Z-isomers), and it is to be understood that the invention encompasses all such optical, diastereoisomers and geometric isomers. The invention also comprises all tautomeric forms of the compounds disclosed herein. Where compounds of the invention include chiral centers, the invention encompasses the enantiomerically pure isomers of such compounds, the enantiomerically enriched mixtures of such compounds, and the racemic and scalemic mixtures of such compounds. Preferably in enantiomerically enriched mixtures there is greater or equal to 80% of one enantiomer, more preferably greater than 90%, 95%, or 98%.

The present invention also includes prodrugs of compounds of the invention. The term "prodrug" is intended to represent covalently bonded carriers, which are capable of releasing the active ingredient when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of the invention include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like.

The compounds of the invention may be administered as is or as a prodrug, for example in the form of an in vivo hydrolyzable ester or in vivo hydrolyzable amide. An in vivo hydrolyzable ester of a compound of the invention containing carboxy or hydroxy group is, for example, a pharmaceutically acceptable ester which is hydrolyzed in the human or animal body to produce the parent acid or alcohol. Suitable pharmaceutically acceptable esters for carboxy include C$_{1-6}$-alkoxymethyl esters (e.g., methoxymethyl), C$_{1-6}$-alkanoyloxymethyl esters (e.g., for example pivaloyloxymethyl), phthalidyl esters, C$_{3-8}$-cycloalkoxycarbonyloxyC$_{1-6}$-alkyl esters (e.g., 1-cyclohexylcarbonyloxyethyl); 1,3-dioxolen-2-onylmethyl esters (e.g., 5-methyl-1,3-dioxolen-2-onylmethyl; and C$_{1-6}$-alkoxycarbonyloxyethyl esters (e.g., 1-methoxycarbonyloxyethyl) and may be formed at any carboxy group in the compounds of this invention.

An in vivo hydrolyzable ester of a compound of the invention containing a hydroxy group includes inorganic esters such as phosphate esters and a-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolyzable ester forming groups for hydroxy include alkanoyl, benzoyl, phenylacetyl and substituted benzoyl and phenylacetyl, alkoxycarbonyl (to give alkyl carbonate esters), dialkylcarbamoyl and N—(N,N-dialkylaminoethyl)-N-alkylcarbamoyl (to give carbamates), N,N-dialkylaminoacetyl and carboxyacetyl. Examples of substituents on benzoyl include morpholino and piperazino linked from a ring nitrogen atom via a methylene group to the 3- or 4-position of the benzoyl ring. A suitable value for an in vivo hydrolyzable amide of a compound of the invention containing a carboxy group is, for example, a N—C$_{1-6}$-alkyl or N,N-di-C$_{1-6}$-alkyl amide such as N-methyl, N-ethyl, N-propyl, N,N-dimethyl, N-ethyl-N-methyl or N,N-diethyl amide.

The foregoing merely summarizes some aspects and preferred embodiments thereof and is not intended to be limiting in nature. These aspects and preferred embodiments thereof are described more fully below.

Compounds

In one aspect, the invention comprises compounds of formula I:

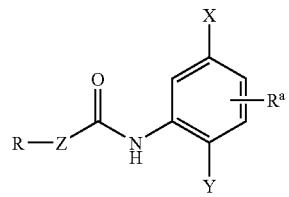

and N-oxides, hydrates, solvates, pharmaceutically acceptable salts, prodrugs or complexes thereof, and racemic and scalemic mixtures, diastereomers and enantiomers thereof, wherein in embodiment (I):

X is phenyl, thienyl, pyridyl, or pyrimidyl, each of which is optionally substituted with one to three substituents independently selected from halo, —CN, —CH=N(OH), hydroxy, C$_1$-C$_3$-hydrocarbyl, —O—C$_1$-C$_4$alkyl, —(CH$_2$)$_{0-3}$—N(R$^3$)(R$^4$), methoxy, or mono-, di-, or tri-halo substituted alkyl, or, when there are two optional substituents bonded to adjacent atoms of the phenyl, thienyl, or pyridyl they, together with the atoms to which they are bonded, optionally form a 5- or 6-membered cycloalkyl or heterocycle having 1, 2, or 3 annular heteroatoms, which cycloalkyl or heterocycle is optionally substituted with oxo, alkyl and —C(O)—O-alkyl-heteroaryl;

Y is —NH$_2$ or OH;

R$^a$ is H or halo (preferably F);

Z is selected from the group consisting of a bond, phenyl, furyl, benzofuryl, pyridyl, —C$_1$-C$_3$alkyl-phenyl, -phenyl-C$_1$-C$_3$alkyl-heterocyclyl, -phenyl-alkenyl-, -phenyl-alkyl-, heterocyclyl and cycloalkyl, each of which is optionally substituted with C$_1$-C$_3$alkyl, —OMe or halo;

R is selected from the group consisting of H, —(CH$_2$)$_{0-3}$—N(R$^3$)(R$^4$), —(CH$_2$)—C(O)—N(R$^3$)(R$^4$), —(CH$_2$)$_{0-2}$—C(O)—O—(CH$_2$)$_{2-3}$—N(R$^3$)(R$^4$), —(CH$_2$)$_{0-2}$—C(O)O—(CH$_2$)$_{0-3}$-heteroaryl, —(CH$_2$)$_{0-2}$—C(O)—O—(CH$_2$)$_{0-3}$-aryl, —SO$_2$—(CH$_2$)$_{0-3}$-aryl, —SO$_2$—N(R$^3$)(R$^4$), —SO$_2$—(CH$_2$)$_{0-3}$-heteroaryl, —SO$_2$—(CH$_2$)$_{0-3}$- heterocyclyl, indole, cyclooctaincole, —$(CH_2)_{2-3}$-heterocyclyl, —$(CH_2)_{0-3}$-aryl, —$(CH_2)_{0-3}$-heteroaryl, —$(CH_2)_{1-3}$—O—C(O)—$C_{1-6}$alkyl (wherein the alkyl is optionally substituted with a moiety selected from the group consisting of —$N(R^{30})(R^{31})$, —$(CR^{32}R^{33})_s$—$N(R^{30})(R^{31})$, —$Y^{31}$—$X^{30}$, and —O—$(CH_2)_{2-3}$—N$(R^3)(R^4)$, and wherein the aryl, heteroaryl, heterocyclyl are each optionally substituted; or —Z—R is selected from the group consisting —$C_1$-$C_8$alkyl, -phenyl-heterocyclyl, -phenyl-dibenzo-oxazepine, -benzofuryl-heterocyclyl, -benzofuryl-O—$(CH_2)_{2-3}$-heterocyclyl, -benzothienyl-O—$(CH_2)_{2-3}$-heterocyclyl, or -benzofuryl-O—$(CH_2)_{2-3}$—$N(R^3)(R^4)$, each of which is optionally substituted; and $R^3$ and $R^4$ are independently selected from the group consisting of H, —$C_1$-$C_6$ alkyl, —$C_2$-$C_3$ alkyl-$OR^5$, aryl, heteroaryl, -heteroaryl-heteroaryl, -heteroaryl-aryl, -aryl-heteroaryl, —C(O)-aryl, —$C_1$-$C_3$-alkoxy-$C_1$-$C_3$-alkyl, —$C_2$-$C_3$alkyl-O—$C_1$-$C_3$alkyl, —$C_2$-$C_3$-alkyl-$NR^5R^6$, —$CH_2$—$C(CH_3)_2$—$NR^5R^6$, wherein aryl and heteroaryl are optionally substituted with one, two or three amino, methoxy, hydroxyl, —S—$CH_2$-heterocyclyl, —$NR_3S(O)_2$—$C_1$-$C_3$alkyl, or $R^3$ and $R^4$, together with the nitrogen to which they are both bonded, form a 4- or 6-membered heterocyclyl with 1 or 2 annular heteroatoms (including the nitrogen to which $R^3$ and $R^4$ are bonded), which heterocyclyl is optionally substituted with 1 to 3 substituents independently selected from the group consisting of H, hydroxy, oxo, amino, —N=$C(NR^3R^4)_2$, one, two or three $C_1$-$C_6$ alkyl, aryl, heteroaryl, —$C_1$-$C_6$ alkyl-aryl, —$C_1$-$C_6$ alkyl-heteroaryl, —$C_1$-$C_3$-alkoxy-$C_1$-$C_3$-alkyl, —$C_0$-$C_3$-alkyl-$SR^7$, —$C_2$-$C_3$-alkyl-OH, —$C_2$-$C_3$-alkyl-O—$C_1$-$C_4$-alkyl, —$C_5$-$C_6$-cycloalkyl, —$C_0$-$C_3$-alkyl-$N(R^3)$—C(O)—$C_1$-$C_3$alkyl, —$C_{0-3}$alkyl-$N(R^3)$—C(O)-tihalomethyl, —$C_0$-$C_3$-alkyl-$NR^3C(O)O$—$C_1$-$C_3$alkyl-aryl, —$C_0$-$C_3$-alkyl-$CF_3$, —$C_0$-$C_3$-alkyl-$NR^3C(O)O$—$C_1$-$C_3$alkyl-heteroaryl and —$C_0$-$C_3$-alkyl-$N(R^7)(R^8)$, wherein said heterocyclyl is optionally fused to an aryl or heteroaryl;

$R^5$, $R^6$, $R^7$, and $R^8$ are independently selected from —H, —$C_0$-$C_3$-alkyl-aryl, —$C_0$-$C_3$-alkyl-heteroaryl, —$C_0$-$C_3$-alkyl-heterocycyl, —$C_0$-$C_3$-alkyl-cycloalkyl and $C_1$-$C_6$-alkyl;

s is an integer from 0 (in which case the nitrogen is directly bonded to the moiety that is substituted) to 6;

$R^{32}$ and $R^{33}$ are each independently selected from the group consisting of hydrogen, halo, hydroxyl, —$C_0$-$C_3$alkyl-aryl, —$C_0$-$C_3$alkyl-heteroaryl, —$C_0$-$C_3$alkyl-heterocyclyl, —$C_0$-$C_3$alkyl-cycloalkyl and $C_1$-$C_4$alkyl;

$R^{30}$ and $R^{31}$ are each independently selected from the group consisting of hydrogen, cyano, oxo, hydroxyl, —$C_1$-$C_8$alkyl, $C_1$-$C_8$heteroalkyl, $C_1$-$C_8$alkenyl, carboxamido, $C_1$-$C_3$alkyl-carboxamido-, carboxamido-$C_1$-$C_3$alkyl-, amidino, $C_2$-$C_8$hydroxyalkyl-, $C_1$-$C_3$alkylaryl-, aryl-$C_1$-$C_3$alkyl-, $C_1$-$C_3$alkylheteroaryl-, heteroaryl-$C_1$-$C_3$alkyl-, $C_1$-$C_3$alkylheterocyclyl-, heterocyclyl-$C_1$-$C_3$alkyl, $C_1$-$C_3$alkylcycloalkyl-, cycloalkyl-$C_1$-$C_3$alkyl-, $C_2$-$C_8$alkoxy, $C_2$-$C_8$alkoxy-$C_1$-$C_4$alkyl-, $C_1$-$C_8$alkoxycarbonyl-, aryloxycarbonyl, aryl-$C_1$-$C_3$alkoxycarbonyl-, heteroaryloxycarbonyl, heteroaryl-$C_1$-$C_8$alkoxycarbonyl-, $C_1$-$C_8$acyl, $C_0$-$C_8$alkyl-carbonyl-, aryl-$C_0$-$C_8$alkyl-carbonyl-, heteroaryl-$C_0$-$C_8$alkyl-carbonyl-, cycloalkyl-$C_0$-$C_8$alkyl-carbonyl-, $C_0$-$C_8$alkyl-NH-carbonyl-, aryl-$C_0$-$C_8$alkyl-NH-carbonyl-, heteroaryl-$C_0$-$C_8$alkyl-NH-carbonyl-, cycloalkyl-$C_0$-$C_8$alkyl-NH-carbonyl-, $C_0$-$C_8$alkyl-O-carbonyl-, aryl-$C_0$-$C_8$alkyl-O-carbonyl-, heteroaryl-$C_0$-$C_8$alkyl-O-carbonyl-, cycloalkyl-$C_0$-$C_8$alkyl-O-carbonyl-, $C_1$-$C_8$alkylsulfonyl-, arylalkylsulfonyl-, arylsulfonyl-, heteroarylalkylsulfonyl-, heteroarylsulfonyl-, $C_1$-$C_8$alkyl-NH-sulfonyl-, arylalkyl-NH-sulfonyl-, aryl-NH-sulfonyl-, heteroarylalkyl-NH-sulfonyl-, heteroaryl-NH-sulfonyl-, aroyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl- and a protecting group, wherein each of the foregoing is further optionally substituted with one more moieties selected from halo, cyano, oxo, carboxy, formyl, nitro, amino, amidino and guanidino; or $R^{30}$ and $R^{31}$ taken together with the N to which they are attached form a heterocyclyl or heteroaryl, each of which is optionally substituted with from 1 to 3 substituents selected from the group consisting of halo, cyano, oxo, carboxy, formyl, nitro, amino, amidino, guanidino, a protecting group, and ($X^{30}$—$Y^{31}$—), wherein said heterocyclyl may also be bridged (forming a bicyclic moiety with a methylene, ethylene or propylene bridge);

$X^{30}$ is selected from the group consisting of $C_1$-$C_8$alkyl-, $C_2$-$C_8$alkenyl-, $C_2$-$C_8$alkynyl-, $C_0$-$C_3$alkyl-$C_2$-$C_8$alkenyl-$C_0$-$C_3$alkyl-, $C_0$-$C_3$alkyl-$C_2$-$C_8$alkynyl-$C_0$-$C_3$alkyl-, $C_0$-$C_3$alkyl-O—$C_0$-$C_3$alkyl-, HO—$C_0$-$C_3$alkyl-, $C_0$-$C_4$alkyl-$N(R^{30})$—$C_0$-$C_3$alkyl-, $N(R^{30})(R^{31})$—$C_0$-$C_3$alkyl-, $N(R^{30})(R^{31})$—$C_0$-$C_3$alkenyl-, $N(R^{30})(R^{31})$—$C_0$-$C_3$alkynyl-, $(N(R^{30})(R^{31}))_2$—C=N—, $C_0$-$C_3$alkyl-$S(O)_{0-2}$—$C_0$-$C_3$alkyl-, $CF_3$—$C_0$-$C_3$alkyl-, $C_1$-$C_8$heteroalkyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl- and $N(R^{30})(R^{31})$-heterocyclyl-$C_1$-$C_3$alkyl-, wherein the aryl, cycloalkyl, heteroaryl and heterocycyl are optionally substituted with from 1 to 3 substituents from halo, cyano, oxo, carboxy, formyl, nitro, amino, amidino and guanidino; and $Y^{31}$ is selected from the group consisting of a direct bond, —O—, —$N(R^{30})$—, —C(O)—, —O—C(O)—, —C(O)—O—, —$N(R^{30})$—C(O)—, —C(O)—N$(R^{30})$—, —$N(R^{30})$—C(S)—, —C(S)—$N(R^{30})$—, —$N(R^{30})$—C(O)—$N(R^{31})$—, —$N(R^{30})$—C($NR^{31}$)—$N(R^{31})$—, —$N(R^{30})$—$C(NR^{31})$—, —$C(NR^{31})$—$N(R^{30})$, —$N(R^{30})$—C(S)—$N(R^{31})$—, —$N(R^{30})$—C(O)—O—, —O—C(O)—$N(R^{31})$—, —$N(R^{30})$—C(S)—O—, —O—C(S)—$N(R^{31})$—, —$S(O)_{0-2}$—, —$SO_2N(R^{31})$—, —$N(R^{31})$—$SO_2$— and —$N(R^{30})$—$SO_2N(R^{31})$—;

provided that $Y^{31}$ and $X^{30}$ are not linked to form —O—O— or —O—N—;

in embodiment (II):

X is thienyl (preferably thien-2-yl);

Y is —$NH_2$;

Z is pyridyl (preferably pyrid-3-yl), furyl, heterocyclyl, or cycloalkyl; and

R is —C(=NH)($N(R^3)(R^4)$), —$C(NH_2)$(=NOMe), —$C(NH_2)$(=NOH), —$NR^3SO_2NR^3R^4$, —C≡C—$C_1$-$C_3$alkyl-$NR^3R^4$, —$C_0$-$C_3$alkyl-aryl or —$C_0$-$C_3$alkyl-(5- or 6-membered heterocyclyl) optionally substituted with $C_1$-$C_3$-alkyl or —$N(R^3)(R^4)$, wherein $R^3$ and $R^4$ are defined as in embodiment (I), above;

in embodiment (III):

X is thienyl (preferably thienyl-2-yl), phenyl or pyridyl, each of which is optionally substituted with $C_1$-$C_3$alkyl or halo;

Y is —NH$_2$;
Z is phenyl, pyridyl (preferably pyrid-2-yl), furyl, thienyl, heterocyclyl, or cycloalkyl; and
R is an optionally substituted —C$_0$-C$_3$alkyl-aryl, —C(O)-aryl, —C$_0$-C$_3$alkyl-N(R$^3$)-aryl, —C$_0$-C$_3$alkyl-(5- or 6-membered aryl or heteroaryl) (preferably optionally substituted with from 1 to 3 C$_1$-C$_3$-alkoxy);
wherein R$^3$ is defined as in embodiment (I), above
in embodiment (IV):
X is thienyl (preferably (thien-2-yl), phenyl, pyridyl, or pyridyl-N-oxide, wherein the thienyl may also be optionally substituted with halo or CN, and the phenyl and pyridyl moities are optionally substituted with one or more halo;
Y is —NH$_2$;
R$^a$ is H or F;
Z is aryl, 5- to 9-membered heterocyclyl, heteroaryl, or cycloalkyl, each of which is optionally substituted with one or two substituents selected from halo, oxo, CN, hydroxy, C$_1$-C$_3$-hydrocarbyl, methoxy, or mono-, di-, or tri-halo substituted alkyl, or, when there are two optional substituents bonded to adjacent atoms of the aryl, heteroaryl, or heterocyclyl they, together with the atoms to which they are bonded, optionally form a 5- or 6-membered cycloalkyl or heterocycle having 1, 2, or 3 annular heteroatoms; and
R is H, halo, hydroxyl, C$_1$-C$_3$alkyl-OH, cyano, alkyoxy, —C$_0$-C$_3$alkyl-N(R$^3$)(R$^4$), —C$_0$-C$_3$alkyl-N(R$^3$)—C$_1$-C$_3$alkyl-CH(OH)—CH$_2$OH, —C$_0$-C$_2$-alkyl-aryl or —C$_0$-C$_2$-alkyl-(5- or 6-membered heteroaryl or heterocyclyl), wherein the aryl, heteroaryl and heterocyclyl are optionally substituted with one to three independently selected moieties selected from the group consisting of methyl, halo, hydroxy, oxo-, —Y$^{31}$—X$^{30}$, or —(CR$^{32}$R$^{33}$)$_s$—N(R$^{30}$)(R$^{31}$);
wherein R$^3$, R$^4$, R$^{30}$, R$^{31}$, R$^{32}$, R$^{33}$, s, Y$^{31}$ and X$^{30}$ are defined as in embodiment (I), above
in embodiment (V):
X is thienyl (preferably thien-2-yl);
Y is —NH$_2$;
R$^a$ is H or F;
Z is phenyl, heterocyclyl or cycloalkyl;
R is —(CH$_2$)—N(R$^3$)(R$^4$);
R$^3$ and R$^4$ are independently H, C$_1$-C$_6$ alkyl, (5- or 6-membered heteroaryl)-C$_0$-C$_2$-alkyl-; or
R$^3$ and R$^4$, together with the nitrogen to which they are both bonded, form a 5- or 6-membered heterocyclyl with 1 or 2 annular heteroatoms (including the nitrogen to which R$^3$ and R$^4$ are bonded), which heterocyclyl is optionally substituted with at least one (preferably one, two, or three) moieties independently selected from hydroxy, oxo, C$_1$-C$_6$ alkyl, C$_1$-C$_6$ alkyloxy, —N(R$^5$)(R$^6$), C$_1$-C$_6$ alkyloxyC$_1$-C$_6$ alkyl, —NR$^7$—C(O)—C$_1$-C$_2$-alkyl, NR$^7$R$^8$—C$_0$-C$_3$-alkyl, or (5- or 6-membered aryl, heterocyclyl or heteroaryl)-C$_0$-C$_2$-alkyl; and
R$^5$, R$^6$, R$^7$, and R$^8$ are independently selected from —H and C$_1$-C$_6$-alkyl;
wherein R$^3$ and R$^4$ are defined as in embodiment (I), above
in embodiment (VI):
X is thienyl (preferably thien-2-yl), thiazolyl, pyridyl, pyrimidyl or phenyl optionally substituted with one, two or three halo, amino or methoxy;
Y is —NH$_2$ or —OH;
Z is phenyl, heterocyclyl or cycloalkyl;
R is N(R$^3$)(R$^4$)—C$_0$-C$_1$-alkyl- or N(R$^5$)(R$^6$)—C$_1$-C$_3$-alkyl-S—, N(R$^{30}$)(R$^{31}$)—(CR$^{32}$R$^{33}$)$_s$—, or X$^{30}$—Y$^{31}$—;

R$^3$ and R$^4$ are independently —H, —C$_1$-C$_6$ alkyl, —C(O)—C$_0$-C$_3$ alkyl-aryl, aryl, -heteroaryl-aryl, -arylheteroaryl, aryl or heteroaryl and are optionally substituted with one, two or three halo, CF$_3$, amino or hydroxyl; or
R$^3$ and R$^4$, together with the nitrogen to which they are both bonded, form a 5- or 6-membered heterocyclyl with 1 or 2 annular heteroatoms (including the nitrogen to which R$^3$ and R$^4$ are bonded), which heterocyclyl is optionally substituted with C$_1$-C$_6$ alkyl, C$_1$-C$_3$-alkoxy-C$_1$-C$_3$-alkyl-, —N═C(NR$^3$R$^4$)$_2$, —C(O)O—C$_0$-C$_3$alkyl-aryl, —C(O)O—C$_0$-C$_3$alkyl-heteroaryl, hydroxyl, —N(R$^5$)(R$^6$), —C$_0$-C$_2$-alkyl-aryl, —C$_0$-C$_2$-alkyl-(5- or 6-membered cycloalkyl, aryl, heterocyclyl or heteroaryl), —NH-aryl, or —NH-(5- or 6-membered cycloalkyl, heterocyclyl or heteroaryl); and
R$^5$ and R$^6$ are, independently, H, —C$_0$-C$_3$alkyl-aryl, heteroaryl-C$_0$-C$_3$alkyl-heteroaryl, —SO$_2$-Me, —C(O)—C$_1$-C$_4$alkyl or C$_1$-C$_3$-alkyl; wherein R$^{30}$, R$^{31}$, R$^{32}$, R$^{33}$, s, Y$^{31}$ and X$^{30}$ are defined as in embodiment (I), above
in embodiment (VII)
X is thienyl (preferably thien-2-yl), phenyl, pyrimidyl or pyridyl;
Y is —NH$_2$;
R$^a$ is H or F;
Z is pyrimid-5-yl, heterocyclyl, or cycloalkyl;
R is C$_1$-C$_3$-alkoxy or —N(R$^3$)(R$^4$); and
R$^3$ and R$^4$, together with the nitrogen to which they are both bonded, form a 5- or 6-membered heterocyclyl, or bridged heterocyclyl, with 1 or 2 annular heteroatoms (including the nitrogen to which R$^3$ and R$^4$ are bonded), which heterocyclyl is optionally substituted with amino, hydroxyl, C$_1$-C$_6$ alkyl, —C$_0$-C$_2$-alkyl-aryl or —C$_0$-C$_2$-alkyl-(5- or 6-membered cycloalkyl, heterocyclyl or heteroaryl), wherein the aryl is optionally substituted with one to three independently selected substituents selected from the group consisting of halo, methoxy, CF$_3$, CN and alkyl;
in embodiment (VIII):
X is aryl or a 5- or 6-membered heteroaryl optionally substituted with amino;
Y is —NH$_2$ or NHSO$_2$NH$_2$;
R$^a$ is H or F;
Z is phenyl, thienyl, heterocyclyl or cycloalkyl; and
R is C$_1$-C$_3$-alkoxy, aryl or a 5- or 6-membered heteroaryl;
in embodiment (IX):
X is aryl or 5- or 6-membered heteroaryl optionally substituted by one or two independently selected halo or CN;
Y is —NH$_2$;
R$^a$ is H or F;
Z is phenyl, heterocyclyl or cycloalkyl; and
R is a —C$_0$-C$_1$-alkyl-(aryl, heteroaryl or 5-10-membered heterocyclyl) optionally substituted by methyl or oxo;
in embodiment (X):
X is thienyl;
Y is —NH$_2$;
R$^a$ is H or F;
Z is phenyl, heterocyclyl or cycloalkyl;
R is R$^8$—C(O)—C$_0$-C$_3$-alkyl- or Ac—NH—, and Z is further optionally substituted with —OH; and
R$^8$ is —OH, HO—NH—, or CH$_3$—O—;

in embodiment (XI):
X is cyclopentenyl optionally substituted with oxo or hydroxy;
Y is —NH$_2$;
R$^a$ is H or F;
Z is benzyl, —C$_0$-C$_3$alkyl-phenyl heterocyclyl or cycloalkyl; and
R is —C$_0$-C$_3$alkyl-morpholinyl;
in embodiment (XII):
X is aryl or 5- or 6-membered heteroaryl optionally substituted by one, two or three independently selected hydroxyl, —O—C$_1$-C$_3$alkyl, amino, —NR$^3$R$^4$, —CN, —CF$_3$, —C$_1$-C$_4$alkyl, —S(O)$_{0-2}$R$^5$, —O—CF$_3$ or halo;
Y is —NH$_2$ or —OH;
R$^a$ is H or F;
Z is phenyl, heteroaryl, heterocyclyl, or cycloalkyl;
R is R$^9$—(C$_{0-6}$alkyl)N—C(O)—N(H)—(CH$_2$)$_t$—, C$_{0-6}$alkyl-S(O)$_2$—N(H)-phenyl-C(O)—N(H) —(CH$_2$)$_t$—, R$^9$—O—C(O)—N(H)—(CH$_2$)$_t$— or R$^9$—O—C(O)—(CH$_2$)$_t$— wherein t is 0-2; and
R$^9$ is R$^{10}$—C$_0$-C$_2$-alkyl-, wherein R$^{10}$ is aryl, 5- or 6-membered heterocyclyl or heteroaryl or N(X$^1$)(X$^2$)—C$_{0-3}$ alkyl- wherein X$^1$ and X$^2$ are independently H, C$_1$-C$_4$-alkyl or 5- or 6-membered heteroaryl, or X$^1$ and X$^2$, together with the N to which they are bonded form a 5- or 6-membered heterocyclyl optionally substituted with methyl, which heterocyclyl and heteroaryl are optionally substituted with alkyl; provided that when R$^{10}$ is heterocyclyl attached through the N atoms, then R$^9$ is R$^{10}$—C$_2$-alkyl-;
wherein R$^3$ and R$^4$ are defined as in embodiment (I), above
in embodiment (XIII):
X is aryl or 5- or 6-membered cycloalkyl, heterocyclyl, or heteroaryl optionally substituted with hydroxy, oxo, or one or two halo;
Y is —OH or —NH$_2$;
Z is phenyl, pyridyl, benzofuryl, heterocyclyl, or cycloalkyl optionally substituted with hydroxy, OMe or one or two halo, wherein when there are two optional substituents bonded to adjacent atoms of the phenyl, or benzofuryl they, together with the atoms to which they are bonded, optionally form a 5- or 6-membered cycloalkyl or heteroalkyl having 1, 2, or 3 annular heteroatoms; and
R is —OH, —OMe, —O—C$_0$-C$_3$alkyl-heterocyclyl or —OAc; and
in embodiment (XIV):
X is thienyl;
Y is —NH$_2$;
R$^a$ is H;
Z is phenyl, heterocyclyl or cycloalkyl;
R is R$^{20}$—C(O)—(C$_2$-C$_3$-alkyl or C$_2$-C$_3$-alkenyl)-; and
R$^{20}$ is HO—, HO—NH—, or MeO—;
in embodiment (XV):
X is pyridyl;
Y is —NH$_2$;
R$^a$ is H or F;
Z is phenyl, heterocyclyl, cycloalkyl or heteroaryl, wherein phenyl, heterocyclyl, cycloalkyl or heteroaryl are optionally substituted with hydroxy, alkyloxy, or halo; and
R is —O—C$_0$-C$_4$-alkyl or —O—C$_2$-C$_4$-alkyl-heterocyclyl.
in embodiment (XVI):
X is aryl, -aryl-heteroaryl, heterocyclyl, -heteroaryl-aryl or heteroaryl, wherein said aryl or heteroaryl is optionally substituted;

Y is NH$_2$;
R$^a$ is H or halogen;
Z is benzofuryl, -benzofuryl-aryl, benzofuryl-heteroaryl, benzothiophene or phenyl, optionally substituted with one or more groups independently selected from C$_1$-C$_7$alkyl, hydroxy, C$_1$-C$_7$alkoxy, halo, CN and amino; and
R is H, —(CR$^{32}$R$^{33}$)$_s$—N(R$^{30}$)(R$^{31}$), —Y$^{31}$—X$^{30}$, —O-heterocyclyl, —O—C$_2$-C$_4$alkyl-N(R$^{30}$)(R$^{31}$), —(CH$_2$), —N(R$^{30}$)(R$^{31}$) or —O—C$_1$-C$_3$alkyl;
wherein R$^{30}$, R$^{31}$, R$^{32}$, R$^{33}$, s, Y$^{31}$ and X$^{30}$ are defined as in embodiment (I), above.

In another aspect, the invention comprises compounds according to the previous embodiments—in which Z is

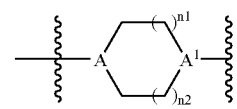

wherein A and A$^1$ are independently CR$^{11}$ or N, wherein R$^{11}$ is —OH, alkyl, alkenyl, alkynyl or aryl, and n1 and n2 are each independently 0-3, provided that when n1 and n2 are 0, then A and A$^1$ are not both N. In certain preferred embodiments of this aspect of the invention, Z includes a 0 to 3 carbon bridge between non-adjacent carbon ring atoms. Preferred embodiments of Z in this aspect of the invention are

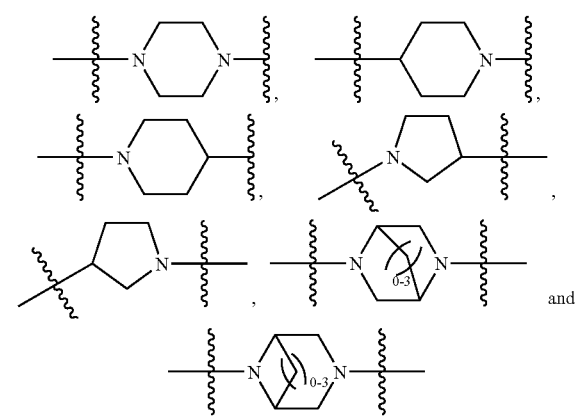

and

In another aspect, the invention comprises compounds according to the previous embodiments in which Z is

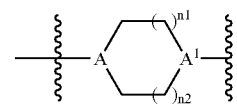

wherein A and A$^1$ are independently CR$^{11}$ or N, wherein R$^{11}$ is —OH, alkyl, alkenyl, alkynyl or aryl, n1 and n2 are each independently 0-3, and R is R$^{20}$—X$^{50}$—, wherein R$^{20}$ is aryl, -alkyl-aryl, heteroaryl, -alkyl-heteroaryl, cycloalkyl, -alkyl-cycloalkyl, -alkyl-heterocyclyl or heterocyclyl and X$^{50}$ is C$_0$-C$_3$-alkyl-X$^{51}$—C$_0$-C$_3$alkyl, wherein X$^{51}$ selected from the group consisting of —SO$_2$—, —NH—SO$_2$—, —C(O)—, —NH—C(O)—, —O—C(O)—, —C(S)—, —NH—C(S)—, —O—C(S)—, —NH—C(O)—NH—, —O—C(O)—NH— and —NH—C(O)—O, provided that when n1 and n2 are 0, then A and A$^1$ are not both N. In certain preferred embodiments of this aspect of the invention, Z includes a 0 to 3 carbon bridge between non-adjacent carbon ring atoms. Preferred embodiments of Z in this aspect of the invention are

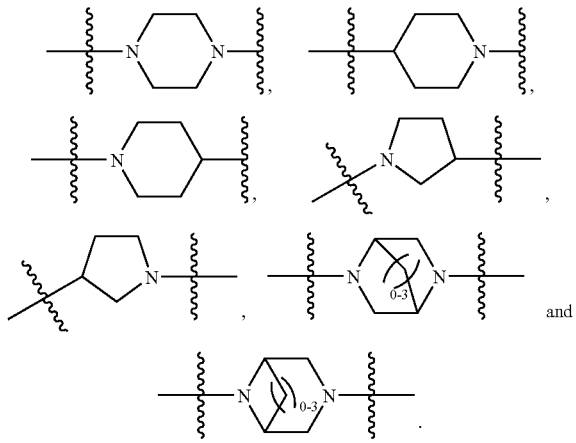

In another aspect, the invention comprises compounds according to the previous embodiments, wherein Z is selected from the group consisting of

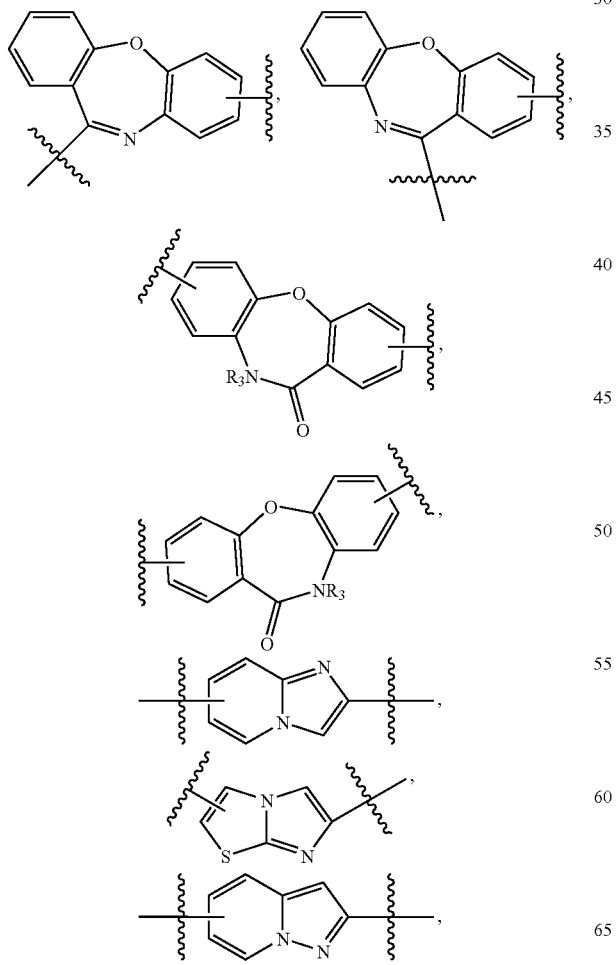

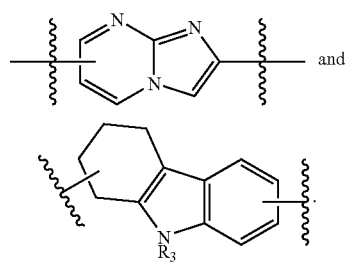

Preferably, in embodiment (I):

X is thienyl (preferably thien-2-yl), pyridyl (preferably pyrid-3-yl or 4-yl), or phenyl, each optionally substituted as described for embodiment (I), and/or R is morpholinyl, pyrrolidinyl, 2,5-diazabicyclo[2.2.1]heptane, azetidine, piperidinyl, or piperazinyl (preferably piperazin-4-yl), each of which is optionally substituted with hydroxy, $C_1$-$C_6$ alkyl, $C_1$-$C_3$-alkoxy-$C_1$-$C_3$-alkyl, $C_5$-$C_6$-cycloalkyl, or $NR^7R^8$—$C_0$-$C_3$-alkyl.

Preferably, in embodiment (I):

—Z—R is -phenyl-heterocyclyl, optionally oxo substituted.

In a preferred embodiment of the present invention, Formula I has a generic structure

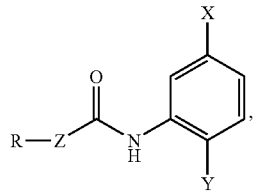

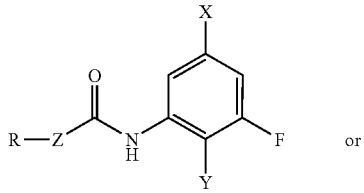

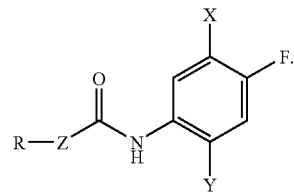

Preferably in embodiment (IV), R is

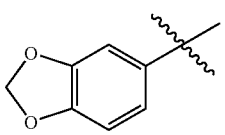 or 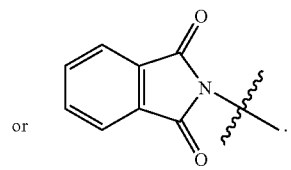

Preferably in embodiment (IV), Z is
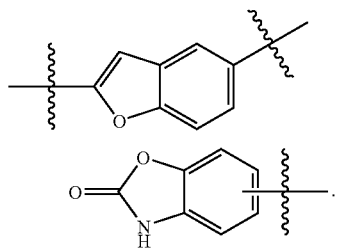 or
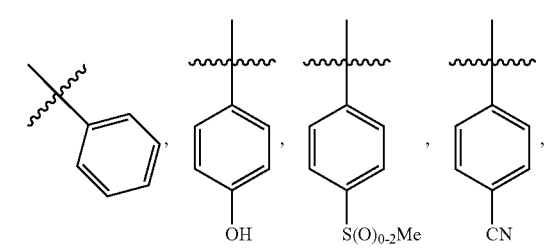
In a preferred embodiment of the compounds according to the present invention, X is selected from the group consisting of
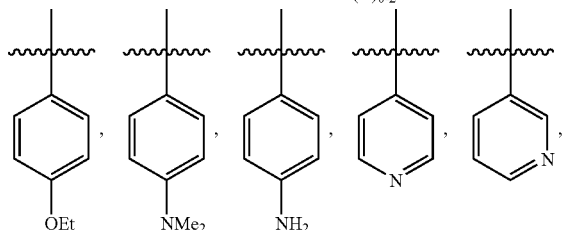
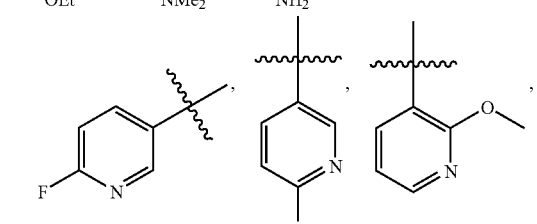
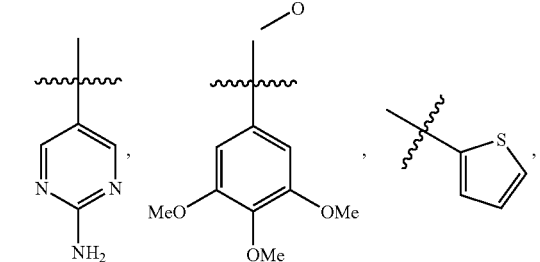
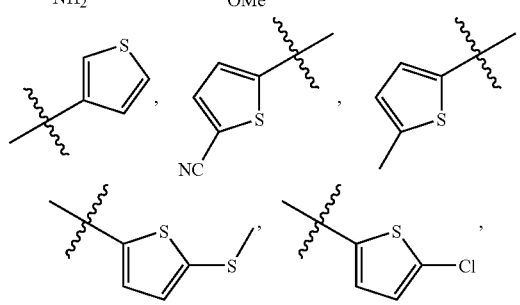
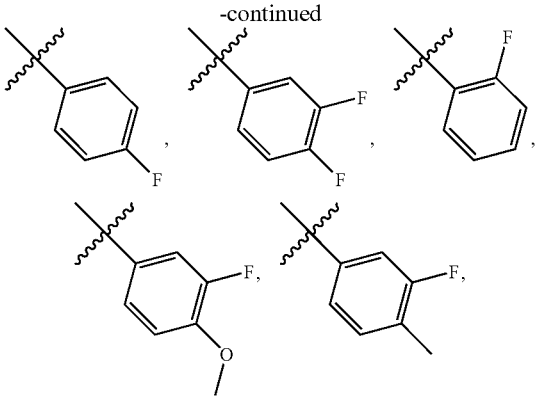
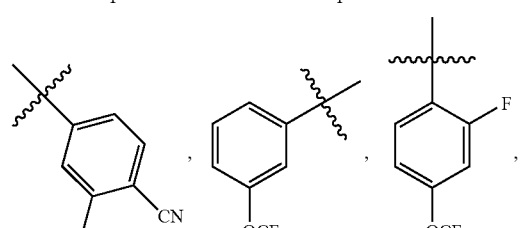
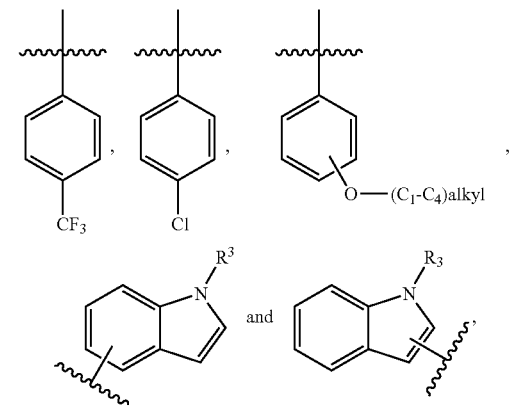
and/or R is selected from the group consisting of
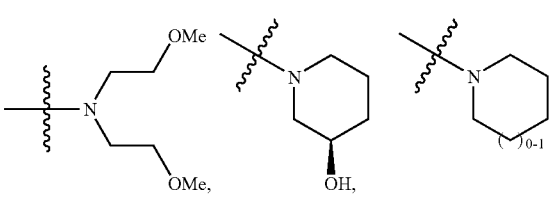

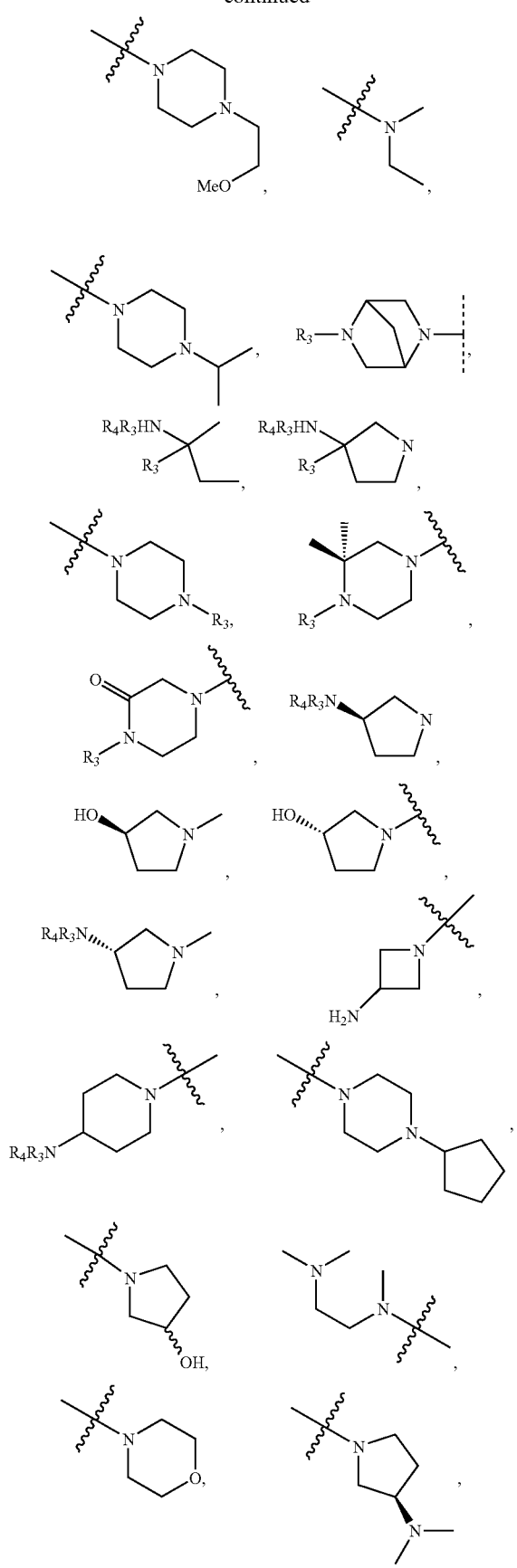
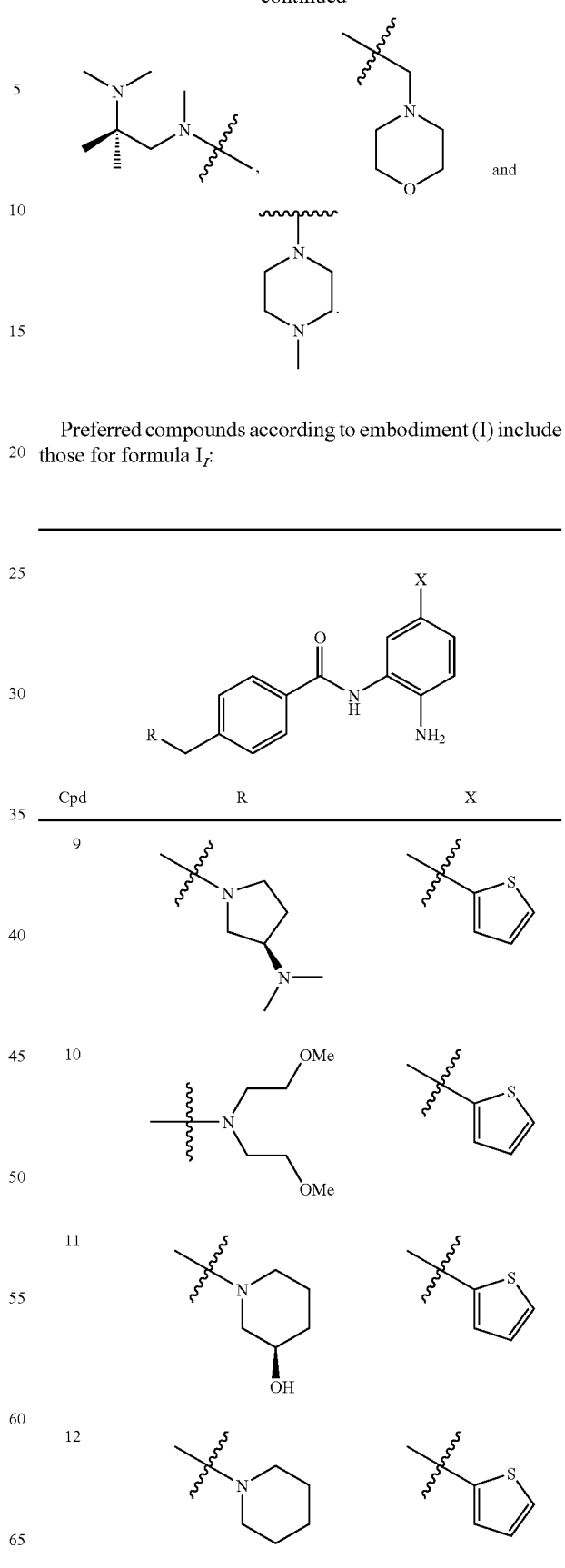
Preferred compounds according to embodiment (I) include those for formula I$_f$:

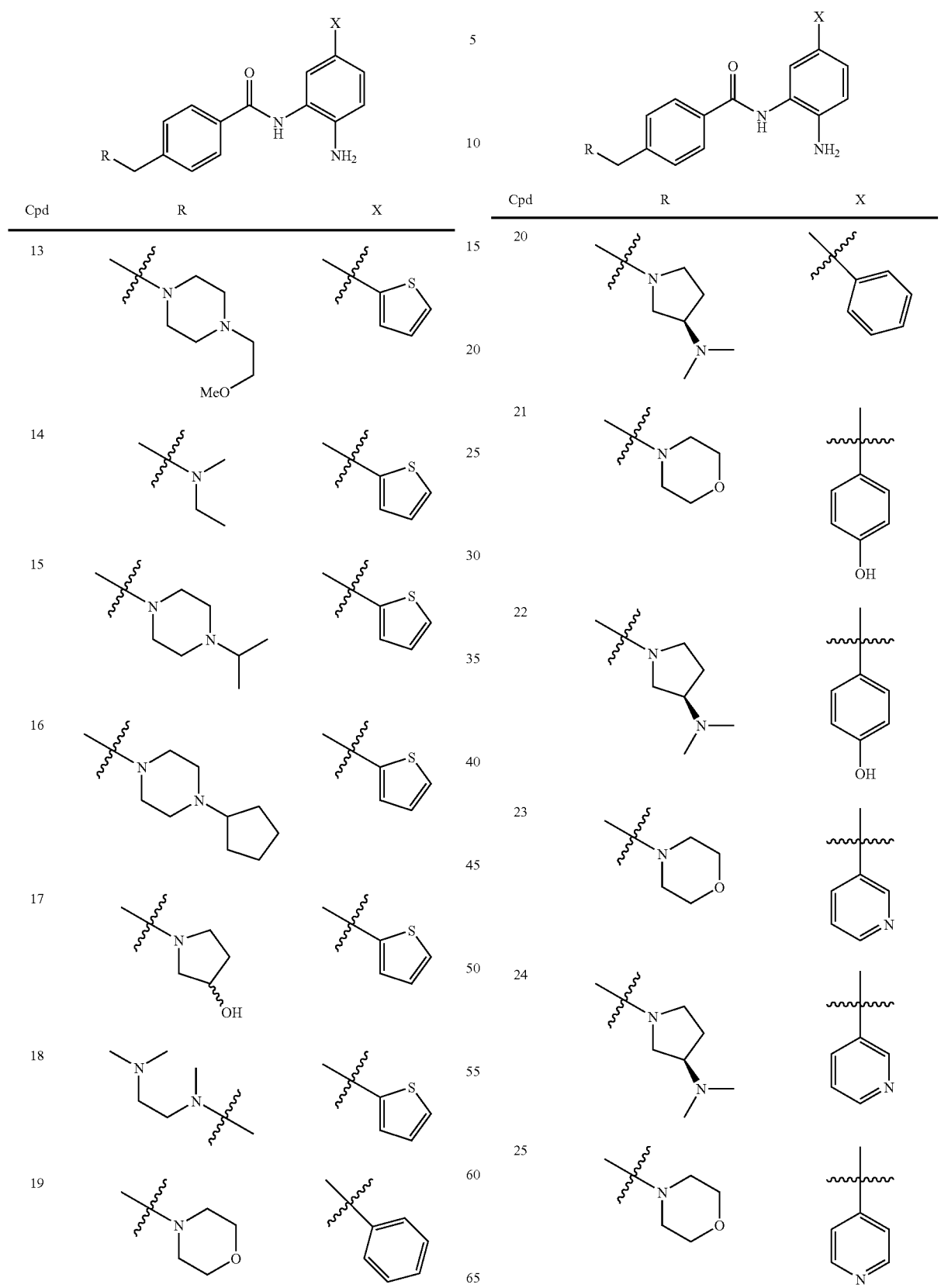

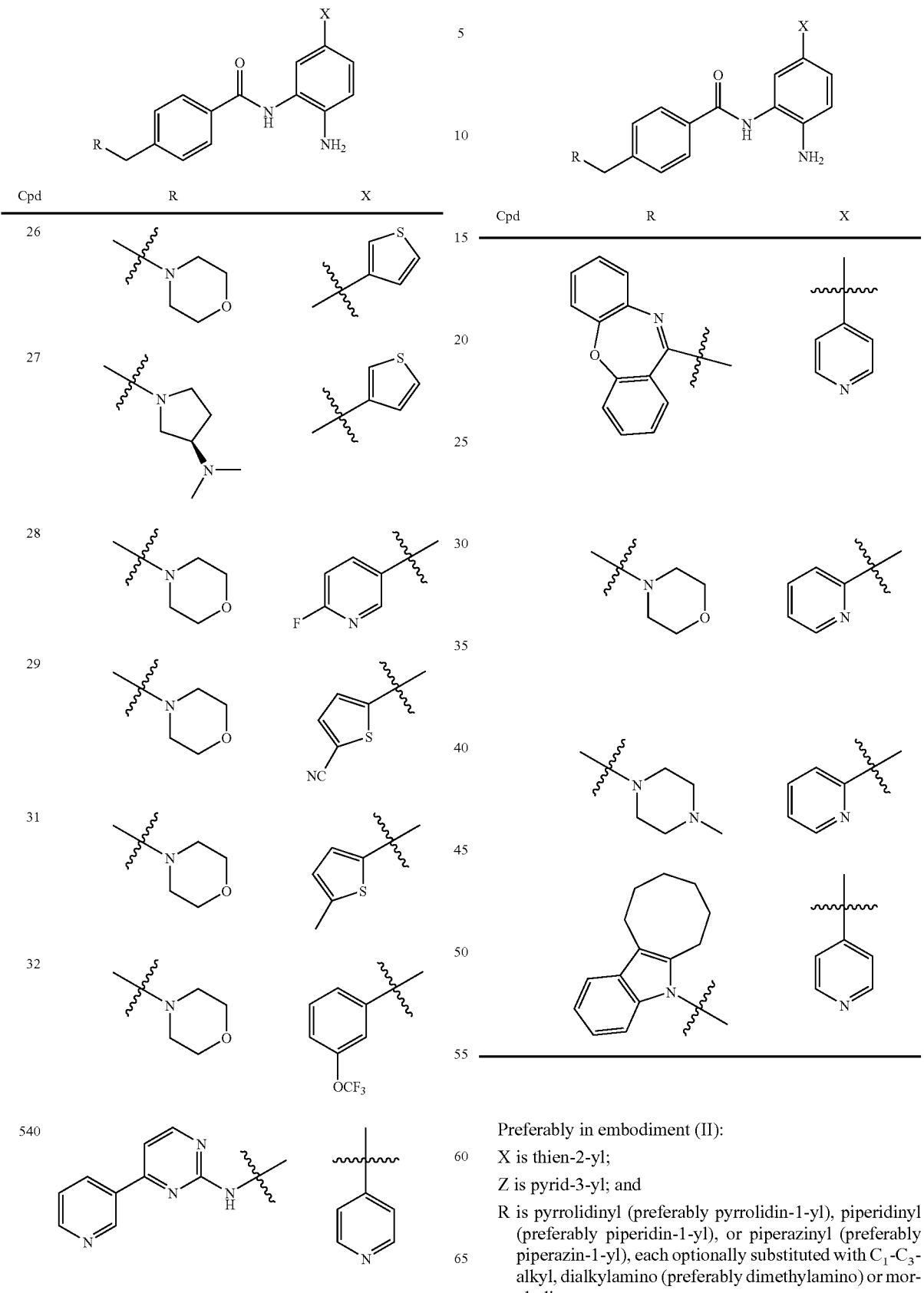
Preferably in embodiment (II):
X is thien-2-yl;
Z is pyrid-3-yl; and
R is pyrrolidinyl (preferably pyrrolidin-1-yl), piperidinyl (preferably piperidin-1-yl), or piperazinyl (preferably piperazin-1-yl), each optionally substituted with $C_1$-$C_3$-alkyl, dialkylamino (preferably dimethylamino) or morpholino.

Preferred compounds according to embodiment (II) include those of formula I$_{II}$:

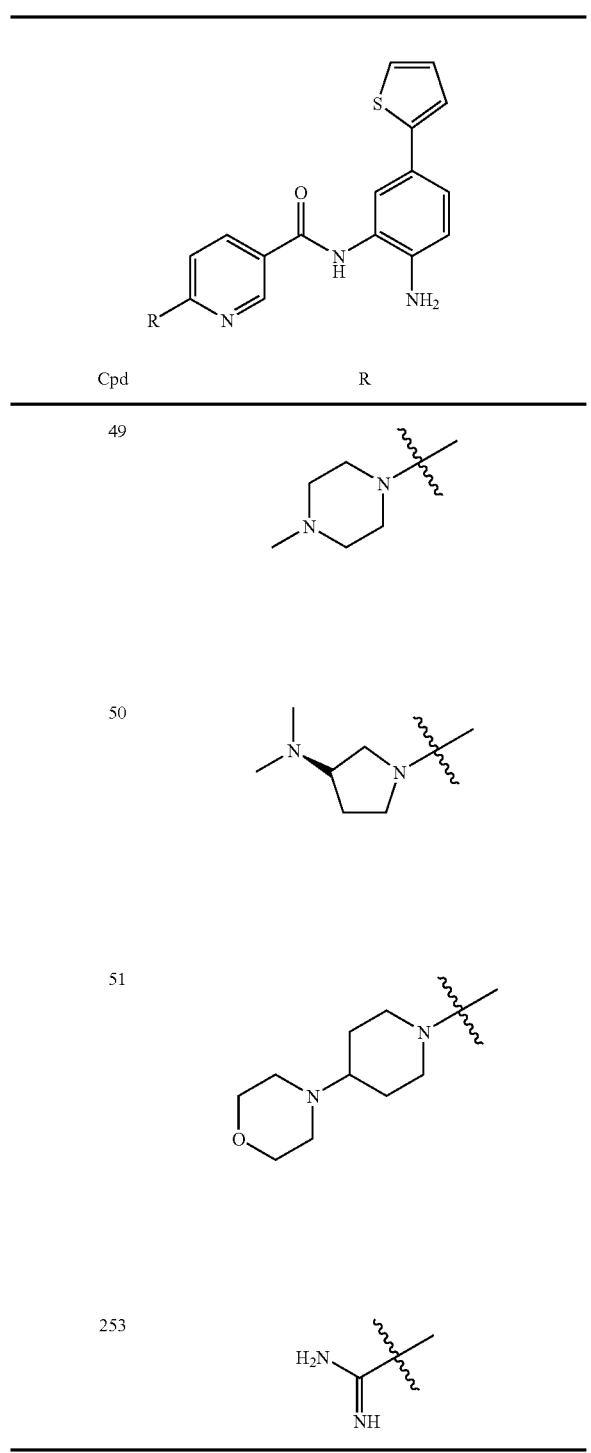

Preferably in embodiment (III)

X is thien-2-yl;

Z is phenyl or pyridin-2-yl, and

R is thienyl (preferably thien-2-yl), 1H-pyrazolyl (preferably 1H-pyrazoly-4-yl), or phenyl optionally substituted with from 1 to 3 $C_1$-$C_3$-alkoxy (preferably methoxy).

Preferred compounds according to embodiment (III) include those of formula I$_{III}$:

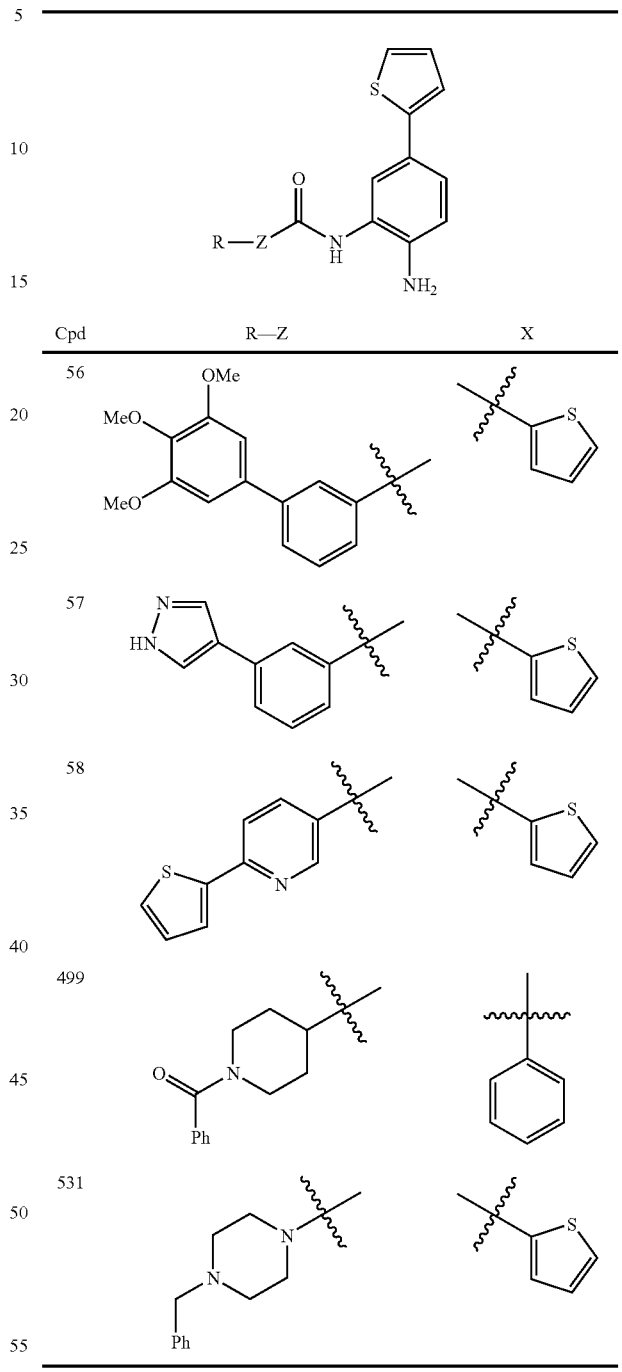

Preferably in embodiment (IV):

X is thien-2-yl;

Z is phenyl, thienyl (preferably thien-2-yl), pyridyl (preferably pyrid-2-yl, -3-yl or 4-yl), furyl (preferably furan-2-yl), and R is pyridyl (preferably pyridine-2-yl), pyrrolidinyl-$C_0$-$C_2$-alkyl (pyrrolidine-2-ylethyl)), morpholino-$C_0$-$C_1$-alkyl, pyrrolyl (preferably pyrrol-1-yl), pyrazolyl (preferably pyrazol-1-yl), halo, or cyano;

Preferred compounds according to embodiment (IV) include those of formula I$_{IVa}$:
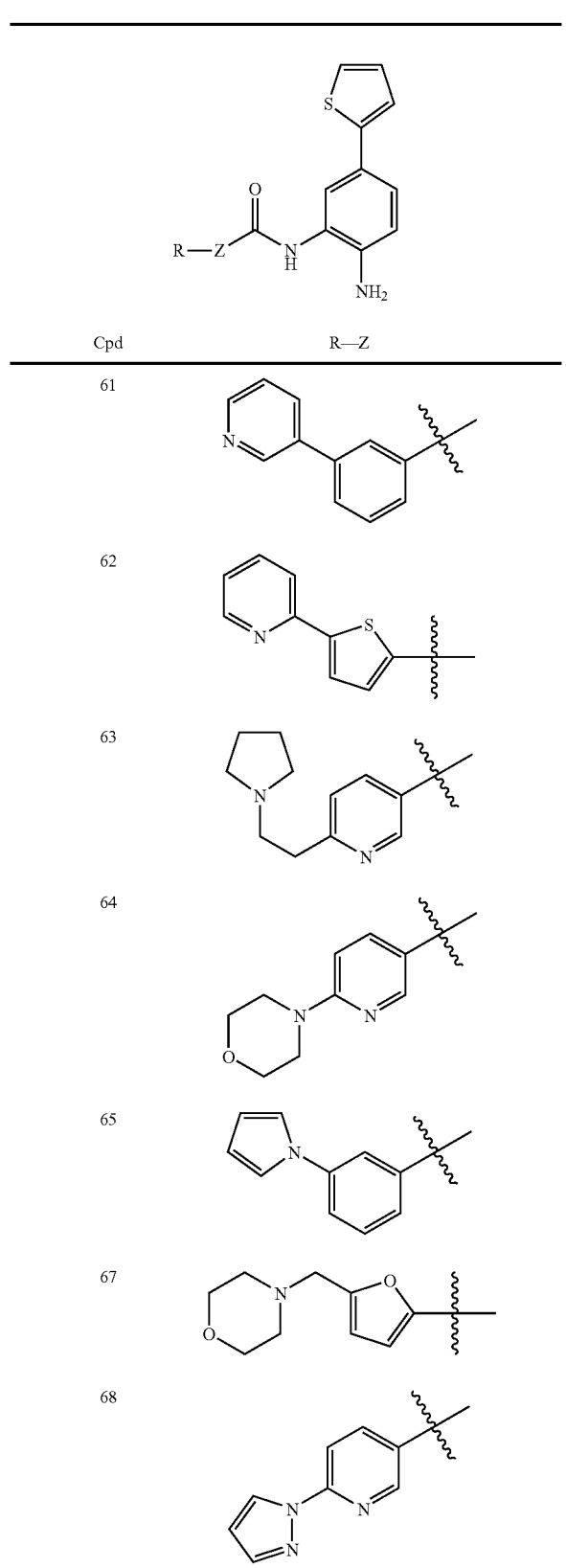
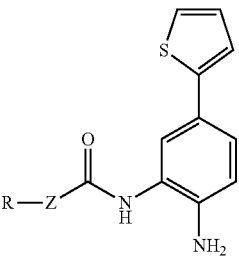
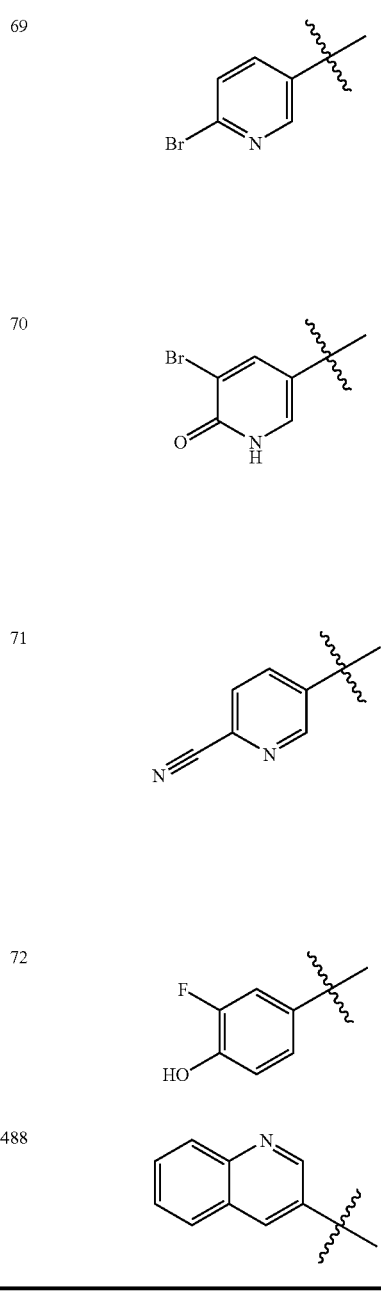

Preferred compounds according to embodiment (IV) include those of formula I$_{IVb}$
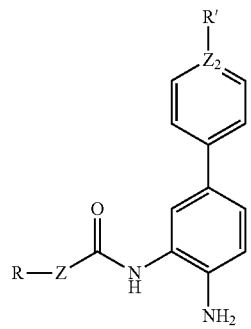
| Cpd | R | Z | Z$_2$ | R' |
|---|---|---|---|---|
| 529 | 4-ethylpiperazin-1-yl | 1,4-phenylene | C | H |
| 484 | 3-oxopiperazin-1-yl | 1,4-phenylene | C | H |
| 491 | imidazol-1-yl | 1,4-phenylene | C | H |
| 498 | pyridin-2-yl | thiophene-2,5-diyl | C | F |
| 494 | phenyl | furan-2,5-diyl | C | F |
| 476 | piperazin-1-yl | 1,4-phenylene | C | H |

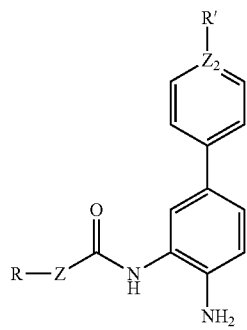
| Cpd | R | Z | $Z_2$ | R' |
|---|---|---|---|---|
| 464 | H | quinoxaline-2,7-diyl | N | — |
| 465 | H | quinoxaline-2,6-diyl | C | H |
| 539 | Bn | 2-oxo-pyridine-1,5-diyl | C | F |
| 552 | piperazin-1-yl | dibenzo[b,f][1,4]oxazepine | N | — |
| 551 | piperazin-1-yl | dibenzo[b,f][1,4]oxazepine | C | H |
| 544 | H | 2,3,4,9-tetrahydro-1H-carbazole-diyl | C | H |

-continued

| Cpd | R | Z | Z₂ | R' |
|---|---|---|---|---|
| | H | imidazo[1,2-a]pyridine-2,6-diyl | C | H |
| | H | imidazo[1,2-a]pyridine-2,6-diyl | N | — |
| | H | imidazo[2,1-b]thiazole-2,6-diyl | C | H |
| | H | imidazo[2,1-b]thiazole-2,6-diyl | N | — |
| | H | pyrazolo[1,5-a]pyridine-2,6-diyl | C | H |
| | H | pyrazolo[1,5-a]pyridine-2,6-diyl | C | F |
| | H | pyrazolo[1,5-a]pyridine-2,6-diyl | N | — |
| | H | imidazo[1,2-a]pyrimidine-2,6-diyl | C | H |
| | MeO— | pyridine-2,5-diyl | C | H |
| | morpholinomethyl | thiophene-2,5-diyl | C | H |

-continued
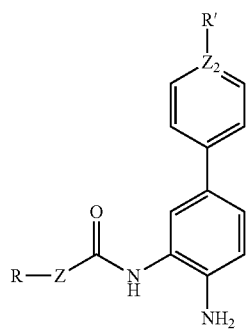
| Cpd | R | Z | $Z_2$ | R' |
|---|---|---|---|---|
| 538 | HOCH$_2$— | 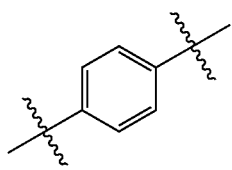 [SMILES: *c1ccc(*)cc1] | C | H |
| 463 | MeO— | 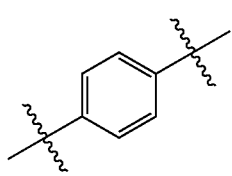 [SMILES: *c1ccc(*)cc1] | N$^+$ | —O$^-$ |
|  | 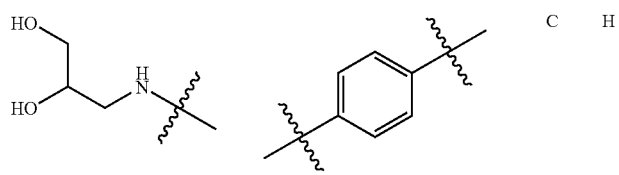 |  | C | H |
|  | 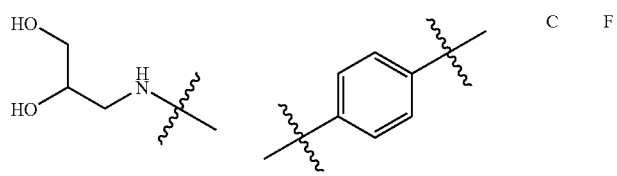 |  | C | F |
Preferably in embodiment (V):
X is thienyl-2-yl; and
R is —(CH$_2$)-(piperidinyl, piperazinyl, or pyrrolidinyl), optionally described for embodiment (V), above.
Preferred compounds according to embodiment (V) include those of formula I$_V$:

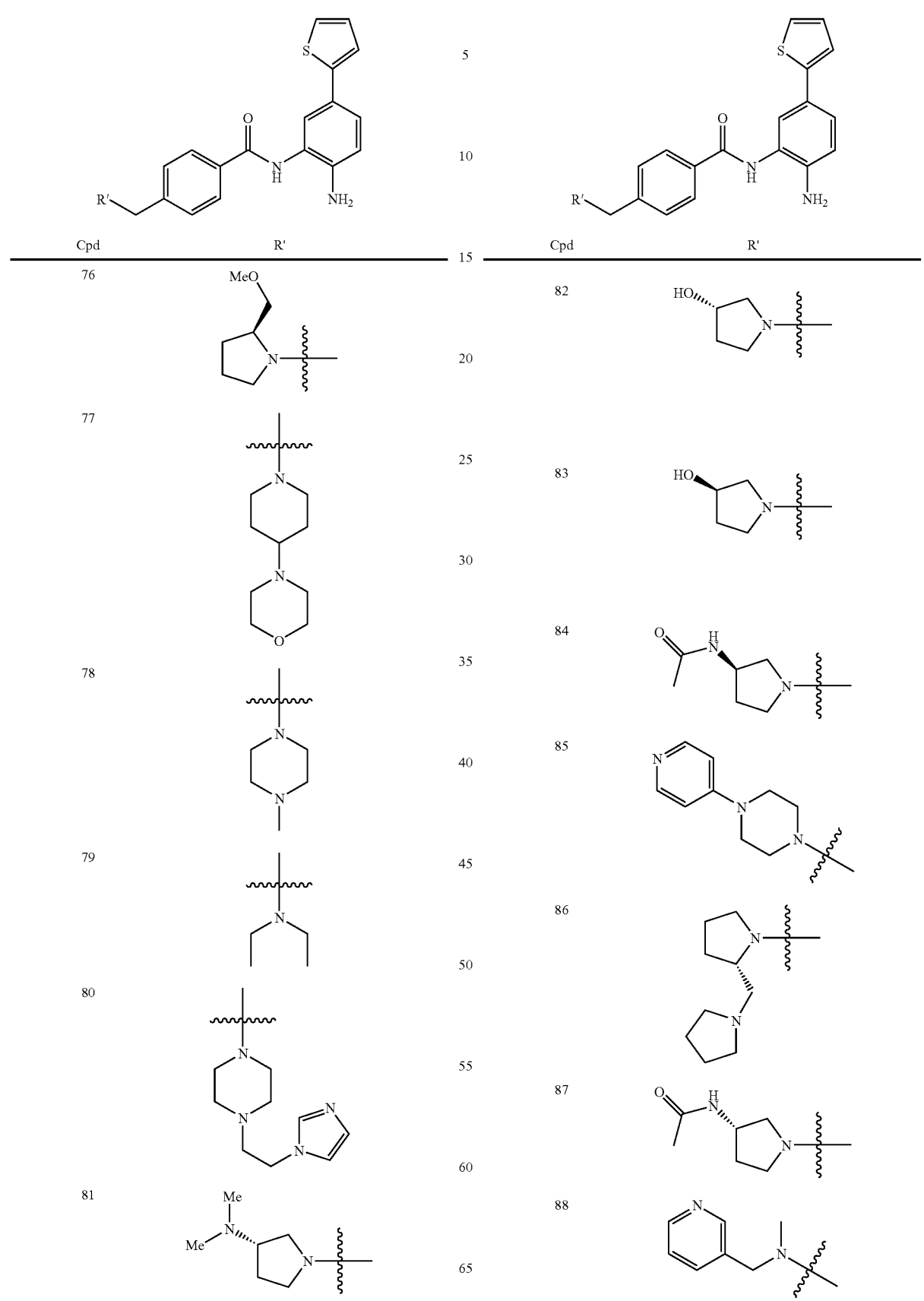

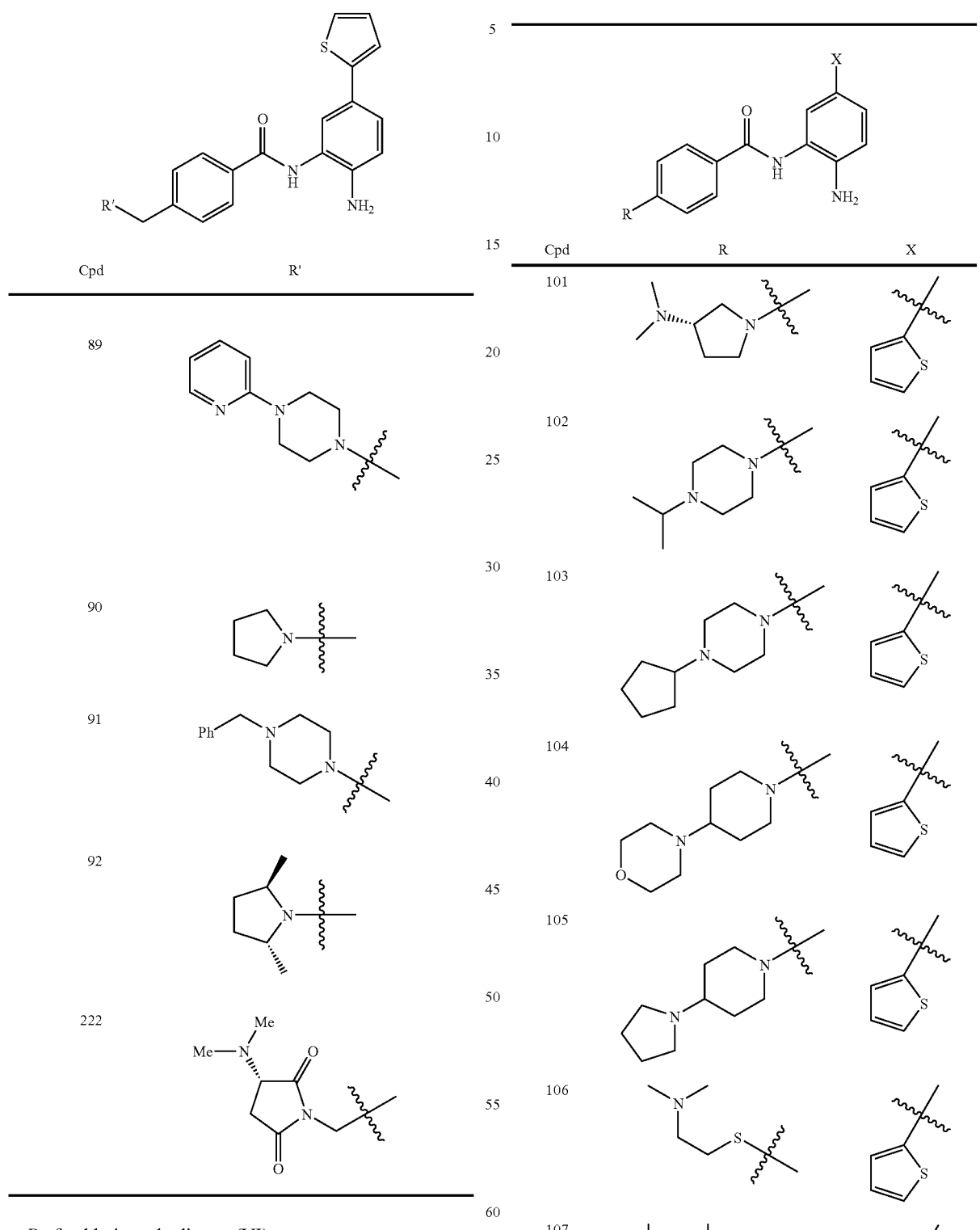

Preferred compounds according to embodiment (VI) include those of formula I$_{VI}$:

Preferably in embodiment (VI):

X is thienyl-2-yl optionally substituted with halo; and

R is piperidinyl (preferably piperidin-1-yl), piperazinyl, or pyrolidinyl, each optionally substituted with the optional substituents described for the heterocyclyl in the definition of R$^3$ and R$^4$ in embodiment (VI), above.

-continued

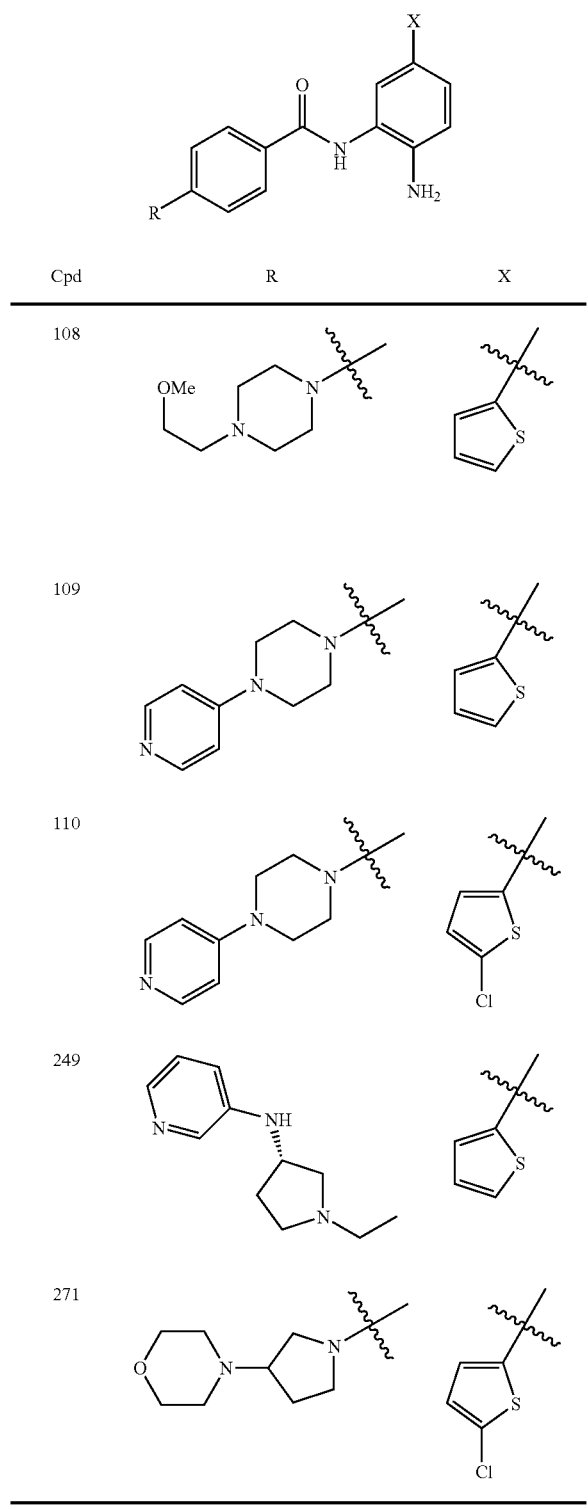

Preferably in embodiment (VII):

X is thiophen-2-yl;

R is morpholino, or piperidinyl or piperazinyl each optionally substituted with the substituents of the heterocyclyl in the definition of $R^3$ and $R^4$ in embodiment (VII).

Preferred compounds of embodiment (VII) include those of formula $I_{VII}$:

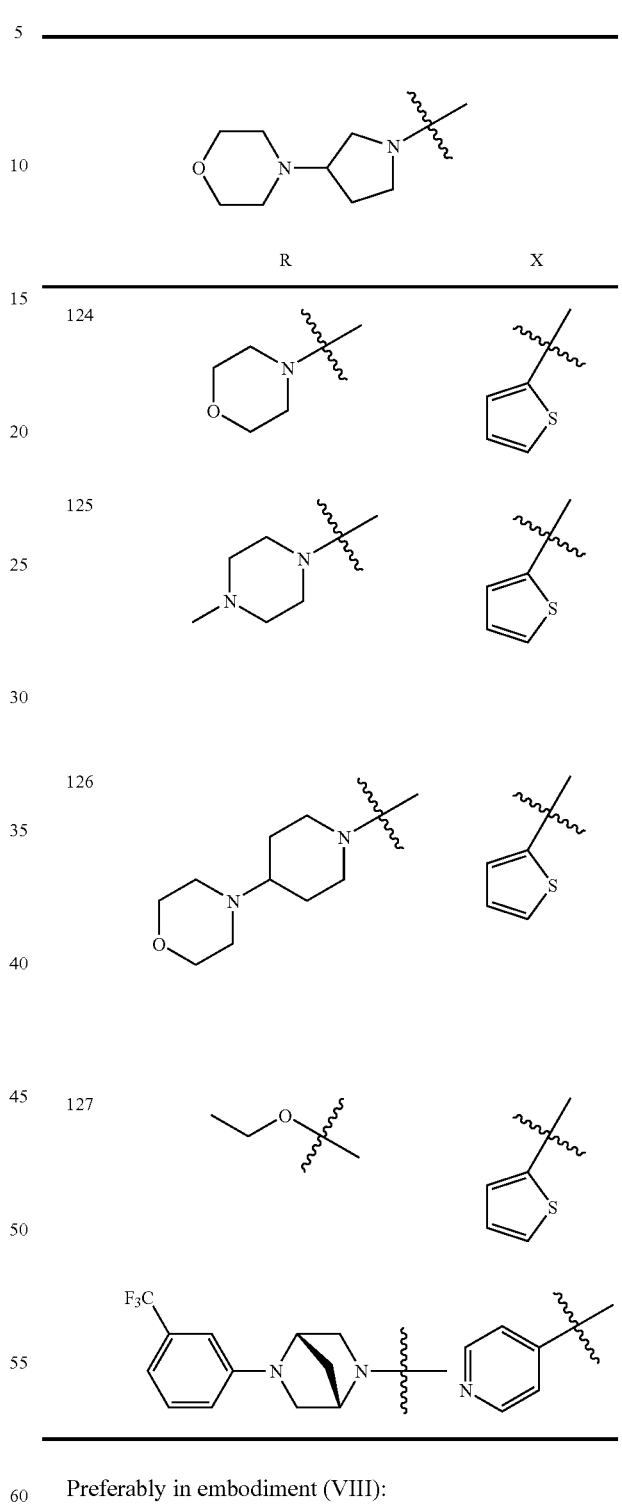

Preferably in embodiment (VIII):

X is thienyl (preferably thien-2-yl), phenyl, pyrrolyl (preferably pyrrol-2-yl), or 1H-pyrazolyl (preferably 1H-pyrazol-4-yl), each optionally substituted with amino;

Y is amino or F; and

R is methoxy or pyridyl (preferably pyridin-1-yl).

Preferred compounds according to embodiment (VIII) include those of formula $I_{VIII}$:

Preferred compounds according to embodiment (IX) include those of formula $I_{IX}$:

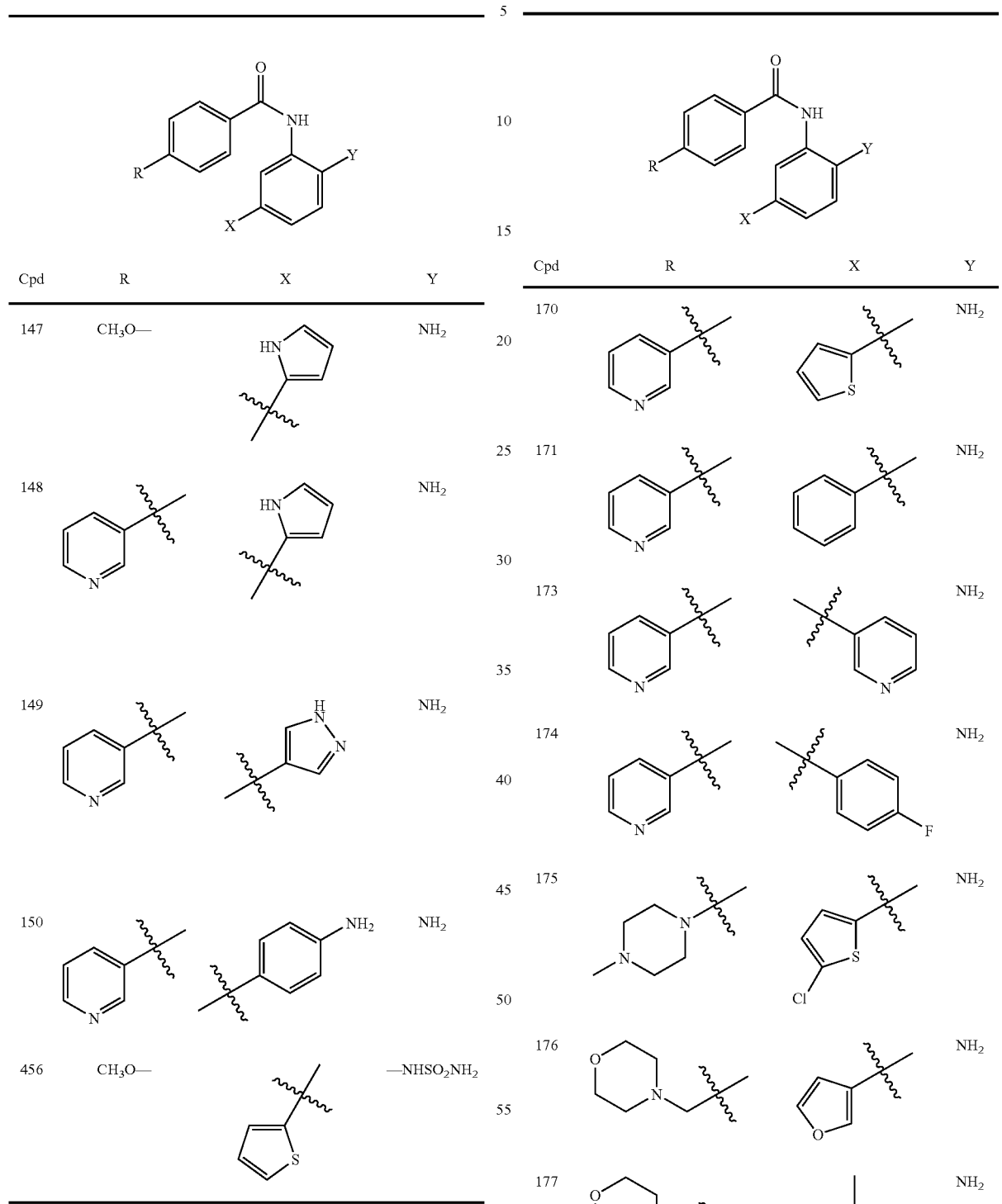

Preferably in embodiment (IX):

X is thienyl (preferably thien-2-yl), phenyl, pyridyl (preferably pyridine-2-yl), or furyl, each of which is optionally substituted with halo; and R is pyridyl (preferably pyridine-2-yl), piperidinyl optionally N-substituted with methyl, or morpholinomethyl.

-continued

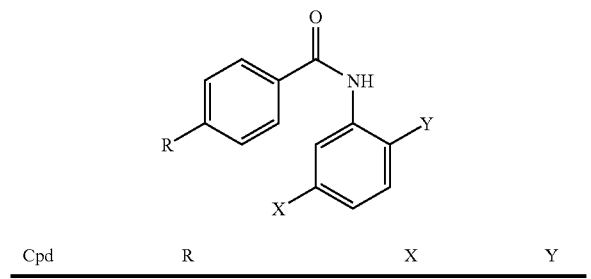

| Cpd | R | X | Y |
|---|---|---|---|
| 178 | 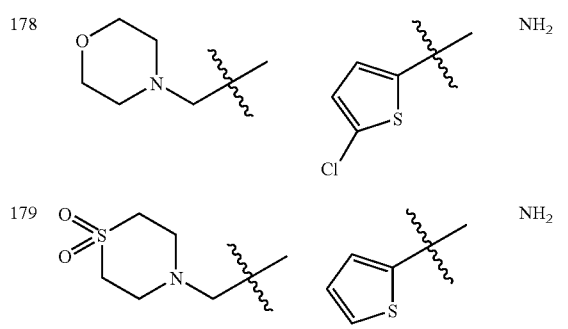 | | NH₂ |
| 179 | | | NH₂ |

Preferred compounds of embodiment (X) include those of formula $I_X$:

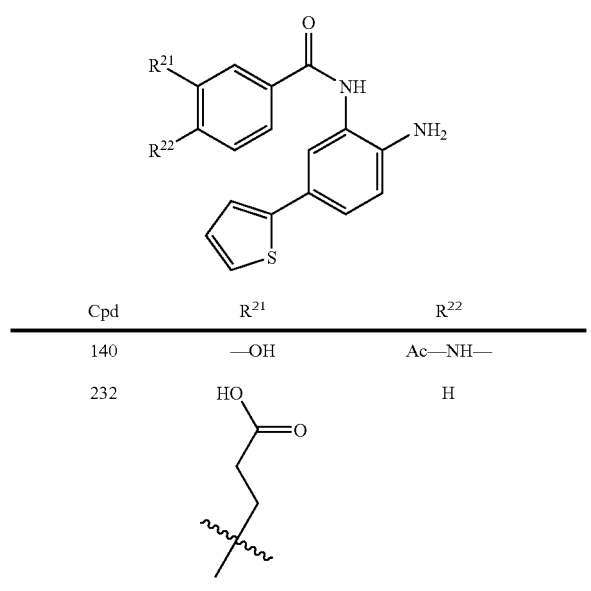

| Cpd | $R^{21}$ | $R^{22}$ |
|---|---|---|
| 140 | —OH | Ac—NH— |
| 232 | 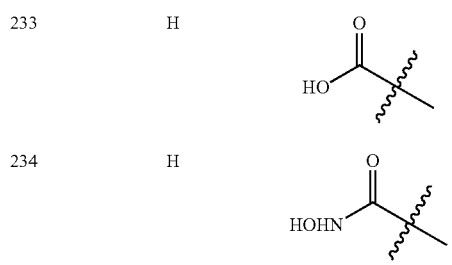 | H |
| 233 | H | |
| 234 | H | |

-continued

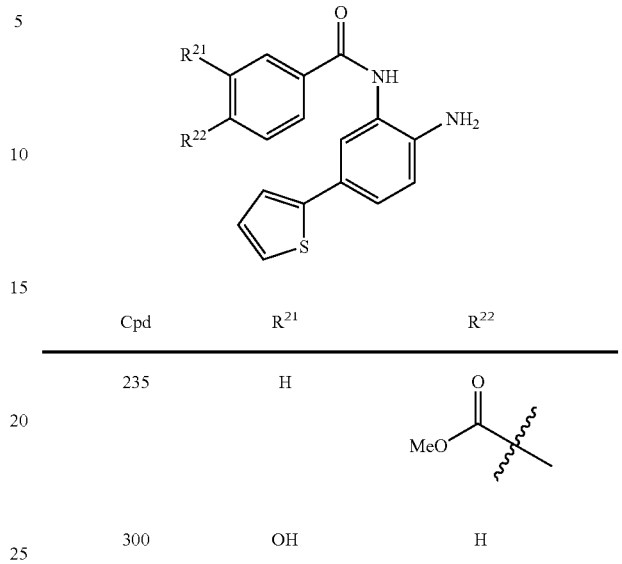

| Cpd | $R^{21}$ | $R^{22}$ |
|---|---|---|
| 235 | H | |
| 300 | OH | H |

Preferred compounds of embodiment (XI) include those of formula $I_{XI}$:

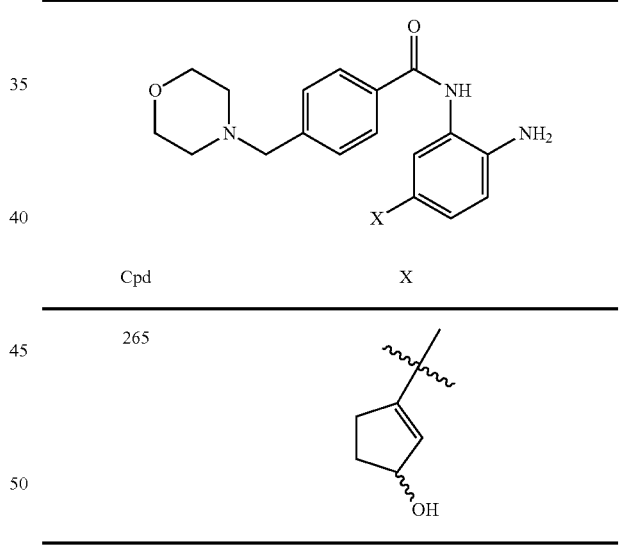

| Cpd | X |
|---|---|
| 265 | |

Preferably in embodiment (XII):

X is thienyl (preferably thien-2 or 3-yl), phenyl, pyridyl (preferably pyridine-2-yl) optionally substituted with 1 or 2 halo;

Y is —NH₂; and $R^{10}$ is —N($C_1$-$C_3$-alkyl)($C_1$-$C_3$-alkyl) (preferably dimethylamino);

Preferred compounds according to embodiment (XII) are those of formula I$_{XII}$:
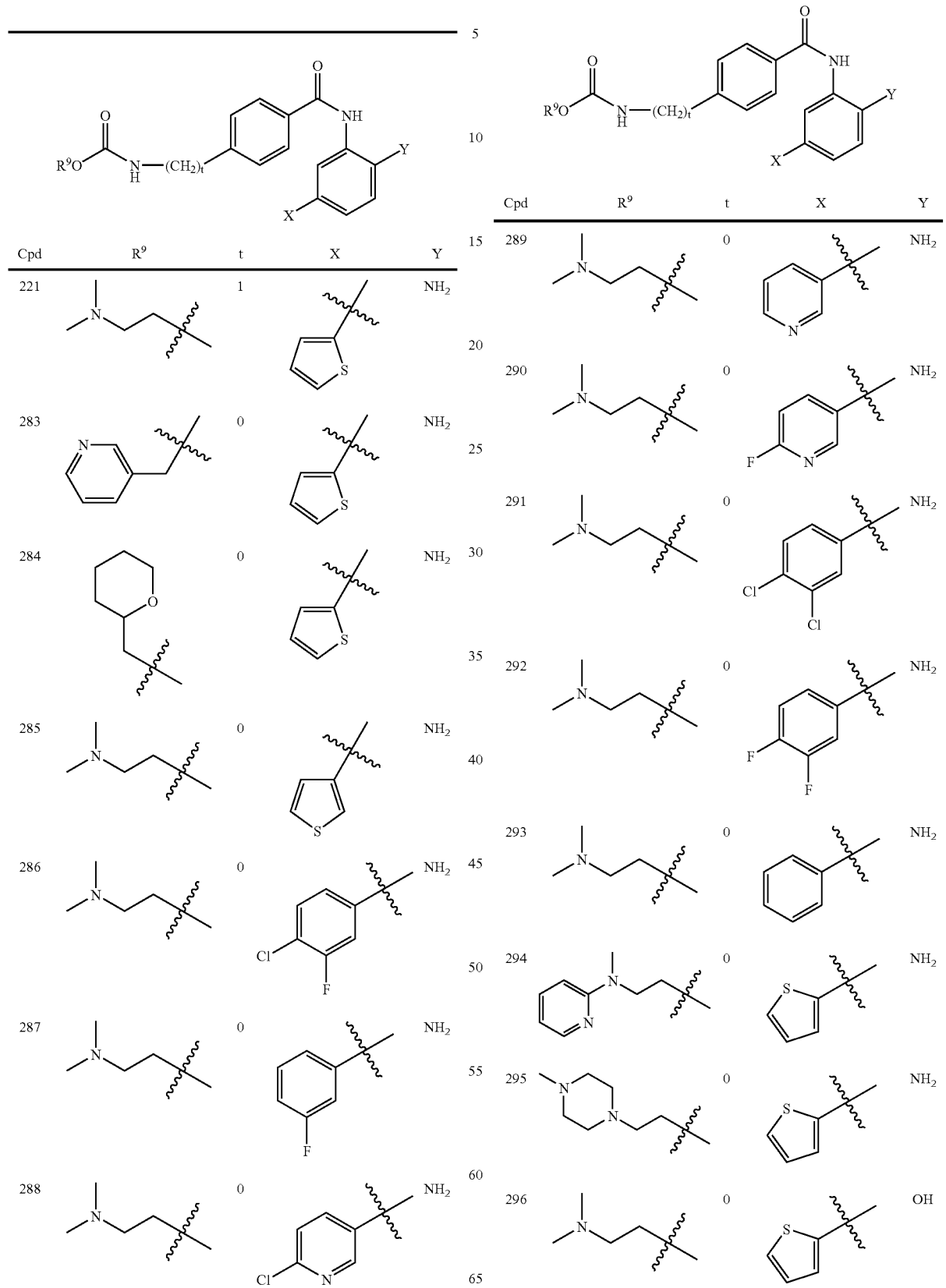

-continued

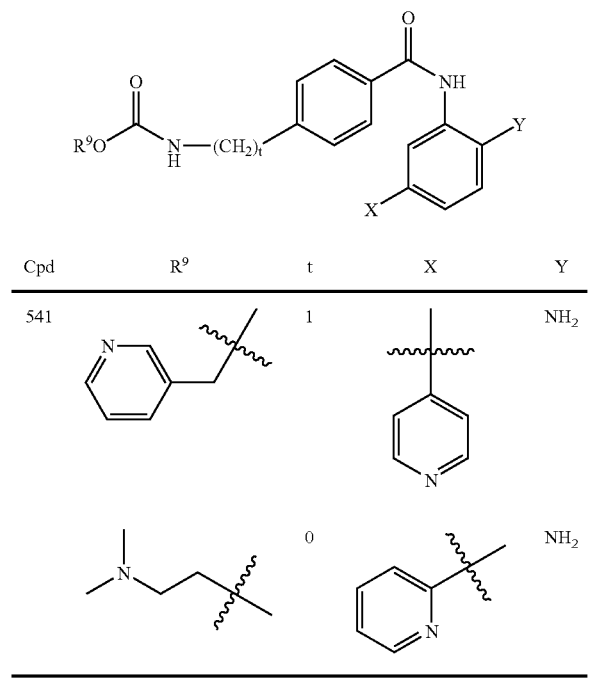

| Cpd | R⁹ | t | X | Y |
|---|---|---|---|---|
| 541 | (3-pyridylmethyl) | 1 | (pyridin-4-yl) | NH₂ |
| | (2-dimethylaminoethyl) | 0 | (pyridin-2-yl) | NH₂ |

Preferably in embodiment (XIII):

X is thienyl (preferably thien-2-yl), pyridyl (preferably pyridine-2-yl), 3-oxo-cyclopent-1-yl, or phenyl, each of which is optionally substituted with 1 or two halo; and Y is —NH₂ or —OH.

Preferred compounds of embodiment (XIII) include those of formula I_{XIII}:

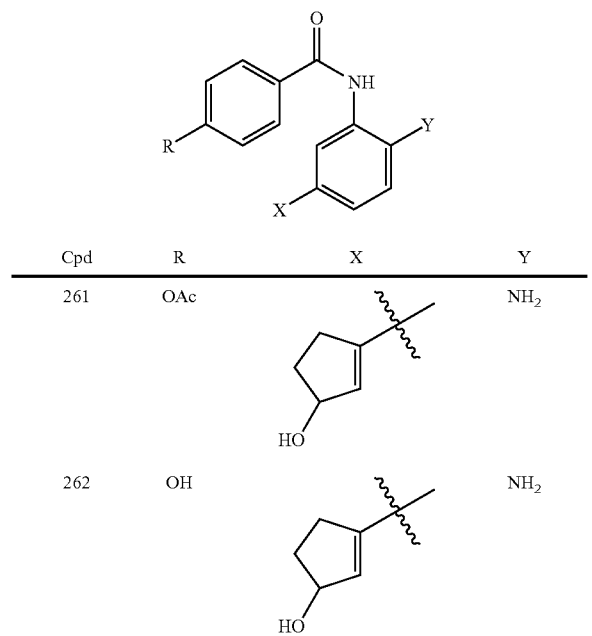

| Cpd | R | X | Y |
|---|---|---|---|
| 261 | OAc | (3-hydroxycyclopent-1-enyl) | NH₂ |
| 262 | OH | (3-hydroxycyclopent-1-enyl) | NH₂ |

-continued

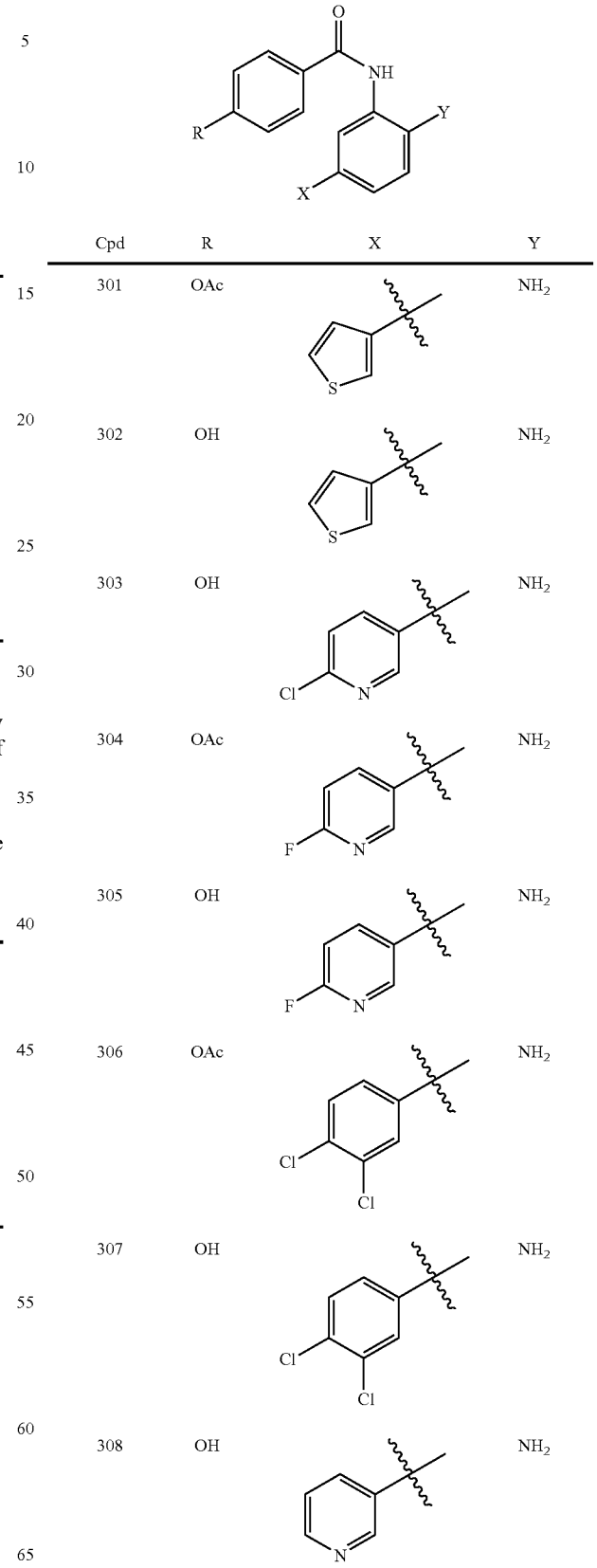

| Cpd | R | X | Y |
|---|---|---|---|
| 301 | OAc | (thien-3-yl) | NH₂ |
| 302 | OH | (thien-3-yl) | NH₂ |
| 303 | OH | (6-chloropyridin-3-yl) | NH₂ |
| 304 | OAc | (6-fluoropyridin-3-yl) | NH₂ |
| 305 | OH | (6-fluoropyridin-3-yl) | NH₂ |
| 306 | OAc | (3,4-dichlorophenyl) | NH₂ |
| 307 | OH | (3,4-dichlorophenyl) | NH₂ |
| 308 | OH | (pyridin-3-yl) | NH₂ |

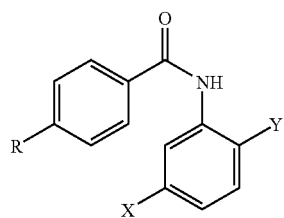

| Cpd | R | X | Y |
|---|---|---|---|
| 309 | OH | (phenyl) | NH$_2$ |
| 310 | OH | (thiophen-2-yl) | OH |

Preferably in embodiment (XIV):
R is $R^{20}$—C(O)-ethyl or $R^{20}$—C(O)-ethenyl.

Preferred compounds of embodiment (XIV) include those of formula I, wherein:

| Cpd | R |
|---|---|
| 226 | HO—C(O)—CH=CH— |
| 227 | HO—NH—C(O)—CH=CH— |
| 230 | MeO—C(O)—CH$_2$—CH$_2$— |
| 231 | HO—C(O)—CH$_2$—CH$_2$— |

Preferably in embodiment (XVI) X is phenyl or pyridyl, each of which is optionally substituted.

Preferably in embodiment (XVI) X is optionally substituted with one or two halogen, preferably F.

Preferably in embodiment (XVI) R is H, alkoxy, —O—(CH$_2$)$_{2-3}$-heterocycle or —O—(CH$_2$)$_{2-3}$—N(R$^3$)(R$^4$), wherein preferably the heterocycle moiety is morpholine or piperidine.

In a preferred embodiment of the compounds according to Formula (I), X is optionally substituted with one, two or three substituents independently selected from the group consisting of halo, oxo, hydroxy, C$_1$-C$_3$-hydrocarbyl, methoxy, HalCH$_2$—O—, Hal$_2$CH—O—, Hal$_3$C—O— (preferably F$_3$C—O—), NH$_2$—, —N(C$_1$-C$_3$alkyl)$_2$, —CN, —S(O)$_{0-2}$—C$_1$-C$_4$alkyl, —CF$_3$, and mono-, di-, or tri-halo substituted alkyl, or, when there are two optional substituents bonded to adjacent atoms of the phenyl, thienyl, or pyridyl they, together with the atoms to which they are bonded, optionally form a 5- or 6-membered cycloalkyl or heteroalkyl having 1, 2, or 3 annular heteroatoms.

Preferred compounds of embodiment (XVI) include those of formula I$_X$:

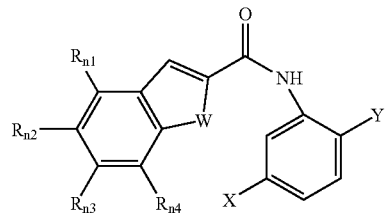

| Cpd | R$_{n1}$ | R$_{n2}$ | R$_{n3}$ | R$_{n4}$ | W | X | Y |
|---|---|---|---|---|---|---|---|
| 378 | —OMe | —H | —OMe | —H | O | (pyridin-4-yl) | —NH$_2$ |
| 398 | —H | —H | —O—CH$_2$CH$_2$-piperidinyl | —H | O | (pyridin-4-yl) | —NH$_2$ |

-continued
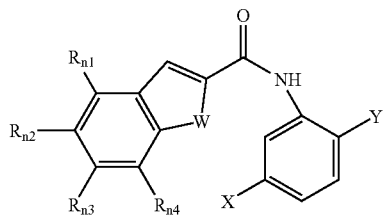
| Cpd | R$_{n1}$ | R$_{n2}$ | R$_{n3}$ | R$_{n4}$ | W | X | Y |
|---|---|---|---|---|---|---|---|
| 466 | —H | —H | ⤳O-CH$_2$CH$_2$-morpholine | —H | O | 4-pyridyl | —NH$_2$ |
| 467 | —H | —H | ⤳O-CH$_2$CH$_2$-N(CH$_3$)$_2$ | —H | O | 4-pyridyl | —NH$_2$ |
| 468 | —H | —H | ⤳O-CH$_2$CH$_2$-morpholine | —H | { | phenyl | —NH$_2$ |
| 469 | —H | —H | ⤳O-CH$_2$CH$_2$-morpholine | —H | O | 4-F-phenyl | —NH$_2$ |
| 470 | —H | —H | ⤳O-CH$_2$CH$_2$-morpholine | —H | O | 3,4-diF-phenyl | —NH$_2$ |

-continued
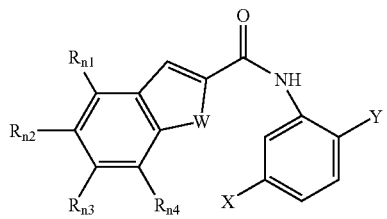
| Cpd | R$_{n1}$ | R$_{n2}$ | R$_{n3}$ | R$_{n4}$ | W | X | Y |
|---|---|---|---|---|---|---|---|
| 471 | —H | —OMe | —OMe | —H | O | 4-pyridyl | —NH$_2$ |
| 472 | —H | —OMe | —OMe | —H | O | phenyl | —NH$_2$ |
| 473 | —H | —OMe | —OMe | —H | O | 4-fluorophenyl | —NH$_2$ |
| 491 | H | H | 4-piperidinyloxy | H | O | phenyl | —NH$_2$ |
| 553 | H | H | 4-piperidinyloxy | H | O | 4-fluorophenyl | —NH$_2$ |
|  | —H | —OMe | —OMe | —H | S | phenyl | —NH$_2$ |

-continued
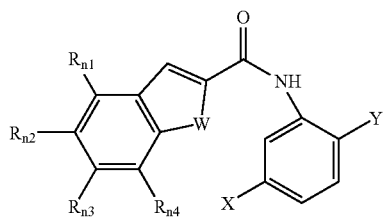
| Cpd | R$_{n1}$ | R$_{n2}$ | R$_{n3}$ | R$_{n4}$ | W | X | Y |
|---|---|---|---|---|---|---|---|
| | H | 2-morpholinoethoxy | H | H | O | phenyl | —NH$_2$ |
| | H | 2-(piperidin-1-yl)ethoxy | H | H | O | phenyl | —NH$_2$ |
| | H | 2-(piperidin-1-yl)ethoxy | H | H | O | 4-fluorophenyl | —NH$_2$ |
| | H | —OMe | H | morpholinomethyl | O | phenyl | —NH$_2$ |
| | H | —OMe | H | morpholinomethyl | O | 4-fluorophenyl | —NH$_2$ |

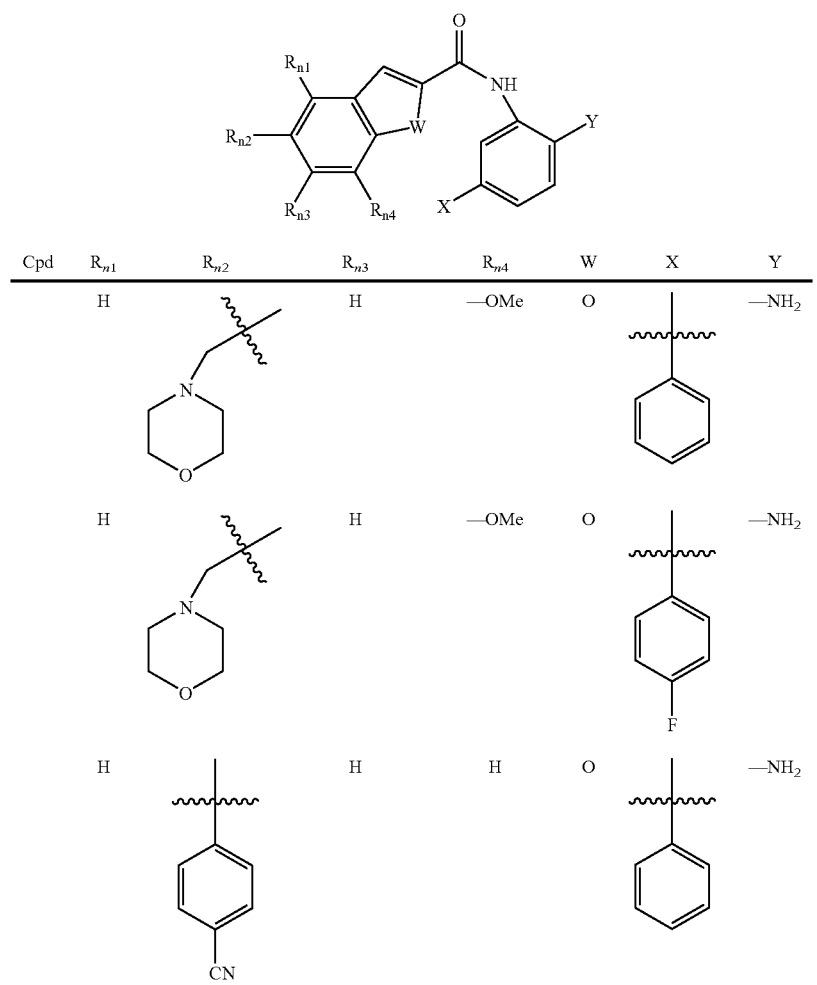

Other preferred compounds of embodiment (XVI) include those of formula $I_{XI}$, where in X is aryl, -aryl-heteroaryl, heteroaryl-aryl, heterocyclyl or heteroaryl, wherein said aryl or heteroaryl is optionally substituted with one to three alkyl, halo, CN, alkyloxy, alkyl-OH, —OH, alkyl-$NH_2$, —N(alkyl)$_2$, alkyl-O-alkyl, —S(O)$_{0-2}$alkyl, —C$_0$-C$_3$alkyl-NR$_3$C(O)alkyl, —C(O)NR$_3$alkyl, -alkyl-CN, CF$_3$, —O—CF$_3$, —C$_0$-C$_3$alkyl-C(O)OR$_3$, —C$_0$-C$_3$alkyl-NR$_3$C(O)Oalkyl, —C(O)Oalkyl, —S(O)$_2$NHalky or —S(O)$_2$NH$_2$:

Other preferred compounds of embodiment (XVI) include those of formula $I_{XII}$, where in X is aryl, -aryl-heteroaryl, heteroaryl-aryl, heterocyclyl or heteroaryl, wherein said aryl or heteroaryl is optionally substituted with one to three alkyl, halo, CN, alkyloxy, alkyl-OH, —OH, alkyl-$NH_2$, —N(alkyl)$_2$, alkyl-O-alkyl, —S(O)$_{0-2}$alkyl, —C$_0$-C$_3$alkyl-NR$_3$C(O)alkyl, —C(O)NR$_3$alkyl, -alkyl-CN, CF$_3$, —O—CF$_3$, —C$_0$-C$_3$alkyl-C(O)OR$_3$, —C$_0$-C$_3$alkyl-NR$_3$C(O)Oalkyl, —C(O)Oalkyl, —S(O)$_2$NHalky or —S(O)$_2$NH$_2$:

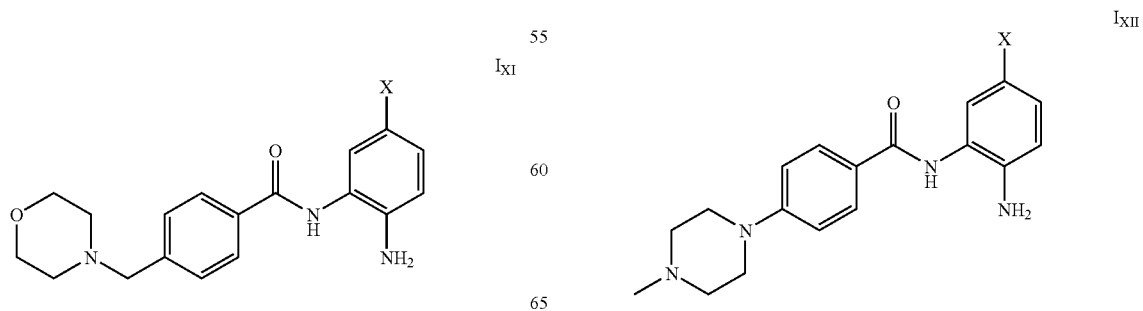

In another aspect, the invention comprises compounds of formula II:

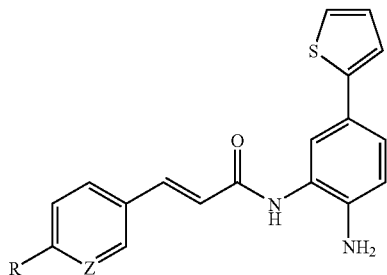

and N-oxides, hydrates, solvates, pharmaceutically acceptable salts, prodrugs or complex thereof, and racemic and scalemic mixtures, diastereomers and enantiomers thereof, wherein Z is N or CH;

R is —$CH_2OR^3$, —$C_0$-$C_3$alkyl-N($R^3$)—$C_0$-$C_3$alkyl-heteroaryl, —$C_0$-$C_3$alkyl-N($R^3$)—$C_0$-$C_3$alkyl-aryl, —$(CH_2)_m$-aryl, —$(CH_2)_m$-heteroaryl or (5- or 6-membered heteroaryl)-$(CH_2)_m$—, wherein the aryl and heteroaryl rings are optionally substituted with 1, 2, or 3 methoxy;

m is 0 or 1;

wherein $R^3$ is as defined in embodiment (I) above.

Preferably, compounds of formula II are those in which R is pyridyl (preferably pyridine-2-yl), phenyl, or morpholino.

Preferred compounds for formula II include the following:

| Cpd | Z | m | R |
|---|---|---|---|
| 42 | N | 0 | ![](MeO, MeO phenyl) |
| 43 | N | 0 | ![](MeO, MeO, OMe phenyl) |
| 44 | N | 0 | |
| 96 | CH | 1 | |
| 166 | N | 1 | |
| | CH | 0 | —$CH_2OH$ |

In a preferred embodiment of the compounds according to Formula (II), the

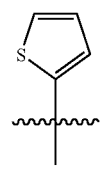

moiety is optionally substituted with one, two or three substituents independently selected from the group consisting of halo, oxo, hydroxy, $C_1$-$C_3$-hydrocarbyl, methoxy, $HalCH_2$—O—, $Hal_2CH$—O—, $Hal_3C$—O—(preferably $F_3C$—O—), $NH_2$—, —N($C_1$-$C_3$alkyl)$_2$, —CN, —S(O)$_{0-2}$—$C_1$-$C_4$alkyl, —$CF_3$, and mono-, di-, or tri halo substituted alkyl, or, when there are two optional substituents bonded to adjacent atoms of the phenyl, thienyl, or pyridyl they, together with the atoms to which they are bonded, optionally form a 5- or 6-membered cycloalkyl or heteroalkyl having 1, 2, or 3 annular heteroatoms.

In another aspect, the invention comprises compounds of formula III

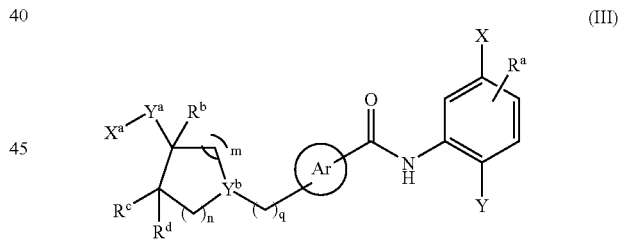

(III)

and N-oxides, hydrates, solvents, pharmaceutically acceptable salts, prodrugs or complexes thereof, and racemic and scalemic mixtures, diastereomers and enantiomers thereof wherein X is aryl, cycloalkyl, heteroaryl or heterocyclyl, each of which is optionally substituted;

Ar is aryl, heteroaryl, cycloalkyl or heterocyclyl, each of which is optionally substituted;

$R^a$ is H or halo;

$R^b$, $R^c$ and $R^d$ are each independently hydrogen, $C_1$-$C_8$ alkyl, aryl, heteroaryl, cycloalkyl, heterocyclyl or halo; or $R^b$ and $R^c$ together with the atoms to which they are bonded, optionally form a 5- or 6-membered cycloalkyl or heteroalkyl having 1 or 2 annular heteroatoms; each of which is optionally substituted with from 1 to 3 substituents;

Y is —$NH_2$ or —OH;

$Y^b$ is —N— or —CH—;

$Y^a$ is direct bond, —O—, —$N(R^{34})$—, —C(O)—, —OC(O)—, —C(O)O—, —$N(R^{34})$—C(O)—, —C(O)—$N(R^{34})$—, —$N(R^{34})$—C(S)—, —C(S)—$N(R^{34})$—, —$N(R^{34})$—C(O)—$N(R^{35})$—, —$N(R^{34})$—$C(NR^{34})$—$N(R^{35})$—, —$N(R^{34})$—$C(NR^{35})$—, —$C(NR^{35})$—$N(R^{34})$—, —$N(R^{34})$—C(S)—$N(R^{35})$—, —$N(R^{34})$—C(O)—O—, —O—C(O)—$N(R^{34})$—, —$N(R^{34})$—C(S)O—, —O—C(S)—$N(R^{35})$—, —$S(O)_{0-2}$—, —$SO_2N(R^{35})$—, —$N(R^{35})$—$SO_2$—, —$N(R^{34})$—$S(O)_2$—$N(R^{35})$—, —O—$C_1$-$C_3$alkyl-, —$N(R^{34})$—$C_1$-$C_3$alkyl-, —C(O)—$C_1$-$C_3$alkyl- or —O—C(O)—$C_1$-$C_3$alkyl-;

$X^a$ is $C_1$-$C_8$alkyl-, $C_1$-$C_8$alkenyl-, $C_1$-$C_8$alkynyl-, $C_0$-$C_3$alkyl-$C_1$-$C_8$alkenyl-$C_0$-$C_3$alkyl-, $C_0$-$C_3$alkyl-$C_1$-$C_8$alkynyl-$C_0$-$C_3$alkyl-, $C_1$-$C_3$alkyl-O—$C_1$-$C_3$alkyl-, HO—$C_1$-$C_3$alkyl-, $C_1$-$C_4$alkyl-$N(R^{34})$—$C_0$-$C_3$alkyl-, $N(R^{34})(R^{35})$—$C_0$-$C_3$alkyl-, $C_1$-$C_3$alkyl-$S(O)_{0-2}$—$C_1$-$C_3$alkyl-, $CF_3$—$C_0$-$C_3$alkyl-, $CF_2H$—$C_0$-$C_3$alkyl-, $C_1$-$C_8$heteroalkyl-, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, aryl-$C_0$-$C_2$alkyl-heterocyclyl-$C_0$-$C_2$alkyl-, heteroaryl-$C_0$-$C_2$alkyl-heterocyclyl-$C_0$-$C_2$alkyl-, $N(R^{34})(R^{35})$-heterocyclyl-$C_0$-$C_3$alkyl-, heteroaryl-$C_0$-$C_3$alkyl-heterocyclyl- or $C_1$-$C_4$alkyl-$CH(N(R^{34})(R^{35}))$—C(O)—$N(R^{34})$-aryl-, wherein the aryl, cycloalkyl, heteroaryl and heterocycyl are optionally substituted with from 1 to 3 independently selected substituents;

or $X^a$—$Y^a$— is selected from the group consisting of H—, halo-, HO—, HS—, HC(O)—, HOC(O)—, $C_1$-$C_4$alkyl-, $H_2N$—, $(R^{34})(R^{35})N$—, $C_1$-$C_4$alkyl-NH—, $(C_1$-$C_4$alkyl$)_2$-N—, $HC(O)N(R^{34})$—, $(R^{34})(R^{35})N$—$S(O)_2$—$N(R^{36})$—, $(R^{34})(R^{35})N$—C(O)—, $H_2N$—C(O)—, $HC(S)N(R^{34})$—, $(R^{34})(R^{35})N$—C(S)—, $H_2N$—C(S)—, $(R^{34})(R^{35})N$—C(O)—O—, $(R^{34})(R^{35})N$—C(S)—O—, $(R^{34})(R^{35})N$—C(O)—$N(R^{36})$, $(C_1$-$C_3$alkylN$)_2$—C=N—, $(R^{34})(R^{35})N$—$C(NR^{37})$—$N(R^{36})$—, $(R^{34})(R^{35})N$—$C(NR^{36})$—, cycloalkyl-$C_0$-$C_2$alkyl-$C(NR^{36})$—, heterocyclyl-$C_0$-$C_2$alkyl-$C(NR^{36})$—, aryl-$C_0$-$C_2$alkyl-$C(NR^{36})$—, heteroaryl-$C_0$-$C_2$alkyl-$C(NR^{36})$—, $C_0$-$C_3$alkyl-$C(NR^{36})$—, $C_1$-$C_4$alkyl-$S(O)_2$—$N(R^{36})$—, $CF_3$—$C_0$-$C_4$alkyl-$S(O)_2$—$N(R^{36})$—, $CF_3$—$C_0$-$C_4$alkyl-C(O)—$N(R^{36})$—, aryl-$C_0$-$C_4$alkyl-$S(O)_2$—$N(R^{36})$—, heteroaryl-$C_0$-$C_4$alkyl-$S(O)_2$—$N(R^{36})$—, cycloalkyl-$C_0$-$C_4$alkyl-$S(O)_2$—$N(R^{36})$—, heterocyclyl-$C_0$-$C_4$alkyl-$S(O)_2$—$N(R^{36})$—, $C_1$-$C_4$alkyl-O—C(O)—NH—, $C_1$-$C_4$alkyl-O—C(O)—N(H)—$C_1$-$C_4$alkyl-, $C_1$-$C_4$alkyl-N(H)—C(O)—N(H)—, $C_1$-$C_4$alkyl-NH—C(O)—O—, $C_1$-$C_4$alkyl-C(O)—N(H)—, $C_1$-$C_4$alkyl-O—C(S)—N(H)—, $C_1$-$C_4$alkyl-N(H)—C(S)—N(H)—, $C_1$-$C_4$alkyl-N(H)—C(S)—O—, $C_1$-$C_4$alkyl-C(S)—N(H)—, Me-C(O)—O—, Me-C(O)—N(H)—, aryl-$C_0$-$C_4$alkyl-O—C(O)—N(H)—, aryl-$C_0$-$C_4$alkyl-O—C(O)—$N(C_1$-$C_4$alkyl)-, aryl-$C_0$-$C_4$alkyl-C(O)—N(H)—, heteroaryl-$C_0$-$C_4$alkyl-O—C(O)—N(H)—, heteroaryl-$C_0$-$C_4$alkyl-O—C(O)—$N(C_1$-$C_4$alkyl)-, heteroaryl-$C_0$-$C_4$alkyl-C(O)—N(H)—, aryl-$C_0$-$C_4$alkyl-N(H)—C(O)—O—, heteroaryl-$C_0$-$C_4$alkyl-N(H)—C(O)—O—, heterocyclyl-$C_0$-$C_4$alkyl-O—C(O)—N(H)—, heterocyclyl-$C_0$-$C_4$alkyl-O—C(O)—$N(C_1$-$C_4$alkyl)-, heterocyclyl-$C_0$-$C_4$alkyl-C(O)—N(H)—, cycloalkyl-$C_0$-$C_4$alkyl-O—C(O)—N(H)—, cycloalkyl-$C_0$-$C_4$alkyl-O—C(O)—$N(C_1$-$C_4$alkyl)-, cycloalkyl-$C_0$-$C_4$alkyl-C(O)—N(H)—, heterocyclyl-$C_0$-$C_4$alkyl-N(H)—C(O)—O—, cycloalkyl-$C_0$-$C_4$alkyl-N(H)—C(O)—O—, heterocyclyl-$C_0$-$C_4$alkyl-C(O)—N(H)—, aryl-$C_0$-$C_4$alkyl-N(H)—C(O)—N(H)—, aryl-$C_0$-$C_4$alkyl-N(H)—, aryl-$C_0$-$C_4$alkyl-O—, aryl-$C_0$-$C_4$alkyl-$S(O)_{0-2}$—, heteroaryl-$C_0$-$C_4$alkyl-N(H)—C(O)—N(H)—, heteroaryl-$C_0$-$C_4$alkyl-N(H)—, heteroaryl-$C_0$-$C_4$alkyl-O—, heteroaryl-$C_0$-$C_4$alkyl-$S(O)_{0-2}$—, heterocyclyl-$C_0$-$C_4$alkyl-N(H)—C(O)—N(H)—, heterocyclyl-$C_0$-$C_4$alkyl-N(H)—, heterocyclyl-$C_0$-$C_4$alkyl-O—, heterocyclyl-$C_0$-$C_4$alkyl-$S(O)_{0-2}$—, cycloalkyl-$C_0$-$C_4$alkyl-N(H)—C(O)—N(H)—, cycloalkyl-$C_0$-$C_4$alkyl-N(H)—, cycloalkyl-$C_0$-$C_4$alkyl-O—, cycloalkyl-$C_0$-$C_4$alkyl-$S(O)_{0-2}$—, aryl-$C_0$-$C_4$alkyl-C(S)—N(H)—, heteroaryl-$C_0$-$C_4$alkyl-C(S)—N(H)—, aryl-$C_0$-$C_4$alkyl-O—C(S)—N(H)—, heteroaryl-$C_0$-$C_4$alkyl-O—C(S)—N(H)—, aryl-$C_0$-$C_4$alkyl-N(H)—C(S)—O—, heteroaryl-$C_0$-$C_4$alkyl-N(H)—C(S)—O—, heterocyclyl-$C_0$-$C_4$alkyl-C(S)—N(H)—, cycloalkyl-$C_0$-$C_4$alkyl-C(S)—N(H)—, heterocyclyl-$C_0$-$C_4$alkyl-O—C(S)—N(H)—, cycloalkyl-$C_0$-$C_4$alkyl-O—C(S)—N(H)—, heterocyclyl-$C_0$-$C_4$alkyl-N(H)—C(S)—O—, cycloalkyl-$C_0$-$C_4$alkyl-N(H)—C(S)—O—, heterocyclyl-$C_0$-$C_4$alkyl-C(S)—N(H)—, aryl-$C_0$-$C_4$alkyl-N(H)—C(S)—NH—, heteroaryl-$C_0$-$C_4$alkyl-N(H)—C(S)—N(H)—, heterocyclyl-$C_0$-$C_4$alkyl-N(H)—C(S)—N(H)—, cycloalkyl-$C_0$-$C_4$alkyl-N(H)—C(S)—N(H)—, $C_1$-$C_4$alkyl-O—$C_1$-$C_4$alkyl-C(O)—N(H)—, $C_1$-$C_4$alkyl-O—$C_2$-$C_4$alkyl-O—C(O)—N(H)—, $C_1$-$C_4$alkyl-O—$C_2$-$C_4$alkyl-N(H)—C(O)—N(H)—, $C_1$-$C_4$alkyl-O—$C_2$-$C_4$alkyl-N(H)—, $C_1$-$C_4$alkyl-O—$C_2$-$C_4$alkyl-O—, $C_1$-$C_4$alkyl-O—$C_2$-$C_4$alkyl-N(H)—C(O)—O—, HO—$C_1$-$C_4$alkyl-C(O)—N(H)—, HO—$C_1$-$C_4$alkyl-N(H)—, HO—$C_1$-$C_4$alkyl-$N(R^3)$—, HO—$C_1$-$C_4$alkyl-O—, HO—$C_1$-$C_4$alkyl-$S(O)_{0-2}$—, HO—$C_2$-$C_4$alkyl-O—C(O)—N(H)—, HO—$C_2$-$C_4$alkyl-N(H)—C(O)—N(H)—, HO—$C_2$-$C_4$alkyl-N(H)—C(O)—O—, $C_1$-$C_4$alkyl-O—$C_1$-$C_4$alkyl-C(S)—N(H)—, $C_1$-$C_4$alkyl-O—$C_2$-$C_4$alkyl-O—C(S)—N(H)—, $C_1$-$C_4$alkyl-O—$C_2$-$C_4$alkyl-N(H)C(S)—N(H)—, $C_1$-$C_4$alkyl-O—$C_2$-$C_4$alkyl-N(H)—C(S)—O—, HO—$C_2$-$C_4$alkyl-O—C(S)—N(H)—, HO—$C_2$-$C_4$alkyl-N(H)—C(S)—N(H)—, HO—$C_2$-$C_4$alkyl-N(H)—C(S)—O—, $(C_1$-$C_4$alkyl$)_2$N—$C_1$-$C_4$alkyl-C(O)—N(H)—, $(C_0$-$C_4$alkyl)-O—$C_1$-$C_4$alkyl-C(O)—N(H)—, $(C_0$-$C_4$alkyl)-O—$C_1$-$C_4$alkyl-C(S)—N(H)—, $(C_0$-$C_4$alkyl)-O—$C_1$-$C_4$alkyl-C(O)—O—, $(C_0$-$C_4$alkyl)-O—$C_2$-$C_4$alkyl-N(H)—C(O)—N(H)—, $(C_0$-$C_4$alkyl)-O—$C_2$-$C_4$alkyl-O—C(O)—N(H)—, $(C_0$-$C_4$alkyl)-O—$C_2$-$C_4$alkyl-N(H)—C(NH)—N(H)—, $(C_0$-$C_4$alkyl)-O—$C_2$-$C_4$alkyl-N(H)—C(O)—, $(C_1$-$C_4$alkyl$)_2$N—$C_2$-$C_4$alkyl-O—C(O)—N(H)—, $(C_1$-$C_4$alkyl$)_2$N—$C_2$-$C_4$alkyl-N(H)—, $(C_1$-$C_4$alkyl$)_2$N—$C_2$-$C_4$alkyl-O—, $(C_1$-$C_4$alkyl$)_2$N—$C_2$-$C_4$alkyl-$S(O)_{0-2}$—, $(C_1$-$C_4$alkyl$)_2$N—$C_2$-$C_4$alkyl-N(H)—C(O)—N(H)—, $(C_1$-$C_4$alkyl$)_2$N—$C_2$-$C_4$alkyl-N(H)—C(O)—O—, $(C_1$-$C_4$alkyl$)_2$N—$C_1$-$C_4$alkyl-C(S)—N(H)—, $(C_1$-$C_4$alkyl$)_2$N—$C_2$-$C_4$alkyl-N(H)—C(S)—N(H)—, $(C_1$-$C_4$alkyl$)_2$N—$C_2$-$C_4$alkyl-N(H)—C(S)—O—, $(C_1$-$C_4$alkyl)-O—$C(O)C_1$-$C_8$alkyl-C(O)—(H)—, HO—$C(O)C_1$-$C_8$alkyl-C(O)—N(H)—, HO—NH—$C(O)C_1$-$C_8$alkyl-C(O)—N(H)—, $CF_2H$—$C_0$-$C_4$alkyl-C(O)—N(H)—, $CF_3$—$C_0$-$C_4$alkyl-C(O)—N(H)—, $CF_3$—$C_0$-$C_4$alkyl-N(H)—, $CF_3$—$C_0$-$C_4$alkyl-$N(R^3)$—, $CF_3$—$C_0$-$C_4$alkyl-O—, $CF_3$—$C_0$-$C_4$alkyl-$S(O)_{0-2}$—, $CF_3$—$C_0$-$C_4$alkyl-O—C(O)—N(H)—, $CF_3$—$C_0$-$C_4$alkyl-N(H)C(O)—N(H)—, $CF_3$—$C_0$-$C_4$alkyl-N(H)—C(O)—O—, $CF_3$—$C_0$-$C_4$alkyl-O—C(S)—N (H)—, $CF_3$—$C_0$-$C_4$alkyl-N(H)—C(S)—N(H)—, $CF_3$—$C_0$-$C_4$alkyl-N(H)—C(S)—O—, $CF_3$—$C_0$-$C_4$alkyl-C(S)—N(H)—, $CF_2H$—$C_0$-$C_4$alkyl-N(H)—, $CF_2H$—$C_0$-$C_4$alkyl-O—, $CF_2H$—$C_0$-$C_4$alkyl-S(O)$_{0-2}$—, $CF_2H$—$C_0$-$C_4$alkyl-O—C(O)—N(H)—, $CF_2H$—$C_0$-$C_4$alkyl-N(H)C(O)—N(H)—, $CF_2H$—$C_0$-$C_4$alkyl-N(H)—C(O)—O—, $CF_2H$—$C_0$-$C_4$alkyl-O—C(S)—N(H)—, $CF_2H$—$C_0$-$C_4$alkyl-N(H)—C(S)—N(H)—, $CF_2H$—$C_0$-$C_4$alkyl-N(H)—C(S)—O—, $CF_2H$—$C_0$-$C_4$alkyl-C(S)—N(H)—, (H)($R^{34}$)N—$C_1$-$C_3$alkyl-, (H)($R^{34}$)N—$C_1$-$C_3$alkyl-, HO—$C_1$-$C_3$alkyl-, (H)($R^{34}$)N—S(O)$_2$—N($R^{35}$)—, (H)($R^{35}$)N—S(O)$_2$—, (H)($R^{34}$)N—C(S)—O—, (H)($R^{34}$)N—C(O)—O—, (H)($R^{34}$)N—C(S)—N($R^{35}$)—, (H)($R^{34}$)N—C(N$R^{35}$)—, (H)($R^{34}$)N—C(N$R^{34}$)—N($R^{38}$)—, (H)($R^{34}$)N—C(O)—N($R^{35}$)—, HO—C(O)—$C_1$-$C_3$alkyl-, $C_1$-$C_4$alkyl-S(O)$_2$—NH— and (($R^{34}$)($R^{35}$)N)$_2$—C=N—;

m and n are independently 0, 1, 2 or 3;

q is 0, 1 or 2;

$R^{34}$, $R^{35}$, $R^{36}$ and $R^{37}$ are each independently selected from the group consisting of hydrogen, cyano, oxo, hydroxyl, —$C_1$-$C_8$alkyl, $C_1$-$C_8$heteroalkyl, $C_1$-$C_8$alkenyl, carboxamido, $C_1$-$C_3$alkyl-carboxamido-, carboxamido-$C_1$-$C_3$alkyl-, amidino, $C_2$-$C_8$hydroxyalkyl, $C_1$-$C_3$alkylaryl-, aryl-$C_1$-$C_3$alkyl-, $C_1$-$C_3$alkylheteroaryl-, heteroaryl-$C_1$-$C_3$alkyl-, $C_1$-$C_3$alkylheterocyclyl-, heterocyclyl-$C_1$-$C_3$alkyl-, $C_1$-$C_3$alkylcycloalkyl-, cycloalkyl-$C_1$-$C_3$alkyl-, $C_2$-$C_8$alkoxy-, $C_2$-$C_8$alkoxy-$C_1$-$C_4$alkyl-, $C_1$-$C_8$alkoxycarbonyl-, aryloxycarbonyl-, aryl-$C_1$-$C_3$alkoxycarbonyl-, heteroaryloxycarbonyl-, heteroaryl-$C_1$-$C_3$alkoxycarbonyl-, $C_1$-$C_8$acyl, $C_0$-$C_8$alkyl-carbonyl-, aryl-$C_0$-$C_8$alkyl-carbonyl-, heteroaryl-$C_0$-$C_8$alkyl-carbonyl-, cycloalkyl-$C_0$-$C_8$alkyl-carbonyl-, $C_0$-$C_8$alkyl-N(H)-carbonyl-, aryl-$C_0$-$C_8$alkyl-N(H)-carbonyl-, heteroaryl-$C_0$-$C_8$alkyl-N(H)-carbonyl-, cycloalkyl-$C_0$-$C_8$alkyl-N(H)-carbonyl-, $C_0$-$C_8$alkyl-O-carbonyl-, aryl-$C_0$-$C_8$alkyl-O-carbonyl-, heteroaryl-$C_0$-$C_8$alkyl-O-carbonyl-, cycloalkyl-$C_0$-$C_8$alkyl-O-carbonyl-, $C_1$-$C_8$ alkylsulfonyl-, arylalkylsulfonyl-, arylsulfonyl-, heteroarylalkylsulfonyl-, heteroarylsulfonyl-, $C_1$-$C_8$alkyl-N(H)-sulfonyl-, arylalkyl-N(H)-sulfonyl-, aryl-N(H)-sulfonyl-, heteroarylalkyl-N(H)-sulfonyl-, heteroaryl-N(H)-sulfonyl, aroyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$ alkyl-, heteroaryl-$C_1$-$C_3$ alkyl-, and a protecting group, wherein each of the foregoing is further optionally substituted with one more moieties; or $R^{34}$ and $R^{35}$ taken together with the N to which they are attached form a heterocyclyl or heteroaryl, each of which is optionally substituted with from 1 to 3 substituents, wherein the heterocyclyl may also be bridged (forming a bicyclic moiety with a methylene, ethylene or propylene bridge), provided that 1) when $Y^b$ is N, then m is not 0 if $Y^a$ is bound to the ring comprising Y, via a N, S or O in $Y^a$, or 2) when m and n are both 0 then $Y^b$ is —CH—.

In a preferred embodiment of the compounds according to Formula (III), X is optionally substituted with one, two or three substituents independently selected from the group consisting of halo, oxo, hydroxy, $C_1$-$C_3$-hydrocarbyl, methoxy, HalCH$_2$—O—, Hal$_2$CH—O—, Hal$_3$C—O— (preferably $F_3C$—O—), NH$_2$—, —N($C_1$-$C_3$alkyl)$_2$, —CN, —S(O)$_{0-2}$—$C_1$-$C_4$alkyl, —CF$_3$, and mono-, di-, or tri-halo substituted alkyl, or, when there are two optional substituents bonded to adjacent atoms of the phenyl, thienyl, or pyridyl they, together with the atoms to which they are bonded, optionally form a 5- or 6-membered cycloalkyl or heteroalkyl having 1, 2, or 3 annular heteroatoms.

In a preferred embodiment of the compounds according to Formula (III), X is selected from the group consisting of phenyl, pyridyl, thienyl and furyl, each of which is optionally substituted with one, two or three independently selected substituents.

In a preferred embodiment of the compounds according to Formula (III), X is selected from the group consisting of phenyl, pyridyl, thienyl and furyl, each of which is optionally substituted with one, two or three substituents independently selected from the group consisting of halo, oxo, hydroxy, $C_1$-$C_3$-hydrocarbyl, methoxy, HalCH$_2$—O—, Hal$_2$CH—O—, Hal$_3$C—O— (preferably $F_3C$—O—), NH$_2$—, —N($C_1$-$C_3$alkyl)$_2$, —CN, —S(O)$_{0-2}$—$C_1$-$C_4$alkyl, —CF$_3$, and mono-, di-, or tri-halo substituted alkyl, or, when there are two optional substituents bonded to adjacent atoms of the phenyl, thienyl, or pyridyl they, together with the atoms to which they are bonded, optionally form a 5- or 6-membered cycloalkyl or heteroalkyl having 1, 2, or 3 annular heteroatoms.

In a preferred embodiment of the compounds according to Formula (III), Ar is optionally substituted with one or two substituents independently selected from the group consisting of halo, nitro, hydroxy, $C_1$-$C_3$-hydrocarbyl, methoxy, HalCH$_2$—O—, Hal$_2$CH—O—, Hal$_3$C—O— (preferably $F_3C$—O—), and mono-, di-, or tri-halo substituted alkyl.

In a preferred embodiment of the compounds according to Formula (III), Ar is selected from the group consisting of phenyl, pyridyl, pyrimidyl, benzofuryl, benzothienyl, thienyl and furanyl, each of which is optionally substituted with one or two substituents.

In a preferred embodiment of the compounds according to Formula (III), Ar is selected from the group consisting of phenyl, pyridyl, pyrimidyl, benzofuryl, benzothienyl, thienyl and furanyl, each of which is optionally substituted with one or two substituents independently selected from the group consisting of halo, nitro, hydroxy, $C_1$-$C_3$-hydrocarbyl, methoxy, HalCH$_2$—O—, Hal$_2$CH—O—, Hal$_3$C—O— (preferably $F_3C$—O—), and mono-, di-, or tri-halo substituted alkyl.

In a preferred embodiment of the compounds according to Formula (III), $X^a$ comprises a moiety selected from the group consisting of aryl, cycloalkyl, heteroaryl and heterocycyl, each of which is optionally substituted with from 1 to 3 independently selected substituents.

In a preferred embodiment of the compounds according to Formula (III), $X^a$ comprises a moiety selected from the group consisting of aryl, cycloalkyl, heteroaryl and heterocycyl, each of which is optionally substituted with from 1 to 3 substituents independently selected from the group consisting of —OH, —NH$_2$, —O—$C_0$-$C_3$alkylCH$_3$, halo, oxo, —C(O)NH$_2$, —NHC(O)CH$_3$.

In a preferred embodiment of the compounds according to Formula (III), $X^a$—$Y^a$— is selected from the group consisting of CH$_3$—SO$_2$—, CF$_3$—C(O)—NH—, CH$_3$—C(O)—NH—, ((CH$_3$)$_2$N)$_2$—C=N—, (CH$_3$)$_2$N—, CH$_3$—O—CH$_2$—C(O)—NH—, (CH$_3$)$_2$N—CH$_2$—C(O)—NH—, CH$_3$CH$_2$—N(CH$_3$)—, CF$_3$CH$_2$—NH—, H—, HO—, CH$_3$—O—C(O)—NH—, H$_2$N—, CH$_3$CH$_2$—NH—, H$_2$N—C(O)—, phenyl-CH$_2$—O—C(O)—N(CH$_2$CH$_3$)—, CH$_3$CH$_2$—NH—, F, CH$_3$—O—CH$_2$—C(O)—NH—, heterocyclyl-heterocyclyl, heterocyclyl-heteroaryl, aryl-NH—, heteroaryl-NH—, (CH$_3$)$_2$N—CH$_2$—C(O)—NH— and HO—CH$_2$CH$_2$—NH—.

In a preferred embodiment of the compounds according to Formula (III), the compounds are represented by the formula (III-a):

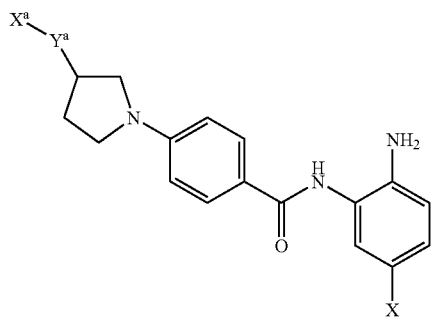

(III-a)

wherein X, $X^a$ and $Y^a$ are as defined for Formula (III).

In a preferred embodiment of the compounds according to Formula (III), the compounds are represented by the formula (III-b):

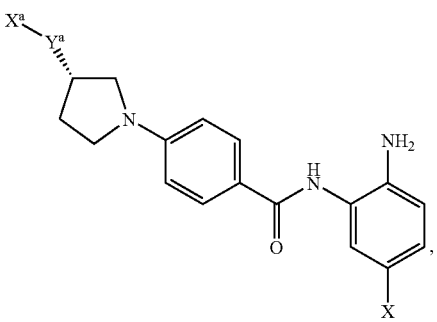

(III-b)

wherein X, $X^a$ and $Y^a$ are as defined for Formula (III).

In a preferred embodiment of the compounds according to Formula (III), the compounds are represented by the formula (III-c):

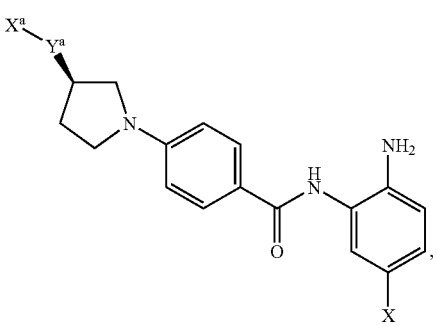

(III-c)

wherein X, $X^a$ and $Y^a$ are as defined for Formula (III).

In a preferred embodiment of the compounds according to Formula (III), the compounds are represented by the formula (III-d):

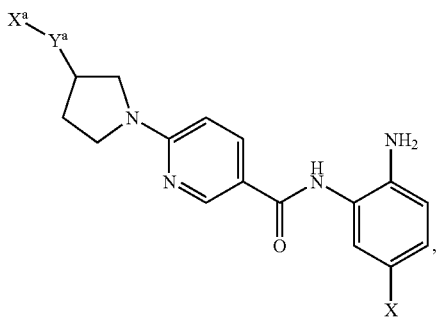

(III-d)

wherein X, $X^a$ and $Y^a$ are as defined for Formula (III).

In a preferred embodiment of the compounds according to Formula (III), the compounds are represented by the formula (III-e):

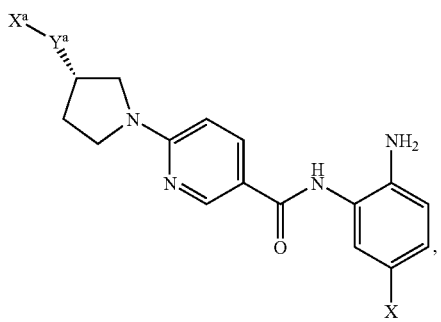

(III-e)

wherein X, $X^a$ and $Y^a$ are as defined for Formula (III).

In a preferred embodiment of the compounds according to Formula (III), the compounds are represented by the formula (III-f):

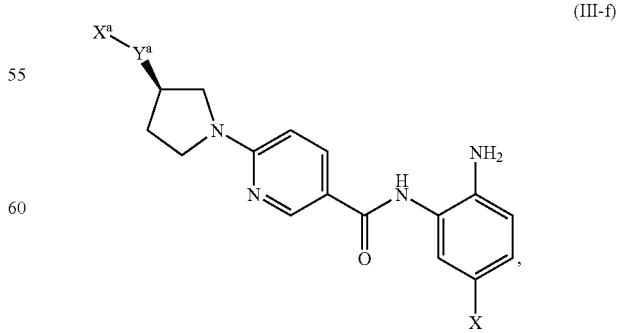

(III-f)

wherein X, $X^a$ and $Y^a$ are as defined for Formula (III).

In a preferred embodiment of the compounds according to Formula (III), the compounds are represented by the formula (III-g):

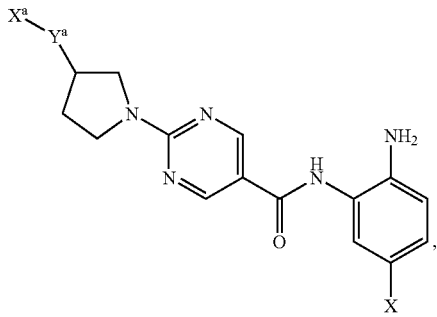
(III-g)

wherein X, $X^a$ and $Y^a$ are as defined for Formula (III).

In a preferred embodiment of the compounds according to Formula (III), the compounds are represented by the formula (III-h):

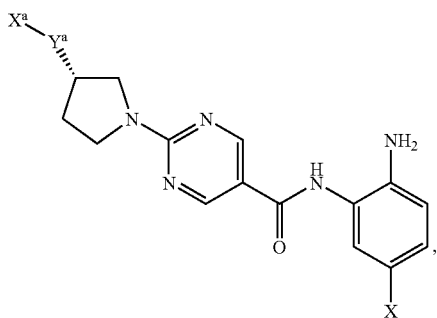
(III-h)

wherein X, $X^a$ and $Y^a$ are as defined for Formula (III).

In a preferred embodiment of the compounds according to Formula (III), the compounds are represented by the formula (III-i):

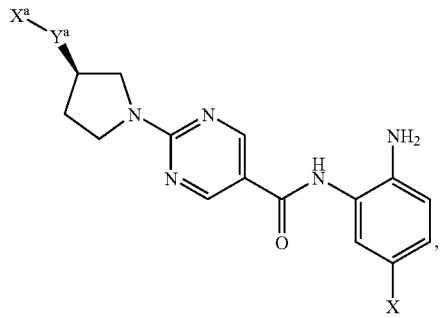
(III-i)

wherein X, $X^a$ and $Y^a$ are as defined for Formula (III).

In a preferred embodiment of the compounds according to the present invention, when a moiety is defined as —N($R^x$)($R^y$), wherein $R^x$ and $R^y$, together with the N atom to which they are attached optionally form a heterocycle with one or more annular heteroatoms, said heterocycle is selected from the group consisting of

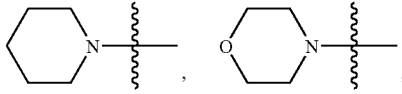

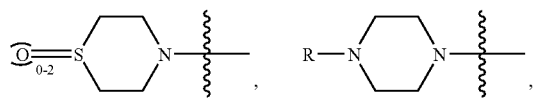

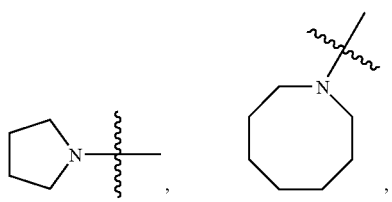

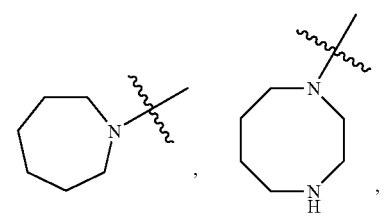

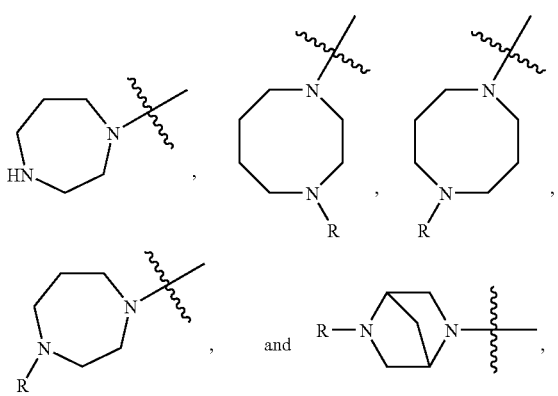

wherein R is the substituent as defined for a particular embodiment.

In another embodiment, the invention comprises the following compounds:

| Cpd | Name |
|---|---|
| 30 | N-(2-amino-5-(benzo[d][1,3]dioxol-5-yl)phenyl)-4-(morpholinomethyl)benzamide |
| 33 | (E)-N-(2-amino-5-(3-methoxyprop-1-enyl)phenyl)-4-(morpholinomethyl)benzamide |
| 66 | N-(2-amino-5-(thiophen-2-yl)phenyl)-1,3-dimethyl-1H-thieno[2,3-c]pyrazole-5-carboxamide |
| 72 | 2-(4-((6-chloro-5-fluoro-1H-benzo[d]imidazol-2-ylthio)methyl)benzamido)-4-(thiophen-2-yl)benzoic acid |
| 132 | N-(2-Amino-5-(thiophen-2-yl)phenyl)-2-oxo-2,3-dihydrobenzo[d]oxazole-6-carboxamide |
| 161 | (S)-2-(5-(2-Amino-5-(thiophen-2-yl)phenylcarbamoyl)-2-methyl-1H-benzo[d]imidazol-1-yl)ethyl 2-(tert-butoxycarbonylamino)-3-methylbutanoate |
| 172 | 2-(4-((6-chloro-5-fluoro-1H-benzo[d]imidazol-2-ylthio)methyl)benzamido)-4-(thiophen-2-yl)benzoic acid |
| 184 | N-1-(2-Amino-5-(thiophen-2-yl)phenyl)-N8-(biphenyl-3-yl)octanediamide |
| 193 | N-(2-Amino-5-(5-(((2-hydroxyethylamino)methyl)thiophen-2-yl)phenyl)-4-methoxybenzamide |
| 194 | N-(5-(5-((1H-pyrazol-5-ylamino)methyl)thiophen-2-yl)-2-aminophenyl)-4-methoxybenzamide |
| 201 | N-(2-Amino-5-(5-((hydroxyimino)methyl)thiophen-2-yl)phenyl)-4-(pyridin-3-yl)benzamide |
| 205 | N-(2-Amino-5-(thiophen-2-yl)phenyl)-2-(1-benzylpiperidin-4-ylidene)acetamide |
| 210 | N-(4-Amino-4'-(methylsulfinyl)biphenyl-3-yl)-4-methoxybenzamide |
| 216 | Pyridin-3-ylmethyl 6-(2-amino-5-(thiophen-2-yl)phenylcarbamoyl)-3,4-dihydroquino-line-1(2H)-carboxylate |
| 222 | N-(2-amino-5-(thiophen-2-yl)phenyl)-4-((3-(2-(dimethylamino)ethyl)-3-methylureido)methyl)benzamide |
| 279 | N-(2-Amino-5-(thiophen-2-yl)phenyl)-4-(1-(benzo[d][1,3]dioxol-5-ylmethyl)pyrrolidin-3-yl)butanamide |
| 316 | N-(2-Amino-5-(thiophen-2-yl)phenyl)-4-(benzo[d][1,3]dioxol-5-ylmethyl)piperazine-1-carboxamide |
| 320 | N-(4-Aminobiphenyl-3-yl)-1-(4-nitrophenylsulfonyl)piperidine-4-carboxamide |

In preferred embodiments of the present invention, the invention comprises the ing compounds:
N-(2-amino-5-(1H-indol-5-yl)phenyl)-4-methoxybenzamide,
(tetrahydro-2H-pyran-2-yl)methyl 4-(2-amino-5-(thiophen-2yl)phenylcarbamoyl)phenylcarbamate,
N-(2-amino-5-(thiophen-2-yl)phenyl)-3-(pyridin-3-yl)benzamide,
N-(2-amino-5-(1H-pyrrol-2-yl)phenyl)-4-methoxybenzamide,
N-(2-amino-5-(1H-pyrrol-2-yl)phenyl)-4-(pyridin-3-yl)benzamide,
N-(2-amino-5-(pyridin-3-yl)phenyl)-4-(pyridin-3-yl)benzamide,
pyridin-3-ylmethyl 4-(2-amino-5-(thiophen-2-yl)phenylcarbamoyl)phenylcarbamate,
N-(2-amino-5-(thiophen-2-yl)phenyl)-5-(pyridin-2-yl)thiophene-2-carboxamide,
N-(4,4'-diaminobiphenyl-3-yl)-4-(pyridin-3-yl)benzamide,
(S)-2-(5-(2-amino-5-(thiophen-2-yl)phenylcarbamoyl)-2-methyl-1H-benzo[d]imidazol-1-yl)ethyl 2-amino-3-methylbutanoate,
N-(4-amino-4'-fluorobiphenyl-3-yl)-4-(pyridin-3-yl)benzamide,
N-(2-amino-5-(thiophen-2-yl)phenyl)-3',4',5'-trimethoxybiphenyl-3-carboxamide,
N-(2-amino-5-(thiophen-2-yl)phenyl)-3-(1H-pyrazol-4-yl)benzamide,
N-(2-amino-5-(1H-pyrazol-4-yl)phenyl)-4-(pyridin-3-yl)benzamide,
N-(2-amino-5-(thiophen-2-yl)phenyl)-2-oxo-2,3-dihydrobenzo[d]oxazole-6-carboxamide,
2-(4-((6-chloro-5-fluoro-1H-benzo[d]imidazol-2-ylthio)methyl)benzamido)-4-(thiophen-2-yl)benzoic acid,
4-acetamido-N-(2-amino-5-(thiophen-2-yl)phenyl)-3-hydroxybenzamide,
N1-(2-amino-5-(thiophen-2-yl)phenyl)-N8-(biphenyl-3-yl)octanediamide,
N-(4-aminobiphenyl-3-yl)-4-(morpholinomethyl)benzamide,
N-(4-aminobiphenyl-3-yl)-4-(pyridin-3-yl)benzamide,
N-(2-amino-5-(5-((2-hydroxyethylamino)methyl)thiophen-2-yl)phenyl)-4-methoxybenzamide,
N-(5-(5-((1H-pyrazol-5-ylamino)methyl)thiophen-2-yl)-2-aminophenyl)-4-methoxybenzamide,
N-(2-amino-5-(5-chlorothiophen-2-yl)phenyl)-4-(pyridin-3-yl)benzamide,
(E)-N-(2-amino-5-(thiophen-2-yl)phenyl)-3-(6-(3,4,5-trimethoxyphenyl)pyridin-3-yl)acrylamide,
(E)-3-(2,3'-bipyridin-5-yl)-N-(2-amino-5-(thiophen-2-yl)phenyl)acrylamide,
(E)-N-(2-amino-5-(thiophen-2-yl)phenyl)-3-(6-(3,4-dimethoxyphenyl)pyridin-3-yl)acrylamide,
N-(2-amino-5-(thiophen-2-yl)phenyl)-6-chloronicotinamide,
N-(2-amino-5-(thiophen-2-yl)phenyl)-4-(piperidin-1-ylmethyl)benzamide,
N-(2-amino-5-(thiophen-2-yl)phenyl)-6-morpholinonicotinamide,
N-(2-amino-5-(thiophen-2-yl)phenyl)-4-((3-hydroxypyrrolidin-1-yl)methyl)benzamide,
(R)—N-(2-amino-5-(thiophen-2-yl)phenyl)-4-((3-(dimethylamino)pyrrolidin-1-yl)methyl)benzamide,
(S)—N-(2-amino-5-(thiophen-2-yl)phenyl)-4-(3-(dimethylamino)pyrrolidin-1-yl)benzamide,
N-(2-amino-5-(thiophen-2-yl)phenyl)-6-(4-methylpiperazin-1-yl)nicotinamide,
(Z)—N-(2-amino-5-(5-((hydroxyimino)methyl)thiophen-2-yl)phenyl)-4-(pyridin-3-yl)benzamide,
N-(2-amino-5-(thiophen-2-yl)phenyl)-2-ethoxypyrimidine-5-carboxamide,
N-(4-amino-4'-(methylthio)biphenyl-3-yl)-4-methoxybenzamide,
N-(4-amino-4'-(methylsulfinyl)biphenyl-3-yl)-4-methoxybenzamide,
N-(2-amino-5-(thiophen-2-yl)phenyl)-4-((ethyl(methyl)amino)methyl)benzamide,
N-(2-amino-5-(thiophen-2-yl)phenyl)-4-((4-isopropylpiperazin-1-yl)methyl)benzamide,
N-(2-amino-5-(thiophen-2-yl)phenyl)-4-((4-(2-methoxyethyl)piperazin-1-yl)methyl)benzamide,
N-(2-amino-5-(thiophen-2-yl)phenyl)-4-((4-cyclopentylpiperazin-1-yl)methyl)benzamide, N-(2-amino-5-(thiophen-2-yl)phenyl)-2-morpholinopyrimidine-5-carboxamide,
N-(2-amino-5-(thiophen-2-yl)phenyl)-2-(4-methylpiperazin-1-yl)pyrimidine-5-carboxamide,
(R)—N-(2-amino-5-(thiophen-2-yl)phenyl)-4-((3-hydroxypiperidin-1-yl)methyl)benzamide,
N-(2-amino-5-(pyridin-3-yl)phenyl)-4-(morpholinomethyl)benzamide,
N-(2-amino-5-(thiophen-2-yl)phenyl)-1,3-dimethyl-1H-thieno[2,3-c]pyrazole-5-carboxamide,
N-(2-amino-5-(pyridin-4-yl)phenyl)-4-(morpholinomethyl)benzamide,
(R)—N-(2-amino-5-(pyridin-3-yl)phenyl)-4-((3-(dimethylamino)pyrrolidin-1-yl)methyl)benzamide,
N-(2-amino-5-(thiophen-2-yl)phenyl)-4-(4-(2-methoxyethyl)piperazin-1-yl)benzamide,
N-(2-amino-5-(thiophen-2-yl)phenyl)-4-(2-(dimethylamino)ethylthio)benzamide,
N-(4-amino-4'-hydroxybiphenyl-3-yl)-4-(morpholinomethyl)benzamide,
(R)—N-(4-aminobiphenyl-3-yl)-4-((3-(dimethylamino)pyrrolidin-1-yl)methyl)benzamide,
N-(2-amino-5-(thiophen-2-yl)phenyl)-4-(4-cyclopentylpiperazin-1-yl)benzamide,
N-(2-amino-5-(thiophen-2-yl)phenyl)-4-(4-(pyrrolidin-1-yl)piperidin-1-yl)benzamide,
(R)—N-(4-amino-4'-hydroxybiphenyl-3-yl)-4-((3-(dimethylamino)pyrrolidin-1-yl)methyl)benzamide,
N-(2-amino-5-(thiophen-2-yl)phenyl)-4-((bis(2-methoxyethyl)amino)methyl)benzamide,
N-(2-amino-5-(thiophen-2-yl)phenyl)-4-(4-isopropylpiperazin-1-yl)benzamide,
N-(2-amino-5-(thiophen-2-yl)phenyl)-4-(4-morpholinopiperidin-1-yl)benzamide,
(R)—N-(2-amino-5-(thiophen-2-yl)phenyl)-6-(3-(dimethylamino)pyrrolidin-1-yl)nicotinamide,
N-(2-amino-5-(thiophen-2-yl)phenyl)-6-(2-(pyrrolidin-1-yl)ethyl)nicotinamide,
N-(2-amino-5-(thiophen-2-yl)phenyl)-4-(2-(diethylamino)ethylthio)benzamide,
(S)—N-(2-amino-5-(thiophen-2-yl)phenyl)-4-((2-(methoxymethyl)pyrrolidin-1-yl)methyl)benzamide,
2-(dimethylamino)ethyl 4-(2-amino-5-(thiophen-2-yl)phenylcarbamoyl)benzylcarbamate,
N-(2-amino-5-(thiophen-2-yl)phenyl)-2-(4-morpholinopiperidin-1-yl)pyrimidine-5-carboxamide,
N-(2-amino-5-(thiophen-2-yl)phenyl)-4-((4-morpholinopiperidin-1-yl)methyl)benzamide,
N-(2-amino-5-(thiophen-2-yl)phenyl)-4-(((2-(dimethylamino)ethyl)(methyl)amino)methyl)benzamide,
(E)-N-(2-amino-5-(thiophen-2-yl)phenyl)-3-(6-morpholinopyridin-3-yl)acrylamide,
N-(2-amino-5-(thiophen-2-yl)phenyl)-4-((4-methylpiperazin-1-yl)methyl)benzamide,
N-(2-amino-5-(thiophen-2-yl)phenyl)-4-((diethylamino)methyl)benzamide,
4-((4-(2-(1H-imidazol-1-yl)ethyl)piperazin-1-yl)methyl)-N-(2-amino-5-(thiophen-2-yl)phenyl)benzamide,
N-(2-amino-5-(thiophen-2-yl)phenyl)quinoline-3-carboxamide,
3-(2-amino-5-(thiophen-2-yl)phenylcarbamoyl)phenyl acetate,
N-(2-amino-5-(thiophen-2-yl)phenyl)-3-hydroxybenzamide,
N-(2-amino-5-(thiophen-2-yl)phenyl)-4-(isoindolin-2-ylmethyl)benzamide,
(S)—N-(2-amino-5-(thiophen-2-yl)phenyl)-4-((3-(dimethylamino)pyrrolidin-1-yl)methyl)benzamide,
(S)—N-(2-amino-5-(thiophen-2-yl)phenyl)-4-((3-hydroxypyrrolidin-1-yl)methyl)benzamide,
N-(2-amino-5-(thiophen-2-yl)phenyl)-4-((3-(2-(dimethylamino)ethyl)-3-methylureido)methyl)benzamide,
N-(2-amino-5-(thiophen-3-yl)phenyl)-4-(morpholinomethyl)benzamide,
(R)-4-((3-acetamidopyrrolidin-1-yl)methyl)-N-(2-amino-5-(thiophen-2-yl)phenyl)benzamide
(R)—N-(2-amino-5-(thiophen-2-yl)phenyl)-4-((3-hydroxypyrrolidin-1-yl)methyl)benzamide
(R)—N-(2-amino-5-(thiophen-3-yl)phenyl)-4-((3-(dimethylamino)pyrrolidin-1-yl)methyl)benzamide,
N-(2-amino-5-(thiophen-2-yl)phenyl)-4-((4-(pyridin-4-yl)piperazin-1-yl)methyl)benzamide,
(S)—N-(2-amino-5-(thiophen-2-yl)phenyl)-4-((2-(pyrrolidin-1-ylmethyl)pyrrolidin-1-yl)methyl)benzamide,
N-(2-amino-5-(thiophen-2-yl)phenyl)-5-(morpholinomethyl)furan-2-carboxamide,
(S)-4-((3-acetamidopyrrolidin-1-yl)methyl)-N-(2-amino-5-(thiophen-2-yl)phenyl)benzamide,
(S)—N-(2-amino-5-(thiophen-2-yl)phenyl)-4-(3-(pyridin-3-ylamino)pyrrolidin-1-yl)benzamide,
3-(3-(2-amino-5-(thiophen-2-yl)phenylcarbamoyl)phenyl)propanoic acid,
3-(4-(2-amino-5-(thiophen-2-yl)phenylcarbamoyl)phenyl)propanoic acid,
N-(2-amino-5-(furan-3-yl)phenyl)-4-(morpholinomethyl)benzamide,
N-(4-amino-4'-chlorobiphenyl-3-yl)-4-(morpholinomethyl)benzamide,
(S)—N-(2-amino-5-(thiophen-2-yl)phenyl)-4-((3-(dimethylamino)-2,5-dioxopyrrolidin-1-yl)methyl)benzamide,
N-(2-amino-5-(6-fluoropyridin-3-yl)phenyl)-4-(morpholinomethyl)benzamide,
N-(2-amino-5-(thiophen-2-yl)phenyl)-4-((methyl(pyridin-3-ylmethyl)amino)methyl)benzamide,
N-(2-amino-5-(thiophen-2-yl)phenyl)-4-((4-(pyridin-2-yl)piperazin-1-yl)methyl)benzamide,
N-(2-amino-5-(thiophen-2-yl)phenyl)-4-(pyrrolidin-1-ylmethyl)benzamide,
N-(2-amino-5-(5-cyanothiophen-2-yl)phenyl)-4-(morpholinomethyl)benzamide,
(S)—N-(2-amino-5-(thiophen-2-yl)phenyl)-4-((3-(pyridin-3-ylamino)pyrrolidin-1-yl)methyl)benzamide,
methyl 3-(4-(2-amino-5-(thiophen-2-yl)phenylcarbamoyl)phenyl)propanoate,
N-(2-amino-5-(thiophen-2-yl)phenyl)-6-(1H-pyrazol-1-yl)nicotinamide,
N-(2-amino-5-(benzo[d][1,3]dioxol-5-yl)phenyl)-4-(morpholinomethyl)benzamide,
N-(2-amino-5-(5-methylthiophen-2-yl)phenyl)-4-(morpholinomethyl)benzamide,
pyridin-3-ylmethyl 6-(2-amino-5-(thiophen-2-yl)phenylcarbamoyl)-3,4-dihydroquinoline-1(2H)-carboxylate,
N-(4-amino-3'-(trifluoromethoxy)biphenyl-3-yl)-4-(morpholinomethyl)benzamide,
N-(2-amino-5-(thiophen-2-yl)phenyl)-6-bromonicotinamide,
N-(2-amino-5-(thiophen-2-yl)phenyl)-6-(4-morpholinopiperidin-1-yl)nicotinamide,
N-(2-amino-5-(thiophen-2-yl)phenyl)-4-((4-benzylpiperazin-1-yl)methyl)benzamide,
N-(2-amino-5-(thiophen-2-yl)phenyl)-4-(((2R,5R)-2,5-dimethylpyrrolidin-1-yl)methyl)benzamide, (E)-3-(4-(2-amino-5-(thiophen-2-yl)phenylcarbamoyl)phenyl)acrylic acid,
(E)-N-(2-amino-5-(thiophen-2-yl)phenyl)-4-(3-(hydroxyamino)-3-oxoprop-1-enyl)benzamide,
N-(2-amino-5-(5-chlorothiophen-2-yl)phenyl)-4-(morpholinomethyl)benzamide,
N-(2-amino-5-(3-hydroxycyclopent-1-enyl)phenyl)-4-(morpholinomethyl)benzamide,
4-(2-amino-5-(thiophen-2-yl)phenylcarbamoyl)benzoic acid,
N-(2-amino-5-(5-chlorothiophen-2-yl)phenyl)-4-(4-methylpiperazin-1-yl)benzamide,
N-(2-amino-5-(5-chlorothiophen-2-yl)phenyl)-4-(3-morpholinopyrrolidin-1-yl)benzamide,
methyl 4-(2-amino-5-(thiophen-2-yl)phenylcarbamoyl)benzoate,
N1-(2-amino-5-(thiophen-2-yl)phenyl)-N4-hydroxyterephthalamide,
4-(2-amino-5-(3-hydroxycyclopent-1-enyl)phenylcarbamoyl)phenyl acetate,
N-(2-amino-5-(3-hydroxycyclopent-1-enyl)phenyl)-4-hydroxybenzamide,
N-(2-amino-5-(thiophen-2-yl)phenyl)-5-bromo-6-oxo-1,6-dihydropyridine-3-carboxamide,
N-(2-amino-5-(thiophen-2-yl)phenyl)-6-cyanonicotinamide,
2-(dimethylamino)ethyl 4-(2-amino-5-(thiophen-3-yl)phenylcarbamoyl)phenylcarbamate,
2-(dimethylamino)ethyl 4-(4-amino-4'-chloro-3'-fluorobiphenyl-3-ylcarbamoyl)phenylcarbamate,
2-(dimethylamino)ethyl 4-(4-amino-3'-fluorobiphenyl-3-ylcarbamoyl)phenylcarbamate,
4-(2-amino-5-(thiophen-3-yl)phenylcarbamoyl)phenyl acetate,
N-(2-amino-5-(thiophen-3-yl)phenyl)-4-hydroxybenzamide,
N-(2-amino-5-(thiophen-3-yl)phenyl)acetamide,
N-(2-amino-5-(thiophen-2-yl)phenyl)-6-carbamimidoylnicotinamide,
N-(2-amino-5-(thiophen-2-yl)phenyl)-6-(thiophen-2-yl)nicotinamide,
N-(2-amino-5-(thiophen-2-yl)phenyl)-4-(4-(pyridin-4-yl)piperazin-1-yl)benzamide,
2-(dimethylamino)ethyl 4-(2-amino-5-(6-chloropyridin-3-yl)phenylcarbamoyl)phenylcarbamate,
N-(2-amino-5-(6-chloropyridin-3-yl)phenyl)-4-hydroxybenzamide,
2-(dimethylamino)ethyl 4-(2-amino-5-(pyridin-3-yl)phenylcarbamoyl)phenylcarbamate,
N-(2-amino-5-(thiophen-2-yl)phenyl)-3-fluoro-4-hydroxybenzamide,
N-(2-amino-5-(6-fluoropyridin-3-yl)phenyl)-4-hydroxybenzamide,
2-(dimethylamino)ethyl 4-(2-amino-5-(6-fluoropyridin-3-yl)phenylcarbamoyl)phenylcarbamate,
N-(2-amino-5-(pyridin-3-yl)phenyl)-4-hydroxybenzamide,
4-(2-amino-5-(6-fluoropyridin-3-yl)phenylcarbamoyl)phenyl acetate,
N-(2-amino-5-(5-chlorothiophen-2-yl)phenyl)-4-(4-(pyridin-4-yl)piperazin-1-yl)benzamide,
pyridin-3-ylmethyl 3-(2-amino-5-(thiophen-2-yl)phenylcarbamoyl)phenylcarbamate,
2-(dimethylamino)ethyl 4-(4-amino-3',4'-dichlorobiphenyl-3-ylcarbamoyl)phenylcarbamate,
2-morpholinoethyl 4-(2-amino-5-(thiophen-2-yl)phenylcarbamoyl)phenylcarbamate,
2-(pyrrolidin-1-yl)ethyl 4-(2-amino-5-(thiophen-2-yl)phenylcarbamoyl)phenylcarbamate,
(S)-(1-methylpyrrolidin-2-yl)methyl 4-(2-amino-5-(thiophen-2-yl)phenylcarbamoyl)phenylcarbamate,
(2E,4Z)—N-(2-amino-5-(thiophen-2-yl)phenyl)-4-(1-(benzo[d][1,3]dioxol-5-ylmethyl)pyrrolidin-3-ylidene)but-2-enamide,
(E)-N-(2-amino-5-(thiophen-2-yl)phenyl)-3-(4-(morpholinomethyl)phenyl)acrylamide,
4-(4-amino-3',4'-dichlorobiphenyl-3-ylcarbamoyl)phenyl acetate,
2-(dimethylamino)ethyl 4-(4-amino-3',4'-difluorobiphenyl-3-ylcarbamoyl)phenylcarbamate,
N-(2-amino-5-(thiophen-2-yl)phenyl)-4-(1-(benzo[d][1,3]dioxol-5-ylmethyl)pyrrolidin-3-yl)butanamide,
4-(4-amino-3',4'-difluorobiphenyl-3-ylcarbamoyl)phenyl acetate,
N-(2-amino-5-(thiophen-2-yl)phenyl)-4-(4-(pyridin-3-yl)thiazol-2-ylamino)benzamide,
N-(4-amino-3',4'-difluorobiphenyl-3-yl)-4-hydroxybenzamide,
2-(dimethylamino)ethyl 4-(4-aminobiphenyl-3-ylcarbamoyl)phenylcarbamate,
N-(2-amino-5-(thiophen-2-yl)phenyl)-5-(3-(dimethylamino)prop-1-ynyl)nicotinamide,
N-(2-amino-5-(thiophen-2-yl)phenyl)-4-(pyrrolidin-1-yl)benzamide,
(E)-N-(2-amino-5-(thiophen-2-yl)phenyl)-3-(4-(hydroxymethyl)phenyl)acrylamide,
(S)—N-(4-aminobiphenyl-3-yl)-4-(3-aminopyrrolidin-1-yl)benzamide,
N-(4-aminobiphenyl-3-yl)-4-hydroxybenzamide,
2-(methyl(pyridin-2-yl)amino)ethyl 4-(2-amino-5-(thiophen-2-yl)phenylcarbamoyl)phenylcarbamate,
N-(2-amino-5-(thiophen-2-yl)phenyl)-5-((4-morpholinopiperidin-1-yl)methyl)furan-2-carboxamide,
2-(4-methylpiperazin-1-yl)ethyl 4-(2-amino-5-(thiophen-2-yl)phenylcarbamoyl)phenylcarbamate,
2-(dimethylamino)ethyl 4-(2-hydroxy-5-(thiophen-2-yl)phenylcarbamoyl)phenylcarbamate,
4-hydroxy-N-(2-hydroxy-5-(thiophen-2-yl)phenyl)benzamide,
N-(4-aminobiphenyl-3-yl)-1-(4-nitrophenylsulfonyl)piperidine-4-carboxamide,
N-(2-amino-5-(thiophen-2-yl)phenyl)-4-(piperazin-1-ylmethyl)benzamide,
N-(2-amino-5-(thiophen-2-yl)phenyl)-4-(benzo[d][1,3]dioxol-5-ylmethyl)piperazine-1-carboxamide,
(S)—N-(2-amino-5-(thiophen-2-yl)phenyl)-4-(3-aminopyrrolidin-1-yl)benzamide,
N-(2-amino-5-(thiophen-2-yl)phenyl)-4-(piperidin-1-yl)benzamide,
N-(2-hydroxy-5-(thiophen-3-yl)phenyl)-4-(morpholinomethyl)benzamide,
3-(dimethylamino)propyl 4-(2-amino-5-(thiophen-2-yl)phenylcarbamoyl)phenylcarbamate,
2-morpholinoethyl 4-(4-aminobiphenyl-3-ylcarbamoyl)phenylcarbamate,
N-(2-amino-5-(thiophen-2-yl)phenyl)-4-(piperazin-1-yl)benzamide,
2-(dimethylamino)ethyl 4-(2-hydroxy-5-(thiophen-3-yl)phenylcarbamoyl)phenylcarbamate,
2-(dimethylamino)ethyl 4-(2-amino-5-(5-chlorothiophen-2-yl)phenylcarbamoyl)phenylcarbamate,
2-(pyrrolidin-1-yl)ethyl 3-(2-amino-5-(thiophen-2-yl)phenylcarbamoyl)phenylcarbamate, (E)-3-(4-(((2-(1H-indol-3-yl)ethyl)(2-hydroxyethyl)amino)methyl)phenyl)-N-(2-amino-5-(thiophen-2-yl)phenyl)acrylamide,
1-methylpiperidin-4-yl 4-(2-amino-5-(thiophen-2-yl)phenylcarbamoyl)phenylcarbamate,
(R)-1-methylpyrrolidin-3-yl 4-(2-amino-5-(thiophen-2-yl)phenylcarbamoyl)phenylcarbamate,
2-(dimethylamino)ethyl 4-(2-amino-5-(6-methoxypyridin-3-yl)phenylcarbamoyl)phenylcarbamate,
2-(dimethylamino)ethyl 4-(2-amino-5-(pyridin-4-yl)phenylcarbamoyl)phenylcarbamate,
2-(dimethylamino)ethyl 4-(2-amino-5-(2-methoxypyridin-3-yl)phenylcarbamoyl)phenylcarbamate,
2-(dimethylamino)ethyl 4-(4-amino-3'-(trifluoromethoxy)biphenyl-3-ylcarbamoyl)phenylcarbamate,
N-(4-(4-aminobiphenyl-3-ylcarbamoyl)benzyl)-2-(methylsulfonamido)benzamide,
N-(2-amino-5-(thiophen-2-yl)phenyl)-4-(4-(pyridin-3-ylmethyl)piperazin-1-yl)benzamide,
2-(dimethylamino)ethyl 4-(4-amino-4'-(trifluoromethoxy)biphenyl-3-ylcarbamoyl)phenylcarbamate,
2-(dimethylamino)ethyl 4-(4-amino-3'-fluoro-4'-methoxybiphenyl-3-ylcarbamoyl)phenylcarbamate,
2-(dimethylamino)ethyl 4-(4-amino-4'-fluorobiphenyl-3-ylcarbamoyl)phenylcarbamate,
N-(2-amino-5-(thiophen-2-yl)phenyl)-4-(4-(pyridin-4-ylmethyl)piperazin-1-yl)benzamide,
2-(dimethylamino)ethyl 4-(4-amino-4'-chlorobiphenyl-3-ylcarbamoyl)phenylcarbamate,
2-(dimethylamino)ethyl 4-(2-amino-5-(thiophen-2-yl)phenylcarbamoyl)piperidine-1-carboxylate,
N-(2-amino-5-(pyridin-3-yl)phenyl)-1-(2,6-difluorobenzyl)-1H-1,2,3-triazole-4-carboxamide,
2-(dimethylamino)ethyl (1r,4r)-4-(2-amino-5-(thiophen-2-yl)phenylcarbamoyl)cyclohexylcarbamate,
2-(dimethylamino)ethyl 4-(4-amino-3'-fluoro-4'-hydroxybiphenyl-3-ylcarbamoyl)phenylcarbamate,
N-(2-amino-5-(thiophen-2-yl)phenyl)-1-(2,6-difluorobenzyl)-1H-1,2,3-triazole-4-carboxamide,
2-(dimethylamino)ethyl 4-(4-amino-2',4'-difluorobiphenyl-3-ylcarbamoyl)phenylcarbamate,
2-(dimethylamino)ethyl 4-(4-amino-4'-(trifluoromethyl)biphenyl-3-ylcarbamoyl)phenylcarbamate,
2-(dimethylamino)ethyl 4-(4-amino-2'-fluorobiphenyl-3-ylcarbamoyl)phenylcarbamate,
2-(dimethylamino)ethyl 4-(4-amino-4'-hydroxybiphenyl-3-ylcarbamoyl)phenylcarbamate,
2-(dimethylamino)ethyl 4-(4-amino-3',4',5'-trifluorobiphenyl-3-ylcarbamoyl)phenylcarbamate,
2-(dimethylamino)ethyl 4-(4-amino-4'-(dimethylamino)biphenyl-3-ylcarbamoyl)phenylcarbamate,
2-(dimethylamino)ethyl 4-(4-amino-4'-(methylthio)biphenyl-3-ylcarbamoyl)phenylcarbamate,
2-(dimethylamino)ethyl 4-(4-amino-4'-cyanobiphenyl-3-ylcarbamoyl)phenylcarbamate,
2-(dimethylamino)ethyl 5-(2-amino-5-(thiophen-2-yl)phenylcarbamoyl)thiophen-2-ylcarbamate,
2-(dimethylamino)ethyl 4-(4-amino-2'-fluoro-4'-methoxybiphenyl-3-ylcarbamoyl)phenylcarbamate,
2-(dimethylamino)ethyl 4-(4-amino-3'-fluoro-4'-methylbiphenyl-3-ylcarbamoyl)phenylcarbamate,
2-(dimethylamino)ethyl 4-(2-amino-5-(thiazol-2-yl)phenylcarbamoyl)phenylcarbamate,
N-(2-amino-5-(thiazol-2-yl)phenyl)-4-(4-methylpiperazin-1-yl)benzamide,
2-(dimethylamino)ethyl 4-(4-amino-2',4',5'-trifluorobiphenyl-3-ylcarbamoyl)phenylcarbamate,
2-(dimethylamino)ethyl 4-(4-amino-4'-(methylsulfinyl)biphenyl-3-ylcarbamoyl)phenylcarbamate,
2-(dimethylamino)ethyl 4-(4-amino-2'-fluoro-4'-(trifluoromethyl)biphenyl-3-ylcarbamoyl)phenylcarbamate,
2-(dimethylamino)ethyl 4-(4-amino-4'-(methylsulfonyl)biphenyl-3-ylcarbamoyl)phenylcarbamate,
2-(dimethylamino)ethyl 4-(4,4'-diaminobiphenyl-3-ylcarbamoyl)phenylcarbamate,
N-(2-amino-5-(thiophen-2-yl)phenyl)-1-(benzo[d][1,3]dioxol-5-ylmethyl)-1H-1,2,3-triazole-4-carboxamide,
2-(dimethylamino)ethyl 4-(4-amino-4'-ethoxybiphenyl-3-ylcarbamoyl)phenylcarbamate,
2-(dimethylamino)ethyl 4-(2-amino-5-(5-(methylthio)thiophen-2-yl)phenylcarbamoyl)phenylcarbamate,
4-methoxy-N-(2-(sulfamoylamino)-5-(thiophen-2-yl)phenyl)benzamide,
(S)-4-(3-acetamidopyrrolidin-1-yl)-N-(4-aminobiphenyl-3-yl)benzamide,
(S)-4-(3-acetamidopyrrolidin-1-yl)-N-(4-amino-4'-fluorobiphenyl-3-yl)benzamide,
2-(dimethylamino)ethyl 4-(4-amino-4'-cyano-3'-fluorobiphenyl-3-ylcarbamoyl)phenylcarbamate,
N-(2-amino-5-(thiophen-2-yl)phenyl)-3-(4-(morpholinomethyl)phenyl)propanamide,
(S)—N-(4-amino-4'-fluorobiphenyl-3-yl)-4-(3-aminopyrrolidin-1-yl)benzamide,
(S)—N-(4-aminobiphenyl-3-yl)-4-(3-(bis(dimethylamino)methyleneamino)pyrrolidin-1-yl)benzamide,
2-(dimethylamino)ethyl 4-(2-amino-5-(2-aminopyrimidin-5-yl)phenylcarbamoyl)phenylcarbamate,
(S)—N-(4-amino-4'-fluorobiphenyl-3-yl)-4-(3-(bis(dimethylamino)methyleneamino)pyrrolidin-1-yl)benzamide,
N-(2-amino-5-(pyridin-4-yl)phenyl)-3-methoxybenzamide,
N-(2-amino-5-(pyridin-4-yl)phenyl)-4-(dimethylamino)benzamide,
N-(2-amino-5-(pyridin-4-yl)phenyl)benzofuran-2-carboxamide,
N-(4-amino-3',4'-difluorobiphenyl-3-yl)-1-benzylpiperidine-4-carboxamide,
2-(dimethylamino)ethyl 4-(3-fluoro-2-hydroxy-5-(thiophen-2-yl)phenylcarbamoyl)phenylcarbamate,
N-(4-amino-3',4'-difluorobiphenyl-3-yl)-4-(1,3-dioxoisoindolin-2-yl)benzamide,
N-(2-amino-5-(pyridin-4-yl)phenyl)benzo[d][1,3]dioxole-5-carboxamide,
N-(2-amino-5-(pyridin-4-yl)phenyl)-4,6-dimethoxybenzofuran-2-carboxamide,
N-(2-amino-5-(pyridin-4-yl)phenyl)-6-(2-morpholinoethoxy)benzofuran-2-carboxamide,
N-(4-amino-3',4'-difluorobiphenyl-3-yl)-5-(morpholinomethyl)furan-2-carboxamide,
N-(2-amino-5-(pyridin-4-yl)phenyl)-4-((3,4-dimethoxyphenylamino)methyl)benzamide,
N-(2-amino-5-(pyridin-4-yl)phenyl)-6-(2-(dimethylamino)ethoxy)benzofuran-2-carboxamide,
N-(4-aminobiphenyl-3-yl)-6-(2-morpholinoethoxy)benzofuran-2-carboxamide,
(S)-benzyl 1-(4-(2-amino-5-(pyridin-4-yl)phenylcarbamoyl)phenyl)pyrrolidin-3-ylcarbamate,
(S)-4-(3-acetamidopyrrolidin-1-yl)-N-(2-amino-5-(pyridin-4-yl)phenyl)benzamide,
(S)—N-(2-amino-5-(pyridin-4-yl)phenyl)-4-(3-aminopyrrolidin-1-yl)benzamide,
N-(4-aminobiphenyl-3-yl)-5-methyl-4-(morpholinomethyl)furan-2-carboxamide,
N-(4-aminobiphenyl-3-yl)-5-(pyridin-2-yl)thiophene-2-carboxamide, N-(4-aminobiphenyl-3-yl)-3-(pyridin-3-yl)benzamide,
N-(4-amino-4'-fluorobiphenyl-3-yl)-6-(2-morpholinoethoxy)benzofuran-2-carboxamide,
N-(2-amino-5-(pyridin-4-yl)phenyl)-3-fluoro-4-methoxybenzamide,
N-(4-aminobiphenyl-3-yl)-1-benzylpiperidine-4-carboxamide,
(S)—N-(4-aminobiphenyl-3-yl)-4-(3-(methylsulfonamido)pyrrolidin-1-yl)benzamide,
N-(4-aminobiphenyl-3-yl)-4-(4-methylpiperazin-1-yl)benzamide,
N-(4-aminobiphenyl-3-yl)-4-(pyrrolidin-1-yl)benzamide,
(R)—N-(4-aminobiphenyl-3-yl)-4-(3-aminopyrrolidin-1-yl)benzamide,
(S)—N-(4-aminobiphenyl-3-yl)-4-(3-(2,2,2-trifluoroacetamido)pyrrolidin-1-yl)benzamide,
N-(4-aminobiphenyl-3-yl)-4-(4-methylpiperazin-1-ylsulfonyl)benzamide,
N-(4-amino-3',4'-difluorobiphenyl-3-yl)-6-(2-morpholinoethoxy)benzofuran-2-carboxamide,
N-(2-amino-5-(pyridin-4-yl)phenyl)-6-(2-(piperidin-1-yl)ethoxy)benzofuran-2-carboxamide,
N-(4-aminobiphenyl-3-yl)-1-benzoylpiperidine-4-carboxamide,
(S)—N-(4-aminobiphenyl-3-yl)-4-(3-(dimethylamino)pyrrolidin-1-yl)benzamide,
N-(2-amino-5-(thiophen-2-yl)phenyl)-4-benzylpiperazine-1-carboxamide,
(R)—N-(4-aminobiphenyl-3-yl)-4-(3-hydroxypyrrolidin-1-yl)benzamide,
(S)-methyl 1-(4-(4-aminobiphenyl-3-ylcarbamoyl)phenyl)pyrrolidin-3-ylcarbamate,
N-(2-amino-5-(pyridin-4-yl)phenyl)-5,6-dimethoxybenzofuran-2-carboxamide,
N-(4-aminobiphenyl-3-yl)-5,6-dimethoxybenzofuran-2-carboxamide,
N-(4-aminobiphenyl-3-yl)-4-(4-ethylpiperazin-1-yl)benzamide,
N-(4-aminobiphenyl-3-yl)-4-(4-aminopiperidin-1-yl)benzamide,
N-(4-aminobiphenyl-3-yl)-4-(3-oxopiperazin-1-yl)benzamide,
(S)—N-(4-aminobiphenyl-3-yl)-4-(3-hydroxypyrrolidin-1-yl)benzamide,
(S)-benzyl 1-(4-(4-aminobiphenyl-3-ylcarbamoyl)phenyl)pyrrolidin-3-yl(ethyl)carbamate,
(S)—N-(4-aminobiphenyl-3-yl)-4-(3-(ethylamino)pyrrolidin-1-yl)benzamide,
N-(4-aminobiphenyl-3-yl)-4-(1H-imidazol-1-yl)benzamide,
N-(4-amino-4'-fluorobiphenyl-3-yl)-5-(pyridin-2-yl)thiophene-2-carboxamide,
(R)—N-(4-amino-4'-fluorobiphenyl-3-yl)-4-(3-aminopyrrolidin-1-yl)benzamide,
1-(4-(4-aminobiphenyl-3-ylcarbamoyl)phenyl)piperidine-4-carboxamide,
(S)—N-(4-aminobiphenyl-3-yl)-4-(3-fluoropyrrolidin-1-yl)benzamide,
N-(4-aminobiphenyl-3-yl)-4-(3,3-difluoropyrrolidin-1-yl)benzamide,
N-(4-amino-4'-fluorobiphenyl-3-yl)-5-phenylfuran-2-carboxamide,
(R)—N-(4-amino-4'-fluorobiphenyl-3-yl)-4-(3-(2-methoxyacetamido)pyrrolidin-1-yl)benzamide,
(R)—N-(4-amino-4'-fluorobiphenyl-3-yl)-4-(3-(methylsulfonamido)pyrrolidin-1-yl)benzamide,
(S)—N-(4-aminobiphenyl-3-yl)-4-(3-(2-methoxyacetamido)pyrrolidin-1-yl)benzamide,
(S)—N-(4-aminobiphenyl-3-yl)-4-(3-(2-(dimethylamino)acetamido)pyrrolidin-1-yl)benzamide,
(R)-4-(3-acetamidopyrrolidin-1-yl)-N-(4-amino-4'-fluorobiphenyl-3-yl)benzamide,
(R)-methyl 1-(4-(4-amino-4'-fluorobiphenyl-3-ylcarbamoyl)phenyl)pyrrolidin-3-ylcarbamate,
N-(4-aminobiphenyl-3-yl)-4-(piperazin-1-yl)benzamide,
N-(2-amino-5-(pyridin-4-yl)phenyl)quinoxaline-6-carboxamide,
N-(4-aminobiphenyl-3-yl)quinoxaline-6-carboxamide,
pyridin-3-ylmethyl 4-(2-amino-5-(pyridin-4-yl)phenylcarbamoyl)benzylcarbamate,
N-(4-amino-4'-fluorobiphenyl-3-yl)-1-benzyl-6-oxo-1,6-dihydropyridine-3-carboxamide,
N-(2-amino-5-(pyridin-4-yl)phenyl)-4-((4-(pyridin-3-yl)pyrimidin-2-ylamino)methyl)benzamide,
(Z)—N-(2-amino-5-(pyridin-4-yl)phenyl)-4-(dibenzo[b,f][1,4]oxazepin-11-yl)benzamide,
(E)-N-(2-amino-5-(pyridin-4-yl)phenyl)-11-(4-methylpiperazin-1-yl)dibenzo[b,f][1,4]oxazepine-8-carboxamide,
(E)-N-(4-aminobiphenyl-3-yl)-11-(4-methylpiperazin-1-yl)dibenzo[b,f][1,4]oxazepine-8-carboxamide,
(S)—N-(4-aminobiphenyl-3-yl)-4-(3-(2-hydroxyethylamino)pyrrolidin-1-yl)benzamide,
N-(4-aminobiphenyl-3-yl)-5-methoxypicolinamide,
N-(4-aminobiphenyl-3-yl)-5-(morpholinomethyl)thiophene-2-carboxamide,
(S)—N-(4-aminobiphenyl-3-yl)-4-(3-(2,2,2-trifluoroethylamino)pyrrolidin-1-yl)benzamide,
(R)—N-(4-aminobiphenyl-3-yl)-4-(3-(dimethylamino)pyrrolidin-1-yl)benzamide,
(R)—N-(4-aminobiphenyl-3-yl)-4-(3-(ethylamino)pyrrolidin-1-yl)benzamide,
N-(4-aminobiphenyl-3-yl)-4-(hydroxymethyl)benzamide,
(R)—N-(4-aminobiphenyl-3-yl)-4-(3-methoxypyrrolidin-1-yl)benzamide,
N-(4-amino-4'-fluorobiphenyl-3-yl)-5,6-dimethoxybenzofuran-2-carboxamide,
(S)-methyl 8-(1-(4-(2-amino-5-(thiophen-2-yl)phenylcarbamoyl)phenyl)pyrrolidin-3-ylamino)-8-oxooctanoate,
N-(4-aminobiphenyl-3-yl)-6-(piperidin-4-yloxy)benzofuran-2-carboxamide,
4-(4-amino-3-(4-methoxybenzamido)phenyl)pyridine 1-oxide,
N-(4-aminobiphenyl-3-yl)-2,3,4,9-tetrahydro-1H-carbazole-6-carboxamide,
N-(4-aminobiphenyl-3-yl)-5,6-dimethoxybenzo[b]thiophene-2-carboxamide,
N-(4-amino-4'-fluorobiphenyl-3-yl)-6-(piperidin-4-yloxy)benzofuran-2-carboxamide,
N-(4-aminobiphenyl-3-yl)-4-(3-hydroxyazetidin-1-yl)benzamide,
N-(4-aminobiphenyl-3-yl)-4-(2,3-dihydroxypropylamino)benzamide,
N-(4-aminobiphenyl-3-yl)-5-(2-morpholinoethoxy)benzofuran-2-carboxamide,
N-(4-amino-4'-fluorobiphenyl-3-yl)-5-(2-morpholinoethoxy)benzofuran-2-carboxamide,
N-(4-aminobiphenyl-3-yl)-5-(2-(piperidin-1-yl)ethoxy)benzofuran-2-carboxamide,
N-(4-aminobiphenyl-3-yl)imidazo[1,2-a]pyridine-2-carboxamide,
N-(4-amino-4'-fluorobiphenyl-3-yl)-4-(2,3-dihydroxypropylamino)benzamide,
N-(4-amino-4'-fluorobiphenyl-3-yl)-4-(3-hydroxyazetidin-1-yl)benzamide, N-(4-amino-4'-fluorobiphenyl-3-yl)-5-(2-(piperidin-1-yl)ethoxy)benzofuran-2-carboxamide,
(S)—N-(4-amino-4'-fluorobiphenyl-3-yl)-4-(3-hydroxypyrrolidin-1-yl)benzamide,
N-(2-amino-5-(pyridin-4-yl)phenyl)imidazo[1,2-a]pyridine-2-carboxamide,
N-(4-aminobiphenyl-3-yl)imidazo[2,1-b]thiazole-6-carboxamide,
N-(2-amino-5-(pyridin-2-yl)phenyl)-4-methoxybenzamide,
2-(dimethylamino)ethyl 4-(2-amino-5-(pyridin-2-yl)phenylcarbamoyl)phenylcarbamate,
N-(2-amino-5-(pyridin-2-yl)phenyl)-4-(morpholinomethyl)benzamide,
N-(2-amino-5-(pyridin-4-yl)phenyl)imidazo[2,1-b]thiazole-6-carboxamide,
N-(2-amino-5-(pyridin-4-yl)phenyl)-2-((1S,4S)-5-(3-(trifluoromethyl)phenyl)-2,5-diazabicyclo[2.2.1]heptan-2-yl)pyrimidine-5-carboxamide,
(S)—N-(2-amino-5-(pyridin-2-yl)phenyl)-4-(3-aminopyrrolidin-1-yl)benzamide,
N-(2-amino-5-(pyridin-2-yl)phenyl)-4-(4-methylpiperazin-1-yl)benzamide,
N-(4-aminobiphenyl-3-yl)-7-methoxy-5-(morpholinomethyl)benzofuran-2-carboxamide,
N-(2-amino-5-(pyridin-2-yl)phenyl)-4-(4-aminopiperidin-1-yl)benzamide,
(S)—N-(2-amino-5-(pyridin-2-yl)phenyl)-4-(3-hydroxypyrrolidin-1-yl)benzamide,
N-(4-aminobiphenyl-3-yl)pyrazolo[1,5-a]pyridine-2-carboxamide,
N-(4-amino-4'-fluorobiphenyl-3-yl)-7-methoxy-5-(morpholinomethyl)benzofuran-2-carboxamide and
N-(4-aminobiphenyl-3-yl)-5-(4-cyanophenyl)benzofuran-2-carboxamide.

In the second aspect, the invention provides a composition comprising a compound according to—the present invention together with a pharmaceutically acceptable excipient.

The third aspect of the invention provides a method of inhibiting histone deacetylase, the method comprising contacting the histone deacetylase with a compound according to the present invention, or with a composition according to the present invention. Inhibition of the histone deacetylase can be in a cell or a multicellular organism. If in a multicellular organism, the method according to this aspect of the invention comprises administering to the organism a compound according—to the present invention, or a composition according to the present invention. Preferably the organism is a mammal, more preferably a human.

The data presented herein demonstrate the anti-tumor effects of the HDAC inhibitors of the invention. Recent publications reporting on HDAC inhibitor human clinical trials suggest that these inhibitors can effectively treat human solid tumors or cancer (lung, colon, prostrate, stomach, breast, leukemia), including complete remissions of transformed lymphoma (SAHA, ASCO Abstract No. 2321, 2003) and peripheral T-cell lymphoma (depsipeptide/FR901228 ASCO Abstract No. 88, 2002). Together with the data presented herein demonstrating surprising efficacy at inhibiting HDAC-1 and tumor growth inhibition in vivo, these data lead one to reasonably expect that the -inhibitors of the invention are useful not only for inhibition of HDAC, but as therapeutic agents for the treatment of cancer as well.

All of the compounds in this application were named using Chemdraw Ultra version 9 or 10, which is available through Cambridgesoft.co, 100 Cambridge Park Drive, Cambridge, Mass. 02140.

We have unexpectedly found that when HDAC inhibitors including within them the benzamide moiety:

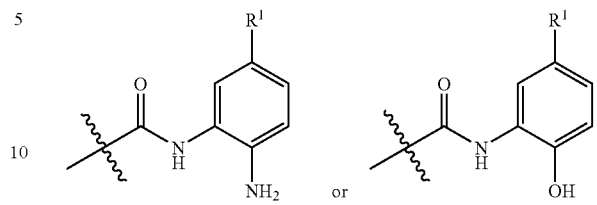

are substituted on the aniline or phenol ring at the 5-position (para to the —NH$_2$ or —OH group) with a substantially planar ring or ring system (aryl or heteroaryl), the compound's HDAC inhibitory activity (as measured by the human HDAC-1 inhibition assay described below) increases by from 3 to 10 times or more compared to similar compounds in which the aniline or phenol ring is unsubstituted or substituted with a smaller, non-planar moiety, or if the planar moiety is at other than the 5-position of the aninlinyl or phenol ring. Additionally, we have found that the planar moiety itself can be substituted. Accordingly, R$^1$ in the compounds of the invention is a mono-, bi-, or tri-cyclic aryl or heteroaryl moiety, which moiety is optionally substituted. In some preferred embodiments R$^1$ is not further substituted. In other preferred embodiments, R$^1$ is substituted with a moiety of from 1-5 atoms, e.g., methyl, hydroxymethyl, halomethyl, halo, hydroxy, amino, etc. In other embodiments, R$^1$ is substituted with a larger moiety, e.g., from 6-25 atoms.

This is surprising in view of T. Suzuki et. al., *J. Med. Chem.*, 1999, 42, 3001-3003, which teaches that the substitution pattern on the aniline ring of the benzamide fragment of known HDACs (wherein the amino group is ortho to the amide nitrogen) is highly sensitive to substitutions. Substituents such as Me and OMe ortho- or meta-relative to the amino group are detrimental to HDAC inhibitory activity, causing complete loss of HDAC potency. The same type of substituents in the para-position relative to the amino group did not cause significant drop of potency which allowed assuming that only small substituents such as Me, MeO, F, Cl might be tolerated.

Furthermore, we have surprisingly found that the HDAC inhibitory activity of such compounds (i.e., compounds comprising the chemical moiety

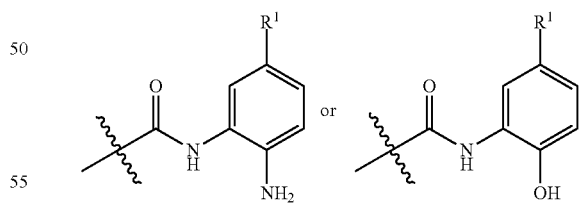

and having a substantially planar ring or ring system at the 5-position of the aniline ring) is substantially independent of the identity of the chemical moiety bound to the carbonyl of this chemical moiety.

The following are representative examples of the compounds according to the embodiments described above.

Pharmaceutical Compositions

In a second aspect, the invention provides pharmaceutical compositions comprising an inhibitor of histone deacetylase according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain preferred embodiments, compounds of the invention are administered intravenously in a hospital setting. In certain other preferred embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salts refers to salts that retain the desired biological activity of the above-identified compounds and exhibit minimal or no undesired toxicological effects. Examples of such salts include, but are not limited to acid addition salts formed with inorganic acids (for Example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate). As used herein, the term "salt" is also meant to encompass complexes, such as with an alkaline metal or an alkaline earth metal.

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

Inhibition of Histone Deacetylase

In a third aspect, the invention provides a method of inhibiting histone deacetylase in a cell, comprising contacting a cell in which inhibition of histone deacetylase is desired with an inhibitor of histone deacetylase according to the invention. Because compounds of the invention inhibit histone deacetylase, they are useful research tools for in vitro study histone deacetylases and their role in biological processes. In addition, the compounds of the invention selectively inhibit certain isoforms of HDAC.

Measurement of the enzymatic activity of a histone deacetylase can be achieved using known methodologies. For Example, Yoshida et al., J. Biol. Chem., 265: 17174-17179 (1990), describes the assessment of histone deacetylase enzymatic activity by the detection of acetylated histones in trichostatin A treated cells. Taunton et al., Science, 272: 408-411 (1996), similarly describes methods to measure histone deacetylase enzymatic activity using endogenous and recombinant HDAC-1.

In some preferred embodiments, the histone deacetylase inhibitor interacts with and reduces the activity of all histone deacetylases in the cell. In some other preferred embodiments according to this aspect of the invention, the histone deacetylase inhibitor interacts with and reduces the activity of fewer than all histone deacetylases in the cell. In certain preferred embodiments, the inhibitor interacts with and reduces the activity of one histone deacetylase (e.g., HDAC-1), but does not interact with or reduce the activities of other histone deacetylases (e.g., HDAC-2, HDAC-3, HDAC-4, HDAC-5, HDAC-6, HDAC-7, and HDAC-8). As discussed below, certain particularly preferred histone deacetylase inhibitors are those that interact with, and reduce the enzymatic activity of, a histone deacetylase that is involved in tumorigenesis. Certain other preferred histone deacetylase inhibitors interact with and reduce the enzymatic activity of a fungal histone deacetylase.

Preferably, the method according to the third aspect of the invention causes an inhibition of cell proliferation of the contacted cells. The phrase "inhibiting cell proliferation" is used to denote an ability of an inhibitor of histone deacetylase to retard the growth of cells contacted with the inhibitor as compared to cells not contacted. An assessment of cell proliferation can be made by counting contacted and non-contacted cells using a Coulter Cell Counter (Coulter, Miami, Fla.) or a hemacytometer. Where the cells are in a solid growth (e.g., a solid tumor or organ), such an assessment of cell proliferation can be made by measuring the growth with calipers and comparing the size of the growth of contacted cells with non-contacted cells.

Preferably, growth of cells contacted with the inhibitor is retarded by at least 50% as compared to growth of non-contacted cells. More preferably, cell proliferation is inhibited by 100% (i.e., the contacted cells do not increase in number). Most preferably, the phrase "inhibiting cell proliferation" includes a reduction in the number or size of contacted cells, as compared to non-contacted cells. Thus, an inhibitor of histone deacetylase according to the invention that inhibits cell proliferation in a contacted cell may induce the contacted cell to undergo growth retardation, to undergo growth arrest, to undergo programmed cell death (i.e., to apoptose), or to undergo necrotic cell death.

The cell proliferation inhibiting ability of the histone deacetylase inhibitors according to the invention allows the synchronization of a population of asynchronously growing cells. For Example, the histone deacetylase inhibitors of the invention may be used to arrest a population of non-neoplastic cells grown in vitro in the G1 or G2 phase of the cell cycle. Such synchronization allows, for Example, the identification of gene and/or gene products expressed during the G1 or G2 phase of the cell cycle. Such synchronization of cultured cells may also be useful for testing the efficacy of a new transfection protocol, where transfection efficiency varies and is dependent upon the particular cell cycle phase of the cell to be transfected. Use of the histone deacetylase inhibitors of the invention allows the synchronization of a population of cells, thereby aiding detection of enhanced transfection efficiency.

In some preferred embodiments, the contacted cell is a neoplastic cell. The term "neoplastic cell" is used to denote a cell that shows aberrant cell growth. Preferably, the aberrant cell growth of a neoplastic cell is increased cell growth. A neoplastic cell may be a hyperplastic cell, a cell that shows a lack of contact inhibition of growth in vitro, a benign tumor cell that is incapable of metastasis in vivo, or a cancer cell that is capable of metastasis in vivo and that may recur after attempted removal. The term "tumorigenesis" is used to denote the induction of cell proliferation that leads to the development of a neoplastic growth. In some embodiments, the histone deacetylase inhibitor induces cell differentiation in the contacted cell. Thus, a neoplastic cell, when contacted with an inhibitor of histone deacetylase may be induced to differentiate, resulting in the production of a non-neoplastic daughter cell that is phylogenetically more advanced than the contacted cell.

In some preferred embodiments, in neoplastic cells, antitumor activity of an HDAC inhibitor can be assessed by analyzing expression of certain tumor suppressor genes, such as $p21^{WAF1/Cip1}$. HDAC inhibitors induce $p21^{WAF1/Cip1}$ expression in human cancer cells, which leads to retardation of cell proliferation.

In some preferred embodiments, the contacted cell is in an animal. Thus, the invention provides a method for treating a cell proliferative disease or condition in an animal, comprising administering to an animal in need of such treatment a therapeutically effective amount of a histone deacetylase inhibitor of the invention. Preferably, the animal is a mammal, more preferably a domesticated mammal. Most preferably, the animal is a human.

The term "cell proliferative disease or condition" is meant to refer to any condition characterized by aberrant cell growth, preferably abnormally increased cellular proliferation. Examples of such cell proliferative diseases or conditions include, but are not limited to, cancer, restenosis, and psoriasis. In particularly preferred embodiments, the invention provides a method for inhibiting neoplastic cell proliferation in an animal comprising administering to an animal having at least one neoplastic cell present in its body a therapeutically effective amount of a histone deacetylase inhibitor of the invention.

It is contemplated that some compounds of the invention have inhibitory activity against a histone deacetylase from a protozoal source. Thus, the invention also provides a method for treating or preventing a protozoal disease or infection, comprising administering to an animal in need of such treatment a therapeutically effective amount of a histone deacetylase inhibitor of the invention. Preferably the animal is a mammal, more preferably a human. Preferably, the histone deacetylase inhibitor used according to this embodiment of the invention inhibits a protozoal histone deacetylase to a greater extent than it inhibits mammalian histone deacetylases, particularly human histone deacetylases.

The present invention further provides a method for treating a fungal disease or infection comprising administering to an animal in need of such treatment a therapeutically effective amount of a histone deacetylase inhibitor of the invention. Preferably the animal is a mammal, more preferably a human. Preferably, the histone deacetylase inhibitor used according to this embodiment of the invention inhibits a fungal histone deacetylase to a greater extent than it inhibits mammalian histone deacetylases, particularly human histone deacetylases.

The term "therapeutically effective amount" is meant to denote an amount which elicits the desired therapeutic effect, for example, a dosage sufficient to cause inhibition of histone deacetylase activity in the cells of the subject, or a dosage sufficient to inhibit cell proliferation or to induce cell differentiation in the subject. The therapeutic effect is dependent upon the disease being treated and the results desired. As such, the therapeutic effect can be a decrease in the severity of symptoms associated with the disease and/or inhibition (partial or complete) of progression of the disease. The amount needed to elicit the therapeutic response can be determined based on the age, health, size and sex of the patient. Optimal amounts can also be determined based on monitoring of the patient's response to treatment. Administration may be by any route, including, without limitation, parenteral, oral, sublingual, transdermal, topical, intranasal, intratracheal, or intrarectal. In certain particularly preferred embodiments, compounds of the invention are administered intravenously in a hospital setting. In certain other preferred embodiments, administration may preferably be by the oral route.

When administered systemically, the histone deacetylase inhibitor is preferably administered at a sufficient dosage to attain a blood level of the inhibitor from about 0.01 µM to about 100 µM, more preferably from about 0.05 µM to about 50 µM, still more preferably from about 0.1 µM to about 25 µM, and still yet more preferably from about 0.5 µM to about 25 µM. For localized administration, much lower concentrations than this may be effective, and much higher concentrations may be tolerated. One of skill in the art will appreciate that the dosage of histone deacetylase inhibitor necessary to produce a therapeutic effect may vary considerably depending on the tissue, organ, or the particular animal or patient to be treated.

In certain preferred embodiments of the third aspect of the invention, the method further comprises contacting the cell with an antisense oligonucleotide that inhibits the expression of a histone deacetylase. The combined use of a nucleic acid level inhibitor (e.g., antisense oligonucleotide) and a protein level inhibitor (i.e., inhibitor of histone deacetylase enzyme activity) results in an improved inhibitory effect, thereby reducing the amounts of the inhibitors required to obtain a given inhibitory effect as compared to the amounts necessary when either is used individually. The antisense oligonucleotides according to this aspect of the invention are complementary to regions of RNA or double-stranded DNA that encode HDAC-1, HDAC-2, HDAC-3, HDAC-4, HDAC-5, HDAC-6, HDAC-7, HDAC-8, HDAC-9, HDAC-10 and/or HDAC-11 (see e.g., GenBank Accession Number U50079 for HDAC-1, GenBank Accession Number U31814 for HDAC-2, and GenBank Accession Number U75697 for HDAC-3).

For purposes of the invention, the term "oligonucleotide" includes polymers of two or more deoxyribonucleosides, ribonucleosides, or 2'-substituted ribonucleoside residues, or any combination thereof. Preferably, such oligonucleotides have from about 6 to about 100 nucleoside residues, more preferably from about 8 to about 50 nucleoside residues, and most preferably from about 12 to about 30 nucleoside residues. The nucleoside residues may be coupled to each other by any of the numerous known internucleoside linkages. Such internucleoside linkages include without limitation phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleoside linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/or having additional substituents, including without limitation lipophilic groups, intercalating agents, diamines and adamantane.

For purposes of the invention the term "2'-substituted ribonucleoside" includes ribonucleosides in which the hydroxyl group at the 2' position of the pentose moiety is substituted to produce a 2'-O-substituted ribonucleoside. Preferably, such substitution is with a lower alkyl group containing 1-6 saturated or unsaturated carbon atoms, or with an aryl or allyl group having 2-6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups. The term "2'-substituted ribonucleoside" also includes ribonucleosides in which the 2'-hydroxyl group is replaced with an amino group or with a halo group, preferably fluoro.

Particularly preferred antisense oligonucleotides utilized in this aspect of the invention include chimeric oligonucleotides and hybrid oligonucleotides.

For purposes of the invention, a "chimeric oligonucleotide" refers to an oligonucleotide having more than one type of internucleoside linkage. One preferred Example of such a chimeric oligonucleotide is a chimeric oligonucleotide comprising a phosphorothioate, phosphodiester or phosphorodithioate region, preferably comprising from about 2 to about 12 nucleotides, and an alkylphosphonate or alkylphosphonothioate region (see e.g., Pederson et al. U.S. Pat. Nos. 5,635,377 and 5,366,878). Preferably, such chimeric oligonucleotides contain at least three consecutive internucleoside linkages selected from phosphodiester and phosphorothioate linkages, or combinations thereof.

For purposes of the invention, a "hybrid oligonucleotide" refers to an oligonucleotide having more than one type of nucleoside. One preferred Example of such a hybrid oligonucleotide comprises a ribonucleotide or 2'-substituted ribonucleotide region, preferably comprising from about 2 to about 12 2'-substituted nucleotides, and a deoxyribonucleotide region. Preferably, such a hybrid oligonucleotide contains at least three consecutive deoxyribonucleosides and also contains ribonucleosides, 2'-substituted ribonucleosides, preferably 2'-O-substituted ribonucleosides, or combinations thereof (see e.g., Metelev and Agrawal, U.S. Pat. No. 5,652, 355).

The exact nucleotide sequence and chemical structure of an antisense oligonucleotide utilized in the invention can be varied, so long as the oligonucleotide retains its ability to inhibit expression of the gene of interest. This is readily determined by testing whether the particular antisense oligonucleotide is active. Useful assays for this purpose include quantitating the mRNA encoding a product of the gene, a Western blotting analysis assay for the product of the gene, an activity assay for an enzymatically active gene product, or a soft agar growth assay, or a reporter gene construct assay, or an in vivo tumor growth assay, all of which are described in detail in this specification or in Ramchandani et al. (1997) Proc. Natl. Acad. Sci. USA 94: 684-689.

Antisense oligonucleotides utilized in the invention may conveniently be synthesized on a suitable solid support using well known chemical approaches, including H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG) (see, e.g., Pon, R. T. (1993) Methods in Molec. Biol. 20: 465-496).

Particularly preferred oligonucleotides have nucleotide sequences of from about 13 to about 35 nucleotides. Yet additional particularly preferred oligonucleotides have nucleotide sequences of from about 15 to about 26 nucleotides.

The following Examples are intended to further illustrate certain preferred embodiments of the invention, and are not intended to limit the scope of the invention.

EXAMPLES

Example 1a (R)—N-(2-Amino-5-(thiophen-2-yl)phenyl)-4-((3-(dimethylamino)pyrrolidin-1-yl)methyl)benzamide (9)

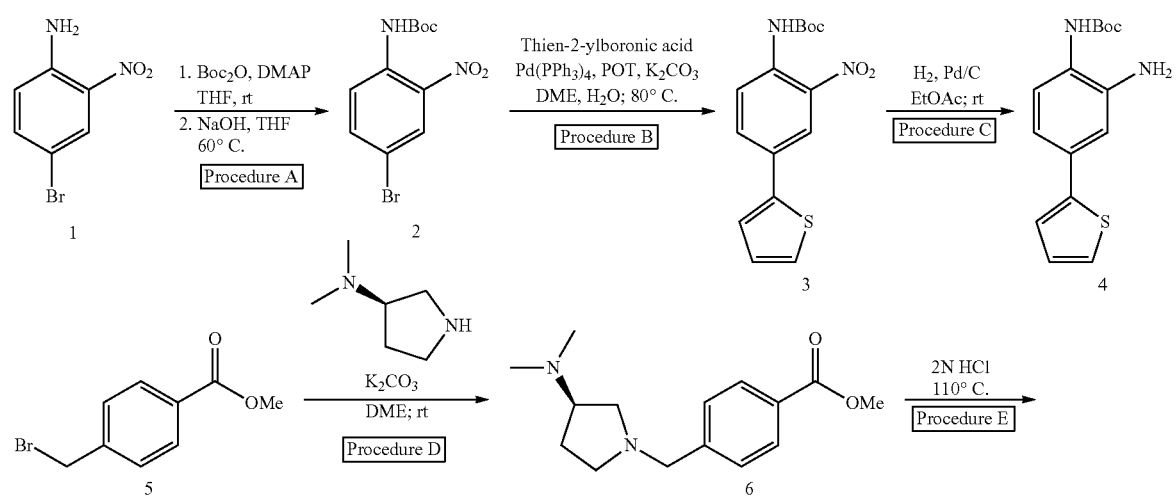

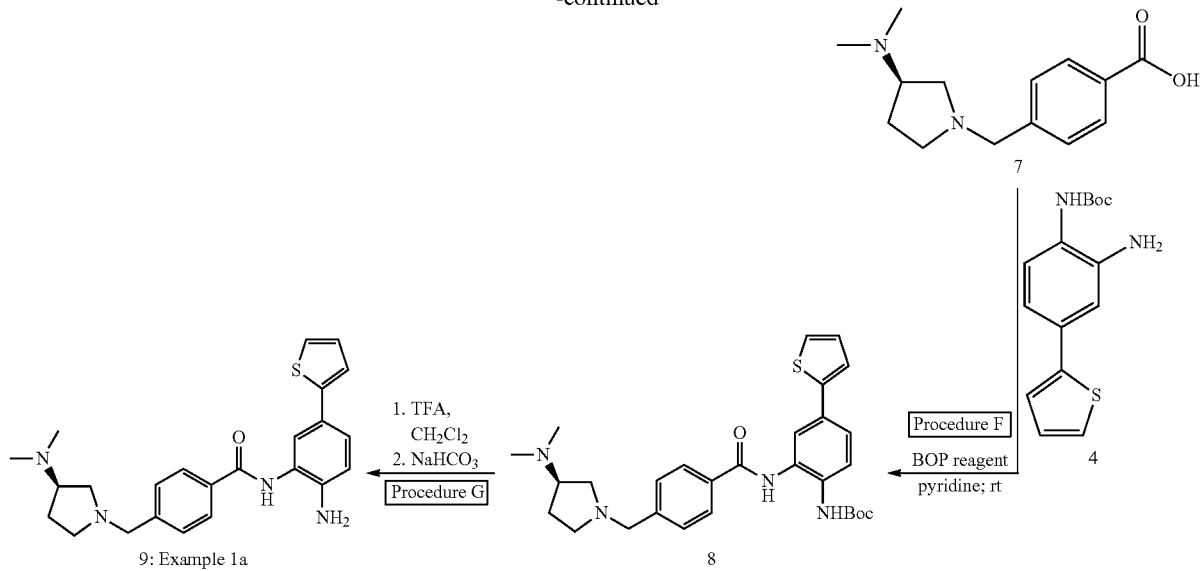

Step 1. tert-Butyl 4-bromo-2-nitrophenylcarbamate (2)

To a solution of 4-bromo-2-nitroaniline 1 (10.0 g; 46.1 mmol) and Boc-anhydride (20.11 g, 92.2 mmol) in THF (100 mL) stirred at room temperature was added a catalytic amount of 4-(dimethylamino)pyridine (DMAP). The reaction mixture was allowed to stir for 90 min, the solvent was removed in vacuo and the residue was dried under vacuum to produce colorless oil. The oil was dissolved in THF (46 mL), treated with an aqueous sodium hydroxide solution (2N, 46 mL) and heated to 65° C. for 18 h. Solid sodium hydroxide (1.8 g, 46.1 mmol) was added to the reaction mixture and heating was continued for 4 h; then the THF was removed in vacuo and a yellow solid crashed from the aqueous solution. The solid was filtered, washed with $H_2O$ and dried under vacuum to afford title compound 2 (15 g, >99% yield).

$^1$H NMR (DMSO-$d_6$) δ (ppm): 9.67 (s, 1H), 8.05 (d, J=2.2 Hz, 1H), 7.78 (dd, J=8.8, 2.2 Hz, 1H), 7.57 (d, J=8.8 Hz, 1H), 1.43 (s, 9H).

Step 2. tert-Butyl 2-nitro-4-(thiophen-2-yl)phenylcarbamate (3)

A suspension of 2-thiophene boronic acid (3.93 g, 30.7 mmol), bromoarene 2 (7.31 g, 23.1 mmol), tri-o-tolyl-phosphine (2.16 g, 7.1 mmol) and potassium carbonate (9.81 g, 70.9 mmol) in degassed ethyleneglycol dimethylether (DME) (120 mL) and $H_2O$ (40 mL) was treated with tetrakis(triphenylphosphine)palladium(0) (1.78 g, 1.5 mmol). The mixture was stirred in a preheated oil bath at 80° C. for 18 h, diluted with AcOEt (200 mL), washed with brine, dried over $MgSO_4$ and concentrated. The crude material was either purified by flash chromatography (eluent: 10% AcOEt in hexane) or triturated in a mixture AcOEt:hexane (10:1, 100 mL) to give title compound 3 (6.74 g, 90% yield).

$^1$H NMR (DMSO-$d_6$) δ (ppm): 9.63 (s, 1H), 8.12 (d, J=2.3 Hz, 1H), 7.92 (dd, J=8.6, 2.3 Hz, 1H), 7.62 to 7.59 (m, 2H), 7.59 to 7.52 (m, 1H), 7.15 (dd, J=4.9, 3.5 Hz, 1H), 1.45 (s, 9H).

Step 3: tert-Butyl 2-amino-4-(thiophen-2-yl)phenylcarbamate (4)

Compound 3 was suspended in AcOEt and placed under nitrogen atmosphere; then 10% palladium on carbon (catalytic amount) was added. The reaction mixture was placed under vacuum for a few min then opened up under a balloon of hydrogen and stirred at ambient temperature for 18 h. The reaction mixture was filtered through Celite® and concentrated to give compound 4 (0.393 g, 95% yield).

$^1$H NMR (DMSO-$d_6$) δ (ppm): 8.33 (s, 1H), 7.42 (dd, J=4.9, 0.98 Hz, 1H), 7.27 (dd, J=3.5, 0.98 Hz, 1H), 7.06 (dd, J=5.1, 3.7 Hz, 1H), 6.95 (d, J=2.2 Hz, 1H), 6.82 (dd, J=8.0 Hz, 2.0 Hz, 1H), 5.01 (s, 2H), 1.47 (s, 9H).

Step 4: (R)-Methyl 4-((3-(dimethylamino)pyrrolidin-1-yl)methyl)benzoate (6)

Methyl 4-(bromomethyl)benzoate 5 (0.5 g, 2.2 mmol), (R)—N,N-dimethylpyrrolidin-3-amine (0.523 g, 4.6 mmol) and potassium carbonate (0.392 g, 2.8 mmol) were stirred at room temperature for 18 h in ethyleneglycol dimethylether (3 mL) then diluted with DCM (20 mL), washed with brine, dried over $MgSO_4$ and concentrated to give title compound 6 (0.57 g, 96% yield).

$^1$H NMR (DMSO-$d_6$) δ (ppm): 7.88 (d, J=8.4 Hz, 2H), 7.41 (d, J=8.4 Hz, 2H), 3.82 (s, 3H), 3.60 (abq, J=44.0, 13.5 Hz, 2H), 2.69 to 2.61 (m, 2H), 2.58 to 2.50 (m, 1H), 2.48 to 2.39 (m, 1H), 2.26 to 2.23 (m, 1H), 2.05 (s, 6H), 1.85 to 1.81 (m, 1H), 1.62 to 1.56 (m, 1H).

Step 5: (R)-4-((3-(Dimethylamino)pyrrolidin-1-yl)methyl)benzoic acid (7)

Compound 6 (0.55 g, 2.1 mmol) was heated to 110° C. in 2N aqueous hydrochloric acid (7 mL) for 18 h then cooled to −78° C. and lyophilized to give compound 7 as a grey solid (0.65 g, 97% yield). LRMS: 248.2 (calc), 249.0 (obs).

Step 6: (R)-tert-Butyl 2-(4-((3-(dimethylamino)pyrrolidin-1-yl)methyl)benzamido)-4-(thiophen-2-yl)phenylcarbamate (8)

A solution of acid 7 (0.20 g, 0.62 mmol), amine 4 (0.164 g, 0.56 mmol) and BOP reagent (0.30 g, 0.68 mmol) in pyridine (4 mL) was stirred for 18 h, concentrated, diluted with AcOEt, washed with aqueous sodium bicarbonate (NaHCO$_3$), brine, dried over MgSO$_4$, filtered and concentrated. Flash chromatography purification of the residue (eluent: 1:1 MeOH:AcOEt with 1% triethylamine) gave compound 8 (0.198 g, 67% yield).

$^1$H NMR (DMSO-d$_6$) δ (ppm): 9.86 (s, 1H), 8.72 (s, 1H), 7.92 (d, J=8.2 Hz, 2H), 7.79 (d, J=2.0 Hz, 1H), 7.59 (d, J=8.6 Hz, 1H), 7.51 (d, J=1.2 Hz, 1H), 7.50 (d, J=1.2 Hz, 1H), 7.46 to 7.43 (m, 3H), 7.11 (dd, J=5.1, 3.5 Hz, 1H), 3.64 (abq, J=40.5, 13.3 Hz, 2H), 2.84 to 2.75 (m, 1H), 2.67 to 2.63 (m, 1H), 2.33 (m, 2H), 2.13 (s, 6H), 1.99 to 1.88 (m, 1H), 1.66 (m, 1H), 1.45 (s, 9H), 1.25 (m, 1H).

Step 7: (R)—N-(2-Amino-5-(thiophen-2-yl)phenyl)-4-((3-(dimethylamino)pyrrolidin-1-yl)methyl)benzamide (9)

To a solution of compound 8 (0.198 g, 0.38 mmol) in DCM (3 mL) was added neat trifluoroacetic acid (1 mL). The solution was allowed to stir at room temperature for 90 min, concentrated (without heating), taken up in AcOEt, washed with saturated aqueous NaHCO$_3$, brine, dried over MgSO$_4$, filtered and concentrated to give title compound 9 (0.038 g, 24% yield).

$^1$H NMR: (DMSO-d$_6$) δ (ppm) 9.69 (s, 1H), 7.94 (s, J=7.8 Hz, 2H), 7.43 (t, J=8.0 Hz, 3H), 7.34 (d, J=5.1 Hz, 1H), 7.28 (dd, J=8.2, 2.0 Hz, 1H), 7.22 (d, J=3.3 Hz, 1H), 7.03 (t, J=3.5 Hz, 1H), 6.79 (d, J=8.4 Hz, 1H), 5.15 (s, 2H), 3.63 (q, J=36.8, 14.1 Hz, 2H), 2.67 to 2.63 (m, 1H), 2.45-2.37 (m, 2H), 2.33 to 2.19 (m, 7H), 1.90 (m, 2H), 1.68 (m, 1H).

TABLE 1

Characterization of compounds prepared according to Scheme 1

| Cpd | Ex | R | X | Name | Characterization |
|---|---|---|---|---|---|
| 10 | 1b | N,N-bis(2-methoxyethyl)aminomethyl (N(CH$_2$CH$_2$OMe)$_2$) | thiophen-2-yl | N-(2-amino-5-(thiophen-2-yl)phenyl)-4-((bis(2-methoxyethyl)amino)methyl)-benzamide | $^1$H NMR (DMSO-d$_6$) δ (ppm): 9.69 (s, 1H), 7.93 (d, J = 8.2 Hz, 2H), 7.45 (s, 1H), 7.43 (d, J = 8.4 Hz, 2H), 7.34 (dd, J = 5.1, 1.2 Hz, 1H), 7.28 (dd, J = 8.2, 2.2 Hz, 1H), 7.22 (dd, J = 3.5, 1.2 Hz, 1H), 7.03 (dd, J = 5.1, 3.5 Hz, 1H), 6.79 (d, J = 8.4 Hz, 1H), 5.14 (s, 2H), 3.71 (s, 2H), 3.40 (t, J = 6.1 Hz, 4H), 3.20 (s, 6H), 2.63 (t, J = 6.1 Hz, 4H). LRMS: 439.19 (calc) 440.2 (obs). |
| 11 | 1c | (3-hydroxypiperidin-1-yl) | thiophen-2-yl | (R)-N-(2-amino-5-(thiophen-2-yl)phenyl)-4-((3-hydroxypiperidin-1-yl)methyl)-benzamide | $^1$H NMR (DMSO-d$_6$) δ (ppm): 9.69 (s, 1H), 7.94 (d, J = 8.2 Hz, 2H), 7.45 (d, J = 2.2 Hz, 1H), 7.41 (d, J= 8.2 Hz, 2H), 7.34 (dd, J = 5.1, 0.98 Hz, 1H), 7.28 (dd, J = 8.4, 2.2 Hz, 1H), 7.22 (dd, J = 3.7, 1.2 Hz, 1H), 7.03 (dd, J = 5.1, 3.5 Hz, 1H), 6.79 (d, J = 8.4 Hz, 1H), 5.14 (s, 2H), 4.59 (d, J = 5.1 Hz, 1H), 3.52 (abq, J = 36.8, 13.3 Hz, 2H), 3.44 to 3.43 (m, 1H), 2.76 (d, J = 10.4 Hz, 1H), 2.63 (d, J = 11.3 Hz, 1H), 1.87 to 1.69 (m, 3H), 1.62 to 1.58 (m, 1H), 1.45 to 1.39 (m, 1H), 1.06 to 1.04 (m, 1H). LRMS: 407.17 (calc) 408.0 (obs). |
| 12 | 1d | piperidin-1-yl | thiophen-2-yl | N-(2-amino-5-(thiophen-2-yl)phenyl)-4-(piperidin-1-ylmethyl)-benzamide | $^1$H NMR (DMSO-d$_6$) δ (ppm): 9.87, (s, 1H), 9.34 (s, 1H), 8.07 (d, J = 8.2 Hz, 2H), 7.62 (d, J = 7.8 Hz, 2H), 7.46 (s, 1H), 7.36 (s, J = 5.1 Hz, 1H), 7.33 (d, J = 8.4 Hz, 1H), 7.25 (d, J = 3.5 Hz, 1H), 7.04 (dd, J = 5.1, 3.5 Hz, 1H), 6.86 (d, J = 8.2 Hz, 1H), 4.36 (d, J = 5.1 Hz, 2H), 3.39 to 3.31 (m, 2H), 2.93 to 2.86 (m, 2H), 1.83 (d, J = 14.1 Hz, 2H), 1.71 to 1.57 (m, 3H), 1.38 to 1.34 (m, 1H). LRMS: 391.17 (calc) 392.1 (obs). |
| 13 | 1e | (4-(2-methoxyethyl)piperazin-1-yl) | thiophen-2-yl | N-(2-amino-5-(thiophen-2-yl)phenyl)-4-((4-(2-methoxyethyl)piperazin-1-yl)methyl)-benzamide | $^1$H NMR (DMSO-d$_6$) δ (ppm): 9.70 (s, 1H), 7.94 (d, J = 8.2 Hz, 2H), 7.45 (d, J = 2.0 Hz, 1H), 7.41 (d, J = 8.2 Hz, 2H), 7.34 (dd, J = 5.1, 0.98 Hz, 1H), 7.28 (dd, J = 8.2, 2.2 Hz, 1H), 7.22 (dd, J = 3.5, 0.98 Hz, 1H), 7.03 (dd, J = 5.1, 3.7 Hz, 1H), 6.79 (d, J = 8.4 Hz, 1H), 5.14 (s, 2H), 3.52 (s, 2H), 3.40 (t, J = 5.8 Hz, 3H), 3.20 (s, 3H), 2.38 (m, 9H). LRMS: 450.21 (calc) 451.1 (obs). |

TABLE 1-continued

Characterization of compounds prepared according to Scheme 1

| Cpd | Ex | R | X | Name | Characterization |
|---|---|---|---|---|---|
| 14 | 1f | N-ethyl-N-methyl-amino | thiophen-2-yl | N-(2-amino-5-(thiophen-2-yl)phenyl)-4-((ethyl(methyl)amino)methyl)-benzamide | $^1$H NMR (DMSO-d$_6$) δ (ppm): 9.71, (s, 1H), 7.95 (d, J = 7.8 Hz, 2H), 7.45 to 7.42 (m, 4H), 7.34 (d, J = 4.1 Hz, 1H), 7.28 (dd, J = 8.2, 2.2 Hz, 1H), 7.23 (d, J = 2.5 Hz, 1H), 7.03 (dd, J = 5.1, 3.5 Hz, 1H), 6.79 (d, J = 8.2 Hz, 1H), 5.14 (s, 2H), 3.53 (m, 2H), 2.40 (m, 2H), 2.13 (s, 3H), 1.03 (t, J = 7.0 Hz, 3H). LRMS: 365.16 (calc) 366.0 (obs). |
| 15 | 1g | 4-isopropylpiperazin-1-yl | thiophen-2-yl | N-(2-amino-5-(thiophen-2-yl)phenyl)-4-((4-isopropyl-piperazin-1-yl)methyl)-benzamide | $^1$H NMR (DMSO-d$_6$) δ (ppm): 9.70 (s, 1H), 7.49 (d, J = 8.0 Hz, 2H), 7.45 (d, J = 2.2 Hz, 1H), 7.42 (d, J = 8.2 Hz, 2H), 7.34 (dd, J = 5.1, 1.2 Hz, 1H), 7.28 (dd, J = 8.4, 2.2 Hz, 1H), 7.22 (dd, J = 3.5, 1.2 Hz, 1H), 7.03 (dd, J = 5.1, 3.5 Hz, 1H), 6.79 (d, J = 8.4 Hz, 1H), 5.14 (s, 2H), 3.53 (s, 2H), 2.65 (m, 1H), 2.31 to 1.97 (m, 8H), 0.98 (m, 6H). LRMS: 434.60 (calc) 435.1 (obs). |
| 16 | 1h | 4-cyclopentylpiperazin-1-yl | thiophen-2-yl | N-(2-amino-5-(thiophen-2-yl)phenyl)-4-((4-cyclopentyl-piperazin-1-yl)methyl)-benzamide | $^1$H NMR (DMSO-d$_6$) δ (ppm): 9.70 (s, 1H), 7.95 (d, J = 7.8 Hz, 2H), 7.44 (d, J = 4.3 Hz, 2H), 7.41 (s, 1H), 7.34 (d, J = 5.1 Hz, 1H), 7.28 (dd, J = 8.4, 2.0 Hz, 1H), 7.22 (d, J = 3.1 Hz, 1H), 6.79 (d, J = 8.4 Hz, 1H), 5.14 (s, 2H), 3.55 (s, 2H), 2.31 (m, 9H), 1.80 (m, 2H), 1.60 (m, 2H), 1.48 (m, 2H), 1.35 (m, 2H). LRMS: 460.23 (calc) 461.1 (obs). |
| 17 | 1i | 3-hydroxypyrrolidin-1-yl | thiophen-2-yl | N-(2-amino-5-(thiophen-2-yl)phenyl)-4-((3-hydroxy-pyrrolidin-1-yl)methyl)-benzamide | $^1$H NMR (DMSO-d$_6$) δ (ppm): 9.69 (s, 1H), 7.93 (m, 2H), 7.42 (t, J = 9.2 Hz, 3H), 7.34 (dd, J = 5.1, 1.2 Hz, 1H), 7.28 (dd, J = 8.4, 2.3 Hz, 1H), 7.22 (m, 1H), 7.03 (dd, J = 5.1, 3.5 Hz, 1H), 6.79 (d, J = 8.4 Hz, 1H), 5.15 (s, 2H), 4.70 (d, J = 4.5 Hz, 1H), 4.19 (m, 1H), 3.62 (q, J = 23.7, 13.3 Hz, 2H), 2.68 (m, 1H), 2.57 (m, 1H), 2.39 (m, 1H), 2.30 (m, 1H), 2.01 (m, 1H), 1.55 (m, 1H). LRMS: 393.15 (calc) 394.1 (obs). |
| 18 | 1j | ((2-(dimethylamino)ethyl)(methyl)amino)methyl | thiophen-2-yl | N-(2-amino-5-(thiophen-2-yl)phenyl)-4-(((2-(dimethylamino)-ethyl)(methyl)-amino)methyl)-benzamide | $^1$H NMR (CD$_3$OD) δ (ppm): 7.97 (d, J = 8.2 Hz, 2H), 7.50 (d, J = 8.5 Hz, 2H), 7.49 (d, J = 2.2 Hz, 1H), 7.35 (dd, J = 8.4, 2.2 Hz, 1H), 7.23 (dd, J = 5.1, 1.0 Hz, 1H), 7.21 (dd, J = 3.5, 1.0 Hz, 1H), 7.01 (dd, J = 5.1, 3.7 Hz, 1H), 6.91 (d, J = 8.4 Hz, 1H), 3.62 (s, 2H), 2.62-2.55 (m, 8H), 2.30 (s, 6H), 2.25 (s, 3H). LRMS: 408.57 (calc) 409.2 (obs). |
| 19 | 1k | morpholino | phenyl | N-(4-aminobiphenyl-3-yl)-4-(morpholinomethyl)-benzamide | $^1$H NMR (CD$_3$OD) δ (ppm): 7.97 (d, 2 H, J = 8.2 Hz), 7.57-7.48 (mult, 5H), 7.37 (t, 3 H, J = 2.2 Hz), 7.24 (td, 1 H, J = 1.2 & 7.2 Hz), 6.97 (d, 1 H, J = 8.2 Hz), 3.71 (t, 4 H, J = 4.3 Hz), 3.62 (s, 2H), 2.50 (s, 4H). LRMS: 387.47 (calc) 388.3 and 194.8 (obs). |
| 20 | 1l | (R)-3-(dimethylamino)pyrrolidin-1-yl | phenyl | (R)-N-(4-aminobiphenyl-3-yl)-4-((3-(dimethylamino)-pyrrolidin-1-yl)methyl)-benzamide | $^1$H NMR (DMSO-d$_6$) δ (ppm): 9.70 (s, 1H), 7.94 (d, J = 8.0 Hz, 2H), 7.54 (d, J = 7.2 Hz, 2H), 7.50 (s, 1H), 7.43 to 7.35 (m, 4H), 7.31 (dd, J = 8.4, 2.2 Hz, 1H), 7.22 (t, J = 7.3 Hz, 1H), 6.85 (d, J = 8.4 Hz, 1H), 5.08 (s, 2H), 3.61 (abq, J = 41.9, 13.3 Hz, 2H), 2.65 to 2.53 (m, 2H), 2.43 (m, 1H), 2.31 (m, 1H), 2.07 (s, 6H), 1.89 to 1.84 (m, 1H), 1.61 (m, 1H), 1.21 (m, 1H). LRMS: 414.24 (calc), 415.2 (obs). |

TABLE 1-continued

Characterization of compounds prepared according to Scheme 1

| Cpd | Ex | R | X | Name | Characterization |
|---|---|---|---|---|---|
| 21 | 1m | morpholine | 4-hydroxyphenyl | N-(4-amino-4'-hydroxybiphenyl-3-yl)-4-(morpholinomethyl)-benzamide | $^1$H NMR (DMSO-d$_6$) δ (ppm): 9.69 (s, 1H), 9.33 (s, 1H), 7.95 (d, J = 8.0 Hz, 2H), 7.43 (d, J = 8.2 Hz, 2H), 7.38 (d, J = 2.0 Hz, 1H), 7.33 (d, J = 8.4 Hz, 2H), 7.20 (dd, J = 8.2, 2.2 Hz, 1H), 6.80 (d, J = 8.2 Hz, 1H), 6.76 (d, J = 8.8 Hz, 2H), 4.94 (s, 2H), 3.60 (t, J = 4.5 Hz, 4H), 3.53 (s, 2H), 2.47 to 2.35 (m, 4H). LRMS: 403.19 (calc) 404.1 (obs). |
| 22 | 1n | (3-(dimethylamino)pyrrolidin-1-yl) | 4-hydroxyphenyl | (R)-N-(4-amino-4'-hydroxy-biphenyl-3-yl)-4-((3-(dimethylamino)pyrrolidin-1-yl)methyl)-benzamide | $^1$H NMR (DMSO-d$_6$) δ (ppm): 9.68 (s, 1H), 9.33 (s, 1H), 7.93 (d, J = 8.2 Hz, 2H), 7.41 (d, J = 8.2 Hz, 2H), 7.34 (s, 1H), 7.33 (d, J = 8.4 Hz, 2H), 7.20 (dd, J = 8.2, 2.2 Hz, 1H), 6.80 (d, J = 8.4 Hz, 1H), 6.76 (d, J = 8.6 Hz, 2H), 4.94 (s, 2H), 3.61 (abq, J = 40.5, 13.1 Hz, 2H), 2.65 to 2.61 (m, 2H), 2.57 to 2.53 (m, 2H), 2.31 (m, 2H), 2.09 (s, 6H), 1.97 to 1.86 (m, 1H). LRMS: 430.24 (calc) 431.2 (obs). |
| 23 | 1o | morpholine | pyridin-3-yl | N-(2-amino-5-(pyridin-3-yl)phenyl)-4-(morpholinomethyl)-benzamide | $^1$H NMR (DMSO-d$_6$) δ (ppm): 9.72 (s, 1H), 8.77 (d, J = 2.2 Hz, 1H), 8.42 (dd, J = 4.7, 1.4 Hz, 1H), 7.96 (d, J = 8.2 Hz, 2H), 7.92 (dt, J = 8.2, 2.2 Hz, 1H), 7.55 (d, J = 2.2 Hz, 1H), 7.44 (d, J = 8.0 Hz, 2H), 7.38 (dt, J = 7.4, 2.5 Hz, 2H), 6.88 (d, J = 8.2 Hz, 1H), 5.20 (s, 2H), 3.57 (t, J = 4.4 Hz, 4H), 3.53 (s, 2H), 2.35 (m, 4H). |
| 24 | 1p | (3-(dimethylamino)pyrrolidin-1-yl) | pyridin-3-yl | (R)-N-(2-amino-5-(pyridin-3-yl)phenyl)-4-((3-(dimethylamino)pyrrolidin-1-yl)methyl)-benzamide | $^1$H NMR (DMSO-d$_6$) δ (ppm): 10.94 (s, 1H), 9.82 (s, 1H), 8.88 (s, 1H), 8.52 (d, J = 5.1 Hz, 1H), 8.05 (d, J = 7.6 Hz, 2H), 7.60 (s, 2H), 7.58 (d, J = 5.1 Hz, 2H), 7.46 (dd, J = 8.4, 2.3 Hz, 1H), 6.91 (d, J = 8.4 Hz, 1H), 3.92 (m, 2H), 2.78 (s, 6H), 2.65 (m, 2H), 2.53 to 2.51 (m, 2H), 2.43 (m, 1H), 2.31 to 2.30 (m, 2H). LRMS: 415.24 (calc) 416.2 (obs). |
| 25 | 1q | morpholine | pyridin-4-yl | N-(2-amino-5-(pyridin-4-yl)phenyl)-4-(morpholinomethyl)-benzamide | $^1$H NMR (DMSO-d$_6$) δ (ppm): 9.73 (s, 1H), 8.51 (dd, J = 4.7, 1.6 Hz, 2H), 7.98 (d, J = 8.0 Hz, 2H), 7.68 (d, J = 2.0 Hz, 1H), 7.58 (dd, J = 4.5, 1.6 Hz, 2H), 7.51 (dd, J = 8.4, 2.2 Hz, 1H), 7.46 (d, J = 8.2 Hz, 2H), 6.88 (d, J = 8.4 Hz, 1H), 5.39 (s, 2H), 3.59 (t, J = 4.4 Hz, 4H), 3.55 (s, 2H), 2.37 (m, 4H). LRMS: 388.2 (calc) 389.1 (obs). |
| 26 | 1r | morpholine | thiophen-3-yl | N-(2-amino-5-(thiophen-3-yl)phenyl)-4-(morpholinomethyl)-benzamide | $^1$H NMR (DMSO-d$_6$) δ (ppm): 9.74 (s, 1H), 7.97 (d, J = 8.0 Hz, 2H), 7.58 to 7.57 (m, 1H), 7.56 (t, J = 2.0 Hz, 1H), 7.51 (d, J = 2.0 Hz, 1H), 7.45 (d, J = 8.2 Hz, 2H), 7.42 (dd, J = 4.9, 2.0 Hz, 1H), 7.36 (dd, J = 8.4, 2.2 Hz, 1H), 6.81 (d, J = 8.4 Hz, 1H), 5.04 (s, 2H), 3.59 (t, J = 4.5 Hz, 4H), 3.55 (s, 2H), 2.37 (m, 4H). LRMS: 393.2 (calc) 394.1 (obs) |

TABLE 1-continued

Characterization of compounds prepared according to Scheme 1

| Cpd | Ex | R | X | Name | Characterization |
|---|---|---|---|---|---|
| 27 | 1s | (R)-3-(dimethylamino)pyrrolidin-1-yl | thiophen-3-yl | (R)-N-(2-amino-5-(thiophen-3-yl)phenyl)-4-((3-(dimethylamino)pyrrolidin-1-yl)methyl)-benzamide | $^1$H NMR (DMSO-d$_6$) δ (ppm): 9.72 (s, 1H), 7.96 (d, J = 8.2 Hz, 2H), 7.58 to 7.55 (m, 2H), 7.51 (d, J = 2.0 Hz, 1H), 7.44 (s, 1H), 7.43 to 7.41 (m, 2H), 7.36 (dd, J = 8.4, 2.2 Hz, 1H), 6.81 (d, J = 8.4 Hz, 1H), 5.04 (s, 2H), 3.62 (abq, J = 42.6, 13.5 Hz, 2H), 2.73 (m, 1H), 2.67 to 2.63 (m, 1H), 2.61 to 2.55 (m, 1H), 2.47 to 2.43 (m, 1H), 2.30 to 2.26 (m, 1H), 2.09 (s, 6H), 1.92 to 1.82 (m, 1H), 1.66 to 1.58 (m, 1H). LRMS: 420.2 (calc) 421.1 (obs) |
| 28 | 1t | morpholino | 6-fluoropyridin-3-yl | N-(2-amino-5-(6-fluoropyridin-3-yl)phenyl)-4-(morpholino-methyl)-benzamide | $^1$H NMR (DMSO-d$_6$) δ (ppm): 8.34 (s, 1H), 7.92 (m, 1H), 7.88 (d, J = 9.0 Hz, 2H), 7.57 (s, 1H), 7.43 (d, J = 9.1 Hz, 2H), 7.24 (m, 1H), 6.92 (m, 2H), 4.01 (s, 2H), 3.72 (t, J = 4.5 Hz, 5H), 3.58 (s, 1H) 2.43 (m, 5H). LRMS: 406.45 (calc) 407.1 (obs) |
| 29 | 1u | morpholino | 5-cyanothiophen-2-yl | N-(2-amino-5-(5-cyanothiophen-2-yl)phenyl)-4-(morpholino-methyl)-benzamide | $^1$H NMR (DMSO-d$_6$) δ (ppm): 7.92 (s, 1H), 7.82 (d, J = 8.1 Hz, 2H), 7.51 (s, 1H), 7.42 (d, J = 3.9 Hz, 1H), 7.41 (d, J = 8.0 Hz, 2H), 7.28 (m, 1H), 7.07 (d, J = 4.1 Hz, 1H), 6.31 (d, J = 8.41 Hz, 1H), 4.09 (m, 2H), 3.62 (m, 4H), 2.39 (m, 4H). LRMS: 418.51 (calc) 419.2 (obs) |
| 30 | 1v | morpholino | benzo[d][1,3]dioxol-5-yl | N-(2-amino-5-(benzo[d][1,3]-dioxol-5-yl)-phenyl)-4-(morpholino-methyl)-benzamide | $^1$H NMR (CDCl$_3$) δ (ppm): 7.89 (m, 2H), 7.42 (m, 2H), 7.21 (m, 1H), 7.01 (m, 2H), 6.82 (dd, J = 20.0, 8.2 Hz, 2H), 6.01 (s, 2H), 3.98 (s, 2H), 3.78 (t, J = 4.2 Hz, 4H), 3.59 (s, 2H), 2.42 (m, 4H), 1.61 (s, 1H). LRMS: 431.48 (calc) 432.2 (obs). |
| 31 | 1w | morpholino | 5-methylthiophen-2-yl | N-(2-amino-5-(5-methylthiophen-2-yl)phenyl)-4-(morpholino-methyl)-benzamide | $^1$H NMR (CDCl$_3$) δ (ppm): 8.15 (s, 1H), 7.84 (d, J = 8.1 Hz, 2H), 7.44 (s, 1H), 7.40 (d, J = 8.0 Hz, 2H), 7.24 (m, 1H), 6.93 (d, J = 3.5 Hz, 1H), 6.78 (d, J = 8.0 Hz, 2H), 6.67 (m, 1H), 4.01 (m, 2H), 3.71 (t, J = 5.0 Hz, 4H), 3.53 (s, 2H), 2.48 (s, 3H), 2.43 (m, 3H). LRMS: 407.17 (calc) 408.1 (obs). |
| 32 | 1x | morpholino | 3-(trifluoromethoxy)phenyl | N-(4-amino-5'-(trifluoromethoxy)-biphenyl-3-yl)-4-(morpholino-methyl)-benzamide | $^1$H NMR (CDCl$_3$) δ (ppm): 7.91 (d, J = 8.0 Hz, 2H), 7.57 (s, 1H), 7.48 (m, 2H), 7.37 (m, 2H), 7.13 (m, 1H), 6.92 (d, J = 8.0 Hz, 1H), 4.01 (s, 2H), 3.71 (t, J = 4.1 Hz, 4H), 3.57 (s, 2H), 2.48 (m, 3H), 1.61 (s, 1H). LRMS: 471.47 (calc) 472.2 (obs). |
| 33 | 1y | morpholino | (E)-3-methoxyprop-1-enyl | (E)-N-(2-amino-5-(3-methoxy-prop-1-enyl)phenyl)-4-(morpholino-methyl)-benzamide | $^1$H NMR (CDCl$_3$) δ (ppm): 7.89 to 7.84 (m, 3H), 7.46 (d, J = 8.2 Hz, 2H), 7.33 (s, 1H), 7.15 (dd, J = 8.2, 2.0 Hz, 1H), 6.78 (d, J = 8.2 Hz, 1H), 6.48 (d, J = 15.8 Hz, 1H), 6.11 (m, 1H), 4.04 (dd, J = 6.3, 1.4 Hz, 2H), 3.82 (bs, 2H), 3.72 (t, J = 4.6 Hz, 4H), 3.56 (s, 2H), 3.36 (s, 3H), 2.45 (t, J = 4.5 Hz, 4H). LRMS: 381.2 (calc) 381.2 (obs). |

Example 2a (E)-N-(2-Amino-5-(thiophen-2-yl)phenyl)-3-(6-(3,4-dimethoxyphenyl)pyridin-3-yl)acrylamide (42)

Step 2: (E)-tert-Butyl 3-(6-(3,4-dimethoxyphenyl)pyridin-3-yl)acrylate (39)

To a degassed solution of bromide 37 (0.47 g, 1.6 mmol), tert-butyl acrylate 38 (1.12 mL, 7.7 mmol), POT (0.34 g, 1.1

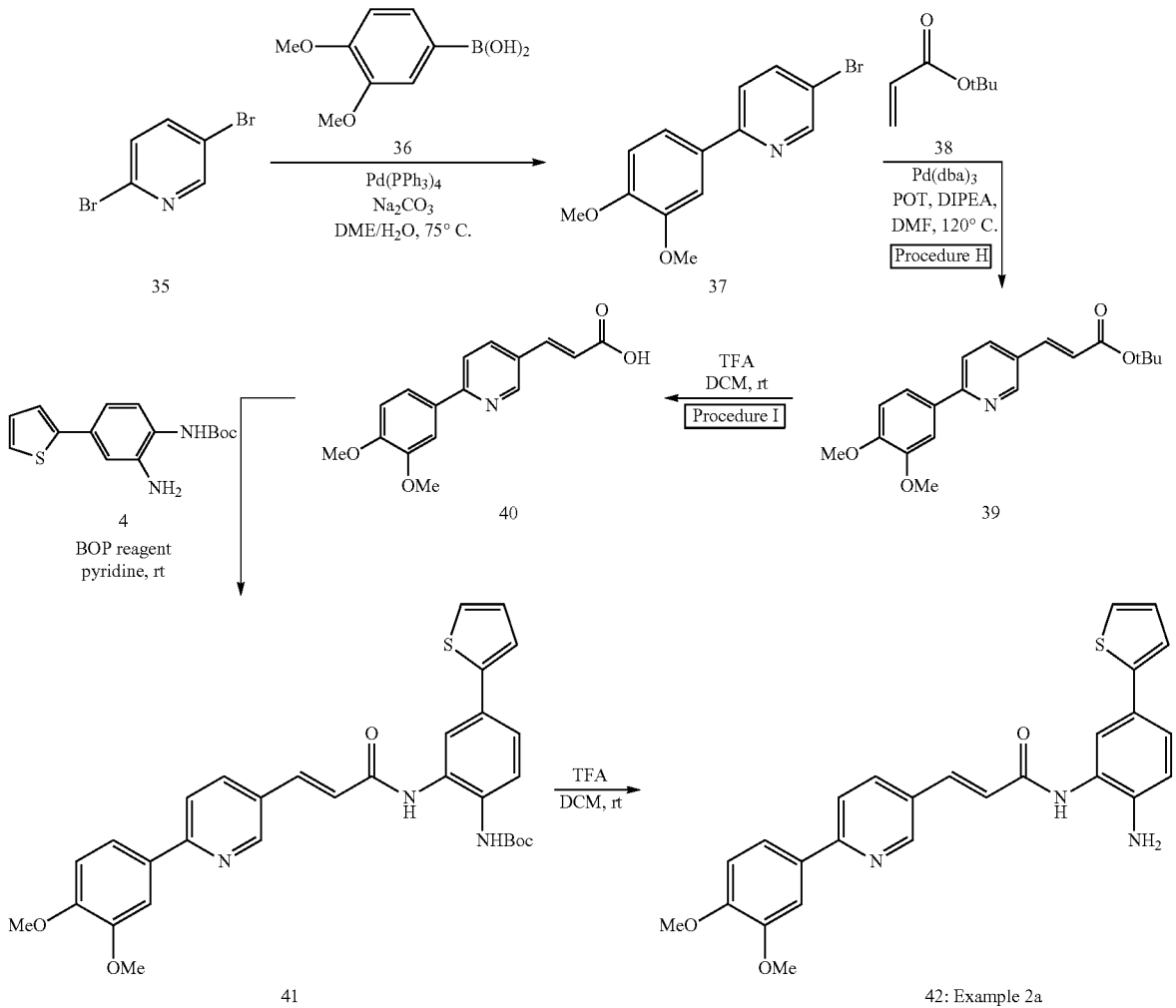

Scheme 2

Step 1: 5-Bromo-2-(3,4-dimethoxyphenyl)pyridine (37)

To a degassed solution of 2,5-dibromopyridine 35 (0.50 g, 2.11 mmol), 3,4-dimethoxyphenylboronic acid 36 (0.50 g, 2.74 mmol) and sodium carbonate (0.67 g, 6.3 mmol) in ethyleneglycol dimethylether (7 mL) and H$_2$O (2 mL) was added tetrakis(triphenylphosphine)-palladium(0) (0.16 g, 0.14 mmol) and the solution was stirred at 75° C. for 18 h. The reaction mixture was filtered, concentrated, diluted with AcOEt, washed with brine, dried over MgSO$_4$, filtered and concentrated. Flash chromatography of the residue (eluent: 3:1 hexane:AcOEt) provided title compound 37 (0.47 g, 76% yield).

$^1$H NMR (DMSO-d$_6$) δ (ppm): 8.70 (d, J=2.3 Hz, 1H), 8.04 (dd, J=8.6, 2.5 Hz, 1H), 7.91 (d, J=8.6 Hz, 1H), 7.65 to 7.61 (m, 2H), 7.04 (d, J=8.2 Hz, 1H), 3.83 (s, 3H), 3.80 (s, 3H).

mmol) and Hunig's base (1.11 mL, 6.4 mmol) in DMF (8 mL) was added tris(dibenzylideneacetone)dipalladium (0) (0.124 g, 0.16 mmol). The solution was placed in a preheated oil bath at 120° C., stirred for 18 h and concentrated. Flash chromatography purification of the residue (eluent: 3:1 hexane:AcOEt) afforded title compound 39 (0.45 g, 83% yield).

$^1$H NMR (DMSO-d$_6$) δ (ppm): 8.84 (d, J=2.0 Hz, 1H), 8.19 (dd, J=8.4, 2.2 Hz, 1H), 7.98 (d, J=8.6 Hz, 1H), 7.72 to 7.69 (m, 2H), 7.59 (d, J=8.2 Hz, 1H), 7.05 (d, J=8.2 Hz, 1H), 6.67 (d, J=16.0 Hz, 1H), 3.85 (s, 3H), 3.81 (s, 3H).

Step 3: (E)-3-(6-(3,4-Dimethoxyphenyl)pyridin-3-yl)acrylic acid compound with 2,2,2-trifluoroacetic acid (1:1) (40)

To a solution of tert-butyl ester 39 (0.45 g, 1.3 mmol) in DCM (5 mL) was added neat trifluoroacetic acid (1.7 mL).

The reaction was allowed to stir at room temperature for 18 h then concentrated; the residue was triturated with diethyl ether, to give title compound 40 (0.376 g, 92% yield).

$^1$H NMR (DMSO-d$_6$) δ (ppm): 8.86 (s, 1H), 8.22 (d, J=8.4 Hz, 1H), 8.01 (d, J=8.4 Hz, 1H), 7.72 (d, J=2.0 Hz, 1H), 7.70 (d, J=2.0 Hz, 1H), 7.64 (d, J=15.8 Hz, 1H), 7.06 (d, J=8.2 Hz, 1H), 6.69 (d, J=16.0 Hz, 1H), 3.85 (s, 3H), 3.82 (s, 3H).

Step 4: (E)-tert-butyl 2-(3-(6-(3,4-dimethoxyphenyl) pyridin-3-yl)acrylamido)-4-(thiophen-2-yl)phenyl-carbamate (41)

A solution of acid 40 (0.10 g, 0.25 mmol), amine 4 (72.7 mg, 0.25 mmol) and BOP reagent (0.133 g, 3.0 mmol) in pyridine (2 mL) was stirred 18 h at room temperature. The reaction mixture was concentrated and the residue was purified by flash chromatography (eluent: 1:1 hexane:AcOEt) to give title compound 41 (0.14 g, 61% yield).

1H NMR (DMSO-d$_6$) δ (ppm): 9.82 (s, 1H), 8.85 (s, 1H), 8.61 (s, 1H), 8.05 (t, J=12.9 Hz, 2H), 7.89 (s, 1H), 7.75 to 7.73 (m, 2H), 7.70 (d, J=5.9 Hz, 1H), 7.66 (m, 1H), 7.51 (dd, J=5.1, 1.2 Hz, 1H), 7.48 to 7.46 (m, 1H), 7.42 (dd, J=3.7, 1.2 Hz, 1H), 7.12 (dd, J=5.1, 3.5 Hz, 1H), 7.07 (d, J=8.4 Hz, 2H), 3.86 (s, 3H), 3.82 (s, 3H), 1.48 (s, 9H).

Step 5: (E)-N-(2-Amino-5-(thiophen-2-yl)phenyl)-3-(6-(3,4-dimethoxyphenyl)pyridin-3-yl)acrylamide (42)

To a solution of compound 41 (85.2 mg, 0.15 mmol) in DCM (2 mL) was added neat trifluoroacetic acid (0.7 mL). The reaction was allowed to stir at room temperature for 2 h then concentrated, diluted with AcOEt, washed with saturated aqueous NaHCO$_3$, brine, dried over MgSO4, filtered and concentrated to give title compound 42 (38 mg, 54% yield).

1H NMR (DMSO-d$_6$) δ (ppm): 9.51 (s, 1H), 8.83 (s, 1H), 8.05 (s, J=2.3 Hz, 2H), 7.74 (s, 1H), 7.71 (d, J=8.4 Hz, 1H), 7.66 (d, J=9.8 Hz, 1H), 7.61 (s, 1H), 7.35 (dd, J=5.1, 1.2 Hz, 1H), 7.24 (dd, J=8.4, 2.2 Hz, 1H), 7.21 (dd, J=3.5, 1.2 Hz, 1H), 7.08 to 7.02 (m, 2H), 6.98 (s, 1H), 6.77 (d, J=8.2 Hz, 1H), 5.22 (s, 2H), 3.86 (s, 3H), 3.82 (s, 3H).

TABLE 2

Characterization of compounds prepared according to Scheme 2

| Cpd | Ex | R | Name | Characterization |
|---|---|---|---|---|
| 43 | 2b | 3,4,5-trimethoxyphenyl (MeO, MeO, OMe) | (E)-N-(2-amino-5-(thiophen-2-yl)phenyl)-3-(6-(3,4,5-trimethoxyphenyl)pyridin-3-yl)acrylamide | $^1$H NMR (DMSO-d$_6$) δ (ppm): 9.52 (s, 1H), 8.86 (s, 1H), 8.11 (d, J = 3.1 Hz, 2H), 7.67 (d, J = 2.3 Hz, 1H), 7.63 (s, 1H), 7.45 (s, 2H), 7.35 (dd, J = 5.1, 1.2 Hz, 1H), 7.26 to 7.23 (m, 1H), 7.21 (dd, J = 3.5, 1.2 Hz, 1H), 7.05 to 7.00 (m, 2H), 6.78 (d, J = 8.4 Hz, 1H), 5.22 (s, 2H), 3.89 (s, 6H), 3.72 (s, 3H). LRMS: 487.16 (calc) 488.3 (obs). |
| 44 | 2c | pyridin-3-yl | (E)-3-(2,3'-bipyridin-5-yl)-N-(2-amino-5-(thiophen-2-yl)phenyl)-acrylamide | $^1$H NMR (DMSO-d$_6$) δ (ppm): 9.54 (s, 1H), 9.30 (s, 1H), 8.94 (s, 1H), 8.64 (dd, J = 4.7, 1.6 Hz, 1H), 8.48 (d, J = 8.8 Hz, 1H), 8.16 (s, 2H), 7.68 (t, J = 3.3 Hz, 1H), 7.65 (s, 1H), 7.54 (dd, J = 8.2. 4.8 Hz, 1H), 7.35 (dd, J = 4.9, 0.98 Hz, 1H), 7.26 to 7.24 (m, 1H), 7.22 (dd, J = 3.5, 1.2 Hz, 1H), 7.08 (s, 1H), 7.04 (t, J = 3.5 Hz, 1H), 6.78 (d, J = 8.4 Hz, 1H). LRMS: 398.12 (calc) 399.2 (obs). |

Example 3a

N-(2-amino-5-(thiophen-2-yl)phenyl)-6-chloronicotinamide (47)

Example 3b

N-(2-amino-5-(thiophen-2-yl)phenyl)-6-(4-methylpiperazin-1-yl)nicotinamide (49)

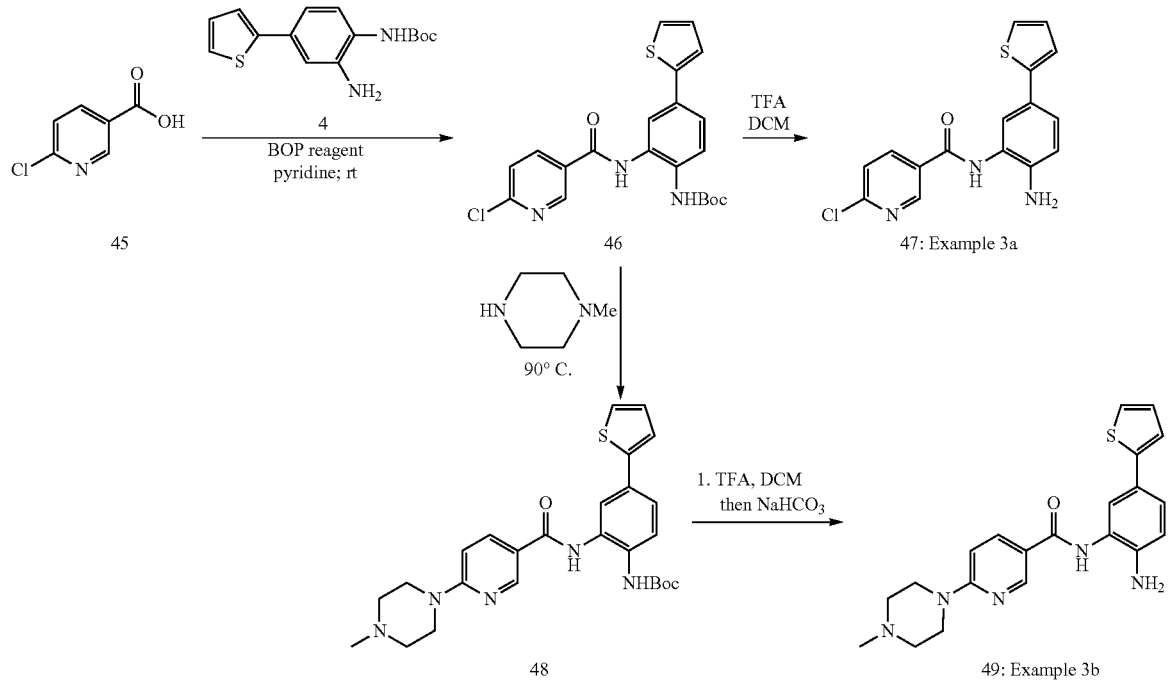

Scheme 3

Step 1: tert-Butyl 2-(6-chloronicotinamido)-4-(thiophen-2-yl)phenylcarbamate (46)

Following the same procedure as described in Example 1a, step 6 (scheme 1) but substituting compound 7 for compound 45, title compound 46 was obtained (75% yield).

$^1$H NMR (DMSO-d$_6$) δ ppm: 10.08 (s, 1H), 8.97 (d, J=2.3 Hz, 1H), 8.80 (s, 1H), 8.36 (dd, J=8.4, 2.5 Hz, 1H), 7.75 to 7.68 (m, 3H), 7.52 (dd, J=6.1, 2.2 Hz, 1H), 7.51 (t, J=2.5 Hz, 1H), 7.44 (dd, J=3.7, 1.2 Hz, 1H), 7.11 (dd, J=5.1, 3.7 Hz, 1H), 1.44 (s, 9H).

Step 2: N-(2-Amino-5-(thiophen-2-yl)phenyl)-6-chloronicotinamide (47)

Following the same procedure as described in Example 1a, step 7 (scheme 1), but substituting compound 8 for compound 46, the title compound 47 was obtained (21% yield).

$^1$H NMR: (DMSO-d$_6$) δ (ppm): 9.91 (s, 1H), 8.97 (d, J=2.2 Hz, 1H), 8.36 (dd, J=8.2, 2.3 Hz, 1H), 7.68 (d, J=8.2 Hz, 1H), 7.43 (s, 1H), 7.33 (d, J=5.1 Hz, 1H), 7.29 (dd, J=8.4, 2.0 Hz, 1H), 7.22 (d, J=3.3 Hz, 1H), 7.03 (t, J=3.7 Hz, 1H), 6.78 (d, J=8.4 Hz, 1H), 5.28 (s, 2H).

Step 3: tert-Butyl 2-(6-(4-methylpiperazin-1-yl)nicotinamido)-4-(thiophen-2-yl)phenylcarbamate (48)

A mixture of chloride 46 (0.15 g, 0.35 mmol) and N-methylpiperazine (0.5 mL, 4.5 mmol) was heated to 90° C. in a sealed tube for 18 h. The reaction mixture was then diluted with AcOEt, washed with saturated aqueous NaHCO$_3$, brine, dried over MgSO$_4$, filtered and concentrated. The residue was purified by flash chromatography (eluent: 2:1 AcOEt:hexane) to afford title compound 48 (65 mg, 38% yield).

$^1$H NMR: (DMSO-d$_6$) δ (ppm): 9.71 (s, 1H), 8.72 (s, 1H), 8.65 (s, 1H), 8.04 (d, J=8.8 Hz, 1H), 7.76 (s, 1H), 7.60 (d, J=8.6 Hz, 1H), 7.51 to 7.46 (m, 2H), 7.43 (d, J=3.5 Hz, 1H), 7.11 (t, J=3.7 Hz, 1H), 6.93 (d, J=8.8 Hz, 1H), 3.64 (s, 3H), 2.39 (m, 4H), 2.22 (m, 4H), 1.46 (s, 9H).

Step 4: N-(2-Amino-5-(thiophen-2-yl)phenyl)-6-(4-methylpiperazin-1-yl)nicotinamide (49)

Following the same procedure as described in Example 1a, Step 7, but substituting compound 8 for compound 48, the title compound 49 was obtained (19% yield).

$^1$H NMR: (DMSO-d$_6$) δ (ppm): 9.49 (s, 1H), 8.72 (d, J=2.2 Hz, 1H), 8.07 (d, J=9.0 Hz, 1H), 7.43 (s, 1H), 7.33 (d, J=5.1 Hz, 1H), 7.26 (d, J=8.4 Hz, 1H), 7.22 (d, J=9.5 Hz, 1H), 7.04 to 7.02 (m, 1H), 6.89 (d, J=9.2 Hz, 1H), 6.78 (d, J=8.2 Hz, 1H), 5.13 (s, 2H), 3.62 (s, 4H), 2.44 to 2.38 (m, 4H), 2.22 (s, 3H).

TABLE 3

Characterization of compounds prepared according to Scheme 3

| Cpd | Ex | R | Name | Characterization |
|---|---|---|---|---|
| 50 | 3c | (R)-3-(dimethylamino)pyrrolidin-1-yl | (R)-N-(2-amino-5-(thiophen-2-yl)phenyl)-6-(3-(dimethylamino)pyrrolidin-1-yl)nicotinamide | $^1$H NMR (DMSO-$d_6$) δ (ppm): 9.47 (s, 1H), 8.72 (d, J = 2.3 Hz, 1H), 8.05 (dd, J = 9.0, 2.3 Hz, 1H), 7.44 (d, J = 2.2 Hz, 1H), 7.34 (dd, J = 5.1, 1.2 Hz, 1H), 7.26 (dd, J = 8.4, 2.2 Hz, 1H), 7.23 (dd, J = 3.5, 1.2 Hz, 1H), 7.03 (dd, J = 5.1, 3.5 Hz, 1H), 6.78 (d, J = 8.4 Hz, 1H), 6.52 (d, J = 9.2 Hz, 1H), 5.11 (s, 2H), 3.37 to 3.35 (m, 1H), 3.19 to 3.12 (m, 2H), 2.80 to 2.74 (m, 2H), 2.20 (s, 6H), 2.18 to 2.12 (m, 1H), 1.85 to 1.78 (m, 1H). LRMS: 407.18 (calc) 408.2 (obs). |
| 51 | 3d | 4-morpholinopiperidin-1-yl | N-(2-amino-5-(thiophen-2-yl)phenyl)-6-(4-morpholinopiperidin-1-yl)nicotinamide | $^1$H NMR (DMSO-$d_6$) δ (ppm): 8.75 (d, J = 2.3 Hz, 1H), 8.09 (dd, J1 = 9.0 Hz, J2 = 2.3 Hz, 1H), 2.99 (d, J = 2.2 Hz, 1H), 7.34 (dd, J1 = 8.4 Hz, J2 = 2.2 Hz, 1), 7.21 (ddd, J1 = 9.6 Hz, J2 = 5.1 Hz, J3 = 1.0 Hz, 2H), 7.01 (dd, J1 = 5.1 Hz, J2 = 3.7 Hz, 1H), 6.88 (dd, J1 = 8.2 Hz, J2 = 5.1 Hz, 2H), 4.55 (d, J = 14 Hz, 2H), 3.73 (t, J = 4.5 Hz, 4H), 2.96 (td, J1 = 13 Hz, J2 = 2.2 Hz, 2H), 2.69 (bs, 4H), 2.62 (m, 1H), 2.04 (d, J = 12 Hz, 2H), 1.49 (qd, J1 = 12 Hz, J2 = 3.7 Hz, 2H). LRMS: 463.2 (calc) 464.1 (obs) |

Example 6a (S)—N-(2-Amino-5-(thiophen-2-yl)phenyl)-4-((2-(methoxymethyl)pyrrolidin-1-yl)methyl)benzamide (76)

Scheme 6

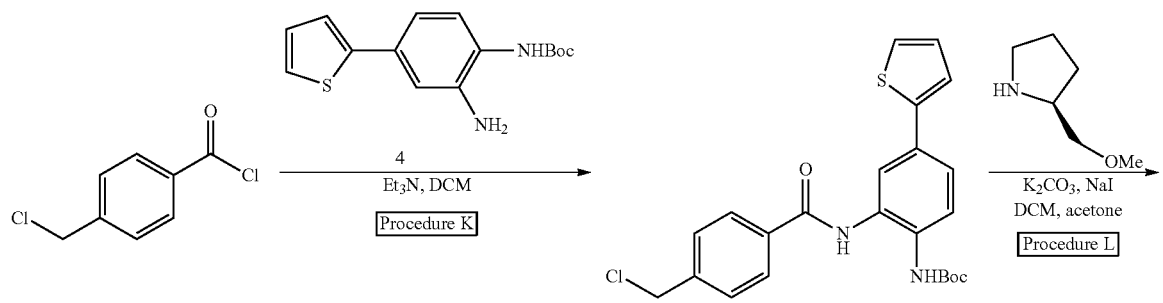

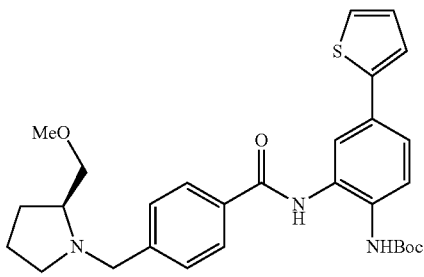

75

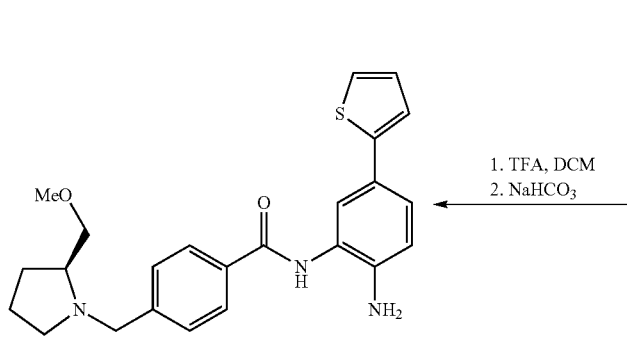

76: Example 6a

Step 1: tert-Butyl 2-(4-(chloromethyl)benzamido)-4-(thiophen-2-yl)phenylcarbamate (74)

To a suspension of amine 4 (0.45 g, 1.55 mmol) in DCM (6.84 mL), cooled to −20° C., was added triethylamine (0.65 mL, 4.65 mmol) followed by a solution of 4-(chloromethyl)benzoyl chloride 73 (0.322 g, 1.71 mmol) in DCM (2.28 mL) via canula. The cold bath was then removed and the reaction mixture was stirred at room temperature for 1 h, washed with saturated NH₄Cl, saturated NaHCO₃, brine, dried over MgSO₄, filtered and concentrated. The crude material was recrystallized from 30% AcOEt in hexane to give title compound 74 (0.431 g, 63% yield).

¹H NMR (DMSO-d₆) δ (ppm): 9.92 (s, 1H), 8.73 (s, 1H), 7.97 (s, J=8.2 Hz, 2H), 7.80 (d, J=1.9 Hz, 1H), 7.61 (d, J=8.4 Hz, 1H), 7.60 (d, J=8.4 Hz, 2H), 7.51 (dd, J=4.9, 1.0 Hz, 1H), 7.50 (dd, J=5.3, 2.3 Hz, 1H), 7.44 (dd, J=3.7, 1.3 Hz, 1H), 7.11 (d, J=5.1, 3.5 Hz, 1H), 4.84 (s, 2H), 1.44 (s, 9H).

Step 2: (S)-tert-Butyl 2-(4-((2-(methoxymethyl)pyrrolidin-1-yl)methyl)benzamido)-4-(thiophen-2-yl)phenylcarbamate (75)

To a solution of chloride 74 (0.30 g, 0.68 mmol) in DCM (7 mL) was added (S)-2-(methoxymethyl)pyrrolidine (86 mg, 0.75 mmol), K₂CO₃ (0.31 g, 2.24 mmol) and NaI (12 mg, 0.075 mmol). Acetone (3 mL) was added and the reaction mixture was heated to reflux for 3 days then concentrated. The residue was taken up in AcOEt, washed with H₂O, brine, dried over MgSO₄, filtered and concentrated to give title compound 75 (0.323 g, 91% yield).

¹H NMR (DMSO-d₆) δ (ppm): 9.87 (s, 1H), 8.72 (s, 1H), 7.91 (d, J=8.4 Hz, 2H), 7.80 (d, J=2.2 Hz, 1H), 7.59 (d, J=8.6 Hz, 1H), 7.51 (dd, J=4.9, 1.0 Hz, 1H), 7.49 (dd, J=8.4, 2.3 Hz, 1H), 7.45 (d, J=8.6 Hz, 2H), 7.44 (dd, J=3.7, 1.0 Hz, 1H), 7.11 (dd, J=12.5 Hz, 1H), 3.39 (q, J=5.7 Hz, 1H), 2.79 to 2.75 (m, 1H), 2.73 to 2.67 (m, 1H), 2.15 (q, J=7.6 Hz, 1H), 1.86 (dq, J=11.9, 7.8 Hz, 1H), 1.66 to 1.58 (m, 1H), 1.54 to 1.46 (m, 1H), 1.44 (s, 9H).

Step 3: (S)—N-(2-Amino-5-(thiophen-2-yl)phenyl)-4-((2-(methoxymethyl)pyrrolidin-1-yl)methyl)benzamide (76)

Following the same procedure as described in Example 1a, step 7 (scheme 1), but substituting compound 8 for 75, the title compound 76 was obtained (82% yield).

1H NMR (DMSO-d₆) δ (ppm): 9.69 (s, 1H), 7.93 (d, J=8.2 Hz, 2H), 7.45 (d, J=1.8 Hz, 1H), 7.41 (d, J=8.2 Hz, 2H), 7.33 (dd, J=5.1, 1.0 Hz, 1H), 7.28 (dd, 8.2, 2.2 Hz, 1H), 7.23 (dd, J=3.5, 1.0 Hz, 1H), 7.03 (dd, J=4.9, 3.5 Hz, 1H), 3.43-3.37 (m, 2H), 3.27-3.21 (m, 1H), 3.24 (s, 3H), 2.79-2.74 (m, 1H), 2.71-2.66 (m, 1H), 1.65-1.59 (m, 1H), 1.58-1.47 (m, 1H).

TABLE 6

Characterization of compounds prepared according to Scheme 6

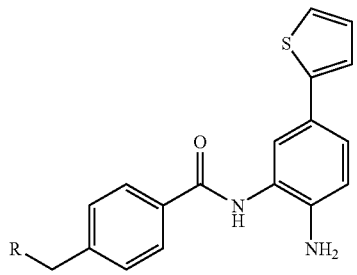

| Cpd | Ex | R | Name | Characterization |
|---|---|---|---|---|
| 77 | 6b | (4-morpholinopiperidin-1-yl) | N-(2-amino-5-(thiophen-2-yl)phenyl)-4-((4-morpholino-piperidin-1-yl)-methyl)-benzamide | $^1$H NMR (DMSO-$d_6$) δ (ppm): 9.83 (s, 1H), 8.08 (d, J = 7.4 Hz, 2H), 7.63-7.60 (m, 2H), 7.44 (d, J = 2.0 Hz, 1H), 7.35 (dd, J = 5.1, 1.0 Hz, 1H), 7.31 (dd, J = 8.2, 2.2 Hz, 1H), 7.23 (dd, J = 3.5, 1.0 Hz, 1H), 7.04 (dd, J = 5.1, 3.5 Hz, 1H), 6.81 (d, J = 8.4 Hz, 1H), 4.43-4.32 (m, 2H), 4.05-3.82 (m, 2H), 3.76-3.60 (m, 2H), 3.60-3.27 (m, 5H), 3.06-2.87 (m, 4H), 2.28-2.19 (m, 2H), 1.92-1.78 (m, 2H). LRMS: 476.6 (calc) 477.1 obs |
| 78 | 6c | (4-methylpiperazin-1-yl) | N-(2-amino-5-(thiophen-2-yl)phenyl)-4-((4-methylpiperazin-1-yl)methyl)-benzamide | $^1$H NMR (DMSO-$d_6$) δ (ppm): 9.70 (s, 1H), 7.94 (d, J = 8.0 Hz, 2H), 7.44 (d, J = 2.0 Hz, 1H), 7.41 (d, J = 8.2 Hz, 2H), 7.34 (dd, J = 5.1, 1.0 Hz, 1H), 7.28 (dd, J = 8.4, 2.3 Hz, 1H), 7.22 (J = 3.5, 1.2 Hz, 1H), 7.03 (dd, J = 5.1, 3.5 Hz, 1H), 6.79 (d, J = 8.4 Hz, 1H), 5.14 (s, 2H), 3.52 (s, 2H), 2.52-2.31 (m, 4H), 2.22-2.17 (m, 4H), 2.07 (s, 3H). LRMS: 406.6 (calc) 407.1 (obs) |
| 79 | 6d | (diethylamino) | N-(2-amino-5-(thiophen-2-yl)phenyl)-4-((diethylamino)-methyl)benzamide | $^1$H NMR (DMSO-$d_6$) δ (ppm): 9.69 (s, 1H), 7.93 (d, J = 7.4 Hz, 2H), 7.45 (d, J = 2.2 Hz, 1H), 7.43 (d, J = 8.6 Hz, 2H), 7.34 (dd, J = 5.1, 1.2 Hz, 1H), 7.28 (dd, J = 8.2, 2.2 Hz, 1H), 7.22 (dd, J = 3.7, 1.2 Hz, 1H), 7.03 (dd, J = 5.1, 3.5 Hz, 1H), 6.79 (d, J = 8.2 Hz, 1H), 5.14 (s, 2H), 3.58 (s, 2H), 2.45 (q, J = 7.2 Hz, 4H), 0.97 (t, J = 6.7 Hz, 6H). LRMS: 379.5 (calc) 380.1 (obs). |
| 80 | 6e | (4-(2-(1H-imidazol-1-yl)ethyl)piperazin-1-yl) | 4-((4-(2-(1H-imidazol-1-yl)ethyl)-piperazin-1-yl)-methyl)-N-(2-amino-5-(thiophen-2-yl)phenyl)-benzamide | $^1$H NMR (DMSO-$d_6$) δ (ppm): 9.70 (s, 1H), 7.95 (d, J = 8.0 Hz, 2H), 7.65 (s, 1H), 7.45 (d, J = 2.1 Hz, 1H), 7.41 (d, J = 8.2 Hz, 2H), 7.34 (dd, J = 5.1, 4.1 Hz, 1H), 7.28 (dd, J = 8.4, 2.2 Hz, 1H), 7.22 (dd, J = 3.5, 1.2 Hz, 1H), 7.17 (s, 1H), 7.03 (dd, J = 5.1, 3.5 Hz, 1H), 6.86 (s, 1H), 6.79 (d, J = 8.4 Hz, 1H), 5.14 (s, 2H), 4.04 (t, J = 6.5 Hz, 2H), 3.54 (s, 2H), 2.59 (t, J = 6.3 Hz, 2H), 2.47-2.38 (m, 8H). LRMS: 486.6 (calc) 487.1 (obs) |
| 81 | 6f | (S)-(3-(dimethylamino)pyrrolidin-1-yl) | (S)-N-(2-amino-5-(thiophen-2-yl)phenyl)-4-((3-(dimethylamino)-pyrrolidin-1-yl)methyl)-benzamide | $^1$H NMR (DMSO-$d_6$) δ (ppm): 9.70 (s, 1H), 7.94 (d, J = 8.2 Hz, 2H), 7.45 (d, J = 2.2 Hz, 1H), 7.41 (d, J = 8.4 Hz, 2H), 7.34 (dd, J = 5.1, 1.0 Hz, 1H), 7.28 (dd, J = 8.4, 2.2 Hz, 1H), 7.22 (dd, J = 3.5, 1.0 Hz, 1H), 7.03 (dd, J = 5.1, 3.7 Hz, 1H), 6.79 (d, J = 8.4 Hz, 1H), 5.14 (s, 2H), 3.66 (d, J = 13.4 Hz, 1H), 3.55 (d, J = 13.5 Hz, 1H), 2.72-2.60 (m, 2H), 2.60-2.54 (m, 1H), 2.48-2.41 (m, 1H), 2.28-2.22 (m, 1H), 1.88-1.79 (m, 1H), 1.63-1.55 (m, 1H). LRMS: 420.6 (calc) 421.1 (obs) |

TABLE 6-continued

Characterization of compounds prepared according to Scheme 6

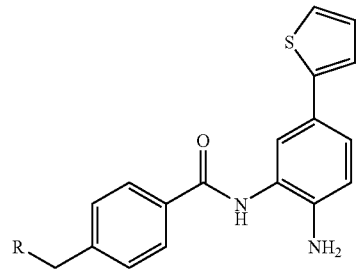

| Cpd | Ex | R | Name | Characterization |
|---|---|---|---|---|
| 82 | 6g | HO,,,/pyrrolidine | (S)-N-(2-amino-5-(thiophen-2-yl)phenyl)-4-((3-hydroxy-pyrrolidin-1-yl)methyl)-benzamide | $^1$H NMR (DMSO-$d_6$) δ (ppm): 9.71 (s, 1H), 7.94 (d, J = 8.0 Hz, 2H), 7.45 (d, J = 1.8 Hz, 1H), 7.42 (d, J = 8.0 Hz, 2H), 7.34 (dd, J = 5.1, 1.2 Hz, 1H), 7.28 (dd, J = 8.4, 2.2 Hz, 1H), 7.23 (dd, J = 3.5, 1.0 Hz, 1H), 7.03 (dd, J = 5.1, 1.6 Hz, 1H), 6.79 (d, J = 8.4 Hz, 1H), 5.14 (s, 2H), 4.74-4.68 (m, 1H), 4.23-4.17 (m, 1H), 3.69-3.57 (m, 2H), 2.72-2.36 (m, 1H), 2.62-2.53 (m, 1H), 2.43-2.36 (m, 1H), 2.34-2.29 (m, 1H), 1.99 (sext, J = 6.8 Hz, 1H), 1.58-1.50 (m, 1H). LRMS: 393.5 (calc) 394.10 (obs) |
| 83 | 6h | HO,/pyrrolidine | (R)-N-(2-amino-5-(thiophen-2-yl)phenyl)-4-((3-hydroxy-pyrrolidin-1-yl)methyl)-benzamide | $^1$H NMR (DMSO-$d_6$) δ (ppm): 9.71 (s, 1H), 7.94 (d, J = 8.2 Hz, 2H), 7.45 (d, J = 2.2 Hz, 1H), 7.43 (d, J = 8.2 Hz, 2H), 7.34 (dd, J = 5.1, 1.2 Hz, 1H), 7.28 (dd, J = 8.2, 2.2 Hz, 1H), 7.23 (dd, J = 3.5, 1.0 Hz, 1H), 7.03 (dd, J = 5.1, 3.5 Hz, 1H), 6.79 (d, J = 8.4 Hz, 1H), 5.14 (s, 2H), 4.76-4.69 (m, 1H), 4.24-4.16 (m, 1H), 3.70-3.57 (m, 2H), 2.72-2.63 (m, 1H), 2.63-2.53 (m, 1H), 2.46-2.36 (m, 1H), 2.35-2.28 (m, 1H), 1.99 (sext, J = 7.2 Hz, 1H), 1.59-1.52 (m, 1H). LRMS: 393.5 (calc) 394.1 (obs) |
| 84 | 6i | acetamido-pyrrolidine | (R)-4-((3-acetamido-pyrrolidin-1-yl)methyl)-N-(2-amino-5-(thiophen-2-yl)phenyl)-benzamide | $^1$H NMR (DMSO-$d_6$) δ (ppm): 9.70 (s, 1H), 8.00 (d, J = 6.9 Hz, 1H), 7.94 (d, J = 8.0 Hz, 2H), 7.45 (d, J = 2.2 Hz, 1H), 7.43 (d, J = 8.2 Hz, 2H), 7.34 (dd, J = 5.1, 1.2 Hz, 1H), 7.28 (dd, J = 8.2, 2.2 Hz, 1H), 7.23 (dd, J = 3.7, 1.2 Hz, 1H), 7.03 (dd, J = 5.1, 3.5 Hz, 1H), 6.79 (d, J = 8.4 Hz, 1H), 5.14 (s, 2H), 4.16-4.07 (m, 1H), 3.64 (d, J = 13.3 Hz, 1H), 6.79 (d, J = 8.4 Hz, 1H), 2.67-2.58 (m, 2H), 2.41-2.35 (m, 1H), 2.28 (dd, J = 9.4, 4.3 Hz, 1H), 2.11-2.03 (m, 1H), 1.75 (s, 3H), 1.60-1.50 (m, 1H). LRMS: 434.6 (calc) 435.1 (obs) |
| 85 | 6j | pyridinyl-piperazine | N-(2-amino-5-(thiophen-2-yl)phenyl)-4-((4-(pyridin-4-yl)piperazin-1-yl)methyl)-benzamide | $^1$H NMR (DMSO-$d_6$) δ (ppm): 9.71 (s, 1H), 8.13 (d, J = 6.7 Hz, 2H), 7.97 (d, J = 8.0 Hz, 2H), 7.46 (d, J = 8.2 Hz, 2H), 7.45 (s, 1H), 7.34 (dd, J = 5.1, 1.2 Hz, 1H), 7.28 (dd, J = 8.4, 2.2 Hz, 1H), 7.23 (dd, J = 3.5, 1.2 Hz, 1H), 7.03 (dd, J = 5.1, 1.6 Hz, 1H), 6.79 (d, J = 8.4 Hz, 2H), 6.79 (d, J = 4.6 Hz, 1H), 5.14 (s, 2H), 3.60 (s, 2H), 3.36-3.28 (m, 8H). LRMS: 469.6 (calc) 470.1 (obs) |
| 86 | 6k | pyrrolidinylmethyl-pyrrolidine | (S)-N-(2-amino-5-(thiophen-2-yl)phenyl)-4-((2-(pyrrolidin-1-ylmethyl)-pyrrolidin-1-yl)methyl)-benzamide | $^1$H NMR (DMSO-$d_6$) δ (ppm): 9.74 (s, 1H), 7.97 (d, J = 8.0 Hz, 2H), 7.47 (d, J = 8.4 Hz, 2H), 7.45 (d, J = 2.0 Hz, 1H), 7.34 (dd, J = 5.1, 1.2 Hz, 1H), 7.29 (dd, J = 8.2, 2.2 Hz, 1H), 7.03 (dd, J = 5.1, 3.5 Hz, 1H), 6.80 (d, J = 8.4 Hz, 1H), 5.15 (s, 2H), 4.13 (d, J = 13.5 Hz, 1H), 4.47 (d, J = 13.9 Hz, 1H), 3.33-3.20 (m, 5H), 3.16-3.12 (m, 1H), 3.08-2.96 (m, 1H), 2.84-2.80 (m, 1H), 2.33-2.27 (m, 1H), 2.12-2.02 (m, 1H), 1.96-1.88 (m, 4H), 1.78-1.63 (m, 3H). LRMS: 460.6 (calc) 461.2 (obs). |

TABLE 6-continued

Characterization of compounds prepared according to Scheme 6

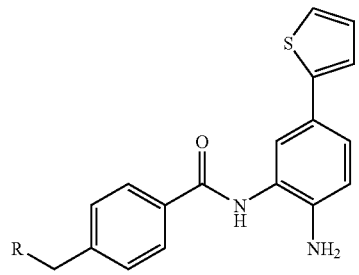

| Cpd | Ex | R | Name | Characterization |
|---|---|---|---|---|
| 87 | 6l | (acetamido-pyrrolidinyl-methyl group) | (S)-4-((3-acetamido-pyrrolidin-1-yl)methyl)-N-(2-amino-5-(thiophen-2-yl)phenyl)-benzamide | $^1$H NMR (DMSO-$d_6$) δ (ppm): 9.69 (s, 1H), 7.99 (d, J = 6.3 Hz, 1H), 7.94 (d, J = 8.2 Hz, 2H), 7.45 (d, J = 2.2 Hz, 1H), 7.43 (d, J = 8.4 Hz, 2H), 7.34 (dd, J = 5.1, 1.2 Hz, 1H), 7.28 (dd, J = 8.2, 2.2 Hz, 1H), 7.22 (dd, J = 3.5, 1.2 Hz, 1H), 7.03 (dd, J = 5.1, 3.5 Hz, 1H), 6.79 (d, J = 8.4 Hz, 1H), 5.14 (s, 2H), 4.17-4.07 (m, 2H), 3.64 (d, J = 13.3 Hz, 1H), 3.60 (d, J = 13.7 Hz, 1H), 2.66-2.57 (m, 2H), 2.39 (q, J = 8.6 Hz, 1H), 2.28 (dd, J = 9.2, 4.1 Hz, 1H), 2.33-2.03 (m, 1H), 1.75 (s, 3H), 1.55 (sext, J = 6.8 Hz, 1H). LRMS: 434.6 (calc) 435.1 (obs). |
| 88 | 6m | (methyl(pyridin-3-ylmethyl)amino group) | N-(2-amino-5-(thiophen-2-yl)phenyl)-4-((methyl(pyridin-3-ylmethyl)amino)methyl)-benzamide | $^1$H NMR (DMSO-$d_6$) δ (ppm): 9.70 (s, 1H), 8.53 (s, 1H), 8.47 (dd, J = 4.7, 1.8 Hz, 1H), 7.97 (d, J = 8.0 Hz, 2H), 7.76 (d, J = 7.8, 4.7 Hz, 1H), 7.47 (d, J = 8.0 Hz, 2H), 7.45 (d, J = 2.0 Hz, 1H), 7.37 (dd, J = 7.8, 4.7 Hz, 1H), 7.34 (dd, J = 4.9, 1.0 Hz, 1H), 7.28 (dd, J = 8.2, 2.2 Hz, 1H), 7.22 (dd, J = 3.5, 1.0 Hz, 1H), 7.03 (dd, J = 5.3, 3.7 Hz, 1H), 6.79 (d, J = 8.2 Hz, 1H), 5.13 (s, 2H), 3.59 (s, 2H), 3.55 (s, 2H), 2.09 (s, 3H). LRMS: 428.6 (calc) 429.1 (obs). |
| 89 | 6n | (4-(pyridin-2-yl)piperazin-1-yl group) | N-(2-amino-5-(thiophen-2-yl)phenyl)-4-((4-(pyridin-2-yl)piperazin-1-yl)methyl)-benzamide | $^1$H NMR (DMSO-$d_6$) δ (ppm): 9.71 (s, 1H), 8.08 (dd, J = 4.9, 1.2 Hz, 1H), 7.97 (d, J = 8.0 Hz, 1H), 7.51 (dd, J = 7.2, 2.2 Hz, 1H), 7.49 (dd, J = 6.9, 1.8 Hz, 1H), 7.47 (d, J = 8.2 Hz, 2H), 7.34 (dd, J = 5.1, 1.2 Hz, 1H), 7.28 (d, J = 8.1, 2.3 Hz, 1H), 7.23 (dd, J = 3.7, 1.2 Hz, 1H), 7.03 (dd, J = 5.1, 3.5 Hz, 1H), 6.79 (d, J = 8.4 Hz, 1H), 6.61 (dd, J = 6.5, 4.9 Hz, 1H), 5.15 (s, 2H), 3.59 (s, 2H), 3.49-3.46 (m, 4H), 2.48-2.45 (m, 4H). LRMS: 469.6 (calc) 470.2 (obs). |
| 90 | 6o | (pyrrolidin-1-yl group) | N-(2-amino-5-(thiophen-2-yl)phenyl)-4-(pyrrolidin-1-ylmethyl)-benzamide | $^1$H NMR (DMSO-$d_6$) δ (ppm): 9.71 (s, 1H), 7.95 (d, J = 7.0 Hz, 2H), 7.45 (s, 3H), 7.34 (dd, J = 5.1, 1.0 Hz, 1H), 7.28 (dd, J = 8.4, 2.2 Hz, 1H), 7.23 (dd, J = 9.3, 0.78 Hz, 1H), 7.03 (dd, J = 5.1, 3.7 Hz, 1H), 6.80 (d, J = 8.4 Hz, 1H), 5.14 (s, 2H), 3.65 (bs, 2H), 2.47 (bs, 4H), 1.72 (bs, 4H). LRMS: 377.5 (calc) 378.1 (obs). |
| 91 | 6p | (4-benzylpiperazin-1-yl group) | N-(2-amino-5-(thiophen-2-yl)phenyl)-4-((4-benzylpiperazin-1-yl)methyl)-benzamide | $^1$H NMR (DMSO-$d_6$) δ (ppm): 9.70 (s, 1H), 7.94 (d, J = 8.2 Hz, 2H), 7.45 (s, 1H), 7.41 (d, J = 8.0 Hz, 2H), 7.34 (d, J = 5.1 Hz, 1H), 7.32-7.26 (m, 5H), 7.23-7.20 (m, 2H), 7.03 (dd, J = 5.1, 3.7 Hz, 1H), 6.79 (d, J = 8.4 Hz, 1H), 5.14 (s, 2H), 3.53 (s, 2H), 3.44 (s, 2H), 2.48-2.37 (m, 8H). LRMS: 482.7 (calc) 483.1 (obs). |
| 92 | 6q | ((2R,5R)-2,5-dimethylpyrrolidin-1-yl group) | N-(2-amino-5-(thiophen-2-yl)phenyl)-4-(((2R,5R)-2,5-dimethyl-pyrrolidin-1-yl)methyl)-benzamide | $^1$H NMR (DMSO-$d_6$) δ (ppm): 9.18 (s, 1H), 8.02 (d, J = 8.0 Hz, 2H), 7.66 (d, J = 2.5 Hz, 1H), 7.59-7.51 (m, 2H), 7.34 (dd, J = 8.2, 2.2 Hz, 1H), 7.29 (dd, J = 5.3, 1.2 Hz, 1H), 7.25 (dd, J = 3.5, 1.2 Hz, 1H), 7.04 (dd, J = 5.1, 3.5 Hz, 1H), 6.92 (d, J = 8.4 Hz, 1H), 4.87 (bs, 2H), 3.93 (d, J = 12.5 Hz, 1H), 3.67 (d, J = 12.5 Hz, 1H), 3.05 (bs, 2H), 2.05 (bs, 2H), 1.38 (bs, 2H), 0.99 (bs, 6H). LRMS: 405.6 (calc) 406.1 (obs). |

Example 7a

(E)-N-(2-Amino-5-(thiophen-2-yl)phenyl)-3-(4-(morpholinomethyl)phenyl)acrylamide (96)

with 5% KHSO$_4$, saturated NaHCO$_3$, dried over MgSO$_4$, filtered and concentrated to provide title compound 94 (0.415 g, 24% yield) after purification by flash chromatography (eluent: 30% to 50% AcOEt in hexanes). LRMS: 448.2 (calc) 471.0 (M+Na, obs)

Scheme 7

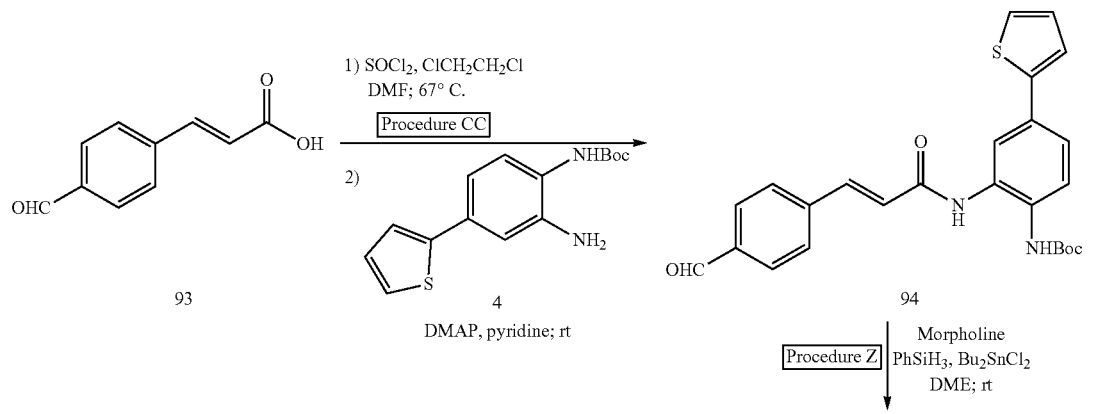

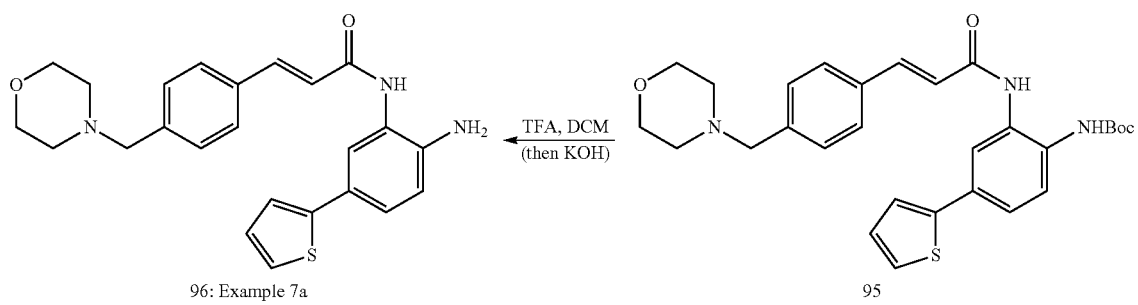

96: Example 7a

95

Step 1: (E)-tert-Butyl 2-(3-(4-formylphenyl)acrylamido)-4-(thiophen-2-yl)phenyl-carbamate (94)

A suspension of (E)-3-(4-formylphenyl)acrylic acid 93 (1.046 g, 5.94 mmol) in 1,2-dichloroethane (30 mL) was treated with neat thionyl chloride (SOCl$_2$) (0.9 mL, 12.3 mmol) and stirred at 67° C. then dimethyl formamide (0.3 mL) was slowly added; and the reaction mixture was allowed to stir at 67° C. for 30 min, cooled to room temperature, concentrated, diluted with dry benzene (40 mL) and concentrated again. The yellow residue was stored under vacuum for 3 h then suspended in pyridine (25 mL) and treated with amine 4 (1.113 g, 3.83 mmol) and 4-dimethylamino pyridine (DMAP) (156 mg). The suspension was stirred at room temperature for 3 days, diluted with H$_2$O (10 mL) then stirred for additional 5 h. The solution was diluted with DCM, washed

Step 2: (E)-tert-Butyl 2-(3-(4-(morpholinomethyl)phenyl)acrylamido)-4-(thiophen-2-yl)phenylcarbamate (95)

A mixture of aldehyde 94 (0.205 g, 0.458 mmol) and dibutyltin dichloride (87 mg, 0.28 mmol) was suspended in ethyleneglycol dimethylether (1.5 mL) and stirred for 15 minutes then treated with phenyl silane (0.15 mL, 1.18 mmol) and the yellow suspension was stirred at room temperature for 15 h. The reaction mixture was quenched with MeOH, stirred for 3 h, concentrated then purified by column chromatography (eluent: 5% isopropanol in DCM) followed by trituration with a diethyl ether and pentane mixture to provide title compound 95 (0.124 g, 100% yield). LRMS: 519.2 (calc) 520.1 (obs)

Step 3: (E)-N-(2-Amino-5-(thiophen-2-yl)phenyl)-3-(4-(morpholinomethyl)phenyl)-acrylamide (96)

Following the same procedure as described in Example 1, step 7 (scheme 1), but substituting compound 8 for compound 95, the title compound 96 was obtained (0.161 g, 67% yield).

¹H NMR (DMSO-d₆) δ (ppm): 9.46 (s, 1H), 7.70 (d, J=2.2 Hz, 1H), 7.60 to 7.55 (m, 3H), 7.40 to 7.35 (m, 3H), 7.26 to 7.22 (m, 2H), 7.05 (dd, J=5.1, 3.5 Hz, 1H), 6.89 (d, J=15.7 Hz, 1H), 6.78 (d, J=8.4 Hz, 1H), 5.22 (s, 2H), 3.58 (t, J=4.5 Hz, 4H), 3.49 (s, 2H), 2.36 (m, 4H). LRMS: 419.2 (calc) 420.0 (obs)

Example 8a (S)—N-(2-Amino-5-(thiophen-2-yl)phenyl)-4-(3-(dimethylamino)pyrrolidin-1-yl)benzamide (101)

¹H NMR (DMSO-d₆) δ (ppm): 7.67 (d, J=9.0 Hz, 2H), 6.52 (d, J=9.0 Hz, 2H), 3.50 (dd, J=9.8, 7.2 Hz, 1H), 3.45 to 3.39 (m, 1H), 3.30 to 3.24 (m, 1H), 3.06 (t, J=8.2 Hz, 1H), 2.83 to 2.75 (m, 1H), 2.20 (s, 6H), 2.17 to 2.14 (m, 1H), 1.86 to 1.76 (m, 1H), 1.51 (s, 9H).

Step 2: (S)-4-(3-(Dimethylamino)pyrrolidin-1-yl)benzoic acid (99)

A solution of tert-butyl ester 98 (0.595 g, 2.05 mmol) in 1:1 trifluoroacetic acid:DCM (6 mL) was stirred at room tem-

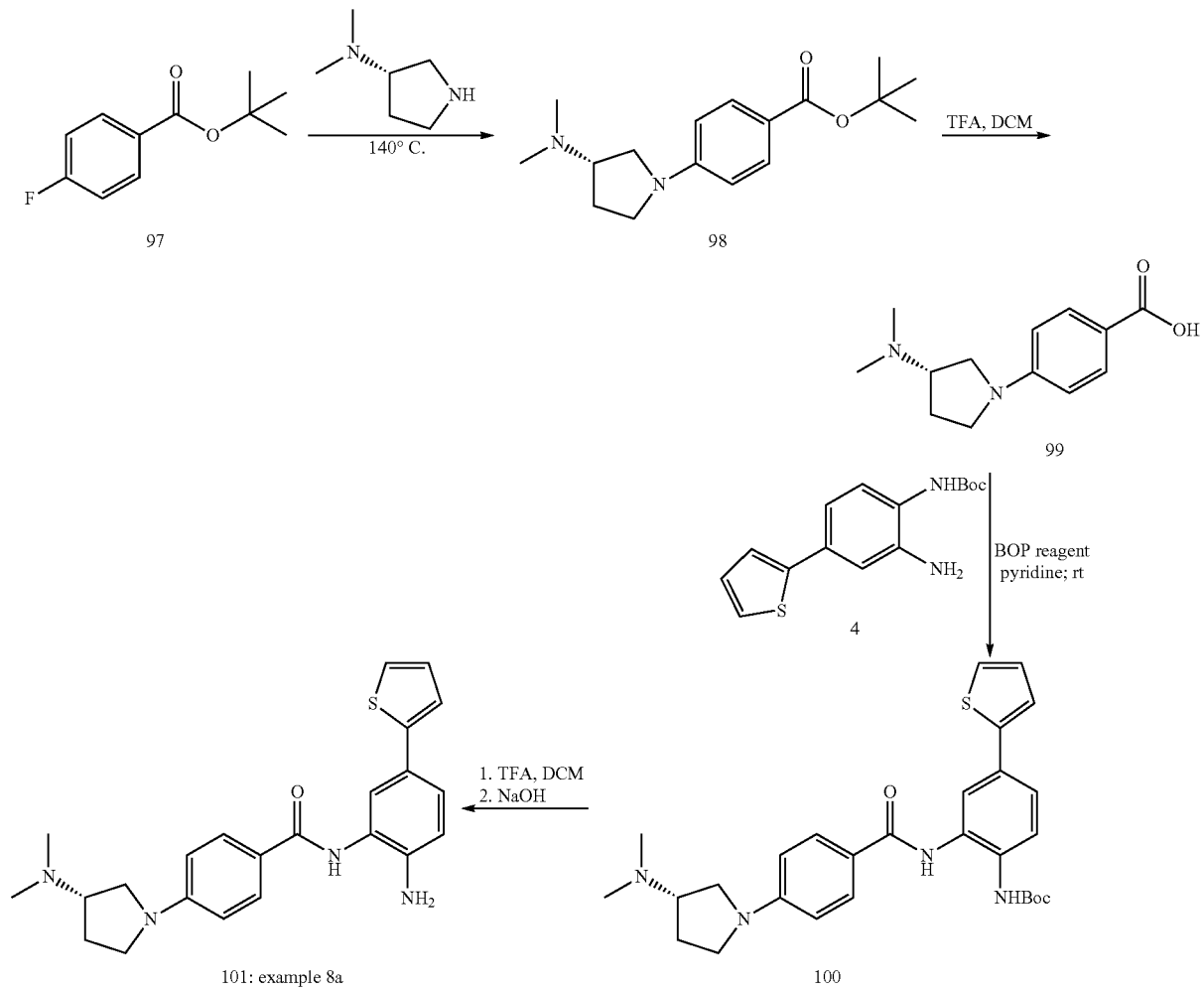

Scheme 8 perature for 3 h then concentrated to give title compound 99 (used as is in the next reaction). LRMS: 234.14 (calc) 235.1 (obs)

Step 3: (S)-tert-Butyl 2-(4-(3-(dimethylamino)pyrrolidin-1-yl)benzamido)-4-(thiophen-2-yl)phenylcarbamate (100)

Following the same procedure as described in Example 1a, step 6 (scheme 1) and using compound 4 but substituting compound 7 for compound 99, the title compound 100 was obtained (0.407 g, 68% yield) [after flash chromatography (eluent: 10% isopropanol in DCM with 0.1% triethylamine)].

Step 1: (S)-tert-Butyl 4-(3-(dimethylamino)pyrrolidin-1-yl)benzoate (98)

A mixture of fluoride 97 (2.196 g, 11.2 mmol) and (S)—N,N-dimethylpyrrolidin-3-amine (1.369 g, 11.99 mmol) was stirred at 140° C. under nitrogen atmosphere for 3 h then diluted with DCM, washed with saturated NaHCO₃, dried over MgSO₄, filtered and concentrated. The crude compound was purified by flash chromatography (eluent: 50% AcOEt in DCM then 50% isopropanol in DCM with 0.1% triethylamine) to give title compound 98 (1.36 g, 42% yield).

1H NMR (DMSO-d₆) δ (ppm): 9.63 (s, 1H), 8.67 (s, 1H), 7.82 (d, J=8.8 Hz, 2H), 7.78 (d, J=2.0 Hz, 1H), 7.54 (d, J=8.4 Hz, 1H), 7.50 (dd, J=8.4 Hz, 1H), 7.46 (d, J=2.2 Hz, 1H), 7.45 to 7.42 (m, 1H), 7.12 to 7.09 (m, 1H), 6.60 (d, J=9.0 Hz, 2H), 3.56 to 3.52 (m, 1H), 3.46 (t, J=8.8 Hz, 1H), 3.92 to 3.27 (m, 1H), 3.16 to 3.04 (m, 1H), 2.83 to 2.76 (m, 1H), 2.21 (s, 6H), 2.16 (m, 1H), 1.87 to 1.77 (m, 1H), 1.46 (s, 9H).

Step 4: (S)—N-(2-Amino-5-(thiophen-2-yl)phenyl)-4-(3-(dimethylamino)pyrrolidin-1-yl)benzamide (101)

Following the same procedure as described in Example 1a, step 7 (scheme 1), but substituting compound 8 for compound 100, the title compound 101 was obtained (0.229 g, 70% yield). [Crude product was triturated with diethyl ether while the mother liquor was concentrated and purified by flash chromatography (eluent: 5% to 10% isopropanol in DCM)].

¹H NMR (DMSO-d₆) δ (ppm): 9.41 (s, 1H), 7.86 (d, J=8.6 Hz, 2H), 7.44 (d, J=2.2 Hz, 1H), 7.34 (dd, J=5.1, 0.98 Hz, 1H), 7.25 (dd, J=8.2, 2.2 Hz, 1H), 7.23 (dd, J=3.5, 0.98 Hz, 1H), 7.04 to 7.02 (m, 1H), 6.79 (d, J=8.4 Hz, 1H), 6.58 (d, J=8.8 Hz, 2H), 5.07 (s, 2H), 3.56 to 3.51 (m, 1H), 3.46 (t, J=8.4 Hz, 1H), 3.32 to 3.27 (m, 1H), 3.09 (t, J=8.2 Hz, 1H), 2.84 to 2.76 (m, 1H), 2.22 (s, 6H), 2.19 to 2.16 (m, 1H), 1.88 to 1.78 (m, 1H). LRMS: 406.1 (calc), 407.1 (obs).

TABLE 7

Characterization of compounds prepared according to Scheme 8

| Cpd | Ex | R₁ | R₂ | Name | Characterization |
|---|---|---|---|---|---|
| 102 | 8b | 4-isopropyl-piperazin-1-yl | thiophen-2-yl | N-(2-amino-5-(thiophen-2-yl)phenyl)-4-(4-isopropyl-piperazin-1-yl)benzamide | ¹H NMR (DMSO-d₆) δ (ppm): 9.50 (s, 1H), 7.89 (d, J = 9.0 Hz, 2H), 7.46 (d, J = 2.2 Hz, 1H), 7.36 (dd, J = 5.1, 1.2 Hz, 1H), 7.28 (dd, J = 8.2, 2.2 Hz, 1H), 7.24 (dd, J = 3.5, 0.98 Hz, 1H), 7.05 (dd, J = 5.1, 3.5 Hz, 1H), 7.00 (d, J = 9.0 Hz, 2H), 6.80 (d, J = 8.2 Hz, 1H), 5.10 (s, 2H), 3.28 to 3.26 (m, 4H), 2.70 (m, 1H), 2.58 (m, 4H), 1.01 (d, J = 6.5 Hz, 6H). LRMS: 420.2 (calc) 421.2 (obs). |
| 103 | 8c | 4-cyclopentyl-piperazin-1-yl | thiophen-2-yl | N-(2-amino-5-(thiophen-2-yl)phenyl)-4-(4-cyclopentyl-piperazin-1-yl)-benzamide | ¹H NMR (DMSO-d₆) δ (ppm): 9.51 (s, 1H), 7.89 (d, J = 8.4 Hz, 2H), 7.45 (d, J = 2.3 Hz, 1H), 7.36 (dd, J = 5.1, 0.98 Hz, 1H), 7.28 (dd, J = 8.2, 2.2 Hz, 1H), 7.24 (dd, J = 3.5, 1.2 Hz, 1H), 7.05 (dd, J = 5.1, 3.5 Hz, 1H), 7.01 (m, 2H), 6.81 (d, J = 8.4 Hz, 1H), 5.10 (s, 2H), 3.31 to 3.28 (m, 4H), 2.55 to 2.52 (m, 4H), 1.82 (m, 2H), 1.64 (m, 3H), 1.53 (m, 2H), 1.37 to 1.34 (m, 2H). LRMS: 446.2 (calc) 447.2 (obs). |
| 104 | 8d | 4-morpholino-piperidin-1-yl | thiophen-2-yl | N-(2-amino-5-(thiophen-2-yl)phenyl)-4-(4-morpholino-piperidin-1-yl)benzamide | ¹H NMR (DMSO-d₆) δ (ppm): 9.49 (s, 1H), 7.87 (d, J = 9.0 Hz, 2H), 7.45 (d, J = 2.2 Hz, 1H), 7.36 (dd, J = 5.1, 1.2 Hz, 1H), 7.28 (dd, J = 8.4, 2.3 Hz, 1H), 7.24 (dd, J = 3.5, 1.2 Hz, 1H), 7.05 (dd, J = 5.1, 3.7 Hz, 1H), 7.00 (d, J = 9.2 Hz, 2H), 6.80 (d, J = 8.4 Hz, 1H), 5.09 (s, 2H), 3.92 (d, J = 13.7 Hz, 2H), 3.57 (t, J = 4.3 Hz, 4H), 2.81 (t, J = 11.3 Hz, 2H), 2.48 to 2.46 (m, 4H), 2.36 to 2.32 (m, 1H), 1.87 to 1.84 (m, 2H), 1.49 to 1.41 (m, 2H). LRMS: 462.2 (calc) 463.2 (obs). |
| 105 | 8e | 4-(pyrrolidin-1-yl)piperidin-1-yl | thiophen-2-yl | N-(2-amino-5-(thiophen-2-yl)phenyl)-4-(4-(pyrrolidin-1-yl)piperidin-1-yl)benzamide | ¹H NMR (DMSO-d₆) δ (ppm): 9.49 (s, 1H), 7.88 (d, J = 9.0 Hz, 2H), 7.45 (d, J = 2.2 Hz, 1H), 7.36 (dd, J = 5.1, 1.2 Hz, 1H), 7.28 (dd, J = 8.4, 2.3 Hz, 1H), 7.25 (dd, J = 3.7, 1.2 Hz, 1H), 7.05 (dd, J = 5.1, 3.5 Hz, 1H), 7.00 (d, J = 9.2 Hz, 2H), 6.80 (d, J = 8.4 Hz, 1H), 5.09 (s, 2H), 3.81 (m, 2H), 3.31 to 3.28 (m, 2H), 2.87 (t, J = 11.0 Hz, 2H), 2.67 to 2.66 (m, 1H), 2.46 to 2.45 (m, 1H), 2.33 to 2.32 (m, 1H), 1.91 (m, 2H), 1.69 (m, 4H), 1.49 to 1.47 (m, 2H). LRMS: 446.2 (calc) 447.2 (obs). |

TABLE 7-continued

Characterization of compounds prepared according to Scheme 8

| Cpd | Ex | R₁ | R₂ | Name | Characterization |
|---|---|---|---|---|---|
| 106 | 8f | (dimethylaminoethylthio) | (thiophen-2-yl) | N-(2-amino-5-(thiophen-2-yl)phenyl)-4-(2-(dimethylamino)ethylthio)-benzamide | $^1$H NMR (Acetone-d$_6$) δ (ppm): 9.33 (bs, 1H), 8.14 (d, J = 8.4 Hz, 2H), 7.77 (d, J = 2.3 Hz, 1H), 7.60 (d, j = 8.4 Hz, 2H), 7.48 (dd, J = 8.4, 2.2 Hz, 1H), 7.42 (dd, J = 5.1, 1.2 Hz, 1H), 7.37 (dd, J = 3.7, 1.2 Hz, 1H), 7.18 (dd, J = 5.1, 3.5 Hz, 1H), 7.05 (d, J = 8.4 Hz, 1H), 4.99 (bs, 2H), 3.41-3.37 (m, 2H), 2.87 (t, J = 7.4 Hz, 2H), 2.50 (s, 6H). LRMS: 397.56 (calc) 398.1 (obs). |
| 107 | 8g | (diethylaminoethylthio) | (thiophen-2-yl) | N-(2-amino-5-(thiophen-2-yl)phenyl)-4-(2-(diethylamino)-ethylthio)-benzamide | $^1$H NMR (DMSO-d$_6$) δ (ppm): 9.69 (s, 1H), 7.92 (d, J = 8.4 Hz, 2H), 7.44 (d, J = 2.0 Hz, 1H), 7.41 (d, J = 8.6 Hz, 2H), 7.34 (dd, J = 5.1, 1.2 Hz, 1H), 7.28 (dd, J = 8.4, 2.3 Hz, 1H), 7.22 (d, J = 1.2 Hz, 1H) 7.03 (dd, J = 5.1, 3.7 Hz, 1H), 6.79 (d, J = 8.4 Hz, 1H), 5.14 (s, 2H), 3.12 (t, J = 6.8 Hz, 2H), 2.68-2.62 (m, 2H), 2.48 (q, J = 7.2 Hz, 4H), 0.94 (t, J = 7.0 Hz, 6H). LRMS: 425.62 (calc) 426.1 (obs). |
| 108 | 8h | 4-(2-methoxyethyl)-piperazin-1-yl | (thiophen-2-yl) | N-(2-amino-5-(thiophen-2-yl)phenyl)-4-(4-(2-methoxyethyl)-piperazin-1-yl)benzamide | $^1$H NMR (Acetone-d$_6$) δ (ppm): 8.01 (d, J = 9.0 Hz, 2H), 7.68 (d, J = 2.3 Hz, 1H), 7.38 (dd, J = 3.5, 1.2 Hz, 1H), 7.10-7.07 (m, 3H), 6.95 (d, J = 8.2 Hz, 1H), 3.61 (t, J = 5.7 Hz, 2H), 3.44-3.38 (m, 2H), 3.35 (s, 3H), 2.80-2.65 (m, 8H). LRMS: 436.58 (calc) 437.1 (obs). |
| 109 | 8i | 4-(pyridin-4-yl)piperazin-1-yl | (thiophen-2-yl) | N-(2-amino-5-(thiophen-2-yl)phenyl)-4-(4-(pyridin-4-yl)piperazin-1-yl)benzamide | $^1$H NMR (DMSO-d$_6$) δ (ppm): 9.55, (s, 1H), 8.22 (d, J = 6.1 Hz, 2H), 7.93 (d, J = 9.0 Hz, 2H), 7.46 (d, J = 2.2 Hz, 1H), 7.36 (dd, J = 5.1, 1.2 Hz, 1H), 7.29 (dd, J = 8.2, 2.2 Hz, 1H), 7.25 (dd, J = 3.5, 1.2 Hz, 1H), 7.07 to 7.04 (m, 3H), 6.99 (d, J = 6.3 Hz, 2H), 6.81 (d, J = 8.4 Hz, 1H), 5.11 (s, 2H), 3.61 (t, J = 4.3 Hz, 4H), 3.49 to 3.46 (m, 4H). LRMS: 455.1 (calc) 456.0 (obs). |
| 110 | 8j | 4-(pyridin-4-yl)piperazin-1-yl | (5-chlorothiophen-2-yl) | N-(2-amino-5-(5-chloro-thiophen-2-yl)phenyl)-4-(4-(pyridin-4-yl)piperazin-1-yl)benzamide | $^1$H NMR (DMSO-d$_6$) δ (ppm): 9.53 (s, 1H), 8.20 (d, J = 6.3 Hz, 2H), 8.16 (s, 1H, from formic acid salt), 7.92 (d, J = 9.0 Hz, 2H), 7.40 (d, J = 2.2 Hz, 1H), 7.23 (dd, J = 8.4, 2.3 Hz, 1H), 7.11 (d, J = 3.9 Hz, 1H), 7.08 to 7.05 (m, 3H), 6.90 (d, J = 6.5 Hz, 2H), 6.80 (d, J = 8.4 Hz, 1H), 5.20 (s, 2H), 3.53 to 3.50 (m, 4H), 3.46 to 3.44 (m, 4H). LRMS: 490.2 (calc) 490.0 and 492.0 (obs). |

Example 10a

N-(2-Amino-5-(thiophen-2-yl)phenyl)-2-morpholinopyrimidine-5-carboxamide (124)

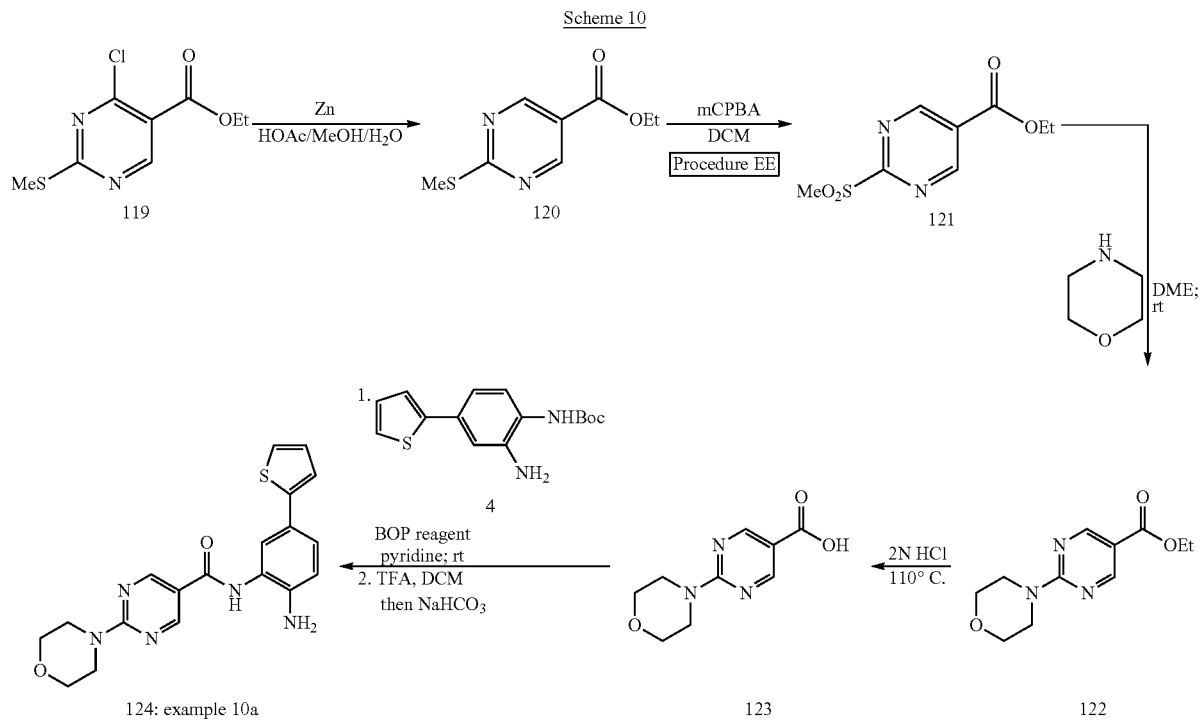

Scheme 10

Step 1: Ethyl 2-(methylthio)pyrimidine-5-carboxylate (120)

A solution of chloride 119 (1.51 g, 6.5 mmol) in acetic acid (5 mL) was treated with Zn(0) dust (0.969 g, 14.82 mmol). The suspension was stirred at room temperature for 24 h then diluted with DCM, filtered through Celite®, and concentrated. The residue was taken up in DCM, washed with saturated NaHCO3, dried over MgSO4, filtered and concentrated to give title compound 120 (0.424 g, 33% yield).

1H NMR (DMSO-$d_6$) δ (ppm): 9.00 (s, 1H), 4.36 to 4.29 (m, 2H), 3.33 (s, 1H), 2.58 (s, 3H), 1.35-1.32 (m, 3H).

Step 2: Ethyl 2-(methylsulfonyl)pyrimidine-5-carboxylate (121)

A solution of sulfide 120 (0.424 g, 2.14 mmol) in DCM (9 mL) was treated with a solution of 3-chloroperoxybenzoic acid (mCPBA) (2.0 g) in DCM (9 mL) then the reaction mixture was stirred at room temperature for 100 min, quenched with a solution of $Na_2S_2O_3$ in $H_2O$, diluted with DCM and washed with saturated NaHCO3, dried over MgSO4, filtered and concentrated to give compound 121 (0.374 g, 76% yield).

MS: 230.1 (calc) 230.9 (obs)

Step 3: Ethyl 2-morpholinopyrimidine-5-carboxylate (122)

A solution of sulfone 121 (0.184 g, 0.80 mmol) in ethyleneglycol dimethylether (5 mL) was treated with neat morpholine (0.3 mL, 3.4 mmol) and the mixture was stirred at room temperature for 48 h. The reaction mixture was then diluted with DCM and washed with saturated NaHCO3 in brine, dried over MgSO4, filtered, concentrated and stored under vacuum to give intermediate 122 (0.205 g, >99% yield).

1H NMR (DMSO-$d_6$) δ (ppm): 8.78 (s, 2H), 4.26 (q, J=7.0 Hz, 2H), 3.83 (t, J=4.7 Hz, 4H), 3.66 (t, J=5.1 Hz, 4H), 1.30 (t, J=7.0 Hz, 3H).

Step 4: 2-Morpholinopyrimidine-5-carboxylic acid (123)

A solution of ester 122 (0.205 g, 0.86 mmol) in 2N HCl in $H_2O$ (10 mL) was stirred at 110° C. in a pressure vessel for 6 h, cooled to −78° C. and lyophilized for 2 days. The resulting amorphous solid was further dried using a mixture of dry acetonitrile (10 mL) and dry benzene (10 mL) followed by concentration (this was repeated 3 times) to give compound 123 (0.193 g, 92% yield). LRMS: 209.1 (calc) 210.0 (obs).

Steps 5 & 6: N-(2-Amino-5-(thiophen-2-yl)phenyl)-2-morpholinopyrimidine-5-carboxamide (124)

Following the same procedures as described in Example 1a, steps 6 and 7 (scheme 1), but substituting compound 7 for compound 123, the title compound 124 was obtained (Step 5: 66% yield, Step 6: 58% yield).

¹H NMR: (DMSO-d₆) δ (ppm): 9.60 (s, 1H), 8.94 (s, 2H), 7.45 (d, J=2.2 Hz, 1H), 7.35 (dd, J=5.1, 0.98 Hz, 1H), 7.29 (dd, J=8.4, 2.2 Hz, 1H), 7.24 (dd, J=3.5, 0.98 Hz, 1H), 7.05 (dd, J=4.9, 3.5 Hz, 1H), 6.79 (d, J=8.4 Hz, 1H), 5.22 (s, 2H), 3.84 to 3.82 (m, 4H), 3.69 to 3.67 (m, 4H). LRMS: 381.1 (calc), 382.0 (obs).

TABLE 9

Characterization of compounds prepared according to Scheme 10

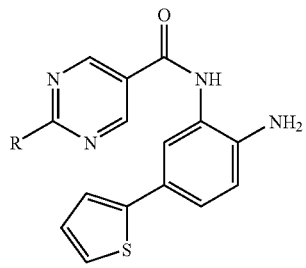

| Cpd | Ex | R | Name | Characterization |
|---|---|---|---|---|
| 125 | 10b | (4-methylpiperazin-1-yl) | N-(2-amino-5-(thiophen-2-yl)phenyl)-2-(4-methylpiperazine-1-yl)pyrimidine-5-carboxamide | ¹H NMR (DMSO-d₆) δ (ppm): 9.62 (s, 1H), 8.94 (s, 2H), 7.45 (d, J = 2.2 Hz, 1H), 7.35 (dd, J = 5.1, 1.2 Hz, 1H), 7.30 (dd, J = 8.4, 2.3 Hz, 1H), 7.24 (dd, J = 3.5, 0.98 Hz, 1H), 7.05 (dd, J = 5.1, 3.5 Hz, 1H), 6.79 (d, J = 8.4 Hz, 1H), 5.23 (s, 2H), 3.93 to 3.92 (m, 4H), 3.11 to 3.05 (m, 4H), 2.41 (s, 3H). LRMS: 394.1 (calc) 395.1 (obs). |
| 126 | 10c | (4-morpholinopiperidin-1-yl) | N-(2-amino-5-(thiophen-2-yl)phenyl)-2-(4-morpholinopiperidin-1-yl)pyrimidine-5-carboxamide | ¹H NMR (DMSO-d₆) δ (ppm): 9.56 (s, 1H), 8.90 (s, 2H), 7.44 (d, J = 2.2 Hz, 1H), 7.35 (dd, J = 4.9, 0.98 Hz, 1H), 7.29 (dd, J = 8.4, 2.3 Hz, 1H), 7.24 (dd, J = 3.5, 0.98 Hz, 1H), 7.05 (dd, J = 5.1, 3.5 Hz, 1H), 6.79 (d, J = 8.4 Hz, 1H), 5.22 (s, 2H), 4.75 (d, J = 13.3 Hz, 2H), 3.56 (t, J = 4.1 Hz, 4H), 3.00 (t, J = 11.3 Hz, 2H), 2.47 (m, 4H), 2.34 to 2.32 (m, 1H), 1.91 to 1.87 (m, 2H), 1.37 to 1.28 (m, 2H). LRMS: 464.20 (calc) 465.2 (obs). |
| 127 | 10d | ethoxy | N-(2-amino-5-(thiophen-2-yl)phenyl)-2-ethoxypyrimidine-5-carboxamide | ¹H NMR (DMSO-d₆) δ (ppm): 9.83 (s, 1H), 9.13 (s, 2H), 7.46 (d, J = 2.2 Hz, 1H), 7.35 (dd, J = 5.1, 1.2 Hz, 1H), 7.31 (dd, J = 8.4, 2.3 Hz, 1H), 7.24 (dd, J = 3.5, 0.98 Hz, 1H), 7.05 (dd,, J = 5.1, 3.5 Hz, 1H), 6.79 (d, J = 8.4 Hz, 1H), 5.30 (s, 2H), 4.45 (q, J = 7.0 Hz, 2H), 1.37 (t, J = 6.8 Hz, 3H). LRMS: 340.10 (calc) 341.17 (obs). |

Example 11a

N-(2-Amino-5-(thiophen-2-yl)phenyl)-2-oxo-2,3-dihydrobenzo[d]oxazole-6-carboxamide (132)

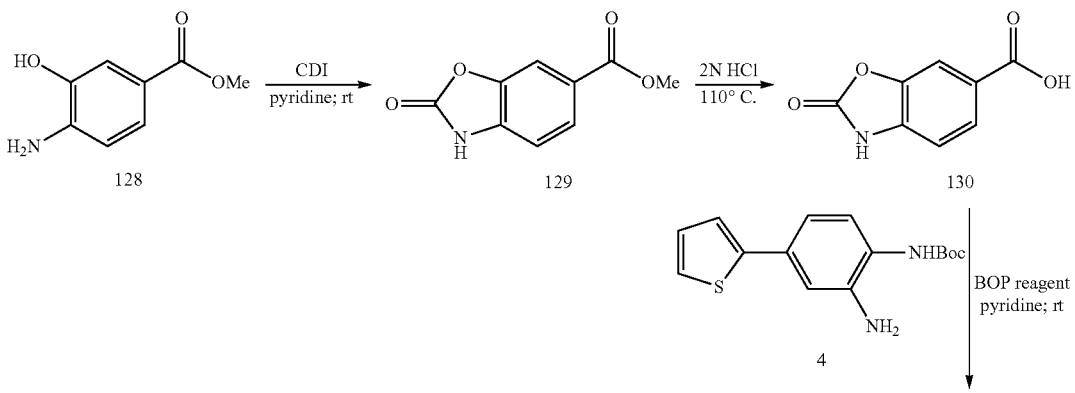

Scheme 11

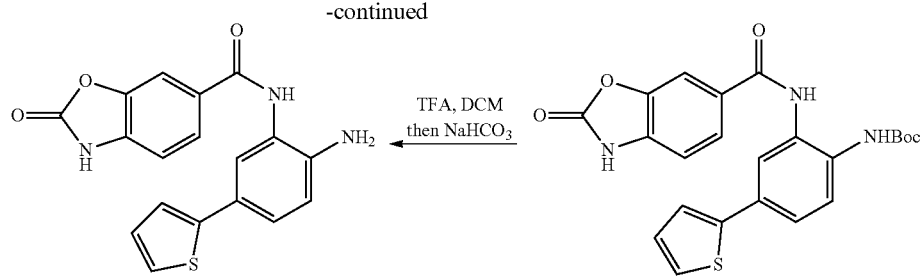

132: Example 11a   ←   131

Step 1: Methyl 2-oxo-2,3-dihydrobenzo[d]oxazole-6-carboxylate (129)

A solution of hydroxyaniline 128 (1.085 g, 6.49 mmol) and carbonyl diimidazole (1.409 g, 8.69 mmol) in pyridine (3 mL) was stirred at room temperature for 36 h then diluted with AcOEt, washed with 5% KHSO4 (pH=2), saturated NaHCO3, brine, dried over MgSO4, filtered and concentrated to give title compound 129 (1.19 g, 95% yield).

1H NMR (DMSO-$d_6$) δ (ppm): 7.80 to 7.78 (m, 1H), 7.74 to 7.73 (m, 1H), 7.18 to 7.16 (m, 1H), 3.83 (s, 3H).

Step 2: 2-Oxo-2,3-dihydrobenzo[d]oxazole-6-carboxylic acid (130)

Following the same procedure as described in Example 10a, step 4 (scheme 10), but substituting compound 122 for compound 129, acid 130 was obtained (quantitative).

1H NMR (DMSO-$d_6$) δ (ppm): 7.78 (dd, J=8.0 Hz, 1H), 7.72 to 7.71 (m, 1H), 7.16 (d, J=8.0 Hz, 1H).

Step 3: tert-Butyl 2-(2-oxo-2,3-dihydrobenzo[d]oxazole-6-carboxamido)-4-(thiophen-2-yl)phenylcarbamate (131)

Following the same procedure as described in Example 1, step 6 (scheme 1), but substituting compound 7 for compound 130, intermediate 131 was obtained (99% yield).

1H NMR (DMSO-$d_6$) δ (ppm): 9.86 (s, 1H), 8.71 (s, 1H), 7.87 (d, J=1.2 Hz, 1H), 7.82 (dd, J=8.2, 1.6 Hz, 1H), 7.78 (d, J=2.2 Hz, 1H), 7.61 (d, J=8.4 Hz, 1H), 7.52 to 7.50 (m, 1H), 7.49 (d, J=2.2 Hz, 1H), 7.44 (dd, J=3.5, 0.98 Hz, 1H), 7.21 (d, J=8.2 Hz, 1H), 7.11 (dd, J=5.1, 3.5 Hz, 1H), 1.46 (s, 9H).

Step 4: N-(2-Amino-5-(thiophen-2-yl)phenyl)-2-oxo-2,3-dihydrobenzo[d]oxazole-6-carboxamide (132)

Following the same procedure as described in Example 1, Step 7 (scheme 1), but substituting compound 8 for compound 131, the title compound 132 was obtained (89% yield).

1H NMR (DMSO-$d_6$) δ (ppm): 11.95 (s, 1H), 9.67 (s, 1H), 7.91 (s, 1H), 7.85 (d, J=6.5 Hz, 1H), 7.43 (s, 1H), 7.34 (d, J=3.7 Hz, 1H), 7.28 (d, J=6.5 Hz, 1H), 7.23 (s, 1H), 7.18 (d, J=7.8 Hz, 1H), 7.03 (s, 1H), 6.79 (d, J=8.0 Hz, 1H), 5.17 (s, 2H). LRMS: 351.4 (calc) 352.1 (obs).

Example 13a

4-Acetamido-N-(2-amino-5-(thiophen-2-yl)phenyl)-3-hydroxybenzamide (140)

Scheme 13

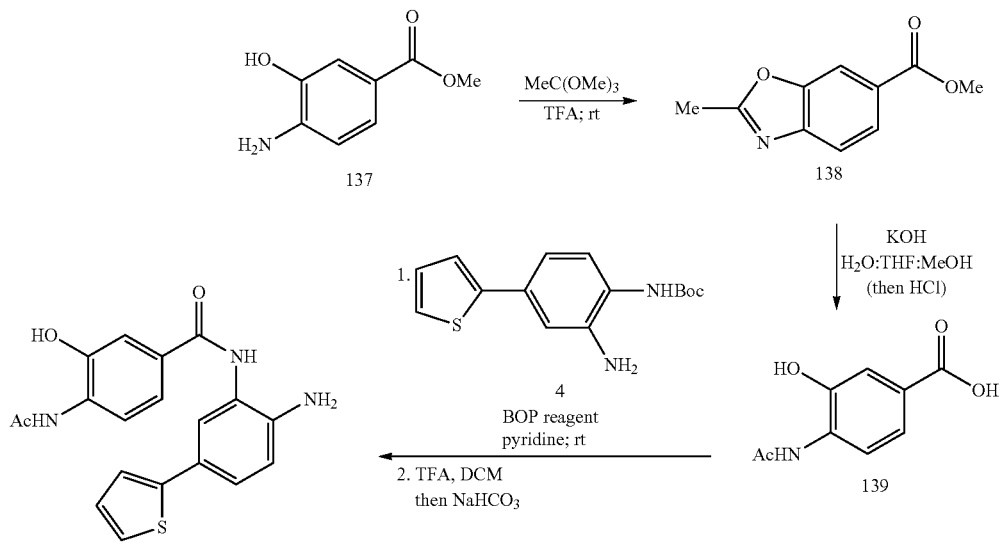

140: example 13a

Step 1: Methyl 2-methylbenzo[d]oxazole-6-carboxylate (138)

A solution of hydroxylamine 137 (0.805 g, 4.815 mmol) was dissolved in trimethyl orthoacetate (MeC(OMe)$_3$) (10 mL, 78.55 mmol) was treated with TFA (0.6 mL, 7.8 mmol) then stirred at room temperature for 90 min. The reaction mixture was diluted with DCM, washed with saturated NaHCO$_3$, brine, dried over MgSO$_4$ and concentrated to give compound 138 (0.911 g, 99% yield).
$^1$H NMR (DMSO-d$_6$) δ (ppm): 8.19 (s, J=0.98 Hz, 1H), 7.95 (dd, J=8.4, 1.6 Hz, 1H), 7.76 (d, J=8.2 Hz, 1H), 3.88 (s, 3H), 2.67 (s, 3H).

Step 2: 2-Methylbenzo[d]oxazole-6-carboxylic acid (139)

A solution of compound 138 (920 mg, 4.815 mmol) in THF:MeOH (30 mL of a 1:1 solution) was treated with a solution of potassium hydroxide (0.698 g, 17.86 mmol) in H$_2$O (15 mL). The reaction mixture was stirred for 65 min at room temperature then quenched with 1N HCl (18 mL, 18.6 mmol) (final pH of 2.5), THF was removed under reduced pressure and the remaining aqueous solution was cooled to −78° C. and lyophilized to give compound 139 (940 mg, quantitative).

Steps 3 & 4: N-(2-Amino-5-(thiophen-2-yl)phenyl)-2-methylbenzo[d]oxazole-6-carboxamide (140)

Following the same procedure as described in Example 1, steps 6 and 7 (scheme 1) but substituting compounds 7 for compounds 139, the title compound 140 was obtained in 48% yield (combined for the steps 2-4).
1H NMR (DMSO-d$_6$) δ (ppm): 10.16 (s, 1H), 9.59 (s, 1H), 9.38 (s, 1H), 7.97 (d, J=8.6 Hz, 1H), 7.46 to 7.44 (m, 3H), 7.34 (dd, J=5.1, 1.2 Hz, 1H), 7.27 (dd, J=8.2, 2.2 Hz, 1H), 7.23 (dd, J=3.5, 1.2 Hz, 1H), 7.05 to 7.02 (m, 1H), 6.79 (d, J=8.4 Hz, 1H), 5.13 (s, 2H), 3.34 (s, 3H). LRMS: 367.4 (calc) 368.1 (obs).

Example 14a

N-(2-Amino-5-(1H-pyrrol-2-yl)phenyl)-4-methoxybenzamide (147)

Scheme 14

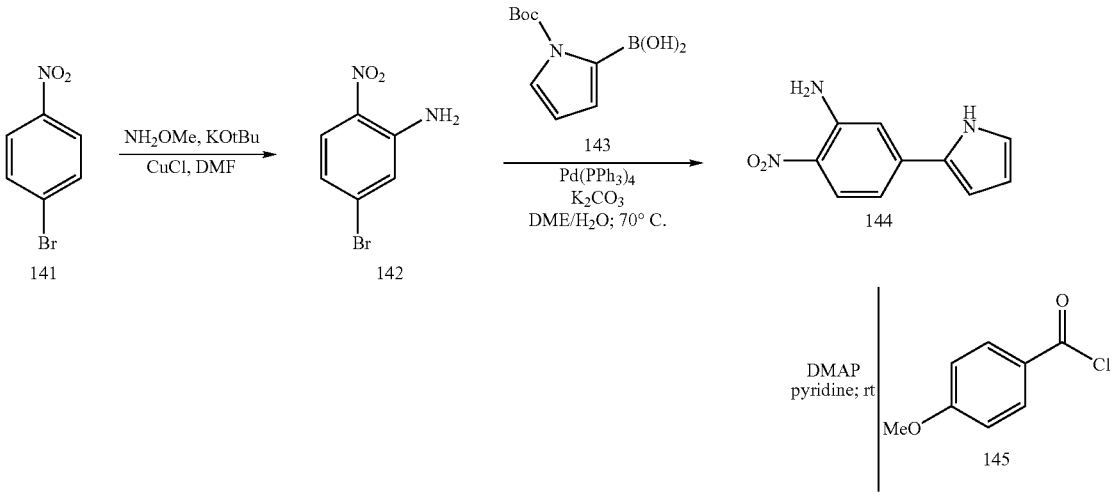

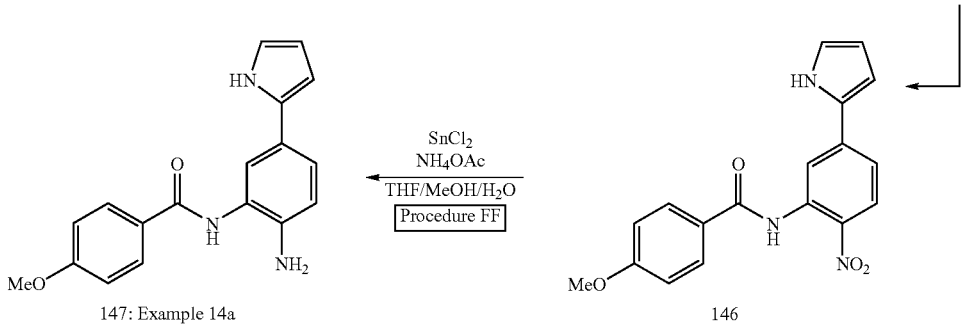

Step 1: 5-Bromo-2-nitrobenzenamine (142)

To a solution of potassium tert-butoxide (21.92 g, 195 mmol) and copper (I) chloride (2.36 g, 23.8 mmol) in ethyleneglycol dimethylether (170 mL), stirred at 0° C. under nitrogen, a solution of 1-bromo-4-nitrobenzene (141, 8.69 g, 43.0 mmol) in DMF (45 mL) was added drop wise over 50 min. After complete addition the cooling bath was removed and the mixture was allowed to stir at room temperature for 4 h, diluted with DCM, washed with aqueous NH$_4$Cl, dried over MgSO$_4$, filtered and concentrated to give compound 142 (7.85 g, 84% yield).
$^1$H NMR (CDCl$_3$) δ (ppm): 7.98 (d, J=9.2 Hz, 1H), 7.02 (d, J=2.0 Hz, 1H), 6.82 (dd, J=9.2, 2.0 Hz, 1H), 6.12 (bs, 2H).

Step 2: 2-Nitro-5-(1H-pyrrol-2-yl)benzenamine (144)

Following the same procedure as described in Example 1, step 2 (scheme 1), but substituting compound 2 for compound 142 and 2-thiophene boronic acid for the compound 143, compound 144 was obtained in 10% yield.
1H NMR (DMSO-d$_6$) δ (ppm): 11.54 (s, 1H), 7.93 (d, J=9.0 Hz, 1H), 7.37 (s, 2H), 7.11 (d, J=1.8 Hz, 1H), 6.98 to 6.96 (m, 1H), 6.92 (dd, J=9.2, 1.9 Hz, 1H), 6.61 to 6.59 (m, 1H), 6.19 to 6.17 (m, 1H).

Step 3: 4-Methoxy-N-(2-nitro-5-(1H-pyrrol-2-yl)phenyl)benzamide (146)

A solution of 4-methoxybenzoyl chloride (145, 0.175 g, 1.0 mmol), aniline 144 (79.2 mg, 0.39 mmol) and 4-(dimethylamino)pyridine (catalytic amount) was stirred at room temperature for 24 h. The reaction mixture was diluted with DCM, treated with saturated NaHCO3, stirred for 3 h and diluted with AcOEt. Organic phase was collected, washed with saturated NaHCO3, dried over MgSO4, filtered and concentrated to provide compound 146 (0.133 g, 100% yield).
MS: 337.33 (calc) 338.0 (obs)

Step 4: N-(2-Amino-5-(1H-pyrrol-2-yl)phenyl)-4-methoxybenzamide (147)

A solution of nitro compound 146 (0.1326 g, 0.39 mmol) in a 8.5:5:1 mixture of THF:MeOH:H$_2$O (14.5 mL) was treated with tin(II) chloride dihydrate (0.602 g, 2.67 mmol) and ammonium acetate (0.818 g, 10.6 mmol) then heated to 55° C. for 60 min. The reaction mixture was cooled to room temperature, diluted with AcOEt, washed with 5% KHSO4, saturated NaHCO3, brine, dried over MgSO4, filtered and concentrated. The title compound 147 was obtained after purification by chromatotron (14.7 mg, 12% yield, eluent: 50% AcOEt in hexane).

Alternative method. Following the same procedure as described in Example 1, step 3 (scheme 1) but substituting compound 3 for compound 146, the title compound can be obtained. $^1$H NMR (DMSO-d$_6$) δ (ppm): 10.94 (s, 1H), 9.60 (s, 1H), 7.97 (d, J=8.8 Hz, 2H), 7.38 (d, J=1.8 Hz, 1H), 7.23 (dd, J=8.4, 2.2 Hz, 1H), 7.03 (d, J=8.8 Hz, 2H), 6.75 (d, J=8.4 Hz, 1H), 6.69 to 6.67 (m, 1H), 6.23 to 6.21 (m, 1H), 6.02 to 6.00 (m, 1H), 4.85 (s, 2H), 3.83 (s, 3H). LRMS: 307.3 (calc) 308.3 (obs).

TABLE 10

Characterization of compounds prepared according to Scheme 14

| Cpd | Ex | R | X | Y | Name | Characterization |
|---|---|---|---|---|---|---|
| 148 | 14b | pyridin-3-yl | 1H-pyrrol-2-yl (HN) | NH$_2$ | N-(2-amino-5-(1H-pyrrol-2-yl)phenyl)-4-(pyridin-3-yl)benzamide | $^1$H NMR (DMSO-d$_6$) δ (ppm): 10.96 (s, 1H), 9.81 (s, 1H), 8.98 (d, J = 1.6 Hz, 1H), 8.60 (dd, J = 4.7, 1.6 Hz, 1H), 8.19 to 8.16 (m, 1H), 8.12 (d, J = 8.0 Hz, 2H), 7.90 (d, J = 8.4 Hz, 2H), 7.52 (dd, J = 7.8, 4.7 Hz, 1H), 7.42 (s, 1H), 7.26 (dd, J = 8.2, 2.0 Hz, 1H), 6.77 (d, J = 8.2 Hz, 1H), 6.69 to 6.68 (m, 1H), 6.23 to 6.01 (m, 1H), 4.92 (s, 2H). LRMS: 354.4 (calc) 355.2 (obs). |
| 149 | 14c | pyridin-3-yl | 1H-pyrazol-4-yl | NH$_2$ | N-(2-amino-5-(1H-pyrazol-4-yl)phenyl)-4-(pyridin-3-yl)benzainide | $^1$H NMR (DMSO-d$_6$) δ (ppm): 8.99 (d, J = 2.0 Hz, 1H), 8.63 (dd, J = 4.7, 1.6 Hz, 1H), 8.59 (s, 1H), 8.22 (d, J = 0.6 Hz, 1H), 8.20 to 8.17 (m, 1H), 8.14 (d, J = 8.2 Hz, 2H), 7.93 (d, J = 8.2 Hz, 2H), 7.56 to 7.52 (m, 1H), 6.89 (d, J = 2.0 Hz, 1H), 6.85 to 6.83 (m, 1H), 6.53 (d, J = 7.8 Hz, 1H), 4.69 (s, 2H), 4.54 (s, 1H), 1.04 (d, J = 6.0 Hz, 1H). LRMS: 355.4 (calc) 356.3 (obs). |

TABLE 10-continued

Characterization of compounds prepared according to Scheme 14

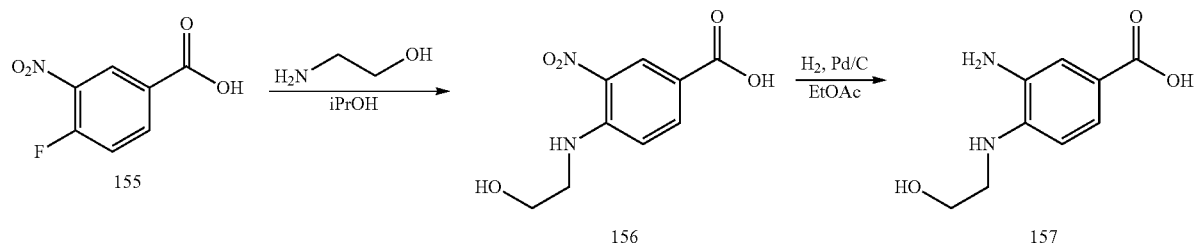

| Cpd | Ex | R | X | Y | Name | Characterization |
|---|---|---|---|---|---|---|
| 150 | 14d | 3-pyridyl | 4-aminophenyl (NH₂) | NH₂ | N-(4,4'-diaminobiphenyl-1-3-yl-4-(pyridin-3-yl)benzamide | $^1$H NMR (DMSO-$d_6$) δ (ppm): 9.80 (s, 1H), 8.98 (d, J = 1.4 Hz, 1H), 8.60 (dd, J = 4.7, 1.6 Hz, 1H), 8.18 to 8.16 (m, 1H), 8.12 (d, J = 8.2 Hz, 2H), 7.89 (d, J = 8.4 Hz, 2H), 7.54 to 7.50 (m, 1H), 7.38 (s, 1H), 7.22 (d, J = 8.4 Hz, 2H), 7.18 (dd, J = 8.2, 2.0 Hz, 1H), 6.80 (d, J = 8.4 Hz, 1H), 6.58 (d, J = 8.6 Hz, 2H), 5.05 (s, 2H), 4.92 (d, 2H). LRMS: 380.44 (calc) 381.2 (obs). |

Example 16a (S)-2-(5-(2-Amino-5-(thiophen-2-yl)phenylcarbamoyl)-2-methyl-1H-benzo[d]imidazol-1-yl)ethyl 2-(tert-butoxycarbonylamino)-3-methylbutanoate (161)

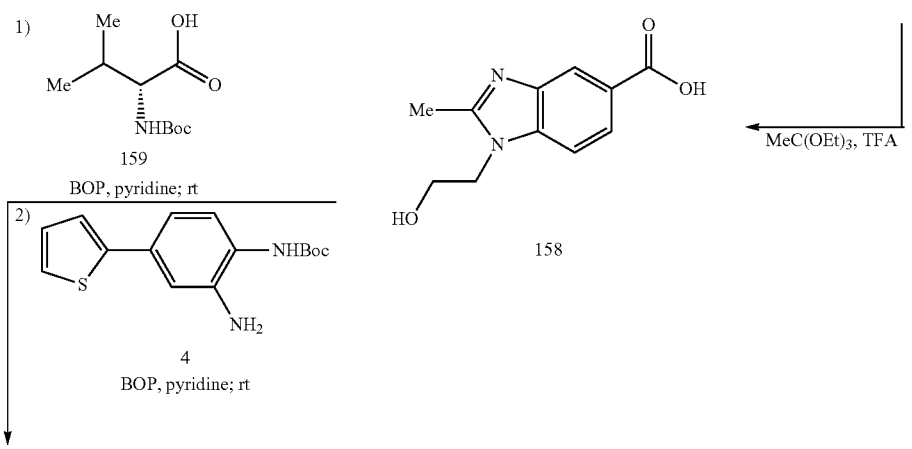

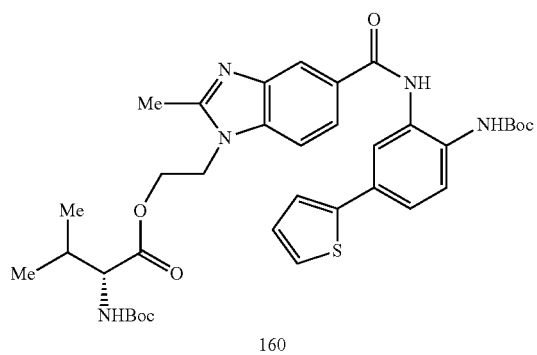

160

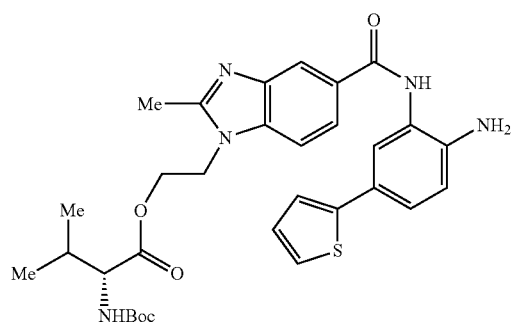

161: example 16a

Step 1: 4-(2-Hydroxyethylamino)-3-nitrobenzoic acid (156)

A solution of fluoride 155 (1.13 g, 6.08 mmol) in isopropanol (12 mL) was treated with neat ethanolamine (3.0 mL, 49.7 mmol) added dropwise then it was stirred at room temperature for 18 h. The reaction mixture was suspended in AcOEt and washed with 5% KHSO4, brine, dried over MgSO4, filtered and concentrated to give intermediate 156 (1.334 g, 97% yield).

LRMS: 226.2 (calc) 225.1 (obs, M–H)

Step 2: 3-Amino-4-(2-hydroxyethylamino)benzoic acid (157)

A solution of intermediate 156 (1.33 g, 5.9 mmol) in AcOEt/MeOH was stirred under $H_2$ in the presence of 10% palladium on carbon for 18 h, filtered through Celite®, concentrated and then triturated with DCM to give compound 157 (1.18 g, >99% yield).

LRMS: 196.2 (calc) 197.1 (obs)

Step 3: 1-(2-Hydroxyethyl)-2-methyl-1H-benzo[d]imidazole-5-carboxylic acid (158)

Following the same procedure as described in Example 13, step 1 (scheme 13), but substituting compound 137 for compound 157, title compound 158 was obtained (0.701 g, 53% yield) after purification by preparative HPLC [Gilson, column aquasil C18 (5 µM), 250×21.2 mm; gradient 10% to 80% MeOH in water, UV detection)].

Steps 4 & 5: (R)-2-(5-(2-(tert-Butoxycarbonylamino)-5-(thiophen-2-yl)phenylcarbamoyl)-2-methyl-1H-benzo[d]imidazol-1-yl)ethyl 2-(tert-butoxycarbonylamino)-3-methylbuta-noate (160)

Following the same procedure as described in Example 1, step 6 (scheme 1), but substituting compound 4 for compound 158 and compound 7 for compound 159, an ester intermediate was obtained (structure not shown in the scheme 16). Following the same procedure as described in Example 1, step 6 (scheme 1), but substituting compound 7 for the above mentioned ester intermediate, compound 160 was obtained (19% yield over two steps) after purification by chromatotron (eluent: 5% iso-PrOH in DCM).

LRMS: 691.84 (calc) 692.5 (obs).

Step 6: (R)-2-(5-(2-Amino-5-(thiophen-2-yl)phenylcarbamoyl)-2-methyl-1H-benzo[d]imidazol-1-yl)ethyl 2-(tert-butoxycarbonylamino)-3-methylbutanoate (161)

Following the same procedure as described in Example 1, step 7 (scheme 1), but substituting compound 8 for compound 160, title compound 161 was obtained (84% yield).

1H NMR (DMSO-$d_6$) δ (ppm): 9.70 (s, 1H), 8.23 (s, 1H), 7.88 (d, J=1.6 Hz, 1H), 7.86 (d, J=1.6 Hz, 1H), 7.65 (d, J=8.0 Hz, 1H), 7.48 (d, J=2.2 Hz, 1H), 7.34 (dd, J=5.1, 1.2 Hz, 1H), 7.28 (dd, J=8.2, 2.2 Hz, 1H), 7.24 (dd, J=3.5, 1.2 Hz, 1H), 7.04 (dd, J=5.1, 3.5 Hz, 1H), 6.81 (d, J=8.2 Hz, 1H), 5.14 (s, 2H), 4.55 (d, J=4.9 Hz, 2H), 4.38 (d, J=4.5 Hz, 2H), 2.99 (d, J=5.3 Hz, 1H), 2.61 (s, 3H), 1.68 to 1.63 (m, 2H), 0.71 (d, J=6.8 Hz, 3H), 0.64 (d, J=6.8 Hz, 3H). LRMS: 491.6 (calc) 492.4 (obs).

Example 17a

(E)-N-(2-Amino-5-(thiophen-2-yl)phenyl)-3-(6-morpholinopyridin-3-yl)acrylamide (166)

Scheme 17

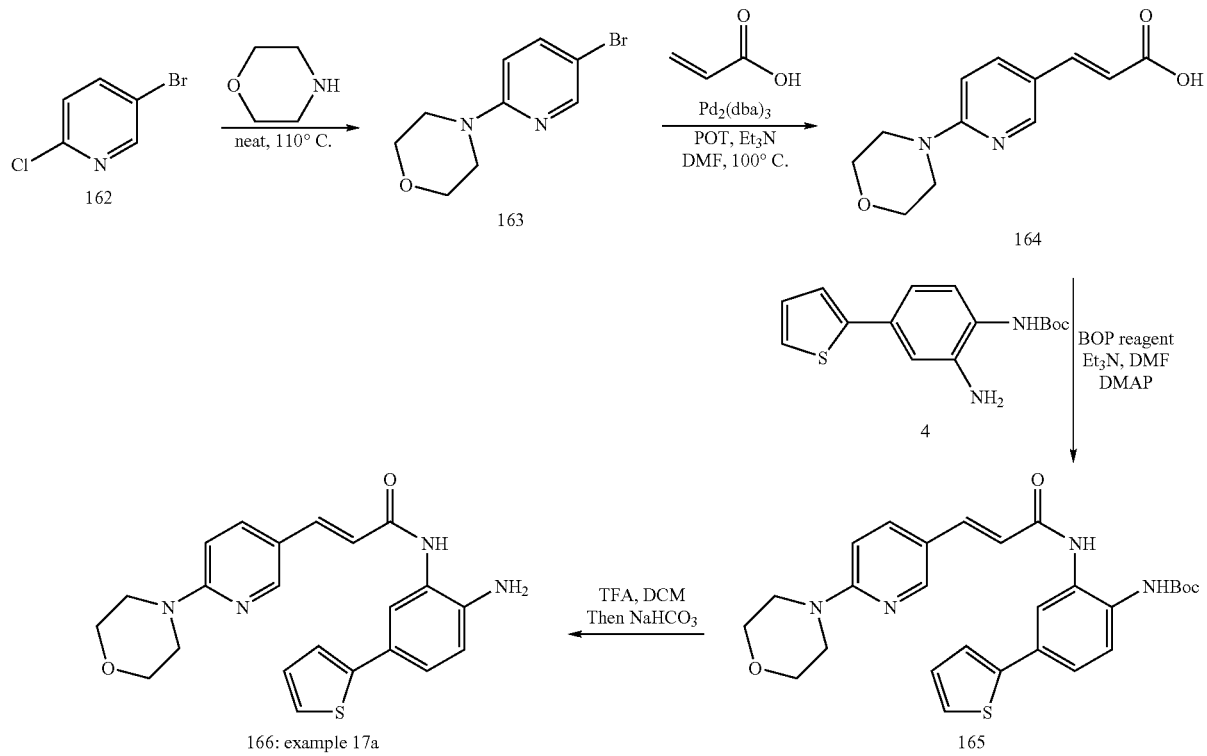

Step 1: 4-(5-Bromopyridin-2-yl)morpholine (163)

Following the same procedure as described in Example 3, step 3 (scheme 3), but substituting N-methylpiperazine for morpholine and compound 46 for compound 162, title compound 163 was obtained in 57% yield.

1H NMR (DMSO-d$_6$) δ (ppm): 8.13 (d, J=2.2 Hz, 1H), 7.63 (dd, J=9.0, 2.5 Hz, 1H), 6.74 (d, J=9.0 Hz, 1H), 3.76 (t, J=4.7 Hz, 4H), 3.45 (t, J=4.9 Hz, 4H). LRMS: 243.10 (calc) 243.0/245.0 (obs).

Step 2: (E)-3-(6-Morpholinopyridin-3-yl)acrylic acid (164)

Following the same procedure as described in Example 2, step 2 (scheme 2), but substituting compound 37 for compound 163, and compound 38 for acrylic acid, title compound 164 was obtained in 41% yield.

1H NMR (DMSO-d$_6$) δ (ppm): 12.14 (bs, 1H), 8.32 (d, J=2.3 Hz, 1H), 7.92 (dd, J=9.2, 2.5 Hz, 1H), 7.47 (d, J=15.8 Hz, 1H), 6.85 (d, J=9.0 Hz, 1H), 6.33 (d, J=15.8 Hz, 1H), 3.67 to 3.65 (m, 4H), 3.54 to 3.52 (m, 4H). LRMS: 234.27 (calc) 235.1 (obs).

Step 3: (E)-tert-Butyl 2-(3-(6-morpholinopyridin-3-yl)acrylamido)-4-(thiophen-2-yl)phenylcarbamate (165)

To a solution of 164 (0.275 g, 1.17 mmol) in DMF (10 mL) was added triethylamine (0.168 mL, 1.21 mmol) and BOP reagent (0.563 g, 1.27 mmol) and the mixture was stirred at room temperature for 30 min. Then amine 4 (0.309 g, 1.06 mmol) and excess triethylamine (0.443 mL, 3.18 mmol) were added and the reaction mixture was allowed to stir for 18 h at room temperature. Then 4-(dimethylamino)pyridine (catalytic amount) was added and the reaction mixture was heated to 50-60° C. for 24 h. The solution was concentrated, diluted with AcOEt, washed with saturated NaHCO3, H2O, brine, dried over MgSO4, filtered and concentrated. The resulting yellow solid was triturated from ethyl ether to give compound 165 (0.435 g, 81% yield).

1H NMR (DMSO-d$_6$) δ (ppm): 9.68 (s, 1H), 8.58 (bs, 1H), 8.35 (d, J=2.3 Hz, 1H), 7.85 (d, J=2.0 Hz, 1H), 7.82 (d, J=2.0 Hz, 1H), 7.61 (d, J=9.0 Hz, 1H), 7.52 (d, J=15.5 Hz, 1H), 7.51 (dd, J=5.1, 1.2 Hz, 1H), 7.44 (dd, J=8.4, 2.3 Hz, 1H), 7.41 (dd, J=3.5, 1.2 Hz, 1H), 7.11 (dd, J=5.1, 3.5 Hz, 1H), 6.92 (d, J=9.4 Hz, 1H), 6.71 (d, J=15.4 Hz, 1H), 4.02 to 3.97 (m, 4H), 3.69 to 3.67 (m, 4H), 1.45 (s, 9H). LRMS: 506.62 (calc) 507.1 (obs).

Step 4: (E)-N-(2-Amino-5-(thiophen-2-yl)phenyl)-3-(6-morpholinopyridin-3-yl)acrylamide (166)

Following the same procedure as described in Example 1, step 7 (scheme 1), but substituting compound 8 for compound 165, the title compound 166 was obtained in 92% yield.

1H NMR (DMSO-d$_6$) δ (ppm): 9.33 (s, 1H), 8.33 (d, J=2.0 Hz, 1H), 7.80 (dd, J=8.8, 2.5 Hz, 1H), 7.66 (d, J=1.8 Hz, 1H), 7.48 (d, J=15.4 Hz, 1H), 7.34 (dd, J=5.1, 1.0 Hz, 1H), 7.22 (dd, J=9.0, 2.2 Hz, 1H), 7.20 (dd, J=3.5, 1.2 Hz, 1H), 7.03 (d, J=5.1, 3.5 Hz, 1H), 6.92 (d, J=9.0 Hz, 1H), 6.76 (d, J=8.4 Hz, 1H), 6.70 (d, J=15.7 Hz, 1H), 5.18 (s, 2H), 3.69-3.66 (m, 4H), 3.54-3.51 (m, 4H). LRMS: 406.51 (calc) 407.1 (obs).

Example 18a

N-(2-Amino-5-(5-chlorothiophen-2-yl)phenyl)-4-(pyridin-3-yl)benzamide (170)

Steps 3 & 4: N-(2-Amino-5-(5-chlorothiophen-2-yl)phenyl)-4-(pyridin-3-yl)benzamide (170)

Following the same procedure as described in Example 1, steps 6 & 7 (scheme 1), but substituting compounds 4 and 7

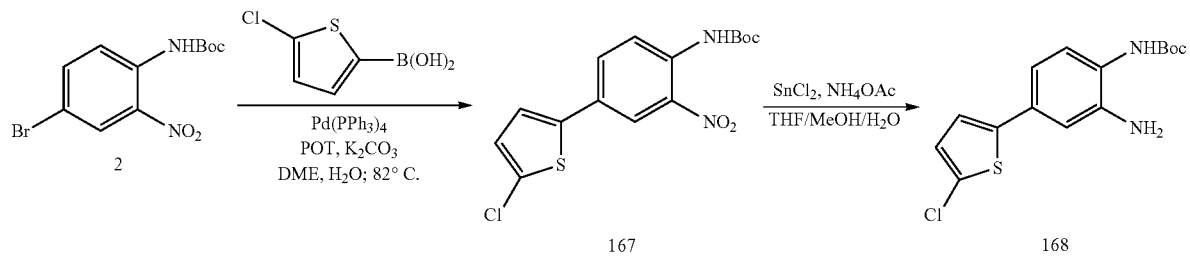

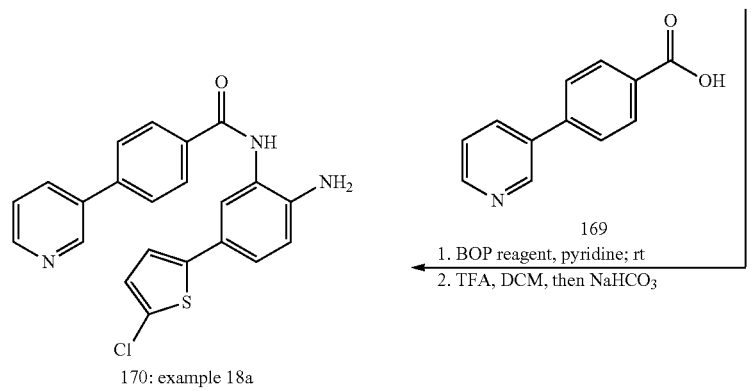

Step 1: tert-Butyl 4-(5-chlorothiophen-2-yl)-2-nitrophenylcarbamate (167)

Following the same procedure as described in Example 1, step 2 (scheme 1), but substituting 2-thiophene boronic acid for 5-chloro-2-thiophene boronic acid, title compound 167 was obtained after purification by column chromatography (45% yield, eluent: 5% isopropanol in DCM).

1H NMR (DMSO-d$_6$) δ (ppm): 9.67 (s, 1H), 8.10 (s, J=2.2 Hz, 1H), 7.88 to 7.85 (m, 1H), 7.64 (d, J=8.6 Hz, 1H), 7.51 (d, J=3.9 Hz, 1H), 7.19 (d, J=3.9 Hz, 1H), 1.45 (s, 9H). LRMS: 354.04 (calc) 377.0 (obs M+Na).

Step 2: tert-Butyl 2-amino-4-(5-chlorothiophen-2-yl)phenylcarbamate (168)

Following the same procedure as described in Example 14, step 4 (scheme 14), but substituting compound 146 for compound 167, title compound 168 was obtained in quantitative yield.
LRMS: 268.01 (calc M-tBu) 269.0 (obs M-tBu).

for compounds 168 and 169 respectively, the title compound 170 was obtained in 76% yield (purified by column chromatography, eluent: 5 to 10% isopropanol in DCM).

1H NMR (DMSO-d$_6$) δ (ppm): 9.80 (s, 1H), 8.98 (d, J=2.3 Hz, 1H), 8.60 (dd, J=4.7, 1.4 Hz, 1H), 8.17 (dt, J=8.0, 1.6 Hz, 1H), 8.11 (d, J=8.4 Hz, 2H), 7.89 (d, J=8.4 Hz, 2H), 7.52 (dd, J=7.8, 4.7 Hz, 1H), 7.42 (d, J=2.0 Hz, 1H), 7.24 (dd, J=8.2, 2.2 Hz, 1H), 7.11 (d, J=3.9 Hz, 1H), 7.04 (d, J=3.9 Hz, 1H), 6.80 (d, J=8.2 Hz, 1H), 5.29 (s, 2H). LRMS: 405.1 (calc) 406.1 (obs).

TABLE 11

Characterization of compound prepared according to Scheme 18

| Cpd | Ex | R | X | Y | Name | Characterization |
|---|---|---|---|---|---|---|
| 171 | 18b | pyridin-3-yl | phenyl | NH₂ | N-(4-aminobiphenyl-3-yl)-4-(pyridin-3-yl)benzamide | $^1$H NMR (DMSO-d$_6$) δ (ppm): 10.48 (s, 1H), 9.15 (s, 1H), 8.74 (d, 1H, J = 5.1 Hz), 8.52 (d, 1H, J = 7.8 Hz), 8.26 (d, 2H, J = 8.2 Hz), 7.98 (d, 2H, J = 8.4 Hz), 7.80 (d, 2H, J = 8.2 Hz), 7.62 (d, 2H, J = 7.2 Hz), 7.51 (d, 1H, J = 8.4 Hz), 7.44 (t, 2H, J = 7.4 Hz), 7.32 (t, 2H, J = 7.2 Hz). LRMS: 365.43 (calc) 366.3 and 183.6 (obs). |
| 172 | 18c | (6-chloro-5-fluoro-1H-benzo[d]imidazol-2-ylthio)methyl | thiophen-2-yl | CO₂H | 2-(4-((6-chloro-5-fluoro-1H-benzo[d]imidazol-2-ylthio)methyl)-benzamido)-4-(thiophen-2-yl)benzoic acid | $^1$H NMR (DMSO-d$_6$) δ (ppm): 12.91 (d, J = 12.5 Hz, 1H), 12.33 (s, 1H), 9.05 (s, 1H), 8.04 (d, J = 8.2 Hz, 1H), 7.89 (d, J = 7.8 Hz, 2H), 7.74 to 7.51 (m, 6H), 7.19 (s, 1H), 4.65 (s, 2H). LRMS: 537.04 (calc), 538.2 (obs). |
| 173 | 18d | pyridin-3-yl | pyridin-3-yl | NH₂ | N-(2-amino-5-(pyridin-3-yl)phenyl)-4-(pyridin-3-yl)benzamide | $^1$H NMR (DMSO-d$_6$) δ (ppm): 9.83 (s, 1H), 8.97 (s, 1H), 8.78 (s, 1H), 8.60 (s, 1H), 8.42 (s, 1H), 8.17 (d, J = 7.6 Hz, 1H), 8.13 (d, J = 8.0 Hz, 2H), 7.94 (d, J = 8.6 Hz, 1H), 7.90 (d, J = 8.6 Hz, 2H), 7.58 (s, 1H), 7.52 (dd, J = 8.0, 4.5 Hz, 1H), 7.40 (d, J = 7.6 Hz, 2H), 6.89 (d, J = 8.2 Hz, 1H), 5.25 (d, J = 0.4 Hz, 2H), LRMS: 366.42 (calc) 367.3 (obs). |
| 174 | 18e | pyridin-3-yl | 4-fluorophenyl | NH₂ | N-(4-amino-4'-fluorobiphenyl-3-yl)-4-(pyridin-3-yl)benzamide | $^1$H NMR (DMSO-d$_6$) δ (ppm): 9.80 (s, 1H), 8.98 (d, J = 1.57 Hz, 1H), 8.60 (dd, J = 4.5, 1.4 Hz, 1H), 8.17 (d, J = 7.8 Hz, 1H), 8.12 (d, J = 8.2 Hz, 2H), 7.89 (d, J = 8.6 Hz, 2H), 7.62 (m, 6H), 7.30 (dd, J = 10.6, 8.4 Hz, 1H), 7.20 (t, J = 8.8 Hz, 2H), 6.85 (d, J = 8.02 Hz, 1H), 5.14 (s, 2H). LRMS: 383.42 (calc) 384.2 (obs). |
| 175 | 18f | (4-methylpiperazin-1-yl)methyl | 5-chlorothiophen-2-yl | NH₂ | N-(2-amino-5-(5-chlorothiophen-2-yl)phenyl)-4-(4-methylpiperazin-1-yl)benzamide | $^1$H NMR (DMSO-d$_6$) δ (ppm): 9.50 (s, 1H), 7.88 (d, J = 9.0 Hz, 2H), 7.40 (d, J = 2.2 Hz, 1H), 7.22 (dd, J = 8.4, 2.3 Hz, 1H), 7.11 (d, J = 3.9 Hz, 1H), 7.05 (d, J = 3.9 Hz, 1H), 7.01 (d, J = 9.2 Hz, 2H), 6.80 (d, J = 8.4 Hz, 1H), 5.19 (s, 2H), 3.28 (t, J = 4.7 Hz, 4H), 2.45 (t, J = 4.9 Hz, 4H), 2.22 (s, 3H). LRMS: 426.1 (calc) 427.0 (obs). |
| 176 | 18g | morpholinomethyl | furan-3-yl | NH₂ | N-(2-amino-5-(furan-3-yl)phenyl)-4-(morpholinomethyl)benzamide | $^1$H NMR (DMSO-d$_6$) δ (ppm): 7.92 (s, 1H), 7.88 (d, J = 8.0 Hz, 2H), 7.63 (s, 1H), 7.44 (m, 3H), 7.22 (dd, J = 7.9, 2.2 Hz, 1H), 6.85 (d, J = 8.1 Hz, 1H), 6.62 (s, 1H), 3.91 (b, 2H), 3.72 (t, J = 5.1 Hz, 4H), 3.57 (s, 2H), 2.43 (t, J = 5.2 Hz, 4H), 1.62 (s, 1H). LRMS: 377.4 (calc) 378.1 (obs) |

TABLE 11-continued

Characterization of compound prepared according to Scheme 18

| Cpd | Ex | R | X | Y | Name | Characterization |
|---|---|---|---|---|---|---|
| 177 | 18h | morpholinomethyl | 4-chlorophenyl | NH$_2$ | N-(4-amino-4'-chlorobiphenyl-3-yl)-4-(morpholinomethyl)benzamide | $^1$H NMR (CDCl$_3$) δ (ppm): 7.88 (m, 3H), 7.42 (m, 6H), 6.90 (d, J = 8.1 Hz, 1H), 3.92 (s, 2H), 3.72 (t, J = 5.1 Hz, 4H), 3.57 (s, 2H), 2.42 (t, J = 5.1 Hz, 4H), 1.64 (s, 1H). LRMS: 421.1 (calc) 422.1 (obs). |
| 178 | 18i | morpholinomethyl | 5-chlorothiophen-2-yl | NH$_2$ | N-(2-amino-5-(5-chlorothiophen-2-yl)phenyl)-4-(morpholinomethyl)benzamide | $^1$H NMR (DMSO-d$_6$) δ (ppm): 9.71 (s, 1H), 7.92 (d, J = 8.7 Hz, 2H), 7.42 (d, J = 8.1 Hz, 2H), 7.31 (s, 1H), 7.22 (m, 1H), 7.07 (dd, J = 23.0, 4.1 Hz, 2H), 6.81 (d, J = 9.1 Hz, 1H), 5.22 (s, 2H), 3.58 (t, J = 3.4 Hz, 4H), 3.51 (s, 2H), 2.70 (s, 4H). LRMS: 427.95 (calc) 428.0 (obs). |
| 179 | 18j | 1,1-dioxothiomorpholinomethyl | thiophen-2-yl | NH$_2$ | N-(2-amino-5-(thiophen-2-yl)phenyl)-4-(1'1'-dioxothiomorpholinomethyl)-benzamide | $^1$H NMR (CD$_3$OD) δ (ppm): 9.76 (s, 1H), 7.98 (d, J = 8.0 Hz, 2H), 7.48 (d, J = 8.2 Hz, 2H), 7.46 (d, J = 2.0 Hz, 1H), 7.35 (dd, J = 5.1, 1.2 Hz, 1H), 7.30 (dd, J = 8.4, 2.3 Hz, 1H), 7.24 (dd, J = 3.5, 1.0 Hz, 1H), 7.04 (dd, J = 5.1, 3.5 Hz, 1H), 6.82 (d, J = 8.4 Hz, 1H), 3.81 (s, 2H), 3.15 (bs, 4H), 2.93 (bs, 4H). LRMS: 441.57 (calc) 442.0 (obs). |

Example 19a

N1-(2-Amino-5-(thiophen-2-yl)phenyl)-N8-(biphenyl-3-yl)octanediamide (184)

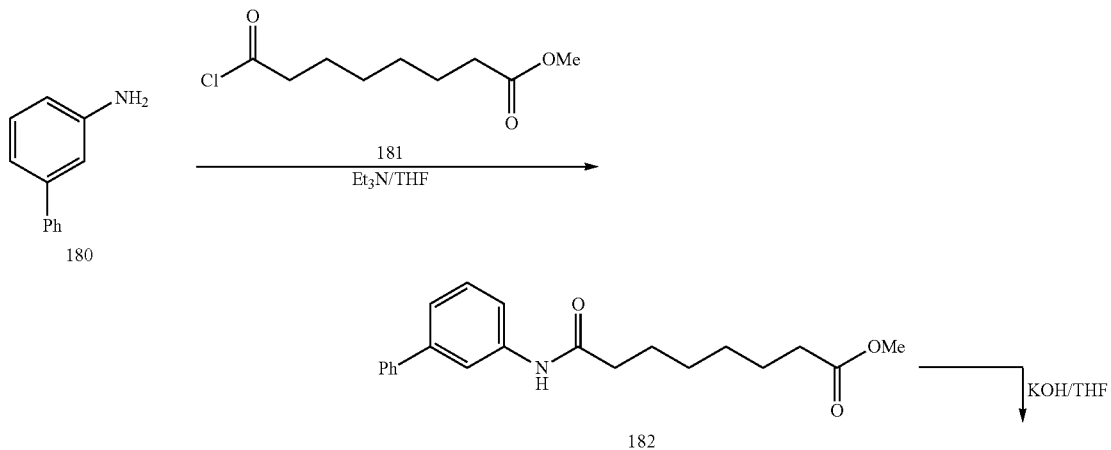

Scheme 19

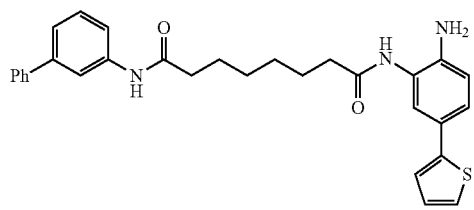

184: Example 19a

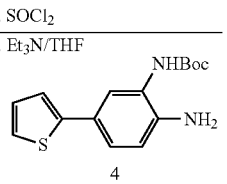

4

-continued

1. SOCl₂
2. Et₃N/THF

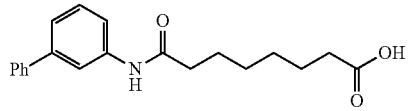

183

Step 1: Methyl 8-(biphenyl-3-ylamino)-8-oxooctanoate (182)

A solution of biphenyl-3-amine (180) (0.171 g, 1.01 mmol) in THF (3 mL) was cooled to 0° C. then treated with methyl 8-chloro-8-oxooctanoate (181) and stirred for 2 h. The reaction mixture was then diluted with AcOEt, washed with saturated NH₄Cl, dried over MgSO₄, filtered and concentrated. The residue was purified by flash chromatography (eluent: 30 to 40% AcOEt in hexane), to provide title compound 182 (0.212 g, 69% yield).

LRMS: 339.18 (calc) 340.3 (obs).

Step 2: 8-(Biphenyl-3-ylamino)-8-oxooctanoic acid (183)

A solution of compound 182 (0.212 g, 0.62 mmol) in THF (10 mL) was treated with potassium hydroxide (5 mL of a 3.5% aqueous solution) and stirred at room temperature for 72 h then concentrated, diluted with diethyl ether and acidified with citric acid. The acidic mixture was extracted with AcOEt, washed with H2O, dried over MgSO4, filtered, and concentrated to give title compound 183 (0.182 g, 90% yield).

LRMS: 325.17 (calc) 326.1 (obs).

Step 3: N1-(2-Amino-5-(thiophen-2-yl)phenyl)-N8-(biphenyl-3-yl)octanediamide (184)

Acid 183 (0.103 g, 0.32 mmol) in thionyl chloride (3 mL) with a few drops of DMF was stirred at room temperature for 15 min then concentrated, diluted with dry THF (10 mL), cooled to 0° C. then treated with amine 4 (0.12 g, 0.41 mmol) and triethylamine (0.086 mL, 0.61 mmol). The reaction mixture was stirred at 0° C. for 30 min then quenched with aqueous NH4Cl, extracted with AcOEt, dried over MgSO4, filtered and concentrated. The residue was purified by flash chromatography (eluent: 50% AcOEt-hexane) to give the title compound 184 (0.111 g, 52% yield).

1H NMR (DMSO-$d_6$) δ(ppm): 9.97 (s, 1H), 9.14 (s, 1H), 7.59 to 7.55 (m, 3H), 7.48 to 7.43 (m, 3H), 7.38 to 7.30 (m, 4H), 7.21 to 7.17 (m, 2H), 7.01 (dd, J=5.1, 3.5 Hz, 1H), 6.72 (d, J=8.2 Hz, 1H), 5.06 (s, 2H), 2.32 (t, J=7.6 Hz, 4H), 1.61 (m, 4H), 1.35 (m, 4H). LRMS: 497.21 (calc) 498.4 (obs).

Example 20a

N-(2-Amino-5-(5-((2-hydroxyethylamino)methyl) thiophen-2-yl)phenyl)-4-methoxybenzamide (193)

Scheme 20

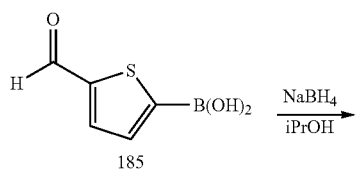

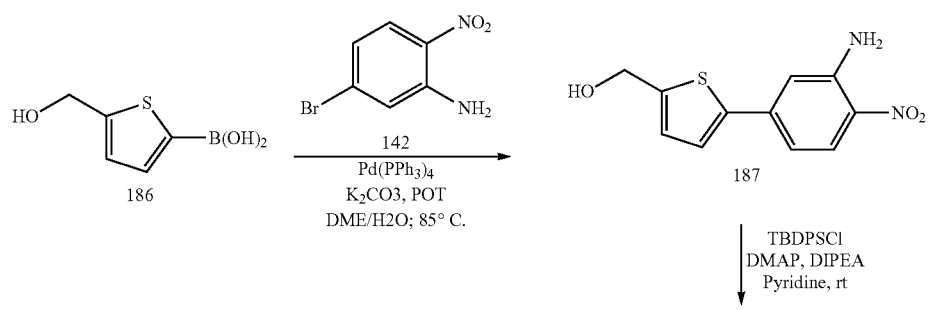

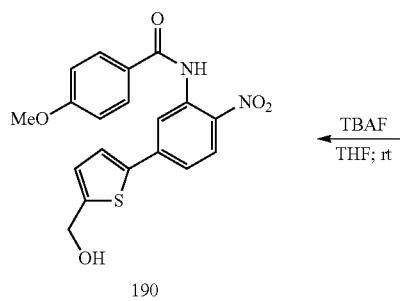

190

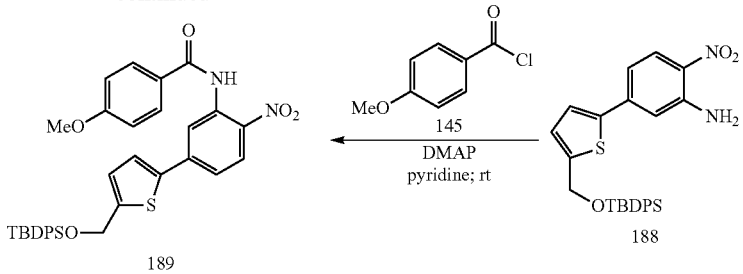

189

188

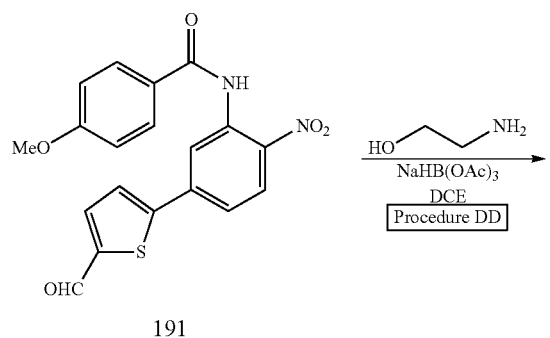

191

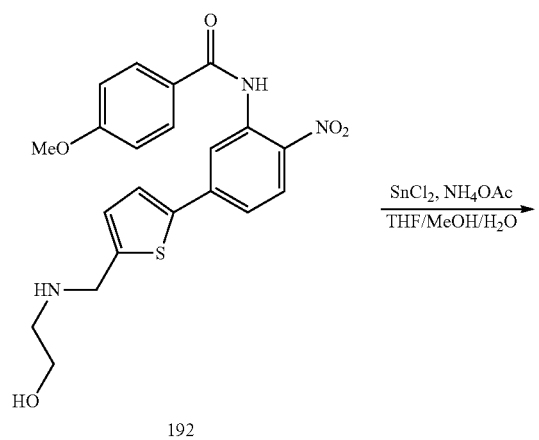

192

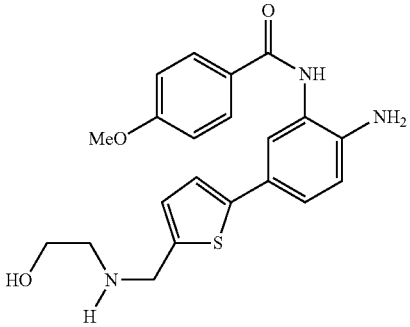

193: Example 20a

Step 1: 5-(Hydroxymethyl)thiophen-2-ylboronic acid (186)

A suspension of 5-formylthiophen-2-ylboronic acid 185 (1.096 g, 7.03 mmol) in isopropanol (10 mL), stirred at 0° C., was treated with solid sodium borohydride (0.336 g, 8.88 mmol) added portion-wise at 0° C. then stirred for 75 min. The reaction was quenched with acetone and concentrated to give compound 186 (used directly in Step 2).
LRMS: 158.0 (calc) 159.1 (obs).

Step 2: (5-(3-Amino-4-nitrophenyl)thiophen-2-yl) MeOH (187)

Following the same procedure as described in Example 1, step 2 (scheme 1), but substituting 2-thiophene boronic acid for 5-(hydroxymethyl)thiophen-2-ylboronic acid (186) and bromoarene 2 for 5-bromo-2-nitrobenzenamine (142), intermediate 187 was obtained after purification by column chromatography (84% yield, eluent: 40 to 60% AcOEt in hexane).

1H NMR (DMSO-$d_6$) δ (ppm): 7.96 (d, 9.0 Hz, 1H), 7.49 (s, 2H), 7.44 (d, J=3.7 Hz, 1H), 7.21 (d, J=2.0 Hz, 1H), 6.99 (dt, J=3.7, 0.98 Hz, 1H), 6.94 (dd, J=9.0, 2.2 Hz, 1H), 5.61 (t, J=5.8 Hz, 1H), 4.65 (dd, J=5.7, 0.78 Hz, 2H). LRMS: 250.3 (calc) 251.0 (obs).

Step 3: 5-(5-((tert-Butyldiphenylsilyloxy)methyl) thiophen-2-yl)-2-nitrobenzenamine (188)

A solution of alcohol 187 (1.217 g, 4.86 mmol), DMAP (catalytic amount) and diisopropylethylamine (1 mL) in pyridine (10 mL) was treated with neat tert-butyldiphenylsilylchloride (1.5 mL, 5.74 mmol) and the mixture was stirred under nitrogen atmosphere for 18 h at room temperature. The reaction mixture was diluted with AcOEt then washed with 5% KHSO4, saturated NaHCO3, brine, dried over MgSO4, filtered and concentrated to give compound 188 (1.75 g, 74% yield).

1H NMR (DMSO-$d_6$) δ (ppm): 7.97 (d, J=9.0 Hz, 1H), 7.66-7.64 (m, 4H), 7.51 to 7.50 (m, 2H), 7.48-7.44 (m, 7H), 7.24 (d, J=2.0 Hz, 1H), 6.98-6.95 (m, 2H), 4.93 (s, 2H), 1.05 (s, 9H). LRMS: 488.7 (calc) 489.2 (obs).

Step 4: N-(5-(5-((tert-Butyldiphenylsilyloxy)methyl)thiophen-2-yl)-2-nitrophenyl)-4-methoxybenzamide (189)

Following the same procedure as described in Example 14a, step 3 (scheme 14), but substituting compound 144 for compound 188, the title compound 189 was obtained (97% yield).

1H NMR (DMSO-$d_6$) δ (ppm): 10.73 (s, 1H), 8.11 (d, J=2.0 Hz, 1H), 8.05 (d, J=8.8 Hz, 1H), 7.95 (d, J=8.8 Hz, 2H), 7.67-7.64 (m, 5H), 7.58 (d, J=3.7 Hz, 1H), 7.48-7.42 (m, 6H), 7.10 (d, J=9.0 Hz, 2H), 7.01 (d, J=3.7 Hz, 1H), 4.95 (s, 2H), 3.86 (s, 3H), 1.05 (s, 9H).

Step 5: N-(5-(5-(Hydroxymethyl)thiophen-2-yl)-2-nitrophenyl)-4-methoxybenzamide (190)

A solution of compound 189 (0.673 g, 1.08 mmol) in a 1M solution of tetrabutylammonium fluoride in THF (1.5 mL, 1.5 mmol) was stirred for 90 min at room temperature. The reaction mixture was diluted with AcOEt, washed with 5% KHSO4, water, dried over MgSO4, filtered and concentrated to give a solid material which was triturated with DCM, to afford title compound 190 (0.805 g, 75% yield). The supernatant was collected, evaporated and the residue was purified by flash column chromatography (eluent: 50% AcOEt in DCM) to afford additional amount of 190 (0.161 g, 15% yield).

1H NMR (DMSO-$d_6$) δ (ppm): 10.73 (s, 1H), 8.17 (d, J=2.0 Hz, 1H), 8.05 (d, J=8.8 Hz, 1H), 7.95 (d, J=9.0 Hz, 2H), 7.63 (dd, J=8.8, 2.2 Hz, 1H), 7.57 (d, J=3.7 Hz, 1H), 7.11 (d, J=9.0 Hz, 2H), 7.04 to 7.03 (m, 1H), 5.65 (t, J=5.7 Hz, 1H), 4.67 (d, J=5.9 Hz, 2H), 3.86 (s, 3H). LRMS: 384.41 (calc) 407.1 (obs M+Na).

Step 6: N-(5-(5-Formylthiophen-2-yl)-2-nitrophenyl)-4-methoxybenzamide (191)

A suspension of alcohol 190 (0.178 g, 0.463 mmol) in DCM (5.0 mL) was treated with solid Dess-Martin periodinane (0.399 g, 0.94 mmol) and stirred under nitrogen atmosphere at room temperature for 20 h. The reaction mixture was quenched with an aqueous solution of Na2S2O3, stirred for 60 min, diluted with DCM/MeOH mixture, washed with saturated NaHCO3, dried over MgSO4, filtered and concentrated to give title compound 191 (0.155 g, 88% yield).

1H NMR (DMSO-$d_6$) δ (ppm): 10.75 (s, 1H), 9.94 (s, 1H), 8.25 (d, J=2.0 Hz, 1H), 8.11 to 8.08 (m, 2H), 7.95 (dd, J=8.8, 1.2 Hz, 2H), 7.91 (dd, J=3.9, 1.2 Hz, 1H), 7.81 (dd, J=8.6, 2.2 Hz, 1H), 7.12 to 7.10 (m, 2H), 3.86 (s, 3H). LRMS: 382.39 (calc) 381.0 (obs M−H).

Step 7: N-(5-(5-((2-Hydroxyethylamino)methyl)thiophen-2-yl)-2-nitrophenyl)-4-methoxybenzamide (192)

A solution of aldehyde 191 (0.155 g, 0.41 mmol) in 1,2-dichloroethane (3.0 mL) was treated with ethanolamine (0.06 mL, 1 mmol) and the mixture was allowed to stir at room temperature for 6 h. The mixture was then treated with solid NaHB(OAc)3 (0.354 g, 1.67 mmol), more 1,2-dichloroethane (3 mL) and stirred a further 17 h at room temperature. The mixture was treated with 10% aqueous K2CO3, extracted with DCM, dried over MgSO4, filtered and concentrated. The residue was purified by flash column chromatography (eluent: 5 to 10% isopropanol in DCM with 1% triethylamine then 5 to 10% MeOH in DCM with 1% triethylamine, to give title compound 192 (77.5 mg, 44% yield).

$^1$H NMR (DMSO-$d_6$) δ (ppm): 10.74 (s, 1H), 8.21 (d, J=2.0 Hz, 1H), 8.07 (d, J=8.6 Hz, 1H), 7.95 (d, J=9.0 Hz, 2H), 7.66 to 7.61 (m, 2H), 7.17 to 7.10 (m, 3H), 7.80 (m, 1H), 4.13 to 4.10 (m, 2H), 3.86 (s, 3H), 3.55 (q, J=5.5 Hz, 2H), 2.78 (m, 2H). LRMS: 427.47 (calc) 428.3 (obs).

Step 8: N-(2-Amino-5-(5-((2-hydroxyethylamino)methyl)thiophen-2-yl)phenyl)-4-methoxybenzamide (193)

Following the same procedure as described in Example 14, step 4 (scheme 14) but substituting compound 146 for compound 192, the title compound 193 was obtained after column chromatography (46% yield, eluent: 50% MeOH in DCM with 1% triethylamine).

1H NMR (DMSO-$d_6$) δ (ppm): 9.58 (s, 1H), 7.97 (d, J=9.0 Hz, 2H), 7.40 (d, J=1.8 Hz, 1H), 7.23 to 7.21 (m, 1H), 7.05 to 7.02 (m, 3H), 6.86 (d, J=3.5 Hz, 1H), 6.77 (d, J=8.4 Hz, 1H), 5.10 (s, 2H), 4.53 (m, 1H), 3.88 (s, 2H), 3.83 (s, 3H), 3.47 (q, J=5.5 Hz, 2H), 2.63 (t, J=5.5 Hz, 2H). LRMS: 397.4 (calc) 795.5 (obs for 2M+H).

TABLE 12

Characterization of compound 194 prepared according to Scheme 20

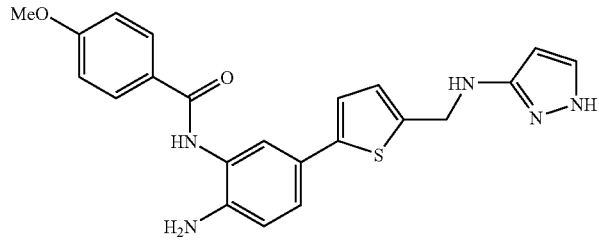

194

| Cpd | Ex | Name | Characterization |
|---|---|---|---|
| 194 | 20b | N-(5-(5-((1H-pyrazol-5-ylamino)methyl)-thiophen-2-yl)-2- | $^1$H NMR (DMSO-$d_6$) δ (ppm): 11.52 (s, 1H), 9.58 (s, 1H), 7.96 (d, J = 8.8 Hz, 2H), 7.37 (d, J = 2.2 Hz, 1H), 7.32 (m, 1H), 7.19 (dd, J = 8.2, 2.2 Hz, 1H), 7.04 to 7.01 (m, 3H), 6.87 (d, J = 3.5 Hz, 1H), 6.76 (d, J = 8.2 Hz, 1H), 5.64 (bs, 1H), 5.47 (s, |

TABLE 12-continued
Characterization of compound 194 prepared according to Scheme 20
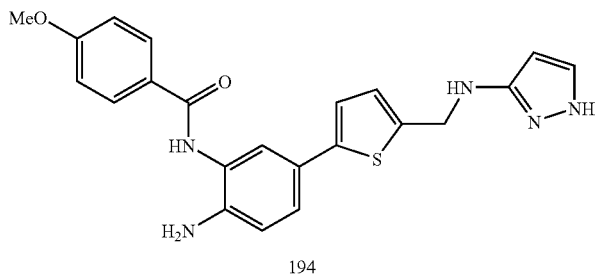 [SMILES: COc1ccc(C(=O)Nc2cc(-c3ccc(CNc4cc[nH]n4)s3)ccc2N)cc1]
194
| Cpd | Ex | Name | Characterization |
|---|---|---|---|
| | | aminophenyl)-4-methoxybenzamide | 1H), 5.08 (s, 2H), 4.33 (d, J = 6.3 Hz, 2H), 3.83 (s, 3H). LRMS: 419.50 (calc) 420.2 (obs). |
Example 21a
N-(2-Amino-5-(5-((hydroxyimino)methyl)thiophen-2-yl)phenyl)-4-(pyridin-3-yl)benzamide (201)
Scheme 21
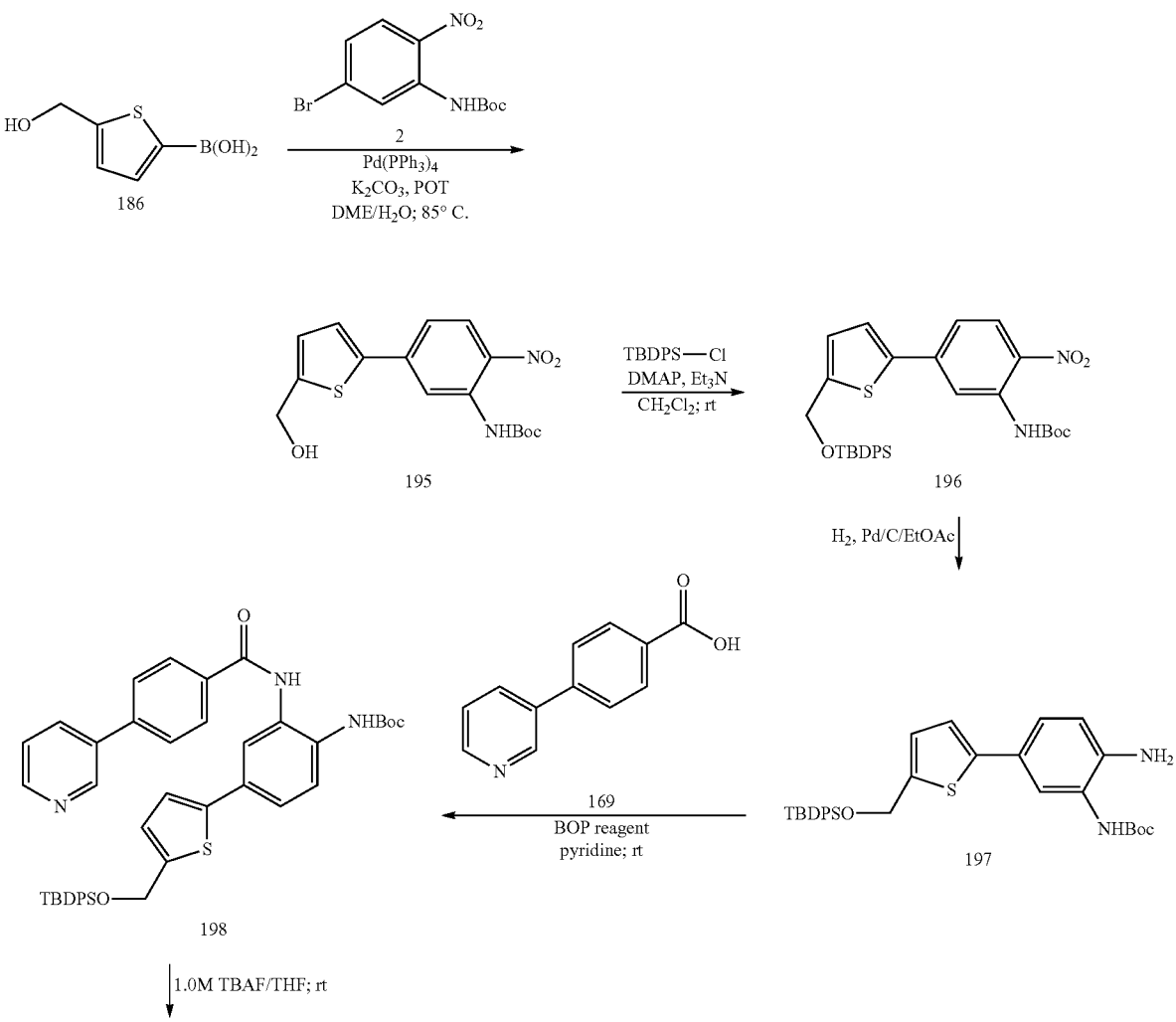

-continued

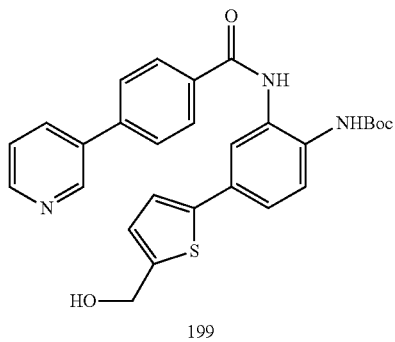
199

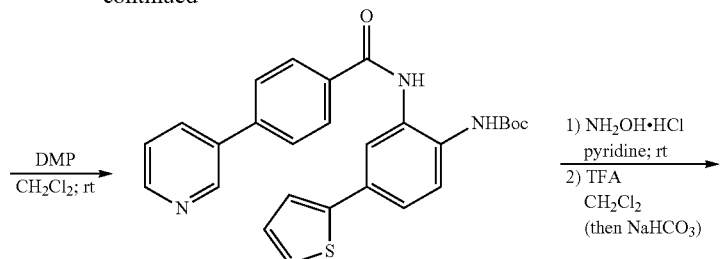
200

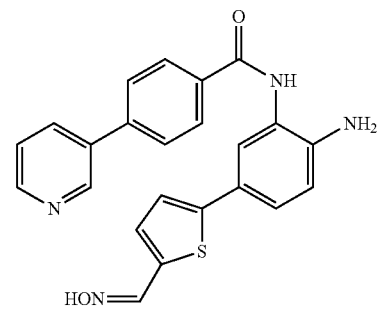
201: example 21a

Step 1: tert-Butyl 5-(5-(hydroxymethyl)thiophen-2-yl)-2-nitrophenylcarbamate (195)

Following the same procedure as described in Example 1, step 2 (scheme 1), but substituting 2-thiophene boronic acid for compound 186, title compound 195 was obtained in 48% yield [after flash chromatography (eluent: 20 to 50% AcOEt in hexane)].

1H NMR (DMSO-d$_6$) δ (ppm): 9.62 (s, 1H), 8.08 (d, J=2.2 Hz, 1H), 7.87 (dd, J=8.6, 2.3 Hz, 1H), 7.64 (d, J=8.6 Hz, 1H), 6.96 (d, J=3.5 Hz, 1H), 5.57 (t, J=5.7 Hz, 1H), 4.63 (d, J=5.7 Hz, 2H), 1.45 (s, 9H). LRMS: 350.09 (calc) 373.1 (obs M+Na).

Step 2: tert-Butyl 5-(5-((tert-butyldiphenylsilyloxy)methyl)thiophen-2-yl)-2-nitrophenylcarbamate (196)

Following the same procedure as described in Example 20, step 3 (scheme 20), but substituting compound 187 for compound 195, diisopropylethyl amine for triethylamine, and pyridine for DCM, title compound 196 was obtained after column chromatography (94% yield, eluent: 50% DCM in hexane).

1H NMR (DMSO-d$_6$) δ (ppm): 9.64 (s, 1H), 8.09 (d, J=2.3 Hz, 1H), 7.89 (dd, J=8.4, 2.2 Hz, 1H), 7.66 to 7.63 (m, 5H), 7.49 to 7.42 (m, 7H), 6.94 (d, J=3.7 Hz, 1H), 4.91 (s, 2H), 1.46 (s, 9H), 1.04 (s, 9H). LRMS: 588.21 (calc) 587.3 (obs M−H).

Step 3: tert-Butyl 2-amino-5-(5-((tert-butyldiphenylsilyloxy)methyl)thiophen-2-yl)phenylcarbamate (197)

Following the same procedure as described in Example 1, step 3 (scheme 1), but substituting compound 3 for compound 196, title compound 197 was obtained (98% yield).

LRMS: 502.17 (calc M-tBu) 503.4 (obs M-tBu).

Step 4: tert-Butyl 4-(5-((tert-butyldiphenylsilyloxy)methyl)thiophen-2-yl)-2-(4-(pyridin-3-yl)benzamido)phenylcarbamate (198)

Following the same procedure as outlined in Example 1, step 6 (scheme 1), but substituting compound 7 for compound 169 and compound 4 for compound 197, and using a catalytic amount of 4-dimethylaminopyridine, title compound 198 was obtained in 76% yield [after column chromatography (eluent: 50% AcOEt in hexane)].

1H NMR (DMSO-d$_6$) δ (ppm): 10.01 (s, 1H), 8.99 (d, J=2.3 Hz, 1H), 8.73 (s, 1H), 8.61 (dd, J=4.9, 1.6 Hz, 1H), 8.19-8.16 (m, 1H), 8.10 (d, J=8.4 Hz, 2H), 7.94 (d, J=8.4 Hz, 2H), 7.78 (d, J=2.2 Hz, 1H), 7.66-7.62 (m, 5H), 7.54-7.41 (m, 8H), 7.29 (d, J=3.7 Hz, 1H), 6.91 (d, J=3.5 Hz, 1H), 4.90 (s, 2H), 1.47 (s, 9H), 1.04 (s, 9H). LRMS: 739.29 (calc) 740.3 (obs).

Step 5: tert-Butyl 4-(5-(hydroxymethyl)thiophen-2-yl)-2-(4-(pyridin-3-yl)benzamido)-phenylcarbamate (199)

Following the same procedure as described in Example 20, step 5 (scheme 20) but substituting compound 189 for compound 198, title compound 199 was obtained in 90% yield [after column chromatography (eluent: 25% AcOEt in DCM)].

1H NMR (DMSO-d$_6$) δ (ppm): 9.97 (s, 1H), 8.99 (d, J=2.3 Hz, 1H), 8.75 (s, 1H), 8.61 (dd, J=4.7, 1.6 Hz, 1H), 8.18 (dq, J=7.8, 1.6 Hz, 1H), 8.10 (d, J=8.4 Hz, 2H), 7.93 (d, J=8.2 Hz, 2H), 7.79 (d, J=2.2 Hz, 1H), 7.60 (d, J=8.4 Hz, 1H), 7.54 to 7.51 (m, 1H), 7.47 (dd, J=8.4, 2.2 Hz, 1H), 7.28 (d, J=3.5 Hz, 1H), 6.93 (d, J=3.5 Hz, 1H), 5.51 (t, J=5.9 Hz, 1H), 4.62 (d, J=5.7 Hz, 2H), 1.47 (s, 9H). LRMS: 501.17 (calc) 502.1 (obs).

Step 6: tert-Butyl 4-(5-formylthiophen-2-yl)-2-(4-(pyridin-3-yl)benzamido)phenylcarbamate (200)

Following the same procedure as described in Example 20, step 6 (scheme 20), but substituting compound 190 for compound 199, title compound 200 was obtained in 24% yield [after column chromatography (eluent: 5% isopropanol in DCM)].
LRMS: 499.2 (calc) 500.1 (obs).

Steps 7 & 8: N-(2-Amino-5-(5-((hydroxyimino)methyl)thiophen-2-yl)phenyl)-4-(pyridin-3-yl)benzamide (201)

A solution of aldehyde 200 (20.4 mgs, 0.41 mmol) in pyridine (4 mL) was treated with solid hydroxylamine hydrochloride (0.344 g, 4.95 mmol) and the solution was stirred at room temperature for 4 h, diluted with DCM, washed with saturated NaHCO3, brine, dried over MgSO4, filtered and concentrated. The residue was purified by chromatotron (eluent: 5% MeOH in DCM) to provide a solid material (25 mg, structure not shown in the scheme 21). LRMS: 514.2 (calc) 515.2 (obs).

Following the same procedure as described in Example 1, step 7 (scheme 1), but substituting compound 8 for the above mentioned material, the title compound 201 was obtained in 62% yield [after column chromatography (eluent: 10% isopropanol in DCM)].

1H NMR (DMSO-$d_6$) δ (ppm): 11.77 (s, 1H), 9.80 (s, 1H), 8.98 (d, J=1.8 Hz, 1H), 8.61 (dd, J=4.7, 1.6 Hz, 1H), 8.18 to 8.16 (m, 1H), 8.12 (d, J=8.4 Hz, 2H), 7.90 (d, J=8.4 Hz, 2H), 7.74 (s, 1H), 7.56 to 7.51 (m, 2H), 7.36 (q, J=3.9 Hz, 2H), 7.26 (d, J=3.9 Hz, 1H), 6.81 (d, J=8.4 Hz, 1H), 5.31 (s, 2H). LRMS: 414.1 (calc), 414.9 (obs).

Example 22a

N-(2-Amino-5-(thiophen-2-yl)phenyl)-2-(1-benzylpiperidin-4-ylidene)acetamide (205)

Scheme 22

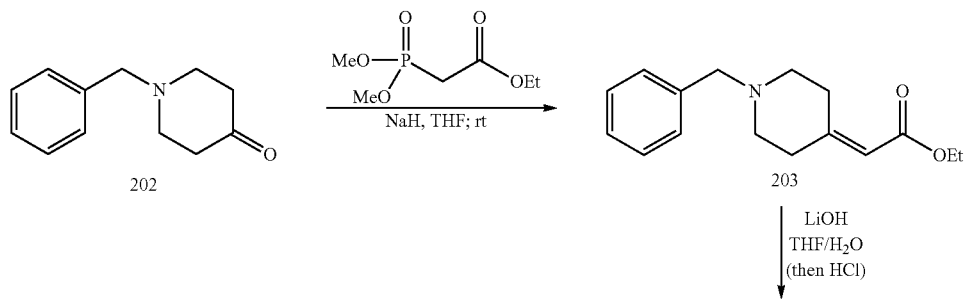

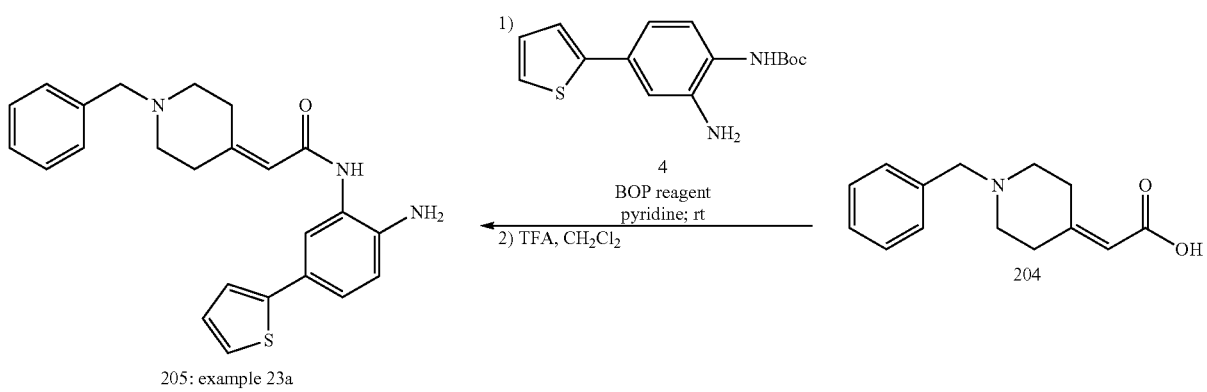

205: example 23a

Step 1: Ethyl 2-(1-benzylpiperidin-4-ylidene)acetate (203)

To a suspension of sodium hydride (4.8 g, 121 mmol) in THF (300 mL) was added a solution of ethyl 2-(dimethoxyphosphoryl)acetate (24.3 mL, 121.2 mmol) in THF (60 mL) drop wise over 30 min. After complete addition the solution was stirred for 10 min then a solution of ketone 202 (15.3 g, 80.8 mmol) in THF (80 mL) was added drop wise over 20 min. After 60 min of stirring at room temperature, the reaction mixture was quenched with H2O, extracted with diethyl ether. The organic phase were washed with H2O, brine, dried over Na2SO4, filtered, and purified by column chromatography (30 to 40% AcOEt in hexane) to give title compound 203 (20.4 g, 98% yield).

LRMS: 259.20 (calc) 260.1 (obs).

Step 2: 2-(1-Benzylpiperidin-4-ylidene)acetic acid (204)

To a solution of ester 203 (8.06 g, 31.1 mmol) in THF (100 mL) was added an aqueous solution of LiOH (1.96 g, 46.6 mmol) in water (30 mL) and the reaction mixture was allowed to stir at 45° C. for 60 min. Then more LiOH (0.5 g, 11.9 mmol) was added to the heating solution. After further heating for 8 h, the reaction mixture was concentrated, extracted with AcOEt. The extract was concentrated and the residue was combined with the white solid which was collected by filtration from the aqueous phase. The combined solid materials were dissolved in DCM, treated with 2N HCl in diethyl ether (10 mL) and the mixture was diluted with benzene, evaporated and dried under vacuum to give (presumably) mono-hydrochloride salt of the acid 204 (8.23 g, 99% yield).

$^1$H NMR (CD$_3$OD) δ (ppm): 7.58 to 7.54 (m, 2H), 7.51 to 7.48 (m, 3H), 5.86 (s, 1H), 4.36 (s, 2H), 3.35 to 3.13 (m, 6H), 2.66 to 2.63 (m, 2H). LRMS: 231.13 (calc) 232.1 (obs).

Steps 3 & 4: N-(2-Amino-5-(thiophen-2-yl)phenyl)-2-(1-benzylpiperidin-4-ylidene)acetamide (205)

Following the same procedure as described in Example 1, steps 6 & 7 (scheme 1), but substituting compound 7 for compound 204, the title compound 205 was obtained (step 3: 34% yield, step 4: 33% yield).

1H NMR (MeOH-d4) δ (ppm): 7.44 (d, J=2.0 Hz, 1H), 7.36-7.27 (m, 6H), 7.22 (dd, J=5.2, 0.8 Hz, 1H), 7.19 (dd, J=3.6, 1.2 Hz, 1H), 7.01 (dd, J=5.2, 3.6 Hz, 1H), 6.85 (d, J=8.4 Hz, 1H), 5.94 (s, 1H), 3.57 (s, 2H), 3.06 (t, J=6.0 Hz, 2H), 2.61-2.54 (m, 4H), 2.40 (t, J=5.6 Hz, 2H) LRMS: 403.5 (calc) 404.2 (obs).

Example 23a

N-(4-Amino-4'-(methylthio)biphenyl-3-yl)-4-methoxybenzamide (209)

And Example 23b

N-(4-Amino-4'-(methylsulfinyl)biphenyl-3-yl)-4-methoxybenzamide (210)

Scheme 23

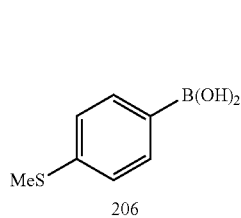
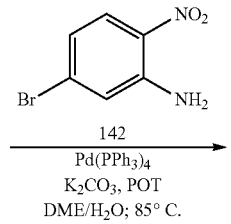

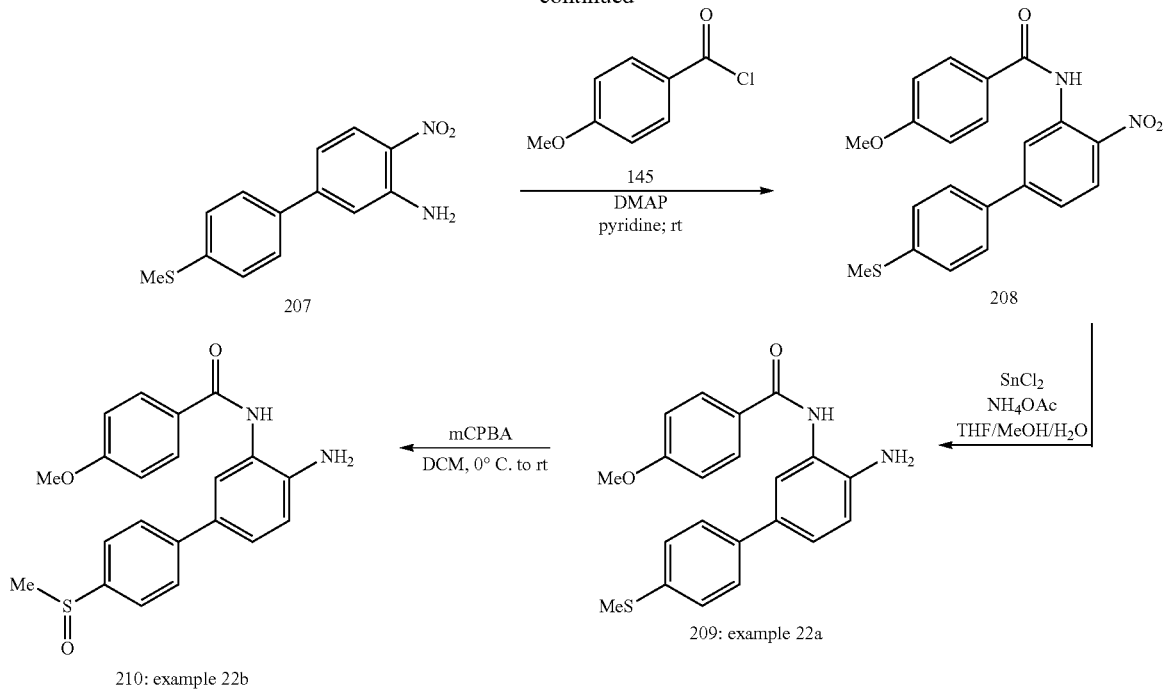

Step 1: 4'-(Methylthio)-4-nitrobiphenyl-3-amine (207)

Following the same procedure as described in Example 1, step 2 (scheme 1), but substituting 2-thiophene boronic acid for compound 206, and compound 2 for compound 142, title compound 207 was obtained in 100% yield [after column chromatography (eluent: 20 to 50% AcOEt in hexane)].

1H NMR: (DMSO-d$_6$) δ (ppm): 8.01 (d, J=9.0 Hz, 1H), 7.59 (dd, J=6.7, 2.0 Hz, 2H), 7.45 (s, 2H), 7.36 (dd, J=6.7, 2.0 Hz, 2H), 7.26 (d, J=2.0 Hz, 1H), 6.91 (dd, J=9.0, 2.0 Hz, 1H), 2.52 (s, 3H).

Step 2: 4-Methoxy-N-(4'-(methylthio)-4-nitrobiphenyl-3-yl)benzamide (208)

Following the same procedure as described in Example 14, step 3 (scheme 14), but substituting compound 144 for compound 207, title compound 208 was obtained (66% yield).

1H NMR (DMSO-d$_6$) δ (ppm): 10.70 (s, 1H), 8.17 (d, J=2.0 Hz, 1H), 8.08 (d, J=8.4 Hz, 1H), 7.95 (dd, J=6.8, 1.8 Hz, 2H), 7.71 (dd, J=8.8, 2.3 Hz, 2H), 7.66 (dd, J=8.4 Hz, 1H), 7.40 (d, J=8.2 Hz, 2H), 7.11 (d, J=8.8 Hz, 2H), 3.86 (s, 3H), 2.54 (s, 3H).

Step 3: 4-Methoxy-N-(4'-(methylthio)-4-nitrobiphenyl-3-yl)benzamide (209)

Following the same procedure as described in Example 14, step 4 (scheme 14), but substituting compound 146 for compound 208, title compound 209 was obtained in 54% yield [after column chromatography (eluent: 5% isopropanol in DCM) and trituration from pentane/diethyl ether].

1H NMR (DMSO-d$_6$) δ (ppm): 9.63 (s, 1H), 7.99 (d, J=8.8 Hz, 2H), 7.52 to 7.48 (m, 3H), 7.32 to 7.27 (m, 3H), 7.06 (d, J=8.8 Hz, 2H), 6.85 (d, J=8.4 Hz, 1H), 5.07 (s, 2H), 3.84 (s, 3H), 2.49 (s, 3H). LRMS: 364.1 (calc), 365.1 (obs).

Step 4: N-(4-amino-4'-(methylsulfinyl)biphenyl-3-yl)-4-methoxybenzamide (210)

Following the same procedure as described in Example 10, step 2 (scheme 10), but substituting compound 120 for compound 209, the title compound 210 was obtained in 57% yield [after column chromatography (5% isopropanol in DCM)].

1H NMR (DMSO-d$_6$) δ (ppm): 9.64 (s, 1H), 8.00 (d, J=9.0 Hz, 2H), 7.76 (d, J=7.69 (d, J=8.6 Hz, 2H), 7.58 (d, J=2.2 Hz, 1H), 7.40 (dd, J=8.4 Hz, 1H), 7.06 (d, J=9.0 Hz, 2H), 6.88 (d, J=8.4 Hz, 1H), 5.21 (s, 2H), 3.84 (s, 3H), 2.76 (s, 3H). LRMS: 380.1 (calc), 380.9 (obs).

Example 24a
Pyridin-3-ylmethyl 6-(2-amino-5-(thiophen-2-yl)phenylcarbamoyl)-3,4-dihydroquino-line-1(2H)-carboxylate (216)
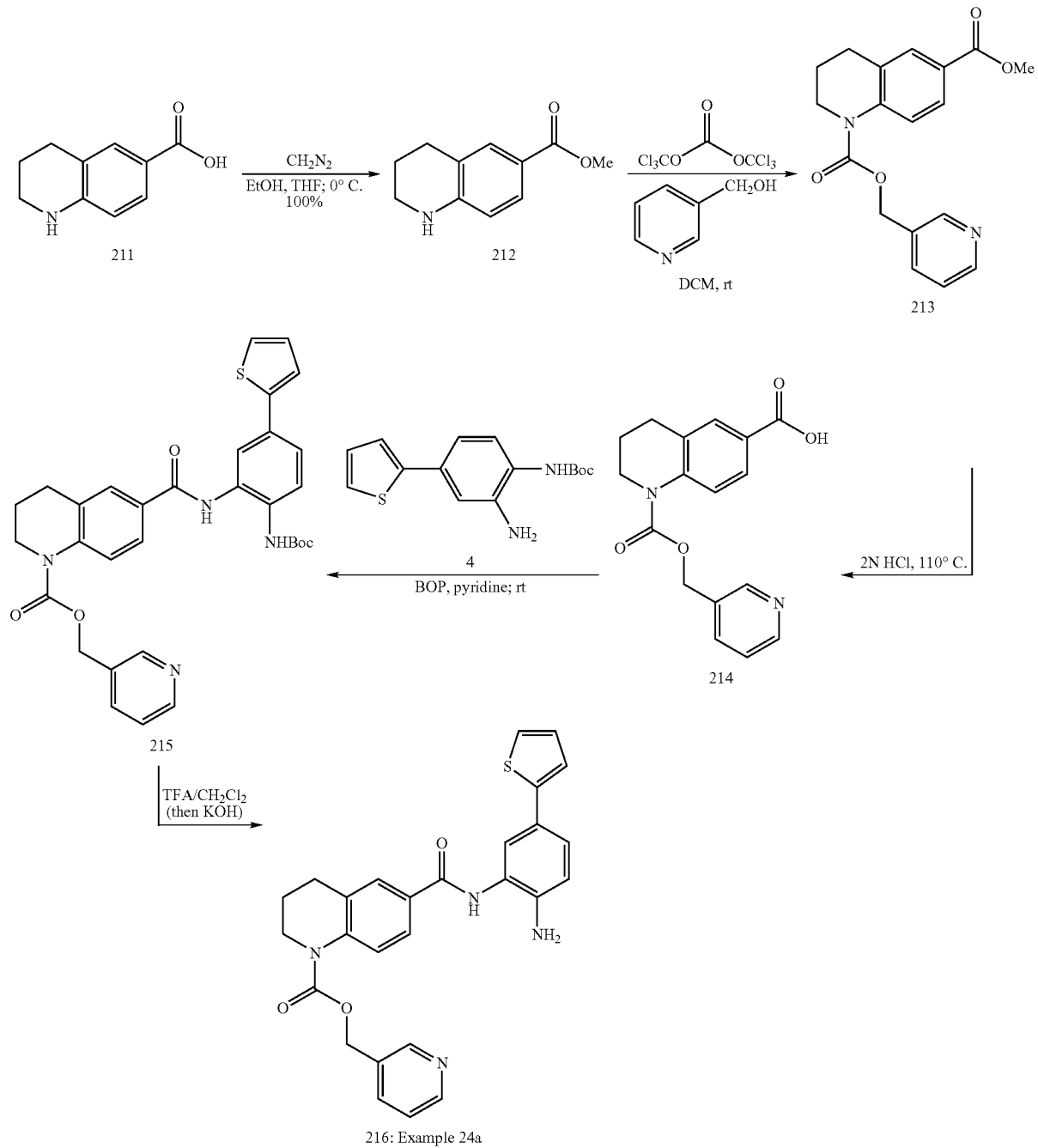
216: Example 24a

Step 1: Methyl 1,2,3,4-tetrahydroquinoline-6-carboxylate (212)

A mixture of 50% potassium hydroxide in H₂O (30 mL) and diethyl ether (100 mL), stirred at 0° C., was treated portion-wise with solid N-nitroso-N-methyl urea (3.0 g, 29.1 mmol). The reaction mixture was stirred for 30 min then transferred into a separatory funnel, the aqueous layer was discarded and the yellow ethereal phase (diazomethane solution) was cooled to −78° C. in an Erlenmeyer flask. To a solution of acid 211 (1.0 g, 5.65 mmol) in THF (100 mL), stirred at 0° C., was added the ethereal solution of diazomethane (kept at −78° C.) drop wise. After the addition, the reaction mixture was stirred at 0° C. for 2 h then at room temperature for 4 h, and concentrated to give title compound 212 as a reddish solid (100% yield).

$^1$H NMR (DMSO-$d_6$) δ (ppm): 7.47 to 7.45 (m, 2H), 6.63 (s, 1H), 6.42 (d, J=8.4 Hz, 1H), 3.71 (s, 3H), 3.24-3.21 (m, 2H), 2.67 (t, J=6.3 Hz, 2H), 1.80-1.74 (m, 2H).

Step 2: 6-Methyl 1-pyridin-3-ylmethyl 3,4-dihydroquinoline-1,6(2H)-dicarboxylate (213)

A solution of triphosgene (0.489 g, 1.61 mmol) in DCM (5 mL) was treated with compound 212 (0.286 g, 1.50 mmol) and the solution was stirred under N₂ atmosphere at room temperature for 18 h. The DCM was removed under reduced pressure, the residue was dissolved in pyridin-3-yl methanol (1.0 mL, 10.3 mmol) and the solution was stirred at room temperature for 8 h then diluted with DCM, washed with saturated NaHCO₃, H₂O, dried over MgSO₄, filtered and concentrated to give title compound 213 (0.527 g, 100% yield).

LRMS: 326.1 (calc) 327.1 (obs)

Step 3: 1-((Pyridin-3-ylmethoxy)carbonyl)-1,2,3,4-tetrahydroquinoline-6-carboxylic acid (214)

A solution of ester 213 (0.489 g, 1.50 mmol) in 2N HCl (10 mL) was stirred at 110° C. for 3 h then concentrated, suspended in dry acetonitrile (20 mL), stirred for 2 h, diluted with dry benzene (20 mL), and stirred for 6 h. The suspension was concentrated then re-suspended in 1:1 acetonitrile and benzene (20 mL). The solid material was collected by filtration to provide title compound 214 (0.460 g, 88% yield).

LRMS: 312.1 (calc) 313.1 (obs)

Step 4: Pyridin-3-ylmethyl 6-(2-(tert-butoxycarbonylamino)-5-(thiophen-2-yl)phenylcarbamoyl)-3,4-dihydroquinoline-1(2H)-carboxylate (215)

Following the same procedure as described in Example 1, step 6 (example 1), but substituting compound 7 for compound 214, title compound 215 was obtained in 55% yield [after flash chromatography (eluent: 50% AcOEt in DCM)].

LRMS: 584.2 (calc) 484.16 (M-tBoc, obs)

Step 5: Pyridin-3-ylmethyl 6-(2-amino-5-(thiophen-2-yl)phenylcarbamoyl)-3,4-dihydroquinoline-1(2H)-carboxylate (216)

Following the same procedure as described in Example 1, step 7 (scheme 1), but substituting compound 8 for compound 215, and NaHCO₃ for KOH, the title compound 216 was obtained in 89% yield.

$^1$H NMR (DMSO-$d_6$) δ (ppm): 9.67 (s, 1H), 8.67 (d, J=1.6 Hz, 1H), 8.56 (dd, J=4.9, 1.8 Hz, 1H), 7.89 to 7.86 (m, 1H), 7.82 to 7.79 (m, 3H), 7.46 to 7.43 (m, 2H), 7.36 (dd, J=5.1, 1.2 Hz, 1H), 7.29 (dd, J=3.5, 2.2 Hz, 1H), 7.24 (dd, J=3.5, 1.2 Hz, 1H), 7.05 (dd, J=5.1, 3.5 Hz, 1H), 6.81 (d, J=8.4 Hz, 1H), 5.27 (s, 2H), 5.14 (s, 2H), 3.78 (t, J=6.1 Hz, 2H), 2.81 (t, J=6.4 Hz, 2H), 1.91 to 1.88 (m, 2H). LRMS: 484.16 (calc) 485.2 (obs).

Example 25a 2-(Dimethylamino)ethyl 4-(2-amino-5-(thiophen-2-yl)phenylcarbamoyl)benzylcar-bamate (221)

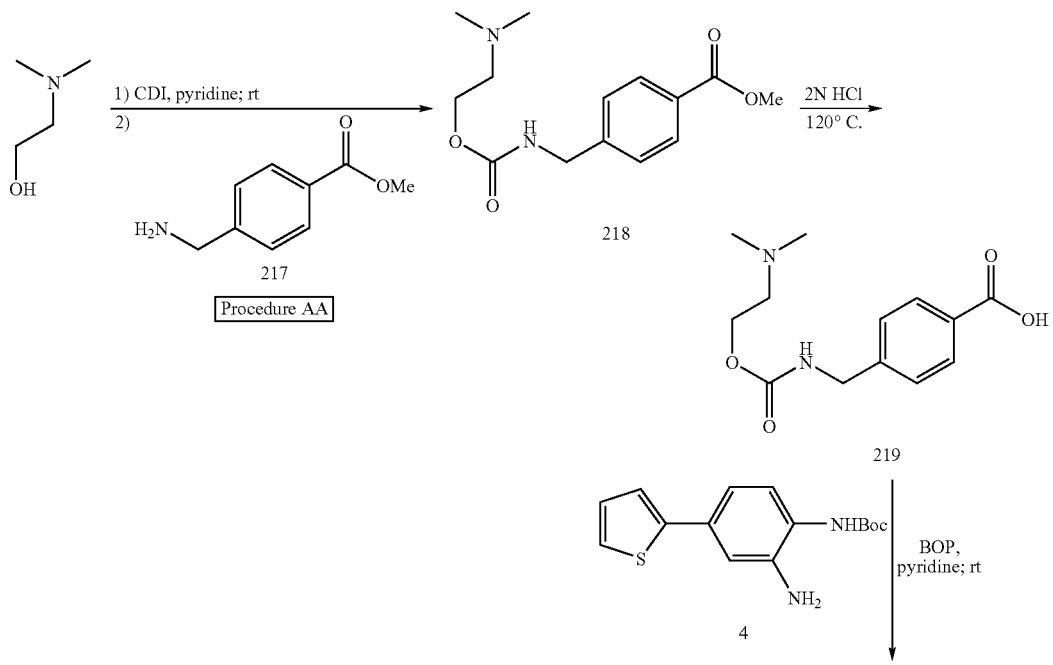

Scheme 25

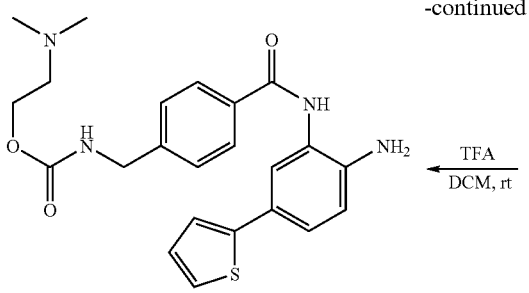

221: Example 25a

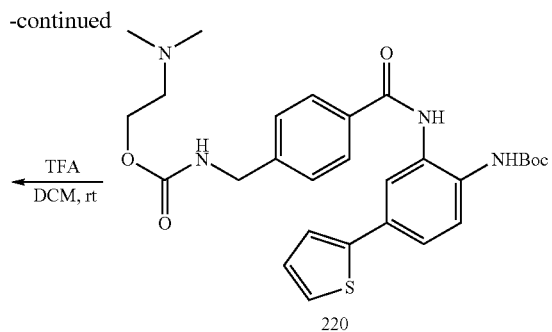

220

Step 1: Methyl 4-(((2-(dimethylamino)ethoxy)carbonylamino)methyl)benzoate (218)

A solution of carbonyl diimadzole (CDI) (609 mg, 3.76 mmol) in pyridine (5 mL) was treated with neat dimethylaminoethanol (400 μL, 3.98 mmol) and the mixture was stirred for 15 h at room temperature. Methyl 4-(aminomethyl)benzoate hydrochloride (217) (794 mg, 3.82 mmol) was then added and the reaction mixture was stirred for further 7 h, diluted with DCM, washed with saturated NaHCO3, dried over MgSO4, filtered and concentrated to produce title compound 218 as a white solid (1.16 g, >100% yield, crude, used without additional purification).

1H NMR (DMSO-$d_6$) δ (ppm): 7.93 to 7.90 (m, 2H), 7.38 (d, J=8.2 Hz, 2H), 4.25 (d, J=6.1 Hz, 2H), 4.04 (t, J=5.9 Hz, 2H), 3.84 (s, 3H), 2.43 (t, J=5.9 Hz, 2H), 2.15 (s, 6H).

Step 2: 4-(((2-(Dimethylamino)ethoxy)carbonylamino)methyl)benzoic acid (219)

Following the same procedure as described in Example 1, step 5 (scheme 1), but substituting compound 6 for compound 218, title compound 219 was obtained in 100% yield.

LRMS: 266.1 (calc) 267.1 (obs)

Step 3: 2-(Dimethylamino)ethyl 4-(2-tert-butoxycarbonyl-amino-5-(thiophen-2-yl)phenylcarbamoyl)benzylcarbamate (220)

Following the same procedure as described in Example 1, step 6 (scheme 1), but substituting compound 7 for compound 219, title compound 220 was obtained (40% yield).

1H NMR (DMSO-$d_6$) δ (ppm): 9.89 (s, 1H), 8.74 (s, 1H), 7.94 (d, J=8.4 Hz, 2H), 7.83 (d, J=2.2 Hz, 2H), 7.61 (d, J=8.4 Hz, 1H), 7.54 to 7.50 (m, 2H), 7.46 (dd, J=3.7, 1.2 Hz, 1H), 7.41 (d, J=8.2 Hz, 2H), 7.13 (dd, J=5.1, 3.7 Hz, 1H), 4.27 (d, J=6.1 Hz, 2H), 4.07 (t, J=5.9 Hz, 2H), 2.48 to 2.47 (m, 2H), 2.19 (s, 6H), 1.46 (s, 9H).

Step 4: 2-(Dimethylamino)ethyl 4-(2-amino-5-(thiophen-2-yl)phenylcarbamoyl)benzylcarbamate (221)

Following the same procedure as described in Example 1, step 7 (scheme 1), but substituting compound 8 for compound 220, the title compound 221 was obtained in 78% yield.

1H NMR: (DMSO-$d_6$) δ (ppm): 9.71 (s, 1H), 7.96 (d, J=9.0 Hz, 2H), 7.82 (t, J=6.1 Hz, 1H), 7.47 (d, J=2.0 Hz, 1H), 7.39 (s, 1H), 7.36 (d, J=1.2 Hz, 1H), 7.35 (d, J=1.2 Hz, 1H), 7.30 (dd, J=8.2, 2.2 Hz, 1H), 7.25 (dd, J=3.5, 1.2 Hz, 1H), 7.05 (dd, J=5.1, 3.5 Hz, 1H), 6.81 (d, J=8.4 Hz, 1H), 5.16 (s, 2H), 4.25 (d, J=6.1 Hz, 2H), 4.06 (t, J=5.8 Hz, 2H), 2.45 (t, J=5.8 Hz, 2H), 2.17 (s, 6H). LRMS: 438.2 (calc) 439.1 (obs)

TABLE 13

Characterization of compound 222 prepared according to Scheme 25

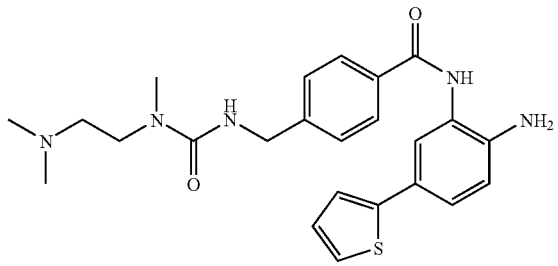

222: Example 25b

| Cpd | Ex | Name | Characterization |
|---|---|---|---|
| 222 | 25b | N-(2-amino-5-(thiophen-2-yl)phenyl)-4-((3-(2-(dimethylamino)ethyl)-3-methylureido)methyl)-benzamide | 1H NMR (DMSO-$d_6$) δ (ppm): 9.70 (s, 1H), 7.94 (d, J = 8.2 Hz, 2H), 7.47 (d, J = 2.0 Hz, 1H), 7.39 to 7.35 (m, 3H), 7.30 (dd, J = 8.2, 2.2 Hz, 1H), 7.25 (dd, J = 3.5, 0.98 Hz, 1H), 7.05 (dd, J = 5.1, 3.5 Hz, 2H), 6.81 (d, J = 8.4 Hz, 1H), 5.76 (s, 2H), 4.30 (d, J = 5.9 Hz, 2H), 3.31 (t, J = 6.7 Hz, 2H), 2.85 (s, 3H), 2.36 (t, J = 6.7 Hz, 2H), 2.18 (s, LRMS: 451.2 (calc) 452.3 (obs) |

Example 26a
(E)-3-(4-(2-Amino-5-(thiophen-2-yl)phenylcarbamoyl)phenyl)acrylic acid (226)
Example 26b
(E)-N-(2-Amino-5-(thiophen-2-yl)phenyl)-4-(3-(hydroxyamino)-3-oxoprop-1-enyl)benzamide (227)
Example 26c
3-(4-(2-Amino-5-(thiophen-2-yl)phenylcarbamoyl)phenyl)propanoic acid (230)
Example 26d
Methyl 3-(4-(2-amino-5-(thiophen-2-yl)phenylcarbamoyl)phenyl)propanoate (231)
Scheme 26
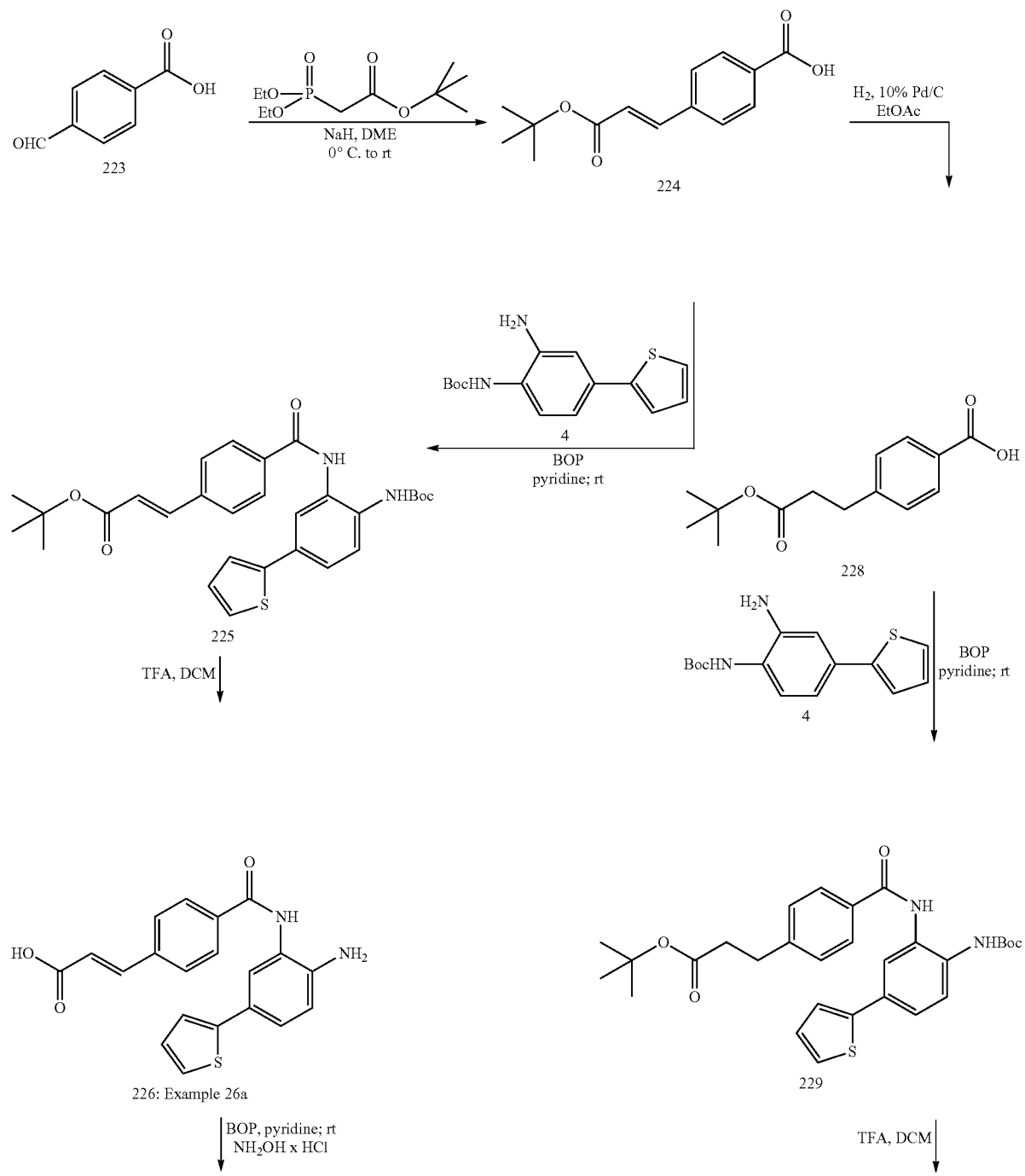

-continued

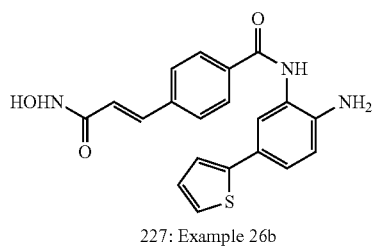

227: Example 26b

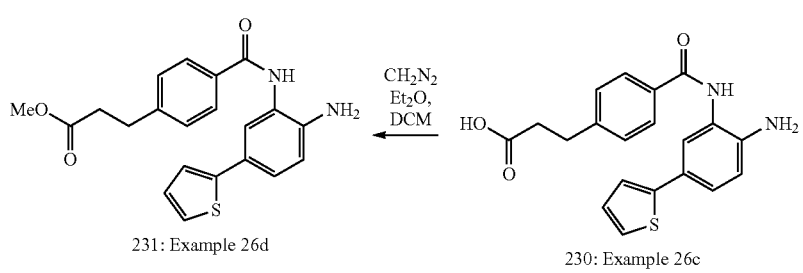

231: Example 26d              230: Example 26c

Step 1: (E)-4-(3-tert-Butoxy-3-oxoprop-1-enyl)benzoic acid (224)

A solution of 4-formylbenzoic acid (223) (306 mg, 2.04 mmol) and tert-butyl 2-(diethoxyphosphoryl)acetate (0.8 mL, 3.23 mmol) in ethyleneglycol dimethylether (15 mL) was stirred at 0° C. then treated with sodium hydride (60% in oil, 312 mg, 7.8 mmol), further stirred for 1 h then at room temperature for 3 h. The reaction mixture was diluted with acetone, stirred 10 min then treated with 5% aqueous KHSO$_4$, extracted with DCM. The extract was dried over MgSO$_4$, filtered and concentrated to provide title compound 224 as a white solid (811.5 mg, >100% yield, crude, used in the next step without additional purification).
LRMS: 248.10 (calc) 247.0 (M−H)

Step 2: (E)-tert-Butyl 3-(4-(2-(tert-butoxycarbonylamino)-5-(thiophen-2-yl)phenylcarbamoyl)phenyl)acrylate (225)

Following the procedure as described in Example 1, step 6 (scheme 1), but substituting compound 7 for compound 224, title compound 225 was obtained in 42% yield (over 2 steps starting from the acid 223).
LRMS: 520.20 (calc) 543.1 (M+Na)

Step 3: (E)-3-(4-(2-Amino-5-(thiophen-2-yl)phenylcarbamoyl)phenyl)acrylic acid trifluoroacetate (1:1) (226)

Following the same procedure as described in Example 1, step 7 (scheme 1), but substituting compound 8 for compound 225, the title compound 226 was obtained as a white solid in quantitative yield.
1H NMR (DMSO-d$_6$) δ (ppm): 9.96 (s, 1H), 8.04 (d, J=8.4 Hz, 2H), 7.86 (d, J=8.6 Hz, 2H), 7.67 (d, J=16.0 Hz, 1H), 7.52 (d, J=1.8 Hz, 1H), 7.41 (dd, J=4.7, 0.98 Hz, 1H), 7.38 (dd, J=8.0, 2.0 Hz, 1H), 7.31 (d, J=2.5 Hz, 1H), 7.07 (dd, J=5.1, 3.5 Hz, 1H), 6.93 (d, J=8.0 Hz, 1H), 6.68 (d, J=16.0 Hz, 1H). LRMS: 364.1 (calc) 364.9 (obs)

Step 4: (E)-N-(2-Amino-5-(thiophen-2-yl)phenyl)-4-(3-(hydroxyamino)-3-oxoprop-1-enyl)benzamide (227)

Following the same procedure as described in Example 1, step 6 (scheme 1), but substituting compound 4 for N-hydroxylamine hydrochloride salt and compound 7 for compound 226, the title compound 227 was obtained as a yellowish solid in 79% yield [purified by flash chromatography (eluent: 5% to 66% MeOH in DCM)].

1H NMR (DMSO-d$_6$) δ (ppm): 9.81 (s, 1H), 8.04 (d, J=8.0 Hz, 2H), 7.69 (d, J=7.6 Hz, 2H), 7.47 (d, J=2.0 Hz, 2H), 7.36 (dd, J=4.9, 0.78 Hz, 1H), 7.30 (dd, J=8.2, 2.3 Hz, 1H), 7.25 (dd, J=3.5, 0.78 Hz, 1H), 7.05 (dd, J=5.1, 3.7 Hz, 1H), 6.81 (d, J=8.4 Hz, 1H), 6.61 (d, J=16.4 Hz, 1H), 5.19 (s, 2H). LRMS: 379.0 (calc) 380.0 (obs).

Step 5: 4-(3-tert-Butoxy-3-oxopropyl)benzoic acid (228)

Following the same procedure as described in Example 1, step 3 (scheme 1), but substituting compound 3 for compound 224, title compound 228 was obtained in quantitative yield.
1H NMR (DMSO-d$_6$) δ (ppm): 7.85 (d, J=8.0 Hz, 2H), 7.34 (d, J=8.4 Hz, 2H), 2.87 (t, J=7.6 Hz, 2H), 2.46 (t, J=7.6 Hz, 2H), 1.34 (s, 9H).

Step 6: tert-Butyl 3-(4-(2-(tert-butoxycarbonylamino)-5-(thiophen-2-yl)phenylcarbamoyl)phenyl)propanoate (229)

Following the same procedure as described in Example 1, step 6 (scheme 1), but substituting compound 7 for compound 228, intermediate 229 was obtained (88% yield).
1H NMR (DMSO-d$_6$) δ (ppm): 9.87 (s, 1H), 8.76 (s, 1H), 7.90 (d, J=8.2 Hz, 2H), 7.82 (d, J=2.2 Hz, 1H), 7.60 (d, J=8.6 Hz, 1H), 7.54 to 7.50 (m, 2H), 7.46 (dd, J=3.7, 1.2 Hz, 1H), 7.41 (d, J=8.4 Hz, 2H), 7.13 (dd, J=5.1, 3.7 Hz, 1H), 2.90 (t, J=7.2 Hz, 2H), 2.58 (t, J=7.2 Hz, 2H), 1.45 (s, 9H), 1.37 (s, 9H).

Step 7: 3-(4-(2-Amino-5-(thiophen-2-yl)phenylcarbamoyl)phenyl)propanoic acid (230)

Following the same procedure as described in Example 1, Step 7 (scheme 1), but substituting compound 8 for intermediate 229, the title compound 230 was obtained as its trifluoroacetic acid salt (88% yield).
1H NMR (DMSO-d$_6$) δ (ppm): 9.68 (s, 1H), 7.92 (d, J=8.2 Hz, 2H), 7.47 (d, J=2.2 Hz, 1H), 7.39 to 7.35 (m, 3H), 7.29 (dd, J=8.4, 2.3 Hz, 1H), 7.24 (dd, J=3.5, 1.2 Hz, 1H), 7.05 (dd, J=5.1, 3.5 Hz, 1H), 6.81 (d, J=8.4 Hz, 1H), 5.15 (s, 2H), 2.90 (t, J=7.6 Hz, 2H), 2.58 (t, J=7.4 Hz, 2H).

Step 8: Methyl 3-(4-(2-amino-5-(thiophen-2-yl)phenylcarbamoyl)phenyl)propanoate (231)

A mixture of 50% potassium hydroxide in H$_2$O (30 mL) and diethyl ether (100 mL), stirred at 0° C., was treated portion wise with solid N-nitroso-N-methyl urea (3.0 g, 29.1 mmol). The reaction mixture was stirred for 30 min then transferred into a separatory funnel, the aqueous layer was discarded and the yellow ethereal phase (diazomethane solution) was cooled to −78° C. in an Erlenmeyer flask. A suspension of the acid 230 (20 mg, 0.055 mmol) in DCM (2 mL) was treated with the diazomethane solution in diethyl ether (3 mL) and the yellow solution was stirred at room temperature for 3 h, concentrated and the residue was purified by flash chromatography (eluent: 2% isopropanol in DCM) to provide title compound 231 (19.7 mg, 94% yield).

$^1$H NMR (DMSO-$d_6$) δ (ppm): 9.69 (s, 1H), 7.92 (d, J=8.2 Hz, 2H), 7.46 (d, J=2.0 Hz, 1H), 7.38 to 7.35 (m, 3H), 7.30 (dd, J=8.2, 2.2 Hz, 1H), 7.24 (dd, J=3.5, 1.2 Hz, 1H), 7.05 (dd, J=5.1, 3.5 Hz, 1H), 6.81 (d, J=8.4 Hz, 1H), 5.16 (s, 2H), 3.59 (s, 3H), 2.93 (t, J=7.4 Hz, 2H), 2.69 (t, J=7.4 Hz, 2H). LRMS: 380.12 (calc) 381.2 (obs).

TABLE 14

Characterization of compounds 232-235 prepared according to Scheme 26

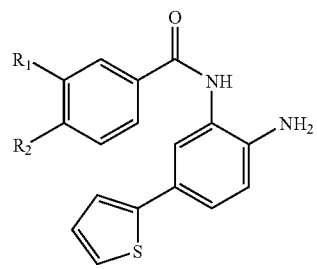

232-235

| Cpd | Ex | R$_1$ | R$_2$ | Name | Characterization |
|---|---|---|---|---|---|
| 232 | 26e | HO-C(=O)-CH$_2$CH$_2$- | H | 3-(3-(2-amino-5-(thiophen-2-yl)phenylcarbamoyl)-phenyl)propanoic acid | $^1$H NMR (DMSO-$d_6$) δ (ppm): 9.91 (s, 1H), 7.89 (s, 1H), 7.84 (d, J = 7.0 Hz, 1H), 7.52 (d, J = 2.2 Hz, 1H), 7.48 to 7.46 (m, 2H), 7.44 to 7.41 (m, 2H), 7.39 (dd, J = 8.2 Hz, 1H), 7.32 (dd, J = 3.5 Hz, 1H), 7.08 (dd, J = 5.1, 3.5 Hz, 1H), 6.95 (d, J = 8.4 Hz, 1H), 2.92 (t, J = 7.6 Hz, 2H), 2.62 (t, J = 7.6 Hz, 2H). LRMS: 366.10 (calc) 367.1 (obs) |
| 233 | 26f | H | HO-C(=O)-C(CH$_3$)- | 2,2,2-trifluoroacetic acid compound with 4-(2-amino-5-(thiophen-2-yl)phenylcarbamoyl)-benzoic acid (1:1) | $^1$H NMR (DMSO-$d_6$) δ (ppm): 10.03 (s, 1H), 8.09 (q, J = 8.6 Hz, 4H), 7.51 (d, J = 2.0 Hz, 1H), 7.40 (dd, J = 4.9, 0.98 Hz, 1H), 7.37 (dd, J = 8.2, 2.2 Hz, 1H), 7.30 (dd, J = 3.3, 0.78 Hz, 1H), 7.07 (dd, J = 5.1, 3.5 Hz, 1H), 6.90 (d, J = 8.4 Hz, 1H). LRMS: 338.1 (calc) 339.0 (obs). |
| 234 | 26g | H | HOHN-C(=O)- | N1-(2-amino-5-(thiophen-2-yl)phenyl)-N4-hydroxyterephthalamide | $^1$H NMR (DMSO-$d_6$) δ (ppm): 9.84 (s, 1H), 8.06 (d, J = 8.4 Hz, 2H), 7.87 (d, J = 8.4 Hz, 2H), 7.47 (d, J = 2.2 Hz, 1H), 7.36 (dd, J = 5.1, 1.2 Hz, 1H), 7.31 (dd, J = 8.4, 2.3 Hz, 1H), 7.25 (dd, J = 3.5, 1.2 Hz, 1H), 7.05 (dd, J = 5.1, 3.5 Hz, 1H), 6.81 (d, J = 8.4 Hz, 1H), 5.21 (s, 2H). LRMS: 353.1 (calc) 354.0 (obs). |
| 235 | 26h | H | MeO-C(=O)- | methyl 4-(2-amino-(thiophen-2-yl)phenylcarbamoyl)-benzoate | $^1$H NMR (DMSO-$d_6$) δ (ppm): 9.94 (s, 1H), 8.11 (q, J = 8.4 Hz, 4H), 7.47 (d, J = 2.2 Hz, 1H), 7.36 (dd, J = 5.1, 0.98 Hz, 1H), 7.31 (dd, J = 8.4, 2.2 Hz, 1H), 7.25 (dd, J = 3.5, 0.98 Hz, 1H), 7.05 (dd, J = 5.1, 3.7 Hz, 1H), 6.81 (d, J = 8.2 Hz, 1H), 5.22 (s, 2H), 3.90 (s, 3H). LRMS: 352.1 (calc) 353.0 (obs) |

Example 27a
(S)—N-(2-Amino-5-(thiophen-2-yl)phenyl)-4-((3-(dimethylamino)-2,5-dioxopyrrolidin-1-yl)methyl)benzamide (242)
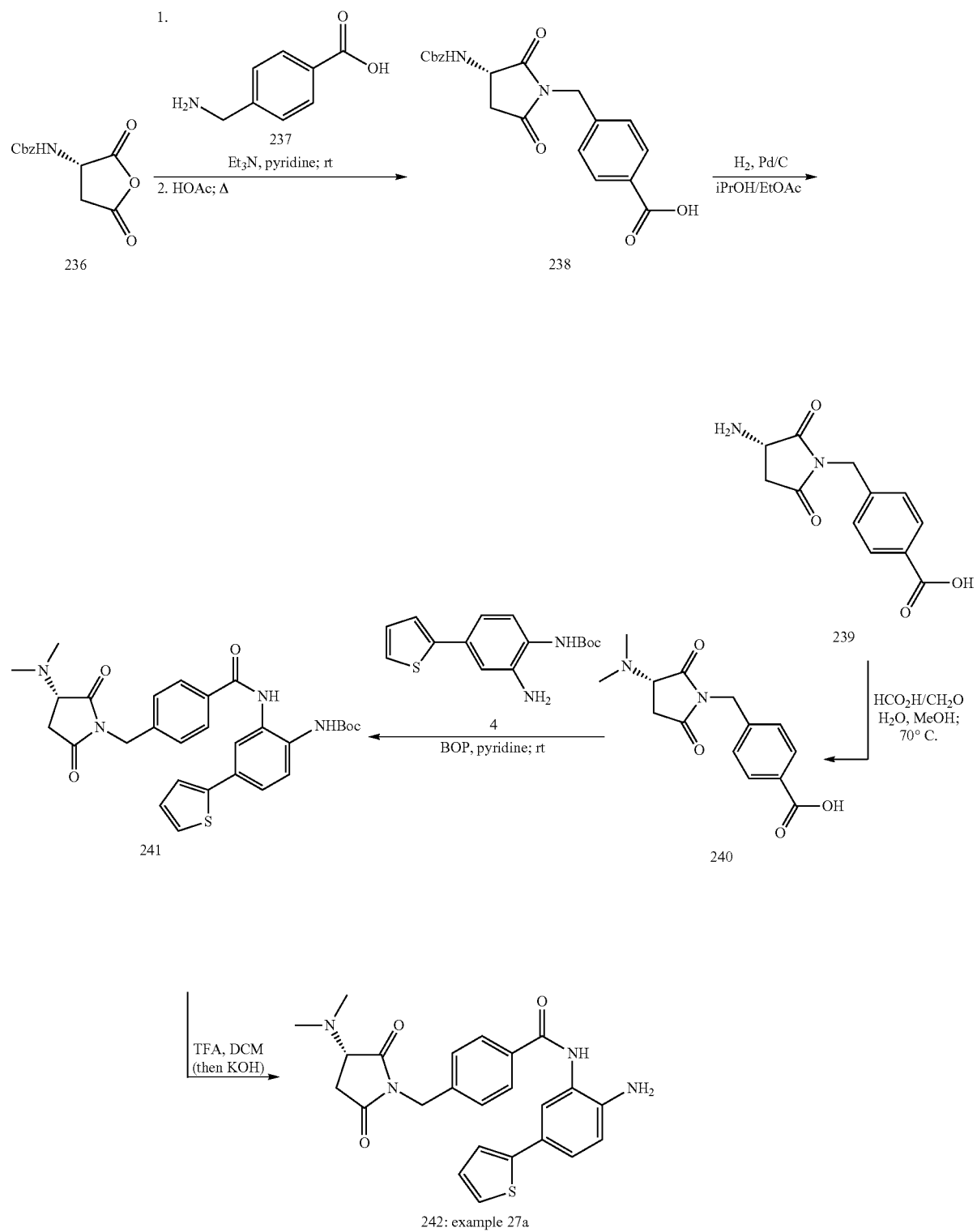
242: example 27a

Step 1: (S)-4-((3-(Benzyloxycarbonylamino)-2,5-dioxopyrrolidin-1-yl)methyl)benzoic acid (238)

A mixture of N-carbobenzyloxy-L-aspartic anhydride (236) (546 mg, 2.19 mmol) and 4-(aminomethyl)benzoic acid hydrochloride (237) (383 mg, 2.53 mmol) was suspended in pyridine (8 mL) and treated with triethylamine (1 mL). The white suspension was stirred at room temperature for 9 h then concentrated under reduced pressure. The residue was dissolved in acetic acid and stirred at 83° C. for 24 h, concentrated, diluted with DCM, washed with an aqueous solution of KHSO4 and H2O then concentrated. The residue was diluted once again with benzene, concentrated and the remaining yellow solid was triturated with MeOH/H2O (1:1) to give title compound 238 (471 mg, 56% yield).
LRMS: 382.1 (calc) 383.0 (M+H)

Step 2: (S)-4-((3-Amino-2,5-dioxopyrrolidin-1-yl)methyl)benzoic acid (239)

Following the same procedure as described in Example 1, step 3 (scheme 1), but substituting AcOEt for a 2:1 mixture of isopropanol-ethylacetate, title compound 239 was obtained in quantitative yield.
LRMS: 248.1 (calc) 249.0 (M+H)

Step 3: (S)-4-((3-(Dimethylamino)-2,5-dioxopyrrolidin-1-yl)methyl)benzoic acid (240)

To a solution of the amino acid 239 (305 mg, 1.23 mmol) in 96% formic acid (30 mL), MeOH (15 mL) and H$_2$O (5 mL) was added solid formaldehyde (77.2 mg, 25.7 mmol) and the mixture was stirred at 70° C. for 3.5 h then more formaldehyde was added (579 mg, 19.3 mmol) and the reaction was further stirred at 70° C. for 4 h. The reaction mixture was cooled to 40° C., stirred under vacuum for 20 h and evaporated under reduced pressure. The residue was suspended in dry MeOH/benzene and the solvents were removed under reduced pressure. The suspension-evaporation procedure was repeated two more times, to provide title compound 240 (339 mg, quantitative yield). The material was used without additional purification in the next step.
LRMS: 276.1 (calc) 277.0 (M+H)

Step 4: (S)-tert-Butyl 2-(4-((3-(dimethylamino)-2,5-dioxopyrrolidin-1-yl)methyl)benzamido)-4-(thiophen-2-yl)phenylcarbamate (241)

Following the same procedure as described in Example 1, step 6 (scheme 1), but substituting compound 7 for compound 240, title compound 241 was obtained in 17% yield (over two steps).
1H NMR (DMSO-d$_6$) δ (ppm): 9.90 (s, 1H), 8.74 (s, 1H), 7.93 (d, J=8.2 Hz, 2H), 7.80 (d, J=2.2 Hz, 1H), 7.62 (d, J=8.6 Hz, 1H), 7.54 to 7.50 (m, 2H), 7.45 (dd, J=3.5, 0.98 Hz, 1H), 7.40 (d, J=8.4 Hz, 2H), 7.13 (dd, J=5.1, 3.5 Hz, 1H), 4.65 (s, 2H), 3.95 (dd, J=8.6, 4.7 Hz, 1H), 2.89 to 2.69 (m, 2H), 2.25 (s, 6H), 1.45 (s, 9H).

Step 5: (S)—N-(2-Amino-5-(thiophen-2-yl)phenyl)-4-((3-(dimethylamino)-2,5-dioxopyrrolidin-1-yl)methyl)benzamide (242)

Following the same procedure as described in Example 1, Step 7, but substituting compound 8 for compound 241, the title compound 242 was obtained (81% yield).
1H NMR (DMSO-d$_6$) δ (ppm): 9.71 (s, 1H), 7.95 (d, J=8.2 Hz, 2H), 7.46 (d, J=2.2 Hz, 1H), 7.38 to 7.35 (m, 3H), 7.30 (dd, J=8.4, 2.2 Hz, 1H), 7.24 (dd, J=3.5, 1.2 Hz, 1H), 7.05 (dd, J=5.1, 3.5 Hz, 1H), 6.80 (d, J=8.4 Hz, 1H), 5.16 (s, 2H), 4.64 (s, 2H), 3.95 (dd, J=8.6, 4.7 Hz, 1H), 2.89 to 2.82 (m, 1H), 2.74 to 2.68 (m, 1H), 2.25 (s, 6H).

Example 28a
(S)—N-(2-Amino-5-(thiophen-2-yl)phenyl)-4-((3-(pyridin-3-ylamino)pyrrolidin-1-yl)methyl)benzamide (249)

Scheme 28

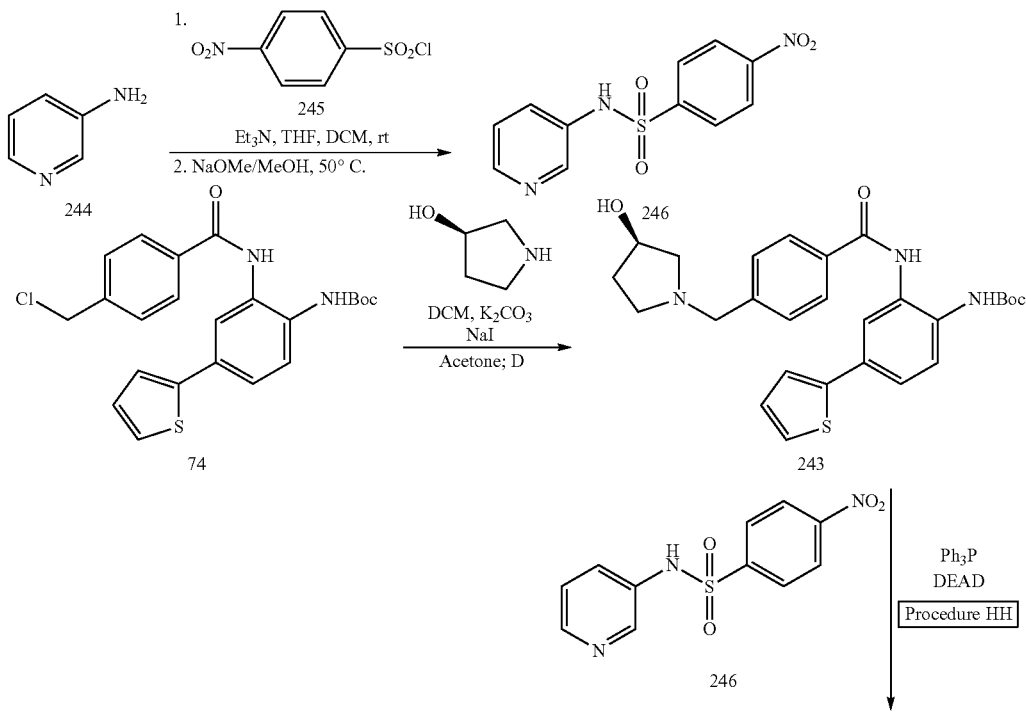

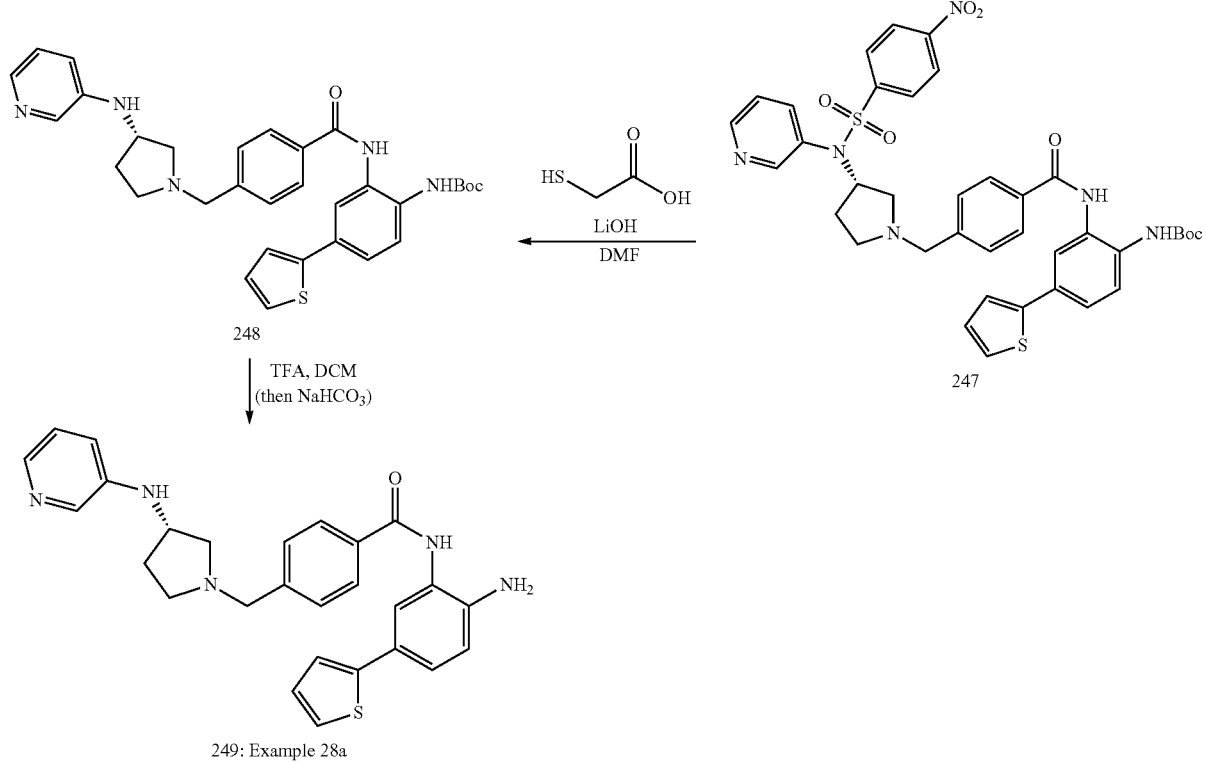

249: Example 28a

Step 1: (R)-tert-Butyl 2-(4-((3-hydroxypyrrolidin-1-yl)methyl)benzamido)-4-(thiophen-2-yl)phenylcarbamate (243)

Following the same procedure as described in Example 6, step 2 (scheme 6), but substituting (S)-2-(methoxymethyl)pyrrolidine for (R)-pyrrolidin-3-ol (0.173 g, 1.99 mmol), compound 243 was obtained in quantitative yield.

LRMS: 493.2 (calc) 494.2 (obs)

Step 2: 4-Nitro-N-(pyridin-3-yl)benzenesulfonamide (246)

To a solution of 3-aminopyridine 244 (3.03 g, 32.23 mmol) in THF (70 mL) and DCM (135 mL) was added 4-nitrobenzene sulfonyl chloride 245 (1.5 g, 67.68 mmol), triethylamine (7.17 g, 70.9 mmol) and dimethylamino pyridine (catalytic amount). The reaction mixture was allowed to stir at room temperature for 1 h then concentrated. The residue was taken up in MeOH (200 mL) then solid sodium methoxide (20 g) was added and the reaction mixture was stirred at 50° C. for 3 h, carefully neutralized with 1N HCl until pH 7. The formed precipitate was collected by filtration to give the title compound 246 (7.67 g, 85% yield).

1H NMR (DMSO-$d_6$) δ (ppm): 10.88 (s, 1H), 8.36 (d, J=9.0 Hz, 2H), 8.28 (dd, J=6.1, 1.4 Hz, 1H), 8.27 (d, J=2.5 Hz, 1H), 7.50 (ddd, J=8.4, 2.7, 1.6 Hz, 1H), 7.30 (ddd, J=8.2, 4.7, 0.8 Hz, 1H).

Step 3: (S)-tert-Butyl 2-(4-((3-(4-nitro-N-(pyridin-3-yl)phenylsulfonamido)pyrrolidin-1-yl)methyl)benzamido)-4-(thiophen-2-yl)phenylcarbamate (247)

To a solution of 243 (0.98 g, 1.81 mmol) in THF (10 mL) at 0° C., was added compound 246 (0.61 g, 2.17 mmol), triphenylphosphine (0.76 g, 2.89 mmol) and diethyl azodicarboxylate (DEAD) (0.51 g, 2.90 mmol), the ice bath was removed and the reaction mixture was allowed to stir at room temperature for 18 h. The reaction mixture was partitioned between EtOAc and H2O, organic phase was collected, washed successively with saturated NH4Cl and brine, dried over MgSO4, filtered and concentrated to give a light brown oil which was purified by flash chromatography (eluent: 50% AcOEt in hexanes to 100% AcOEt) to give intermediate 247 (0.65 g, 47% yield).

1H NMR (DMSO-$d_6$) δ (ppm): 9.84 (s, 1H), 8.71 (s, 1H), 8.65 (dd, J=4.5, 1.4 Hz, 1H), 8.40 (d, J=9.0 Hz, 2H), 8.30 (d, J=2.3 Hz, 1H), 7.96 (d, J=9.0 Hz, 2H), 7.82 (d, J=8.4 Hz, 2H), 7.80 (d, J=2.2 Hz, 1H), 7.96 (d, J=9.0 Hz, 2H), 7.82 (d, J=8.4 Hz, 2H), 7.80 (d, J=2.2 Hz, 1H), cannot evaluate this region because of the presence of residual Ph$_3$PO (7.63-7.51), 7.48 (dd, J=9.2, 4.7 Hz, 1H), 7.44 (dd, J=3.5, 1.2 Hz, 1H), 7.12 (dd, J=5.1, 3.5 Hz, 1H), 7.09 (d, J=8.0 Hz, 2H), 4.85 (bs, 1H), 3.49 (d, J=13.9 Hz, 1H), 3.39 (d, J=13.7 Hz, 1H), 2.57-2.54 (m, 1H), 2.47-2.43 (m, 1H), 2.37-2.31 (m, 1H), 2.19-2.14 (m, 1H), 1.65-1.60 (m, 1H), 1.43-1.40 (m, 1H).

Step 4: (S)-tert-Butyl 2-(4-((3-(pyridin-3-ylamino)pyrrolidin-1-yl)methyl)benzamido)-4-(thiophen-2-yl)phenylcarbamate (248)

To a solution of 247 (0.65 g, 0.86 mmol) in DMF (5 mL) was added mercaptoacetic acid (0.103 g, 1.12 mmol) followed by solid lithium hydroxide (0.108 g, 2.58 mmol). The reaction mixture was allowed to stir at room temperature for 18 h and then at 70° C. for 4 h. The reaction mixture was concentrated, diluted with AcOEt and extracted with H2O, saturated NaHCO3, brine, dried over MgSO4, filtered and concentrated to give a yellow oil which was purified by flash chromatography (eluents: 100% EtOAc then 2.5% MeOH/ 1% Et3N/96.5% EtOAc and finally, 5% MeOH/1% Et3N/ 94% EtOAc) to provide title compound 248 (0.333 g, 68% yield).

1H NMR (DMSO-$d_6$) δ (ppm): 9.87 (s, 1H), 8.73 (s, 1H), 7.92 (d, J=7.8 Hz, 2H), 7.91 (d, J=3.7 Hz, 1H), 7.79 (d, J=2.0 Hz, 1H), 7.72 (dd, J=4.5, 1.2 Hz, 1H), 7.59 (d, J=8.6 Hz, 1H), 7.52-7.46 (m, 4H), 7.43 (dd, J=3.5, 1.0 Hz, 1H), 7.11 (dd, J=5.1, 3.5 Hz, 1H), 7.03 (d, J=8.3, 4.5 Hz, 1H), 6.85 (dd, J=8.6, 1.2 Hz, 1H), 6.00 (d, J=7.0 Hz, 1H), 3.93-3.87 (m, 1H), 3.72 (d, J=13.3 Hz, 1H), 3.63 (d, J=13.5 Hz, 1H), 2.79 (dd, J=9.2, 7.0 Hz, 1H), 2.66 (d, J=5.9 Hz, 1H), 2.48-2.44 (m, 1H), 2.37 (dd, J=9.2, 4.1 Hz, 1H), 2.26-2.19 (m, 1H), 1.62-1.58 (m, 1H).

Step 5: (S)—N-(2-Amino-5-(thiophen-2-yl)phenyl)-4-((3-(pyridin-3-ylamino)pyrrolidin-1-yl)methyl)benzamide (249)

Following the procedure as described in Example 1, step 7 (scheme 1), but substituting compound 8 for compound 248, the title compound 249 was obtained (0.14 g, 51% yield).

1H NMR (DMSO-$d_6$) δ (ppm): 9.69 (s, 1H), 7.94 (d, J=8.0 Hz, 2H), 7.92 (d, J=2.5 Hz, 1H), 7.72 (d, J=3.9 Hz, 1H), 7.45-7.43 (m, 3H), 7.33 (dd, J=5.1, 1.2 Hz, 1H), 7.28 (dd, J=8.4, 2.2 Hz, 1H), 7.22 (dd, J=3.5, 1.0 Hz, 1H), 7.05-7.02 (m, 2H), 6.85 (ddd, J=8.2, 2.7, 1.6 Hz, 1H), 6.79 (d, J=8.4 Hz, 1H), 6.00 (d, J=6.8 Hz, 1H), 5.14 (s, 2H), 3.95-3.86 (m, 1H), 3.70 (d, J=13.5 Hz, 1H), 3.62 (d, J=13.5 Hz, 1H), 2.80 (t, J=8.4 Hz, 1H), 2.65 (q, J=5.5 Hz, H), 2.48-2.44 (m, 1H), 2.37 (dd, J=10.0, 4.5 Hz, 1H), 2.23 (sext, J=8.0 Hz, 1H), 1.59 (sext, J=6.3 Hz, 1H).

Example 29a

N-(2-Amino-5-(thiophen-2-yl)phenyl)-4-carbamimidoylbenzamide (253)

Scheme 29

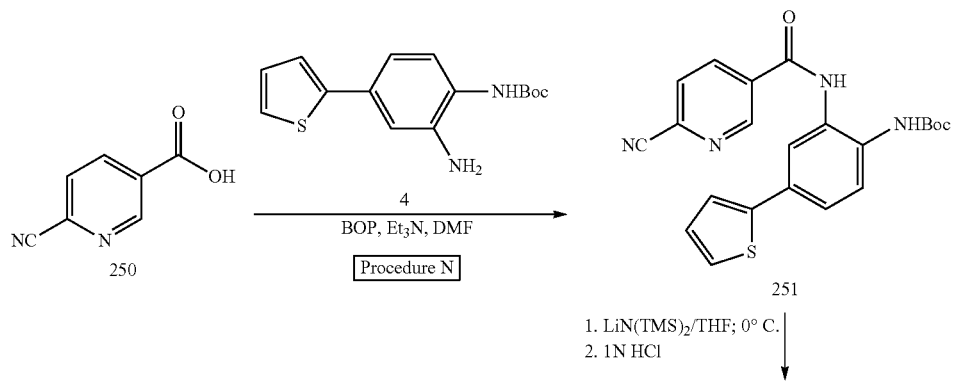

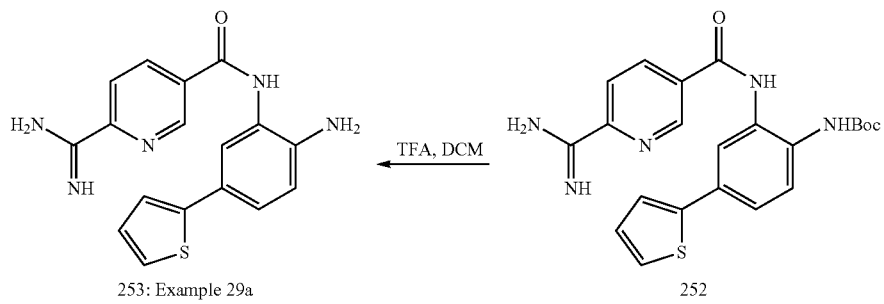

253: Example 29a  252

Step 1: tert-Butyl 2-(6-cyanonicotinamido)-4-(thiophen-2-yl)phenylcarbamate (251)

Following the same procedure as described in Example 1, step 6 (scheme 1), but substituting compound 7 for compound 250, and pyridine for triethyl amine and DMF, title compound 251 was obtained (41% yield).

1H NMR (DMSO-d$_6$) □ (ppm): 10.22 (s, 1H), 9.25 (d, J=1.6 Hz, 1H), 8.84 (s, 1H), 8.53 (dd, J=8.0, 2.4 Hz, 1H), 8.24 (d, J=8.0 Hz, 1H), 7.28 (dd, J=3.6, 1.2 Hz, 1H), 7.75-7.71 (m, 2H), 7.54-7.50 (m, 2H), 7.43 (dd, J=3.6, 1.2 Hz, 1H), 7.11 (dd, J=5.2, 3.6, 1H), 1.43 (s, 9H).

Step 2 tert-Butyl 2-(6-carbamimidoylnicotinamido)-4-(thiophen-2-yl)phenylcarbamate (252)

To a 1M solution of lithium bis(trimethylsilyl)amide in THF (0.0.76 mL, 0.76 mmol) at 0° C. was added compound 251 (0.10 g, 0.24 mmol). The reaction mixture was allowed to warm to room temperature, stirred for 18 h, cooled to 0° C., treated with 1N HCl (15 mL), stirred for 30 min and concentrated. The residue was diluted with AcOEt and extracted with H$_2$O. The aqueous phase was collected, neutralized with 1N NaOH, extracted with AcOEt, dried over MgSO$_4$, filtered and concentrated. The resulting brown solid was triturated with diethyl ether to give intermediate 252 (50 mg, 48% yield).

LRMS: 437.5 (calc) 438.0 (obs)

Step 3: N-(2-Amino-5-(thiophen-2-yl)phenyl)-6-carbamimidoylnicotinamide (253)

Following the procedure as described in Example 1, step 7 (scheme 1), but substituting compound 8 for compound 252, the title compound 253 was obtained in 5% yield [after purification by prep HPLC (eluent: 30% MeOH to 70% MeOH in water).

1H NMR (CD3OD) δ (ppm): 9.37 (d, J=1.6 Hz, 1H), 8.65 (dd, J=8.0, 2.0, 1H), 8.32 (d, J=8.4 Hz, 1H), 7.52 (d, J=2.0 Hz, 1H), 7.40-7.38 (m, 1H), 7.25 (dd, J=5.2, 0.8 Hz, 1H), 7.22 (d, J=3.2 Hz, 1H), 7.03 (dd, J=4.8, 3.2 Hz, 1H), 6.92 (d, J=8.0 Hz, 1H).

Example 30a 4-(2-Amino-5-(3-oxocyclopent-1-enyl)phenylcarbamoyl)phenyl acetate (260)

Example 30b 4-(2-Amino-5-(3-hydroxycyclopent-1-enyl)phenylcarbamoyl)phenyl acetate (261)

Example 30c

N-(2-Amino-5-(3-hydroxycyclopent-1-enyl)phenyl)-4-hydroxybenzamide (262)

Scheme 30

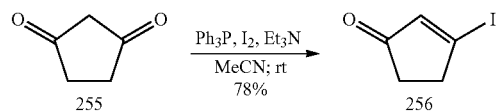

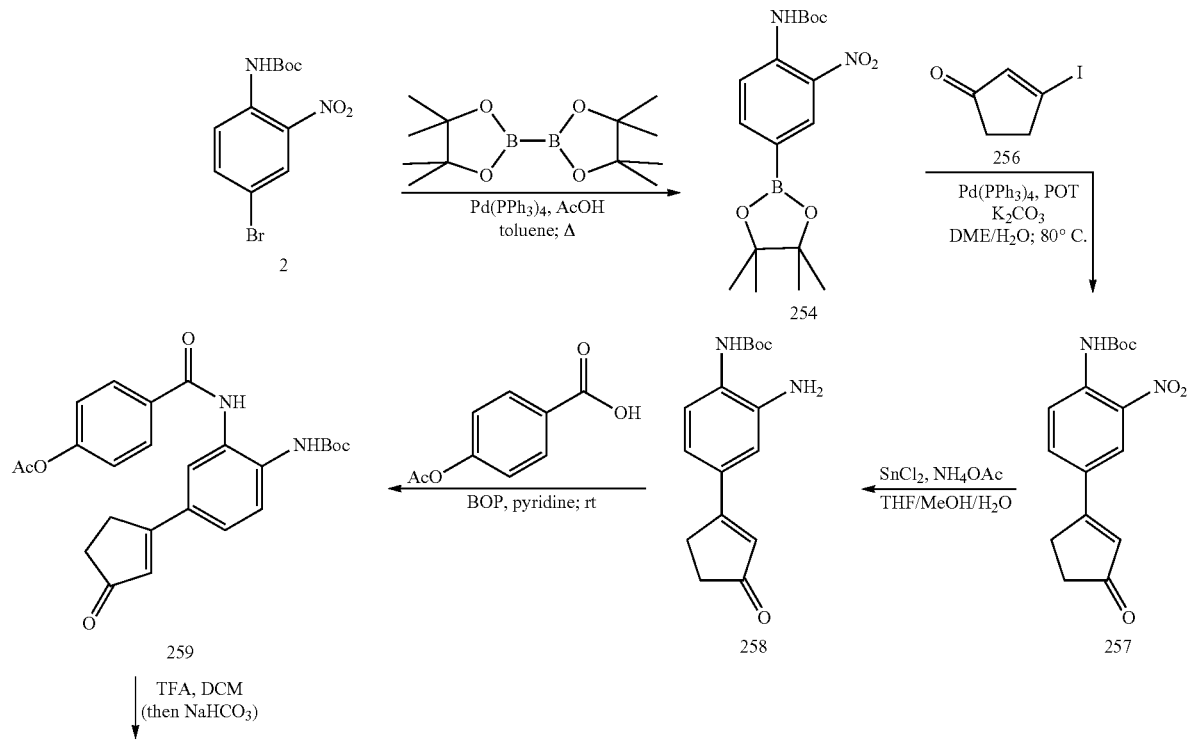

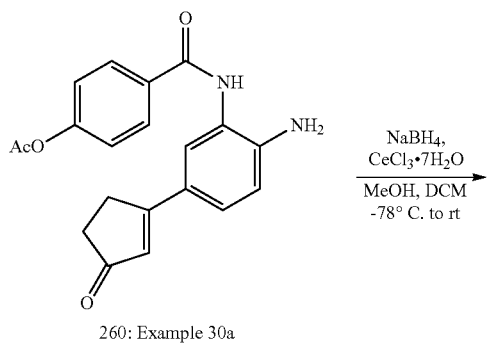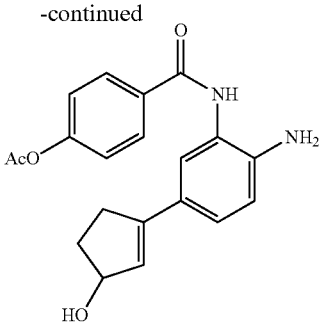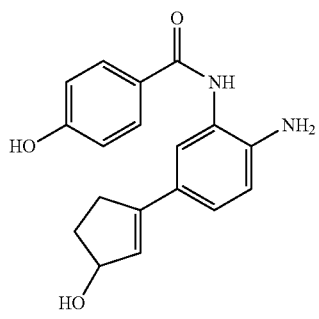

260: Example 30a        261: Example 30b        262: Example 30c

Step 1: tert-Butyl 2-nitro-4-(4,4,5,5-tetramethyl-1,3,2-dioxaborolan-2-yl)phenylcarbamate (254)

To a degassed solution of bromide 2 (1 g, 3.16 mmol), bis(pinacolate)diborane (1.6 g, 6.32 mmol) and acetic acid (0.93 g, 9.5 mmol) in toluene (30 mL) was added tetrakistriphenyl phosphine (0.1 g, 0.64 mmol) and the reaction mixture was immediately heated to 120° C. for 2 h. The reaction mixture was cooled to room temperature, washed with H$_2$O, brine, dried over MgSO$_4$, filtered and concentrated. The residue was purified by flash chromatography to provide title compound 254 as a yellow solid (0.9 g, 78% yield).

$^1$H NMR (CDCl$_3$) δ (ppm): 9.80 (s, 1H), 8.61 (d, J=1.6 Hz, 1H), 8.55 (d, J=8.4 Hz, 1H), 7.96 (dd, J=8.6, 1.6 Hz, 1H), 1.54 (s, 9H), 1.34 (s, 12H). LRMS: 364.16 (calc) 387.1 (M+Na, obs).

Step 2: 3-Iodocyclopent-2-enone (256)

A solution of iodine (6.2 g, 24.5 mmol) and triphenylphosphine (6.6 g, 26.5 mmol) in acetonitrile (200 mL) was stirred at room temperature for 2 h followed by the addition of cyclopentane-1,3-dione 255 (2 g, 20.6 mmol) and triethylamine (2.5 g, 24.5 mmol). The reaction mixture was stirred at 110° C. for 3 h then cooled to room temperature, concentrated and then purified by flash chromatography (eluent: 60% AcOEt in hexanes) to provide title compound 256 as a white solid (3.3 g, 78% yield).

$^1$H NMR (CDCl$_3$) δ (ppm): 6.65 (t, J=2.0 Hz, 1H), 3.06 to 3.03 (m, 2H), 2.47 to 2.45 (m, 2H).

Step 3: tert-Butyl 2-nitro-4-(3-oxocyclopent-1-enyl)phenylcarbamate (257)

Following the same procedure as described in Example 1, step 2 (scheme 1), but substituting compound 2 for compound 256 and 2-thiophene boronic acid for 254, title compound 257 was obtained as a yellow solid in 96% yield [after flash chromatography (eluent: 20% AcOEt in hexanes)].

LRMS: 318.2 (calc) 319.0 (obs).

Step 4: tert-Butyl 2-amino-4-(3-oxocyclopent-1-enyl)phenylcarbamate (258)

Following the same procedure as described in Example 14a, step 4 (scheme 14), but substituting compound 146 for compound 257, title compound 258 was obtained (quantitative yield).

Step 5: 4-(2-(tert-Butoxycarbonylamino)-5-(3-oxo-cyclopent-1-enyl)phenylcarbamoyl)phenyl acetate (259)

Following the same procedure as described in Example 1, step 6 (scheme 1), but substituting compound 4 for compound 258 and compound 7 for 4-acetoxybenzoic acid, title compound 259 was obtained as a yellow oil in 30% yield [after flash chromatography (eluent: 30% AcOEt in hexanes)].

LRMS: 450.2 (calc) 473.0 (obs)

Step 6: 4-(2-Amino-5-(3-oxocyclopent-1-enyl)phenylcarbamoyl)phenyl acetate (260)

Following the same procedure as described in Example 1, step 7 (scheme 1), but substituting compound 8 for compound 259, the title compound 260 was obtained as a yellow solid (89% yield).

$^1$H NMR: (CD$_3$OD) δ (ppm): 8.07 (d, J=8.0 Hz, 2H), 7.62 (d, J=1.2 Hz, 1H), 7.54 (dd, J=5.2, 1.2 Hz, 1H), 7.24 (d, J=8.1 Hz, 2H), 6.90 (d, J=8.0 Hz, 1H), 6.43 (s, 1H), 3.09 (m, 2H), 2.50 (m, 2H), 2.31 (s, 3H). LRMS: 350.4 (calc) 351 (obs)

Step 7: 4-(2-Amino-5-(3-hydroxycyclopent-1-enyl)phenylcarbamoyl)phenyl acetate (261) and N-(2-amino-5-(3-hydroxycyclopent-1-enyl)phenyl)-4-hydroxybenzamide (262)

To a stirring solution of amine 260 (0.11 g, 6.31 mmol) in DCM (9 mL) and cerium (III) chloride heptahydrate (0.37 g, 0.93 mmol) in MeOH (6 mL) at −78° C. was added sodium borohydride (60 mg, 0.93 mmol) in one portion. The reaction mixture was allowed to warm to room temperature and stirred for 15 min then concentrated. Purifications by flash chromatography (eluent: 5% MeOH in DCM) followed by chromatotron (same eluent) provided the title compounds 261 (15 mg, 14% yield) and 262 (15 mg, 16% yield).

Compound 261: $^1$H NMR (CD$_3$OD) δ (ppm): 8.08 (d, J=8.1 Hz, 2H), 7.37 (s, 1H), 7.30 (dd, J=5.1, 1.2, 1H), 7.27 (d, J=8.2 Hz, 2H), 6.87 (d, J=8.2 Hz, 1H), 6.13 (s, 1H), 4.61 (m, 1H), 3.31 (m, 3H), 2.81 (m, 1H), 2.61 (m, 1H), 2.32 (s, 3H), 1.91 (m, 1H). LRMS: 352.14 (calc) 335.0 (M-OH, obs)

Compound 262: $^1$H NMR (CD$_3$OD) δ (ppm): 7.88 (d, J=8.1 Hz, 2H), 7.33 (m, 1H), 7.27 (dd, J=5.2, 1.1 Hz, 1H), 6.88 (m, 3H), 6.13 (s, 1H), 4.61 (s, 1H), 3.34 (m, 3H), 2.81 (m, 1H), 2.61 (m, 1H), 2.31 (m, 1H), 2.12 (s, 1H), 1.92 (m, 1H).

TABLE 15

Characterization of compounds prepared according to Scheme 30.

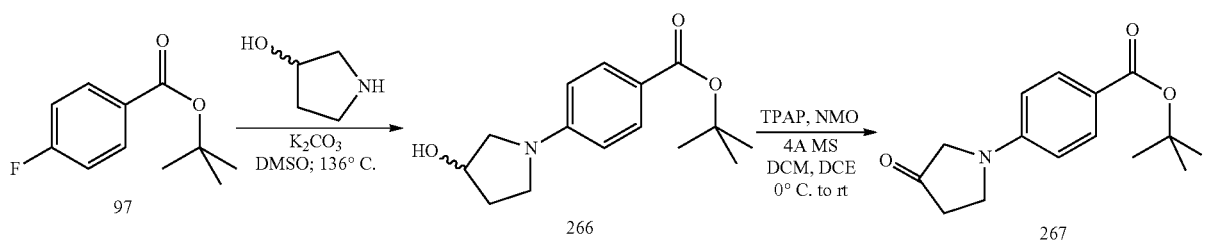

| Cpd | Ex | R | Name | Characterization |
|---|---|---|---|---|
| 265 | 30f | (cyclopentenyl with OH) | N-(2-amino-5-(3-hydroxycyclohex-1-enyl)phenyl)-4-(morpholinomethyl)benzamide | $^1$H NMR(CDCl$_3$) δ (ppm): 8.12 (s, 1H), 7.85 (d, J = 8.0 Hz, 2H), 7.42 (d, J = 8.1 Hz, 2H), 7.34 (s, 1H), 7.20 (dd, J = 8.4, 2.2 Hz, 1H), 6.73 (d, J = 9.1 Hz, 1H), 6.18 (s, 1H), 4.59 (s, 1H), 3.70 (t, J = 5.1 Hz, 4H), 3.57 (s, 2H), 3.32 (s, 3H), 2.72 (m, 1H), 2.49 (m, 4H), 2.29 (m, 1H), 2.12 (s, 2H), 1.90 (m, 1H). LRMS: 393.21 (calc) 376.0 (found)M-18 (deoxygenation). |

Example 31a

N-(2-Amino-5-(5-chlorothiophen-2-yl)phenyl)-4-(3-morpholinopyrrolidin-1-yl)benzamide (271)

Scheme 31

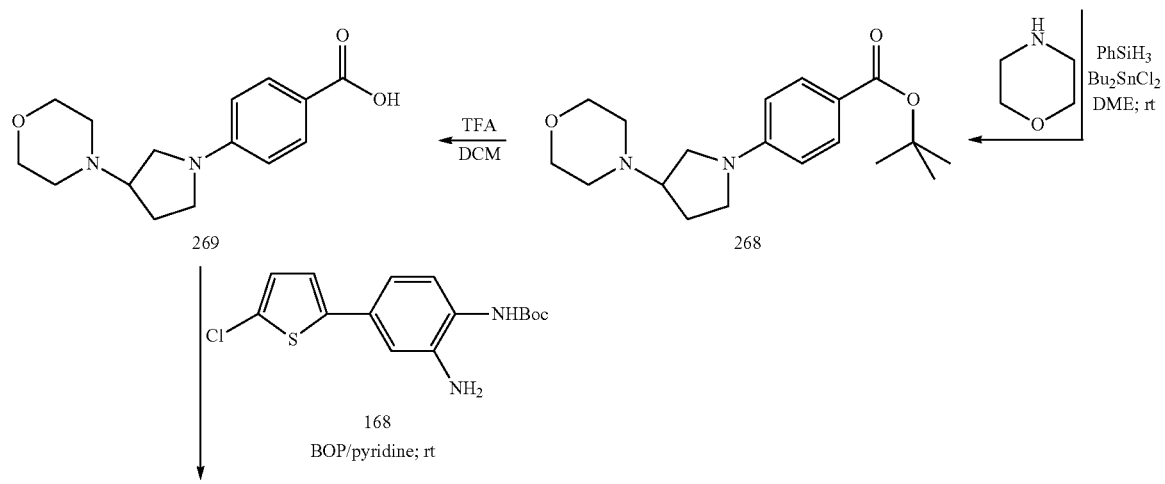

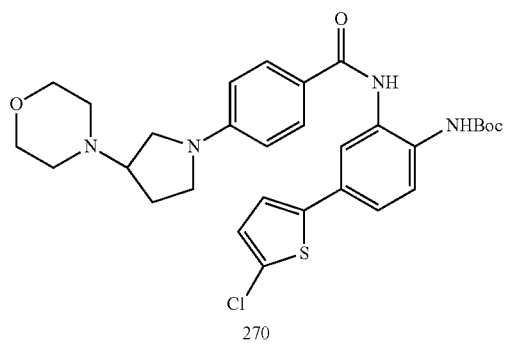
270

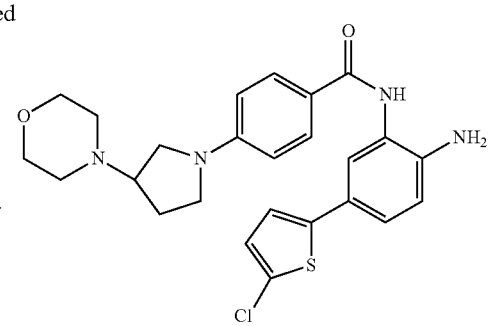
271: Example 31a

Step 1: tert-Butyl 4-(3-hydroxypyrrolidin-1-yl)benzoate (266)

A mixture of fluoride 97 (2.24 g, 11.4 mmol), pyrrolidin-3-ol (1.37 g, 15.8 mmol) and potassium carbonate (2.24 g) was suspended in dimethyl sulfoxide (5 mL) and stirred at 136° C. for 7 h. The reaction mixture was cooled to room temperature, diluted with DCM, washed with $H_2O$, dried over $MgSO_4$, filtered and concentrated to provide title compound 266 (3.93 g, 100%).

LRMS: 263.3 (calc) 264.1 (obs)

Step 2: tert-Butyl 4-(3-oxopyrrolidin-1-yl)benzoate (267)

A mixture of alcohol 266 (2.75 g, 10.45 mmol), NMO (5.8 g, 49 mmol) and 4 Å molecular sieves (8.34 g) was suspended in dry DCM (100 mL) and dry 1,2-dichloroethane (100 mL), stirred at room temperature for 45 min, and then cooled to 0° C. for the addition of solid TPAP (0.36 g, 1.03 mmol). The reaction mixture was stirred at 0° C. for 30 min and then at room temperature for 5 h, filtered through Celite®/silica gel using 50% AcOEt in hexanes as an eluent, then concentrated. The residue was purified by flash chromatography (eluent: 30% to 50% AcOEt in hexane) to provide title compound 267 (0.78 g, 29% yield).

LRMS: 261.3 (calc) 284.1 (M+Na, obs)

Step 3: tert-Butyl 4-(3-morpholinopyrrolidin-1-yl)benzoate (268)

A mixture of ketone 267 (0.40 g, 1.53 mmol), dibutyltin dichloride (0.35 g) and morpholine (0.27 mL) in ethyleneglycol dimethylether (3.5 mL) was stirred at room temperature for 6 h, then cooled to 0° C. for the addition of neat phenyl silane (0.60 mL, 4.72 mmol). The reaction mixture was stirred at room temperature for 18 h then diluted with MeOH (3 mL) and $H_2O$ (0.5 mL), stirred for additional 4 h and concentrated. The residue was purified by flash chromatography (eluent: 5% MeOH in DCM) to provide title compound 268 (0.56 g, >100% yield, crude, used without additional purification).

LRMS: 332.2 (calc) 333.2 (obs)

Step 4: 4-(3-Morpholinopyrrolidin-1-yl)benzoic acid (269)

Following the same procedure as described in Example 8, step 2 (scheme 8), but substituting compound 98 for compound 268, title compound 269 was obtained (used as is in the next reaction).

MS: 276.1 (calc) 277.1 (obs)

Step 5: tert-Butyl 2-(4-(3-morpholinopyrrolidin-1-yl)benzamido)-4-(thiophen-2-yl)phenylcarbamate (270)

Following the same procedure as described in Example 1, step 6 (scheme 1), but substituting compound 4 for compound 168 and compound 7 for compound 269, title compound 270 was obtained in 40% yield.

LRMS: 582.2 (calc) 583.0 (obs)

Step 6: N-(2-Amino-5-(thiophen-2-yl)phenyl)-4-(3-morpholinopyrrolidin-1-yl)benzamide (271)

Following the same procedure as described in Example 1, step 7 (scheme 1), but substituting compound 8 for compound 270, the title compound 271 was obtained in 40% yield.

$^1$H NMR (DMSO-$d_6$) δ (ppm): 9.42 (s, 1H), 7.87 (d, J=9.0 Hz, 2H), 7.40 (d, J=2.2 Hz, 1H), 7.22 (dd, J=8.4, 2.3 Hz, 1H), 7.11 (d, J=3.9 Hz, 1H), 7.05 (d, J=3.9 Hz, 1H), 6.80 (d, J=8.4 Hz, 1H), 6.60 (d, J=8.8 Hz, 2H), 5.17 (s, 2H), 3.61 (t, J=4.5 Hz, 4H), 3.57-3.55 (m, 1H), 3.47 (t, J=8.6 Hz, 1H), 3.32-3.28 (m, 1H), 3.12 (t, J=8.2 Hz, 1H), 2.97-2.89 (m, 1H), 2.47 (m, 4H, overlapped with DMSO-$d_6$), 2.25-2.19 (m, 1H), 1.88-0.78 (m, 1H). LRMS: 482.2 (calc) 483.0 (obs).

193
Example 32a
(2E,4E)-N-(2-Amino-5-(thiophen-2-yl)phenyl)-4-(1-(benzo[d][1,3]dioxol-5-ylmethyl)pyrrolidin-3-ylidene)but-2-enamide (278)
194
Example 32b
N-(2-Amino-5-(thiophen-2-yl)phenyl)-4-(1-(benzo[d][1,3]dioxol-5-ylmethyl)pyrrolidin-3-yl)butanamide (279)
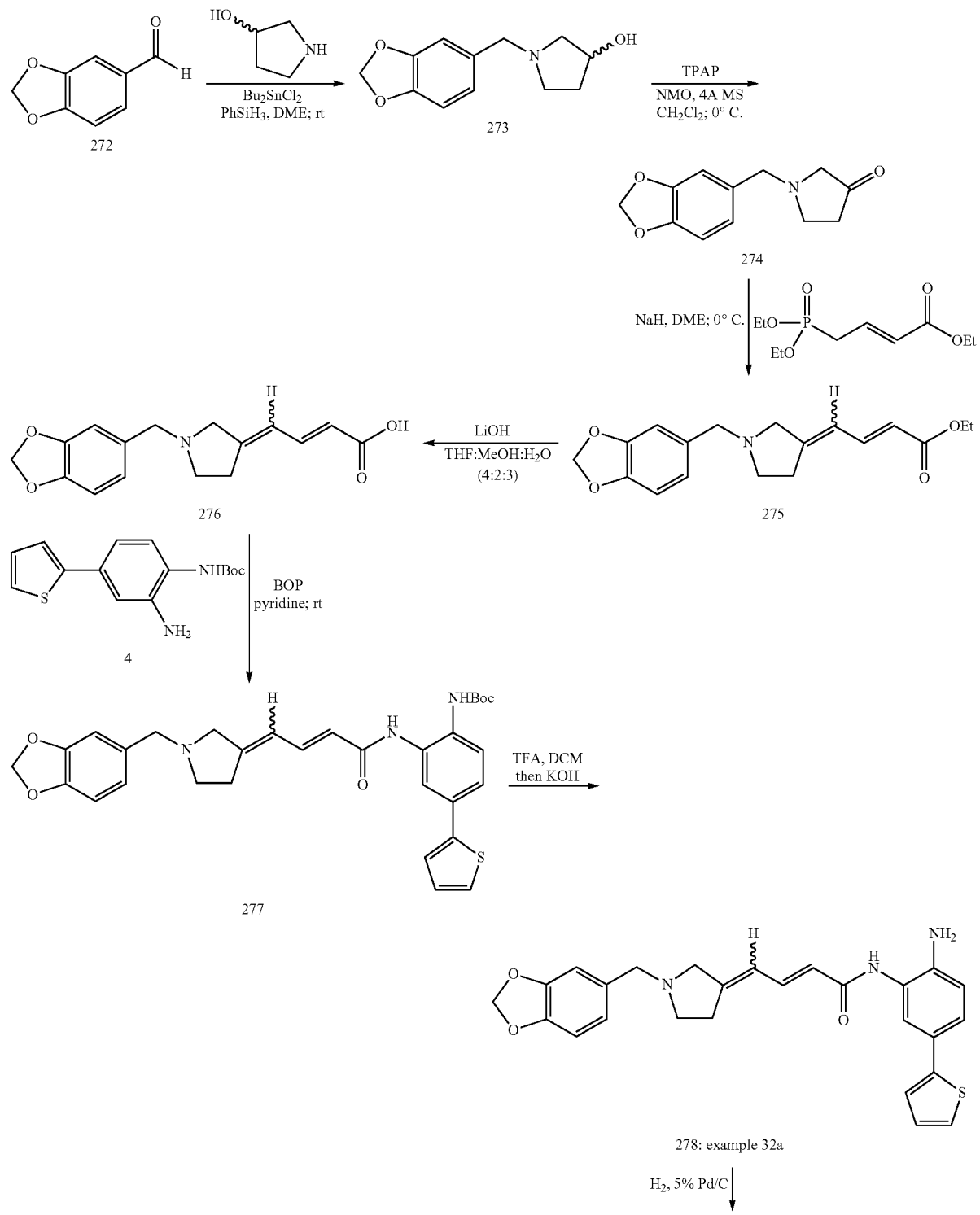

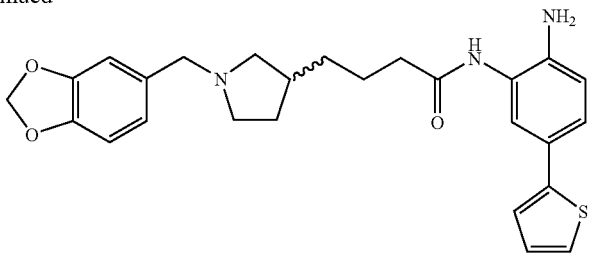

279: example 32b

Step 1: 1-(Benzo[d][1,3]dioxol-5-ylmethyl)pyrrolin-3-ol (273)

A solution of pyrrolidin-3-ol (0.539 g, 6.2 mmol) in ethyleneglycol dimethylether (DME) (5 mL) was treated with benzo[d][1,3]dioxole-5-carbaldehyde (272) (1.08 g, 7.2 mmol) and dibutyldichlorostannane (0.71 g, 2.3 mmol). After the suspension was stirred for 15 min at room temperature, phenylsilane (1.0 mL, 8.6 mmol) was added neat and the mixture was stirred for 18 h. The reaction mixture was diluted with DCM (50 mL), treated with 1N HCl (13 mL) and stirred for 30 min followed by dilution with $H_2O$ (50 mL) and DCM (50 mL). The aqueous layer was collected, basified with solid potassium carbonate ($K_2CO_3$), extracted with DCM, dried over $MgSO_4$, filtered and concentrated to provide title compound 273 (0.82 g, 60% yield).

$^1$H NMR (DMSO-$d_6$) δ (ppm): 6.85 to 6.81 (m, 2H), 6.73 (dd, J=8.0, 1.8 Hz, 1H), 5.97 (s, 2H), 4.69 (d, J=4.3 Hz, 1H), 4.18 to 4.16 (m, 1H), 3.44 (q, J=12.9 Hz, 2H), 2.62 (dd, J=9.8, 6.3 Hz, 1H), 2.55-2.50 (m, 1H), 2.39-2.33 (m, 1H), 2.28 to 2.25 (m, 1H), 2.01-1.93 (m, 1H), 1.55-1.48 (m, 1H).

Step 2: 1-(Benzo[d][1,3]dioxol-5-ylmethyl)pyrrolidin-3-one (274)

A solution of alcohol 273 (0.78 g, 3.53 mmol) in dry DCM (40 mL) was treated with 4 Å molecular sieves (powder, 3.49 g) and 4-methylmorpholine N-oxide (NMO) (2.11 g, 18.03 mmol) and the suspension was stirred under nitrogen atmosphere for 18 h. The reaction mixture was cooled to 0° C. for the addition of solid tetrapropylammonium perruthenate (TPAP) (0.11 g, 0.31 mmol) and stirred for 30 min, then diluted with DCM, filtered through a Celite® pad, washed with saturated $NaHCO_3$, dried over $MgSO_4$, filtered through a pad of $SiO_2$ (eluent: 5% MeOH in DCM) and concentrated to provide title compound 274 (0.65 g, 84% yield).

LRMS: 219.18 (calc) 219.9 (obs)

Step 3: (2E,4E)-Ethyl 4-(1-(benzo[d][1,3]dioxol-5-ylmethyl)pyrrolidin-3-ylidene)but-2-enoate (275)

To a solution of ketone 274 (0.65 g, 2.96 mmol) and (E)-ethyl 4-(diethoxyphosphoryl)but-2-enoate (1.0 mL, 4.33 mmol) in ethyleneglycol dimethylether (50 mL) at 0° C. was added NaH (0.26 g, 6.58 mmol) and the mixture was stirred at 0° C. for 30 min then at room temperature for 2 h. The reaction mixture was quenched with acetone (2 mL) then diluted with DCM and washed with saturated $NaHCO_3$, dried over $MgSO_4$, filtered and concentrated. The residue was purified by flash column chromatography (eluent: 50% AcOEt in DCM) to provide title compound 275 (0.15 g, 16% yield) as a mixture of cis/trans isomers.

$^1$H NMR (DMSO-$d_6$) δ (ppm): 7.26 (dd, J=15.3, 11.5 Hz, 0.5H), 7.12 (dd, J=15.1, 11.5 Hz, 0.5H), 6.88-6.83 (m, 2H), 6.77 (dt, J=9.2, 1.6 Hz, 1H), 6.14 (t, J=11.7 Hz, 1H), 5.99 (d, J=2.9 Hz, 2H), 5.83 (d, J=15.2 Hz, 1H), 4.14-4.07 (m, 2H), 3.53 (d, J=19.2 Hz, 2H), 3.30 (s, 1H), 3.16 (s, 1H), 2.61 (s, 2H), 2.57 (d, J=5.3 Hz, 1H), 1.22-1.18 (m, 4H).

Step 4: (2E,4E)-4-(1-(Benzo[d][1,3]dioxol-5-ylmethyl)pyrrolidin-3-ylidene)but-2-enoic acid (276)

A solution of ester 275 (0.15 g, 0.485 mmol) in 2:1 THF:MeOH (6 mL) was treated with a solution of lithium hydroxide (59 mg, 1.41 mmol) in $H_2O$ (3 mL) and stirred for 18 h. The reaction mixture was quenched with 1N HCl (2.0 mL), concentrated, diluted with $H_2O$, cooled to −78° C. and lyophilized to provide title compound 276 (quantitative, in a mixture with LiCl).

LRMS: 287.1 (calc) 288.0 (obs)

Step 5: tert-Butyl 2-((2E,4E)-4-(1-(benzo[d][1,3]dioxol-5-ylmethyl)pyrrolidin-3-ylidene)but-2-enamido)-4-(thiophen-2-yl)phenylcarbamate (277)

Following the same procedure as described in Example 1, step 6 (scheme 1), but substituting compound 7 for compound 276, title compound 277 was obtained (71% yield) [after column chromatography (eluent: 5% isopropanol in DCM)].

LRMS: 229.21 (calc) 560.1 (obs)

Step 6: (2E,4E)-N-(2-Amino-5-(thiophen-2-yl)phenyl)-4-(1-(benzo[d][1,3]dioxol-5-ylmethyl)pyrrolidin-3-ylidene)but-2-enamide (278)

Following the same procedure as described in Example 1, step 7 (scheme 1), but substituting compound 8 for compound 277 and sodium bicarbonate with potassium hydroxide, the title compound 278 was obtained in quantitative yield.

$^1$H NMR (DMSO-$d_6$) δ (ppm): 9.32 (s, 0.5H), 9.31 (s, 0.5H), 7.65 (d, J=8.2 Hz, 1H), 7.35 (d, J=5.1 Hz, 1H), 7.25-7.18 (m, 3H), 7.05-7.03 (m, 1H), 6.90-6.84 (m, 2H), 6.81-6.74 (m, 2H), 6.18 to 6.12 (m, 2H), 5.99 (s, 2H), 5.17 (s, 1H), 5.16 (s, 1H), 3.56 (s, 1H), 3.51 (s, 1H), 3.29 (s, 1H), 3.17 (s, 1H), 2.63 to 2.59 (s, 4H).

Step 7: N-(2-Amino-5-(thiophen-2-yl)phenyl)-4-(1-(benzo[d][1,3]dioxol-5-ylmethyl)pyrrolidin-3-yl)butanamide (279)

Following the same procedure as described in Example 1, step 3 (scheme 1), but substituting compound 3 for compound 278, and 10% palladium on carbon for 5% palladium on carbon, title compound 279 in 20% yield.

LRMS: 463.2 (calc) 464.0 (obs)

Example 33a

Pyridin-3-ylmethyl 4-(2-amino-5-(thiophen-2-yl)phenylcarbamoyl)phenylcarbamate (283)

to −78° C. and lyophilized to give a solid material which was triturated with acetone to give title compound 281 (3.098 g, 96% yield).

$^1$H NMR (DMSO-d$_6$) δ (ppm): 10.27 (s, 1H), 8.88 (s, 1H), 8.79 (d, J=3.3 Hz, 2H), 7.86 (d, J=8.8 Hz, 3H), 7.56 (d, J=8.8 Hz, 2H), 5.32 (s, 2H).

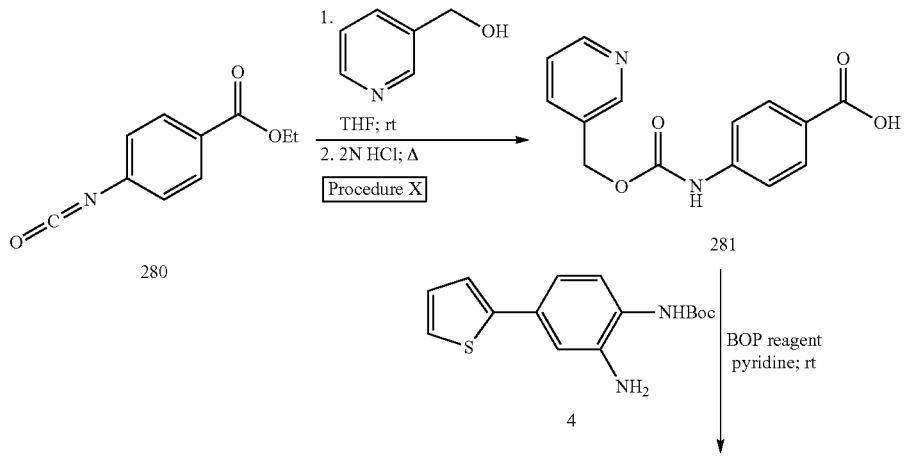

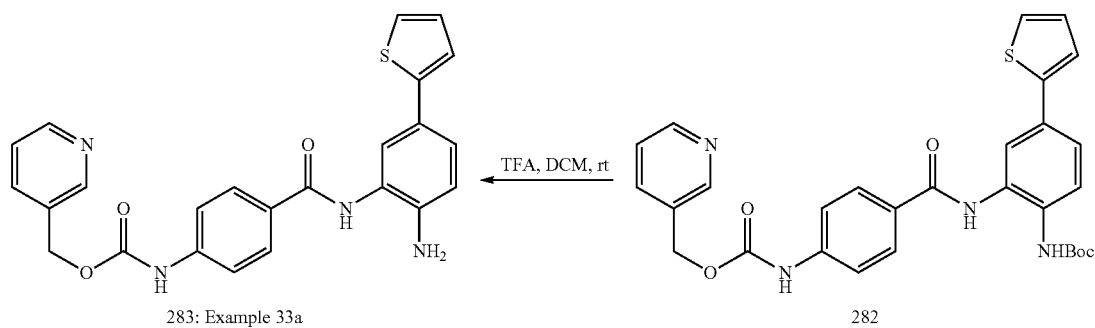

283: Example 33a

282

Step 1: 4-((Pyridin-3-ylmethoxy)carbonylamino)benzoic acid (281)

A solution of ethyl 4-isocyanatobenzoate 280 (2.0 g, 10.46 mmol) and pyridin-3-ylmethanol in THF was stirred at room temperature for 18 h then concentrated. The crude material was taken up in 2N HCl, heated to reflux for 16 h then cooled

Steps 2 & 3: Pyridin-3-ylmethyl 4-(2-amino-5-(thiophen-2-yl)phenylcarbamoyl)phenylcarbamate (283)

Following the same procedure as described in Example 1, steps 6 and 7 (scheme 1), using compound 4 but substituting compounds 7 & 8 for compounds 281 & 282, the title compound 283 was obtained (step 2: 31% yield, step 3: 23% yield).

¹H NMR: (DMSO-d₆) δ (ppm): 10.11 (s, 1H), 9.61 (s, 1H), 8.66 (s, 1H), 8.55 (dd, J=4.7, 1.6 Hz, 1H), 7.93 (d, J=8.6 Hz, 2H), 7.86 (d, J=8.2 Hz, 1H), 7.57 (d, J=8.8 Hz, 2H), 7.44-7.41 (m, 2H), 7.33 (dd, J=5.1, 0.98 Hz, 1H), 7.27 (dd, J=8.2, 2.2 Hz, 1H), 7.22 (dd, J=3.5, 1.2 Hz, 1H), 7.03 (dd, J=5.1, 3.7 Hz, 1H), 6.79 (d, J=8.4 Hz, 1H), 5.22 (s, 2H), 5.13 (s, 2H).

TABLE 16

Characterization of compounds 284-296 prepared according to Scheme 33

| Cpd | Ex | R₁ | R₂ | X | Name | Characterization |
|---|---|---|---|---|---|---|
| 284 | 33b | (tetrahydro-2H-pyran-2-yl)methyl | thiophen-2-yl | NH₂ | (tetrahydro-2H-pyran-2-yl)methyl 4-(2-amino-5-(thiophen-2-yl)phenylcarbamoyl)phenylcarbamate | ¹H NMR (DMSO-d₆) δ (ppm): 10.06 (1H, s), 9.59 (1H, s), 7.92 (2H, d, 8.8), 7.57 (2H, d, 8.6 Hz), 7.44 (1H, s), 7.34 (1H, d, 5.1 Hz), 7.27 (1H, d, 8.2 Hz), 7.23 (1H, d, 3.5 Hz), 7.03 (1H, t, 3.7 Hz), 6.79 (1H, d, 8.4 Hz), 5.12 (2H, s), 4.09-4.00 (2H, m), 3.89-3.86 (1H, m), 3.54 (1H, m), 1.80 (1H, m), 1.60-1.56 (1H, m), 1.48 (3H, m), 1.32-1.23 (2H, m) LRMS: 451.2 (calc) 452.2 (obs). |
| 285 | 33c | 2-(dimethylamino)ethyl | thiophen-3-yl | NH₂ | 2-(dimethylamino)ethyl 4-(2-amino-5-(thiophen-3-yl)phenylcarbamoyl)phenylcarbamate | ¹H NMR (CD₃OD) δ (ppm): 7.97 (d, J = 8.2 Hz, 2H), 7.62 (d, J = 8.1 Hz, 2H), 7.50 (s, 1H), 7.42 (m, 4H), 6.92 (d, J = 8.0 Hz, 1H), 4.31 (t, J = 5.6 Hz, 2H), 2.69 (t, J = 5.51 Hz, 2H), 2.31 (s, 6H). LRMS: 424.16 (calc) 425.0 (obs). |
| 286 | 33d | 2-(dimethylamino)ethyl | 4-chloro-3-fluorophenyl | NH₂ | 2-(dimethylamino)ethyl 4-(4-amino-4'-chloro-5'-fluorobiphenyl-3-ylcarbamoyl)phenylcarbamate | ¹H NMR (CD₃OD) δ (ppm): 7.97 (d, J = 8.1 Hz, 2H), 7.61 (d, J = 8.0 Hz, 2H), 7.45 (m, 3H), 7.37 (m, 2H), 6.94 (d, J = 8.1 Hz, 1H), 4.30 (t, J = 5.2 Hz, 2H), 2.69 (t, J = 5.2 Hz, 2H), 2.32 (s, 6H). LRMS: 470.9 (calc) 471.0 (obs). |
| 287 | 33e | 2-(dimethylamino)ethyl | 3-fluorophenyl | NH₂ | 2-(dimethylamino)ethyl 4-(4-amino-5'-fluorobiphenyl-3-ylcarbamoyl)phenylcarbamate hydrochloride | ¹H NMR (CD₃OD) δ (ppm): 7.98 (d, J = 8.0 Hz, 2H), 7.62 (d, J = 8.0 Hz, 2H), 7.49 (m, 1H), 7.39 (m, 3H), 7.30 (s, 1H), 7.66 (d, J = 8.1 Hz, 2H), 4.49 (t, J = 5.1 Hz, 2H), 3.47 (t, J = 5.1 Hz, 2H), 2.88 (s, 6H). LRMS: 436.19 (calc) 437 (obs). |
| 288 | 33f | 2-(dimethylamino)ethyl | 6-chloropyridin-3-yl | NH₂ | 2-(dimethylamino)ethyl 4-(2-amino-5-(6-chloropyridin-3-yl)phenylcarbamoyl)phenylcarbamate | ¹H NMR (DMSO-d₆) δ (ppm): 10.01 (s, 1H), 9.62 (s, 1H), 8.61 (d, J = 2.1 Hz, 1H) 8.01 (dd, J = 7.2, 1.3 Hz, 1H), 7.92 (d, J = 8.1 Hz, 2H), 7.61 (m, 3H), 7.49 (d, J = 8.1 Hz, 1H), 7.39 (m, 1H), 6.88 (d, J = 5.6 Hz, 1H), 5.25 (s, 2H), 4.18 (t, J = 5.2 Hz, 2H), 3.34 (s, 1H), 2.51 (t, J = 5.1 Hz, 2H), 2.19 (s, 6H). LRMS: 453.92 (calc) 454.0 (obs). |
| 289 | 33g | 2-(dimethylamino)ethyl | pyridin-3-yl | NH₂ | 2-(dimethylamino)ethyl 4-(2-amino-5-(pyridin-3-yl)phenylcarbamoyl)phenylcarbamate | ¹H NMR (CD₃OD) δ (ppm): 8.78 (s, 1H) 8.40 (s, 1H), 8.00 (m, 3H), 7.62 (d, J = 8.0 Hz, 2H), 7.53 (d, J = 3.5 Hz, 1H), 7.42 (m, 2H), 7.01 (d, J = 8.1 Hz, 1H), 4.51 (t, J = 5.1 Hz, 2H), 3.42 (t, J = 5.2 Hz, 2H), 2.91 (s, 6H). LRMS: 419.48 (calc) 420.1 (obs). |

TABLE 16-continued

Characterization of compounds 284-296 prepared according to Scheme 33

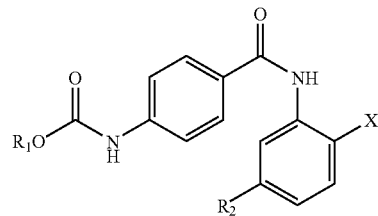

| Cpd | Ex | R₁ | R₂ | X | Name | Characterization |
|---|---|---|---|---|---|---|
| 290 | 33h | (dimethylaminoethyl) | 6-fluoropyridin-3-yl | NH₂ | 2-(dimethylamino)ethyl 4-(2-amino-5-(6-fluoropyridin-3-yl)phenylcarbamoyl)-phenylcarbamate | ¹H NMR (DMSO-d₆) δ (ppm): 10.1 (s, 1H), 9.62 (s, 1H), 8.40 (s, 1H), 8.13 (m, 1H), 7.92 (d, J = 8.0 Hz, 2H), 7.58 (d, J = 8.1 Hz, 2H), 7.52 (s, 1H), 7.32 (dd, J = 7.9, 2.1 Hz, 1H), 7.18 (dd, J = 8.0, 1.8 Hz, 1H), 6.89 (d, J = 8.1 Hz, 1H), 5.20 (s, 1H), 4.18 (t, J = 5.1 Hz, 2H), 3.33 (s, 1H), 2.51 (t, J = 5.1 Hz, 2H), 2.18 (s, 6H). LRMS: 437.47 (calc) 438.0 (obs). |
| 291 | 33i | (dimethylaminoethyl) | 3,4-dichlorophenyl | NH₂ | 2-(dimethylamino)ethyl 4-(4-amino-3',4'-dichlorobiphenyl-3-ylcarbamoyl)phenyl-carbamate | ¹H NMR (DMSO-d₆) δ (ppm): 10.05 (s, 1H), 9.62 (s, 1H), 7.91 (d, J = 8.01 Hz, 2H), 7.78 (s, J = 1.3 HZ, 1H), 7.55 (m, 4H), 7.33 (m, 1H), 6.82 (d, J = 7.2 Hz, 1H), 5.22 (s, 1H), 4.18 (t, J = 5.1 Hz, 2H), 2.52 (t, J = 5.1 Hz, 2H), 2.18 (s, 6H). LRMS: 487.38 (calc) 487.0 (obs). |
| 292 | 33j | (dimethylaminoethyl) | 3,4-difluorophenyl | NH₂ | 2-dimethylamino)ethyl 4-(4-amino-3',4'-difluorobiphenyl-3-ylcarbamoyl)phenyl-carbamate | ¹H NMR (DMSO-d₆) δ (ppm): 10.01 (s 1H), 9.61 (s, 1H), 7.92 (d, J = 8.1 Hz, 2H), 7.58 (m, 3H), 7.50 (s, 1H), 7.39 (m, 3H), 6.81 (d, J = 8.1 Hz, 1H), 5.18 (s, 2H), 4.18 (t, J = 5.1 Hz, 2H), 2.51 (t, J = 5.0 Hz, 2H), 2.18 (s, 6H). LRMS: 454.47 (calc) 455.0 (obs). |
| 293 | 33k | (dimethylaminoethyl) | phenyl | NH₂ | 2-(dimethylamino)-ethyl 4-(4-aminobiphenyl-3-ylcarbamoyl)phenyl-carbamate | ¹H NMR (DMSO-d₆) δ (ppm): 10.01 (s, 1H), 9.68 (s, 1H), 7.92 (d, J = 8.2 Hz, 2H), 7.54 (m, 4H), 7.49 (s, 1H), 7.37 (m, 2H), 7.31 (m, 1H), 7.21 (m, 2H), 6.82 (d, J = 7.9 Hz, 1H), 5.01 (s, 2H), 4.19 (t, J = 5.1 Hz, 2H), 2.53 (t, J = 5.1 hz, 2H), 2.20 (s, 6H). LRMS: 418.49 (calc) 419.1 (obs). |
| 294 | 33l | methyl(pyridin-2-yl)amino ethyl | thiophen-2-yl | NH₂ | 2-(methyl(pyridin-2-yl)amino)ethyl 4-(2-amino-5-(thiophen-2-yl)phenylcarbamoyl)-phenylcarbamate | ¹H NMR (DMSO-d₆) δ (ppm): 10.03 (s, 1H), 9.62 (s, 1H), 8.67 (ddd, J1 = 4.8 Hz, J2 = 2.0 Hz, J3 = 0.8 Hz, 1H), 7.94 (d, J = 8.8 Hz, 2H), 7.57 (d, J = 8.8 Hz, 2H), 7.50 (ddd, J1 = 16.0 Hz, J2 = 7.2 Hz, J3 = 2.0 Hz, 1H), 7.46 (d, J = 2.0 Hz, 1H), 7.36 (dd, J1 = 5.2 Hz, J2 = 1.2 Hz, 1H), 7.29 (dd, J1 = 8.4 Hz, J2 = 2.0 Hz, 1H), 7.24 (dd, J1 = 3.6 Hz, J2 = 1.2 Hz, 1H), 7.05 (dd, J1 = 5.2 Hz, J2 = 3.6 Hz, 1H), 6.80 (d, J = 8.4 Hz, 1H), 6.65 (d, J = 8.8 Hz, 1H), 6.56 (ddd, J1 = 7.6 Hz, J2 = 4.8 Hz, J3 = 0.8 Hz, 1H), 5.14 (s, 2H), 4.28 (t, J = 6.0 Hz, 2H), 3.84 (t, J = 6.0 Hz, 2H), 3.06 (s, 3H). LRMS: 487.57 (calc) 488.0 (obs). |

TABLE 16-continued

Characterization of compounds 284-296 prepared according to Scheme 33

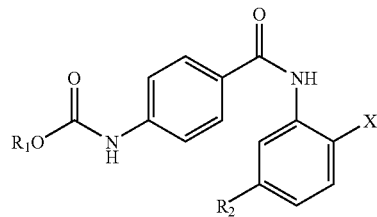

| Cpd | Ex | R₁ | R₂ | X | Name | Characterization |
|---|---|---|---|---|---|---|
| 295 | 33m | 4-methylpiperazin-1-yl-ethyl | thiophen-2-yl | NH₂ | 2-(4-methylpiperazin-1-yl)ethyl 4-(2-amino-5-(thiophen-2-yl)phenylcarbamoyl)-phenylcarbamate | $^1$H NMR (DMSO-d$_6$) δ (ppm): 10.03 (s, 1H), 9.62 (s, 1H), 7.95 (d, J = 8.8 Hz, 2H), 7.60 (d, J = 8.8 Hz, 2H), 7.46 (d, J = 2.4 Hz, 1H), 7.36 (dd, J1 = 5.2 Hz, J2 = 0.8 Hz, 1H), 7.29 (dd, J1 = 8.0 Hz, J2 = 2.0 Hz, 1H), 7.24 (dd, J1 = 3.6 Hz, J2 = 1.2 Hz, 1H), 7.05 (dd, J1 = 4.8 Hz, J2 = 3.6 Hz, 1H), 6.80 (d, J = 8.4 Hz, 1H), 5.14 (s, 2H), 2.59 (t, J = 5.6 Hz, 2H), 2.57-2.16 (m, 7H, overlapped DMSO-d$_6$), 2.16 (s, 4H). LRMS: 479.59 (calc) 480.1 (obs). |
| 296 | 33n | 2-(dimethylamino)ethyl | thiophen-2-yl | OH | 2-(dimethylamino)ethyl 4-(2-hydroxy-5-(thiophen-2-yl)phenylcarbamoyl)-phenylcarbamate | $^1$H NMR (DMSO-d$_6$) δ (ppm): 10.07 (s, 1H), 9.47 (s, 1H), 8.00 (s, 1H), 7.92-7.94 (m, 2H), 7.83 (dt, 1H), 7.59-7.61 (m, 2H), 7.54 (dt, 1H), 7.42 (dd, 1H), 7.27-7.35 (m, 3H), 7.07 (dd, 1H), 6.94 (d, 1H), 4.24 (t, 2H), 2.74 (t, 2H), 2.35 (s, 6H). No J? LRMS 425.14 (calc) 426 (obs). |

TABLE 16a

Characterization of compounds prepared according to Scheme 33

| Cpd | Ex | R | Name | Characterization |
|---|---|---|---|---|
| 585 | 33o | pyridin-3-ylmethyl | pyridin-3-ylmethyl 3-(2-amino-5-thiophen-2-yl)phenyl carbamoyl)phenyl-carbamate | $^1$H NMR (DMSO-d$_6$) δ (ppm): 10.11 (s, 1H), 9.09 (d, J = 2.4 Hz, 1H), 9.05 (d, J = 1.6 Hz, 1H), 8.57 (t, J = 2.0 Hz, 1H), 7.78 (dd, J1 = 3.8 Hz, J2 = 1.0 Hz, 1H), 7.72 (dd, J1 = 5.2 Hz, J2 = 1.2 Hz, 1H), 7.49 (d, J = 2.4 Hz, 1H), 7.36 (dd, J1 = 5.2 Hz, J2 = 1.2 Hz, 1H), 7.33 (dd, J1 = 8.6 Hz, 1H), 7.25 (m, 2H), 7.05 (dd, J1 = 5.2 Hz, J2 = 3.6 Hz, 1H), 6.82 (d, J = 8.4 Hz, 1H), 5.31 (s, 2H). LRMS: 444.51 (calc) 445.0 (found) |
| 586 | 33p | 2-morpholinoethyl | 2-morpholinoethyl 4-(2-amino-5-(thiophen-2-yl)phenylcarbamoyl)-yl)phenylcarbamate | $^1$H NMR (DMSO-d$_6$) δ (ppm): 10.04 (s, 1H), 9.63 (s, 1H), 7.95 (d, J1 = 8.8 Hz, 2H), 7.59 (d, J = 8.8 Hz, 2H), 7.45 (d, J1 = 2.0 Hz, 1H), 7.36 (dd, J1 = 5.2 Hz, J2 = 1.2 Hz, 1H), 7.29 (dd, J1 = 8.4 Hz, J2 = 2.0 Hz, 1H), 7.24 (dd, J1 = 3.6 Hz, J2 = 1.2 Hz, 1H), 7.05 (dd, J1 = 5.2 Hz, J2 = 3.6 Hz, 1H), 6.80 (d, J = 8.4 Hz, 1H), 5.14 (s, 2H), 4.22 (t, J = 5.6 Hz, 2H), 3.57 (t, J = 4.8 Hz, 4H), 2.59 (t, J = 5.6 Hz, 2H), 2.44 (s, 4H). LRMS: 466.55 (calc) 467.0 (found) |

TABLE 16a-continued

Characterization of compounds prepared according to Scheme 33

| Cpd | Ex | R | Name | Characterization |
|---|---|---|---|---|
| 587 | 33q | | 2-(pyrrolidin-1-yl)ethyl 4-(2-amino-5-(thiophen-2-yl)phenylcarbamoyl)-phenylcarbamate | $^1$H NMR (DMSO-d$_6$) δ (ppm): 10.06 (s, 1H), 9.63 (s, 1H), 7.95 (d, J1 = 8.8 Hz, 2H), 7.60 (d, J = 8.8 Hz, 2H), 7.45 (d, J1 = 2.0 Hz, 1H), 7.36 (dd, J1 = 5.2 Hz, J2 = 1.2 Hz, 1H), 7.29 (dd, J1 = 8.4 Hz, J2 = 2.0 Hz, 1H), 7.24 (dd, J1 = 3.6 Hz, J2 = 1.2 Hz, 1H), 7.05 (dd, J1 = 5.2 Hz, J2 = 3.6 Hz, 1H), 6.80 (d, J = 8.4 Hz, 1H), 5.14 (s, 2H), 4.24 (s, 2H), 2.92-2.42 (m, 6H, overlapped DMSO-d$_6$), 1.73 (s,H). LRMS: 450.55 (calc) 451.0 (found) |
| 588 | 33r | | (S)-(1-methylpyrrolidin-2-yl)methyl 4-(2-amino-5-(thiophen-2-yl)phenylcarbamate | $^1$H NMR (DMSO-d$_6$) δ (ppm): 9.99 (s, 1H), 9.63 (s, 1H), 7.95 (d, J1 = 8.8 Hz, 2H), 7.58 (d, J = 8.8 Hz, 2H), 7.46 (d, J1 = 2.0 Hz, 1H), 7.36 (dd, J1 = 5.2 Hz, J2 = 1.2 Hz, 1H), 7.29 (dd, J1 = 8.4 Hz, J2 = 2.0 Hz, 1H), 7.24 (dd, J1 = 3.6 Hz, J2 = 1.2 Hz, 1H), 7.05 (dd, J1 = 4.8 Hz, J2 = 3.6 Hz, 1H), 6.80 (d, J = 8.4 Hz, 1H), 4.14-4.01 (m, 2H), 2.96 (m, 1H), 2.54-2.41 (m, 1H, overlapped DMSO-d$_6$), 2.35 (s, 3H), 2.24-2.12 (m, 1H), 1.97-1.87 (m, 1H), 1.72-1.55 (m, 3H). LRMS: 450.55 (calc) 451.0 (found) |
| 589 | 33s | | 3-(dimethylamino)propyl 4-(2-amino-5-(thiophen-2-yl)phenyl-carbamoyl)-phenylcarbamate | $^1$H NMR (DMSO-d$_6$) δ (ppm): 9.95 (s, 1H), 9.62 (s, 1H), 7.95 (d, J = 8.8 Hz, 2H), 7.59 (d, J = 8.8 Hz, 2H), 7.46 (d, J = 2.0 Hz, 1H), 7.35 (dd, J1 = 5.2 Hz, J2 = 1.2 Hz, 1H), 7.29 (dd, J1 = 8.4 Hz, J2 = 2.0 Hz, 1H), 7.24 (dd, J1 = 3.6 Hz, J2 = 1.2 Hz, 1H), 7.04 (dd, J1 = 5.0 Hz, J2 = 3.4 Hz, 1H), 6.81 (d, J = 8.4 Hz, 1H), 5.13 (s, 2H), 4.14 (t, J = 6.6 Hz, 2H), 2.31 (t, J = 7.0 Hz, 2H), 2.14 (s, 6H), 1.77 (p, J = 6.9 Hz, 2H). LRMS: 438.17 (calc) 439.2 (found) |
| 343 | 33t | | 2-morpholinoethyl 4-(4-aminobiphenyl-3-ylcarbamoyl)-phenylcarbamate | $^1$H NMR (DMSO-d$_6$) δ (ppm): 10.03 (s, 1H), 9.63 (s, 1H), 7.95 (d, J = 8.8 Hz, 2H), 7.60 (d, J = 8.4 Hz, 2H), 7.55 (dd, J1 = 8.4 Hz, J2 = 1.2 Hz, 2H), 7.51 (d, J = 2.4 Hz, 1H), 7.39 (t, J = 7.8 Hz, 2H), 7.32 (dd, J1 = 8.2 Hz, J2 = 2.2 Hz, 1H), 7.24 (tf, J1 = 7.4 Hz, J2 = 1.2 Hz, 1H), 6.86 (d, J = 8.4 Hz, 1H), 5.08 (s, 2H), 4.23 (t, J = 5.6 Hz, 2H), 3.58 (t, J = 4.6 Hz, 4H), 2.59 (t, J = 5.6 Hz, 2H), 2.44 (bt, J = 4.4 Hz, 4H). LRMS: 460.21 (calc) 461.2 (found) |

TABLE 16a-continued

Characterization of compounds prepared according to Scheme 33

| Cpd | Ex | R | Name | Characterization |
|---|---|---|---|---|
| 345 | 33u | | 2-(dimethylamino) ethyl 4-(2-amino-5-(5-chlorothiophen-2-yl)phenyl-carbamoyl)-yl)phenylcarbamate | NMR $^1$HNMR: (DMSO-d$_6$) δ (ppm): 10.02 (s, 1H), 9.61 (s, 1H), 7.94 (d, 2H), 7.59 (d, 2H), 7.40 (d, 1H), 7.23 (dd, 1H), 7.11 (d, 1H), 7.04 (d, 1H), 6.80 (d, 1H), 5.22 (s, 2H), 4.19 (t, 2H), 4.53 (t, 2H), 2.20 (s, 6H). LRMS: 458.2 (calc) 459.2 (found for M + H) |
| 346 | 33v | | 2-(pyrrolidin-1-yl)ethyl 3-(2-amino-5-(thiophen-2-yl)phenyl-carbamoyl)-phenylcarbamate | $^1$H NMR (DMSO-d$_6$) δ (ppm): 9.89 (s, 1H), 9.72 (s, 1H), 8.06 (s, 1H), 7.65 (t, J = 10.0 Hz, 2H), 7.48 (d, J = 2.0 Hz, 1H), 7.42 (t, J = 8.0 Hz, 1H), 7.36 (dd, J1 = 5.0 Hz, J2 = 0.6 Hz, 1H), 7.30 (dd, J1 = 8.2 Hz, J2 = 2.2 Hz, 1H), 7.25 (dd, J1 = 3.6 Hz, J2 = 0.8 Hz, 1H), 7.05 (dd, J1 = 5.0 Hz, J2 = 3.4 Hz, 1H), 6.81 (d, J = 8.4 Hz, 1H), 5.14 (s, 2H), 4.19 (t, J = 5.8 Hz, 2H), 2.69 (t, J = 5.6 Hz, 2H), 2.49 (m, 4H), 1.68 (p, J = 3.2 Hz, 4H). LRMS: 450.17 (calc) 451.2 (found) |
| 347 | 33w | | 2-(dimethylamino)-ethyl 4-(4-amino-4'-chlorobiphenyl-3-ylcarbamoyl)phenyl-carbamate | $^1$H NMR: (DMSO-d$_6$) δ (ppm): 10.00 (s, 1H), 9.61 (s, 1H), 7.94 (d, 2H), 7.59-7.55 (m, 4H), 7.50 (d, 1H), 7.42-7.40 (m, 2H), 7.31 (dd, 1H), 6.84 (d, 1H), 5.14 (s, 2H), 4.17 (t, 2H), 2.52 (t, 2H), 2.18 (s, 6H). LRMS: (calc.) 452.93 (found) 453.2 (MH)+ |
| 348 | 33x | | 1-methylpiperidin-4-yl 4-(2-amino-5-(thiophen-2-yl)phenyl-carbamoyl)-yl)phenyl-carbamate | $^1$H NMR (DMSO-d$_6$) δ (ppm): 9.92 (s, 1H), 9.61 (s, 1H), 7.92 (d, J = 8.4 Hz, 2H), 7.58 (d, J = 8.6 Hz, 2H), 7.45 (s, 1H), 7.35 (d, J = 4.7 Hz, 1H), 7.28 (m, 2H), 7.05 (m, 1H), 6.81 (d, J = 8.3 Hz, 1H), 5.12 (s, 2H), 4.64 (m, 1H), 2.62 (m, 2H), 2.19 (s, 3H), 2.12 (m, 2H), 1.90 (m, 2H), 1.62 (m, 2H). LRMS(ESI): (calc.) 450.55 (found) 451.3 (MH)+ |

TABLE 16a-continued

Characterization of compounds prepared according to Scheme 33

| Cpd | Ex | R | Name | Characterization |
|---|---|---|---|---|
| 349 | 33y | | 2-(dimethylamino)ethyl-4-(4-amino-4'-(dimethylamino)-biphenyl-3-ylcarbamoyl)-phenylcarbamate | $^1$H NMR (DMSO-d$_6$) δ (ppm): 10.01 (s, 1H), 9.61 (s, 1H), 7.95 (d, J = 8.8 Hz, 2H), 7.60 (d, J = 8.8 Hz, 2H), 7.40-7.37 (m, 3H), 7.23 (dd, J1 = 8.4 Hz, J2 = 2.0 Hz, 1H), 6.83-6.75 (m, 3H), 4.90 (s, 2H), 4.20 (t, J = 5.6 Hz, 2H), 2.90 (s, 6H), 2.54 (t, J = 5.6 Hz, 2H), 2.20 (s, 6H). LRMS: (calc.) 461.6 (found) 462.3 (MH)+ |
| 350 | 33z | | (R)-1-methylpyrrolidin-3-yl 4-(2-amino-5-(thiophen-2-yl)phenyl-carbamoyl)-phenyl-carbamate | $^1$H NMR (DMSO-d$_6$) δ (ppm): 10.01 (s, 1H), 9.63 (s, 1H), 7.92 (d, J = 8.5 Hz, 2H), 7.57 (d, J = 8.3 Hz, 2H), 7.44 (s, 1H), 7.42 (d, J = 4.1 Hz, 1H), 7.22 (m, 2H), 7.05 (m, 1H), 6.81 (d, J = 8.4 Hz, 1H), 5.13 (s, 2H), 2.71 (m, 1H), 2.62 (m, 2H), 2.31 (s, 3H), 2.22 (m, 1H), 1.80 (m, 1H). LRMS: (calc.) 436.53 (found) 437.2 (MH)+ |
| 351 | 33aa | | 2-(dimethylamino)ethyl 4-(2-amino-5-(6-methoxypyridin-3-yl)phenyl-carbamoyl)-phenylcarbamate | $^1$HNMR: (DMSO-d$_6$) δ (ppm): 10.00 (s, 1H), 9.63 (s, 1H), 8.33 (dd, 1H), 7.93 (d, 2H), 7.86 (dd, 1H), 7.57 (dd, 2H), 7.44 (d, 1H), 7.27 (dd, 1H), 6.83 (t, 2H), 5.05 (s, 2H), 4.17 (t, 2H), 3.85 (s, 3H), 2.52 (t, 2H), 2.18 (s, 6H). LRMS: (calc.) 449.50 (found) 450.3 (MH)+ |
| 352 | 33bb | | 2-(dimethylamino)-ethyl 4-(2-amino-5-(pyridin-4-yl)phenyl-carbamoyl)yl)phenyl-carbamate | $^1$HNMR: (DMSO-d$_6$) δ (ppm): 10.08 (s, 1H), 9.72 (s, 1H), 8.03 (s, 2H), 7.73 (d, 1H), 7.67-7.63 (m, 4H), 7.55 (dd, 1H), 6.94 (d, 1H), 5.43 (s, 2H), 4.25 (t, 2H), 2.58 (t, 2H), 2.26 (s, 6H). LRMS: (calc.) 419.59 (found) 420.3 (MH)+ |
| 353 | 33cc | | 2-(dimethylamino)-ethyl 4-(2-amino-5-(2-methoxypyridin-3-yl)phenyl-carbamoyl)-phenylcarbamate | $^1$HNMR: (DMSO-d$_6$) δ (ppm): 10.00 (s, 1H), 9.61 (s, 1H), 8.05 (dd, 1H), 7.93 (d, 2H), 7.64 (dd, 1H), 7.57 (dd, 2H), 7.38 (d, 1H), 7.21 (dd, 1H), 7.01 (dd, 1H), 6.81 (d, 1H), 5.07 (s, 2H), 4.17 (t, 2H), 3.85 (s, 3H), 2.52 (t, 2H), 2.18 (s, 6H). LRMS: (calc.) 449.5 (found) 450.3 (MH)+ |

TABLE 16a-continued

Characterization of compounds prepared according to Scheme 33

| Cpd | Ex | R | Name | Characterization |
|---|---|---|---|---|
| 354 | 33dd | | 2-(dimethylamino)ethyl 4-(4-amino-3'-(trifluoromethoxy)biphenyl-3-ylcarbamoyl)phenylcarbamate | $^1$HNMR: (DMSO-$d_6$) δ (ppm): 10.00 (s, 1H), 9.62 (s, 1H), 7.94 (dd, 2H), 7.61-7.57 (m, 3H), 7.55 (d, 2H), 7.52-7.48 (m, 2H), 7.37 (dd, 1H), 7.21-7.19 (m, 1H), 6.86 (d, 1H), 5.19 (s, 2H), 4.19 (t, 2H), 2.52 (t, 2H), 2.18 (s, 6H). LRMS: (calc.) 502.60 (found) 503.2 (MH)+ |
| 355 | 33ee | | 2-(dimethylamino)ethyl 4-(4-amino-4'-(trifluoromethoxy)biphenyl-3-ylcarbamoyl)phenylcarbamate | $^1$HNMR: (DMSO-$d_6$) δ (ppm): 10.00 (s, 1H), 9.61 (s, 1H), 7.94 (d, 2H), 7.66-7.64 (m, 2H), 7.59-7.57 (m, 2H), 7.52 (d, 1H), 7.36-7.30 (m, 3H), 6.85 (d, 1H), 5.14 (s, 2H), 4.17 (t, 2H), 2.52 (t, 2H), 2.18 (s, 6H). LRMS: (calc.) 502.6 (found) 503.3 (MH)+ |
| 356 | 33ff | | 2-(dimethylamino)ethyl 4-(4-amino-3'-fluoro-4'-methoxybiphenyl-3-ylcarbamoyl)phenylcarbamate | $^1$HNMR: (DMSO-$d_6$) δ (ppm): 10.00 (s, 1H), 9.61 (s, 1H), 7.94 (d, 2H), 7.59-7.57 (m, 2H), 7.47 (d, 1H), 7.38 (dd, 1H), 7.30 (dd, 1H), 7.28 (dd, 1H), 7.15 (t, 1H), 6.82 (d, 1H), 5.04 (s, 2H), 4.17 (t, 2H), 3.82 (s, 3H), 2.52 (t, 2H), 2.18 (s, 6H). LRMS: (calc.) 466.62 (found) 467.3 (MH)+ |
| 357 | 33gg | | 2-(dimethylamino)ethyl 4-(4-amino-4'-fluorobiphenyl-3-ylcarbamoyl)ylcarbamate | $^1$H NMR (DMSO-$d_6$) δ (ppm): 10.01 (s, 1H), 9.61 (s, 1H), 7.94 (d, J = 8.8 Hz, 2H), 7.59-7.54 (m, 4H), 7.47 (d, J = 2.2 Hz, 1H), 7.28 (dd, J = 8.2, 2.2 Hz, 1H), 7.19 (t, J = 8.9 Hz, 1H), 6.84 (d, J = 8.2 Hz, 1H), 5.08 (s, 2H), 4.18 (t, J = 5.7 Hz, 2H), 2.52 (t, J = 5.7 Hz, 2H), 2.19 (s, 6H). LRMS: (calc.) 436.59 (found) 437.3 (MH)+ |
| 358 | 33hh | | 2-(dimethylamino)ethyl 4-(4-amino-2',4'-difluorobiphenyl-3-ylcarbamoyl)phenyl-carbamate | $^1$H NMR (DMSO-$d_6$) δ (ppm): 10.01 (s, 1H), 9.61 (s, 1H), 7.94 (d, J = 8.8 Hz, 2H), 7.59 (d, 8.8 Hz, 2H), 7.52-7.46 (m, 1H), 7.37 (s, 1H), 7.31-7.25 (m, 1H), 7.18-7.10 (m, 2H), 6.85 (d, J = 3.2 Hz, 1H), 5.16 (s, 2H), 4.20 (t, J = 5.6 Hz, 2H), 2.57 (t, J = 6.0 Hz, 2H), 2.23 (s, 6H). LRMS: (calc.) 454.20 (found) 455.2 (MH)+ |

TABLE 16a-continued

Characterization of compounds prepared according to Scheme 33

| Cpd | Ex | R | Name | Characterization |
|---|---|---|---|---|
| 359 | 33ii | | 2-(dimethylamino)-ethyl 4-(4-amino-4'-(trifluoromethyl)biphenyl-3-ylcarbamoyl)-phenylcarbamate | $^1$H NMR (DMSO-d$_6$) δ (ppm): 10.01 (s, 1H), 9.61 (s, 1H), 7.96 (d, J = 8.8 Hz, 2H), 7.75 (dd, J1 = 25.6 Hz, J2 = 8.4 Hz, 4H), 7.61-7.59 (m, 3H), 7.42 (dd, J1 = 8.4 Hz, J2 = 2.0 Hz, 1H), 6.88 (d, J = 8.4 Hz, 1H), 5.27 (s, 2H), 4.19 (t, J = 6.0 Hz, 2H), 2.52 (t, J = 6.0 Hz, 2H), 2.19 (s, 6H). LRMS: (calc.) 486.2 (found) 487.2 (MH)+ |
| 360 | 33jj | | 2-(dimethylamino)-ethyl 4-(4-amino-2'-fluorobiphenyl-3-ylcarbamoyl)-phenylcarbamate | $^1$H NMR (DMSO-d$_6$) δ (ppm): 10.03 (s, 1H), 9.64 (s, 1H), 7.96 (s, 2H), 7.60 (s, 2H), 7.46-7.42 (m, 2H), 7.30-7.23 (m, 4H), 6.87 (t, J = 6.3 Hz, 1H), 4.16 (s, 2H), 4.19 (d, J = 4.9 Hz, 2H), 2.5 (m, 2H, overlap with DMSO), 2.20 (s, 6H). LRMS: (calc.) 436.24 (found) 437.2 (MH)+ |
| 361 | 33kk | | 2-(dimethylamino)-ethyl 4-(4-amino-4'-hydroxybiphenyl-ylcarbamoyl)-ylcarbamate | $^1$H NMR (DMSO-d$_6$) δ (ppm): 10.08 (s, 1H), 9.70 (s, 1H), 9.46 (s, 1H), 8.03 (m, 3H), 7.60 (s, 2H), 7.41 (m, 3H), 7.26 (m, 1H), 6.85 (m, 2H), 5.01 (s, 2H), 4.20 (s, 2H), 2.50 (s, 2H), 2.10 (s, 6H). LRMS: (calc.) 434.49 (found) 435.2 (MH)+ |
| 362 | 33ll | | 2-(dimethylamino)-ethyl 4-(4-amino-3',4',5'-trifluorobiphenyl-3-ylcarbamoyl)-phenylcarbamate | $^1$H NMR (DMSO-d$_6$) δ (ppm): 10.01 (s, 1H), 9.61 (s, 1H), 7.96 (d, J = 8.8 Hz, 2H), 7.60 (d, J = 8.8 Hz, 2H), 7.56 (d, J = 1.6 Hz, 1H), 7.52 (dd, J1 = 10.0 Hz, J2 = 6.8 Hz, 1H), 7.39 (dd, J1 = 8.4 Hz, J2 = 2.4Hz, 1H), 6.85 (d, J = 8.4 Hz, 1H), 5.26 (s, 2H), 4.20 (t, J = 5.6 Hz, 2H), 2.54 (t, J = 5.6 Hz, 2H), 2.19 (s, 6H). LRMS: (calc.) 472.5 (found) 473.2 (MH)+ |
| 363 | 33mm | | 2-(dimethylamino)-ethyl 4-(4-amino-4'-(methylthio)biphenyl-3-ylcarbamoyl)-phenylcarbamate | $^1$HNMR: (DMSO-d$_6$) δ (ppm): 10.02 (s, 1H), 9.63 (s, 1H), 7.95 (d, 2H), 7.59 (dd, 2H), 7.53-7.49 (m, 3H), 7.32-7.26 (m, 3H), 6.85 (d, 1H), 5.07 (s, 2H), 4.19 (t, 2H), 2.53 (t, 2H), 2.48 (s, 3H), 2.20 (s, 6H). LRMS: (calc.) 464.6 (found) 465.2 |

TABLE 16a-continued

Characterization of compounds prepared according to Scheme 33

| Cpd | Ex | R | Name | Characterization |
|---|---|---|---|---|
| 364 | 33nn | | 2-(dimethylamino)ethyl 4-(4-amino-4'-cyanobiphenyl-3-ylcarbamoyl)-phenylcarbamate | $^1$HNMR: (DMSO-$d_6$) δ (ppm): 10.02 (s, 1H), 9.62 (s, 1H), 7.95 (d, 2H), 7.83-7.75 (m, 4H), 7.63-7.58 (m, 3H), 7.44 (dd, 1H), 6.88 (dd, 1H), 5.34 (s, 2H), 4.19 (t, 2H), 2.53 (t, 2H), 2.20 (s, 6H). LRMS: (calc.) 443.5 (found) 444.2 (MH)+ |
| 365 | 33oo | | 2-(dimethylamino)-ethyl 4-(4-amino-2'fluoro-4'methoxy-biphenyl-3-ylcarbamoyl)-phenylcarbamate | $^1$H NMR: (DMSO-$d_6$) δ (ppm): 10.00 (s, 1H), 9.60 (s, 1H), 7.92 (d, 2H), 7.57 (d, 2H), 7.36-7.32 (m, 2H), 7.12 (dt, 1H), 6.88-6.80 (m, 3H), 5.05 (s, 2H), 4.18 (t, 2H), 3.77 (s, 3H), 2.51 (t, 2H), 2.18 (s, 6H). LRMS: (calc.) 466.62 (found) 467.3 (MH)+ |
| 366 | 33pp | | 2-(dimethylamino)-ethyl 4-(4-amino-3'fluoro-4'-methylbiphenyl-3-ylcarbamoyl)-phenylcarbamate | $^1$HNMR: (DMSO-$d_6$) δ (ppm): 10.01 (s, 1H), 9.63 (s, 1H), 7.95 (d, 2H), 7.58 (d, 2H), 7.51 (d, 1H), 7.33-7.25 (m, 4H), 6.83 (d, 1H), 5.11 (s, 2H), 4.18 (t, 2H), 2.52 (t, 2H), 2.21 (s, 3H), 2.18 (s, 6H). LRMS: (calc.) 450.62 (found) 451.3 (MH)+ |
| 367 | 33qq | | 2-(dimethylamino)-ethyl 4-(2-amino-5-thiazol-2-yl)phenyl-carbamoyl)-phenylcarbamate | $^1$HNMR: (DMSO-$d_6$) δ (ppm): 10.02 (s, 1H), 9.62 (s, 1H), 7.95 (d, 2H), 7.79 (d, 1H), 7.76 (d, 1H), 7.60-7.55 (m, 4H), 6.83 (d, 1H), 5.48 (s, 2H), 4.19 (t, 2H), 2.52 (t, 2H), 2.19 (s, 6H). LRMS: (calc.) 425.2 (found) 426.2 (MH)+ |
| 368 | 33rr | | 2-(dimethylamino)-ethyl 4-(4-amino-2',4',5'-trifluorobiphenyl-3-ylcarbamoyl)-phenylcarbamate | $^1$HNMR: (DMSO-$d_6$) δ (ppm): 10.01 (s, 1H), 9.62 (s, 1H), 7.94 (d, 2H), 7.61-7.52 (m, 4H), 7.41 (s, 1H), 7.19 (dt, 1H), 6.86 (d, 1H), 5.23 (s, 2H), 4.19 (t, 2H), 2.52 (t, 2H), 2.20 (s, 6H). LRMS: (calc.) 472.46 (found) 473.3 (MH)+ |

TABLE 16a-continued

Characterization of compounds prepared according to Scheme 33

| Cpd | Ex | R | Name | Characterization |
|---|---|---|---|---|
| 369 | 33ss | | 2-(dimethylamino)-ethyl 4-(4-amino-2'-fluoro-4'-(trifluoromethyl)-biphenyl-3-ylcarbamoyl)-phenylcarbamate | $^1$HNMR: (DMSO-d$_6$) δ (ppm): 10.00 (s, 1H), 9.62 (s, 1H), 7.94 (d, 2H), 7.70-7.67 (m, 2H), 7.60-7.57 (m, 3H), 7.47 (m, 1H), 7.26 (dt, 1H), 6.87 (d, 1H), 5.31 (s, 2H), 4.16 (t, 2H), 2.51 (t, 2H), 2.18 (s, 6H). LRMS: (calc.) 504.59 (found) 505.2 (MH)+ |
| 370 | 33tt | | 2-(dimethylamino)-ethyl 4-(4-amino-4'-ethoxybiphenyl-3-ylcarbamoyl)-phenylcarbamate | $^1$H NMR (DMSO-d$_6$) δ (ppm): 10.02 (s, 1H), 9.62 (s, 1H), 7.95 (d, J = 8.8 Hz, 2H), 7.59 (d, J = 8.8 Hz, 2H), 7.48-7.44 (m, 3H), 7.25 (dd, J = 18.4 Hz, J = 22.4 Hz, 1H), 6.96-6.92 (m, 2H), 6.84 (d, J = 8.4 Hz, 1H), 4.98 (s, 2H), 4.19 (t, J = 5.6 Hz, 2H), 4.03 (q, J = 6.8 Hz, 2H), 2.90 (s, 6H), 2.54 (t, J = 5.6 Hz, 2H), 2.20 (s, 6H). LRMS: (calc.) 462.54 (found) 463.2 (MH)+ |
| 371 | 33uu | | 2-(dimethylamino)-ethyl 4-(2-amino-5-(5-(methylthio)-thiophen-2-yl)phenylcarbamoyl)-phenylcarbamate | $^1$H NMR (DMSO-d$_6$) δ (ppm): 10.02 (s, 1H), 9.61 (s, 1H), 7.94 (d, J = 8.8 Hz, 2H), 7.59 (d, J = 8.8 Hz, 2H), 7.38 (d, J = 2.0 Hz, 1H), 7.20 (dd, J1 = 8.4 Hz, J2 = 2.0 Hz, 1H), 7.01 (d, J = 3.2 Hz, 1H), 6.78 (d, J = 8.4 Hz, 1H), 6.73-6.71 (m, 1H), 5.08 (s, 2H), 4.19 (t, J = 5.6 Hz, 2H), 2.54 (t, J = 5.6 Hz, 2H), 2.42 (s, 3H), 2.20 (s, 6H). LRMS: (calc.) 470.61 (found) 439.2 (MH)+ |

Example 34a 3-(2-Amino-5-(thiophen-2-yl)phenylcarbamoyl)phenyl acetate (299)

Example 34b

N-(2-Amino-5-(thiophen-2-yl)phenyl)-3-hydroxybenzamide (300)

Scheme 34

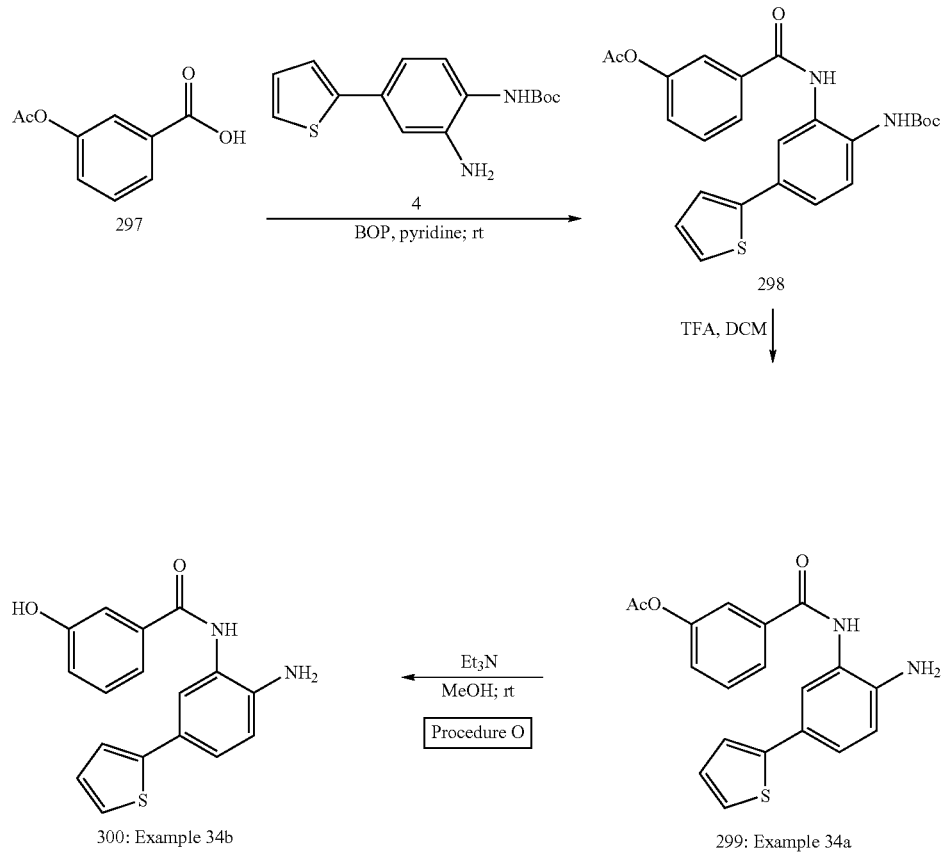

Step 1: 3-(2-(tert-Butoxycarbonylamino)-5-(thiophen-2-yl)phenylcarbamoyl)phenyl acetate (298)

Following the same procedure as described in Example 1, step 6 (scheme 1), using compound 4, but substituting compound 7 for compound 297, title compound 298 was obtained (81% yield).

$^1$H NMR (DMSO-$d_6$) δ (ppm): 9.96 (s, 1H), 8.78 (s, 1H), 7.91 to 7.88 (m, 1H), 7.80 (d, J=2.2 Hz, 1H), 7.72 (t, J=2.0 Hz, 1H), 7.64 to 7.59 (m, 2H), 7.54 to 7.51 (m, 2H), 7.46 (dd, J=3.5, 1.2 Hz, 1H), 7.41 (dd, J=2.3, 0.98 Hz, 0.5H), 7.39 (dd, J=2.3, 0.98 Hz, 0.5H), 7.13 (dd, J=5.1, 3.7 Hz, 1H), 2.32 (s, 3H), 1.46 (s, 9H).

Step 2: 3-(2-Amino-5-(thiophen-2-yl)phenylcarbamoyl)phenyl acetate (296)

Following the same procedure as described in Example 1, step 7 (scheme 1), but substituting compound 8 for compound 295, the title compound 296 was obtained (quantitative yield).

$^1$H NMR (DMSO-$d_6$) δ (ppm): 9.81 (s, 1H), 7.92 (d, J=8.0 Hz, 1H), 7.76 (t, J=1.9 Hz, 1H), 7.57 (t, J=8.0 Hz, 1H), 7.45 (d, J=2.2 Hz, 1H), 7.38 to 7.36 (m, 1H), 7.35 (d, J=1.2 Hz, 1H), 7.31 (dd, J=8.2, 2.2 Hz, 1H), 7.25 (dd, J=3.7, 1.2 Hz, 1H), 7.05 (dd, J=5.1, 3.5 Hz, 1H), 6.81 (d, J=8.2 Hz, 1H), 5.19 (s, 2H), 2.31 (s, 3H).

Step 3: N-(2-Amino-5-(thiophen-2-yl)phenyl)-3-hydroxybenzamide (297)

A suspension of acetate 296 (349 mg, 0.99 mmol) in dry MeOH (6 mL) was treated with triethyl amine (1.5 mL) and stirred at room temperature for 19 h, concentrated under reduced pressure and triturated with diethyl ether to provide the title compound 297 (282.5 mg, 92% yield).

$^1$H NMR (DMSO-$d_6$) δ (ppm): 9.72 (s, 1H), 9.66 (s, 1H), 7.47 to 7.43 (m, 2H), 7.37 (s, 2H), 7.35 to 7.31 (m, 2H), 7.27 (d, J=16.0 Hz, 1H), 7.05 (d, J=2.7 Hz, 1H), 6.97 (d, J=7.8 Hz, 1H), 6.81 (d, J=8.2 Hz, 1H), 5.13 (s, 2H).

TABLE 17

Characterization of compounds 301-310 prepared according to Scheme 34.

| Cpd | Ex | R$_1$ | R$_2$ | X | Name | Characterization |
|---|---|---|---|---|---|---|
| 301 | 34c | OAc | thiophen-3-yl | NH$_2$ | 4-(2-amino-5-(thiophen-3-yl)phenylcarbamoyl)-phenyl acetate | $^1$H NMR (DMSO-d$_6$) δ (ppm):): 9.77 (s, 1H), 8.05 (d, J = 8.6 Hz, 2H), 7.59 to 7.55 (m, 2H), 7.51 (d, J = 2.0 Hz, 1H), 7.42 (dd, J = 4.9, 1.4 Hz, 1H), 7.37 (dd, J = 8.2, 2.2 Hz, 1H), 7.28 (d, J = 8.6 Hz, 2H), 6.81 (d, J = 8.2 Hz, 1H), 5.07 (s, 2H), 2.31 (s, 3H). LRMS: 352.1 (calc) 353.0 (obs). |
| 302 | 34d | OH | thiophen-3-yl | NH$_2$ | N-(2-amino-5-(thiophen-3-yl)phenyl)-4-hydroxybenzamide | $^1$H NMR (DMSO-d$_6$) δ (ppm): 9.54 (s, 1H), 7.88 (d, J = 8.6 Hz, 2H), 7.58 to 7.55 (m, 2H), 7.49 (d, J = 2.2 Hz, 1H), 7.42 (dd, J = 4.7, 1.4 Hz, 1H), 7.34 (dd, J = 8.2, 2.7 Hz, 1H), 6.85 (d, J = 8.8 Hz, 2H), 6.80 (d, J = 8.2 Hz, 1H), 4.99 (s, 2H). LRMS: 310.1 (calc) 311.0 (obs). |
| 303 | 34e | OH | 6-chloropyridin-3-yl | NH$_2$ | N-(2-amino-5-(6-chloropyridin-3-yl)phenyl)-4-hydroxybenzamide | $^1$H NMR (DMSO-d$_6$) δ (ppm): 10.09 (s, 1H), 9.57 (s, 1H), 8.60 (s, 1H), 8.00 (dd, J = 8.4, 2.5 Hz, 1H), 7.84 (d, J = 8.0 Hz, 2H), 7.57 (s, 1H), 7.49 (d, J = 8.1 Hz, 1H), 7.39 (d, J = 7.2 Hz, 1H), 6.84 (m, 3H), 5.11 (s, 2H). LRMS: 339.08 (calc) 339.9 (obs). |
| 304 | 34f | OAc | 6-fluoropyridin-3-yl | NH$_2$ | 4-(2-amino-5-(6-fluoropyridin-3-yl)phenylcarbamoyl)phenyl acetate | $^1$H NMR (CD$_3$OD) δ (ppm): 8.38 (s, 1H), 8.13 (m, 1H), 8.07 (d, J = 8.1 Hz, 2H), 7.50 (s, 1H), 7.38 (dd, J = 8.1, 2.1 Hz, 1H), 7.27 (d, J = 8.0 Hz, 2H), 7.11 (m, 1H), 6.97 (d, J = 8.1 Hz, 1H), 2.32 (s, 3H). LRMS: 365.36 (calc) 366.0 (obs). |
| 305 | 34g | OH | 6-fluoropyridin-3-yl | NH$_2$ | N-(2-amino-5-(6-fluoropyridin-3-yl)phenyl)-4-hydroxybenzamide | $^1$H NMR (CD$_3$OD) δ (ppm): 8.36 (s, 1H), 8.11 (m, 1H), 7.89 (d, J = 8.1 Hz, 2H), 7.43 (s, 1H), 7.34 (dd, J = 8.0, 2.1 Hz, 1H), 7.09 (dd, J = 8.1, 1.9 Hz, 1H), 6.97 (d, J = 8.1 Hz, 1H), 6.87 (d, J = 8.1 Hz, 2H). LRMS: 323.32 (calc) 324.0 (obs). |
| 306 | 34h | OAc | 3,4-dichlorophenyl | NH$_2$ | 4-(4-amino-3',4'-dichlorobiphenyl-3-ylcarbamoyl)phenyl acetate | $^1$H NMR (CD$_3$OD) δ (ppm): 7.98 (d, J = 8.1 Hz, 2H), 7.61 (s, 1H), 7.38 (m, 3H), 7.27 (dd, J = 8.1, 3.2 Hz, 1H), 7.18 (d, J = 8.1 Hz, 2H), 6.88 (d, J = 8.2 Hz, 1H), 2.21 (s, 3H). LRMS: 415.27 (calc) 416.9 (obs). |
| 307 | 34i | OH | 3,4-dichlorophenyl | NH$_2$ | N-(4-amino-4',5'-dichlorobiphenyl-3-yl)-4-hydroxybenzamide | $^1$H NMR (DMSO-d$_6$) δ (ppm): 10.11 (s, 1H), 9.50 (s, 1H), 7.88 (d, J = 8.0 Hz, 2H), 7.75 (s, 1H), 7.62 (d, J = 8.1 Hz, 1H), 7.52 (m, 2H), 7.32 (m, 1H), 6.82 (d, J = 8.1 Hz, 3H), 5.21 (s, 2H). LRMS: 373.23 (calc) 374.9 (obs). |
| 308 | 34j | OH | pyridin-3-yl | NH$_2$ | N-(2-amino-5-(pyridin-3-yl)phenyl)-4-hydroxybenzamide | $^1$H NMR (CD$_3$OD) δ (ppm): 8.65 (s, 1H), 8.32 (d, J = 6.2 Hz, 1H), 7.92 (m, 1H), 7.81 (d, J = 8.0 Hz, 2H), 7.41 (s, 1H), 7.33 (m, 2H), 6.90 (d, J = 8.0 Hz, 1H), 6.79 (d, J = 8.0 Hz, 2H). LRMS: 305.33 (calc) 306.0 (obs). |

TABLE 17-continued

Characterization of compounds 301-310 prepared according to Scheme 34.

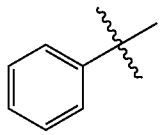 [SMILES: *c1ccccc1]

| Cpd | Ex | R₁ | R₂ | X | Name | Characterization |
|---|---|---|---|---|---|---|
| 309 | 34k | OH | (phenyl) | NH₂ | N-(4-aminobiphenyl-3-yl)-4-hydroxybenzamide | $^1$H NMR (DMSO-d$_6$) δ (ppm): 10.11 (s, 1H), 9.52 (s, 1H), 7.89 (d, J = 8.1 Hz, 2H), 7.52 (d, J = 8.2 Hz, 2H), 7.49 (s, 1H), 7.39 (m, 2H), 7.31 (m, 1H), 7.22 (m, 1H), 6.84 (d, J = 8.1 Hz, 3H), 5.09 (s, 2H). LRMS: 304.34 (calc) 305.0 (found) |
| 310 | 34l | OH | (thiophene) | OH | 4-hydroxy-N-(2-hydroxy-5-(thiophen-2-yl)phenyl)benzamide | $^1$H NMR (DMSO-d$_6$) δ (ppm): 10.11 (s, 1H), 9.39 (s, 1H), 8.01 (s, 1H), 7.85 (d, =8.1 Hz, 2H), 7.42 (d, J = 4.5 Hz, 1H), 7.31 (m, 2H), 7.09 (m, 1H), 6.91 (d, J = 8.2 Hz, 1H), 6.85 (d, J = 8.1 Hz, 2H), 4.11 (s, 1H). LRMS: 331.36 (calc) 312.0 (found) |

Example 35

N-(2-Amino-5-(thiophen-2-yl)phenyl)-4-(benzo[d][1,3]dioxol-5-ylmethyl)piperazine-1-carboxamide (316)

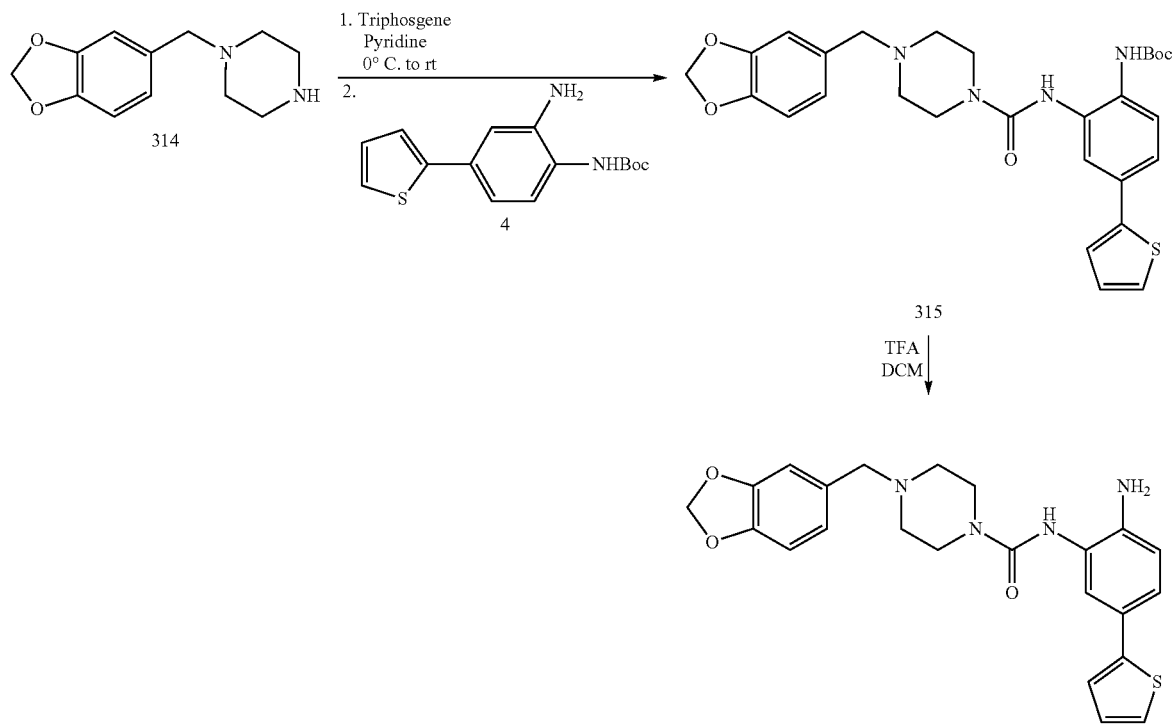

316: Example 35

Step 1. tert-Butyl 2-(4-(benzo[d][1,3]dioxol-5-ylmethyl)piperazine-1-carboxamido)-4-(thiophen-2-yl)phenylcarbamate (315)

A solution of triphosgene (544 mg, 1.83 mmol, 1.05 eq.) in DCM (5 mL) stirred at 0° C. under nitrogen was treated with a solution of 1-(benzo[d][1,3]dioxol-5-ylmethyl)piperazine (314, 1.16 g, 5.24 mmol) in anhydrous pyridine (7 mL), added dropwise over 5 min. The resulting mixture was stirred at 0° C. for 3 h and then at room temperature for 30 min, transferred with a syringe into a flask containing solid amine 4 (832 mg, 2.87 mmol), stirred at room temperature for 21 h, diluted with DCM, washed (saturated $NaHCO_3$ then water), dried over $MgSO_4$, filtered and concentrated. Purification by flash column chromatography (elution with 5% isopropyl alcohol in DCM) gave title compound 315 (165 mg, 11% yield) as a yellow solid.

$^1$H NMR (DMSO-$d_6$) δ (ppm): 8.60 (s, 1H), 8.30 (s, 1H), 7.59 (d, J=2.2 Hz, 1H), 7.51 (dd, J=1.0, 5.0 Hz, 1H), 7.46 (d, J=8.5 Hz, 1H), 7.40 (dd, J=1.0, 3.5 Hz, 1H), 7.39 (dd, J=2.2, 8.5 Hz, 1H), 7.11 (dd, J=3.5, 5.0 Hz, 1H), 6.88 (d, J=1.4 Hz, 1H), 6.86 (d, J=7.8 Hz, 1H), 6.76 (dd, J=1.4, 7.8 Hz, 1H), 5.99 (s, 2H), 3.45 (t, J=4.6 Hz, 1H), 3.43 (s, 2H), 2.38 (t, J=4.6 Hz, 1H), 1.46 (s, 9H). LRMS: (calc.) 536.2; (obt.) 537.1 (MH)$^+$.

Step 2, N-(2-Amino-5-(thiophen-2-yl)phenyl)-4-(benzo[d][1,3]dioxol-5-ylmethyl)piperazine-1-carboxamide (316)

A solution of compound 315 (165 mg, 0.31 mmol) in a mixture DCM-trifluoroacetic acid (3 mL, 2:1 ratio) was stirred at room temperature for 1.5 h; diluted with DCM and washed with a solution of KOH (830 mg, 15 mmol) in brine (15 mL), then brine, dried over $MgSO_4$, filtered and concentrated. Purification by flash column chromatography (elution with 5% to 10% MeOH in DCM) gave title compound 316 (87 mg, 0.20 mmol, 64% yield) as a pale yellow solid.

$^1$H NMR: (DMSO-$d_6$) δ (ppm): 7.92 (s, 1H), 7.33 (dd, J=1.2, 5.1 Hz, 1H), 7.26 (d, J=2.1 Hz, 1H), 7.21-7.18 (m, 2H), 7.03 (dd, J=3.5, 5.1 Hz, 1H), 6.88 (d, J=1.5 Hz, 1H), 6.85 (d, J=8.0 Hz, 1H), 6.76 (dd, J=1.5, 7.8 Hz, 1H), 6.72 (d, J=7.8 Hz, 1H), 5.99 (s, 2H), 4.95 (bs, 2H), 3.44-3.42 (m, 6H), 2.36 (t, J=4.7 Hz, 4H). LRMS: (calc.) 436.2; (obt.) 437.0 (M+H)$^+$.

Example 37a

(S)—N-(4-Aminobiphenyl-3-yl)-4-(3-aminopyrrolidin-1-yl)benzamide (327)

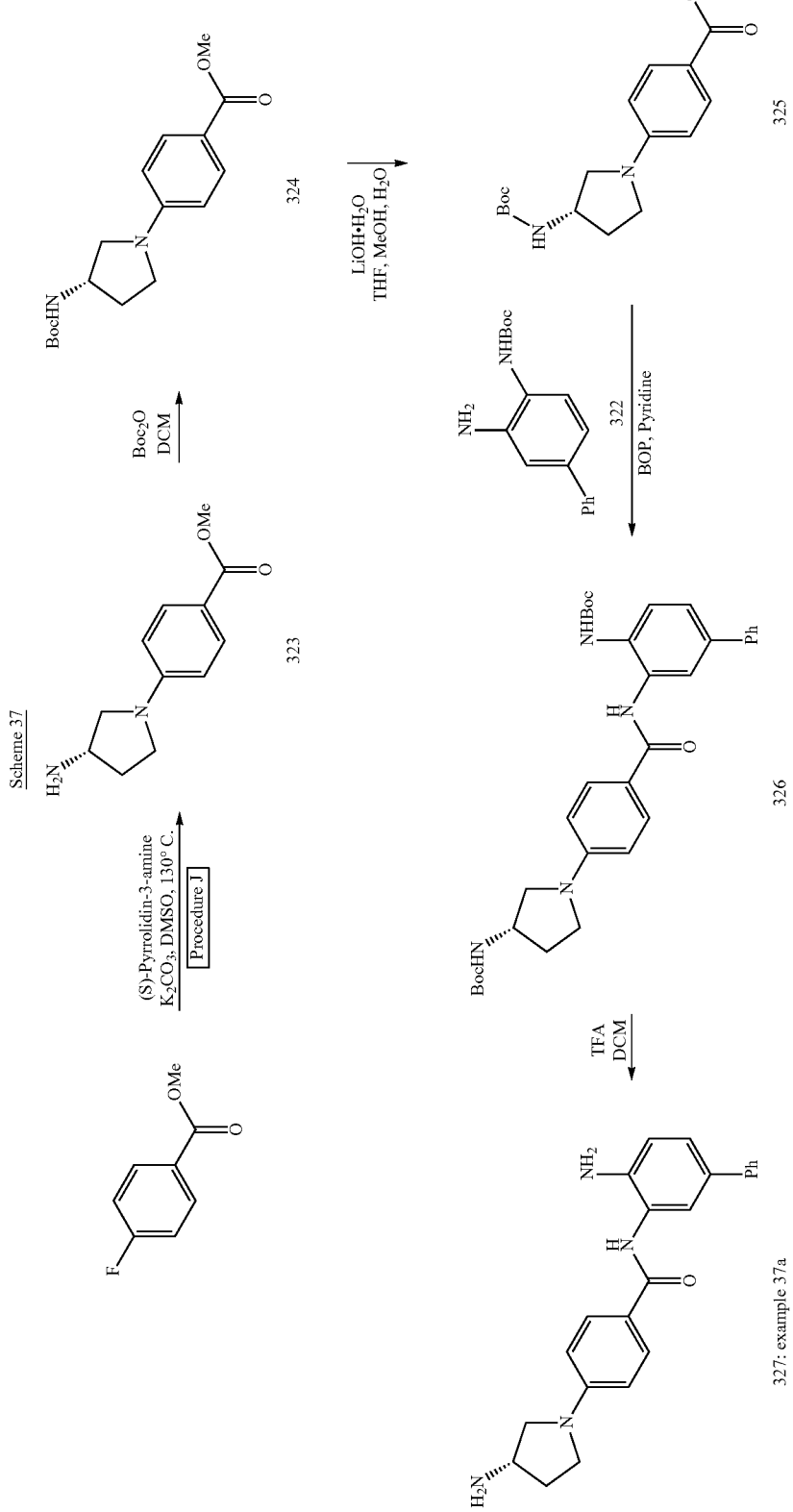

Step 1: (S)-Methyl 4-(3-aminopyrrolidin-1-yl)benzoate (323)

K₂CO₃ (7.71 g, 55.84 mmol) was added to a solution of (S)-pyrrolidin-3-amine (5.0 g, 58.04 mmol) and methyl 4-fluorobenzoate (8.6 g, 55.81 mmol) in DMSO (20 mL). The reaction mixture was stirred for 18 h at 130° C. in a sealed tube. The reaction mixture was cooled, diluted with AcOEt and H₂O, and extracted with AcOEt (3 times). The extract was washed with water, NH₄Cl and brine, dried over MgSO₄, filtered and concentrated to give the title compound 323 (7.98 g, 65% yield) as a pink solid.

¹H NMR (DMSO-d₆) δ (ppm): 7.75 (d, J=9.0 Hz, 2H), 6.52 (d, J=9.0 Hz, 2H), 3.74 (s, 3H), 3.60-3.55 (m, 1H), 3.45-3.41 (m, 2H), 3.32-3.25 (m, 1H), 2.97-2.93 (m, 1H), 2.09-2.01 (m, 1H), 1.72-1.68 (m, 1H). LRMS calc. 220.1; found 221.1 (MH)+.

Step 2: (S)-Methyl 4-(3-(tert-butoxycarbonylamino)pyrrolidin-1-yl)benzoate (324)

A solution of compound 323 (2.00 g, 9.08 mmol) and Boc₂O (2.18 g, 9.99 mmol) in DCM (20 mL) was stirred at room temperature for 18 h. The reaction mixture was concentrated and the residue was purified by flash chromatography (1-2% MeOH in DCM) to give the title compound 324 (2.66 g, 91% yield) as a beige solid.

¹H NMR (DMSO-d₆) δ (ppm): 7.75 (d, J=8.8 Hz, 2H), 7.25 (d, J=6.7 Hz, 1H), 6.54 (d, J=8.8 Hz, 2H), 4.16-4.11 (m, 1H), 3.75 (s, 3H), 3.53-3.49 (m, 1H), 3.46-3.40 (m, 1H), 3.32-3.28 (m, 1H), 3.13-3.09 (m, 1H), 2.17-2.10 (m, 1H), 1.94-1.87 (m, 1H). LRMS calc. 320.2; found 321.1 (MH)+.

Step 3: (S)-4-(3-(tert-Butoxycarbonylamino)pyrrolidin-1-yl)benzoic acid (325)

LiOH.H₂O (1.14 g, 27.26 mmol) and water (5 mL) was added to a solution of 324 (4.36 g, 13.62 mmol) in THF (15 mL) and MeOH (15 mL). The reaction mixture was stirred at room temperature for 22 h, diluted with water and acidified with HCl (pH 4-5). The precipitate obtained was collected by filtration and rinsed with water to give the title compound 325 (3.91 g, 94% yield) as a white solid.

LRMS calc. 306.2; found 307.1 (MH)+.

Step 4: (S)-tert-Butyl 3-(4-(3-tert-butoxycarbonylaminopyrrolidin-1-yl)benzamido)biphenyl-4-ylcarbamate (326)

The acid 325 (3.23 g, 7.03 mmol) and BOP (4.66 g, 10.55 mmol) were added to a solution of 322 (1.2 g, 7.03 mmol) (Compound 322 was synthesized following general procedures B and C starting from compound 2 and phenylboronic acid) in pyridine (40 mL). The reaction mixture was stirred at room temperature for 24 h, concentrated under reduced pressure, diluted with DCM, washed with water, NaHCO₃ and brine. The residue was purified by flash chromatography (2-4% MeOH in DCM) to give the title compound 326 (1.74 g, 43%) as a brown solid.

LRMS calc. 572.3; found 573.1 (MH)+.

Step 5: (S)—N-(4-Aminobiphenyl-3-yl)-4-(3-aminopyrrolidin-1-yl)benzamide (327)

TFA (1 mL) was added to a solution of 326 (370 mg, 0.65 mmol) in DCM (1 mL). The reaction mixture was stirred at room temperature for 24 h, concentrated and the residue was partitioned between EtOAc and NaHCO₃. The aqueous layer was extracted with fresh EtOAc and the comb organic layers were washed with brine, dried over MgSO₄ and concentrated. The residue was purified using the Biotage system, (cartridge Biotage Si 25+M), eluent MeOH/DCM (10% to 40%) to afford the title compound 327 (161 mg, 67% yield).

¹H NMR (CD₃OD) δ (ppm): 7.90 (d, J=8.8 Hz, 2H), 7.56 (d, J=7.8 Hz, 2H), 7.46 (d, J=2.2 Hz, 1H), 7.37 (t, J=7.6 Hz, 2H), 7.35 (dd, J=10.4, 2.3 Hz, 1H), 7.24 (t, J=7.2 Hz, 1H), 6.97 (d, J=8.4 Hz, 1H), 6.65 (d, J=8.8 Hz, 2H), 3.76 (quint, J=5.3 Hz, 1H), 3.61 (dd, J=10.4, 6.3 Hz, 1H), 3.61-3.54 (m, 1H), 3.45-3.39 (m, 1H), 3.20 (dd, J=10.2, 4.5 Hz, 1H), 2.31 (sext, J=6.7 Hz, 1H), 1.94 (sext, J=7.3 Hz, 1H). LRMS calc. 372.5; found 373.2 (MH)+.

TABLE 18

Characterization of compounds prepared according to Scheme 37.

| Cpd | Ex | Structure | Name | Characterization |
|---|---|---|---|---|
| 328 | 37b | 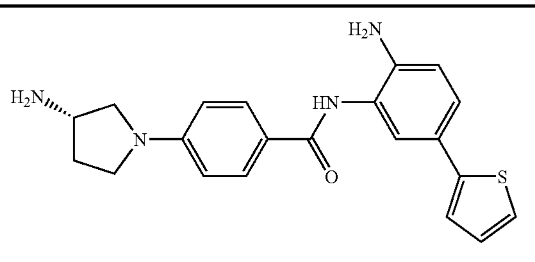 | (S)-N-(2-amino-5-(thiophen-2-yl)phenyl)-4-(3-aminopyrrolidin-1-yl)benzamide | ¹H NMR (DMSO-d6) δ (ppm): 9.42 (s, 1H), 7.88 (d, J = 8.8 Hz, 2H), 7.46 (d, J = 2.2 Hz, 1H), 7.36 (dd, J = 5.1, 1.0 Hz, 1H), 7.27 (dd, J = 8.4, 2.2 Hz, 1H), 7.25 (dd, J = 3.5, 1.0 Hz, 1H), 7.05 (dd, J = 5.1, 3.7 Hz, 1H), 6.81 (d, J = 8.4 Hz, 1H), 6.55 (d, J = 9.0 Hz, 2H), 5.08 (s, 2H), 3.64 (quint, J = 5.4 Hz, 1H), 3.49-3.42 (m, 2H), 3.3 (m, 1H, overlap with DMSO-d6), 3.00 (dd, J = 9.8, 4.5 Hz, 1H), 2.15-2.07 (m, 1H), 1.80-1.73 (m, 1H). LRMS: 378.2 (calc) 379.0(found). |
| 329 | 37c | 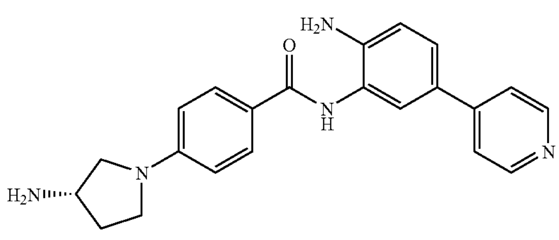 [SMILES: Nc1ccc(-c2ccncc2)cc1NC(=O)c1ccc(N2CC[C@H](N)C2)cc1] | (S)-N-(2-amino-5-(pyridin-4-yl)phenyl)-4-(3-aminopyrrolidin-1-yl)benzainide | ¹H NMR (CD₃OD) δ (ppm): 8.46 (d, J = 6.5 Hz, 2H), 7.89 (d, J = 9.0 Hz, 2H), 7.64 (d, J = 6.5 Hz, 2H), 7.63 (d, J = 2.3 Hz, 1H), 7.51 (dd, J = 8.4, 2.3 Hz, 1H), 6.98 (d, J = 8.4 Hz, 1H), 6.62 (d, J = 9.0 Hz, 2H), 3.68 (quint, J = 5.3 Hz, 1H), 3.58 (dd, J = 10.0, 6.3 Hz, 1H), 3.57-3.52 (m, 1H), 3.42-3.35 (m, 1H), 3.12 (dd, J = 9.8, 4.9 Hz, 1H), 2.25 (sext, J = 4.9 Hz, 1H), 1.89 (sext, J = 6.1 Hz, 1H). LRMS: (calc.) 373.45 (found) 374.3 (MH)+ |

TABLE 18-continued

Characterization of compounds prepared according to Scheme 37.

| Cpd | Ex | Structure | Name | Characterization |
|---|---|---|---|---|
| 330 | 37d | 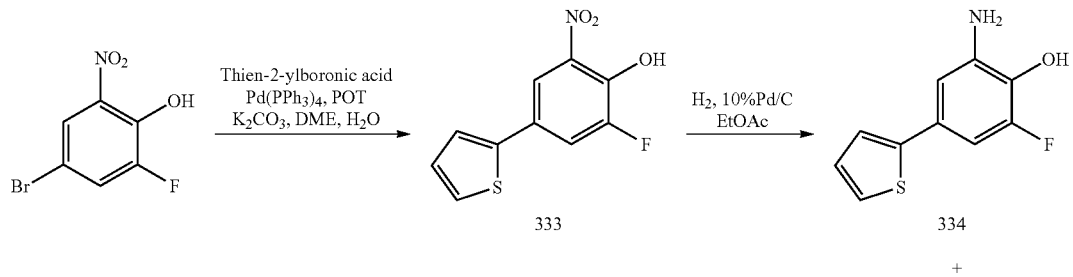 | (S)-N-(4-amino-4'-fluorobiphenyl-3-yl)-4-(3-aminopyrrolidin-1-yl)benzamide | $^1$H NMR (DMSO-$d_6$) δ (ppm): 9.42 (s, 1H), 7.87 (d, J = 8.8 Hz, 2H), 7.56 (dd, J = 9.0, 5.7 Hz, 2H), 7.47 (d, J = 2.2 Hz, 1H), 7.25 (dd, J = 8.2, 2.0 Hz, 1H), 7.20 (t, J = 8.8 Hz, 2H), 6.84 (d, J = 8.2 Hz, 1H), 6.54 (d, J = 8.8 Hz, 2H), 5.01 (d, J = 10.0 Hz, 1H), 3.64 (quint, J = 5.5 Hz, 1H), 3.47 (dd, J = 10.2, 6.3 Hz, 1H), 3.46-3.40 (m, 1H), 3.36-3.29 (m, 1H), 3.01 (dd, J = 10.0, 4.3 Hz, 1H), 2.10 (sext, J = 6.3 Hz, 1H), 1.78 (sext, J = 7.0 Hz, 1H) LRMS: (calc.) 390.45 (found) 391.2 (MH)+ |

Example 38a 2-(Dimethylamino)ethyl 4-(2-hydroxy-5-(thiophen-2-yl)pyridin-3-ylcarbamoyl)phenylcarbamate (336)

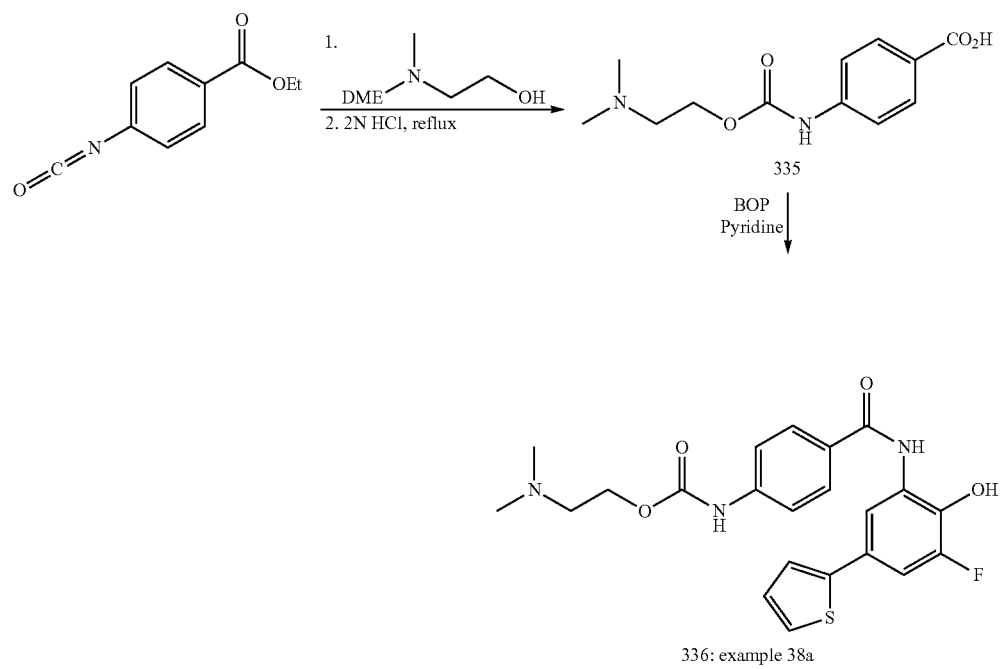

336: example 38a

233

Steps 1-2: 3-Amino-5-(thiophen-2-yl)pyridin-2-ol (334)

Following the same procedure as described in Example 1, steps 2 and 3 (scheme 1), but substituting compound 2 by 4-bromo-2-fluoro-6-nitrophenol, the title compound 334 was obtained as a beige solid (step 1: 53%, step 2: 43%). LRMS: (calc.) 209.0, (obt.) 210.3 (MH)+.

234

Steps 3-4: 2-(Dimethylamino)ethyl 4-(2-hydroxy-5-(thiophen-2-yl)pyridin-3-ylcarbamoyl)-phenylcarbamate (336)

Following the same procedure as described in Example 33a, steps 1 and 2 (scheme 33), but substituting pyridine-3-yl-methanol by 2-(dimethylamino)ethanol and compound 4 by compound 334, the title compound 336 was obtained as a white solid (step 4: 14 mg, 5% yield). $^1$H NMR. $^1$H NMR (DMSO-$d_6$) δ (ppm): 10.1 (s, 1H), 9.82 (s, 1H), 8.22 (s, 1H), 7.92 (b s, 1.0 Hz, 2H), 7.75 (bs, 1H), 7.62 (m, 2H), 7.49 (bs, 1H), 7.40 (m, 2H), 7.11 (s, 1H), 4.21 (m, 2H), 2.58 (m, 2H), 2.22 (s, 6H). LRMS: (calc.) 443.1, (obt.) 444.2 (MH)+.

TABLE 19

Characterization of compounds prepared according to Scheme 38

| Cpd | Ex | Structure | Name | Characterization |
|---|---|---|---|---|
| 337 | 38b | 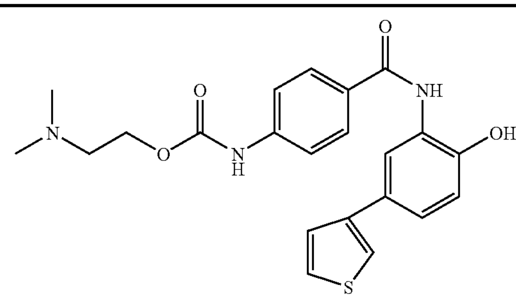 | 2-(dimethylamino) ethyl 4-(2-hydroxy-5-(thiophen-3-yl) phenylcarbamoyl) phenylcarbamate | $^1$H NMR(DMSO-$d_6$) δ (ppm): 10.11 (s, 1H), 9.58 (s, 1H), 7.98 (s, 1H), 7.92 (d, J = 8.7 Hz, 2H), 7.61 (m, 4H), 7.42 (d, J = 6.8 Hz, 1H), 7.38 (d, J = 8.4 Hz, 1H), 6.95 (d, J = 8.7 Hz, 1H), 4.20 (t, J = 5.3 Hz, 2H), 2.51 (t, J = 5.3 Hz, 2H), 2.19 (s, 6H). LRMS: 425.51 (calc) 426.1 (found) |

Example 39a

N-(2-Amino-5-(thiophen-2-yl)phenyl)-4-(4-(pyridin-4-ylmethyl)piperazin-1-yl)benzamide (341)

Scheme 39

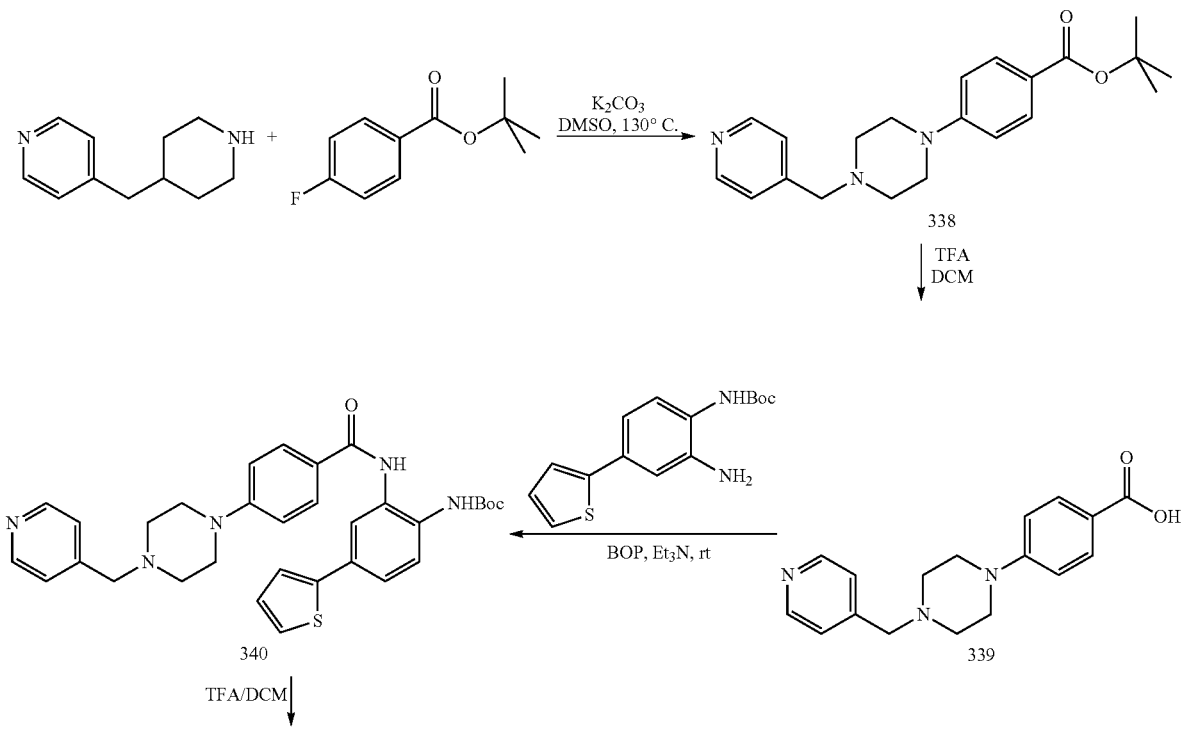

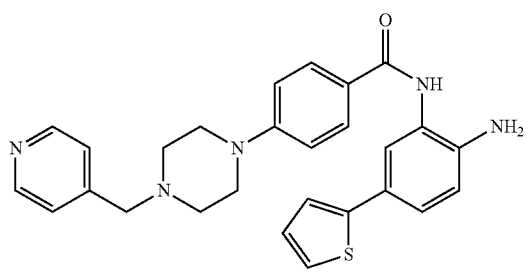

341: example 39a

Step 1: tert-Butyl 4-(4-(pyridin-4-ylmethyl)piperazin-1-yl)benzoate (338)

To a solution of 1-[(4-Pyridyl)methyl]piperazine (1.00 g, 5.6 mmol) in DMSO (4.5 mL) in a pressure vessel was added t-butyl-4-fluorobenzoate (1.05 g, 5.4 mmol) followed by potassium carbonate (0.74 g, 5.4 mmol). The pressure vessel was closed and the mixture was stirred at 130° C. for 21 h. The mixture was diluted with EtOAc (300 mL) and water (50 mL). The organic layer was separated, washed with a saturated NaHCO₃ solution, brine, dried over MgSO₄, and concentrated in vacuo. The residue obtained was purified by flash chromatography using 0-5% MeOH in DCM to afford the title compound 338 as a pink solid (1.34 g, 71% yield).

LRMS: (calc.) 353.2, (obt.) 354.3 (MH)⁺.

Steps 2-4: N-(2-Amino-5-(thiophen-2-yl)phenyl)-4-(4-(pyridin-4-ylmethyl)piperazin-1-yl)benzamide (341)

Following the same procedure as described in Example 2a, steps 3-5 (scheme 2), but substituting compound 39 by compound 338, the title compound 341 was obtained as a beige solid (0.105 g, 62%).

¹H NMR (DMSO-d₆) ☐(ppm): 9.50 (s, 1H), 8.53 (dd, J=4.4, 1.6 Hz, 2H), 7.89 (d, J=8.8 Hz, 2H), 7.46 (d, J=2.4 Hz, 1H), 7.37 (d, J=6.0 Hz, 2H), 7.35 (dd, J=5.2, 1.2 Hz, 1H), 7.28 (dd, J=8.2, 2.2 Hz, 1H), 7.24 (dd, J=3.6, 1.2 Hz, 1H), 7.05 (dd, J=5.2, 3.6 Hz, 1H), 7.01 (d, J=8.8 Hz, 2H), 6.80 (d, J=8.0 Hz, 1H), 5.10 (s, 2H), 3.58 (s, 2H), 3.32 (bt, J=5.2 Hz, 4H), 2.54 (bt, J=5.0 Hz, 4H). LRMS: (calc.) 469.2, (obt.) 470.2 (MH)⁺.

TABLE 20

Characterization of compounds prepared according to Scheme 39.

| Cpd | Ex | Structure | Name | Characterization |
|---|---|---|---|---|
| 342 | 39b | (structure) | N-(2-amino-5-(thiophen-2-yl)phenyl)-4-(4-(pyridin-3-ylmethyl)piperazin-1-yl)benzamide | ¹H NMR (DMSO-d₆) δ (ppm): 9.48 (s, 1H), 8.52 (d, J = 1.6 Hz, 1H), 8.47 (dd, J = 4.9, 1.8 Hz, 1H), 7.87 (d, J = 9.0 Hz, 2H), 7.74 (dt, J = 8.0, 1.8 Hz, 1H), 7.44 (d, J = 2.3 Hz, 1H), 7.37 (ddd, J = 7.6, 4.9, 0.8 Hz, 1H), 7.34 (dd, J = 5.1, 1.2 Hz, 1H), 7.26 (dd, J = 8.4, 2.2 Hz, 1H), 7.22 (dd, J = 3.5, 1.2 Hz, 1H), 7.03 (dd, J = 5.1, 3.5 Hz, 1H), 6.98 (d, J = 9.0 Hz, 2H), 6.79 (d, J = 8.4 Hz, 1H), 5.08 (s, 2H), 3.56 (s, 2H), 3.31-3.27 (m, 4H), 2.52-2.48 (m, 4H). LRMS: (calc.) 469.60 (found) 470.3 (MH)+ |

Example 40

N-(2-Amino-5-(pyridin-4-yl)phenyl)-3-fluoro-4-methoxybenzamide (392)

Scheme 40

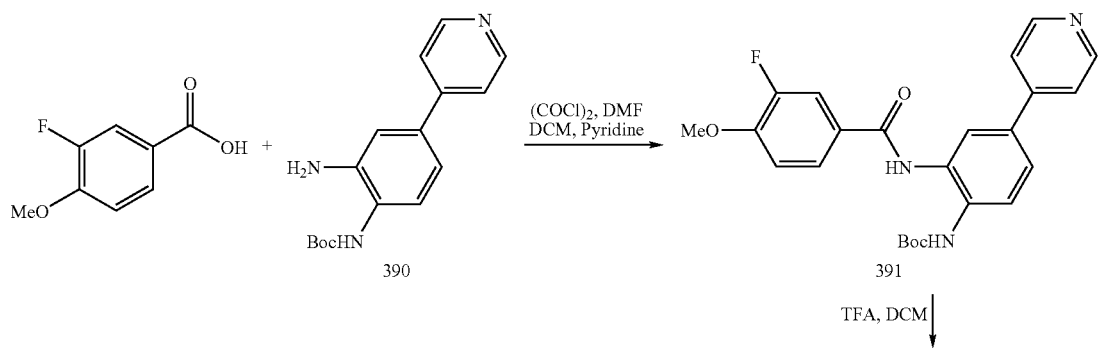

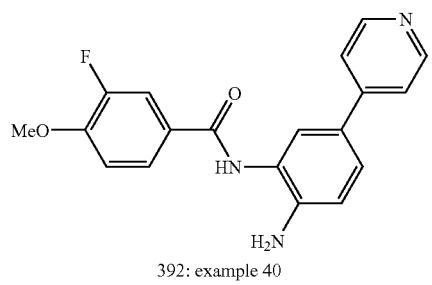

392: example 40

Step 1: tert-Butyl 2-(3-fluoro-4-methoxybenzamido)-4-(pyridin-4-yl)phenylcarbamate (391)

To a suspension of 3-fluoro-4-methoxybenzoic acid (125 mg, 0.736 mmol) in DCM (10 mL), oxalyl chloride (0.442 mL, 0.883 mmol) and DMF (2 drops) were added. The reaction was stirred at room temperature for 30 min and a solution was obtained. A solution of compound 390 (210 mg, 0.736 mmol) (390 was synthesized following general procedures B and C starting from compound 2 and pyridin-4-ylboronic acid) in pyridine (10 mL) was added and the reaction was stirred for an additional hour, quenched with water, dissolved in AcOEt and washed with water. The organic layer was separated and dried with $Na_2SO_4$, filtered and concentrated under vacuum. The residue was purified via Isco (12 g column, 40-100% EtOAc/hexanes solvent gradient) to give the title compound 391 as a light yellowed (60 mg, 18% yield).

$^1$H NMR (DMSO-$d_6$) ppm) 1H, 9.88 (s, 1H), 8.84 (s, 1H), 8.61 (dd, J=4.5, 1.6 Hz, 2H), 7.94-7.91 (m, 1H), 7.85-7.81 (m, 2H), 7.78-7.75 (m, 1H), 7.68-7.65 (m, 3H), 7.34 (t, J=8.6 Hz, 1H), 3.92 (s, 3H), 1.45 (s, 9H).

Step 2. N-(2-Amino-5-(pyridin-4-yl)phenyl)-3-fluoro-4-methoxybenzamide (392)

Following the general procedure G, the title compound was obtained as a yellow solid (25 mg, 27% yield).

$^1$H NMR (MeOD-$d_4$) δ (ppm) 1H, 8.45 (d, J=4.7 Hz, 2H), 7.85-7.76 (m, 2H), 7.65-7.63 (m, 3H), 7.53 (dd, J=8.5, 2.3 Hz, 1H), 7.20 (t, J=8.6 Hz, 1H), 6.97 (d, J=8.6 Hz, 1H), 3.95 (s, 3H). LRMS: (calc.) 337.1 (found) 338.2 (MH)+.

Example 41a

N-(2-amino-5-(pyridin-4-yl)phenyl)-6-(2-(piperidin-1-yl)ethoxy)benzofuran-2-carboxamide (398)

Scheme 41
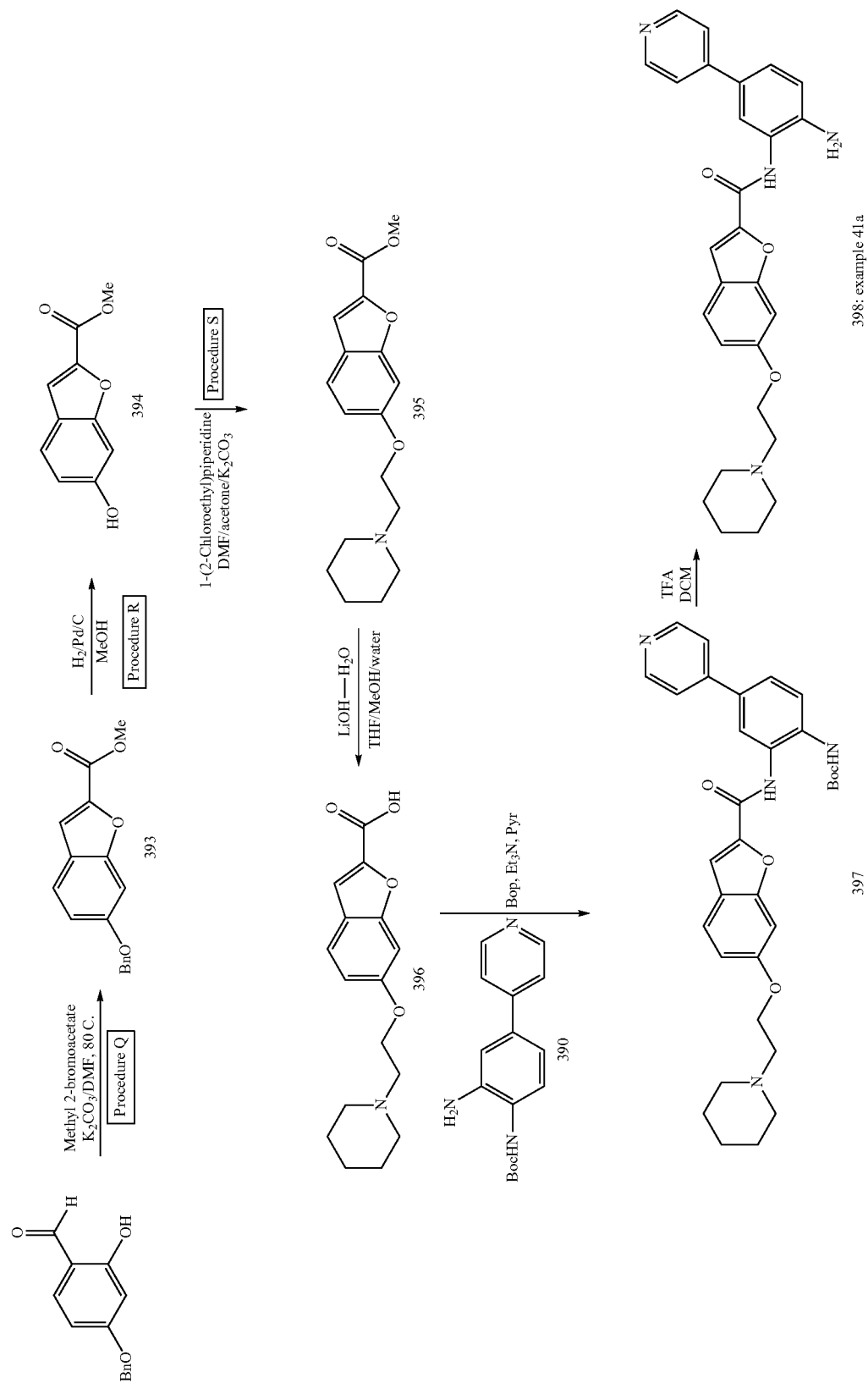
398: example 41a

Step 1. Methyl 6-(benzyloxy)benzofuran-2-carboxylate (393)

To a stirred solution of 4-(benzyloxy)-2-hydroxybenzaldehyde (10 g, 43.9 mmol) in DMF (60 mL), was added methyl bromoacetate (48.3 mmol, 4.57 mL), and potassium carbonate (24.2 g, 175.6 mmol). The solution was heated to 80° C. and stirred for 16 h. The reaction was quenched with water (100 mL) and aqueous extraction was performed with AcOEt (2×50 mL). The organic phase was dried with sodium sulfate and concentrated. Purification was achieved via silica gel chromatography employing 0-30% AcOEt in hexane gradient. This afforded 393 as a light yellow solid (4.5 g, 37%).

$^1$H NMR (DMSO-d$_6$) δ (ppm): 7.68-7.64 (m, 2H), 7.49-7.45 (m, 2H), 7.42-7.31 (m, 4H), 7.07-7.04 (m, 1H), 5.18 (s, 2H), 3.85 (s, 2H).

Step 2. Methyl 6-hydroxybenzofuran-2-carboxylate (394)

To a stirred solution of 393 (1.2 g, 4.26 mmol) in MeOH (20 mL) was added palladium on charcoal (250 mg). The flask was purged with hydrogen gas for 1 minute and then the reaction was stirred under a hydrogen atmosphere for 15 hours. The palladium was filtered off through Celite and the filtrate was evaporated via rotary evaporation, and the resulting solid dried under vacuum to afford 394 as a white solid (700 mg, 86%).

$^1$H NMR (DMSO-d$_6$) δ (ppm): 10.07 (s, 1H), 7.63 (s, 1H), 7.56 (d, J=8.0 Hz, 1H), 6.98 (s, 1H), 6.84 (d, J=9.0 Hz, 1H), 3.84 (s, 3H).

Step 3. Methyl 6-(2-(piperidin-1-yl)ethoxy)benzofuran-2-carboxylate (395)

A solution of 394 (350 mg, 1.82 mmol), 1-(2-Chloroethyl)piperidine (269 mg, 1.82 mmol) and K$_2$CO$_3$ (503 mg, 3.64 mmol) in DMF (10 mL) and acetone (10 mL) was stirred at 60° C. for 3 h and then at room temperature for 3 days (or until completion). The crude product was dissolved in AcOEt and washed with water. The organic layer was separated and dried with Na$_2$SO$_4$, filtered and concentrated under vacuum. The residue was purified via Isco (0-25% MeOH/EtOAc) to afford the title compound 395 as a white solid (330 mg, 60% yield).

$^1$H NMR (DMSO-d$_6$) δ (ppm): 7.68-7.62 (m, 2H), 7.31 (d, J=1.8 Hz, 1H), 6.97 (dd, J=8.8, 2.3 Hz, 1H), 4.12 (t, J=5.9 Hz, 2H), 3.85 (s, 3H), 2.66 (t, J=5.9 Hz, 2H), 2.47-2.40 (m, 4H), 1.48 (quintet, J=5.5 Hz, 4H), 1.39-1.35 (m, 2H).

Steps 4-6. N-(2-Amino-5-(pyridin-4-yl)phenyl)-6-(2-(piperidin-1-yl)ethoxy)benzofuran-2-carboxamide (398)

Following the general procedures P, G and F, the title compound was obtained as a yellow solid (60 mg, 25% yield, last step).

$^1$H NMR (MeOD-d$_4$) δ (ppm): 8.44 (d, J=6.5 Hz, 2H), 7.71 (d, J=2.2 Hz, 1H), 7.62-7.50 (m, 5H), 7.18 (d, J=1.8 Hz, 1H), 6.97 (d, J=8.6 Hz, 2H), 4.17 (t, J=5.7 Hz, 2H), 2.80 (t, J=5.5 Hz, 2H), 2.60-2.50 (m, 4H), 1.63 (quintet, J=5.7 Hz, 4H), 1.50-1.47 (m, 2H). LRMS: (calc.) 456.2 (found) 457.2 (MH)+.

Example 42a (R)—N-(4-Amino-4'-fluorobiphenyl-3-yl)-4-(3-(methylsulfonamido)pyrrolidin-1-yl)benzamide (406)

Example 42b (R)-4-(3-Acetamidopyrrolidin-1-yl)-N-(4-amino-4'-fluorobiphenyl-3-yl)benzamide (408)

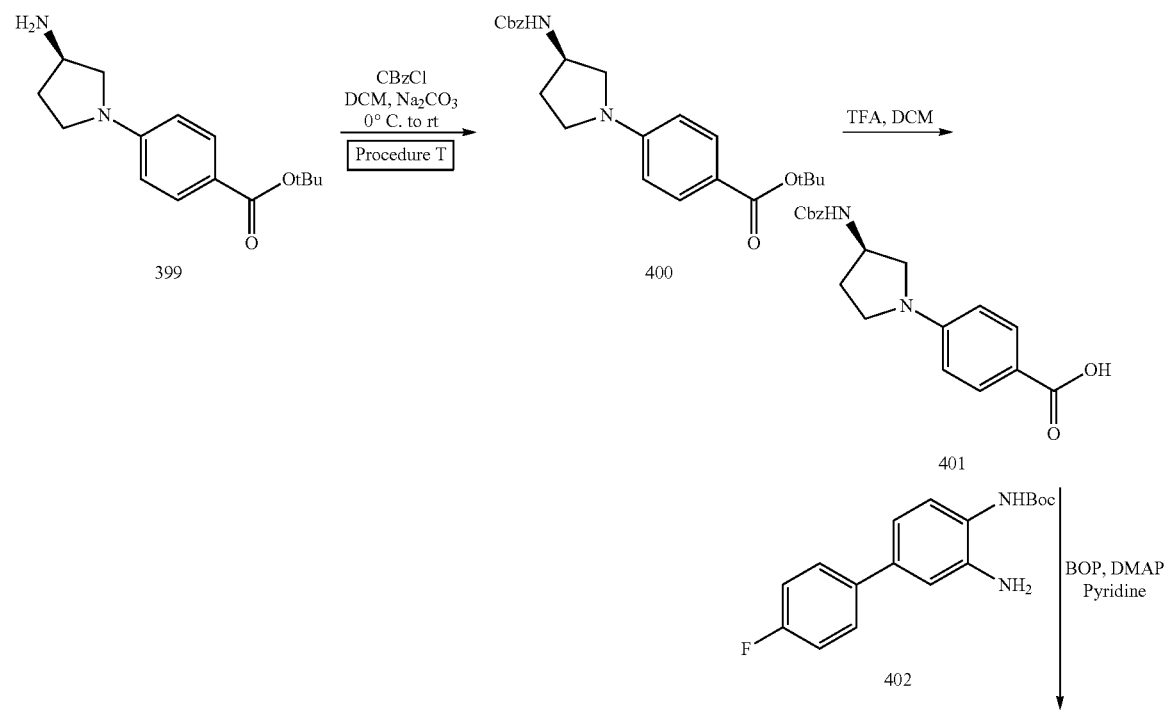

Scheme 42

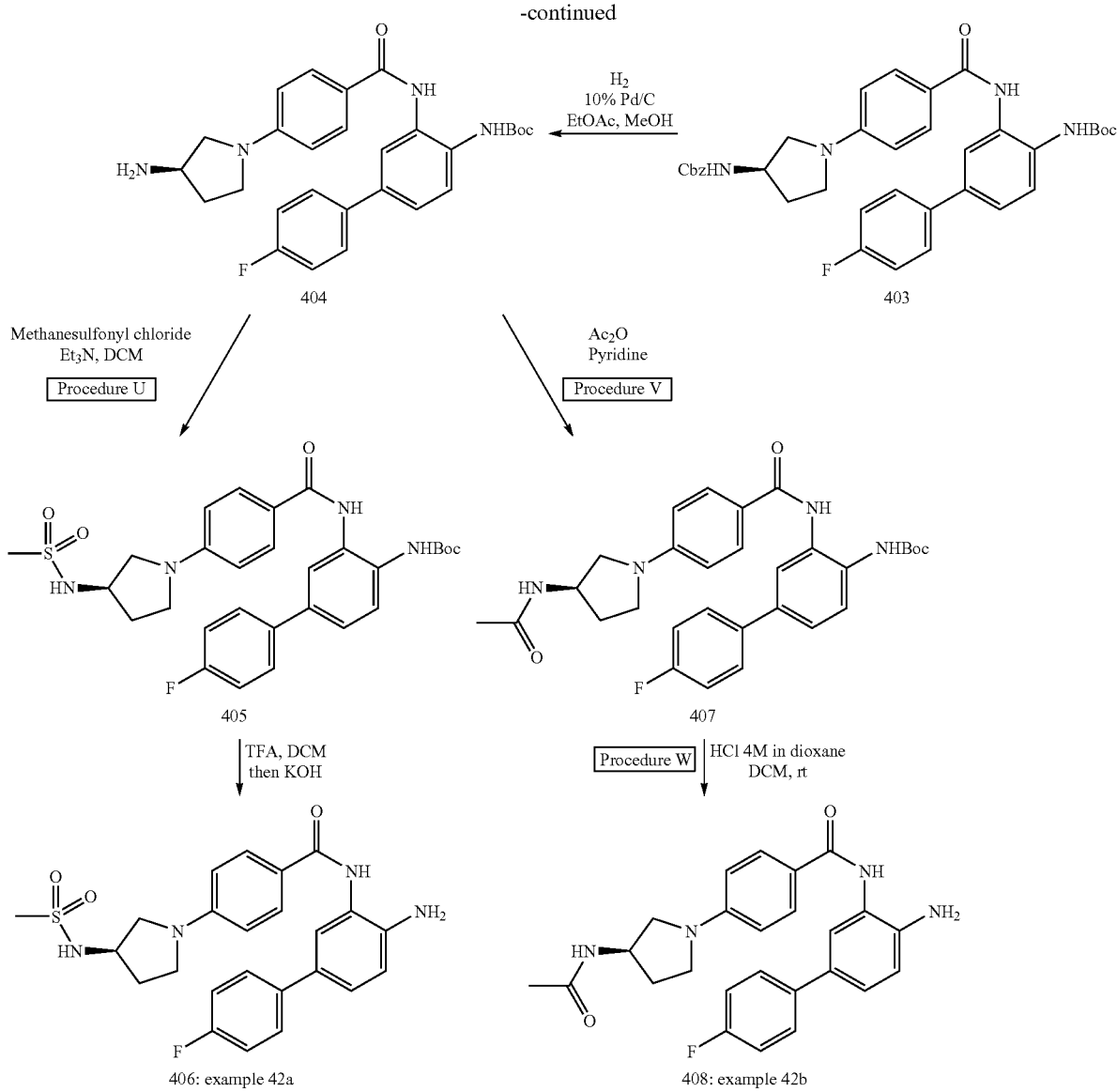

Step 1: (R)-tert-Butyl 4-(3-(benzyloxycarbonylamino)pyrrolidin-1-yl)benzoate (400)

Na$_2$CO$_3$ (7.81 g, 73.7 mmol) then CbzCl (6.88 mL, 48.2 mmol) was added to a solution of 399 (10.28 g, 39.2 mmol) (399 was synthesized following the procedure J starting from (R)-pyrrolidin-3-amine and tert-butyl 4-fluorobenzoate) in DCM (196 mL) at 0° C. The reaction mixture was slowly warmed to room temperature and stirred for 16 h. It was then quenched with saturated NH$_4$Cl, stirred for 30 min, diluted with DCM, washed with brine then H$_2$O, dried with MgSO$_4$, filtered and concentrated to afford the title compound 400 (16.4 g, quant.) as a beige solid.

LRMS calc. 396.2; found 397.2 (MH)$^+$.

Steps 2-4: (R)-tert-Butyl 3-(4-(3-aminopyrrolidin-1-yl)benzamido)-4'-fluorobiphenyl-4-ylcarbamate (404)

Compound 402 was synthesized following general procedures B and C starting from compound 2 and 4-fluorophenylboronic acid. Then following the general procedures I, F, and R, the title compound was obtained (2.0 g, 47% yield, last step).

LRMS calc. 490.2; found 491.3 (MH)$^+$.

Step 5a: (R)-tert-butyl 4'-fluoro-3-(4-(3-(methylsulfonamido)pyrrolidin-1-yl)benzamido)-biphenyl-4-ylcarbamate (405)

A solution of compound 404 (420 mg, 0.856 mmol) in DCM (2 mL) was cooled down to 0° C. and treated with neat methanesulfonyl chloride (148 mg, 1.29 mmol). The mixture was allowed to warm up to room temperature for 18 h. Cooled down to 0° C., treated with sat. NaHCO$_3$ (1 mL), stirred for 1.5 h, diluted with DCM, washed with sat NaHCO$_3$, dried over MgSO$_4$ and concentrated under vacuum to afford the title compound 405 as a brown solid (430 mg, 88%) which was used without further purification LRMS calc. 568.2; found 569.3 (MH)$^+$.

Step 6a: (R)—N-(4-Amino-4'-fluorobiphenyl-3-yl)-4-(3-(methylsulfonamido)pyrrolidin-1-yl)benzamide (406)

Starting from compound 405, the general procedure G was followed to give the title compound 406 as a beige powder (137 mg, 36% yield).

$^1$H NMR: (DMSO-$d_6$) δ (ppm): 9.44 (s, 1H), 7.89 (d, 2H), 7.59-7.56 (m, 2H), 7.48-7.47 (m, 2H), 7.27 (dd, 1H), 7.21 (m, 2H), 6.85 (d, 1H), 6.59 (d, 2H), 5.03 (s, 2H), 4.10-4.40 (m, 1H), 3.65-3.61 (m, 1H), 3.48-3.42 (m, 1H), 3.32-3.29 (m, 1H), 3.22-3.18 (m, 1H), 3.00 (s, 3H), 2.32-2.24 (m, 1H), 2.02-2.19 (m, 1H). LRMS (ESI): (calc.) 468.2 (found) 469.1 (MH)+

Step 5b: (R)-tert-Butyl 3-(4-(3-acetamidopyrrolidin-1-yl)benzamido)-4'-fluorobiphenyl-4-ylcarbamate (407)

To a solution of 404 (0.295 g, 0.601 mmol) in pyridine (3.0 mL) under nitrogen was added acetic anhydride (1.59 mL, 16.84 mmol), and the mixture was stirred for 19 h at room temperature. The solvent was evaporated and the residue obtained was evaporated twice with toluene and triturated with a mixture of Et$_2$O and hexanes. The solid was filtered, air-dried and then dried under vacuum to afford the title compound 407 as a light pink solid (280 mg, 85%).

LRMS calc. 532.3; found 533.3 (MH)+.

Step 6b: (R)-4-(3-Acetamidopyrrolidin-1-yl)-N-(4-amino-4'-fluorobiphenyl-3-yl)benzamide (408)

To a suspension of 407 (0.280 g, 0.526 mmol) in DCM (5 mL) and dioxane (5.0 mL) was added HCl in dioxane (2.4 mL, 9.46 mmol). The mixture was stirred for 3 h at room temperature. The solvent was evaporated and the residue obtained was triturated in Et$_2$O, filtered and dried under vacuum. The light pink solid obtained was suspended in EtOAc, washed with sat NaHCO$_3$, brine, dried over MgSO$_4$, filtered and evaporated to afford a beige solid that was triturated overnight with Et$_2$O. The solid was then filtered and dried under vacuum to give the title compound 408 (167 mg, 69% yield).

$^1$H NMR (DMSO-$d_6$) δ (ppm): 9.42 (s, 1H), 8.18 (d, J=6.8 Hz, 1H), 7.87 (d, J=8.8 Hz, 2H), 7.56 (dd, J=9.0, 5.4 Hz, 2H), 7.47 (d, J=2.0H, 1H), 7.25 (dd, J=8.4, 2.4 Hz, 1H), 7.20 (t, J=8.8 Hz, 2H), 6.84 (d, J=8.4 Hz, 1H), 6.57 (d, J=8.8 Hz, 2H), 5.02 (s, 2H), 4.37 (sext, J=5.8 Hz, 1H), 3.54 (dd, J=10.4, 6.4 Hz, 1H), 3.43 (m, 1H), 3.36 (m, 1H), 3.12 (dd, J=10.4, 4.4 Hz, 1H), 2.17 (sext, J=6.8 Hz, 1H), 1.89 (sext, J=6.2 Hz, 1H), 1.80 (s, 3H). LRMS: calc. 432.20, found: 433.2 (MH)$^+$.

Example 43a (S)—N-(4-Amino-4'-fluorobiphenyl-3-yl)-4-(3-(bis(dimethylamino)methyleneamino)pyrrolidin-1-yl)benzamide (412)

Scheme 43

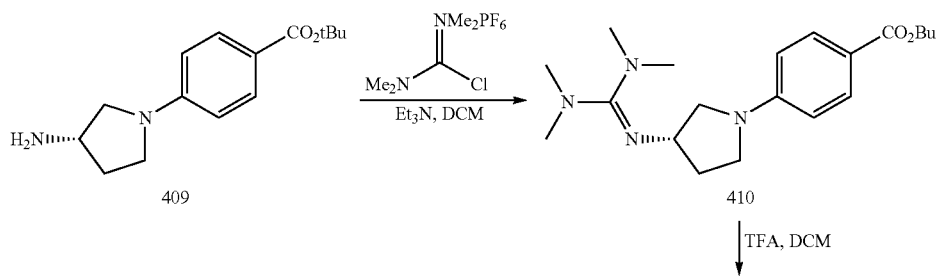

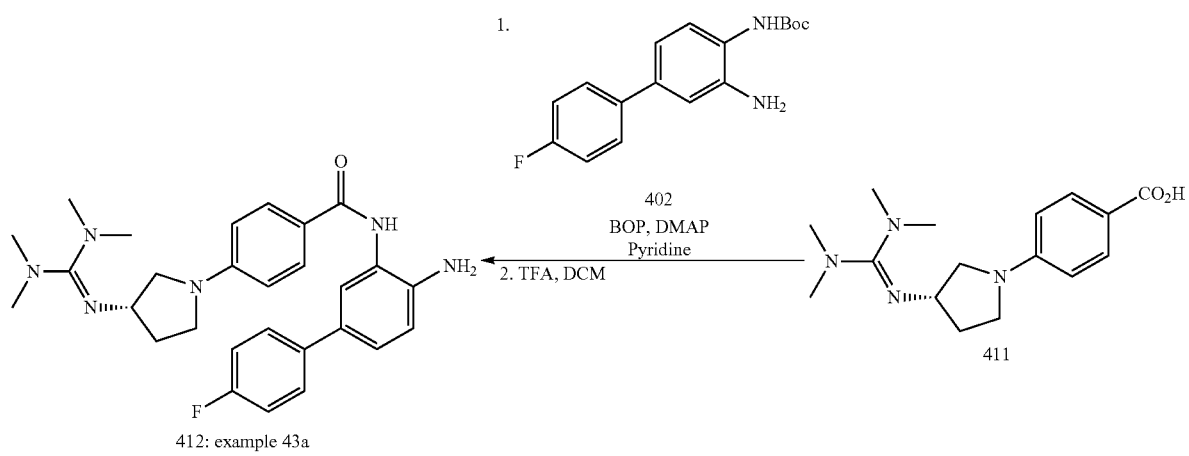

412: example 43a

247

Step 1. (S)-tert-Butyl 4-(3-(bis(dimethylamino)methyleneamino)pyrrolidin-1-yl)benzoate (410)

A solution of chloro N,N,N',N'-tetramethylformamidinium hexafluorophosphate (1.37 g, 4.9 mmol, 1.3 eq.), compound 409 (1.01 g, 3.9 mmol) and TEA (1.3 mL, 10 mmol) in dry DCM (10 mL), was stirred at room temperature for 1.5 h; diluted (DCM), washed with saturated NaHCO$_3$, dried (MgSO$_4$), filtered and concentrated to furnish title compound 410 (1.31 g, 3.6 mmol, 94% yield) as a dark foam, 91-95% pure by HPLC. Used without additional purification. Compound 409 was obtained using general procedure J starting from tert-butyl 4-fluorobenzoate compound with (S)-pyrrolidin-3-amine).

LRMS: (calc.) 360.3 Found: 361.3 (MH)$^+$.

248

Steps 2-4 (S)—N-(4-Amino-4'-fluorobiphenyl-3-yl)-4-(3-(bis(dimethylamino)methylene-amino)pyrrolidin-1-yl)benzamide (412)

Following the general procedures I, F and G, the title compound 412 was obtained as an amorphous solid, formic acid salt after purification by semipreparative HPLC (3.0 mg, 6.1 umol, 8% yield, last step).

$^1$H NMR: (DMSO-d$_6$) δ (ppm): 9.48 (s, 1H), 8.52 (bs, formic acid), 7.90 (d, 2H), 7.59-7.55 (m, 2H), 7.47 (d, 1H), 7.28 (dd, 1H), 7.21 (dt, 2H), 6.85 (d, 1H), 6.63 (d, 2H), 5.04 (s, 2H), 4.23 (m, 1H), 3.69 (m, 1H), 3.51 (m, 2H), 2.93 (bs, 12H), 2.08 (m, 2H), 1.80 (bs, 1H). LRMS: (calc.) 488.4 (found) 489.4 (MH)+

Example 44a (R)—N-(4-Aminobiphenyl-3-yl)-4-(3-methoxypyrrolidin-1-yl)benzamide (416)

Scheme 44

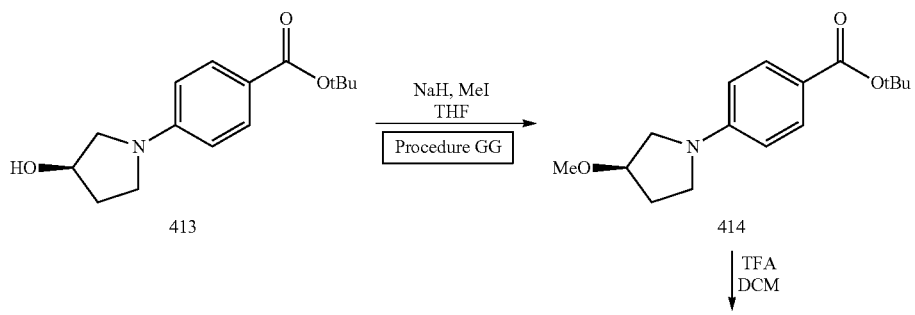

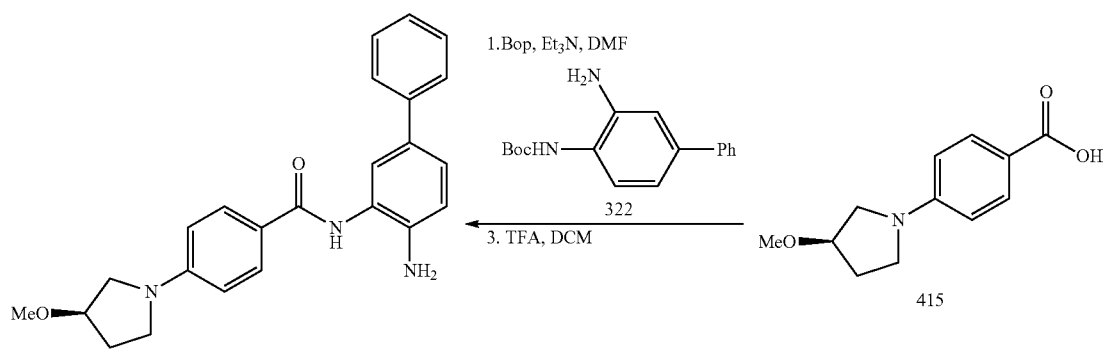

416: example 44

Step 1. (R)-tert-Butyl 4-(3-methoxypyrrolidin-1-yl) benzoate (413)

Starting from tert-butyl 4-fluorobenzoate compound and (R)-pyrrolidin-3-ol, the general procedure J was followed to afford the compound 413. Then, NaH (0.395 g, 9.87 mmol) was added to a solution of compound 413 (2.0 g, 7.59 mmol) in THF (38 ml) at 0° C. The mixture was stirred at 0° C. for 5 min, iodomethane (0.617 ml, 9.87 mmol) was added at 0° C. and stirred at room temperature for 18 h. The mixture was quenched with brine followed by an extraction with EtOAc (3×). The organic layer was dried over Na$_2$SO$_4$ and concentrated to afford the crude product 413 as a yellow solid (1.47 g, quantitative yield) which was used in the next step without further purification.

LRMS: (calc.) 277.2 (found) 278.3 (MH)+

Steps 2-4. (R)—N-(4-Aminobiphenyl-3-yl)-4-(3-methoxypyrrolidin-1-yl)benzamide (416)

Starting from 414, the general procedures I, F (with 322) and G were followed to afford the title compound 416 as a white solid (140 mg, 20%, last step), $^1$H NMR (MeOD-d$_4$) δ (ppm): 7.90 (d, J=9.0 Hz, 2H), 7.56 (dd, J=7.2, 1.2 Hz, 2H), 7.47 (d, J=2.2 Hz, 1H), 7.37 (t, J=7.4 Hz, 2H), 7.36 (dd, J=8.0, 2.4 Hz, 1H), 7.24 (t, J=7.4 Hz, 1H), 6.97 (d, J=8.2 Hz, 1H), 6.64 (d, J=9.0 Hz, 2H), 4.14-4.0 (m, 1H), 3.54 (dd, J=11.0, 4.7 Hz, 1H), 3.48-3.40 (m, 3H), 3.38 (s, 3H), 2.28-2.10 (m, 2H). LRMS: (calc.) 387.2 (found) 388.3 (MH)$^+$.

Example 45a

N-(2-amino-5-(thiophen-2-yl)phenyl)-1-(benzo[d][1,3]dioxol-5-ylmethyl)-1H-1,2,3-triazole-4-carboxamide (422)

Scheme 45

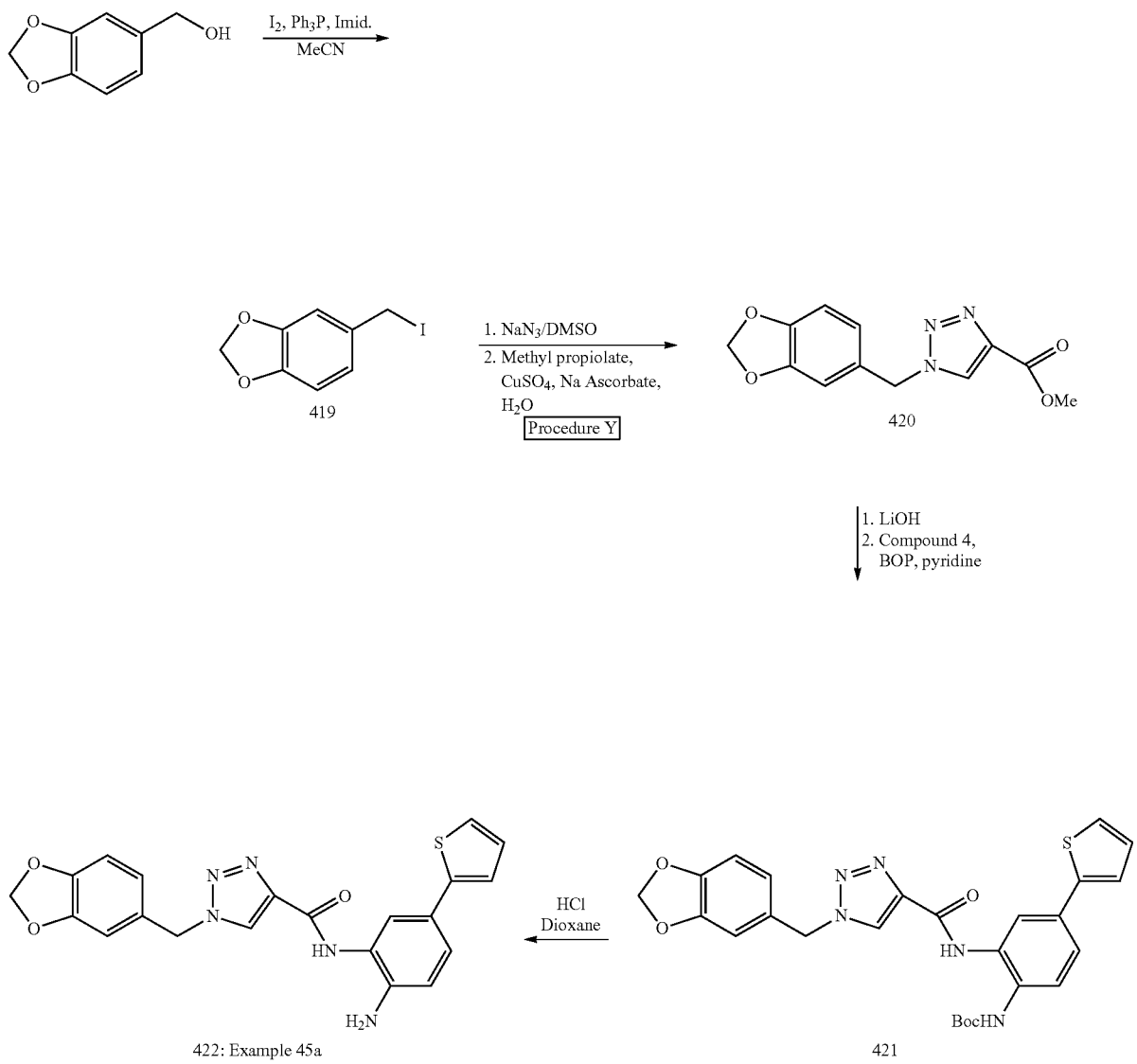

Step 1. 5-(Iodomethyl)benzo[d][1,3]dioxole (419)

Benzo[d][1,3]dioxol-5-ylMeOH (1.0 g, 6.57 mmol) was added in a single portion to a solution of the iodine (2.00 g, 7.89 mmol), imidazole (537 mg, 7.89 mmol) and PPh₃ (2.07 g, 7.89 mmol) in MeCN (10 mL) at 0° C. The reaction was stirred for 1 h and quenched by pouring into a saturated solution of sodium thiosulfate. The product was extracted with AcOEt, washed with brine, dried with MgSO₄ and filtered. Solvent was removed under vacuum and the yellow solid residue was suspended in 25% AcOEt in hexanes and filtered through a silica plug. The filtrate was concentrated to afford the title compound 419 (1.70 g, 99% yield) and was used without further purification.

LRMS: (calc.) 262.0 (found) 134.9 (M-I)+.

Step 2. Methyl 1-(benzo[d][1,3]dioxol-5-ylmethyl)-1H-1,2,3-triazole-4-carboxylate (420)

Compound 419 (1.72 g, 6.57 mmo) was dissolved in a 0.5 M solution of sodium azide 13.1 mL, 6.57 mmol) in DMSO (2 mL), stirred at room temperature overnight and quenched by pouring into a saturated solution of sodium thiosulfate. The compound was extracted with AcOEt, washed with brine, dried over MgSO₄ and filtered to give a yellow solution. Water (2.5 mL) was then added followed by solid sodium ascorbate (130 mg, 0.657 mmol), methyl propionate (553 mg, 0.657 mmol) and 1M aq. CuSO₄ solution (0.2 mL) to give a yellow solution. The reaction mixture was stirred overnight at room temperature to give a mustard-colored suspension. Water was added until a suspension formed, filtered, washed with water, and dried to generate the title compound 420 (1.05 g, 63% yield) as a mustard-colored solid.

LRMS: (calc.) 262.1 (found) 262.2 (MH)+

Steps 3-5 N-(2-Amino-5-(thiophen-2-yl)phenyl)-1-(benzo[d][1,3]dioxol-5-ylmethyl)-1H-1,2,3-triazole-4-carboxamide (422)

Following the general procedures P, F and W, the title compound 422 was obtained as a gray powder (32 mg, 16% yield, last step).

¹H NMR (DMSO-d₆) δ (ppm): 10.3 (s, 1H), 8.84 (s, 1H), 7.7 (s, 1H), 7.54 (m, 2H), 7.44 (m, 1H), 7.27 (d, J=8.4 Hz, 1H), 7.11 (dd, J=3.6, 5.2 Hz, 1H), 7.00 (s, 1H), 6.91 (s, 2H), 6.01 (s, 2H), 5.59 (s, 2H). LRMS: (calc.) 419.1 (found) 420.2 (MH)+

Example 46a

2-(Dimethylamino)ethyl (trans)-4-(2-amino-5-(thiophen-2-yl)phenylcarbamoyl)cyclohexylcarbamate (426)

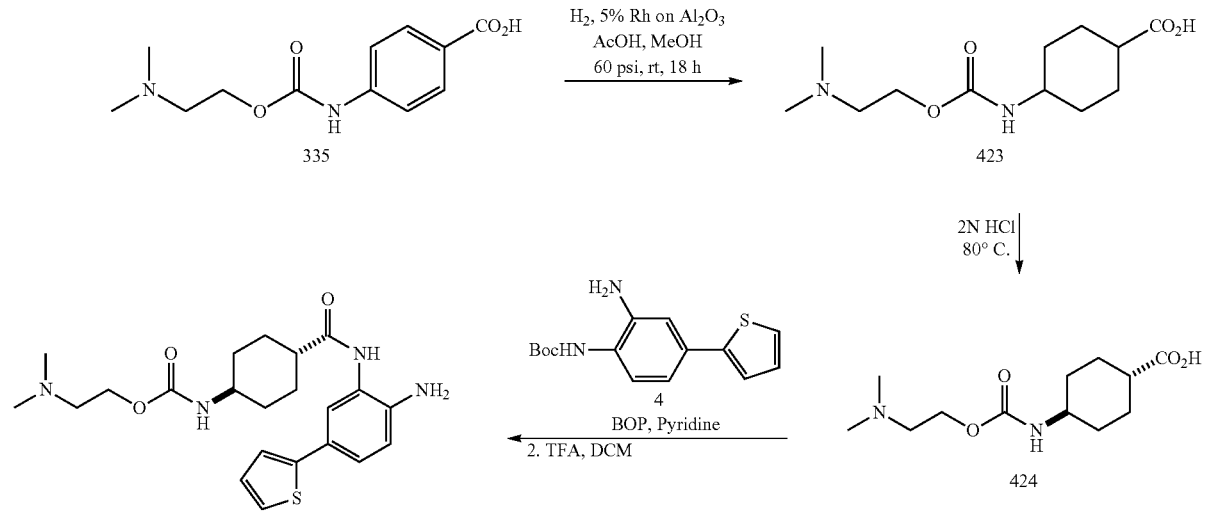

Scheme 46

426: example 46a

Steps 1-2. Trans-4-((2-(Dimethylamino)ethoxy)carbonylamino)cyclohexanecarboxylic acid (424)

A suspension of compound 335 (1.0 g, 3.96 mmol) and 5% Rh on Al₂O₃ (350 mg) in AcOH (5 mL) and MeOH (5 mL) was stirred at room temperature under 60 psi of hydrogen. The reaction mixture was filtered on celite and the filtrate was evaporated to afford the title compound 423 which was dissolved in 2N HCl (920 mL) and stirred at 80° C. for 18 h. The reaction mixture was concentrated, diluted in water, cooled down to −78° C. and lyophilysed during 5 days to afford the title compound 424 as a white solid (820 mg, 82%).

LRMS: (calc.) 258.2 (found) 259.2 (MH)+.

Steps 3-4. 2-(dimethylamino)ethyl (trans)-4-(2-amino-5-(thiophen-2-yl)phenylcarbamoyl)-cyclohexylcarbamate (426)

Following the general procedures F and G, the title compound 426 was obtained as an orange solid (460 mg, 81%, last step).

¹H NMR (DMSO-d₆) δ (ppm): 9.18 (s, 1H), 7.46 (d, J=4.5 Hz, 1H), 7.32 (dd, J=8.1, 2.1 Hz, 1H), 7.18 (m, 2H), 7.05 (m, 1H), 6.74 (d, J=8.2, 1H), 5.05 (s, 2H), 4.01 (t, J=5.1 Hz, 2H), 3.52 (s, 1H), 2.48 (m, 2H), 2.18 (s, 6H), 1.85 (m, 2H), 1.71 (m, 2H), 1.52 (m, 4H). LRMS: (calc.) 430.7 (found) 431.3 (MH)⁺.

Example 47a

N-(2-amino-5-(thiophen-2-yl)phenyl)-4-(4-(pyridin-3-yl)thiazol-2-ylamino)benzamide (430)

LRMS: (calc.) 325.0 (found) 326.0 (MH)⁺.

Steps 2-4. N-(2-Amino-5-(thiophen-2-yl)phenyl)-4-(4-(pyridin-3-yl)thiazol-2-ylamino)-benzamide (430)

Starting from 428, the general procedures P, F and G were followed to afford the title compound 430 as a yellow solid (30 mg, 24%, last step, isolated as a TFA salt).

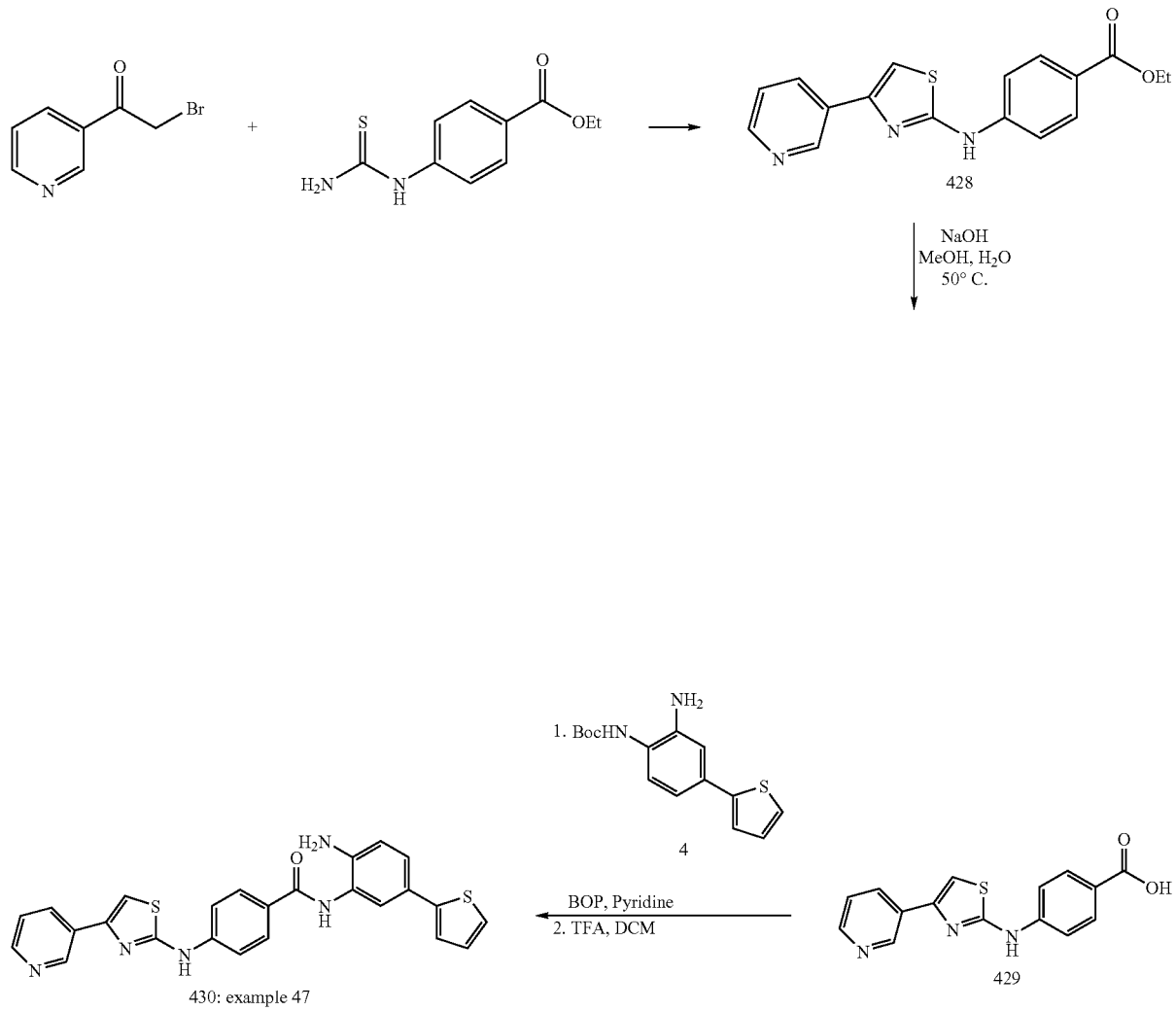

Scheme 47

Step 1. Ethyl 4-(4-(pyridin-3-yl)thiazol-2-ylamino)benzoate (428)

Ethyl 4-thioureidobenzoate (209 mg, 0.935 mmol) was added to a warm solution (50° C.) of 2-bromo-1-(pyridin-3-yl)ethanone (250 mg, 0.88 mmol) in water (5 mL) and stirred at 50° C. for 5 h. The precipitated was filtered out to afford the title compound 428 as a yellow solid (476 mg, wet) which was used without further purification.

$^1$H NMR (DMSO-$d_6$) δ (ppm): 10.77 (s, 1H), 9.77 (s, 1H), 9.23 (s, 1H), 8.63 (d, J=4.5 Hz, 1H), 8.53 (d, J=7.4 Hz, 1H), 8.03 (d, J=8.8 Hz, 2H), 7.85 (d, J=8.8 Hz, 2H), 7.74 (s, 1H), 7.71-7.66 (m, 1H), 7.52 (d, J=2.2 Hz, 1H), 7.39 (dd, J=5.1, 1.0 Hz, 1H), 7.35 (dd, J=8.4, 2.0 Hz, 1H), 7.29 (dd, J=5.1, 1.0 Hz, 1H), 7.06 (dd, J=5.1, 3.5 Hz, 1H), 6.91 (d, J=8.2 Hz, 1H). LRMS: 469.58 (calc) 470.0 (found).

Example 48a

(S)—N-(2-amino-5-(thiophen-2-yl)phenyl)-4-(3-(pyridin-3-ylamino)pyrrolidin-1-yl)benzamide (436)

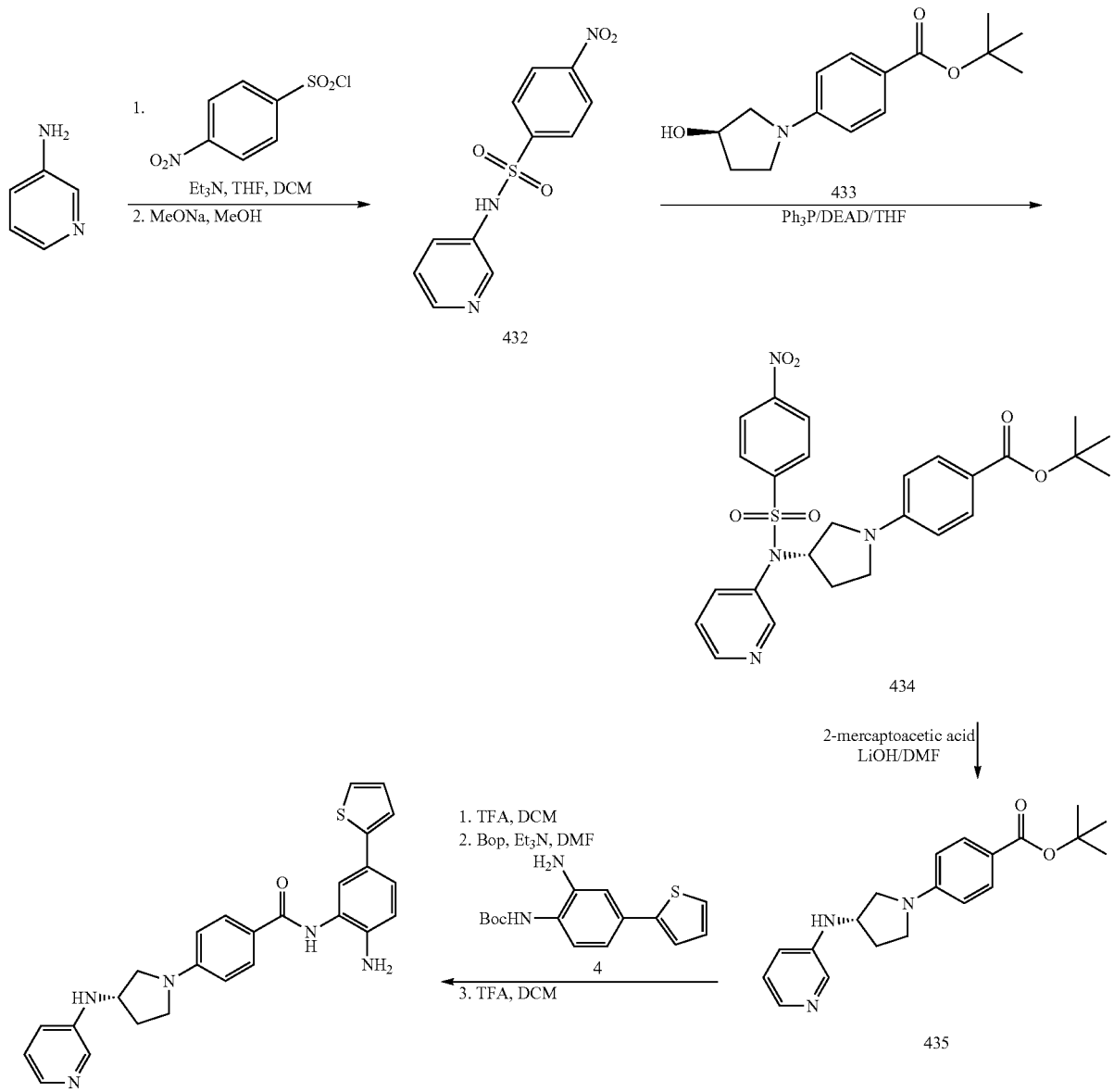

Scheme 48

436: Example 48

Step 1: N-p-Nosyl-3-pyridine (432)

To a stirred solution of 2-aminopyridine (3.03 g, 32.2 mmol) in THF (15 mL) were successively added DCM (30 mL), 4-nitrobenzenesulfonyl chloride (1.50 g, 68.7 mmol), and Et₃N (9.88 mL, 70.9 mmol). The solution turned orange and a precipitate formed. The suspension was allowed to stir at room temperature for 1 h, solvents were evaporated under reduced pressure and the solid residue was suspended in MeOH (200 mL). To the suspension a large excess (>10 eq) of sodium methoxide was added, the mixture was stirred at 50° C. for 3 h, quenched with HCl 1N (2 mL) and concentrated under reduced pressure at 80° C. until the volume became ~50 mL. The concentrated solution was further acidified with 1N HCl until neutral pH. The precipitate formed was filtered to afford the title compound (7.67 g, 85% yield).

$^1$H NMR (DMSO-d$_6$) δ (ppm): 10.88 (s, 1H), 8.36 (d, J=9.0 Hz, 2H), 8.28 (dd, J=6.1, 1.4 Hz, 1H), 8.27 (d, J=2.5 Hz, 1H), 7.50 (ddd, J=8.4, 2.7, 1.6 Hz, 1H), 7.30 (ddd, J=8.2, 4.7, 0.8 Hz, 1H). LRMS: calc. 279.0, found. 280.1 (MH$^+$).

Step 2: tert-Butyl 4-((S)-3-N-p-nosyl (pyridin-3-ylamino)pyrrolidin-1-yl)benzoate (434)

To a solution of compound 432 (6.00 g, 21.5 mmol) in THF (100 mL), were successively added carbinol 433 (5.66 g, 21.5 mmol) (Compound 433 was obtained using procedure J starting from tert-butyl 4-fluorobenzoate compound with (R)-pyrrolidin-3-ol), triphenylphosphine (6.76 g, 25.8 mmol) and diethyl azodicarboxylate (4.06 mL, 25.8 mmol). The mixture was stirred at room temperature for 18 h and the solvent was removed in vacuo. The residue was purified by flash chromatography using EtOAc/Hex (40:60) as an eluent to afford the title compound 434 (4.68 g, 42% yield).

$^1$H NMR (DMSO-$d_6$) ☐ ppm): 8.58 (dd, J=4.7, 1.4 Hz, 1H), 8.48 (d, J=8.0 Hz, 2H), 8.38 (d, J=2.0 Hz, 1H), 8.13 (d, J=9.0, 2H), 7.72 (d, J=9.0 Hz, 2H), 7.61 (ddd, J=8.0, 2.5, 1.6 Hz, 1H), 7.39 (dd, J=8.2, 4.9 Hz, 1H), 6.43 (d, J=9.0 Hz, 2H), 5.17 (quint, J=8.2 Hz, 1H), 3.77 (dd, J=10.4, 7.2 Hz, 1H), 3.36 (dd, J=10.4, 6.7 Hz, 1H), 3.26 (dd, J=15.1, 7.8 Hz, 1H), 3.06 (td, J=12.3, 3.3 Hz, 1H), 2.43-2.38 (m, 1H), 2.02-1.94 (m, 1H), 1.55 (s, 9H). LRMS: calc. 524.2, found 525.3 (MH$^+$).

Step 3: tert-Butyl 4-((S)-3-(pyridin-3-ylamino)pyrrolidin-1-yl)benzoate (435)

To a solution of the nitro compound 434 (4.68 g, 8.92 mmol) in DMF (45 mL), were successively added lithium hydroxide (1.31 g, 31.2 mmol) and thioglycolic acid (930 µL, 13.4 mmol). The mixture was stirred for 3 days at room temperature, the solvent was removed in vacuo at 80° C. and the residue was partitioned between EtOAc and H$_2$O Organic layer was collected and extracted with HCl 1N. Acidic layer was collected and neutralized with a saturated NaHCO$_3$ solution. A white precipitate was formed which was extracted with EtOAc. The EtOAc solution was washed with brine, dried over MgSO4, and concentrated in vacuo to afford the title compound 435 (1.65 g, 54% yield) as a white solid.

$^1$H NMR: (Acetone-$d_6$) δ (ppm): 8.08 (d, J=2.2 Hz, 1H), 7.86 (d, J=4.3 Hz, 1H), 7.79 (d, J=9.0 Hz, 2H), 7.09 (dd, J=8.2, 4.3 Hz, 1H), 7.05 (ddd, J=8.2, 2.7, 1.6 Hz, 1H), 6.57 (d, J=8.8 Hz, 2H), 5.54 (d, J=6.5 Hz, 1H), 4.32 (sext, J=5.3 Hz, 1H), 3.78 (dd, J=10.2, 5.9 Hz, 1H), 3.56 (dd, J=17.0, 7.2 Hz, 1H), 3.47 (td, J=8.0, 5.1 Hz, 1H), 3.31 (dd, J=10.2, 3.9 Hz, 1H), 2.44 (sext., J=7.8 Hz, 1H), 2.13 (sext, J=5.1 Hz, 1H), 1.56 (s, 9H). LRMS: calc. 339.2, found 340.3 (MH$^+$).

Steps 4-6. (S)—N-(2-Amino-5-(thiophen-2-yl)phenyl)-4-(3-(pyridin-3-ylamino)pyrrolidin-1-yl)benzamide (436)

Starting from compound 435, the general procedures I, N and G were followed to afford the title compound 436 as a beige solid (720 mg, 73% yield, last step).

$^1$H NMR (DMSO-$d_6$) δ (ppm): 9.43 (s, 1H), 8.02 (d, J=2.7 Hz, 1H), 7.88 (d, J=8.6 Hz, 2H), 7.79 (d, J=4.3 Hz, 1H), 7.45 (d, J=2.0 Hz, 1H), 7.35 (d, J=5.1 Hz, 1H), 7.26 (dd, J=8.4, 2.0 Hz, 1H), 7.24 (d, J=3.3 Hz, 1H), 7.10 (dd, J=8.2, 4.1 Hz, 1H), 7.04 (dd, J=5.1, 3.3 Hz, 1H), 7.01-6.98 (m, 1H), 6.80 (d, J=8.4 Hz, 1H), 6.61 (d, J=8.4 Hz, 2H), 6.18 (d, J=6.8 Hz, 1H), 5.07 (s, 2H), 4.20 (sext, J=6.8 Hz, 1H), 3.71 (dd, J=9.6, 6.1 Hz, 1H), 3.52-3.48 (m, 1H), 3.44-3.38 (m, 1H), 3.19 (dd, J=9.8, 3.5 Hz, 1H), 2.32 (sext, J=6.3 Hz, 1H), 1.98 (sext, J=5.9 Hz, 1H). LRMS: 455.6 (calc) 456.1 (found).

Example 49a

N-(2-Amino-5-(1H-indol-5-yl)phenyl)-4-methoxybenzamide (441)

Scheme 49

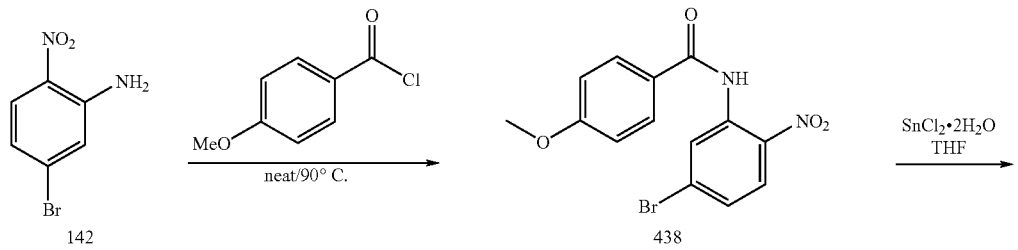

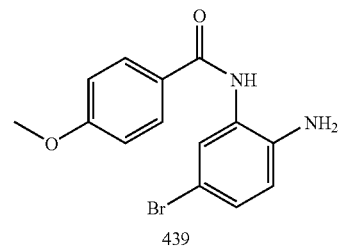

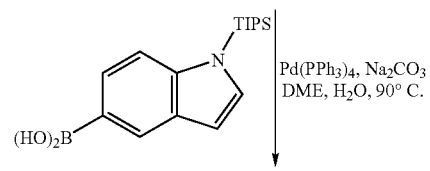

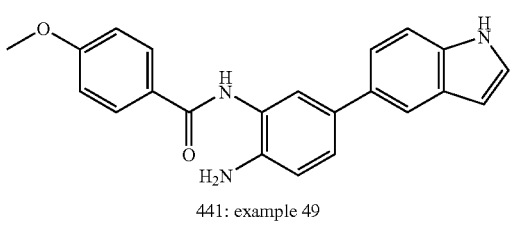

441: example 49

TBAF
THF

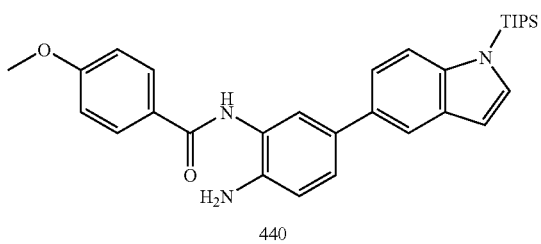

440

Steps 1-2. N-(2-Amino-5-bromo-phenyl)-4-methoxy-benzamide (439)

In a flame dried, round bottom flask, the aniline 142 (10.66 g, 49.09 mmol) and 4-methoxybenzoyl chloride (8.37 g, 49.09 mmol) were added. The mixture was heated to 90° C. The melted solids were stirred overnight to give compound 438 as a yellow-brown solid. THF (250 mL) was then added and the solution was treated with $SnCl_2.2H_2O$ (55.38 g, 245.45 mmol) and stirred at room temperature for 2 h. Approx. half of the THF was evaporated then EtOAc and sat. $NaHCO_3$ were added. The precipitated tin salt was taken out by filtration and a work-up was done on the filtrate with EtOAc. The combined organic layers were washed with water and brine and dried over $MgSO_4$. Most of the EtOAc was evaporated then hexane was added and the precipitate was collected by filtration to give the title compound 439 as a beige powder (13.40 g, 85% yield).

$^1$H NMR (DMSO-$d_6$) δ (ppm): 9.52 (s, 1H), 7.93 (d, J=9.0 Hz, 2H), 7.34 (d, J=2.3 Hz, 1H), 7.08 (dd, J=8.6, 2.3 Hz, 1H), 7.02 (d, J=9.0 Hz, 2H), 6.71 (d, J=8.6 Hz, 1H), 5.10 (s, 2H), 3.82 (s, 3H).

Step 3. N-(2-Amino-5-(1-(triisopropylsilyl)-1H-indol-5-yl)phenyl)-4-methoxybenzamide (440)

Starting from compound 439, the general procedure B was followed (using no POT and $Na_2CO_3$ instead $K_2CO_3$), to afford the title compound 440 (14 mg, 5% yield).

LRMS: 513.3 (calc) 514.5 (found).

Step 4. N-(2-Amino-5-(1H-indol-5-yl)phenyl)-4-methoxybenzamide (441)

TBAF (26 μL) was added to a solution of 440 (14 mg, 0.027 mmol) in THF (50 μL), stirred 1 h at room temperature, diluted with ethyl, washed with water, the organic layer was dried (MgSO$_4$), filtered and concentrated. The compound was purified by preparative TLC to afford the title compound 441 (5.4 mg, 56% yield).

LRMS: 357.4 (calc) 358.3 (found).

Example 50

(S)—N-(4-Aminobiphenyl-3-yl)-4-(3-(2-hydroxyethylamino)pyrrolidin-1-yl)benzamide (444)

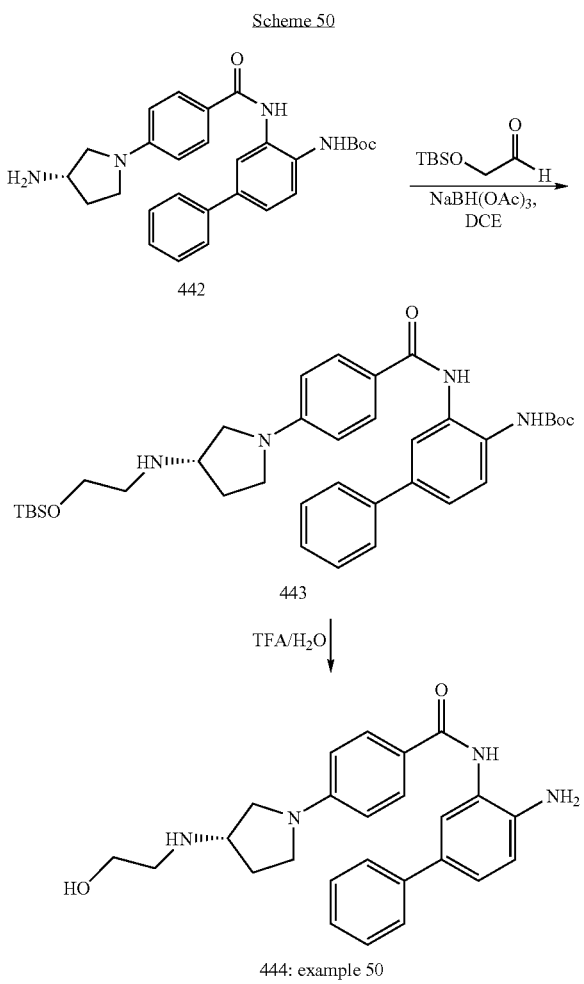

444: example 50

Step 1. (S)-tert-Butyl 3-(4-(3-(2-(tert-butyldimethylsilyloxy)ethylamino)pyrrolidin-1-yl)benzamido)biphenyl-4-ylcarbamate (443)

Starting from (S)-pyrrolidin-3-amine and tert-butyl 4-fluorobenzoate, the compound 442 was synthesized the same way as compound 404 (Scheme 42, example 42a) by following the general procedures J, T, I, F (using compound 322) and R. Then, starting with 442, the general procedure DD was followed to afford the title compound 443 as beige foam (133 mg, 22% yield).

$^1$H NMR (DMSO-d$_6$) δ (ppm): 9.66 (s, 1H), 8.76 (bs, 1H), 7.84 (m, 3H), 7.65 (dd, 7.60 (d, J=8.4 Hz, 1H), 7.48 (m, 1H), 7.45 (d, J=7.6 Hz, 2H), 7.35 (tt, J=7.2 Hz, 1H), 6.59 (d, J=8.8 Hz, 2H), 3.64 (t, J=6.0 Hz, 2H), 3.50 (dd, J=9.8, 6.2 Hz, 1H), 3.42 (m, 2H), 3.31 (m, 1H), 3.07 (dd, J=10.0, 4.8 Hz, 1H), 2.68 (td, J=6.0, 2.8 Hz, 2H), 2.13 (sext, J=6.2 Hz, 1H), 1.81 (sext, J=6.2 Hz, 1H), 1.47 (s, 9H), 0.86 (s, 9H), 0.05 (s, 6H).
LRMS: (Calc): 630.4 (found) 631.4 (MH)$^+$.

Step 2. (S)—N-(4-Aminobiphenyl-3-yl)-4-(3-(2-hydroxyethylamino)pyrrolidin-1-yl)benzamide (444)

A solution of 443 (0.13 g, 0.206 mmol) in TFA (0.392 mL) and water (0.021 mL) was stirred for 2 h at room temperature. The solvent was evaporated and the residue obtained was dissolved in EtOAc, washed with sat NaHCO$_3$ and sat NaCl. The organic layer was dried with MgSO$_4$, filtered and concentrated to a brown solid. Trituration in Et$_2$O generated the title compound 444 as a beige powder (70 mg, 82% yield).

$^1$H NMR (DMSO-d$_6$) δ (ppm): 9.48 (s, 1H), 7.90 (d, J=8.8 Hz, 2H), 7.56 (dd, J=8.4, 1.2 Hz, 2H), 7.51 (d, J=2.4 Hz, 1H), 7.39 (t, J=7.8 Hz, 2H), 7.30 (dd, J=8.2, 2.2 Hz, 1H), 7.24 (tt, J=7.4, 1.3 Hz, 1H), 6.86 (d, J=8.4 Hz, 1H), 6.59 (d, J=8.8 Hz, 2H), 5.04 (bs, 2H), 4.80 (bs, 1H), 3.55 (bs, 3H), 3.45 (m, 1H), 3.30 (m, 1H), 3.21 (m, 1H), 2.79 (bs, 2H), 2.21 (m, 1H), 1.98 (bs, 1H).
LRMS Calc 416.2; Found: 417.3 (MH)$^+$.

Example 51

4-Methoxy-N-(2-(sulfamoylamino)-5-(thiophen-2-yl)phenyl)benzamide (447)

Scheme 51

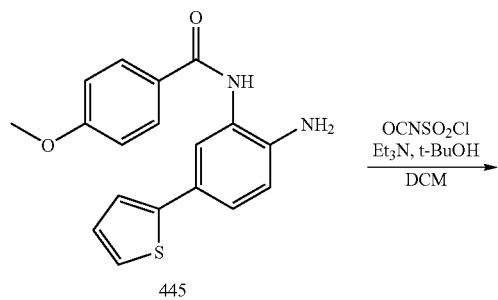

445

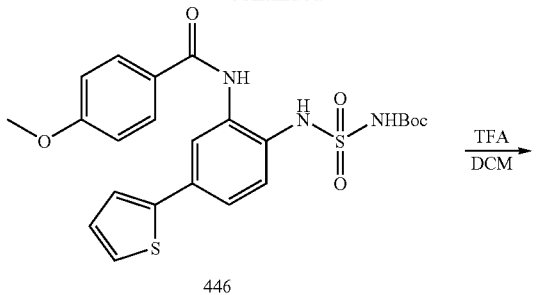

446

447: example 51

Step 1. tert-Butyl N-(2-(4-methoxybenzamido)-4-(thiophen-2-yl)phenyl)sulfamoyl-carbamate (446)

Starting from compound 4 and 4-methoxybenzoyl chloride the compound 445 was synthesized following the general procedure K and G. Then, t-BuOH (0.08 mL, 0.80 mmol) was added dropwise to a solution at 0° C. of sulfurisocyanatidic chloride (0.07 mL, 0.80 mmol) in DCM (20 mL) and stirred for 20 min. A solution of compound 445 (260 mg, 0.80 mmol) in DCM (2 mL) and Et$_3$N (0.3 mL, 2.40 mmol) was added, stirred at room temperature for 18 h, quenched with water, extracted 3 times with DCM, dried over MgSO$_4$ and concentrated. The residue was purified by flash chromatography using 5% MeOH in DCM as an eluent to afford the title compound 446 (365 mg, 90%) as a white solid.
LRMS Calc 503.1; Found: 526.2 (M+Na)$^+$.

Step 2. 4-Methoxy-N-(2-(sulfamoylamino)-5-(thiophen-2-yl)phenyl)benzamide (447)

Following the general procedure G, the title compound 447 was obtained as a white solid (70 mg, 21% yield).
$^1$H NMR (DMSO-d$_6$) δ (ppm): 9.70 (s, 1H), 8.81 (s, 1H), 8.20 (s, 1H), 7.94 (d, J=8.9 Hz, 2H), 7.50 (m, 4H), 7.22 (s, 2H), 7.14 (m, 3H), 3.84 (s, 3H).
LRMS: (calc.) 403.5 (found) 404.0 (MH)$^+$ Example 53

(S)—N-(4-Aminobiphenyl-3-yl)-4-(3-(2,2,2-trifluoroethylamino)pyrrolidin-1-yl)benzamide (460)

Scheme 53

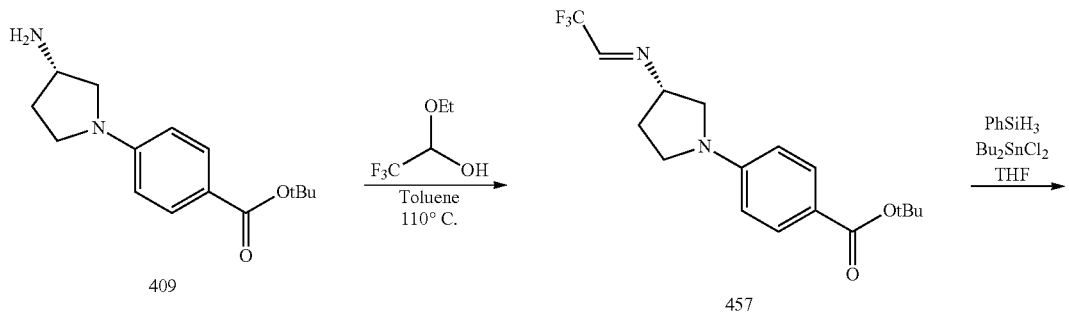

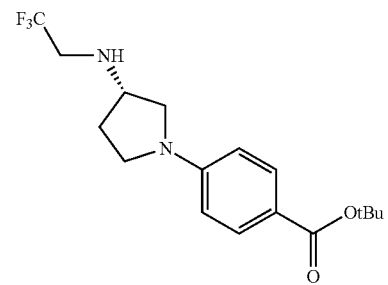

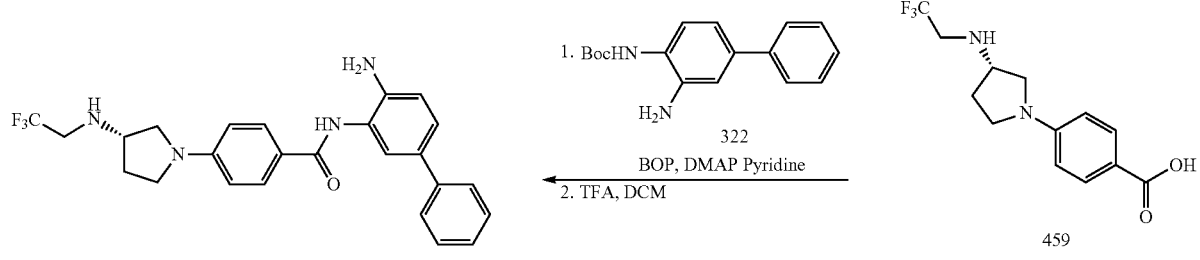

Step 1. 4-(3-(2,2,2-Trifluoroethylideneamino)pyrrolidin-1-yl)benzoate (457)

A solution of compound 409 (1.2 g, 4.57 mmol) and 1-ethoxy-2,2,2-trifluoroethanol (1.65 g, 11.4 mmol) in toluene (23 mL) was heated to 120° C. for 16 h with a Dean-Stark apparatus. More 2,2,2-trifluoroethanol (1.65 g, 11.4 mmol) was added and the reaction 3 was stirred for an extra 2 h. The solvent was then evaporated to afford the title compound 457 (1.26 g, 81% yield)

$^1$H NMR (MeOD-d$_4$) □ (ppm): 8.98 (d, J=5.7 Hz, 2H), 8.57 (t, J=7.8 Hz, 1H), 8.09 (t, J=7.2 Hz, 2H), 7.84 (d, J=1.6 Hz, 1H), 7.59 (dd, J=7.0, 1.4 Hz, 2H), 7.51 (dt, J=7.2, 2.0 Hz, 1H), 7.47-7.40 (m, 2H), 7.40-7.31 (m, 2H), 4.62 (t, J=7.6 Hz, 2H), 2.40 (t, J=7.2 Hz, 2H), 2.02 (quin, J=7.0 Hz, 2H), 1.70 (quin, J=7.0 Hz, 2H), 1.50-1.45 (m, 6H)

Step 2. (S)-tert-Butyl 4-(3-(2,2,2-trifluoroethylamino)pyrrolidin-1-yl)benzoate (458)

Dibutyltin dichloride (28 mg, 0.09 mmol) and phenylsilane (365 mg, 3.37 mmol) were added to a suspension of 457 (1.05 g, 3.07 mmol), in THF (6.1 mL). The reaction mixture was stirred for 48 h at room temperature, diluted with AcOEt, washed with water and brine, dried over MgSO$_4$, filtered and concentrated. The residue was purified by flash chromatography to afford the title compound 458 (647 mg, 61% yield) as a white solid.

LRMS: (calc.) 344.2 (found) 345.2 (MH)+.

Steps 3-5. (S)—N-(4-Aminobiphenyl-3-yl)-4-(3-(2,2,2-trifluoroethylamino)pyrrolidin-1-yl)benzamide (460)

Starting from compound 458 the general procedures I, F and G were followed to afford the title compound 460 (61 mg, 15% yield, last step).

$^1$H NMR (MeOD-d$_4$) □ (ppm): 7.90 (d, J=8.8 Hz, 2H), 7.56 (dd, J=8.2, 1.4 Hz, 2H), 7.46 (d, J=2.2 Hz, 1H), 7.36 (t, J=8.2 Hz, 2H), 7.35 (dd, J=8.2, 2.2 Hz, 1H), 7.23 (tt, J=7.2, 1.4 Hz, 1H), 6.97 (d, J=8.2 Hz, 1H), 6.63 (d, J=9.0 Hz, 2H), 3.64-3.33 (m, 6H), 3.22-3.14 (m, 1H), 3.22-3.14 (m, 1H), 2.32-2.22 (m, 1H), 2.00-1.80 (m, 1H). LRMS: (calc.) 454.49 (found) 455.3 (MH)+

Example 54

4-(4-Amino-3-(4-methoxybenzamido)phenyl)pyridine 1-oxide (463)

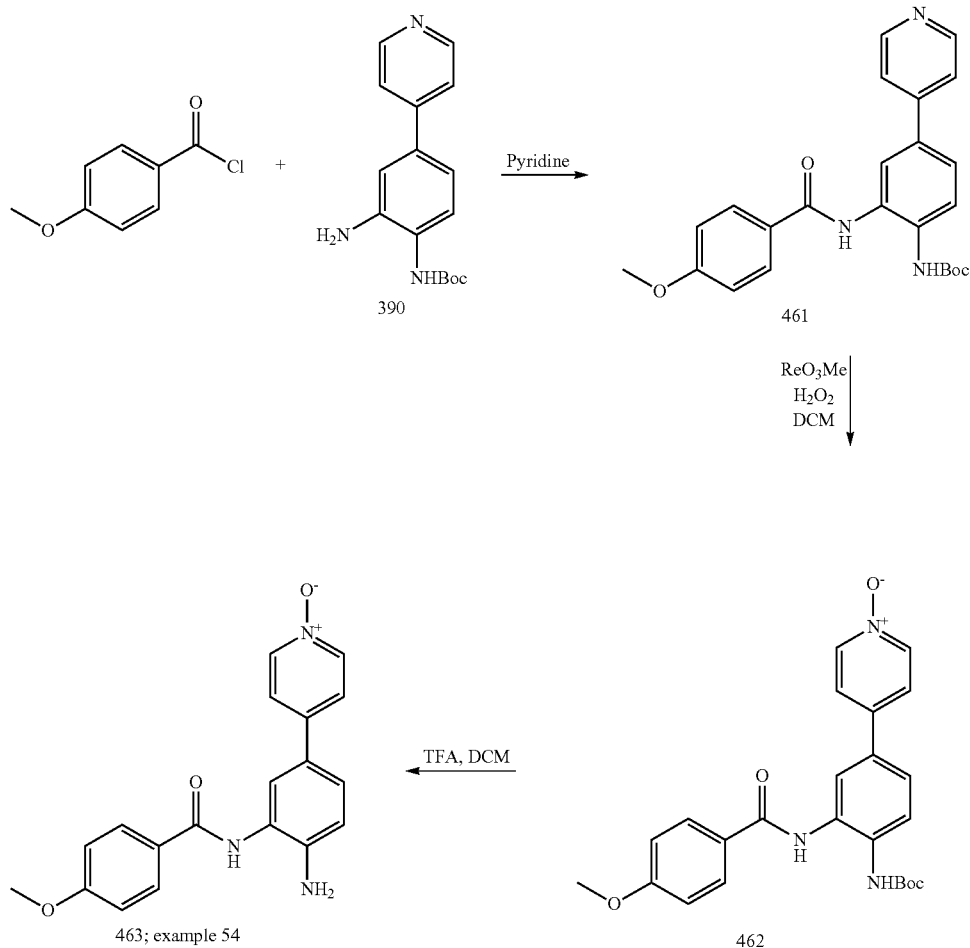

Scheme 54

Step 1. tert-Butyl 2-(4-methoxybenzamido)-4-(pyridin-4-yl)phenylcarbamate (461)

Starting from compound 390 and 4-methoxybenzoyl chloride the general procedure K was followed to afford the title compound 461 as orange foam (560 mg, 76% yield).

$^1$H NMR (DMSO-$d_6$) δ (ppm): 9.85 (br s, 1H), 8.83 (br s, 1H), 8.62-8.59 (m, 2H), 7.98-7.94 (m, 3H), 7.75-7.64 (m, 4H), 7.08 (d, J=9.0 Hz, 2H), 3.84 (s, 3H), 3.33 (s, 3H), 1.45 (s, 9H).

Step 2. 4-(4-(tert-butoxycarbonylamino)-3-(4-methoxybenzamido)phenyl)pyridine 1-oxide (462)

A solution of compound 461 (0.55 g, 1.31 mmol) and ReO$_3$Me (33 mg, 0.13 mmol) in DCM (10 mL) was stirred 5 min, 35% H$_2$O$_2$ (0.14 mL, 1.53 mmol) was added and the reaction was stirred at room temperature for 2 h. The reaction mixture was quenched with water, and AcOEt was added. The white precipitate was filtered and washed with AcOEt and MeOH (5 mL) to afford the title compound 462 (350 mg, 61%) as a white solid.

$^1$H NMR (DMSO-$d_6$) δ (ppm): 9.83 (s, 1H), 8.81 (s, 1H), 8.23 (d, J=7.2 Hz, 2H), 7.96 (d, J=8.8 Hz, 2H), 7.91 (d, J=2.0 Hz, 1H), 7.74-7.70 (m, 3H), 7.64-7.61 (m, 1H), 7.08 (d, J=9.0 Hz, 2H), 3.84 (s, 3H), 1.45 (s, 9H).

Step 3. 4-(4-Amino-3-(4-methoxybenzamido)phenyl)pyridine 1-oxide (463)

Starting from compound 462 the general procedure G was followed to afford the title compound 463 as a dark yellow solid (110 mg, 42% yield).

$^1$H NMR (DMSO-$d_6$) δ (ppm): 9.61 (s, 1H), 8.13 (d, J=7.2 Hz, 2H), 7.98 (d, J=8.8 Hz, 2H), 7.62-7.59 (m, 3H), 7.44 (dd, J=8.6, 2.3 Hz, 1H), 7.04 (d, J=9.0 Hz, 2H), 6.85 (d, J=8.4 Hz, 1H), 5.34 (s, 2H), 3.83 (s, 3H). LRMS: (calc.) 335.1 (found) 336.3 (MH)+

Example 55

(E)-N-(4-Aminobiphenyl-3-yl)-11-(4-methylpiperazin-1-yl)dibenzo[b,f][1,4]oxazepine-8-carboxamide (551)

via rotary evaporation to afford the title compound 545 (7.55 g, 88%) as a light yellow foam.

$^1$H NMR (DMSO-d$_6$) δ (ppm): 8.49 (d, J=2.1 Hz, 1H), 8.08 (dd, J=8.8, 2.2 Hz, 1H), 8.00-7.97 (m, 1H), 7.79-7.74 (m, 1H), 7.49 (td, J=7.6, 1.2 Hz, 1H), 7.41 (dd, J=8.2, 0.8 Hz, 1H), 6.85 (d, J=8.8 Hz, 1H), 3.63 (s, 3H).

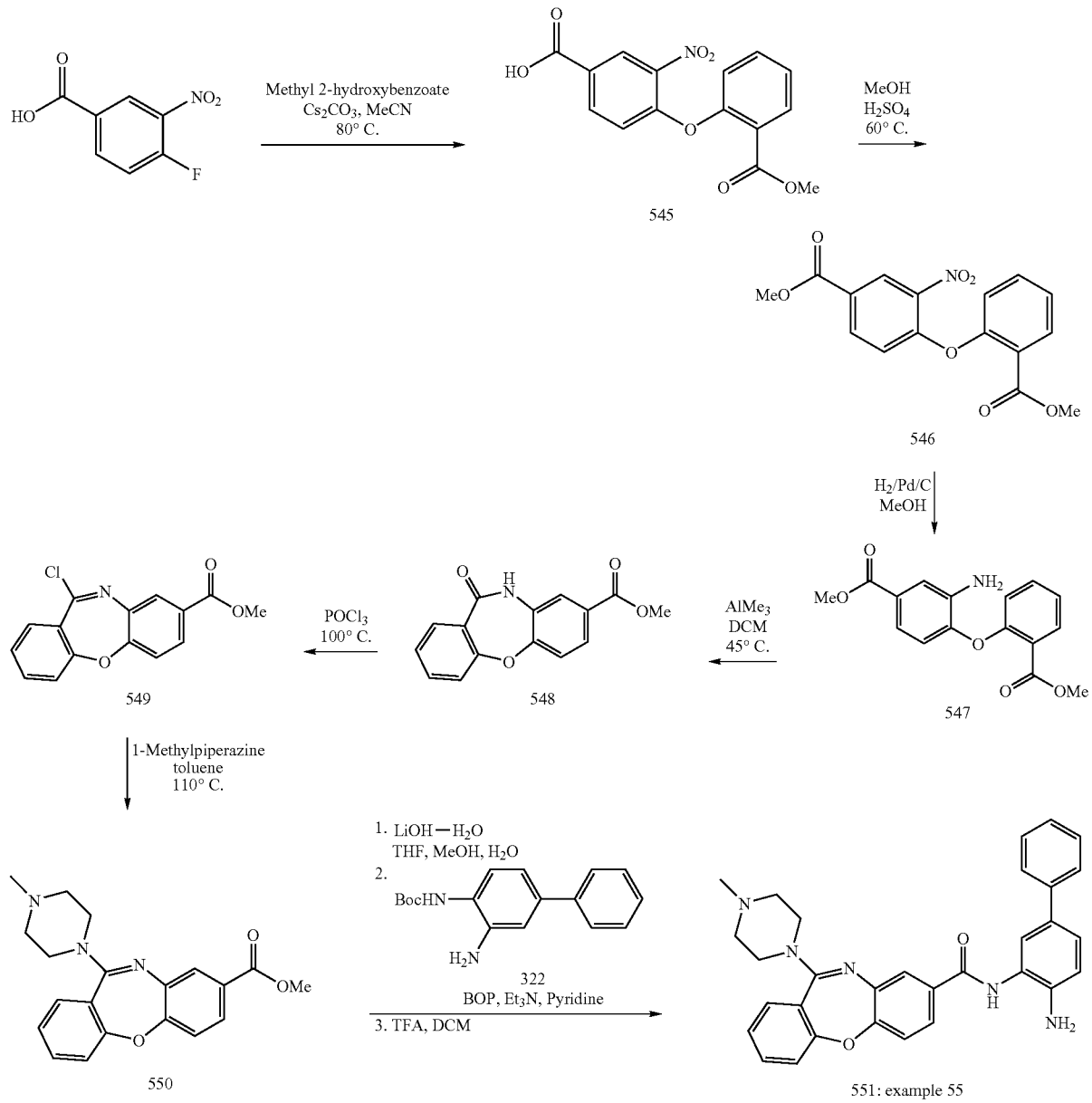

Scheme 55

Step 1. 4-(2-(Methoxycarbonyl)phenoxy)-3-nitrobenzoic acid (545)

4-Fluoro-3-nitrobenzoic acid (5.0 g, 27.0 mmol), methyl 2-hydroxybenzoate (4.11 g, 27.0 mmol) and Cs$_2$CO$_3$ (18.49 g, 56.7 mmol) were dissolved in acetonitrile (100 mL) and stirred at 80° C. for 3 h. The reaction mixture was diluted with AcOEt and washed with 1M HCl and water. The organic layer was separated, dried with Na$_2$SO$_4$, filtered and concentrated

Step 2. Methyl 4-(2-(methoxycarbonyl)phenoxy)-3-nitrobenzoate (546)

Concentrated H$_2$SO$_4$ (3 mL) was added to a solution of compound 545 (7.5 g, 23.64 mmol) in MeOH (80 mL) and stirred at 60° C. for 16 h. MeOH was removed under vacuum and the crude product was dissolved in AcOEt and washed with water. The organic layer was separated, dried with Na₂SO₄, filtered and concentrated via rotary evaporation to afford the title compound 546 (6.2 g, 79%) as a light yellow solid.

¹H NMR (DMSO-d₆) δ (ppm): 8.52 (d, J=2.1 Hz, 1H), 8.09 (dd, J=9.0, 2.4 Hz, 1H), 8.00 (dd, J=8.8, 1.3 Hz, 1H), 7.80-7.75 (m, 1H), 7.50 (td, J=7.4, 1.0 Hz, 1H), 7.42 (dd, J=8.0, 1.0 Hz, 1H), 6.87 (d, J=8.8 Hz, 1H), 3.86 (s, 3H), 3.62 (s, 3H).

Step 3. Methyl 3-amino-4-(2-(methoxycarbonyl)phenoxy)benzoate (547)

Starting from compound 546 the general procedure C was followed to afford the title compound 547 (535 mg, 95% yield) as a yellow oil.

¹H NMR (DMSO-d₆) δ (ppm): 7.82 (dd, J=7.8, 1.6 Hz, 1H), 7.59-7.54 (m, 1H), 7.43 (d, J=2.1 Hz, 1H), 7.25 (td, J=7.6, 1.2 Hz, 1H), 7.11 (dd, J=8.4, 2.1 Hz, 1H), 6.98 (dd, J=8.4, 1.0 Hz, 1H), 6.64 (d, J=8.4 Hz, 1H), 5.31 (br s, 2H), 3.78 (s, 3H), 3.72 (s, 3H).

Step 4. Methyl 11-oxo-10,11-dihydrodibenzo[b,f][1,4]oxazepine-8-carboxylate (548)

A solution of compound 547 (3.2 g, 10.62 mmol) and AlMe₃ (6.37 mL, 12.75 mmol) in DCM (40 mL) was stirred at 45° C. for 16 h and quenched with water. The reaction was diluted with AcOEt, washed with water and 1M HCl. The organic layer was separated, dried with Na₂SO₄, filtered and concentrated via rotary evaporation. The residue was triturated with AcOEt, filtered, washed with AcOEt and was purified via Isco employing a 0 to 50% AcOEt in hexanes solvent gradient to afford the title compound 548 (1.01 g, 35%) as a white solid.

¹H NMR (DMSO-d₆) δ (ppm): 10.68 (s, 1H), 7.79-7.75 (m, 2H), 7.70 (dd, J=8.4, 2.1 Hz, 1H), 7.65-7.60 (m, 1H), 7.45 (d, J=8.4 Hz, 1H), 7.38-7.30 (m, 2H), 3.82 (s, 3H).

Step 5. (E)-Methyl 11-chlorodibenzo[b,f][1,4]oxazepine-8-carboxylate (549)

Compound 548 (1.00 g, 3.71 mmol)) was suspended in POCl₃ (20 mL). The reaction mixture was stirred at 100° C. for 3 h. POCl₃ was removed on rotovap. The crude product was dissolved in ethyl acetate and washed with 2M Na₂CO₃ solution then with NaHCO₃ saturated solution and finally with brine. The organic layer was separated and dried with Na₂SO₄, filtered and concentrated via rotary evaporation to afford compound 549 (1.069 g, 100%) as a orange solid that was taken on without further purification.

Step 6. (E)-Methyl 11-(4-methylpiperazin-1-yl)dibenzo[b,f][1,4]oxazepine-8-carboxylate (550)

Compound 549 (1.06 g, 3.68 mmol) and 1-methylpiperazine (0.818 mL, 7.37 mmol) were dissolved in toluene (40 mL) and stirred at 110° C. for 16 h. The toluene was removed on the rotary evaporator. The crude product was dissolved in ethyl acetate and washed with water. The organic layer was separated and dried with Na₂SO₄, filtered and concentrated via rotary evaporation. The residue was purified via Isco employing a 0 to 50% methanol:ethyl acetate solvent gradient to afford compound 550 (0.86 g, 66%) as a white solid.

¹H NMR (DMSO-d₆) δ (ppm): 7.59-7.53 (m, 3H), 7.42-7.36 (m, 2H), 7.31 (td, J=7.4, 1.2 Hz, 1H), 7.27 (d, J=8.2 Hz, 1H), 3.78 (s, 3H), 3.49 (br s, 4H), 2.47-2.43 (m, 4H), 2.21 (s, 3H).

Steps 7-9. (E)-N-(4-Aminobiphenyl-3-yl)-11-(4-methylpiperazin-1-yl)dibenzo[b,f][1,4]-oxazepine-8-carboxamide (551)

Starting from compound 550 the general procedures P, F and G were followed to afford the title compound 551 as a white solid (120 mg, 90% yield, last step).

¹H NMR (MeOD-d₄) δ (ppm): 7.76 (d, J=2.2 Hz, 1H), 7.66 (dd, J=8.2, 2.2 Hz, 1H), 7.57-7.53 (m, 3H), 7.46-7.44 (m, 2H), 7.38-7.21 (m, 7H), 6.96 (d, J=8.4 Hz, 1H), 3.60 (br s, 4H), 2.61 (br s, 4H), 2.38 (s, 3H). LRMS: (calc.) 503.2 (found) 504.5 (MH)⁺.

Example 56

(Z)—N-(2-amino-5-(pyridin-4-yl)phenyl)-4-(dibenzo[b,f][1,4]oxazepin-11-yl)benzamide (556)

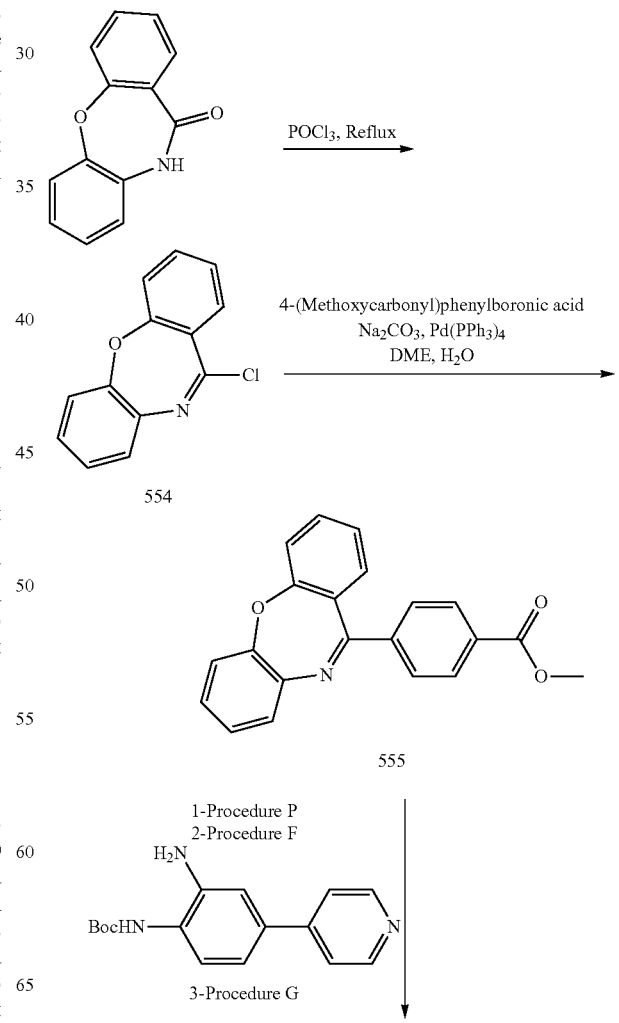

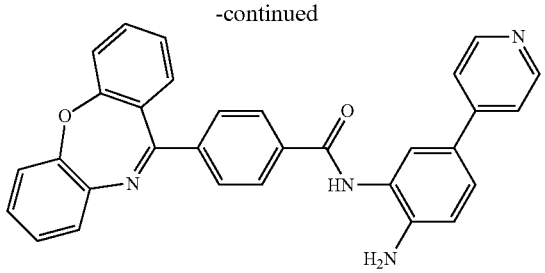

556: Example 56

Step 1: (E)-11-Chlorodibenzo[b,f][1,4]oxazepine (554)

A solution of 10,11-dihydrodibenz[b,f][1,4]oxazepin-11-one (1.00 g, 4.74 mmol) and phosphorus oxychloride (40 mL) was stirred for 5 h at reflux. The reaction mixture was then cooled to room temperature and concentrated under reduced pressure. The residue was dissolved into AcOEt and washed with water and brine. The organic layer was dried ($Na_2SO_4$), filtered and concentrated to give an orange oil. The residue was purified by silica gel column chromatography with EtOAc (10%) in hexanes to afford 554 (939 mg, 86%) as a yellow solid. LRMS (ESI): (calc) 229.0 (found) 230.1 (MH)$^+$.

Step 2: (Z)-Methyl 4-(dibenzo[b,f][1,4]oxazepin-11-yl)benzoate (555)

To a solution of 554 (229 mg, 1.00 mmol) in DME (3 mL) was added 4-methoxycarbonylphenylboronic acid (216 mg, 1.20 mmol), Pd(PPh$_3$)$_4$ (0.065 mg, 0.056 mmol) and 2 N $Na_2CO_{3(aq)}$ (1.5 mL, 3.0 mmol). The reaction mixture was stirred for 2 h at 90° C. The solution was then cooled at room temperature and poured into AcOEt. The organic layer was washed with water, brine and dried ($Na_2SO_4$), filtered and concentrated to give a yellow oil. The residue was purified by silica gel column chromatography with EtOAc (15%) in hexanes to afford 555 (327 mg, 99%) as a yellow foam. LRMS (ESI): (calc) 329.1 (found) 330.3 (MH)$^+$.

Step 3-5: (Z)—N-(2-amino-5-(pyridin-4-yl)phenyl)-4-(dibenzo[b,f][1,4]oxazepin-11-yl)benzamide (556)

Starting from compound 555 the general procedures P, F and G were followed to afford the title compound 556 as a yellow solid (100 mg, 19% yield, last step). $^1$H NMR (DMSO) δ (ppm) 1H, 9.91 (s, 1H), 8.50 (d, J=5.6 Hz, 2H), 8.14 (d, J=8.4 Hz, 2H), 7.89 (d, J=8.4 Hz, 2H), 7.69-7.64 (m, 2H), 7.58 (d, J=6.4 Hz, 2H), 7.52 (dd, J=2.4, 8.4 Hz, 1H), 7.46-7.43 (m, 2H), 7.34-7.27 (m, 4H), 7.19 (dd, J=1.6, 7.6 Hz, 1H), 6.89 (d, J=8.4 Hz, 1H), 5.42 (s, 2H). LRMS (ESI): (calc) 482.5 (found) 483.4 (MH)$^+$.

Example 57

4-(pyridin-4-yl)-2-(2-((1S,4S)-5-(3-(trifluoromethyl)phenyl)-2,5-diazabicyclo[2.2.1]heptan-2-yl)pyrimidine-5-carboxamido)benzenaminium chloride (560)

Scheme 57

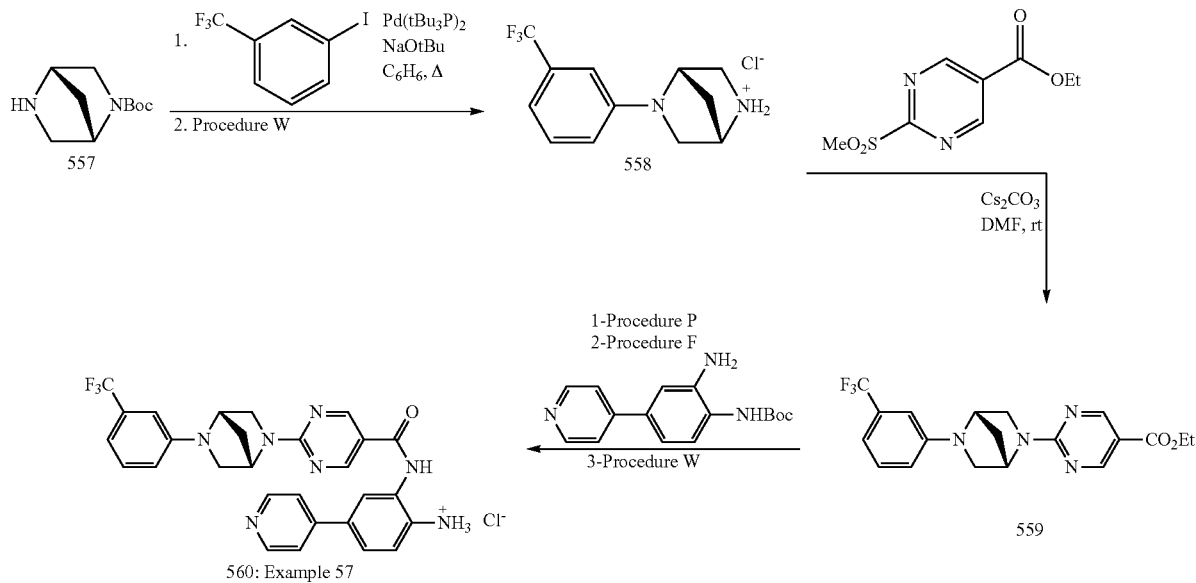

560: Example 57

Step 1: (1S,4S)-5-(3-(trifluoromethyl)phenyl)-5-aza-2-azoniabicyclo[2.2.1]heptane chloride (558)

(S,S)-tert-butyl 2,5-diazabicyclo[2.2.1]heptane-2-carboxylate (557) (7.3 g, 36.8 mmol) and bis(tri-t-butylphosphine)palladium(0) (0.05 g, 0.098 mmol) were dissolved in benzene (60 mL) under a nitrogen atmosphere to give an orange suspension. 3-Iodobenzotrifluoride (6.93 mL, 47.9 mmol), and sodium tert-butoxide (7.78 g, 81 mmol) were then added and the mixture left to stir at 110° C. overnight. The reaction was cooled to room temperature, filtered through Celite® and the filtrate was decolorized with activated charcoal. The solvent was removed in vacuo and the solid residue suspended in hexanes and triturated and filtered to get the carbamate (8.9 g,) as an off-white powder. To this powder was added dioxane (25.7 ml) to give a yellow-orange suspension that was cooled to 0° C. and a solution of hydrogen chloride in dioxane (4M, 64.3 mL, 257 mmol) was added drop-wise. The solid dissolved and the mixture was left to return to room temperature over 4 h. The suspension was filtered to get the hydrochloride salt 558 as a tan solid (6.82 g, 66%). LRMS: 243.1 (calc) 243.1 (found).

Step 2: ethyl 2-((1S,4S)-5-(3-(trifluoromethyl)phenyl)-2,5-diazabicyclo[2.2.1]heptan-2-yl)pyrimidine-5-carboxylate (559)

Compound 558 (500 mg, 1.794 mmol) and cesium carbonate (1461 mg, 4.49 mmol) were suspended in DMF (5 mL) to give a yellow suspension. Ethyl 2-(methylsulfonyl)pyrimidine-5-carboxylate (496 mg, 2.153 mmol) was then added and the reaction was stirred at room temperature for 3 days. The mixture was diluted with water and ethyl acetate. The organic layer was washed twice with water then brine and dried with MgSO$_4$. The solvent was removed in vacuo and the residue was purified by column chromatography (25-50% EtOAc in Hexanes) to obtain compound 559 as a white solid (313 mg, 45%). LRMS: 392.1 (found) 393.2 (MH)$^+$.

Step 3-5: 4-(pyridin-4-yl)-2-(2-((1S,4S)-5-(3-(trifluoromethyl)phenyl)-2,5-diazabicyclo[2.2.1]-heptan-2-yl)pyrimidine-5-carboxamido)benzenaminium chloride (560)

Starting from compound 559 the general procedures P, F and W were followed to afford the title compound 560 as an orange solid (17 mg, 29% yield, last two steps). $^1$H NMR (CD$_3$OD) δ (ppm): 1H, 9.10 (s, 1H), 8.95 (s, 1H), 8.69 (d, J=6 Hz, 2H), 8.28 (d, J=5.6 Hz, 2H), 7.97 (s, 1H), 7.89 (d, J=8.4 Hz, 1H), 7.35 (t, J=7.6 Hz, 1H), 7.20 (d, J=8.4 Hz, 1H), 6.91 (m, 3H), 5.33 (s, 1H), 4.82 (s, 1H), 3.80 (m, 4H), 2.28 (m, 2H). LRMS: (calc) 531.2 (found) 532.6 (MH)$^+$.

Example 58

N-(4-aminobiphenyl-3-yl)-5,6-dimethoxybenzo[b]thiophene-2-carboxamide (563)

Scheme 58

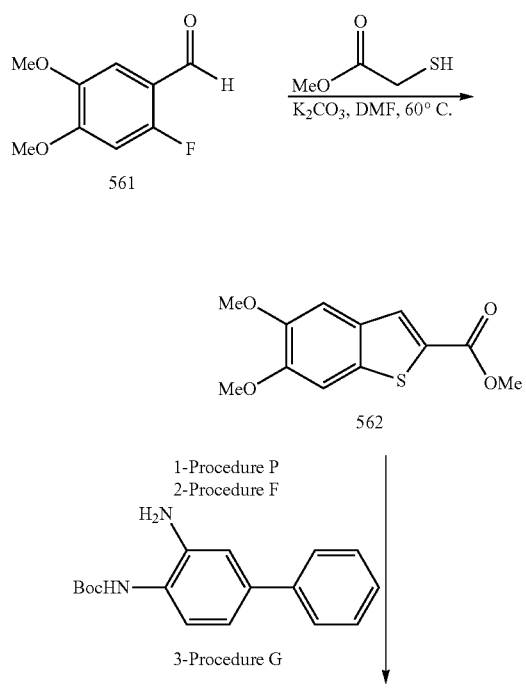

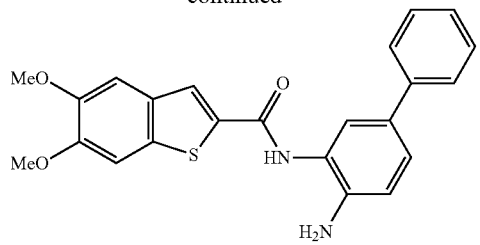

563: Example 58

Step 1: Methyl 5,6-dimethoxybenzo[b]thiophene-2-carboxylate (562)

To a stirred solution of 561 (1.09 g, 5.92 mmol) in DMF (20 mL) was added methyl thioglycolate (6.51 mmol, 0.58 mL) and potassium carbonate (2.45 g, 17.76 mmol). The resulting mixture was heated to 60° C. and left to stir for 15 hours. The DMF was removed via rotary evaporation and aqueous extraction was performed with ethyl acetate and water. The organic phase was separated and dried with sodium sulfate before the solvent was removed under reduced pressure and the resulting solid was dried under vacuum. This afforded 562 as a white solid (1.14 g, 77%). $^1$H NMR (DMSO) δ (ppm): 8.00 (s, 1H), 7.58 (s, 1H), 7.47 (s, 1H), 3.85 (s, 3H), 3.84 (s, 3H), 3.81 (s, 3H).

Step 2-4: N-(4-aminobiphenyl-3-yl)-5,6-dimethoxybenzo[b]thiophene-2-carboxamide (563)

Starting from compound 562 the general procedures P, F and G were followed to afford the title compound 563 as a yellow solid (38.6 mg, 41% yield, step).

$^1$H NMR (DMSO) δ (ppm) 9.90 (s, 1H), 8.18 (s, 1H), 7.60-7.52 (m, 4H), 7.44-7.33 (m, 4H), 7.25 (t, J=7.4 Hz, 1H), 6.88 (d, J=8.4 Hz, 1H), 5.16 (s, 2H), 3.86 (s, 3H), 3.85 (s, 3H). LRMS: (calc) 404.5 (found) 405.4 (MH)$^+$.

The general procedures A to HH used to synthesize compounds of this invention are described in the Table 1. A specific example of each general procedure is provided in the indicated step of a particular example. Substrates and methods may be modified and/or adapted in known ways in order to facilitate the synthesis of the compounds within the scope of the present invention.

TABLE 21

General procedures and reaction conditions

| Proc | Sc | Ex | Step | Reaction Conditions |
|---|---|---|---|---|
| A | 1 | 1a | 1 | $R^1-NH_2$ → $R^1-NH-Boc$ ; 1. Boc$_2$O, DMAP, THF; 2. NaOH, THF, 80° C. |
| B | 1 | 1a | 2 | $Ar^1-Br$ + $Ar^2-B(OH)_2$ → $Ar^1-Ar^2$ ; Pd(PPh$_3$)$_4$, POT, K$_2$CO$_3$, DME, H$_2$O; 80° C. |
| C | 1 | 1a | 3 | $R^1-NO_2$ → $R^1-NH_2$ ; H$_2$, Pd/C, EtOAc or MeOH; or $R^1-CH=CH-R^2$ → $R^1-CH_2-CH_2-R^2$ ; H$_2$, Pd/C, EtOAc or MeOH |
| D | 1 | 1a | 4 | $X-CH_2-R^3$ + $R^1-NH-R^2$ → $R^1-N(R^2)-CH_2-R^3$ ; K$_2$CO$_3$, DME, rt or K$_2$CO$_3$, DMF, rt |
| E | 1 | 1a | 5 | $R^1-CO-OR$ → $R^1-CO-OH$ ; 2N HCl, 110° C. |
| F | 1 | 1a | 6 | $R^1-CO-OR$ + $Ar^1-NH_2$ → $R^1-CO-NH-Ar^1$ ; BOP, Pyridine or BOP, Et$_3$N, Pyridine or BOP, DMAP, Pyridine |
| G | 1 | 1a | 7 | $Ar^1-NH-Boc$ → $Ar^1-NH_2$ ; TFA, DCM |
| H | 2 | 2a | 2 | $Ar^1-X$ + CH$_2$=CH-CO-OR$^2$ → $Ar^1-CH=CH-CO-OR^2$ ; Pd$_2$(dba)$_2$, POT, DIPEA, DMF, 120° C. |
| I | 2 | 2a | 3 | $R^1-CO-OtBu$ → $R^1-CO-OH$ ; TFA, DCM |
| J | 37 | 37a | 1 | $R^1R^2NH$ + $X-Ar^1$ → $R^1R^2N-Ar^1$ ; 90-130° C. or DMSO, 90-130° C. or K$_2$CO$_3$, DMSO, 90-130° C. |
| K | 6 | 6a | 1 | $R^1-CO-Cl$ + $R^2-NH_2$ → $R^1-CO-NH-R^2$ ; Et$_3$N, DCM or Pyridine |
| L | 6 | 6a | 2 | $Br-CH_2-R^3$ + $R^1-NH-R^2$ → $R^1-N(R^2)-CH_2-R^3$ ; K$_2$CO$_3$, NaI, DCM, Acetone |
| M | 10 | 10a | 1 | $R^1R^2NH$ + 2-(methylsulfonyl)pyrimidine-5-carboxylate → 2-($R^1R^2N$)pyrimidine-5-carboxylate (CO$_2$Et); DME, rt |

TABLE 21-continued

General procedures and reaction conditions

| Proc | Sc | Ex | Step | Reaction Conditions |
|---|---|---|---|---|
| N | 29 | 29a | 1 | $R^1COOH + Ar^1NH_2 \xrightarrow{\text{BOP, Et}_3\text{N, DMF}} R^1C(O)NHAr^1$ |
| O | 34 | 34b | 3 | $R^1OAc \xrightarrow{\text{Et}_3\text{N, MeOH or NH}_3\text{, MeOH}} R^1OH$ |
| P | 37 | 37a | 3 | $R^1C(O)OR^2 \xrightarrow{\text{LiOH·H}_2\text{O, MeOH, THF, H}_2\text{O}} R^1COOH$ |
|  |  |  |  | The use of NaOH or KOH instead LiOH·H$_2$O is also considered. |
| Q | 41 | 41a | 1 | Salicylaldehyde (2-hydroxybenzaldehyde, $R^1$-substituted) + Methyl 2-bromoacetate, $K_2CO_3$/DMF, 80° C. → Methyl benzofuran-2-carboxylate ($R^1$-substituted) |
| R | 41 | 41a | 2 | $R^1OBn$ or $R^1NHCbz \xrightarrow{\text{H}_2\text{, Pd/C 10\%, MeOH}} R^1OH$ or $R^1NH_2$ |
| S | 41 | 41a | 3 | $R^1R^2N{-}CH_2CH_2{-}Cl + HO{-}Ar^1 \xrightarrow{\text{K}_2\text{CO}_3\text{, DMF, acetone}} R^1R^2N{-}CH_2CH_2{-}O{-}Ar^1$ |
| T | 42 | 42a | 1 | $R^1{-}NH_2 \xrightarrow{\text{CBzCl, DCM, Na}_2\text{CO}_3, 0°\text{C. to rt}} R^1{-}NHCbz$ |
| U | 42 | 42a | 5a | $R^1{-}NH_2 \xrightarrow{R^2SO_2Cl \text{ or } (R^2SO_2)_2O, \text{Et}_3\text{N, DCM}} R^1{-}NH{-}SO_2{-}R^2$ |
| V | 42 | 42b | 5b | $R^1OH \xrightarrow{\text{Ac}_2\text{O or AcCl, Pyridine}} R^1OAc$ |
| W | 42 | 42b | 6b | $R^1{-}NH{-}Boc \xrightarrow{\text{HCl 4M in Dioxane, Dioxane or DCM}} R^1{-}NH_2$ |
| X | 33 | 33a | 1 | 4-isocyanatobenzoic acid ethyl ester + $R^1OH \xrightarrow{\text{THF, rt}}$ ethyl 4-($R^1$-O-C(O)-NH)benzoate |
| Y | 45 | 45a | 2 | $Ar^1{-}CH_2{-}X \xrightarrow[\text{2) Methyl propriolate, CuSO}_4\text{, Na Ascorbate, H}_2\text{O}]{\text{1) NaN}_3\text{/DMSO}}$ methyl 1-($Ar^1$CH$_2$)-1H-1,2,3-triazole-4-carboxylate |
| Z | 7 | 7a | 2 | $R^3{-}CHO + HNR^1R^2 \xrightarrow{\text{PhSiH}_3\text{, BuSnCl}_2\text{, DME}} R^3{-}CH_2{-}NR^1R^2$ |

TABLE 21-continued
General procedures and reaction conditions
| Proc | Sc | Ex | Step | Reaction Conditions |
|---|---|---|---|---|
| AA | 25 | 25a | 1 | 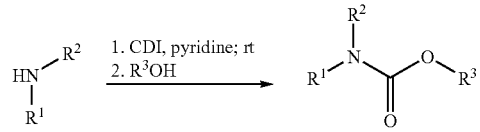 |
| BB | 24 | 24a | 2 | 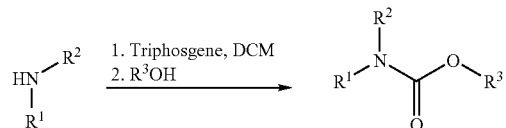 |
| CC | 7 | 7a | 1 | 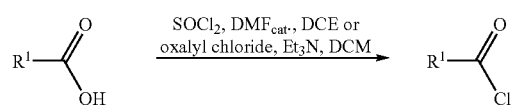 |
| DD | 20 | 20a | 7 | 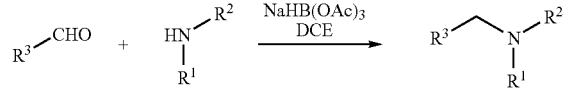 |
| EE | 10 | 10a | 2 |  |
| FF | 14 | 14a | 4 | 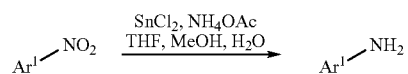 |
| GG | 44 | 44 | 1 |  |
| HH | 28 | 28a | 3 | 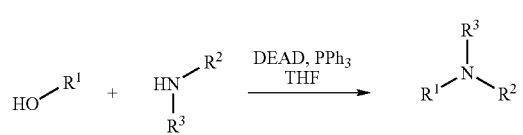 |

Ar¹, Ar², Ar³=Can be a clinical appropriate moiety for this reaction. Those included but are not limited to aryl or heteroaryl, alkenyl and alkynyl.

R¹, R², R³=Can be a clinical appropriate moiety for this reaction. Those included but are not limited to aryl, heteroaryl, alkyl, heterocyclyl, and cycloalkyl.

X=halogen

The compounds 56-58, 61-72, 320 and 372-389 described in this invention are prepared starting from the corresponding starting material and following the preparative sequence (general procedure A to O) indicated in Table 21.

TABLE 22

Characterization and preparative sequence of compounds synthesized

| Ex | Cpd | Starting material | Structure |
|---|---|---|---|
| 4a | 56 | 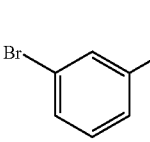 | 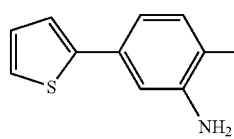 |
| 4b | 57 | 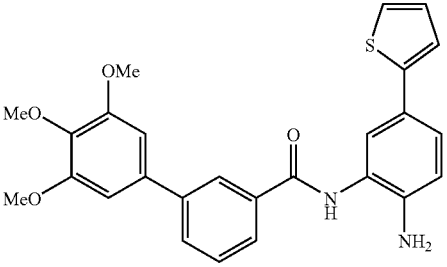 [SMILES: COc1cc(-c2cccc(C(=O)Nc3cc(-c4cccs4)ccc3N)c2)cc(OC)c1OC] | 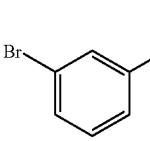 |
| 4c | 58 | 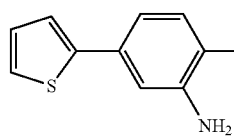 | 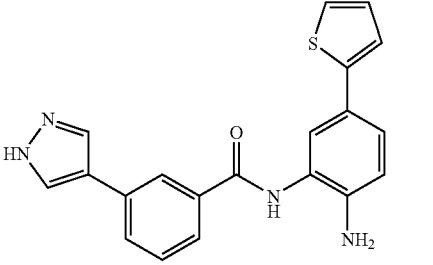 [SMILES: Nc1ccc(-c2cccs2)cc1NC(=O)c1cccc(-c2cn[nH]c2)c1] |
| 5a | 61 | 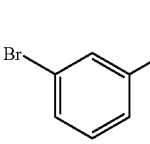 | 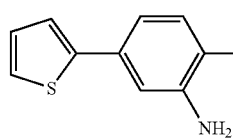 |
| 5b | 62 | 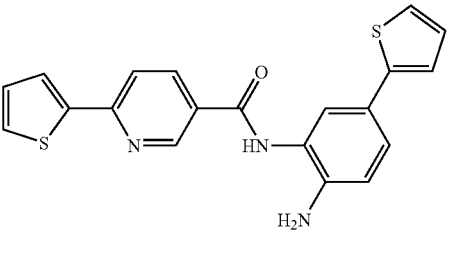 [SMILES: Nc1ccc(-c2cccs2)cc1NC(=O)c1ccc(-c2cccs2)nc1] | 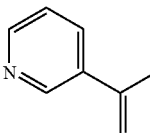 |

TABLE 22-continued
Characterization and preparative sequence of compounds synthesized
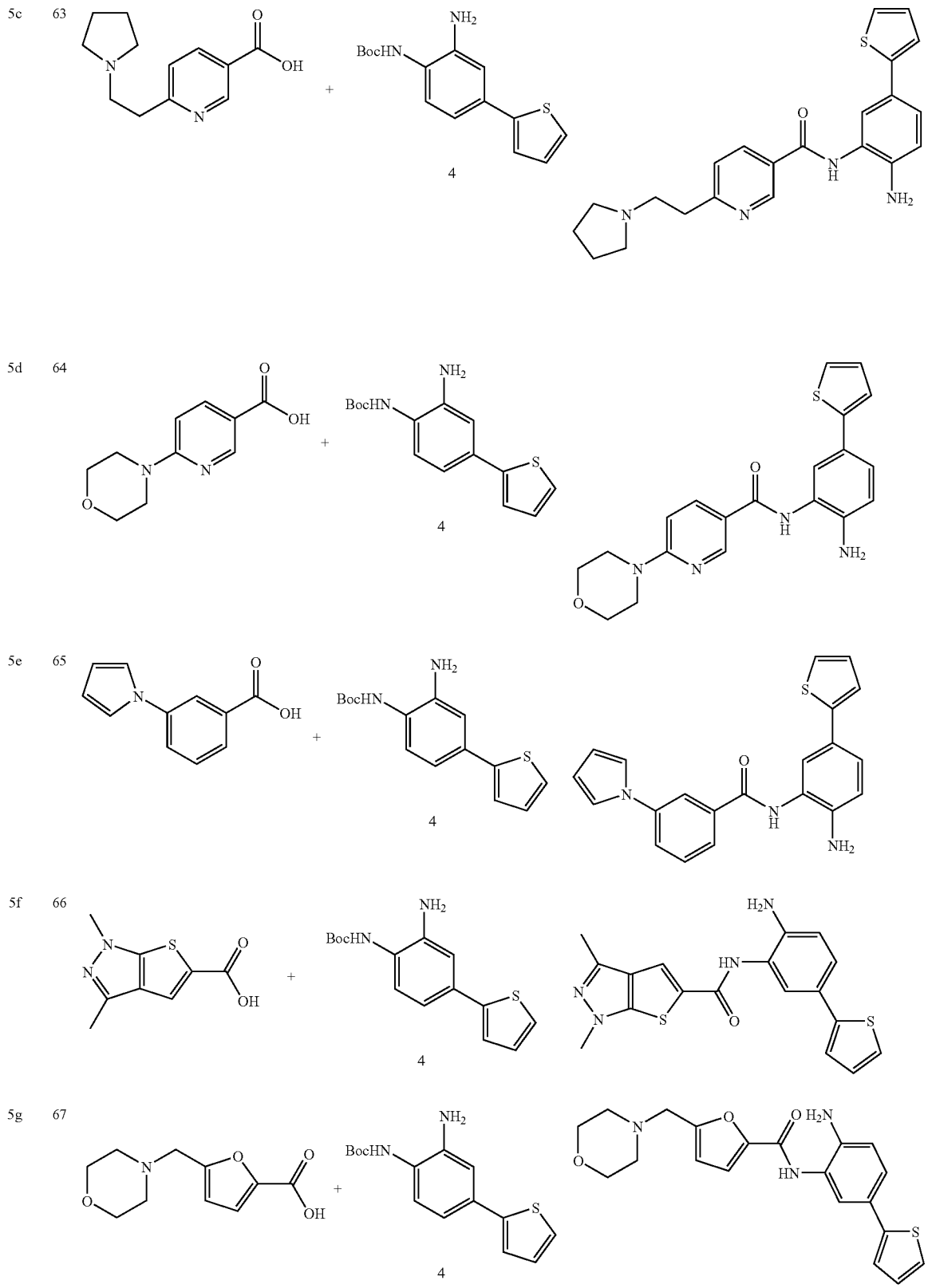

TABLE 22-continued
Characterization and preparative sequence of compounds synthesized
| 5h | 68 | 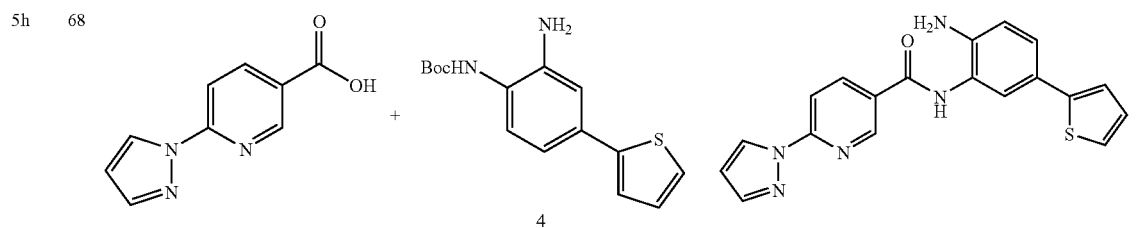 |
| 5i | 69 | 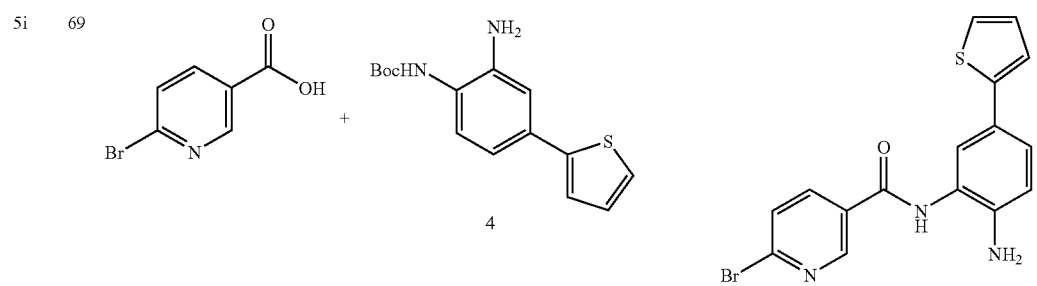 |
| 5j | 70 | 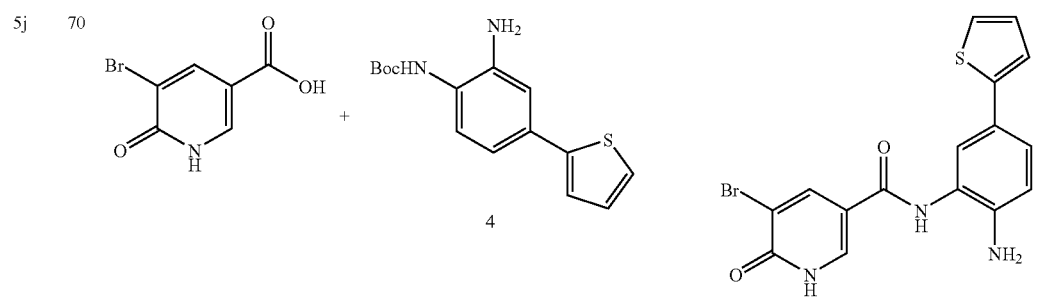 |
| 5k | 71 | 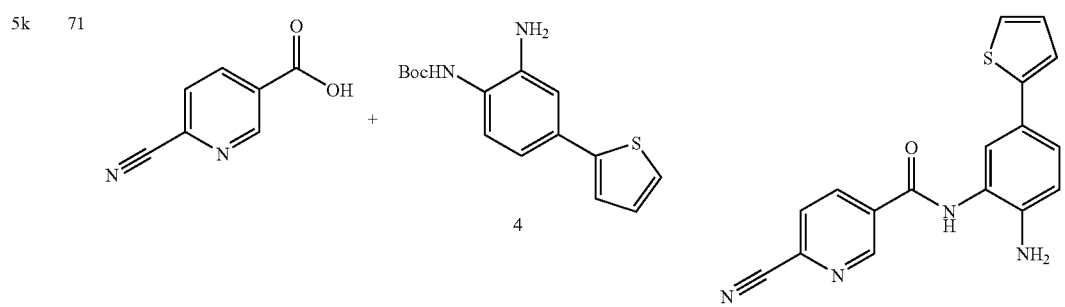 |
| 5l | 72 | 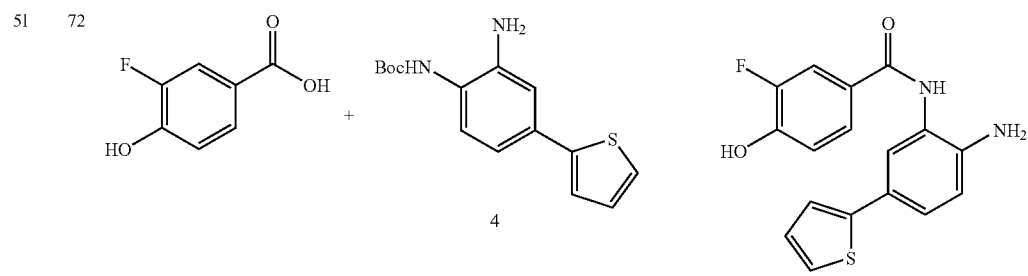 |

TABLE 22-continued
Characterization and preparative sequence of compounds synthesized
5m 372 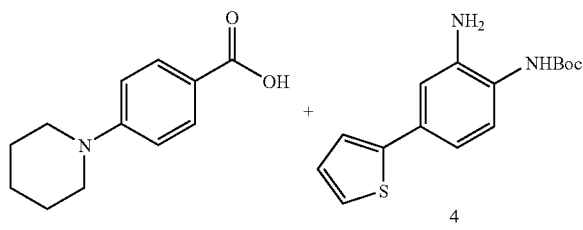 [SMILES: O=C(O)c1ccc(N2CCCCC2)cc1 ; CC(C)(C)OC(=O)Nc1ccc(-c2cccs2)cc1N] 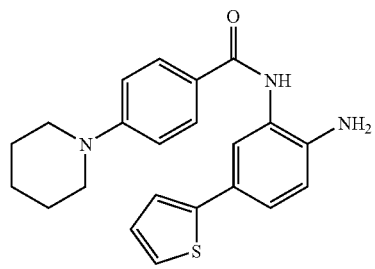 [SMILES: Nc1ccc(-c2cccs2)cc1NC(=O)c1ccc(N2CCCCC2)cc1]
5n 373 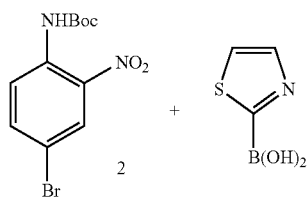 [SMILES: CC(C)(C)OC(=O)Nc1ccc(Br)cc1[N+](=O)[O-] ; OB(O)c1nccs1] 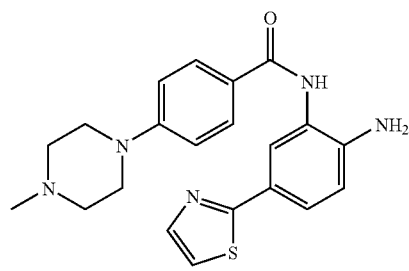 [SMILES: CN1CCN(c2ccc(C(=O)Nc3cc(-c4nccs4)ccc3N)cc2)CC1]
5o 374 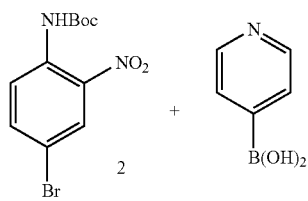 [SMILES: CC(C)(C)OC(=O)Nc1ccc(Br)cc1[N+](=O)[O-] ; OB(O)c1ccncc1] 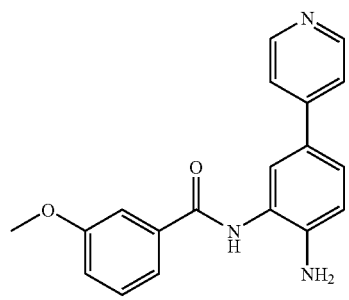 [SMILES: COc1cccc(C(=O)Nc2cc(-c3ccncc3)ccc2N)c1]
5p 375 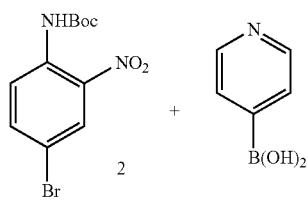 [SMILES: CC(C)(C)OC(=O)Nc1ccc(Br)cc1[N+](=O)[O-] ; OB(O)c1ccncc1] 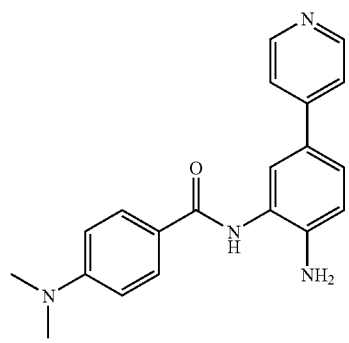 [SMILES: CN(C)c1ccc(C(=O)Nc2cc(-c3ccncc3)ccc2N)cc1]
5q 376 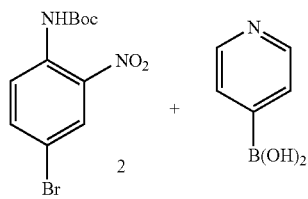 [SMILES: CC(C)(C)OC(=O)Nc1ccc(Br)cc1[N+](=O)[O-] ; OB(O)c1ccncc1] 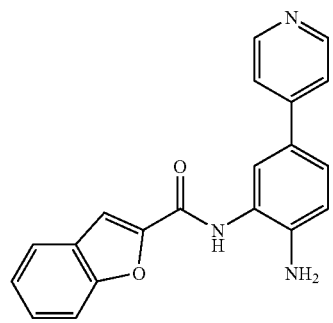 [SMILES: Nc1ccc(-c2ccncc2)cc1NC(=O)c1cc2ccccc2o1]

TABLE 22-continued
Characterization and preparative sequence of compounds synthesized
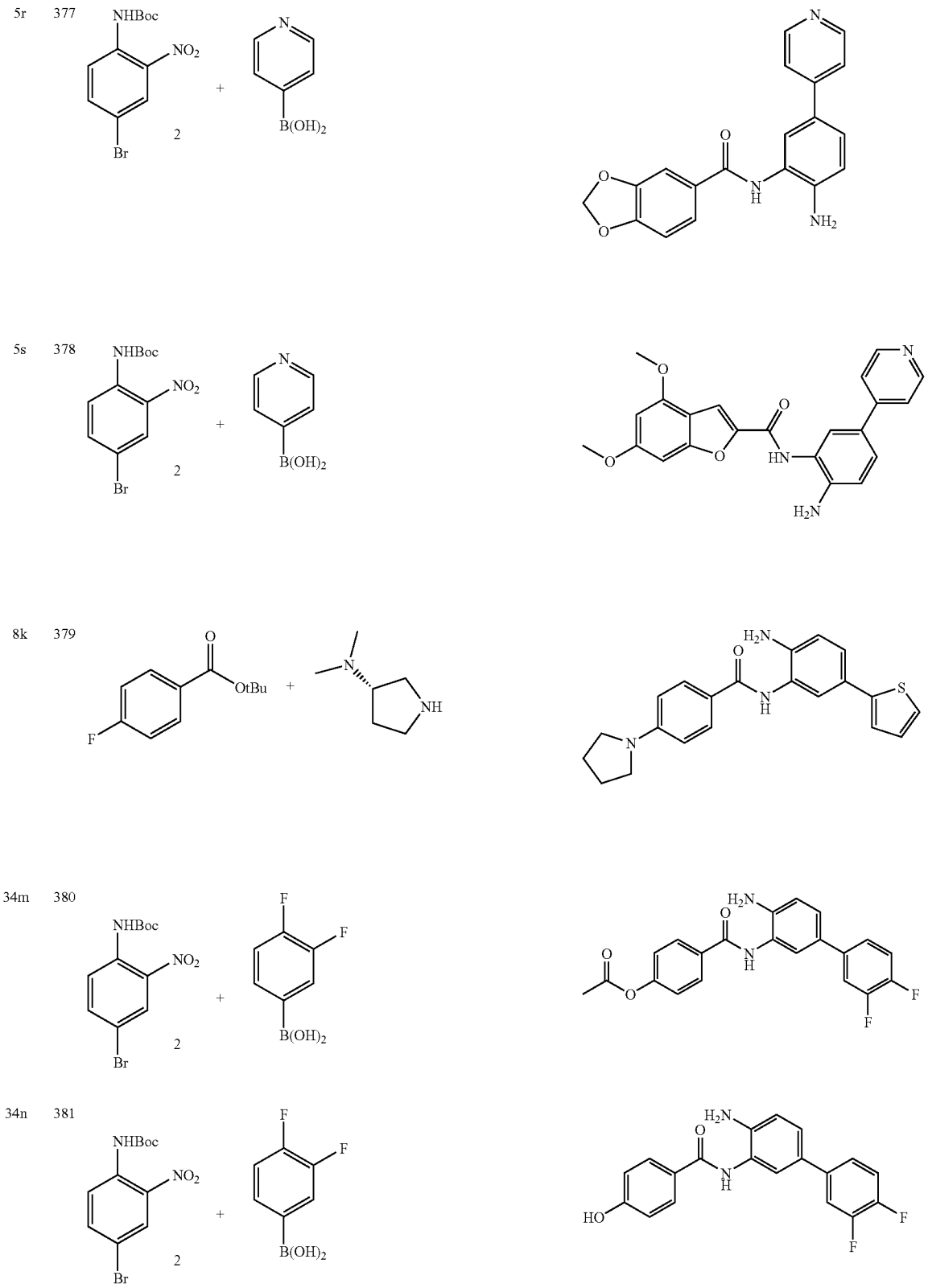

TABLE 22-continued
Characterization and preparative sequence of compounds synthesized
36  320 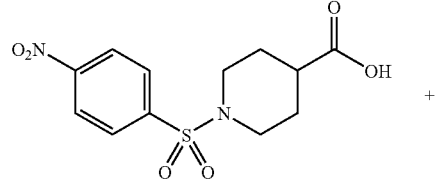 + 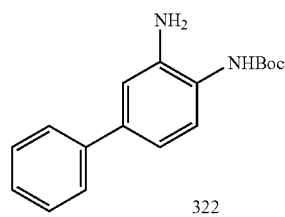 322 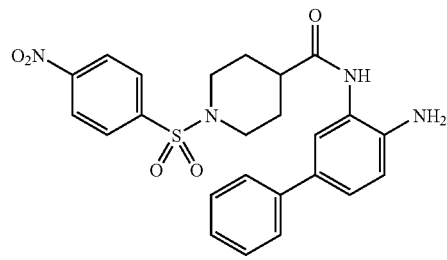 [SMILES: Nc1ccc(-c2ccccc2)cc1NC(=O)C1CCN(S(=O)(=O)c2ccc([N+](=O)[O-])cc2)CC1]
382 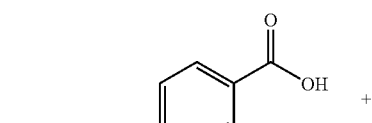 + 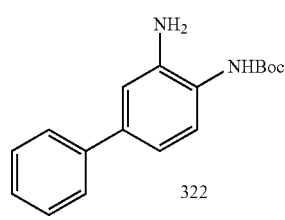 322 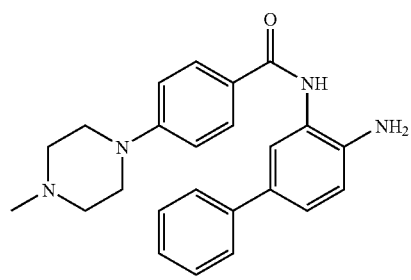 [SMILES: CN1CCN(c2ccc(C(=O)Nc3cc(-c4ccccc4)ccc3N)cc2)CC1]
383 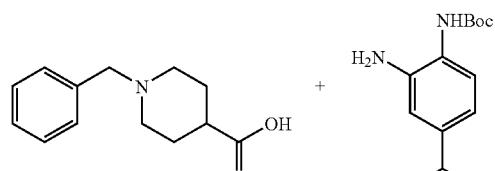 + 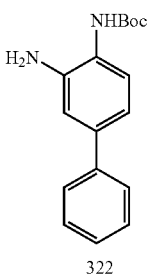 322 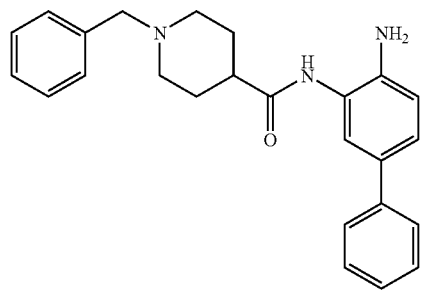 [SMILES: Nc1ccc(-c2ccccc2)cc1NC(=O)C1CCN(Cc2ccccc2)CC1]
384 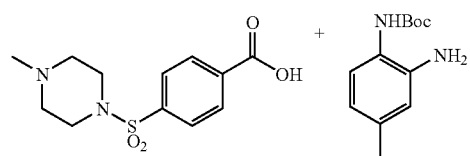 + 322 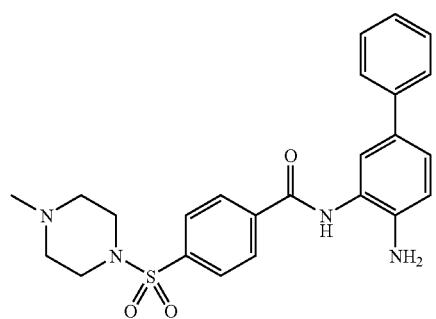 [SMILES: CN1CCN(S(=O)(=O)c2ccc(C(=O)Nc3cc(-c4ccccc4)ccc3N)cc2)CC1]

TABLE 22-continued
Characterization and preparative sequence of compounds synthesized
385 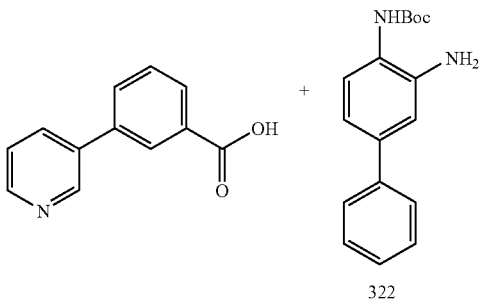 [SMILES: O=C(O)c1cccc(-c2cccnc2)c1 ; CC(C)(C)OC(=O)Nc1ccc(-c2ccccc2)cc1N] 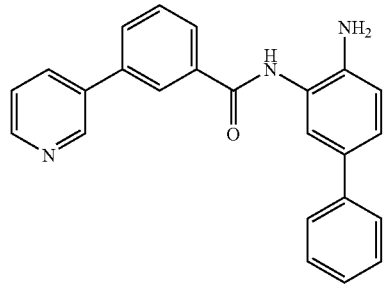 [SMILES: Nc1ccc(-c2ccccc2)cc1NC(=O)c1cccc(-c2cccnc2)c1]
386 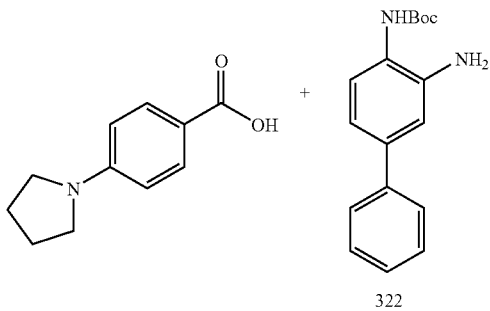 [SMILES: O=C(O)c1ccc(N2CCCC2)cc1 ; CC(C)(C)OC(=O)Nc1ccc(-c2ccccc2)cc1N] 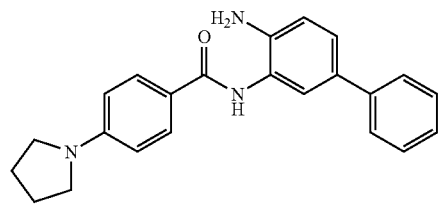 [SMILES: Nc1ccc(-c2ccccc2)cc1NC(=O)c1ccc(N2CCCC2)cc1]
387 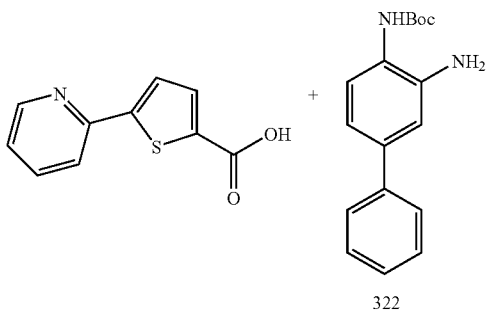 [SMILES: O=C(O)c1ccc(-c2ccccn2)s1 ; CC(C)(C)OC(=O)Nc1ccc(-c2ccccc2)cc1N] 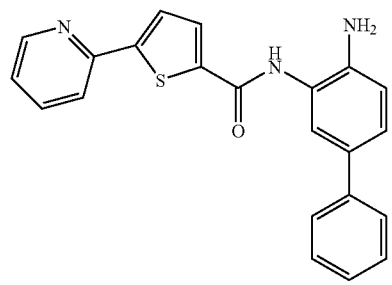 [SMILES: Nc1ccc(-c2ccccc2)cc1NC(=O)c1ccc(-c2ccccn2)s1]
388 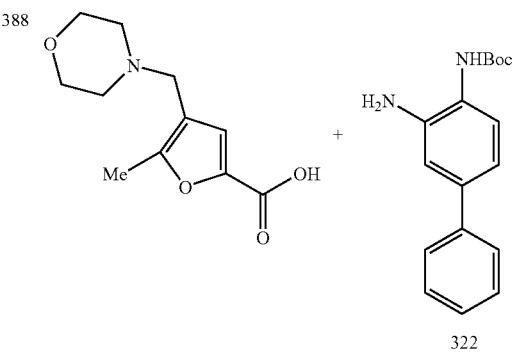 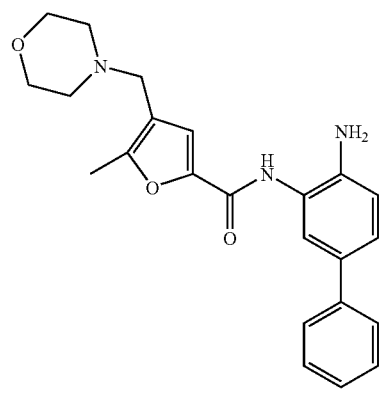 [SMILES: Cc1oc(C(=O)Nc2cc(-c3ccccc3)ccc2N)cc1CN1CCOCC1]

TABLE 22-continued
Characterization and preparative sequence of compounds synthesized
| | | |
|---|---|---|
| 389 | 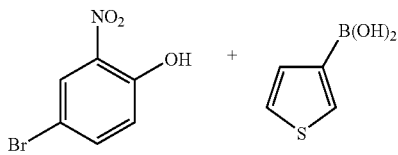 [SMILES: O=[N+]([O-])c1cc(Br)ccc1O ; OB(O)c1ccsc1] | 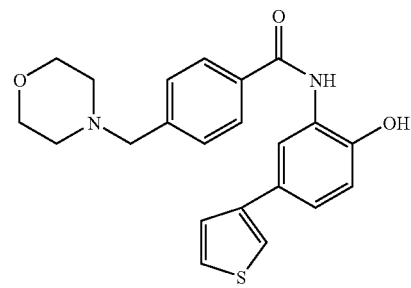 [SMILES: O=C(Nc1cc(-c2ccsc2)ccc1O)c1ccc(CN2CCOCC2)cc1] |
| 464 | 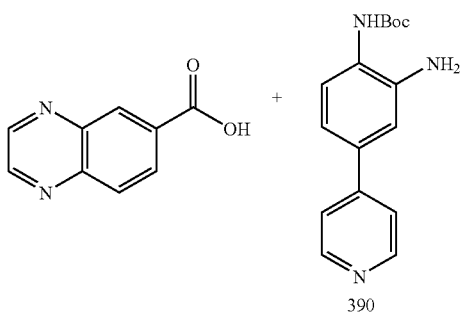 [SMILES: O=C(O)c1ccc2nccnc2c1 ; CC(C)(C)OC(=O)Nc1ccc(-c2ccncc2)cc1N] | 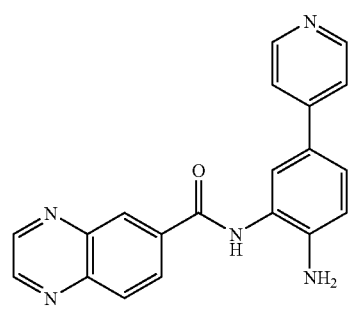 [SMILES: Nc1ccc(-c2ccncc2)cc1NC(=O)c1ccc2nccnc2c1] |
| 465 | 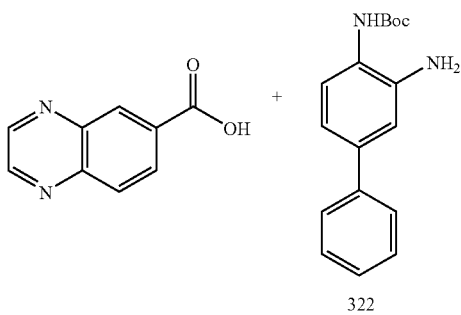 [SMILES: O=C(O)c1ccc2nccnc2c1 ; CC(C)(C)OC(=O)Nc1ccc(-c2ccccc2)cc1N] | 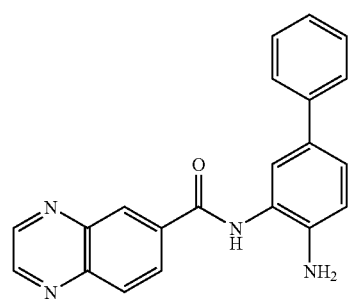 [SMILES: Nc1ccc(-c2ccccc2)cc1NC(=O)c1ccc2nccnc2c1] |
| 466 | 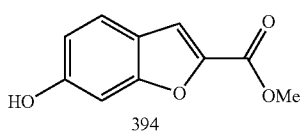 | 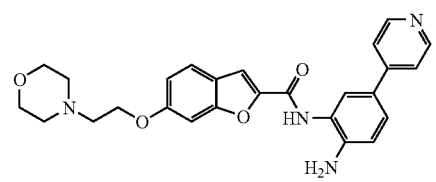 [SMILES: Nc1ccc(-c2ccncc2)cc1NC(=O)c1cc2ccc(OCCN3CCOCC3)cc2o1] |
| 467 | 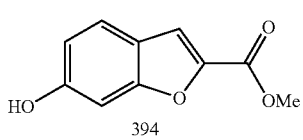 | 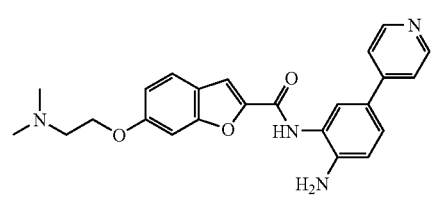 [SMILES: CN(C)CCOc1ccc2cc(C(=O)Nc3cc(-c4ccncc4)ccc3N)oc2c1] |
| 468 | 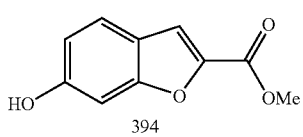 [SMILES: COC(=O)c1cc2ccc(O)cc2o1] | 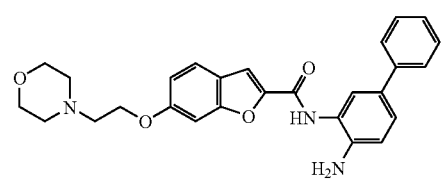 [SMILES: Nc1ccc(-c2ccccc2)cc1NC(=O)c1cc2ccc(OCCN3CCOCC3)cc2o1] |

TABLE 22-continued
Characterization and preparative sequence of compounds synthesized
469 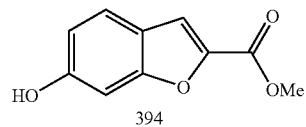 394 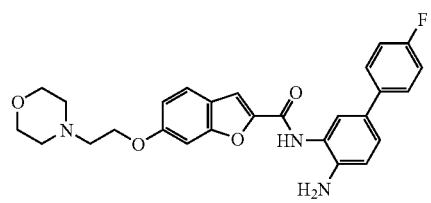 [SMILES: Nc1ccc(-c2ccc(F)cc2)cc1NC(=O)c1cc2ccc(OCCN3CCOCC3)cc2o1]
470 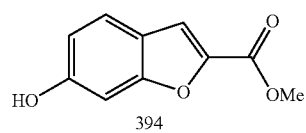 394 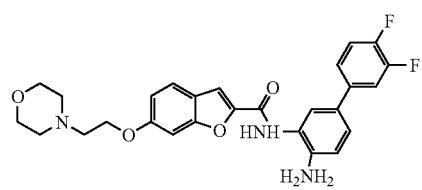
471 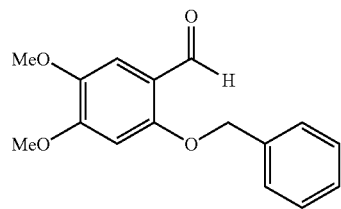 [SMILES: COc1cc(C=O)c(OCc2ccccc2)cc1OC] 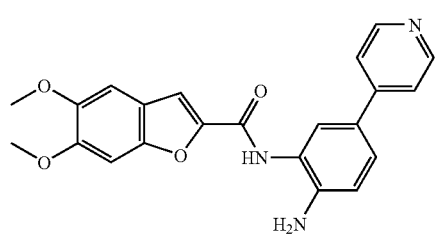 [SMILES: COc1cc2cc(C(=O)Nc3cc(-c4ccncc4)ccc3N)oc2cc1OC]
472 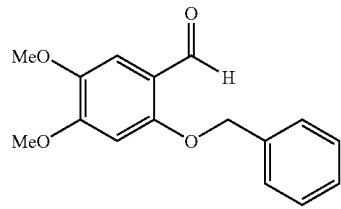 [SMILES: COc1cc(C=O)c(OCc2ccccc2)cc1OC] 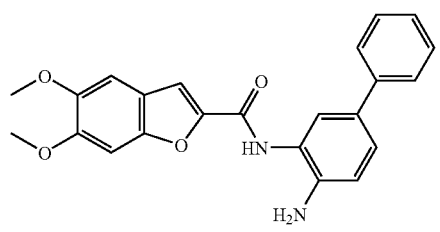 [SMILES: COc1cc2cc(C(=O)Nc3cc(-c4ccccc4)ccc3N)oc2cc1OC]
473 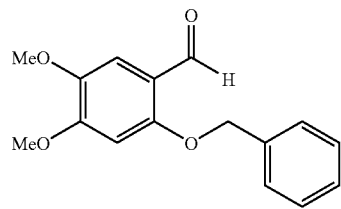 [SMILES: COc1cc(C=O)c(OCc2ccccc2)cc1OC] 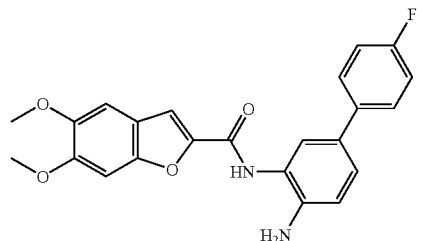
474 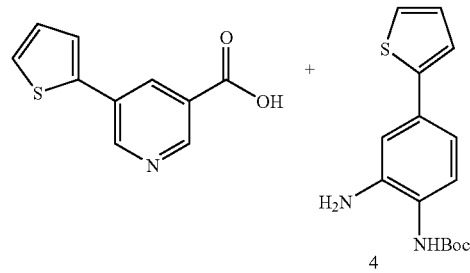 [SMILES: O=C(O)c1cncc(-c2cccs2)c1 ; CC(C)(C)OC(=O)Nc1ccc(-c2cccs2)cc1N] 4 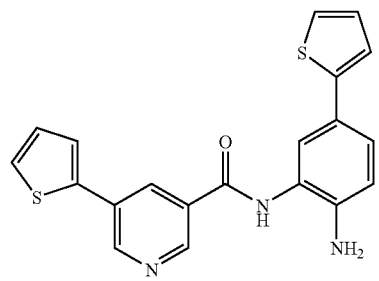 [SMILES: Nc1ccc(-c2cccs2)cc1NC(=O)c1cncc(-c2cccs2)c1]
475 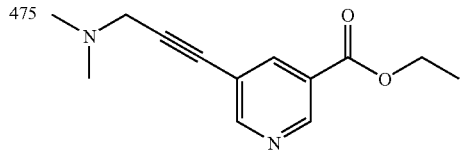 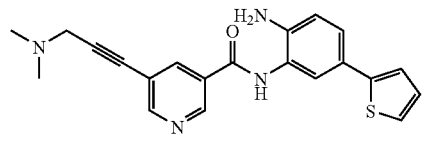 [SMILES: CN(C)CC#Cc1cncc(C(=O)Nc2cc(-c3cccs3)ccc2N)c1]

TABLE 22-continued
Characterization and preparative sequence of compounds synthesized
476 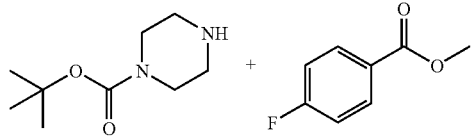 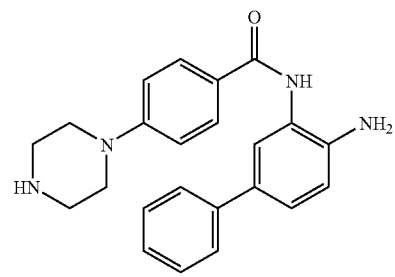 [SMILES: Nc1ccc(-c2ccccc2)cc1NC(=O)c1ccc(N2CCNCC2)cc1]
477 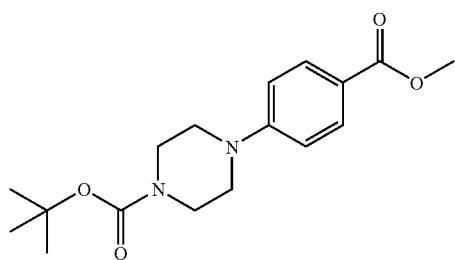 [SMILES: COC(=O)c1ccc(N2CCN(C(=O)OC(C)(C)C)CC2)cc1] 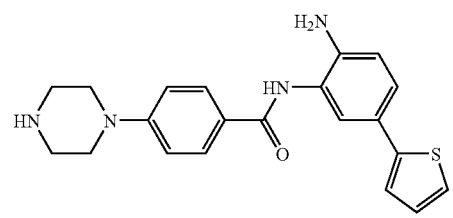 [SMILES: Nc1ccc(-c2cccs2)cc1NC(=O)c1ccc(N2CCNCC2)cc1]
478 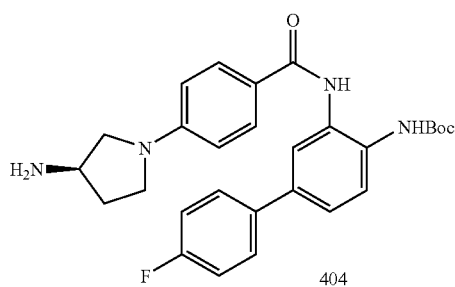 [SMILES: CC(C)(C)OC(=O)Nc1ccc(-c2ccc(F)cc2)cc1NC(=O)c1ccc(N2CC[C@@H](N)C2)cc1] 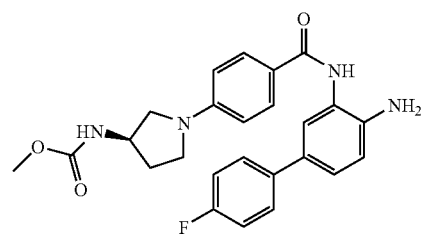 [SMILES: COC(=O)N[C@@H]1CCN(c2ccc(C(=O)Nc3cc(-c4ccc(F)cc4)ccc3N)cc2)C1]
404
479 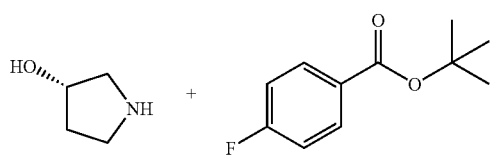 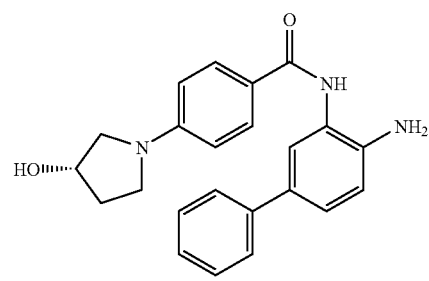 [SMILES: Nc1ccc(-c2ccccc2)cc1NC(=O)c1ccc(N2CC[C@H](O)C2)cc1]
480 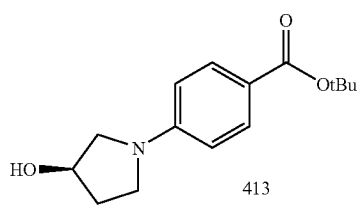 [SMILES: CC(C)(C)OC(=O)c1ccc(N2CC[C@@H](O)C2)cc1] 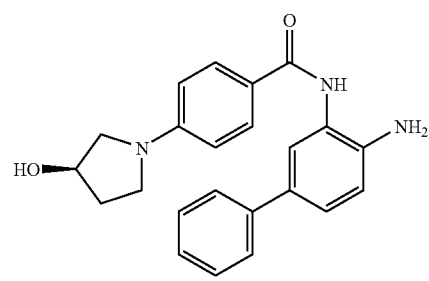 [SMILES: Nc1ccc(-c2ccccc2)cc1NC(=O)c1ccc(N2CC[C@@H](O)C2)cc1]
413

TABLE 22-continued
Characterization and preparative sequence of compounds synthesized
| | | | |
|---|---|---|---|
| 481 | 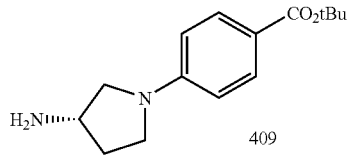 [SMILES: CC(C)(C)OC(=O)c1ccc(N2CC[C@H](N)C2)cc1] 409 | | 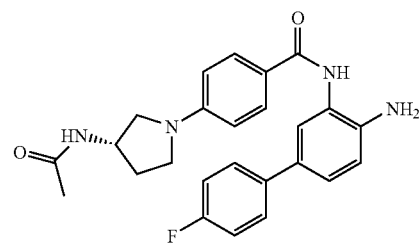 [SMILES: CC(=O)N[C@H]1CCN(c2ccc(C(=O)Nc3cc(-c4ccc(F)cc4)ccc3N)cc2)C1] |
| 482 | 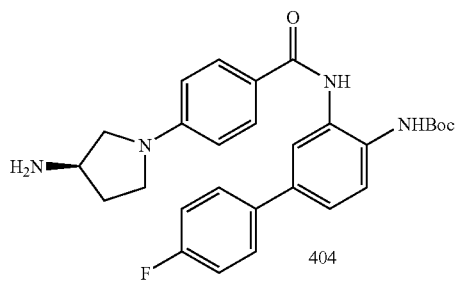 [SMILES: CC(C)(C)OC(=O)Nc1ccc(-c2ccc(F)cc2)cc1NC(=O)c1ccc(N2CC[C@@H](N)C2)cc1] 404 | | 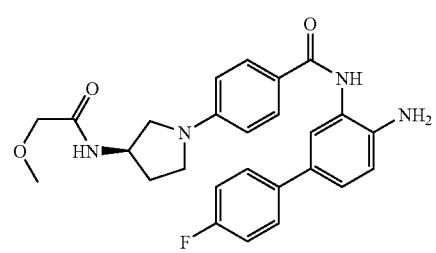 [SMILES: COCC(=O)N[C@@H]1CCN(c2ccc(C(=O)Nc3cc(-c4ccc(F)cc4)ccc3N)cc2)C1] |
| 483 | 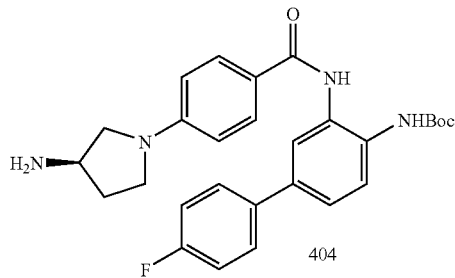 [SMILES: CC(C)(C)OC(=O)Nc1ccc(-c2ccc(F)cc2)cc1NC(=O)c1ccc(N2CC[C@@H](N)C2)cc1] 404 | | 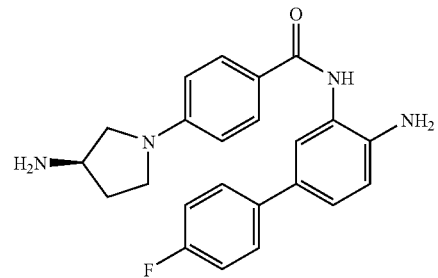 [SMILES: Nc1ccc(-c2ccc(F)cc2)cc1NC(=O)c1ccc(N2CC[C@@H](N)C2)cc1] |
| 484 | 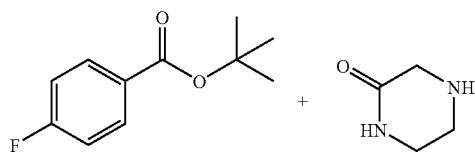 | | 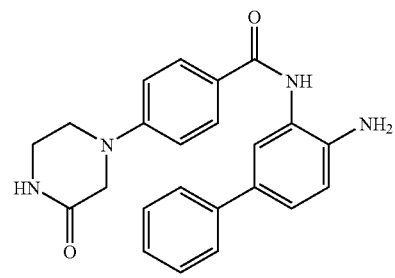 [SMILES: Nc1ccc(-c2ccccc2)cc1NC(=O)c1ccc(N2CCNC(=O)C2)cc1] |
| 485 | 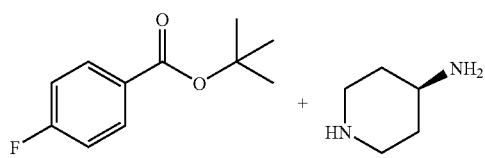 | | 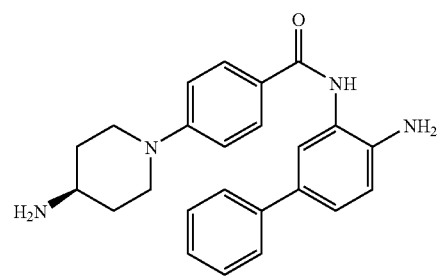 |

TABLE 22-continued
Characterization and preparative sequence of compounds synthesized
486 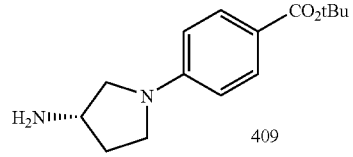 [SMILES: CC(C)(C)OC(=O)c1ccc(N2CC[C@H](N)C2)cc1] 409 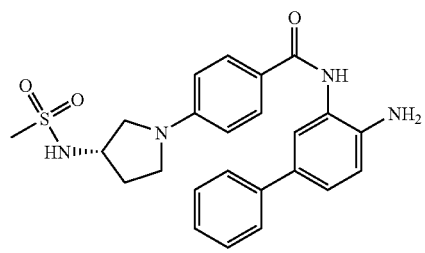 [SMILES: CS(=O)(=O)N[C@H]1CCN(c2ccc(C(=O)Nc3cc(-c4ccccc4)ccc3N)cc2)C1]
487 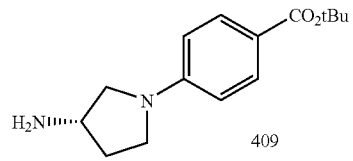 [SMILES: CC(C)(C)OC(=O)c1ccc(N2CC[C@H](N)C2)cc1] 409 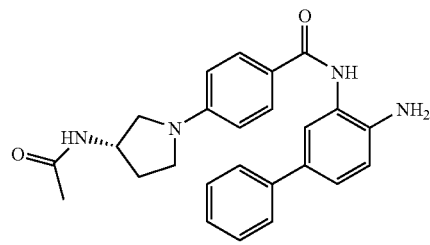 [SMILES: CC(=O)N[C@H]1CCN(c2ccc(C(=O)Nc3cc(-c4ccccc4)ccc3N)cc2)C1]
488 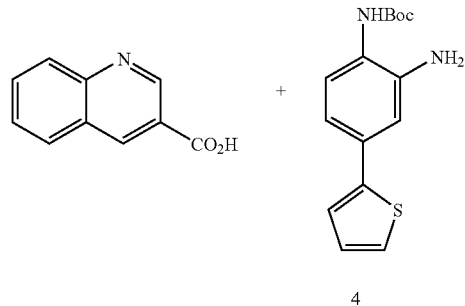 [SMILES: O=C(O)c1cnc2ccccc2c1 ; CC(C)(C)OC(=O)Nc1ccc(-c2cccs2)cc1N] 4 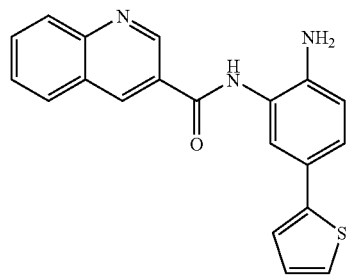 [SMILES: Nc1ccc(-c2cccs2)cc1NC(=O)c1cnc2ccccc2c1]
489 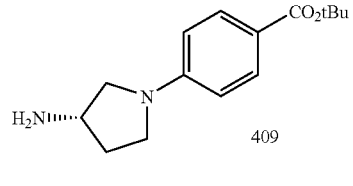 [SMILES: CC(C)(C)OC(=O)c1ccc(N2CC[C@H](N)C2)cc1] 409 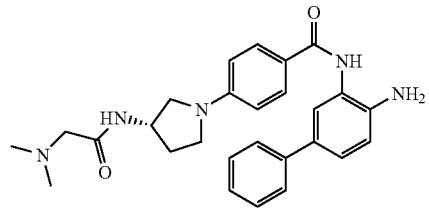 [SMILES: CN(C)CC(=O)N[C@H]1CCN(c2ccc(C(=O)Nc3cc(-c4ccccc4)ccc3N)cc2)C1]
490 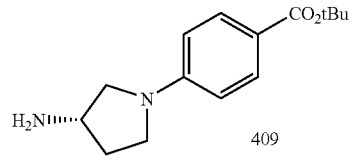 [SMILES: CC(C)(C)OC(=O)c1ccc(N2CC[C@H](N)C2)cc1] 409 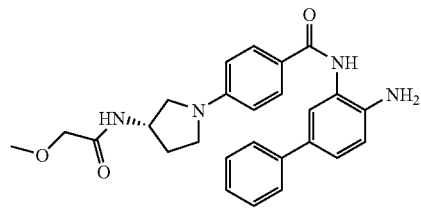 [SMILES: COCC(=O)N[C@H]1CCN(c2ccc(C(=O)Nc3cc(-c4ccccc4)ccc3N)cc2)C1]
491 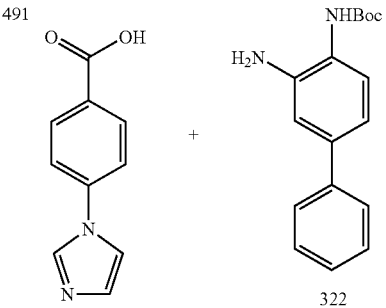 322 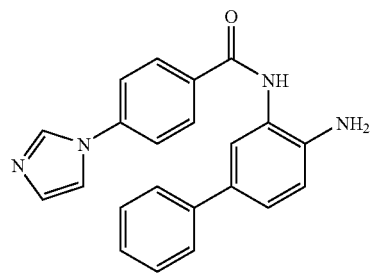 [SMILES: Nc1ccc(-c2ccccc2)cc1NC(=O)c1ccc(-n2ccnc2)cc1]

TABLE 22-continued
Characterization and preparative sequence of compounds synthesized
492 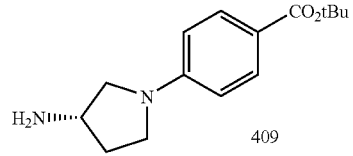 [SMILES: CC(C)(C)OC(=O)c1ccc(N2CC[C@H](N)C2)cc1] 409 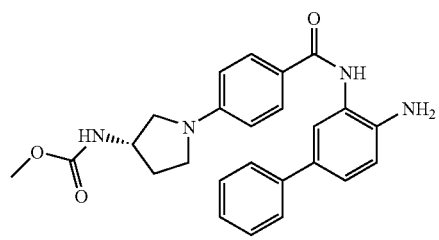 [SMILES: COC(=O)N[C@H]1CCN(c2ccc(C(=O)Nc3cc(-c4ccccc4)ccc3N)cc2)C1]
493 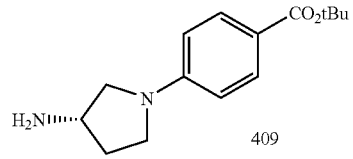 [SMILES: CC(C)(C)OC(=O)c1ccc(N2CC[C@H](N)C2)cc1] 409 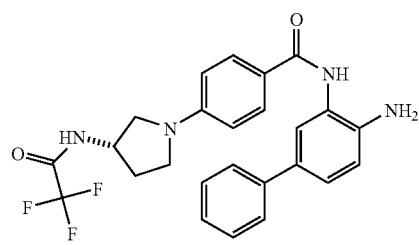 [SMILES: Nc1ccc(-c2ccccc2)cc1NC(=O)c1ccc(N2CC[C@H](NC(=O)C(F)(F)F)C2)cc1]
494 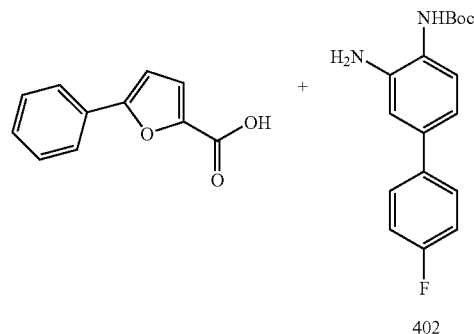 [SMILES: O=C(O)c1ccc(-c2ccccc2)o1 ; CC(C)(C)OC(=O)Nc1ccc(-c2ccc(F)cc2)cc1N] 402 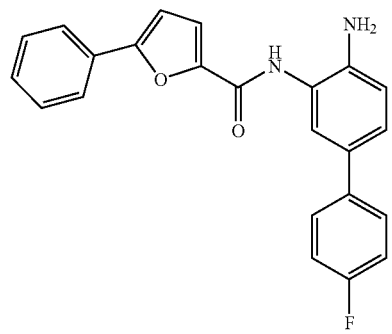 [SMILES: Nc1ccc(-c2ccc(F)cc2)cc1NC(=O)c1ccc(-c2ccccc2)o1]
495 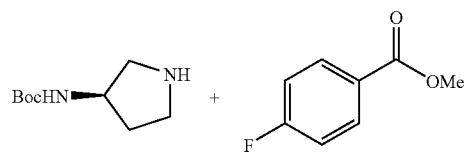 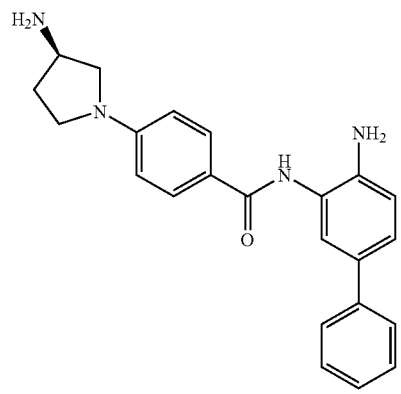 [SMILES: Nc1ccc(-c2ccccc2)cc1NC(=O)c1ccc(N2CC[C@@H](N)C2)cc1]
496 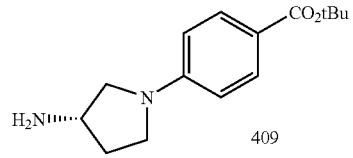 [SMILES: CC(C)(C)OC(=O)c1ccc(N2CC[C@H](N)C2)cc1] 409 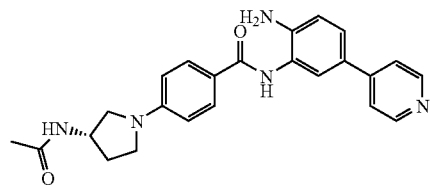 [SMILES: CC(=O)N[C@H]1CCN(c2ccc(C(=O)Nc3cc(-c4ccncc4)ccc3N)cc2)C1]
497 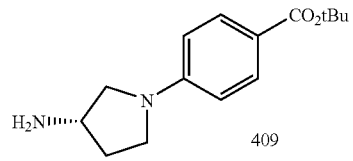 [SMILES: CC(C)(C)OC(=O)c1ccc(N2CC[C@H](N)C2)cc1] 409 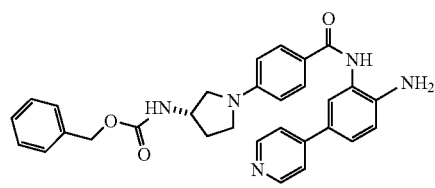 [SMILES: Nc1ccc(-c2ccncc2)cc1NC(=O)c1ccc(N2CC[C@H](NC(=O)OCc3ccccc3)C2)cc1]

TABLE 22-continued
Characterization and preparative sequence of compounds synthesized
498
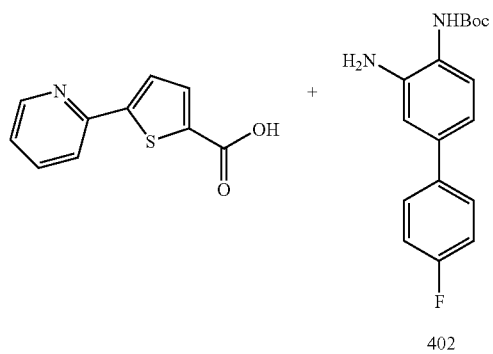 [SMILES: O=C(O)c1ccc(-c2ccccn2)s1 ; CC(C)(C)OC(=O)Nc1ccc(-c2ccc(F)cc2)cc1N] 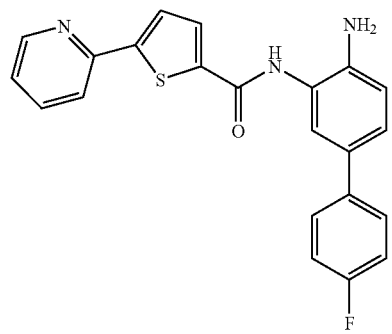 [SMILES: Nc1ccc(-c2ccc(F)cc2)cc1NC(=O)c1ccc(-c2ccccn2)s1]
402
499
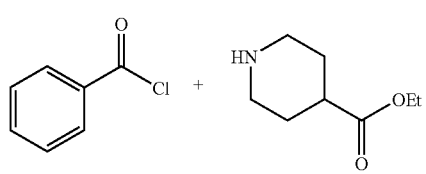 [SMILES: O=C(Cl)c1ccccc1 ; CCOC(=O)C1CCNCC1] 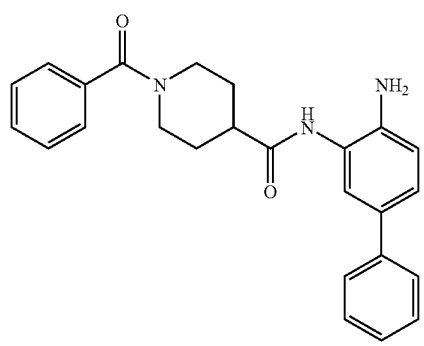 [SMILES: Nc1ccc(-c2ccccc2)cc1NC(=O)C1CCN(C(=O)c2ccccc2)CC1]
500
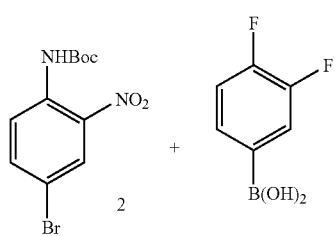 [SMILES: CC(C)(C)OC(=O)Nc1ccc(Br)cc1[N+](=O)[O-] ; OB(O)c1ccc(F)c(F)c1] 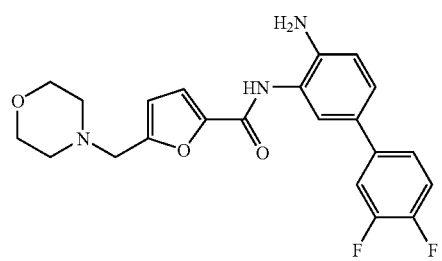 [SMILES: Nc1ccc(-c2ccc(F)c(F)c2)cc1NC(=O)c1ccc(CN2CCOCC2)o1]
501
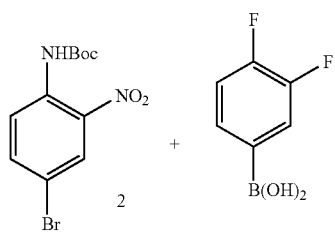 [SMILES: CC(C)(C)OC(=O)Nc1ccc(Br)cc1[N+](=O)[O-] ; OB(O)c1ccc(F)c(F)c1] 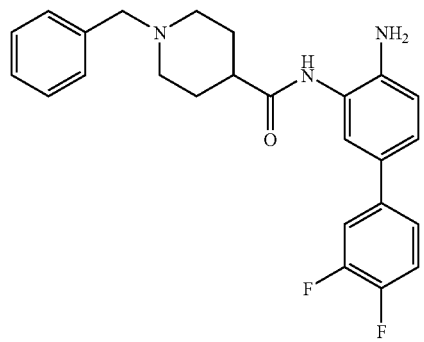 [SMILES: Nc1ccc(-c2ccc(F)c(F)c2)cc1NC(=O)C1CCN(Cc2ccccc2)CC1]
502
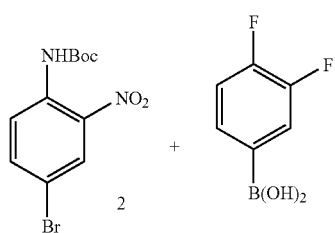 [SMILES: CC(C)(C)OC(=O)Nc1ccc(Br)cc1[N+](=O)[O-] ; OB(O)c1ccc(F)c(F)c1] 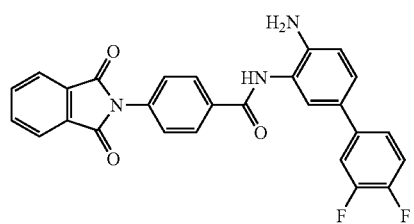 [SMILES: Nc1ccc(-c2ccc(F)c(F)c2)cc1NC(=O)c1ccc(N2C(=O)c3ccccc3C2=O)cc1]

TABLE 22-continued
Characterization and preparative sequence of compounds synthesized
503 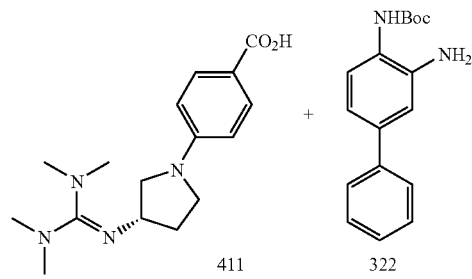 [SMILES: CN(C)C(=N[C@H]1CCN(c2ccc(C(=O)O)cc2)C1)N(C)C ; CC(C)(C)OC(=O)Nc1ccc(-c2ccccc2)cc1N] 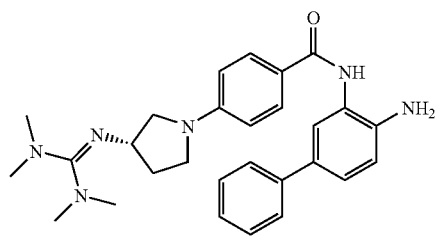 [SMILES: CN(C)C(=N[C@H]1CCN(c2ccc(C(=O)Nc3cc(-c4ccccc4)ccc3N)cc2)C1)N(C)C]
504 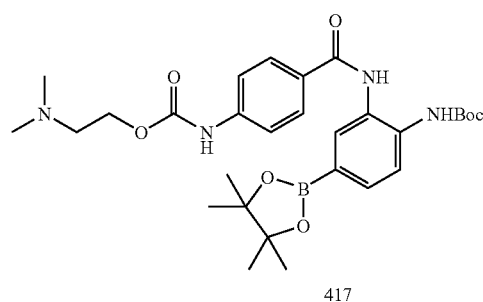 [SMILES: CN(C)CCOC(=O)Nc1ccc(C(=O)Nc2cc(B3OC(C)(C)C(C)(C)O3)ccc2NC(=O)OC(C)(C)C)cc1] 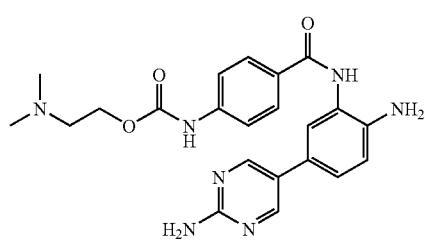 [SMILES: CN(C)CCOC(=O)Nc1ccc(C(=O)Nc2cc(-c3cnc(N)nc3)ccc2N)cc1]
505 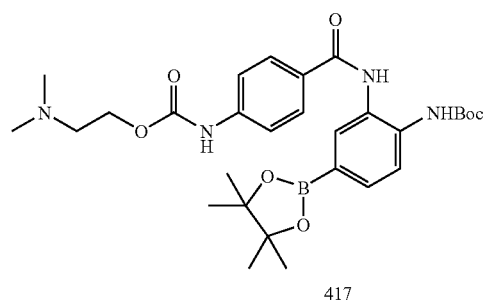 [SMILES: CN(C)CCOC(=O)Nc1ccc(C(=O)Nc2cc(B3OC(C)(C)C(C)(C)O3)ccc2NC(=O)OC(C)(C)C)cc1] 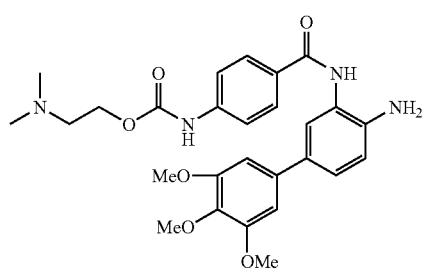 [SMILES: COc1cc(-c2ccc(N)c(NC(=O)c3ccc(NC(=O)OCCN(C)C)cc3)c2)cc(OC)c1OC]
506 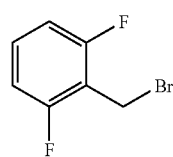 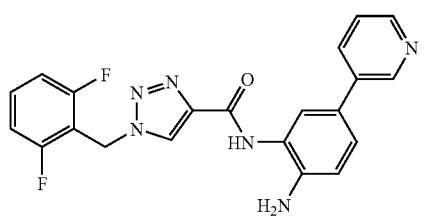 [SMILES: Nc1ccc(-c2cccnc2)cc1NC(=O)c1cn(Cc2c(F)cccc2F)nn1]
507 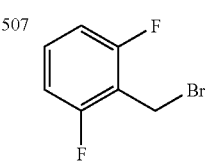 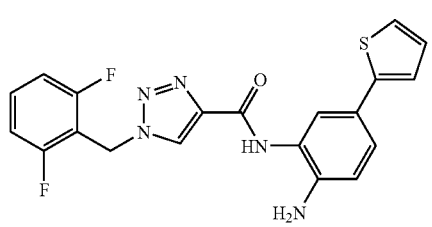 [SMILES: Nc1ccc(-c2cccs2)cc1NC(=O)c1cn(Cc2c(F)cccc2F)nn1]
508 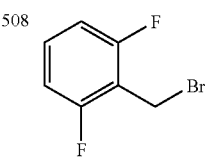 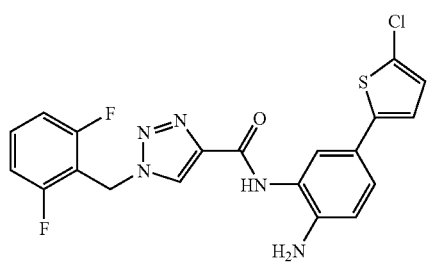 [SMILES: Nc1ccc(-c2ccc(Cl)s2)cc1NC(=O)c1cn(Cc2c(F)cccc2F)nn1]

TABLE 22-continued
Characterization and preparative sequence of compounds synthesized
509 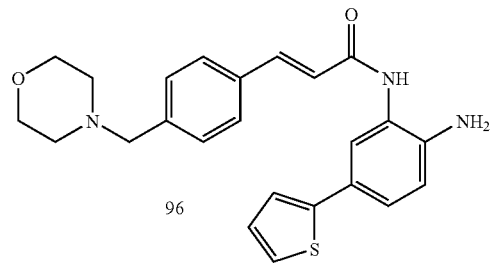 [SMILES: Nc1ccc(-c2cccs2)cc1NC(=O)/C=C/c1ccc(CN2CCOCC2)cc1] 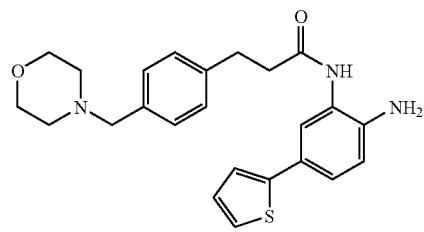 [SMILES: Nc1ccc(-c2cccs2)cc1NC(=O)CCc1ccc(CN2CCOCC2)cc1]
96
510 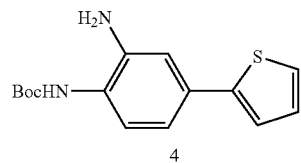 [SMILES: CC(C)(C)OC(=O)Nc1ccc(-c2cccs2)cc1N] 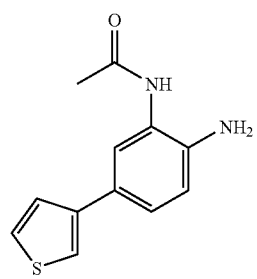 [SMILES: CC(=O)Nc1cc(-c2ccsc2)ccc1N]
4
511 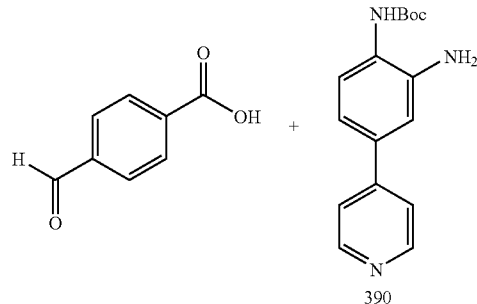 [SMILES: O=Cc1ccc(C(=O)O)cc1 ; CC(C)(C)OC(=O)Nc1ccc(-c2ccncc2)cc1N] 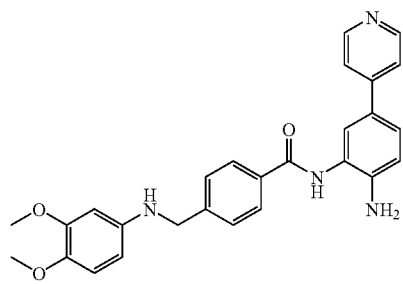 [SMILES: COc1ccc(NCc2ccc(C(=O)Nc3cc(-c4ccncc4)ccc3N)cc2)cc1OC]
390
512 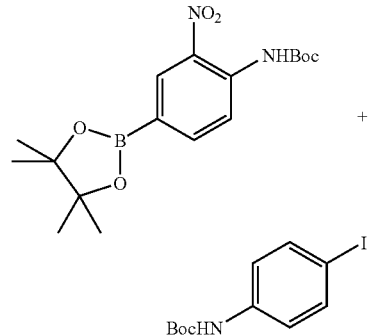 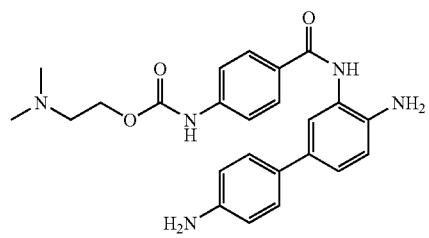 [SMILES: CN(C)CCOC(=O)Nc1ccc(C(=O)Nc2cc(-c3ccc(N)cc3)ccc2N)cc1]
254

TABLE 22-continued
Characterization and preparative sequence of compounds synthesized
513 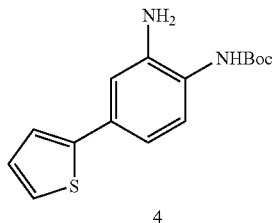 + 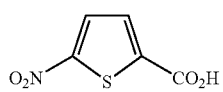 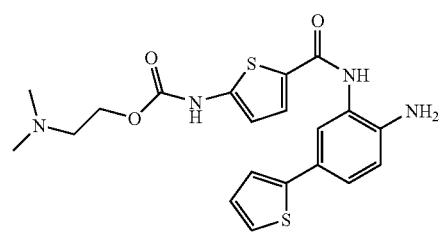 [SMILES: CN(C)CCOC(=O)Nc1ccc(C(=O)Nc2cc(-c3cccs3)ccc2N)s1]
514 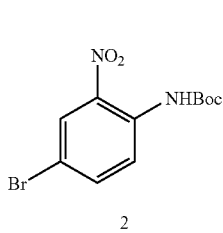 + 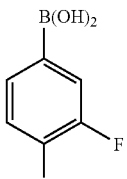 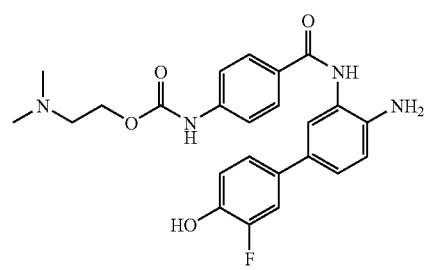 [SMILES: CN(C)CCOC(=O)Nc1ccc(C(=O)Nc2cc(-c3ccc(O)c(F)c3)ccc2N)cc1]
515 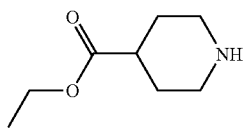 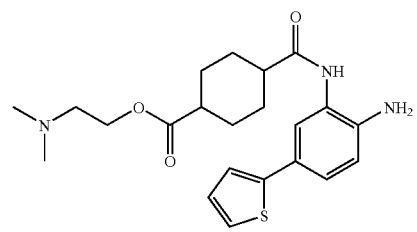 [SMILES: CN(C)CCOC(=O)C1CCC(C(=O)Nc2cc(-c3cccs3)ccc2N)CC1]
516 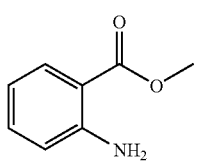 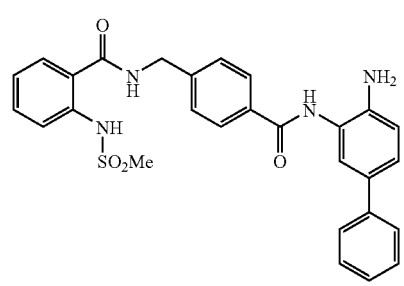 [SMILES: CS(=O)(=O)Nc1ccccc1C(=O)NCc1ccc(C(=O)Nc2cc(-c3ccccc3)ccc2N)cc1]
517 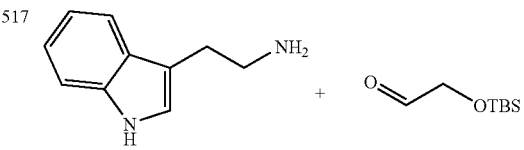 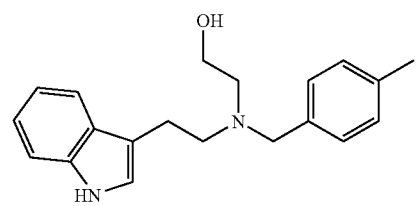
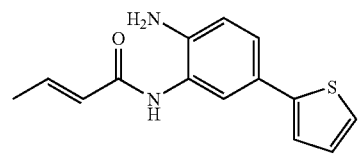

TABLE 22-continued
Characterization and preparative sequence of compounds synthesized
518
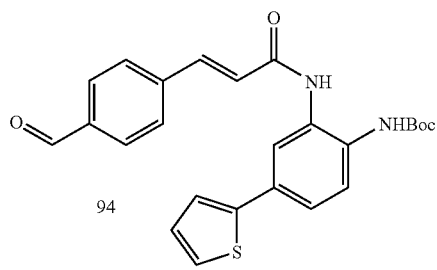 [SMILES: CC(C)(C)OC(=O)Nc1ccc(-c2cccs2)cc1NC(=O)/C=C/c1ccc(C=O)cc1]
94
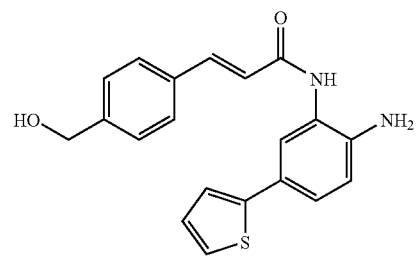 [SMILES: Nc1ccc(-c2cccs2)cc1NC(=O)/C=C/c1ccc(CO)cc1]
519
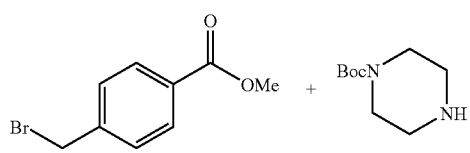 [SMILES: COC(=O)c1ccc(CBr)cc1 ; CC(C)(C)OC(=O)N1CCNCC1]
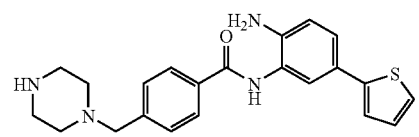 [SMILES: Nc1ccc(-c2cccs2)cc1NC(=O)c1ccc(CN2CCNCC2)cc1]
520
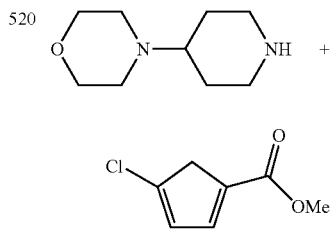
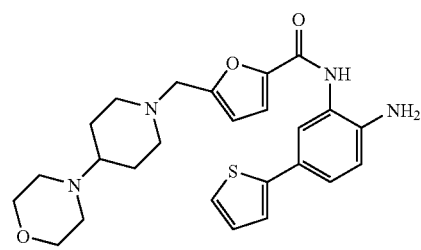 [SMILES: Nc1ccc(-c2cccs2)cc1NC(=O)c1ccc(CN2CCC(N3CCOCC3)CC2)o1]
521
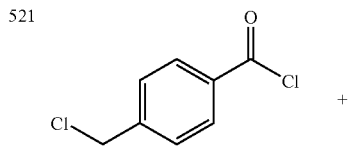
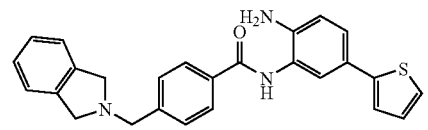 [SMILES: Nc1ccc(-c2cccs2)cc1NC(=O)c1ccc(CN2Cc3ccccc3C2)cc1]
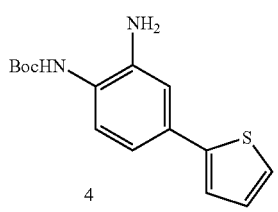
4
522
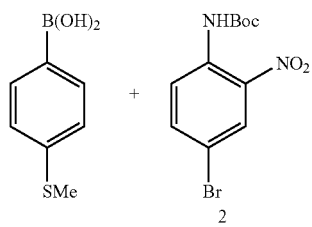 [SMILES: CSc1ccc(B(O)O)cc1 ; CC(C)(C)OC(=O)Nc1ccc(Br)cc1[N+](=O)[O-]]
2
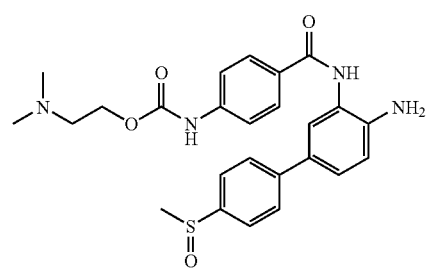 [SMILES: CN(C)CCOC(=O)Nc1ccc(C(=O)Nc2cc(-c3ccc(S(C)=O)cc3)ccc2N)cc1]
523
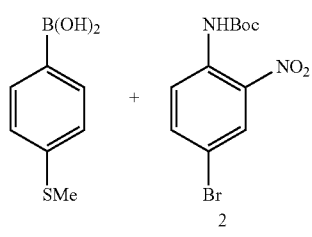 [SMILES: CSc1ccc(B(O)O)cc1 ; CC(C)(C)OC(=O)Nc1ccc(Br)cc1[N+](=O)[O-]]
2
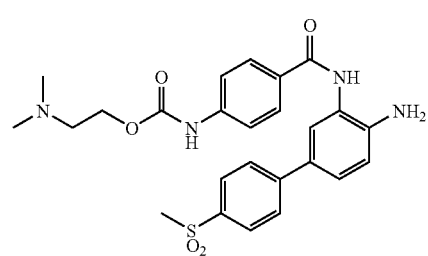 [SMILES: CN(C)CCOC(=O)Nc1ccc(C(=O)Nc2cc(-c3ccc(S(C)(=O)=O)cc3)ccc2N)cc1]

TABLE 22-continued
Characterization and preparative sequence of compounds synthesized
524 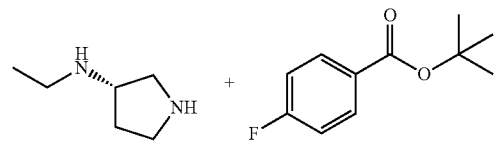 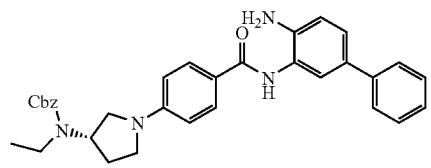 [SMILES: CCN(C(=O)OCc1ccccc1)[C@H]1CCN(c2ccc(C(=O)Nc3cc(-c4ccccc4)ccc3N)cc2)C1]
525 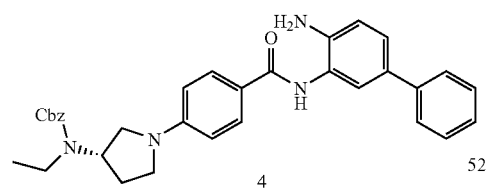 [SMILES: CCN(C(=O)OCc1ccccc1)[C@H]1CCN(c2ccc(C(=O)Nc3cc(-c4ccccc4)ccc3N)cc2)C1] 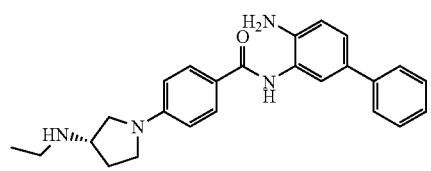 [SMILES: CCN[C@H]1CCN(c2ccc(C(=O)Nc3cc(-c4ccccc4)ccc3N)cc2)C1]
526 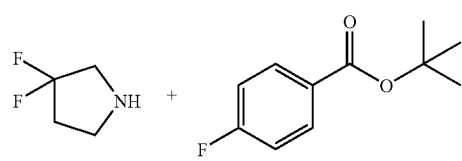 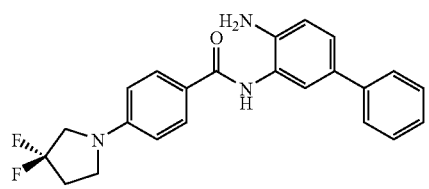
527 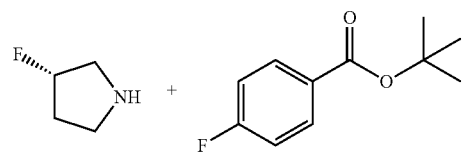 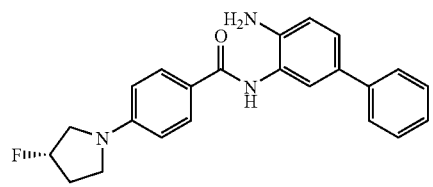 [SMILES: Nc1ccc(-c2ccccc2)cc1NC(=O)c1ccc(N2CC[C@H](F)C2)cc1]
528 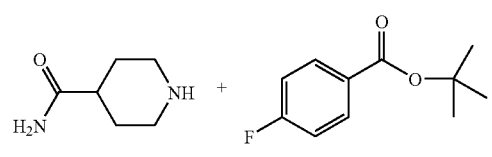 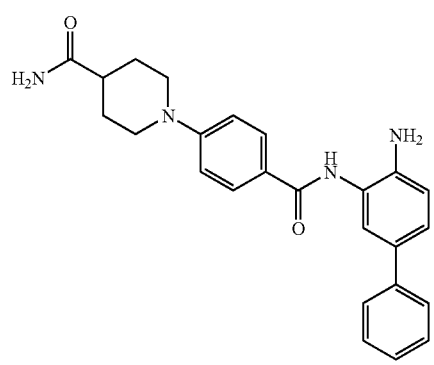 [SMILES: NC(=O)C1CCN(c2ccc(C(=O)Nc3cc(-c4ccccc4)ccc3N)cc2)CC1]
529 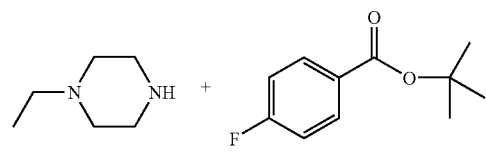 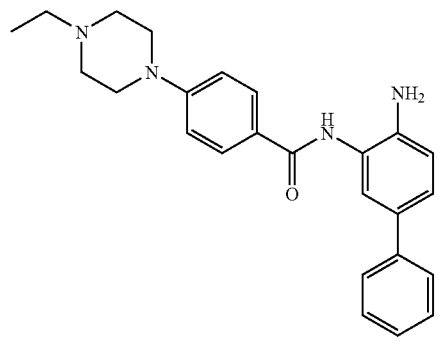 [SMILES: CCN1CCN(c2ccc(C(=O)Nc3cc(-c4ccccc4)ccc3N)cc2)CC1]

TABLE 22-continued
Characterization and preparative sequence of compounds synthesized
530 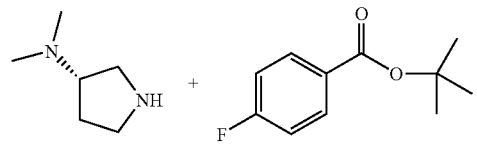 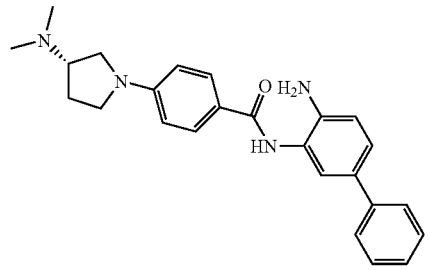 [SMILES: CN(C)[C@H]1CCN(c2ccc(C(=O)Nc3cc(-c4ccccc4)ccc3N)cc2)C1]
531 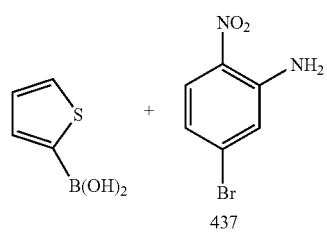 [SMILES: OB(O)c1cccs1 ; Nc1cc(Br)ccc1[N+](=O)[O-]]
437
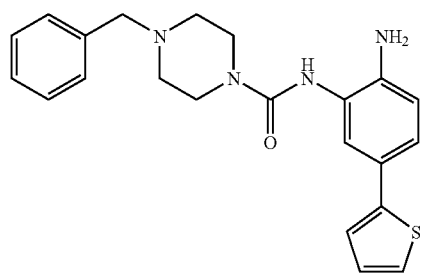 [SMILES: Nc1ccc(-c2cccs2)cc1NC(=O)N1CCN(Cc2ccccc2)CC1]
532 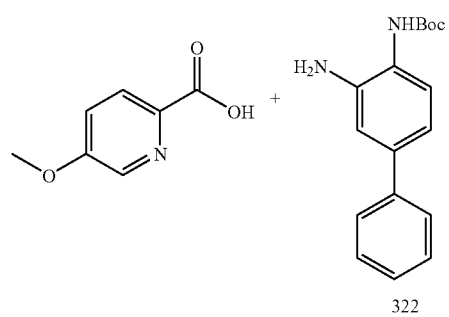 [SMILES: COc1ccc(C(=O)O)nc1 ; CC(C)(C)OC(=O)Nc1ccc(-c2ccccc2)cc1N]
322
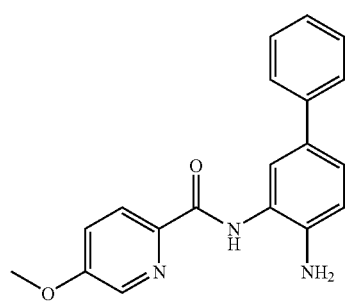 [SMILES: COc1ccc(C(=O)Nc2cc(-c3ccccc3)ccc2N)nc1]
533 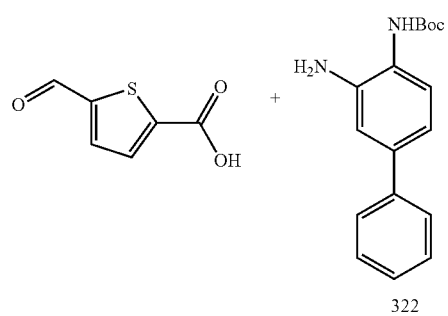 [SMILES: O=Cc1ccc(C(=O)O)s1 ; CC(C)(C)OC(=O)Nc1ccc(-c2ccccc2)cc1N]
322
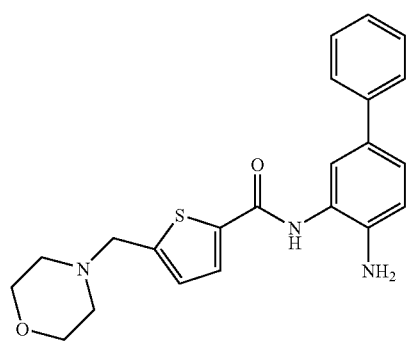 [SMILES: Nc1ccc(-c2ccccc2)cc1NC(=O)c1ccc(CN2CCOCC2)s1]
535 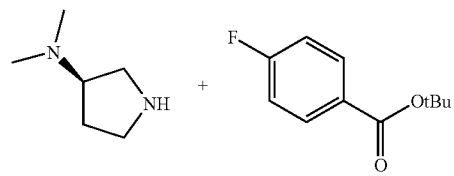 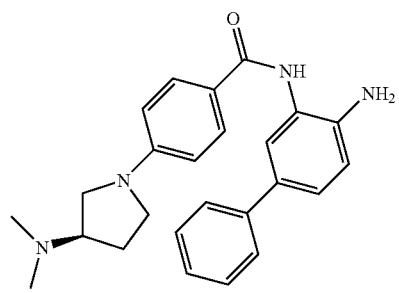 [SMILES: CN(C)[C@@H]1CCN(c2ccc(C(=O)Nc3cc(-c4ccccc4)ccc3N)cc2)C1]

TABLE 22-continued
Characterization and preparative sequence of compounds synthesized
536 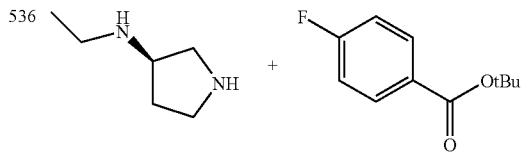 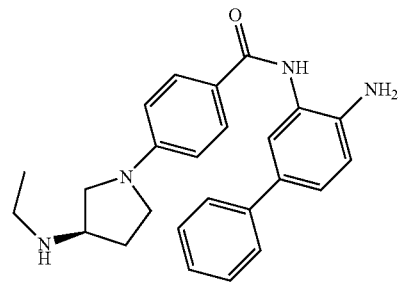 [SMILES: CCN[C@@H]1CCN(c2ccc(C(=O)Nc3cc(-c4ccccc4)ccc3N)cc2)C1]
537 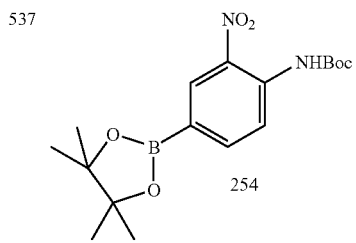 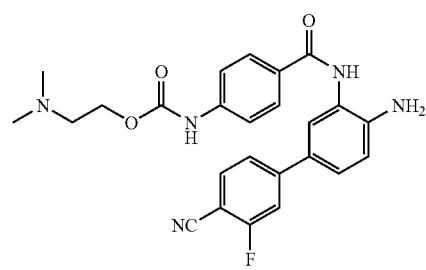
254
538 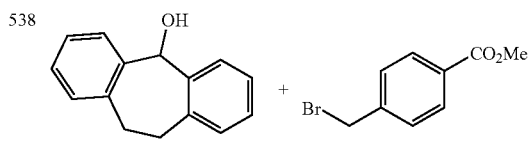 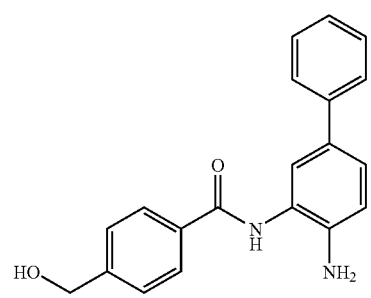 [SMILES: Nc1ccc(-c2ccccc2)cc1NC(=O)c1ccc(CO)cc1]
539 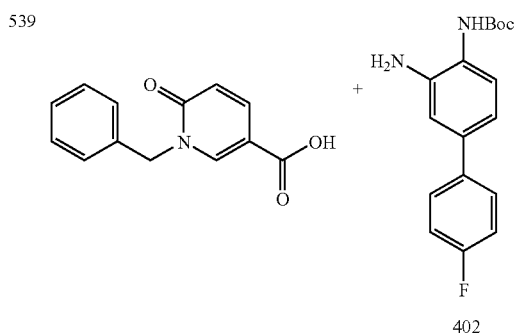 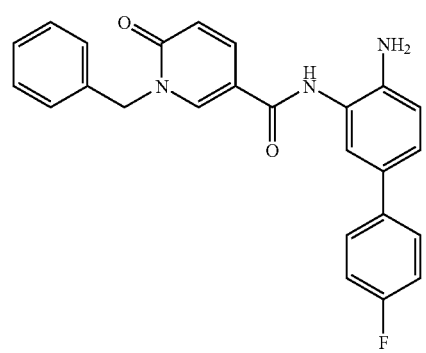 [SMILES: Nc1ccc(-c2ccc(F)cc2)cc1NC(=O)c1ccc(=O)n(Cc2ccccc2)c1]
402
540 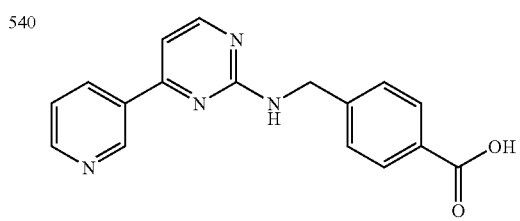 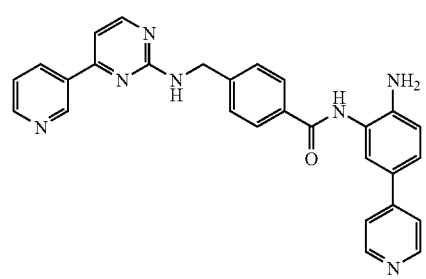 [SMILES: Nc1ccc(-c2ccncc2)cc1NC(=O)c1ccc(CNc2nccc(-c3cccnc3)n2)cc1]
Described in US 2004/0142953

TABLE 22-continued
Characterization and preparative sequence of compounds synthesized
541 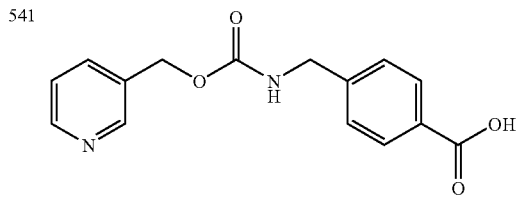
Described in *J. Med. Chem.* 1999, 42, 3001-3003.
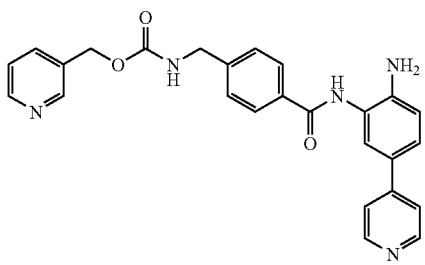 [SMILES: Nc1ccc(-c2ccncc2)cc1NC(=O)c1ccc(CNC(=O)OCc2cccnc2)cc1]
542 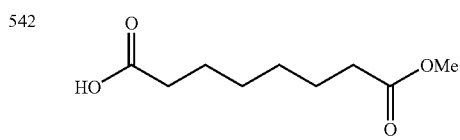
+
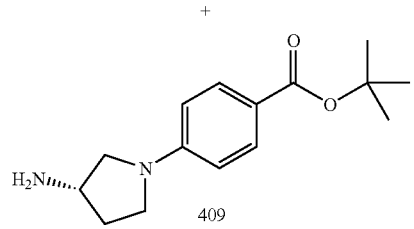
409
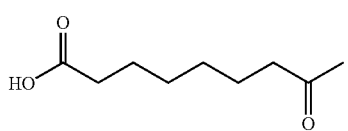
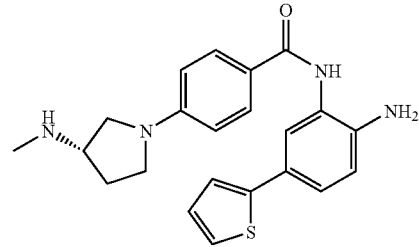
543 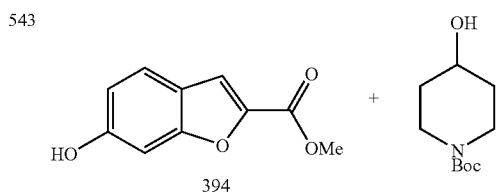
394
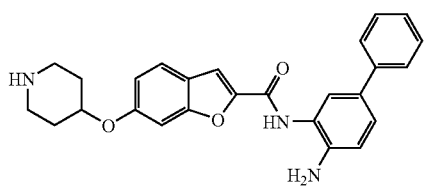 [SMILES: Nc1ccc(-c2ccccc2)cc1NC(=O)c1cc2ccc(OC3CCNCC3)cc2o1]
544 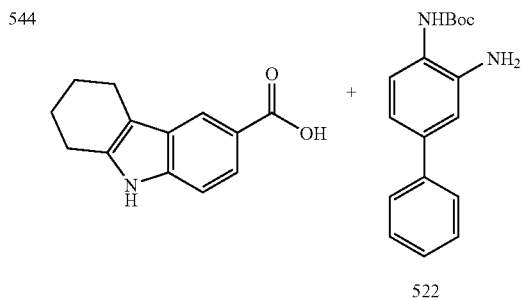
522
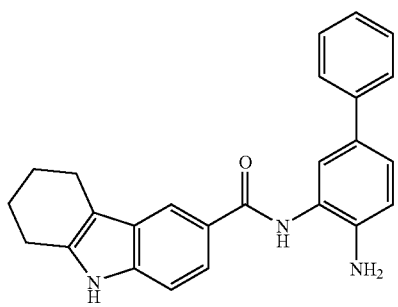 [SMILES: Nc1ccc(-c2ccccc2)cc1NC(=O)c1ccc2[nH]c3c(c2c1)CCCC3]
552 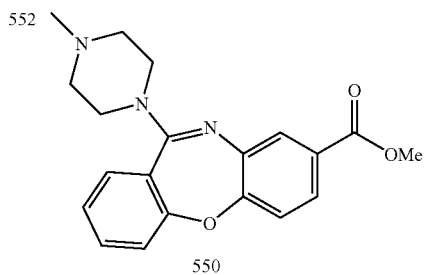
550
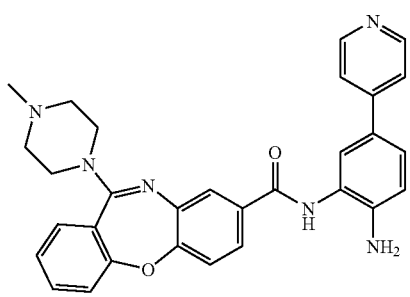 [SMILES: CN1CCN(C2=Nc3cc(C(=O)Nc4cc(-c5ccncc5)ccc4N)ccc3Oc3ccccc32)CC1]

TABLE 22-continued
Characterization and preparative sequence of compounds synthesized
553 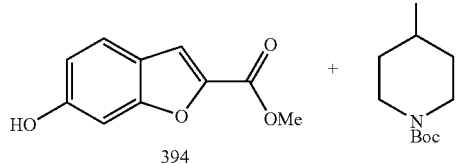 394 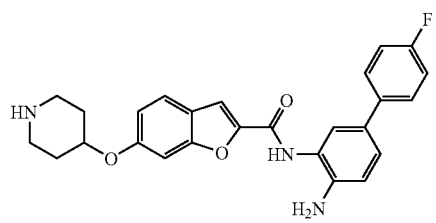 [SMILES: Nc1ccc(-c2ccc(F)cc2)cc1NC(=O)c1cc2ccc(OC3CCNCC3)cc2o1]
554 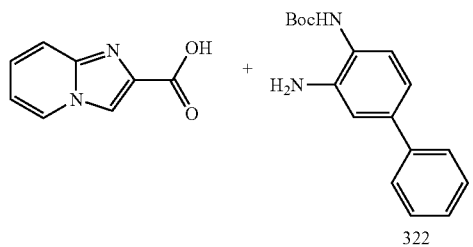 [SMILES: O=C(O)c1cn2ccccc2n1 ; CC(C)(C)OC(=O)Nc1ccc(-c2ccccc2)cc1N] 322 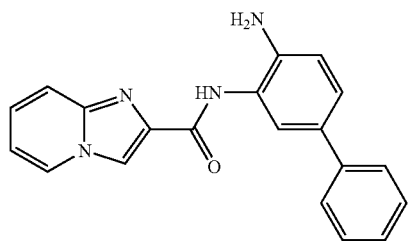 [SMILES: Nc1ccc(-c2ccccc2)cc1NC(=O)c1cn2ccccc2n1]
555 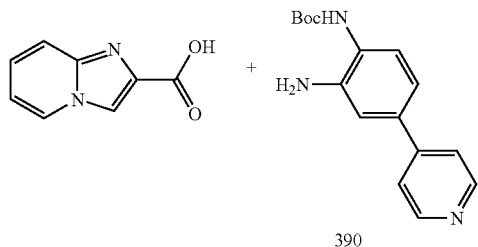 [SMILES: O=C(O)c1cn2ccccc2n1 ; CC(C)(C)OC(=O)Nc1ccc(-c2ccncc2)cc1N] 390 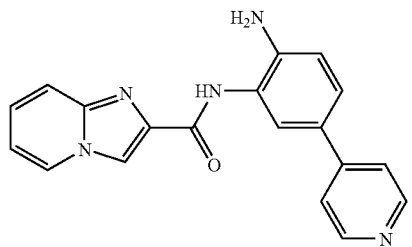 [SMILES: Nc1ccc(-c2ccncc2)cc1NC(=O)c1cn2ccccc2n1]
556 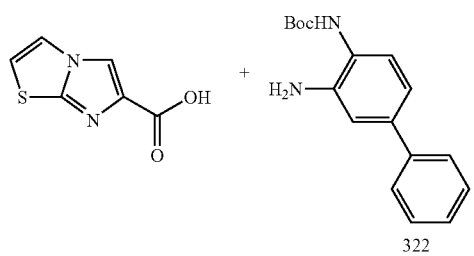 [SMILES: O=C(O)c1cn2ccsc2n1 ; CC(C)(C)OC(=O)Nc1ccc(-c2ccccc2)cc1N] 322 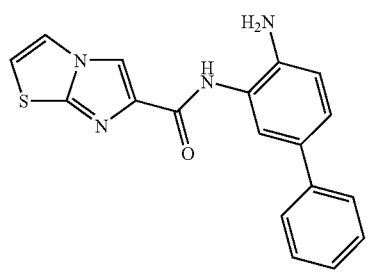 [SMILES: Nc1ccc(-c2ccccc2)cc1NC(=O)c1cn2ccsc2n1]
557 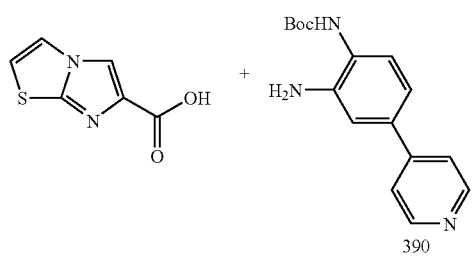 [SMILES: O=C(O)c1cn2ccsc2n1 ; CC(C)(C)OC(=O)Nc1ccc(-c2ccncc2)cc1N] 390 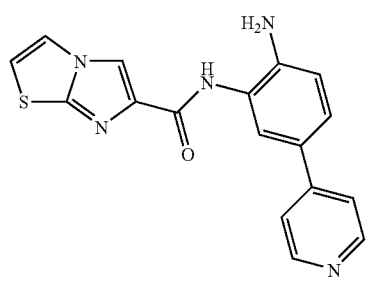 [SMILES: Nc1ccc(-c2ccncc2)cc1NC(=O)c1cn2ccsc2n1]
558 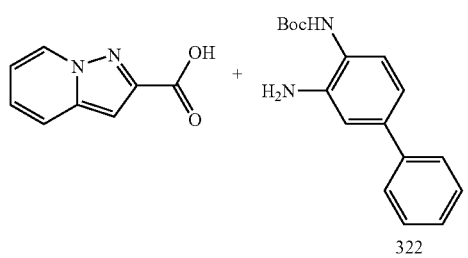 [SMILES: O=C(O)c1cc2ccccn2n1 ; CC(C)(C)OC(=O)Nc1ccc(-c2ccccc2)cc1N] 322 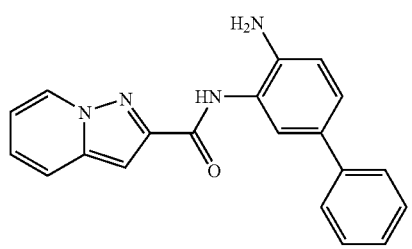 [SMILES: Nc1ccc(-c2ccccc2)cc1NC(=O)c1cc2ccccn2n1]

TABLE 22-continued
Characterization and preparative sequence of compounds synthesized
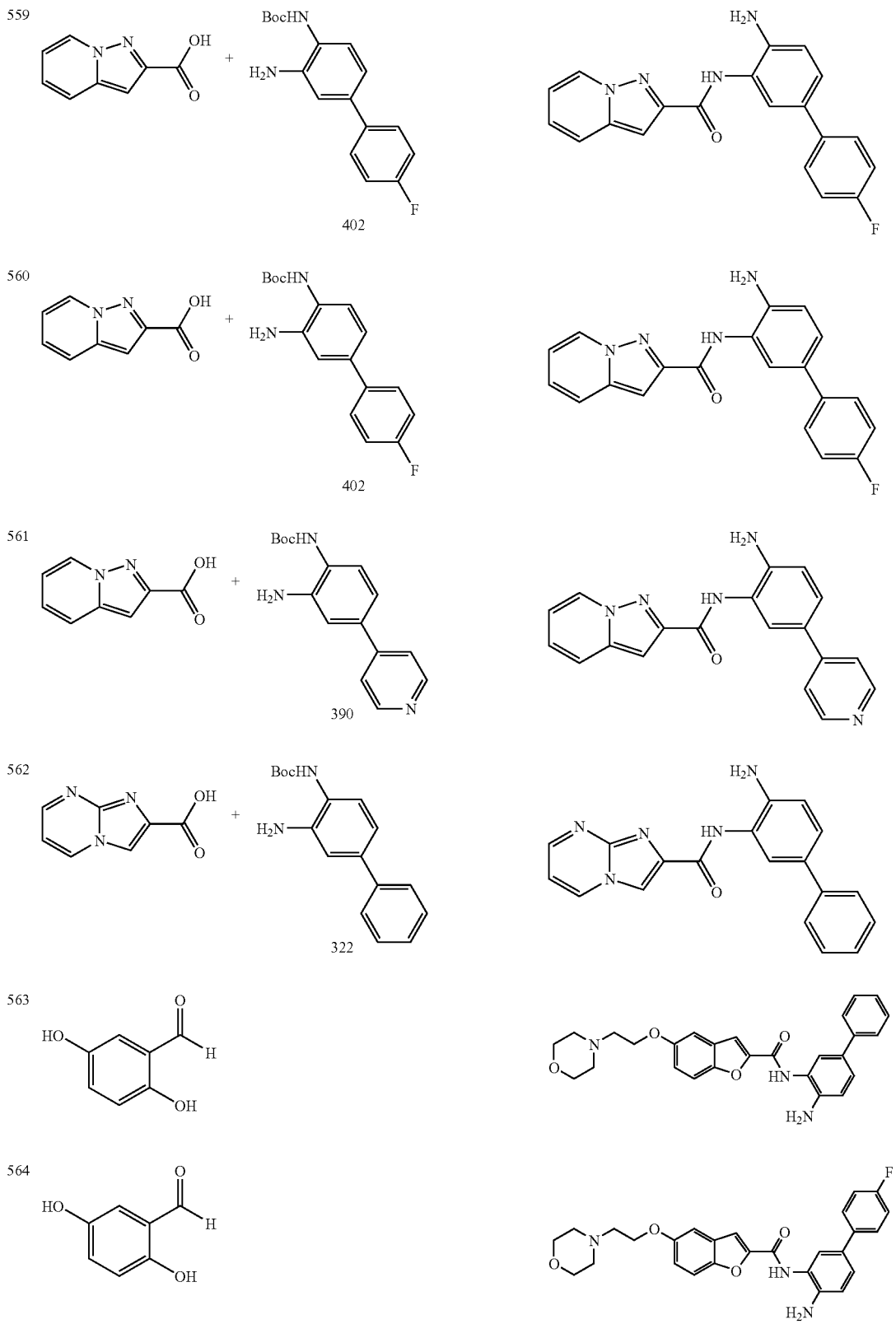

TABLE 22-continued
Characterization and preparative sequence of compounds synthesized
565 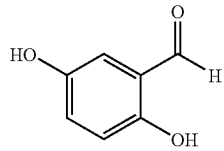 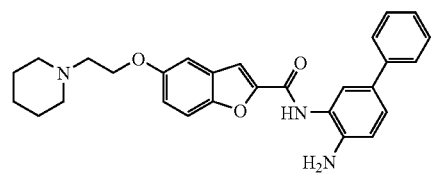 [SMILES: Nc1ccc(-c2ccccc2)cc1NC(=O)c1cc2cc(OCCN3CCCCC3)ccc2o1]
566 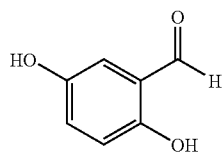 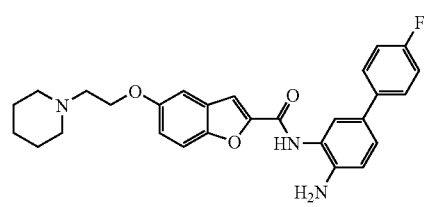 [SMILES: Nc1ccc(-c2ccc(F)cc2)cc1NC(=O)c1cc2cc(OCCN3CCCCC3)ccc2o1]
567 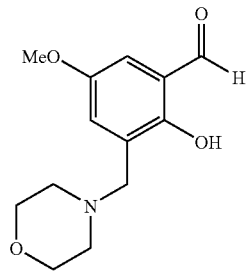 [SMILES: COc1cc(C=O)c(O)c(CN2CCOCC2)c1] 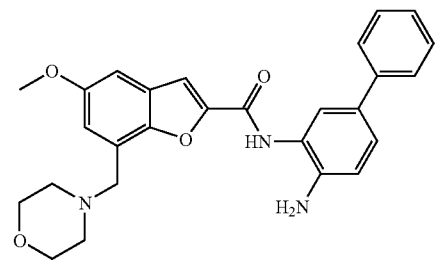 [SMILES: COc1cc(CN2CCOCC2)c2oc(C(=O)Nc3cc(-c4ccccc4)ccc3N)cc2c1]
568 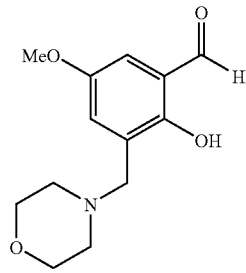 [SMILES: COc1cc(C=O)c(O)c(CN2CCOCC2)c1] 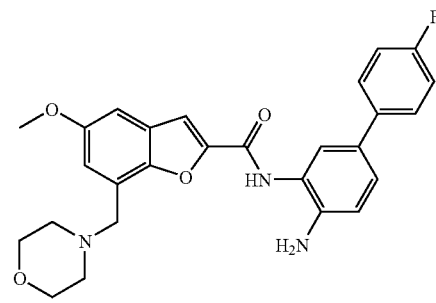 [SMILES: COc1cc(CN2CCOCC2)c2oc(C(=O)Nc3cc(-c4ccc(F)cc4)ccc3N)cc2c1]
569 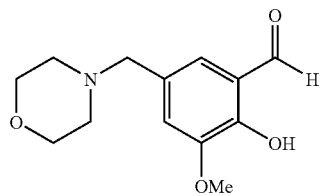 [SMILES: COc1cc(CN2CCOCC2)cc(C=O)c1O] 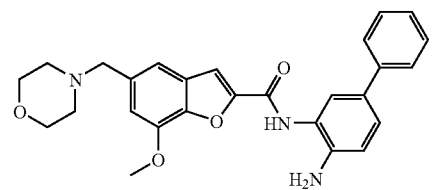 [SMILES: COc1cc(CN2CCOCC2)cc2cc(C(=O)Nc3cc(-c4ccccc4)ccc3N)oc12]
570 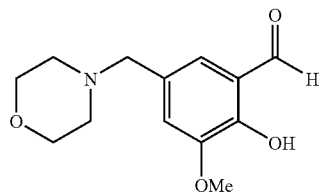 [SMILES: COc1cc(CN2CCOCC2)cc(C=O)c1O] 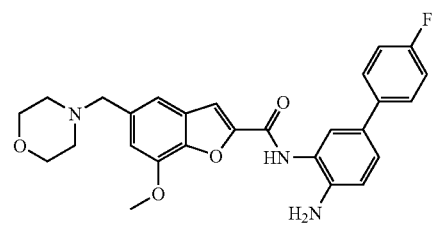 [SMILES: COc1cc(CN2CCOCC2)cc2cc(C(=O)Nc3cc(-c4ccc(F)cc4)ccc3N)oc12]

TABLE 22-continued
Characterization and preparative sequence of compounds synthesized
571
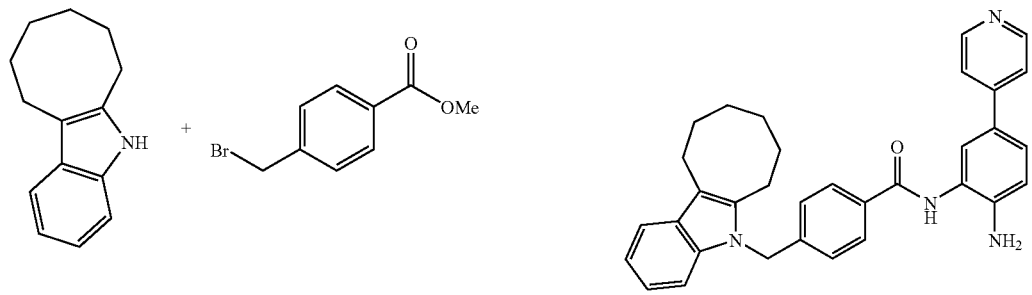
572
573
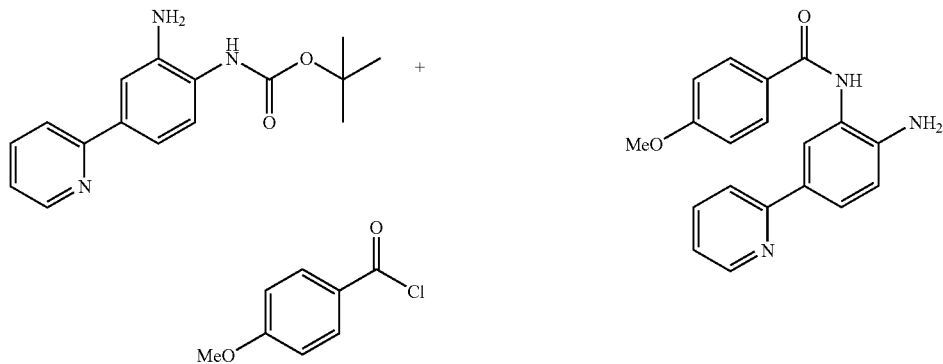
574
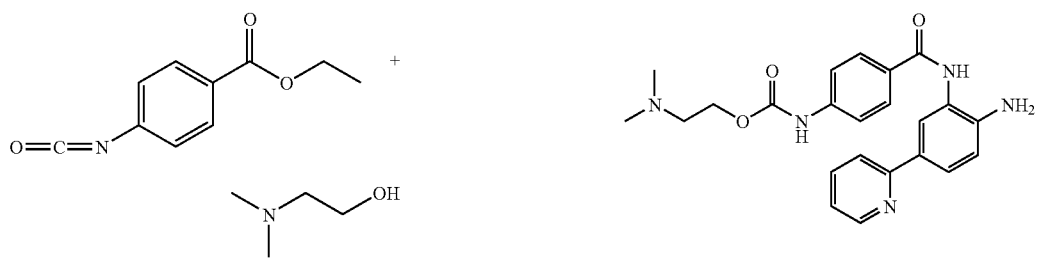
575
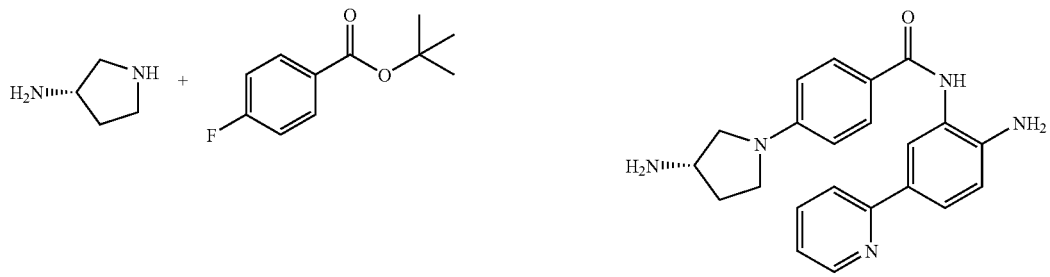

TABLE 22-continued
Characterization and preparative sequence of compounds synthesized
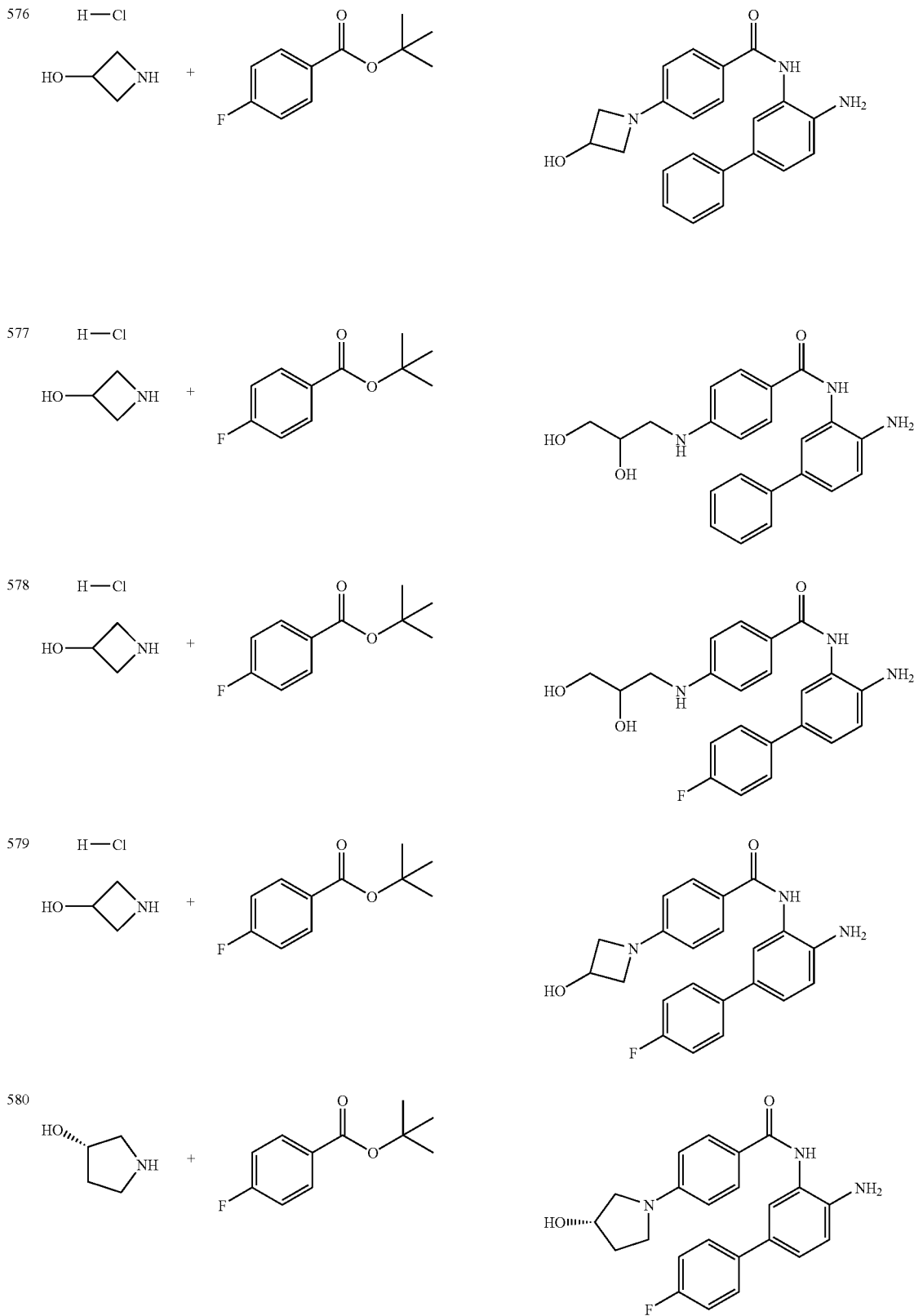

TABLE 22-continued
Characterization and preparative sequence of compounds synthesized
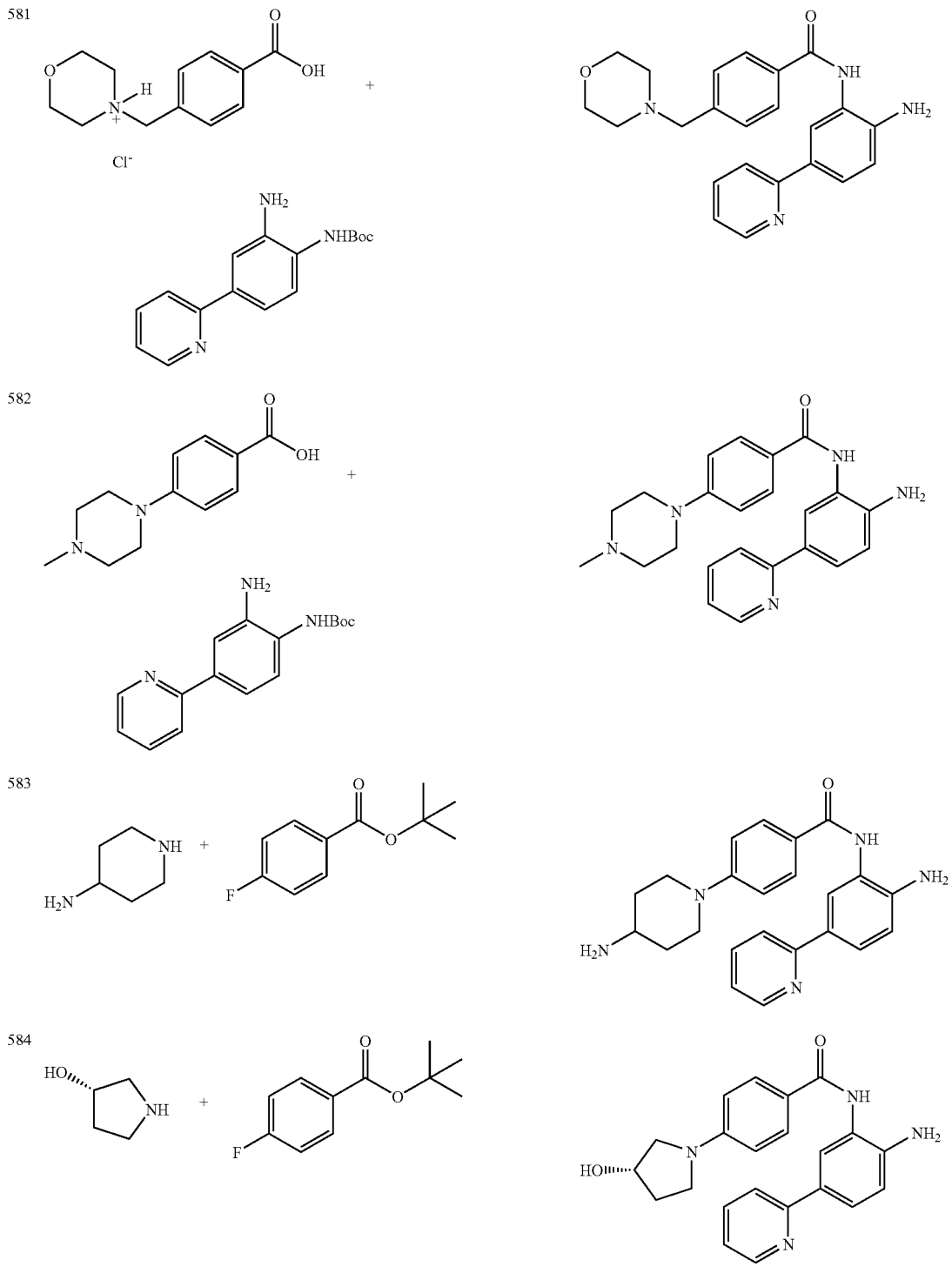
| Ex | Cpd | Name | Characterization | Preparative sequence |
|---|---|---|---|---|
| 4a | 56 | N-(2-Amino-5-(thiophen-2-yl)phenyl)-3',4',5'-trimethoxybi- | $^1$H NMR (DMSO-$d_6$) δ (ppm): 9.82 (s, 1 H), 8.24 (s, 1 H), 7.91 (dd, J = 21.1, 7.6 Hz, 2 H), 7.58 (t, J = 7.8 Hz, 1 H), 7.49 (s, 1 H), 7.35 (d, J = 5.1 Hz, 1 H), 7.31 | K, B, G |

TABLE 22-continued

Characterization and preparative sequence of compounds synthesized

| | | | | |
|---|---|---|---|---|
| | | phenyl-3-carbox-amide 2,2,2-trifluoroacetate | (dd, J = 8.2, 2.0 Hz, 1 H), 7.24 (d, J = 3.3 Hz, 1 H), 7.05 to 7.03 (m, 1 H), 7.01 (s, 2 H), 6.81 (d, J = 8.4 Hz, 1 H), 3.88 (s, 6 H), 3.70 (s, 3 H). LRMS: calc. 460.2, found 461.2 (MH)+. | |
| 4b | 57 | N-(2-amino-5-(thiophen-2-yl)phenyl)-3-(1 H-pyrazol-4-yl)benzamide | $^1$H NMR (DMSO-d$_6$) δ (ppm): 9.69 (s, 1 H), 8.14 (s, 1 H), 8.12 to 8.07 (m, 1 H), 7.71 (t, J = 9.0 Hz, 2 H), 7.40 (t, J = 7.6 Hz, 2 H) 7.28 to 7.27 (m, 1 H), 7.23 (dd, J = 8.4, 2.0 Hz, 1 H), 7.17 (d, J = 2.3 Hz, 1 H), 7.01 (m, 1 H), 6.97 (dd, J = 5.1, 3.5 Hz, 1 H), 6.75 (d, J = 8.2 Hz, 1 H). LRMS: calc. 360.1, found 361.1. | K, B, G |
| 4c | 58 | N-(2-amino-5-(thiophen-2-yl)phenyl)-6-(thiophen-2-yl)nicotinamide | $^1$H NMR (DMSO-d$_6$) δ (ppm): 10.00 (s, 1 H), 9.05 (dd, J = 14.4, 2.4 Hz, 2 H), 8.56 (t, J = 2.0 Hz, 1 H), 7.77 (dd, J = 3.6, 1.2 Hz, 1 H), 7.71 (dd, J = 5.2, 1.2 Hz, 1 H), 7.47 (d, J = 2.4 Hz, 1 H), 7.34 (dd, J = 5.2, 1.2 Hz, 1 H), 7.31 (dd, J = 8.4, 2.4 Hz, 1 H), 7.25-7.22 (m, 2 H), 7.03 (dd, J = 4.8, 3.2 Hz, 1 H), 6.80 (d, J = 8.0 Hz, 1 H), 5.32 (s, 2 H). LRMS: calc. 376.5, found 377.9 | K, B, G |
| 5a | 61 | N-(2-Amino-5-(thiophen-2-yl)phenyl)-3-(pyridin-3-yl)benzamide 2,2,2-trifluoroacetate | $^1$H NMR (DMSO-d$_6$) δ (ppm): 9.99 (s, 1 H), 9.13 (s, 1 H), 8.72 (d, J = 5.1 Hz, 1 H), 8.47 (s, J = 7.6 Hz, 1 H), 8.41 (s, 1 H), 8.03 (dd, J = 21.7.6, 7 Hz, 2 H), 7.76 (t, J = 5.1 Hz, 1 H), 7.69 (t, J = 7.6 Hz, 1 H), 7.51 (s, 1 H), 7.39 to 7.35 (m, 2 H), 7.29 (d, J = 2.5 Hz, 1 H), 7.07 to 7.05 (m, 1 H), 6.90 (d, J = 8.2 Hz, 1 H). | F, G |
| 5b | 62 | N-(2-amino-5-(thiophen-2-yl)phenyl)-5-(pyridin-2-yl)thiophene-2-carboxamide | $^1$H NMR (DMSO-d$_6$) δ (ppm): 9.80 (s, 1 H), 8.57 (s, 1 H), 7.99 (s, 2 H), 7.87 (s, 2 H), 7.44 (s, 1 H), 7.34 to 7.25 (m, 4 H), 7.04 (s, 1 H), 6.81 (s, 1 H), 5.21 (s, 2 H). LRMS: calc. 337.1, found 378.1. | F, G |
| 5c | 63 | N-(2-amino-5-(thiophen-2-yl)phenyl)-6-(2-(pyrrolidin-1-yl)ethyl)nicotin-amide | $^1$H NMR (DMSO-d$_6$) δ (ppm): 9.81 (s, 1 H), 9.04 (d, J = 1.8 Hz, 1 H), 8.23 (d, J = 8.2 Hz, 1 H), 7.45 to 7.43 (m, 2 H), 7.34 (dd, J = 5.1, 1.2 Hz, 1 H), 7.29 (dd, J = 8.2, 2.2 Hz, 1 H), 7.23 (dd, J = 3.5, 0.98 Hz, 1 H), 7.03 (dd, J = 5.1, 3.7 Hz, 1 H), 6.79 (d, J = 8.2 Hz, 1 H), 5.22 (s, 2 H), 2.98 (m, 2 H), 2.82 (m, 1 H), 1.67 (m, 4 H), 1.26-1.22 (m, 3 H), 0.84 (t, J = 6.9 Hz, 2 H). LRMS: calc. 392.2, found 393.2. | F, G |
| 5d | 64 | N-(2-amino-5-(thiophen-2-yl)phenyl)-6-morpholino-nicotinamide | $^1$H NMR (DMSO-d$_6$) δ (ppm): 9.52 (s, 1 H), 8.75 (s, J = 2.3 Hz, 1 H), 8.10 (dd, J = 9.2, 2.5 Hz, 1 H), 7.43 (d, J = 2.0 Hz, 1 H), 7.33 (dd, J = 5.1, 1.2 Hz, 1 H), 7.22 (dd, J = 3.5, 1.2 Hz, 1 H), 7.03 (dd, J = 5.1, 3.5 Hz, 1 H), 6.90 (d, J = 9.0 Hz, 1 H), 6.78 (d, J = 8.4 Hz, 1 H), 5.14 (s, 2 H), 3.70 (t, J = 4.8 Hz, 4 H), 3.58 (t, J = 4.8 Hz, 4 H). LRMS: calc. 380.1, found 381.1. | F, G |
| 5e | 65 | N-(2-amino-5-(thiophen-2-yl)phenyl)-3-(1 H-pyrrol-1-yl)benzamide | $^1$H NMR (DMSO-d$_6$) δ (ppm): 9.85 (s, 1 H), 8.17 (s, 1 H), 7.80 (dd, J = 15.5, 7.4 Hz, 2 H), 7.58 (t, J = 7.8 Hz, 1 H), 7.48 (t, J = 2.2 Hz, 3 H), 7.35 (dd, J = 5.1, 1.2 Hz, 1 H), 7.31 (dd, J = 8.4, | F, G |

TABLE 22-continued

Characterization and preparative sequence of compounds synthesized

| | | | | |
|---|---|---|---|---|
| | | | 2.2 Hz, 1 H), 7.25 (d, J = 3.5 Hz, 1 H), 7.05-7.03 (m, 1 H), 6.82 (d, J = 8.2 Hz, 1 H), 6.30 (t, J = 2.2 Hz, 1 H). LRMS: calc. 359.1, found 360.1. | |
| 5f | 66 | N-(2-amino-5-(thiphen-2-yl)phenyl)-1,3-dimethyl-1 H-thieno[2,3-c]pyrazole-5-carboxamide | $^1$H NMR (DMSO-d$_6$) δ (ppm): 9.75 (s, 1 H), 8.03 (s, 1 H), 7.45 (d, J = 2.2 Hz, 1 H), 7.36 (dd, J = 4.9, 0.98 Hz, 1 H), 7.30 (dd, J = 8.4, 2.3 Hz, 1 H), 7.25 (dd, J = 3.5, 0.98 Hz, 1 H), 7.05 (dd, J = 5.1, 3.5 Hz, 1 H), 6.81 (d, J = 8.4 Hz, 1 H), 5.21 (s, 2 H), 3.89 (s, 3 H), 2.39 (s, 3 H). LRMS: calc. 368.1, found 369.0. | F, G |
| 5g | 67 | N-(2-amino-5-(thiophen-2-yl)phenyl)-5-(morpholinomethyl)furan-2-carboxamide | $^1$H NMR (DMSO-d$_6$) δ (ppm): 9.57 (s, 1 H), 7.40 (d, J = 2.2 Hz, 1 H) 7.34 (dd, J = 5.1, 1.2 Hz, 1 H), 7.27 (dd, J = 8.4, 1.2 Hz, 1 H), 7.26 (d, J = 3.3 Hz, 1 H), 7.22 (dd, J = 3.7, 1.2 Hz, 1 H), 7.03 (dd, J = 5.1, 3.5 Hz, 1 H), 6.78 (d, J = 8.4 Hz, 1 H), 5.12 (s, 2 H), 3.58-3.54 (m, 6 H), 2.42-2.39 (m, 4 H). LRMS: calc. 383.5, found 384.1. | F, G |
| 5h | 68 | N-(2-amino-5-(thiophen-2-yl)phenyl)-6-(1 H-pyrazol-1-yl)nicotinamide | $^1$H NMR (DMSO-d$_6$) δ (ppm) 9.95 (bs, 1 H), 9.07 (d, J = 2.0 Hz, 1 H), 8.73 (d, J = 2.8 Hz, 1 H), 8.55 (dd, J1 = 8.8 Hz, J2 = 2.4 Hz, 1 H), 8.05 (d, J = 8.4 Hz, 1 H), 7.91 (m, 1 H), 7.49 (d, J = 2.4 Hz, 1 H). 7.36 (dd, J = 5.0, 1.0 Hz, 1 H), 7.32 (dd, J = 8.4, 2.4 Hz, 1 H), 7.26 (dd, J = 3.2, 1.2 Hz, 1 H), 7.05 (dd, J = 5.2, 3.6 Hz, 1 H), 6.81 (d, J = 8.4 Hz, 1 H), 6.65 (dd, J = 2.6, 1.8 Hz, 1 H), 5.29 (s, 2 H). LRMS: calc. 361.1, found 362.1. | F, G |
| 5i | 69 | N-(2-amino-5-(thiophen-2-yl)phenyl)-6-bromonicotinamide | $^1$H NMR (DMSO-d$_6$) δ (ppm): 9.95 (s, 1 H), 8.96 (d, J = 2.0 Hz, 1 H), 8.27 (dd, J = 8.4, 2.4 Hz, 1 H), 7.84 (d, J = 8.4 Hz, 1 H), 7.45 (d, J = 2.0 Hz, 1 H), 7.35 (dd, J = 5.2, 1.2 Hz, 1 H), 7.32 (dd, J = 8.4, 2.0 Hz, 1 H), 7.24 (dd, J = 3.6, 0.8 Hz, 1 H), 7.05 (dd, J = 5.2, 3.6 Hz, 1 H), 6.80 (d, J = 8.0 Hz, 1 H), 5.30 (s, 2 H). LRMS: calc. 373.0, found 373.9. | F, G |
| 5j | 70 | N-(2-amino-5-(thiophen-2-yl)phenyl)-5-bromo-6-oxo-1,6-dihydrporyidine-3-carboxamide | $^1$H NMR (DMSO-d$_6$) δ (ppm): 12.29 (s, 1 H), 9.52 (s, 1 H), 8.43 (d, J = 2.4 Hz, 1 H), 8.21 (d, J = 2.8 Hz, 1 H,), 8.36 (d, J = 2.0) Hz, 1 H), 7.33 (dd, J = 5.2, 1.2 Hz, 1 H), 7.27 (dd, J = 8.4, 2.0 Hz, 1 H), 7.21 (dd, J = 3.6, 0.8 Hz, 1 H), 7.02 (dd, J = 5.2, 3.6 Hz, 1 H), 6.75 (d, J = 8.4 Hz, 1 H), 5.21 (s, 2 H). LRMS: calc. 390.3, found 391.8. | F, G |
| 5k | 71 | N-(2-amino-5-(thiophen-2-yl)phenyl)-6-cyanonicotinamide | $^1$H NMR (DMSO-d$_6$) δ (ppm): 10.07 (s, 1 H), 9.26 (d, J = 1.6 Hz, 1 H), 8.22 (t, 7.6 Hz, 1 H) 7.44 (d, J = 2.4 Hz, 1 H), 7.33 (dd, J = 5.2, 0.8 Hz, 1 H), 7.30 (dd, J = 8.0, 2.0 Hz), 7.22 (dd, J = 3.6, 1.2 Hz, 1 H), 7.02 (dd, J = 5.2, 3.6 Hz, 1 H), 7.78 (d, J = 8.4 Hz, 1 H). LRMS: calc. 320.4, found 321.0. | F, G |
| 5l | 72 | N-(2-amino-5-(thiophen-2-yl)phenyl)-3-fluoro-4-hydroxybenzamide | $^1$H NMR (DMSO-d$_6$) δ (ppm): 9.60 (s, 1 H), 7.82 (d, J = 12.1 Hz, 1 H), 7.71 (d, J = 8.4 Hz, 1 H), 7.43 (d, J = 2.2 Hz, 1 H), 7.35 (dd, J = 5.1, 1.2 Hz, 1 H), | F, G |

TABLE 22-continued

Characterization and preparative sequence of compounds synthesized

| | | | | |
|---|---|---|---|---|
| | | | 7.29 (dd, J = 8.4, 2.2 Hz, 1 H), 7.24 (dd, J = 3.5, 1.2 Hz, 1 H), 7.06-7.04 (m, 2 H), 6.80 (d, J = 8.4 Hz, 1 H), 5.15 (s, 2 H). LRMS: calc. 328.1, found 329.0. | |
| 5m | 372 | N-(2-amino-5-(thiophen-2-yl)phenyl)-4-(piperdin-1-yl)benzamide | $^1$H NMR (CDCl$_3$) δ (ppm): 8.21 (s, 1 H), 7.78 (d, J = 8.1 Hz, 2 H), 7.49 (s, 1 H), 7.12 (m, 2 H), 6.91 (m, 3 H), 6.80 (d, J = 8.2 Hz, 1 H), 3.21 (m, 4 H), 1.63 (m, 4 H), 1.58 (m, 2 H). LRMS: calc. 377.5, found 378.1 (MH)+. | F, G |
| 5n | 373 | N-(2-amino-5-(thiazol-2-yl)phenyl)-4-(4-methylpiperizin-1-yl)benzamide | $^1$H NMR: (DMSO-d$_6$) δ (ppm): 9.50 (s, 1 H), 7.89 (d, 2 H), 7.79 (dd, 1 H), 7.76 (d, 1 H), 7.57-7.54 (m, 2 H), 7.00 (d, 1 H), 6.83 (d, 1 H), 5.43 (s, 2 H), 3.28 (t, 4 H), 2.45 (t, 4 H), 2.23 (s, 3 H). LRMS: calc. 393.2, found 394.2 (MH)+ | B, C, F, G |
| 5o | 374 | N-(2-amino-5-(pyridin-4-yl)phenyl)-3-methoxybenzamide | $^1$H NMR (MeOD-d$_4$) (ppm): 8.46 (d, J = 6.3 Hz, 2 H), 7.66-7.63 (m, 3H), 7.60-7.52 (m, 3 H), 7.43 (t, J = 8.0 Hz, 1 H), 7.16-7.13 (m, 1 H), 6.99 (d, J = 8.4 Hz, 1 H), 3.87 (s, 3 H). LRMS: calc. 319.2, found 320.3 (MH)+ | B, C, F, G |
| 5p | 375 | N-(2-amino-5-(pyridin-4-yl)phenyl)-4-(dimethylamino)benzamide | $^1$H NMR (MeOD-d$_4$) (ppm): 8.56-8.40 (m, 2 H), 7.90 (d, J = 9.0 Hz, 2 H), 7.69-7.65 (m, 3 H), 7.53 (dd, J = 8.4, 2.2 Hz, 1 H), 6.98 (d, J = 8.4 Hz, 1 H), 6.79 (d, J = 9.2 Hz, 2 H), 3.05 (s, 6 H). LRMS: calc. 332.2, found 333.3 (MH)+. | B, C, F, G |
| 5q | 376 | N-(2-amino-5-(pyridin-4-yl)phenyl)benzofuran-2-carboxamide | $^1$H NMR (MeOD-d$_4$) (ppm): 8.46-8.43 (m, 2 H), 7.75-7.70 (m, 2 H), 7.65-7.61 (m, 4 H), 7.54-7.45 (m, 2 H), 7.35-7.31 (m, 1 H), 6.98 (d, J = 8.4 Hz, 1 H). LRMS: calc. 329.1, found 330.2 (MH)+ | B, C, F, G |
| 5r | 377 | N-(2-amino-5-(pyridin-4-yl)phenyl)benzo[d][1,3]dioxole-5-carboxamide | $^1$H NMR (DMSO-d$_6$) δ (ppm): 9.59 (s, 1 H), 8.50 (s, 2 H), 7.64-7.48 (m, 6 H), 7.04 (d, J = 8.2 Hz, 1 H), 6.87 (d, J = 8.0 Hz, 1 H), 6.12 (s, 2 H), 5.35 (s, 2 H). LRMS: calc. 333.1, found 334.3 (MH)+ | B, C, F, G |
| 5s | 378 | N-(2-amino-5-(pyridin-4-yl)phenyl)-4,6-dimethoxy-benzofuran-2-carboxamide | $^1$H NMR (MeOD-d$_4$) (ppm): 8.48-8.46 (M, 2h), 7.71 (d, J = 2.1 Hz, 1 H), 7.67-7.65 (m, 2 H), 7.59 (s, 1 H), 7.55 (dd, J = 8.6, 2.4 Hz, 1 H), 6.99 (d, J = 8.6 Hz, 1 H), 6.81-6.80 (m, 1 H), 6.45 (d, J = 2.0 Hz, 1 H), 3.94 (s, 3 H), 3.88 (s, 3 H). LRMS: calc. 389.1, found 390.2 (MH)+. | B, C, F, G |
| 8k | 379 | N-(2-amino-5-(thiophen-2-yl)phenyl)-4-(pyrrolidin-1-yl)benzamide | $^1$H NMR (Acetone-d$_6$) (ppm): 8.92 (s, 1 H), 7.94 (d, J = 9.0 Hz, 2 H), 7.63 (d, J = 2.2 Hz, 1 H), 7.31 (dd, J = 8.4, 2.2 Hz, 1 H), 7.28 (dd, J = 5.1, 1.2 Hz, 1 H), 7.23 (dd, J = 3.5, 1.0 Hz, 1 H), 7.04 (dd, J = 5.1, 3.5 Hz, 1 H), 6.90 (d, J = 8.2 Hz, 1 H), 6.61 (d, J = 8.8 Hz, 2 H,), 4.80 (bs, 2 H), 3.38-3.34 (m, 4 H), 2.06-2.03 (m, 4 H). LRMS: calc. 363.5, found 364.0. | J, I, F, G |
| 34m | 380 | 4-(4-amino-3',4'-difluorbiphenyl-3-ylcarbamoyl)phenyl acetate | $^1$H NMR (Acetone-d$_6$) (ppm): 9.18 (bs, 1 H), 8.11 (d, J = 8.6 Hz, 2 H), 7.66 (t, J = 2.3 Hz, 1 H), 7.52 (ddd, J = 12.3, 7.6, 2.2 Hz, 1 H), 7.43-7.39 (m, 1 H), | B, C, F, G |

TABLE 22-continued

Characterization and preparative sequence of compounds synthesized

| | | | | |
|---|---|---|---|---|
| | | | 7.36 (dd, J = 8.4, 2.3 Hz, 2 H), 7.28 (d J = 8.6 Hz, 2 H). 6.97 (d, J = 8.4 Hz, 1 H), 4.93 (bs, 2 H), 2.33 (s, 3 H). LRMS: calc 382.4, found 383.0. | |
| 34n | 381 | N-(4-amino-3',4'-difluorobiphenyl-3-yl)-4-hydroxybenzamide | $^1$H NMR (DMSO-d$_6$) δ (ppm): 10.07 (s, 1 H), 9.51 (s, 1 H), 7.86 (d, J = 8.8 Hz, 2 H), 7.58 (ddd, J = 12.7, 7.8, 2.2 Hz, 1 H), 7.49 (d, J = 2.3 Hz, 1 H), 7.45-7.35 (m, 2 H), 7.31 (dd, J = 8.4, 2.2 Hz, 1 H), 6.83 (d, J = 8.8 Hz, 2 H), 6.82 (d, J = 8.4 Hz, 1 H), 5.12 (s, 2 H). LRMS: calc. 340.3, found 341.0. | B, C, F, G, O |
| 36 | 320 | N-(4-Aminobiphenyl-3-yl)-1-(4-nitrophenylsulfonly)piperidine-4-carboxamide | $^1$H NMR (DMSO-d$_6$) δ (ppm): 9.14 (s, 1 H), 8.46 (d, J = 8.8 Hz, 2 H), 8.05 (d, J = 8.8 Hz, 2 H), 7.48 (m, 3 H), 7.37 (t, J = 7.6 Hz, 2 H), 7.23 (m, 2 H), 6.78 (d, J = 8.0 Hz, 1 H), 4.98 (s, 2 H), 3.72 (d, J = 12.0 Hz, 2 H), 2.38-2.51 (m, 3 H), 1.94 (dd, J = 14.2, 3.0 Hz, 2 H), 1.63-1.73 (m, 2 H). LRMS: calc. 480.2, found 481.0 (MH)$^+$. | N, G |
| | 382 | N-(4-aminobiphenyl-3-yl)-4-methylpiperazin-1-yl)benzamide | $^1$H NMR (DMSO-d$_6$) δ (ppm): 9.52 (s, 1 H), 7.89 (d, J = 9.2 Hz, 2 H), 7.55 (dd, J = 8.4 Hz, 2 H), 7.51 (m, 1 H), 7.39 (t, J = 8.0 Hz, 2 H), 7.31 (dd, J = 8.4, 2.4 Hz, 1 H), 7.24 (tt, J = 7.4, 1.2 Hz, 1 H), 7.01 (d, J = 9.2 Hz, 2 H), 6.86 (d, J = 8.4 Hz, 1 H), 5.04 (bs, 2 H), 3.28 (t, J = 5.0 Hz, 4 H), 2.45 (t, J = 5.0 Hz, 4 H), 2.23 (s, 3 H). LRMS: calc. 386.2, found 387.2 (MH)+. | F, G |
| | 383 | N-(4-aminobiphenyl-3-yl)-1-benzylpiperdine-4-carboxamide | $^1$H NMR (MeOD-d$_4$) □ (ppm): 7.58-7.53 (m, 2 H), 7.42-7.24 (m,10H), 6.94 (d, J = 8.2 Hz, 1 H), 3.59 (s, 2 H), 3.09-3.00 (m, 2 H), 2.56-2.45 (m, 1 H), 2.22-2.12 (m, 2 H), 2.00-1.90 (m, 4 H). LRMS: calc. 385.5, found 386.5 (MH)+. | F, G |
| | 384 | N-(4-aminobiphenyl-3-yl)-4-(4-methylpiperazin-1-ylsulfonyl)benzamide | $^1$H NMR (DMSO-d$_6$) δ (ppm): 9.96 (s, 1 H), 8.23 (d, J = 8.4 Hz, 2 H), 7.86 (d, J = 8.4 Hz, 2 H), 7.55-7.50 (m, 3 H), 7.40-7.32 (m, 3 H), 7.23 (t, J = 7.4 Hz, 1 H), 6.85 (d, J = 8.4 Hz, 1 H), 5.17-5.14 (m, 2 H), 2.96-2.88 (m, 4 H), 2.38-2.35 (m, 4 H), 2.13 (s, 3 H). LRMS: calc. 450.2, found 451.2 (MH)$^-$. | F, G |
| | 385 | N-(4-aminobiphenyl-3-yl)-3-(pyridin-3-yl)benzamide | $^1$H NMR (MeOD-d$_4$) □ (ppm): 8.96 (d, J = 1.8 Hz, 1 H), 8.60 (dd, J = 4.9, 1.7 Hz, 1 H), 8.38 (t, J = 1.6 Hz, 1 H), 8.28-8.23 (m, 1 H), 8.15-8.09 (m, 1 H), 7.98-7.93 (m, 1 H), 7.72 (t, J = 7.8 Hz, 1 H), 7.63-7.54 (m, 4 H), 7.45-7.38 (m, 3 H), 7.31-7.25 (m, 1 H), 7.02 (d, J = 8.4 Hz, 1 H). LRMS: calc. 365.4, found 366.4 (MH)$^+$. | F, G |
| | 386 | N-(4-aminobiphenyl-3-yl)-4-(pyrrolidin-1-yl)benzamide | Top of Form$^1$H NMR (DMSO-d$_6$) δ(ppm): 9.41 (s, 1 H), 7.86 (d, J = 8.8 Hz, 2 H), 7.54 (d, J = 8.4 Hz, 2 H), 7.50 (d, J = 2.2 Hz, 1 H), 7.37 (d, J = 7.4 Hz, 2 H), 7.28 (dd, J = 8.2, 2.1 Hz, 1 H), 7.22 (t, J = 7.4 Hz, 1 H), 6.85 (d, J = 8.2 Hz, 1 H), 6.57 (d, J = 8.8 Hz, 2 H), 5.00 (d, J = 9.6 | F, G |

TABLE 22-continued

Characterization and preparative sequence of compounds synthesized

| | | | |
|---|---|---|---|
| | | Hz, 2 H), 3.32-3.30 (m, 4 H), 1.98-1.96 (m, 4 H). LRMS: calc. 357.5, found 358.2 (MH)+. | |
| 387 | N-(4-aminobiphenyl-3-yl)-5-(pyridin-2-yl)thiophene-2-carboxamide | ¹H NMR (MeOD-d₄) □ (ppm): 8.60-8.55 (m, 1 H), 7.98-7.86 (m, 3 H), 7.78 (d, J = 4.1 Hz, 1 H), 7.63-7.58 (m, 2 H), 7.52 (d, J = 2.0 Hz, 1 H), 7.44-7.34 (m, 4 H), 7.31-7.24 (m, 1 H), 7.01 (d, J = 8.2 Hz, 1 H). LRMS: calc. 371.5, found, 372.2 (MH)⁺. | F, G |
| 388 | N-(4-aminobiphenyl-3-yl)-5-methyl-4-(morpholinomethyl)furan-2-carboxamide | ¹H NMR (MeOD-d₄) □ (ppm): 7.62-7.56 (m, 2 H), 7.52 (d, J = 2.2 Hz, 1 H), 7.44-7.37 (m, 3 H), 7.30-7.23 (m, 2 H), 6.99 (d, J = 8.2 Hz, 1 H), 3.72 (t, J = 4.5 Hz, 4 H), 3.44 (s, 2 H), 2.57-2.50 (m, 4 H), 2.44 (s, 3 H). LRMS: calc. 391.5, found 392.2 (MH)⁺. | F, G |
| 389 | N-(2-hydroxy-5-(thiophen-3-yl)phenyl)-4-(morpholinomethyl)benzamide | ¹H NMR (DMSO-d₆) δ (ppm): 9.90 (s, 1H ), 9.62 (s, 1 H), 7.91 (m, 3 H), 7.65 (m, 1 H), 7.61 (m, 1 H), 7.42 (m, 4 H), 6.91 (d, J = 8.1 Hz, 1 H), 3.61 (m, H), 3.52 (s, 2 H), 2.39 (m, 4H). LRMS: calc. 394.5, found 395.1 (MH)⁻. | B, C, F |
| 464 | N-(2-amino-5-(pyridin-4-yl)phenyl)quinoxaline-6-carboxamide | ¹H NMR (DMSO-d₄) δ (ppm): 8.99 (d, J = 4.9 Hz, 2 H), 8.79 (s, 1 H), 8.48 (d, J = 6.1 Hz, 2 H), 8.44-8.41 (m, 2 H), 8.24 (d, J = 8.8 Hz, 1 H), 7.74 (s, 1 H), 7.68 (d, J = 5.7 H, 2 H), 7.58 (d, J = 9.0 Hz, 1H), 7.01 (d, J = 8.4 Hz, 1 H). LRMS: calc. 341.2, found 342.4 (MH)⁻. | F, G |
| 465 | N-(4-aminobiphenyl-3-yl)quinoxaline-6-carboxamide | ¹H NMR (MeOD-d₄) δ (ppm): 9.00-8.91 (m, 2 H), 8.78 (d, J = 2.0 Hz, 1 H), 8.42 (dd, J = 8.8, 2.0 Hz, 1 H), 8.23 (d, J = 8.8 Hz, 1H), 7.59-7.55 (m, 3 H), 7.42-7.35 (m, 3 H), 7.27-7.22 (m, 1 H), 7.00 (d, J = 8.2 Hz, 1 H). LRMS: calc. 340.2, found 341.4 (MH)⁺. | F, G |
| 466 | N-(2-amino-5-(pyridin-4-yl)phenyl)-6-(2-morpholinoethoxy)benzofuran-2-carboxamide | ¹H NMR (MeOD-d₄) δ (ppm): 8.46-8.44 (m, 2 H), 7.72 (d, J = 2.2 Hz, 1 H), 7.62-7.60 (m, 2 H), 7.46 (dd, J = 8.4, 2.3 Hz, 1 H), 7.13-7.03 (m, 4 H), 6.94 (d, J = 8.4 Hz, 1 H), 3.84 (s, 2 H), 3.43 (s, 2 H), 2.98-2.92 (m, 4 H). LRMS: calc. 458.2, found 459.3 (MH)⁺. | S, P, F (with 390), G |
| 467 | N-(2-amino-5-(pyridin-4-yl)phenyl)-6-(2-(dimethylamino)ethxy)benzofuran-2-carboxamide | ¹H NMR (MeOD-d₄) δ (ppm): 8.49-8.47 (m, 2 H), 7.73 (d, J = 2.2 Hz, 1 H), 7.68-7.62 (m, 3 H), 7.58-7.54 (m, 2 H), 7.25 (d, J = 1.7 Hz, 1 H), 7.04-6.99 (m, 2 H), 4.20 (t, J = 5.3 Hz, 2 H), 2.83 (t, J = 5.5 Hz, 2 H), 2.37 (s, 6 H). LRMS: calc. 416.2, found,) 417.2 (MH)⁻. | S, P, F (with 390), G |
| 468 | N-(4-aminobiphenyl-3-yl)-6-(2-morpholinoethoxy)benzofuran-2-carboxamide | ¹H NMR (MeOD-d₄) δ (ppm): 7.59 (d, J = 8.6 Hz, 1 H), 7.56-7.53 (m, 4 H), 7.38-7.34 (m, 3 H), 7.25-7.19 (m, 2 H), 7.00-6.95 (m, 2 H), 4.18 (t, J = 5.5 Hz, 2 H), 3.71 (t, J = 4.7 Hz, 4 H), 2.82 (t, J = 5.5 Hz, 2 H), 2.60 (t, J = 4.5 Hz, 4 H). LRMS: calc. 457.2, found 458.4 (MH)⁺. | S, P, F (with 322), G |

TABLE 22-continued

Characterization and preparative sequence of compounds synthesized

| | | | |
|---|---|---|---|
| 469 | N-(4-amino-4'-fluorobiphenyl-3-yl)-6-(2-morpholinoethoxy)benzofuran-2-carboxamide | $^1$H NMR (MeOD-d$_4$) δ (ppm): 7.63 (d, J = 8.8 Hz, 1 H), 7.59-7.55 (m, 3 H), 7.52 (d, J = 2.2 Hz, 1 H), 7.35 (dd, J = 8.4, 2.4 Hz, 1 H), 7.24 (d, J = 2.0 Hz, 1 H), 7.11 (t, J = 8.8 Hz, 2 H), 7.01 (dd, J = 8.8, 2.3 Hz, 1 H), 6.98 (d, J = 8.0 Hz, 1 H), 4.23 (t, J = 5.5 Hz, 2 H), 3.73 (t, J = 4.7 Hz, 4 H), 2.86 (t, J = 5.5 Hz, 2 H), 2.63 (t, J = 4.7 Hz, 4 H). LRMS: calc. 475.2, found 476.5 (MH)$^+$. | S, P, F (with 402), G |
| 470 | N-(4-amino-3',4'-difluorobiphenyl-3-yl)-6-(2-morpholinoethoxy)benzofuran-2-carboxamide | $^1$H NMR (DMSO-d$_6$) □ (ppm): 9.80 (s, 1 H), 7.68-7.54 (m, 4 H), 7.46-7.33 (m, 3 H), 7.26 (d, J = 1.6 Hz, 1 H), 6.98 (dd, J = 8.6, 2.1 Hz, 1 H), 6.88 (d, J = 8.4 Hz, 1 H), 5.24-5.21 (m, 1 H), 4.17 (t, J = 5.7 Hz, 2 H), 3.57 (t, J = 4.7 Hz, 4 H), 2.72 (t, J = 5.6 Hz, 2 H), 2.49-2.47 (m, 4 H). LRMS: calc. 493.2, found 494.5 (MH)$^+$. | S, P, F, G |
| 471 | N-(2-amino-5-(pyridin-4-yl)phenyl)-5,6-dimethoxybenzofuran-2-carboxamide | $^1$H NMR (DMSO-d$_6$) □ (ppm): 9.77 (s, 1 H), 8.50 (d, J = 5.8 Hz, 2 H), 7.69 (s, 1 H), 7.63 (s, 1 H), 7.58 (d, J = 3.5 Hz, 2 H), 6.88 (d, J = 8.4 Hz, 1 H), 5.41 (d, J = 9.0 Hz, 2 H), 3.85 (s, 3 H), 3.81 (s, 3 H). LRMS: calc. 389.1, found 390.1 (MH)$^+$. | R, Q, P, F (with 390), G |
| 472 | N-(4-aminobiphenyl-3-yl)5,6-dimethoxybenzofuran-2-carboxamide | $^1$H NMR (DMSO-d$_6$) □ (ppm): 9.75 (s, 1 H), 7.62 (s, 1 H), 7.55 (d, J = 7.2 Hz, 3 H), 7.40-7.21 (m, 6 H), 6.87 (d, J = 8.4 Hz, 1 H), 5.14 (br s, 2 H), 3.85 (s, 3 H), 3.81 (s, 3 H). LRMS: calc. 388.1, found 389.1 (MH)$^+$. | R, Q, P, F (with 322), G |
| 473 | N-(4-amino-4'-fluorobiphenyl-3-yl)-5,6-dimethoxybenzofuran-2-carboxamide | $^1$H NMR (DMSO-d$_6$) □ (ppm): 9.75 (s, 1 H), 7.62-7.50 (m, 4 H), 7.31-7.27 (m, 3 H), 7.21 (t, J = 8.8 Hz, 2 H), 6.86 (d, J = 8.2 Hz, 1 H), 5.14 (br s, 2 H), 3.84 (s, 3 H), 3.81 (s, 3 H). LRMS: (calc.) 406.1 (found) 407.4 (MH)+ | R, Q, P, F (with 402), G |
| 474 | N-(2-amino-5-(thiophen-2-yl)phenyl)-5-(thiophen-2-yl)nicotinamide | $^1$H NMR (DMSO-d$_6$) □ (ppm): 10.11 (s, 1 H), 9.09 (d, J = 2.4 Hz, 1 H), 9.05 (d, J = 1.6 Hz, 1 H), 8.57 (t, J = 2.0 Hz, 1 H), 7.78 (dd, J = 3.8, 1.0 Hz, 1 H), 7.72 (dd, J = 5.2, 1.2 Hz, 1 H), 7.49 (d, J = 2.4 Hz, 1 H), 7.36 (dd, J = 5.2, 1.2 Hz, 1 H), 7.33 (dd, J = 8.6, 2.2 Hz, 1 H), 7.25 (m, 2 H), 7.05 (dd, J = 5.2, 3.6 Hz, 1 H), 6.82 (d, J = 8.4 Hz, 1 H), 5.31 (s, 2 H). LRMS: calc. 377.1, found 378.0 (MH)$^+$. | N, W |
| 475 | N-(2-amino-5-(thiophen-2-yl)phenyl)-5-(3-(dimethylamino)prop-1-ynyl)nicotinamide | $^1$H NMR (DMSO-d$_6$) □ (ppm): 9.94 (s, 1 H), 9.08 (d, J = 2.0 Hz, 1 H), 8.81 (d, J = 2.0 Hz, 1 H), 8.43 (t, J = 2.2 Hz, 1 H), 7.46 (d, J = 2.0 Hz, 1 H), 7.36 (dd, J = 5.2, 1.2 Hz, 1 H), 7.31 (dd, J = 8.4 Hz, 1 H), 7.24 (dd, J = 3.6, 1.2 Hz, 1 H), 7.05 (dd, J = 5.0, 3.4 Hz, 1 H), 6.79 (d, J = 8.4 Hz, 1 H), 5.30 (s, 2 H), 3.54 (s, 2 H), 2.28 (s, 6 H). LRMS: calc. 376.1, found 377.0 (MH)$^+$. | P, F (with 4), G |
| 476 | N-(4-aminobiphenyl-3-yl-)-4-(piperazin-1-yl)benzamide | $^1$H NMR (DMSO-d$_6$) □ (ppm): 9.51 (s, 1 H), 7.89 (d, J = 9.2 Hz), 2 H), 7.55 (dd, J = 8.4, 1.2 Hz, 2 H), 7.51 (d, J = 2.4 Hz, 1 H), 7.39 (t, J = 7.8 Hz, 2 H), 7.31 (dd, J = 8.4, 2.4 Hz, 1 H), 7.24 | J, P, F (with 322), G |

TABLE 22-continued

Characterization and preparative sequence of compounds synthesized

| | | | |
|---|---|---|---|
| | | (tt, J = 7.4, 1.3 Hz, 1 H), 6.99 (d, J = 9.2 Hz, 2 H), 6.86 (d, J = 8.4 Hz, 1 H), 5.04 (s, 2 H), 3.19 (t, 5.0 Hz, 4 H), 2.83 (t, J = 5.0 Hz, 4 H). LRMS: calc. 372.2, found 373.2 (MH)⁺. | |
| 477 | N-(2-amino-5-(thiophen-2-yl)phenyl)-4-(piperazin-1-yl)benzamide | ¹H NMR (DMSO-d₆) ☐ (ppm): 9.57 (s, 1 H), 7.93 (d, J = 8.8 Hz, 2 H), 7.46 (d, J = 2.3 Hz, 1 H), 7.36 (dd, J = 4.9, 1.0 Hz, 1 H), 7.28 (dd, J = 8.4, 2.3 Hz, 1 H), 7.24 (dd, J = 3.5, 1.0 Hz, 1 H), 7.06-7.03 (m, 3 H), 6.81 (d, J = 8.2 Hz, 1 H), 5.11 (s, 2 H), 3.40 (t, 4.9 Hz, 4 H), 3.06 (t, J = 5.0 Hz, 4 H). LRMS: calc. 378.2, found 379.1 (MH)⁺. | P, N (with 4), W |
| 478 | (R)-methyl 1-(4-(4-amino-4'-fluorobiphenyl-3-ylcarbamoyl)phenyl)pyrrolidin-3-ylcarbamate | ¹H NMR (DMSO-d₆☐ (ppm): 10.3 (s, 1 H), 8.02 (s, J = 8.8 Hz, 2 H), 7.84 (d, J = 2.0 Hz, 1 H), 7.73 (dd, J = 9.0, 5.4 Hz, 2 H), 7.59 (dd, J = 8.4, 2.0 Hz, 1 H), 7.56 (bs, 1 H), 7.53 (d, J = 8.0 Hz, 1 H), 7.33 (t, J = 8.8 Hz, 2 H), 6.61 (d, J = 8.8 Hz, 2 H), 4.21 (sext, J = 5.9 Hz, 1 H), 3.57 (m, 1 H), 3.55 (s, 3 H), 3.46 (m, 1 H), 3.36 (m, 1 H), 3.18 (dd, J = 10.2, 5.0 Hz, 1 H), 2.19 (sext, J = 6.6 Hz, 1 H), 1.94 (sext, J = 6.4 Hz, 1 H). LRMS: calc. 448.2, found 449.2 (MH)⁺. | K, W |
| 479 | (S)-N-(4-aminobiphenyl-3-yl)-4-(3-hydroxypyrrolidin-1-yl)benzamide | ¹H NMR (DMSO-d₆) ☐ (ppm): 9.43 (s, 1 H), 7.88 (d, J = 8.8 Hz, 2 H), 7.56 (dd, J = 8.4, 1.2 Hz, 2 H), 7.51 (d, J = 2.0 Hz, 1 H), 7.39 (t, J = 8.0 Hz, 2 H), 7.30 (dd, J = 8.2, 2.2 Hz, 1 H), 7.24 (tt, J = 7.4, 1.3 Hz, 1 H), 6.86 (d, J = 8.4 Hz, 1 H), 6.57 (d, J = 9.2 Hz, 2 H), 5.02 (d, J = 1.2 Hz, 2 H), 5.01 (s, 1 H), 4.43 (bs, 1 H), 3.47 (dd, J = 10.6, 4.6 Hz 1 H), 3.36-3.42 (m, 2 H), 3.17 (d, J = 10.4 Hz, 1 H), 2.06 (m, 1 H), 1.93 (m, 1 H). LMRS: calc. 373.2, found 374.2 (MH)⁺. | J, V, I, F (with 322), O, G |
| 480 | (R)-N-(4-aminobiphenyl-3-yl)-4-(3-hydroxypyrrolidin-1-yl)benzamide | ¹H NMR (DMSO-d₆) ☐ (ppm): 9.44 (s, 1 H), 7.88 (d, J = 9.2 Hz, 2 H), 7.56 (dd, J = 8.4, 1.2 Hz, 2 H), 7.51 (d, J = 2.4 Hz, 1 H), 7.39 (t, J = 7.8 Hz, 2 H), 7.30 (dd, J = 8.4, 2.4 Hz, 1 H), 7.24 (tt, J = 7.3, 1.4 Hz, 1 H), 6.86 (d, J = 8.4 Hz, 1 H), 6.57 (d, J = 8.8 Hz, 2 H), 5.03 (s, 3 H), 4.43 (bs, 1 H), 3.47 (dd, J = 10.4, 4.8 Hz, 1 H), 3.42-3.56 (m, 2 H), 3.17 (d, J = 10.8 Hz, 1 H), 2.06 (m, 1 H), 1.93 (m, 1 H). LRMS: calc. 373.2, found 374.2 (MH)⁺. | V, I, F (with 322), O, G |
| 481 | (S)-4-(3-acetamidopyrrolidin-1-yl)-N-(4-amino-4'-fluorobiphenyl-3-yl)benzamide | ¹H NMR (DMSO-d₆) ☐ (ppm): 9.44 (s, 1 H), 8.19 (d, J = 6.8 Hz, 1 H), 7.89 (d, J = 9.2 Hz, 2 H), 7.58 (dd, J = 8.8, 5.2 Hz, 2 H), 7.49 (m, 1 H), 7.27 (dd, J = 8.4, 2.0 Hz, 1 H), 7.21 (t, J = 8.8 Hz, 2 H,), 6.85 (d, J = 8.4 Hz, 1 H), 6.59 (d, J = 9.2 Hz, 2 H), 5.02 (m, 2 H), 4.38 (m, J = 5.3 Hz, 1 H), 3.55 (dd, J = 10.0, 6.4 Hz, 1 H), 3.44 (m, 1 H), 3.37 (m, 1 H), 3.14 (dd, J = 10.0, 4.4 Hz, 1 H), 2.19 (sext, J = 6.7 Hz, 1 H), 1.91 (sext, J = 6.1 Hz, 1 H), 1.82 | I, F (with 322), R, V, G |

TABLE 22-continued

Characterization and preparative sequence of compounds synthesized

| | | | |
|---|---|---|---|
| | | (s, 3 H). LRMS: calc. 432.2, found 433.3 (MH)⁻. | |
| 482 | (R)-N-(4-amino-4'-fluorobiphenyl-3-yl)-4-(3-(2-methoxyacetamido)pyrrolidin-1-yl)benzamide | $^1$H NMR: (DMSO-$d_6$) δ (ppm): 9.43 (s, 1 H), 8.10 (d, 1 H), 7.88 (d, 2 H), 7.59-7.56 (m, 2 H), 7.48 (d, 1 H), 7.27 (dd, 1 H), 7.23 (td, 2 H), 6.85 (d, 1 H), 6.58 (d, 2 H), 5.03 (s, 2 H), 4.51-4.46 (m, 1 H), 3.82 (s, 2 H), 3.59-3.55 (m, 1 H), 3.49-3.43 (m, 1 H), 3.31-3.34 (m, 1 H), 3.30 (s, 3 H), 3.24-3.20 (m, 1 H), 2.23-2.17 (m, 1 H), 2.06-1.97 (m, 1 H). LRMS: calc. 462.3, found 463.2 (MH)⁺. | K, G |
| 483 | (R)-N-(4-amino-4'-fluorobiphenyl-3-yl)-4-(3-aminopyrrolidin-1-yl)benzamide | $^1$HNMR: (DMSO-$d_6$) δ (ppm): 9.41 (s, 1 H), 7.78 (d, 2 H), 7.59-7.56 (m, 2 H), 7.48 (d, 1 H), 7.27 (dd, 1 H), 7.23 (td, 2 H), 6.85 (d, 1 H), 6.55 (d, 2 H), 5.03 (s, 2 H), 3.64-3.59 (m, 1 H), 3.49-3.41 (m, 3 H), 2.98 (dd, 1 H), 2.13-2.05 (m, 1 H), 1.79-1.71 (m, 1 H). LRMS: calc. 390.2, found 391.3 (MH)⁺. | G |
| 484 | N-(4-aminobiphenyl-3-yl)-4-(3-oxopiperazin-1-yl)benzamide | $^1$HNMR: (DMSO-$d_6$) δ (ppm): 9.53 (s, 1 H), 8.16 (s, 1 H), 7.92 (dd, 1 H), 7.57-7.54 (m, 2 H), 7.51 (d, 1 H), 7.39 (t, 2 H), 7.31 (dd, 1 H), 7.23 (tt, 1 H), 6.98 (d, 2 H), 6.86 (d, 1 H), 5.05 (s, 2 H), 3.85 (s, 2 H), 3.54 (t, 2 H). LRMS(ESI): (calc.) 386.2 (found) 387.2 (MH)+ | J, I, F (with 322), G |
| 485 | N-(4-aminobiphenyl-3-yl)-4-(4-aminopiperidine-1-yl)benzamide | $^1$HNMR: (DMSO-$d_6$) δ (ppm): 9.48 (s, 1 H), 7.87 (d, J = 9.1 Hz, 2 H), 7.55 (dd, J = 1.3, 8.3 Hz, 2 H), 7.50 (d, J = 2.1 Hz, 1 H), 7.39 (dt, J = 2.1, 7.4 Hz, 2 H), 7.30 (dd, J = 2.1, 8.3 Hz, 1 H), 7.24 (dt, J = 1.3, 7.4 Hz, 1 H), 6.99 (d, J = 9.1 Hz, 2 H), 6.86 (d, J = 8.3 Hz, 1 H), 5.04 (bs, 2 H), 3.82 (d, J = 12.7 Hz, 2 H), 2.86 (dt, J = 2.5, 12.0 Hz, 2 H), 2.81-2.75 (m, 1 H), 1.76 (dd, J = 3.3, 12.5 Hz, 2 H), 1.32-1.22 (m, 2 H). Alkyl NH$_2$ overlapped LRMS(ESI): (calc.) 386.2 (found) 387.2 (MH)+ | J, T, I, F (with 322), R, G |
| 486 | (S)-N-(4-aminobiphenyl-3-yl)-4-(3-(methylsulfonamido)pyrrolidin-1-yl)benzamide | $^1$HNMR: (DMSO-$d_6$) δ (ppm): 9.45 (s, 1 H), 7.89 (d, J = 8.8 Hz, 2 H), 7.57 to 7.51 (m, 3 H), 7.48 (d, J = 6.4 Hz, 1 H), 7.39 (dt, J = 6.4, 1.9 Hz, 2 H), 7.30 (dd, J = 8.4, 2.3 Hz, 1 H), 7.24 (dt, J = 7.4, 1.2 Hz, 1 H), 6.86 (d, J = 8.2 Hz, 1 H), 6.60 (d, J = 8.8 Hz, 2 H), 5.01 (bs, 2 H), 4.08 (dd, J = 6.3, 12.5 Hz, 1 H), 3.63 (dd, J = 6.6, 10.0 Hz, 1 H), 3.48-3.43 (m, 1 H), 3.33 (s, 3 H), 3.20 (dd, J = 5.5, 10.2 Hz, 1 H), 2.3-2.25 (m, 1 H), 2.00-1.96 (m, 1 H). (one overlapped H). LRMS(ESI): (calc.) 450.17 (found) 451.2 (MH)+ | U, I, F (with 322), G |
| 487 | (S)-4-(3-acetamidopyrrolidin-1-yl)-N-(4-aminobiphenyl-3-yl)bezamide | $^1$HNMR: (DMSO-$d_6$) δ (ppm): 9.42 (s, 1 H), 8.20 (d, 1 H), 7.88 (d, 2 H), 7.55 (d, 2 H), 7.50 (s, 1 H), 7.40 (t, 2 H), 7.31 (dd, 1 H), 7.22 (t, 1 H), 6.84 (d, 1 H), 6.59 (d, 2 H), 5.01 (s, 2 H), 4.39 (m, 1 H), 3.52 (m, 1 H), 3.42 (m, 1 H), 3.38 (m, 1 H), 3.11 (dd, 1 H), 2.21 (m, 1 H), 1.90 (m, 1 H), 1.80 (s, 3 H). LRMS: | V, I, F (with 322), G |

TABLE 22-continued

Characterization and preparative sequence of compounds synthesized

| | | | |
|---|---|---|---|
| 488 | N-(2-amino-5-(thiophen-2-yl)phenyl)quinoline-3-carboxamide | (calc.) 414.50 (found) 415.3 (MH)+<br>$^1$H NMR (DMSO-d$_6$) δ (ppm): 10.83 (0.3 H, s), 9.55 (1 H), d J = 1.9 Hz,), 9.27 (1 H, s), 8.23 (1 H, d, J = 8.0 Hz,), 8.19 (1 H, d, J = 8.5 Hz,), 8.02-7.97 (1 H, m), 7.83-7.79 (1 H, m), 7.76 (1 H, s), 7.61 (1 H, d, J = 2 Hz), 7.58 (1 H, d, J = 2 Hz), 7.53 (1 H, d, J = 4.9 Hz), 7.47 (1 H, d, J = 3.5 Hz), LRMS: 345.09 (calc) 346.0 (found) | F, W |
| 489 | (S)-N-(4-aminobiphenyl-3-yl)-4-(3-(2-(dimethylamino)acetamido)pyrrolidin-1-yl)benzamide | $^1$HNMR: (DMSO-d$_6$) δ (ppm): 9.43 (s, 1 H), 8.00 (d, 2 H), 7.88 (d, 2 H), 7.54 (dd, 2 H), 7.49 (d, 1 H), 7.38 (t, 2 H), 7.28 (d, 1 H), 7.24-7.20 (m, 1 H), 6.85 (d, 1 H), 6.57 (d, 2 H), 5.02, 2 H), 4.46-4.42 (m, 1 H), 3.57-3.52 (m, 1 H), 3.44-3.40 (m, 1 H), 3.34 (s, 3 H), 3.20-3.16 (m, 1 H), 2.86 (s, 2 H), 2.20-2.00 (m, 7H), 1.99-1.96 (m, 1 H). LRMS(ESI): (calc.) 457.57 (found) 458.3 (MH)+ | T, I, F (with 322), R, F, G |
| 490 | (S)-N-(4-aminobiphenyl-3-yl)-4-(3-(2-methoxyacetamido)pyrrolidin-1-yl)benzamide | $^1$HNMR: (DMSO-d$_6$) δ (ppm): 9.43 (s, 1 H), 8.09 (d, 2 H), 7.87 (d, 2 H), 7.54 (dd, 2 H), 7.49 (d, 1 H), 7.38 (m, 2 H), 7.28 (d, 1 H), 7.24-7.20 (m, 1 H), 6.84 (d, 1 H), 6.57 (d, 2 H), 5.01 (s, 2 H), 4.49-4.44 (m, 1 H), 3.81 (s, 2 H), 3.57-3.52 (m, 1 H), 3.45 (m, 1 H), 3.34 (s, 3 H), 3.18 (m, 1 H), 2.16 (m, 1 H), 2.04 (m, 1 H). LRMS(ESI): (calc.) 444.53 (found) 445.2 (MH)+ | T, I, F (with 322), R, K, G |
| 491 | (S)-N-(4-aminobiphenyl-3-yl)-4-(3-(2-methoxyacetamido)pyrrolidin-1-yl)benzamide | $^1$HNMR: (DMSO-d$_6$) δ (ppm): 9.81 (s, 1 H), 8.42 (s, 1 H), 8.14 (d, 2 H), 7.85 (s, 1 H), 7.82 (d, 2 H), 7.56-7.51 (m, 3 H), 7.40-7.32 (m, 3 H), 7.22 (m, 1 H), 7.15 (s, 1 H), 6.84 (d, 1 H), 6.86 (d, 2 H), 5.13 (s, 2 H). LRMS(ESI): (calc.) 444.53 (found) 445.2 (MH)+ | F, G |
| 492 | (S)-N-(4-aminobiphenyl-3-yl)-4-(3-(2-methoxyacetamido)pyrrolidin-1-yl)benzamide | $^1$HNMR: (DMSO-d$_6$) δ (ppm): 9.42 (s, 1 H), 7.87 (d, 2 H), 7.55-7.49 (m, 3 H), 7.39 (t, 2 H), 7.32 (dd, 1 H), 7.27-7.20 (m, 1 H), 6.84 (d, 1 H), 6.56 (d, 2 H), 5.01 (s, 2 H), 4.19 (m, 1 H), 3.50-3.52 (m, 4 H), 3.42 (m, 1 H), 3.15 (m 1 H), 2.18 (m, 1 H), 1.93 (m, 1 H). LRMS(ESI): (calc.) 444.53 (found) 445.2 (MH)+ | K, I, F (with 322,), G |
| 493 | (S)-N-(4-aminobiphenyl-3-yl)-4-(3-(2,2,2-trifluoroacetamido)pyrrolidin-1-yl)benzamide | $^1$HNMR: (DMSO-d$_6$) δ (ppm): 9.82 (d, 1 H), 9.53 (s, 1 H), 7.97 (d, 2 H), 7.63-7.58 (m, 3 H), 7.47 (t, 2 H), 7.37 (dd, 1 H), 7.22 (t, 1 H), 7.31 (dt, 1 H), 6.93 (d, 1 H), 6.68 (d, 2 H), 5.10 (s, 2 H), 4.60 (m, 1 H), 3.70 (m, 1 H), 3.56 (m, 1 H), 3.44 (m, 1 H), 2.35 (m, 1 H), 2.15 (m, 1 H). RMS: (calc.) 468.47 (found) 469.1 (MH)+ | K, I, F (with 322), G |
| 494 | N-(4-amino-4'-fluorobiphenyl-3-yl)-5-phenylfuran-2-carboxamide | $^1$H NMR (DMSO-d$_6$) δ (ppm): 9.86 (br, s, 1 H), 8.02 (d, J = 7.2 Hz, 1 H), 7.68-7.60 (m, 2 H), 7.58-7.50 (m, 3 H), 7.47-7.36 (m, 3 H), 7.30-7.20 (m, 3 H), 6.92 (d, J = 8.4 Hz, 1 H), 5.18 (br s, 2 H). LRMS(ESI): (calc.) 372.4 (found) 373.3 (MH)+ | F, G |

TABLE 22-continued

Characterization and preparative sequence of compounds synthesized

| | | | |
|---|---|---|---|
| 495 | (R)-N-(4-aminobiphenyl-3-yl)-4-(3-aminopyrrolidin-1-yl)benzamide | $^1$H NMR (DMSO-d$_6$) □ (ppm): 9.45 (s, 1 H), 7.88 (d, J = 8.6 Hz, 2 H), 7.54 (dd, J = 7.2, 1.2 Hz, 2 H), 7.50 (d, J = 2.4 Hz, 1 H), 7.37 (t, J = 7.4 Hz, 2 H), 7.28 (dd, J = 8.2, 2.2 Hz, 1 H), 7.22 (tt, J = 7.4, 1.2 Hz, 1 H), 6.85 (d, J = 8.2 Hz, 1 H), 6.57 (d, J = 8.8 Hz, 2 H), 5.00 (d, J = 10.2 Hz, 1 H) 3.76 (quint, J = 4.5 Hz, 1 H), 3.54-3.40 (m, 3 H), 3.15 (dd, J = 10.4, 4.1 Hz, 1 H), 2.19 (sext, J = 6.3 Hz, 1 H), 1.91 (sext, J = 5.1 Hz, 1 H). LRMS: (calc.) 372.5 (found) 373.2 (MH)+ | J, P, F (with 322), G |
| 496 | (S)-4-(3-acetamidopyrrolidin-1-yl)-N-(2-amino-5-(pyridin-4-yl phenyl)benzamide | $^1$H NMR (DMSO-d$_6$) δ (ppm): 1 H: 9.43 (s, 1 H), 8.49 (d, J = 6.3 Hz, 2 H), 8.18 (d, J = 6.8 Hz, 1 H), 7.88 (d, J = 9.0 Hz, 2 H), 7.66 (d, J = 2.2 Hz, 1 H), 7.57 (d, J = 6.3 Hz, 2 H), 7.47 (dd, J = 8.6, 2.2 Hz, 1 H), 6.87 (d, J = 8.4 Hz, 1 H), 6.58 (d, J = 9.0 Hz, 2 H), 5.29 (s, 2 H), 4.38 (quint, J = 5.1 Hz, 1 H), 3.54 (dd, J = 9.8, 6.5 Hz, 1 H), 3.47-3.42 (m, 1 H), 3.37-3.32 (m, 1 H), 3.12 (dd, J = 10.2, 4.1 Hz, 1 H), 2.17 (sext, J = 5.1 Hz, 1 H), 1.90-1.87 (m, 1 H), 1.81 (s, 3 H). LRMS: (calc.) 415.5 (found) 416.2 (MH)+ | V, I, F (with 390), G |
| 497 | (S)-benzyl 1-(4-(2-amino-5-(pyridin-4-yl)phenylcarbamoyl)phenyl)pyrrolidin-3-ylcarbamate | $^1$H NMR (CD$_3$OD) δ (ppm): 8.43 (d, J = 6.5 Hz, 2 H), 7.88 (d, J = 8.8 Hz, 2 H), 7.62 (d, J = 2.2 Hz, 1 H), 7.60 (d, J = 6.5 Hz, 2 H), 7.48 (dd, J = 8.4, 2.3 Hz, 1 H), 7.34-7.27 (m, 5 H), 6.96 (d, J = 8.4 Hz, 1 H), 6.57 (d, J = 8.8 Hz, 2 H), 5.48 (s, 2 H), 5.08 (s, 2 H), 4.30 (quint, J = 5.1 Hz, 1 H), 3.59 (dd, J = 10.2, 6.7 Hz, 1 H), 3.46 (dt, J = 9.0, 7.4 Hz, 1 H), 3.35 (q, J = 7.4 Hz, 1 H), 3.21 (dd, J = 9.8, 4.9 Hz, 1 H), 2.26 (sext, J = 7.2 Hz, 1 H), 1.99 (sext, J = 6.8 Hz, 1 H). LRMS: (calc.) 507.6 (found) 508.3 (MH)+ | T, I, F (with 390), G |
| 498 | N-(4-amino-4'-fluorobiphenyl-3-yl)-5-(pyridin-2-yl)thiophene-2-carboxamide | $^1$H NMR(MeOD-d$_4$) δ (ppm): 8.60-8.55 (m, 1 H), 7.98-7.86 (m, 3 H), 7.78 (d, J = 3.9 Hz, 1 H), 7.63-7.56 (m, 2 H), 7.48 (d, J = 2.2 Hz, 1 H), 7.40-7.34 (m, 2 H), 7.19-7.11 (m, 2 H), 7.00 (d, J = 8.4 Hz, 1 H). LRMS(ESI): (calc.) 389.5 (found) 390.2 (MH)+ | F, G |
| 499 | N-(4-aminobiphenyl-3-yl)-1-benzoylpiperidine-4-carboxamide | $^1$H NMR (DMSO-d$_6$) δ (ppm): 9.25 (s, 1 H), 7.60-7.53 (m, 3 H), 7.52-7.46 (m, 3 H), 7.46-7.40 (m, 4 H), 7.32-7.24 (m, 2 H), 6.84 (d, J = 8.2 Hz, 1 H), 4.66-4.45 (br m, 1 H), 3.80-3.62 (br m, 1 H), 3.22-2.84 (br m, 2 H), 2.80-2.70 (m, 1 H), 2.06-1.80 (br m, 2 H), 1.76-1.58 (br m, 2 H). LRMS(ESI): (calc.) 399.5 (found) 400.4 (MH)+ | K, P, F (with 322), G |
| 500 | N-(4-amino-3',4'-difluorobiphenyl-3-yl)-5-(morpholinomethyl)furan-2-carboxamide | $^1$H NMR (MeOD-d$_4$) δ (ppm): 8.46-8.44 (m, 2 H), 7.72 (d, J = 2.2 Hz, 1 H), 7.62-7.60 (m, 2 H), 7.46 (dd, J = 8.4, 2.3 Hz, 1 H), 7.13-7.03 (m, 4 H), 6.94 (d, J = 8.4 Hz, 1 H), 3.84 (s, 2 H), 3.43 (s, 2 H), 2.98-2.92 (m, 4 H). LRMS: (calc.) 413.4 (found) 414.3 (MH)+. | B, C, F, G |

TABLE 22-continued

Characterization and preparative sequence of compounds synthesized

| | | | |
|---|---|---|---|
| 501 | N-(4-amino-3',4'-difluorobiphenyl-3-yl)-1-benzylpiperidine-4-carboxamide | $^1$H NMR (MeOD-d$_4$) δ (ppm): 7.50-7.23 (m, 10 H), 6.96-6.90 (m, 1 H), 3.59 (s, 2 H), 3.09-3.00 (m, 2 H), 2.56-2.44 (m, 1 H), 2.20-2.10 (m, 2 H), 2.00-1.89 (m, 4 H). LRMS: (calc.) 421.5 (found) 422.3 (MH)+ | B, C, F, G |
| 502 | N-(4-amino-3',4'-difluorobiphenyl-3-yl)4-(1,3-dioxoisoindolin-2-yl)benzamide | $^1$H NMR(MeOD-d$_4$) δ (ppm): 9.86 (s, 1 H), 8.22-8.14 (m, 2 H), 8.08-7.94 (m, 4 H), 7.71-7.60 (m, 4 H), 7.52-7.37 (m, 3 H), 6.94-6.86 (m, 1 H), 5.30 (s, 2 H). LRMS: (calc.) 469.4 (found) 470.3 (MH)+ | B, C, F, G |
| 503 | (S)-N-(4-aminobiphenyl-3-yl)-4-(3-(bis(dimethylamino)methyleneamino)pyrrolidin-1-yl)benzamide | $^1$HNMR: (DMSO-d$_6$) δ (ppm): 9.46 (s, 1 H), 7.88 (d, 2 H), 7.55-7.49 (m, 3 H), 7.39 (t, 2 H), 7.29 (dd, 1 H), 7.22 (t, 1 H), 6.85 (d, 1 H), 6.60 (d, 2 H), 5.02 (s, 2 H), 4.18 (m, 1 H), 3.61 (m, 1 H), 3.50 (s, 3 H), 3.21 (m, 1 H), 2.85-2.78 (m, 9H), 2.27 (m, 2 H), 1.97 (m, 2 H). LRMS: (calc.) 470.72 (found) 471.4 (MH)+ | F, G |
| 504 | 2-(dimethylamino)ethyl 4-(2-amino-5-(2-aminopyrimidin-5-yl)phenylcarbamoyl)phenylcarbamate | $^1$H NMR (DMSO-d$_6$) δ (ppm): 10.01 (s, 1 H), 9.64 (s, 1 H), 8.44 (s, 2 H), 7.94 (d, J = 8.8 Hz, 2 H), 7.59 (d, J = 8.8 Hz, 2 H), 7.40 (d, J = 2.0 Hz,), 7.24 (dd, J1 = 8.4 Hz, J2 = 2.0 Hz, 1 H), 6.84 (d, J = 8.4 Hz, 1 H), 6.59 (s, 2 H), 5.01 (s, 2 H), 4.19 (t, J = 6.0 Hz, 2 H), 2.52 (t, J= 5.6 Hz, 2 H, overlapped DMSO-d$_6$), 2.19 (s, 6 H). LRMS: (calc.) 435.38 (found) 436.2 (MH)+ | B, G |
| 505 | 2-(dimethylamino)ethyl 4-(4-amino-3',4',5'-trimethoxybiphenyl-3-ylcarbamoyl)phenylcarbamate | $^1$H NMR (DMSO-d$_6$) δ (ppm): 10.02 (s, 1 H), 9.67 (s, 1 H), 7.95 (d, J = 8.8 Hz, 2 H), 7.59 (d, J = 8.8 Hz, 2 H), 7.46 (d, J = 1.6 Hz, 1 H), 7.34 (dd, J1 = 8.4 Hz, J2 = 2.4 Hz, 1 H), 6.85 (d, J = 8.4 Hz, 1 H), 6.79 (s, 2 H), 5.02 (s, 2 H), 4.19 (t, J = 5.6 Hz, 2 H), 3.83 (s, 6 H), 3.66 (s, 3 H), 2.52 (t, J = 5.6 Hz, 2 H), overlapped DMSO-d$_6$), 2.19 (s, 6 H). LRMS: (calc.) 508.57 (found) 509.2 (MH)+ | B, G |
| 506 | N-(2-amino-5-(pyridin-3-yl)phenyl)-1-(2,6-difluorobenzyl)-1 H-1,2,3-triazole 4-carboxamide | $^1$H NMR (DMSO-d$_6$) δ (ppm): 9.81 (s, 1 H), 8.75 (d, J = 2 Hz, 1 H), 8.73 (s, 1 H), 8.41 (dd, J = 1.6 Hz, 4.4 Hz, 1 H), 7.91 (m, 1 H), 7.58 (d, J = 2 Hz, 1 H), 7.52 (m, 1 H), 7.38 (m, 2 H), 7.20 (t, J = 8 Hz, 2 H), 6.86 (d, J = 8 Hz, 1 H), 5.76 (s, 2 H), 5.17 (s, 2 H). LRMS: (calc.) 406.2 (found) 407.3 (MH)+ | Y, P, F, W |
| 507 | N-(2-amino-5-(thiophen-2-yl)phenyl)-1-(2,6-difluorobenzyl)-1 H-1,2,3-triazole-4-carboxamide | $^1$H NMR (MeOD-d$_4$) δ (ppm): 8.61 (s, 1 H), 7.77 (s, 1 H), 7.70 (d, J = 8.4 Hz, 2 H), 7.43-7.54 (m, 4 H), 7.08-7.13 (m, 3 H), 5.82 (s, 2 H). LRMS: (calc.) 411.1 (found) 412.3 (MH)+ | Y, P, F (with 4), W |
| 508 | N-(2-amino-5-(5-chlorothiophen-2-yl)phenyl)-1-(2,6-difluorobenzyl)-1 H-1,2,3-triazole-4-carboxamide | $^1$H NMR (MeOD-d$_4$) ☐ (ppm): 7.52 (m, 2 H), 7.26 (dd, J = 2.4 Hz, 8.4 hz, 1 H), 7.09 (t, J = 8 Hz, 2 H), 7.01 (d, J = 4 Hz, 1 H), 6.88 (dd, J = 2.4 Hz, 6.4 Hz, 2 H), 5.80 (s, 2 H). LRMS: (calc.) 445.8 (found) 446.3 (MH)+ | Y, P, F (with 168), W |
| 509 | N-(2-amino-5-(thiophen- | $^1$HNMR: (DMSO-d$_6$) δ (ppm): 9.17 (s, 1 H), 7.42 (d, 1 H), 7.34 | C |

TABLE 22-continued

Characterization and preparative sequence of compounds synthesized

| | | | |
|---|---|---|---|
| | 2-yl)phenyl)-3-(4-(morpholinomethyl)phenyl)propanamide | (dd, 1 H), 7.22-7.17 (m, 6 H), 7.04 (dd, 1 H), 6.72 (d, 1 H), 5.02 (s, 2 H), 3.54 (t, 4 H), 3.41 (s, 2 H), 2.90 (t, 2 H), 2.63 (t, 2 H), 2.32-2.27 (m, 4 H). LRMS: (calc.) 421.3 (found) 422.2 (MH)+ | |
| 510 | N-(2-amino-5-(thiophen-3-yl)phenyl)acetamide | $^1$HNMR: (DMSO-d$_6$) δ (ppm): 9.20 (s, 1 H), 7.55 (dd, 1 H), 7.52 (dd, 1 H), 7.48 (d, 1 H), 7.37 (dd, 1 H), 7.26 (dd, 1 H), 6.73 (dd, 1 H), 5.21 (s, 2 H), 2.04 (s, 3 H). LRMS: 232.1 (calc) 233.0 (found for M + H) | V, G |
| 511 | N-(2-amino-5-(pyridin-4-yl)phenyl)-4-((3,4-dimethoxyphenylamino)methyl)benzamide | $^1$H NMR (MeOD-d$_4$) δ (ppm): 8.50-8.38 (m, 2 H), 7.96 (d, J = 8.2 Hz, 2 H), 7.66-7.64 (m, 3 H), 7.55-7.51 (m, 3 H), 6.98 (d, J = 8.4 Hz, 1 H), 6.71 (d, J = 8.6 Hz, 1 H), 6.36 (d, J = 2.5 Hz, 1 H), 6.13 (dd, J = 8.6, 2.5 Hz, 4.37 (s, 2 H), 3.73 (s, 3 H), 3.70 (s, 3 H). LRMS: (calc.) 454.2 (found) 455.3 (MH)+ | F, Z, G |
| 512 | 2-(dimethylamino)ethyl 4-(4,4'-diaminobiphenyl-3-ylcarbamoyl)phenylcarbamate | $^1$H NMR (DMSO-d$_6$) δ (ppm): 10.02 (s, 1 H), 9.62 (s, 1 H), 7.93 (d, J = 8.8 Hz, 2 H), 7.58 (d, J = 8.8 Hz, 2 H), 7.34 (d, J = 2.2 Hz, 1 H), 7.21 (d, J = 6.6 Hz, 2 H), 7.15 (d, J = 8.4 Hz, 1 H), 6.78 (d, J = 8.3 Hz, 1 H), 6.58 (d, J = 8.4 Hz, 2 H), 5.02 (s, 2 H), 4.82 (s, 2 H), 4.17 (t, J = 5.6 Hz, 2 H), 2.53 (t, J = 5.5 Hz, 2 H), 2.18 (s, 6 H). LRMS (ESI): (calc.) 433.13 (found) 434.3 (MH)+ | B, C, F, G |
| 513 | 2-(dimethylamino)ethyl 5-(2-amino-5-(thiophen-2-yl)phenylcarbamoyl)thiophen-2-ylcarbamate | $^1$HNMR: (CD$_3$OD) δ (ppm): 7.66 (d, 1 H), 7.45 (d, H), 7.33 (dd, 1 H), 7.20 (m, 2 H), 7.00 (dd, 1 H), 6.88 (d, 1 H), 6.61 (d, 1 H), 4.31 (t, 2 H), 2.68 (t, 2 H), 2.32 (s, 6 H). LRMS: (calc.) 430.66 (found) 431.1 (MH)+ | F, C, AA, G |
| 514 | 2-(dimethylamino)ethyl 4-(4-amino-3'-fluro-4'-hydroxybiphenyl-3-ylcarbamoyl)phenylcarbamate | $^1$HNRM: (DMSO-d$_6$) δ (ppm): 10.01 (s, 1 H), 9.77 (s, 1 H), 9.61 (s, 1 H), 7.94 (d, 2 H), 7.59-7.57 (m, 2 H), 7.41 (d, 1 H), 7.29 (dd, 1 H), 7.23 (dd, 1 H), 7.17 (dd, 1 H), 6.94 (t, 1 H), 6.81 (d, 1 H), 5.01 (s, 2 H), 4.18 (t, 2 H), 2.52 (t, 2 H), 2.18 (s, 6 H). LRMS: (calc.) 452.59 (found) 453.2 (MH)+ | B, C, F (with 335), G |
| 515 | 2-(dimethylamino)ethyl 4-(2-amino-5-(thiophen-2-yl)phenylcarbamoyl)piperidine-1-carboxylate | $^1$HNMR: (DMSO-d$_6$) δ (ppm): 9.23 (s, 1 H), 7.50 (d, 1 H), 7.32 (dd, 1 H), 7.21-7.17 (m, 2 H), 7.01 (dd, 1 H), 6.72 (d, 1 H), 5.09 (s, 2 H), 4.07 (t, 2 H), 4.01 (m, 2 H), 2.81 (m, (s, 2 H), 2.48 (t, 2 H), 2.18 (s, 6 H), 1.82 (m, 2 H), 1.53 (m, 2 H). LRMS: (calc.) 416.54 (found) 417.2 (MH)+ | BB, E, CC, K (with 4), G |
| 516 | N-(4-(4-aminobiphenyl-3-ylcarbamoyl)benzyl)-2-(methylsufonamido)benzamide | $^1$H NMR (DMSO-d$_6$) δ (ppm): 11.13 (s, 1 H), 10.27 (s, 1 H), 9.58 (t, J = 6.0 Hz, 1 H), 8.05 (d, J = 8.2 Hz, 2 H), 7.94 (d, J = 8.1 Hz, 1 H), 7.71 (d, J = 1.8 Hz, 1 H), 7.65-7.63 (m, 2 H), 7.60-7.50 (m, 5 H), 7.46 (t, J = 7.7 Hz, 2 H), 7.34 (t, J = 7.3 Hz, 1 H), 7.28-7.21 (m, 2 H), 4.58 (d, J = 5.9 Hz, 2 H), 3.12 (s, 3 H). LRMS: Cal.: 514.2; Obt: 515.2 (M + H)+ | U, P, N, P, CC, K (with 322), W |

TABLE 22-continued

Characterization and preparative sequence of compounds synthesized

| | | | |
|---|---|---|---|
| 517 | (E)-3-(4-(((2-(1H-indol-3-yl)ethyl)(2-hydroxyethyl)amino)methyl)phenyl)-N-(2-amino-5-(thiophen-2-yl)phenyl)acrylamide | ¹HNMR: (DMSO-d₆) δ (ppm): 10.75 (s, 1 H), 9.46 (s, 1 H), 8.31 (s, 1 H), 7.71 (d, 1 H), 7.56 (dd, 3 H), 7.44-7.41 (m, 2 H), 7.38-7.35 (m, 2 H), 7.30 (d, 1 H), 7.25-7.22 (m, 2 H), 7.10 (d, 1 H), 7.06-7.01 (m, 2 H), 6.78 (d, 1 H), 5.22 (s, 2 H), 3.74 (s, 2 H), 3.52 (t, 2 H), 2.84-2.79 (m, 2 H), 2.75-2.67 (m, 2 H), 2.66-2.62 (m, 2 H). LRMS: 536.2 (calc) 537.3 (found) | DD, Z, F (with 4), G |
| 518 | (E)-N-(2-amino-5-(thiophen-2-yl)phenyl)-3-(4-(hydroxymethyl)phenyl)acrylamide | ¹HNMR: (DMSO-d₆) δ (ppm): 9.44 (s, 1 H), 7.70 (d, 1 H), 7.60-7.55 (m, 3 H), 7.39 (d, 2 H), 7.36 (dd, 1 H), 7.26-7.22 (m, 2 H), 7.05 (dd, 1 H), 6.88 (d, 1 H), 6.78 (d, 1 H), 5.28 (t, 1 H), 5.21 (s, 2 H), 4.53 (d, 2 H). LRMS: 350.1 (calc) 351.0 (found for M + H) | Z, G |
| 519 | N-(2-amino-5-(thiophen-2-yl)phenyl)-4-(piperazin-1-ylmethyl)benzamide | ¹H NMR (DMSO-d₆) δ (ppm): 10.31 (s, 1 H), 9.58 (s, 2 H), 8.14 (d, J = 8.0 Hz, 2 H), 7.79 (d, J = 7.8 Hz, 2 H), 7.66 (s, 1 H), 7.48 (d, J = 5.1 Hz, 2 H), 7.39 (d, J = 3.1 Hz, 1 H), 7.16 (d, J = 8.4 Hz, 1 H), 7.10 (d, J = 4.9 Hz, 1 H), 7.09 (d, J = 3.7 Hz, 1 H), 4.44 (s, 2 H), 3.55-3.18 (m, 8 H). LRMS(ESI): (calc.) 392.3 (found) 393.3 (MH)+ | D, P, F (with 4), G |
| 520 | N-(2-amino-5-(thiophen-2-yl)phenyl)-5-((4-morpholinopiperidin-1-yl)methyl)furan-2-carboxamide | ¹H NM (DMSO-d₆) δ (ppm): 9.59 (s, 1 H), 7.42 (d, J = 2.4 Hz, 1 H), 7.35 (dd, J1 = 5.2 Hz, J2 = 1.2, 1 H), 7.29 (dd, J1 = 8.4 Hz, J2 = Hz, 1 H), 7.27 (d, J = 3.6 Hz, 1 H), 7.24 (dd, J1 = 3.6 Hz, J2 = 1.2 Hz, 1 H), 7.05 (dd, J1 = 5.2 Hz, J2 = 4.0 Hz, 1 H), 6.80 (d, J = 8.4 Hz, 1 H), 6.48 (d, J = 3.2 Hz, 1 H), 5.14 (s, 2 H), 3.54 (s, 6 H), 2.88 (d, J = 11.6 Hz, 2 H), 2.43 (t, J = 4.4 Hz, 4 H), 2.08 (tt, J1 = 11.2 Hz, J2 = 3.6 Hz, 1 H), 1.99 (t, J = 10.8 Hz, 2 H), 1.74 (d, J = 11.6 Hz, 2 H), 1.38 (qd, J1 = 12.0 Hz, J2 = 3.6 Hz, 2 H). LRMS: 466.6 (calc) 467.1 (found) | D, E, N (with 4), G |
| 521 | N-(2-amino-5-thiophen-2-yl)phenyl)-4-(isoindolin-2-ylmethyl)benzamide | ¹H NMR (DMSO-d₆) δ (ppm): 9.71 (s, 1 H), 7.98 (d, J = 8.4 Hz, 2 H), 7.51 (d, J = 8.4 Hz, 2 H), 7.46 (d, J = 1.8 Hz, 1 H), 7.34 (dd, J = 5.1, 1.2 Hz, 1 H), 7.28 (dd, J = 8.4, 2.2 Hz, 1 H), 7.23 (dd, J = 3.5, 1.2 Hz, 1 H), 7.23-7.16 (m, 4 H), 7.03 (dd, J = 5.1, 3.5 Hz, 1 H), 6.80 (d, J = 8.4 Hz, 1 H), 5.14 (s, 2 H), 3.94 (s, 2 H), 3.85 (s, 4 H). LRMS: 425.55 (calc) 426.1 (found) | K, L, G |
| 522 | 2-(dimethylamino)ethyl 4-(4-amino-4'-(methylsulfinyl)biphenyl-3-ylcarbamoyl)phenylcarbamate | ¹H NMR (DMSO-d₆) □ (ppm): 10.04 (s, 1 H), 9.63 (s, 1 H), 8.58 (s J = 2.0 Hz, 1 H), 7.97 (d, J = 8.8 Hz, 2 H), 7.76-7.67 (m, 2 H), 7.61-7.59 (m, 3 H), 7.41-7.37 (m, 2 H), 6.88 (d, J = 8.4 Hz, 1 H), 5.23 (s, 2 H), 4.22 (t, J = 5.6 Hz, 2 H), 2.75 (s, 3 H), 2.61 (bs, 2 H), 2.26 (s, 6 H).. LRMS: (calc.) 480.58 (found) 481.4 (MH)+ | B, C, F (with 335), G, EE |
| 523 | 2-(dimethylamino)ethyl 4-(4-amino-4'- | ¹H NMR (DMSO-d₆) □ (ppm): 10.18 (s, 1 H), 9.67 (s, 1 H), 7.98 (d, J = 8.8 Hz, 2 H), 7.77-7.68 (m, 4 H), 7.62-7.58 (m, | B, C, F (with 335), G, EE |

TABLE 22-continued

Characterization and preparative sequence of compounds synthesized

| | | | |
|---|---|---|---|
| | (methylsulfonyl) biphenyl-3-ylcarbamoyl) phenylcarbamate | 3 H), 7.40 (dd, J1 = 8.4 Hz, J2 = 2.4 Hz, 1 H), 6.88 (d, J = 8.4 Hz, 1 H), 5.76 (s, 1 H), 5.21 (s, 1 H), 4.61 (t, J = 5.6 Hz, 2 H), 3.67 (bs, overlapped water, 2 H), 3.23 (s, overlapped water, 6 H), 2.75 (s, 3 H) LRMS: (calc.) 496.58 (found) 497.2 (MH)+ | |
| 524 | (S)-benzyl 1-(4-(4-aminobiphenyl-3-ylcarbamoyl) phenyl)pyrrolidin-3-yl(ehtyl)carbamate | $^1$H NMR (DMSO-$d_6$) δ (ppm) 9.43 (s, 1 H), 7.88 (d, J = 9.0 Hz, 2 H), 7.54 (d, J = 7.0 Hz, 2 H), 7.49 (d, J = 2.2 Hz, 1 H), 7.39-7.31 (m, 6 H), 7.29 (dd, J = 8.2, 2,2 Hz, 1 H), 7.22 (t, J = 7.2 Hz, 1 H), 6.85 (d, J = 8.2 Hz, 1 H), 6.60 (d, J = 8.8 Hz, 2 H), 5.11 (s, 1 H), 5.02 (s, 2 H), 4.66 (quint, J = 8.2 Hz, 1 H), 3.51 (t, J = 9.8 Hz, 1 H), 3.51-3.45 (m, 2 H), 3.30-3.24 (m, 4 H), 2.21-2.16 (m, 2 H), 1.09 (t, J = 7.0 Hz, 3 H). LRMS(ESI): (calc.) 534.6 (found) 535.3 (MH)+ | J, T, I, CC, K (with 322), G |
| 525 | (S)-N-(4-aninobiphenyl-3-yl)-4-(3-(ethylamino) pyrrolidin-1-yl)benzamide | $^1$H NMR (DMSO-$d_6$) δ (ppm): 9.41 (s, 1 H), 7.87 (d, J = 9.0 Hz, 2 H), 7.54 (d, J = 7.2 Hz, 2 H), 7.49 (d, J = 2.2 Hz, 1 H), 7.38 (t, J = 7.2 Hz, 2 H), 7.28 (dd, J = 8.4, 2.3 Hz, 1 H), 7.22 (t, J = 7.4 Hz, 1 H), 6.85 (d, J = 8.4 Hz, 1 H), 6.56 (d, J = 9.0 Hz, 2 H), 5.01 (s, 2 H), 3.49 (dd, J = 10.0, 6.3 Hz, 1 H), 3.41-3.38 (m, 2 H), 3.32-3.26 (m, 1 H), 3.08 (dd, J = 10.0, 6.3 Hz, 1 H), 2.78-2.73 (m, 2 H), 2.13 (sext, J = 7.3 Hz, 1 H), 1.83 (sext, J = 6.8 Hz, 1 H), 1.03 (t, J = 7.0 Hz, 3 H). LRMS(ESI): (calc.) 400.52 (found) 401.2 (MH)+ | R |
| 526 | N-(4-aminobiphenyl-3-yl)-4-(3,3-difluoropyrrolidin-1-yl)benzamide | $^1$H NMR (DMSO-$d_6$) δ (ppm): 9.49 (s, 1 H), 7.91 (d, J = 9.0 Hz, 2 H) 7.54 (d, J = 7.2 Hz, 2 H), 7.49 (d, J = 2.0 Hz, 1 H), 7.37 (t, J = 7.4 Hz, 2 H), 7.29 (dd, J = 8.2, 2.2 Hz, 1 H), 7.22 (t, J = 7.4 Hz, 1 H), 6.85 (d, J = 8.2 Hz, 1 H), 6.67 (d, J = 8.8 Hz, 2 H), 5.03 (s, 2 H), 3.78 (t, J = 13.3 Hz, 2 H), 3.56 (t, J = 7.0 Hz, 2 H), 2.56 (sept, J = 7.2 Hz, 2 H). LRMS(ESI): (calc.) 393.2 (found) 394.1 (MH)+ | J, I, CC, K (with 322), G |
| 527 | (S)-N-(4-aminobiphenyl-3-yl)-4-(3-fluoropyrrolidin-1-yl)benzamide | $^1$H NMR (DMSO-$d_6$) δ (ppm): 9.45 (s, 1 H), 7.89 (d, J = 8.8 Hz, 2 H), 7.54 (d, J = 7.4 Hz, 2 H), 7.50 (d, J = 2.2 Hz, 1 H), 7.38 (t, J = 7.4 Hz, 2 H), 7.29 (dd, J = 8.2, 2.2 Hz, 1 H), 7.22 (t, J = 7.2 Hz, 1 H), 6.85 (d, J = 8.2 Hz, 1 H), 6.63 (d, J = 9.0 Hz, 2 H), 5.47 (d, J = 54.0 Hz, 1 H), 5.02 (s, 2 H), 3.66-3.48 (m, 3 H), 3.49-3.36 (m, 1 H), 2.29-2.16 (m, 2 H). LRMS(ESI): (calc.) 375.2 (found) 376.2 (MH)+ | J, I, F (with 322), G |
| 528 | 1-(4-(4-aminobiphenyl-3-ylcarbamoyl) phenyl)piperdine-4-carboxamide | $^1$H NMR (DMSO-$d_6$ δ (ppm): 7.92 (d, J = 8.8 Hz, 2 H), 7.56 (d, J = 7.4 Hz, 2 H), 7.47 (d, J = 1.2 Hz, 1 H), 7.37 (t, J = 7.4 Hz, 2 H), 7.36 (d, J = 8.0 Hz, 1 H), 7.24 (t, J = 7.2 Hz, 1 H), 7.03 (d, J = 8.8 Hz, 2 H), 6.97 (d, J = 8.4 Hz, 1 H), 3.98 (d, J = 13.2 Hz, 2 H), 2.89 (t, J = 11.3 Hz, 2 H), 2.50-2.40 (m, 1 H), 1.90 (d, J = 13.5 Hz, 2 H), 1.80 (qd, J = 11.9, 3.7 Hz, | J, I, F (with 322), G |

TABLE 22-continued

Characterization and preparative sequence of compounds synthesized

| | | | |
|---|---|---|---|
| 529 | N-(4-aminobiphenyl-3-yl)-4-(4-ethylpiperazin-1-yl)benzamide | 2 H). LRMS(ESI): (calc.) 414.2 (found) 415.2 (MH)+ <br> $^1$H NMR (DMSO-d$_6$) δ (ppm): 9.50 (s, 1 H), 7.88 (d, J = 9.0 Hz, 2 H), 7.54 (dd, J = 7.0, 1.2 Hz, 2 H), 7.49 (d, J = 2.2 Hz, 1 H), 7.37 (t, J = 7.4 Hz, 2 H), 7.29 (dd, J = 8.2, 2.2 Hz, 1 H), 7.22 (tt, J = 7.4 Hz, 1.2 Hz, 1 H), 7.00 (d, J = 9.0 Hz, 2 H), 6.85 (d, J = 8.2 Hz, 1 H), 5.03 (s, 2 H), 3.30-3.20 (m, 4 H), 2.41-2.30 (m, 2 H), 1.03 (t, J = 7.2 Hz, 3 H). Signal for 4 H overlapped with signal of DMSO LRMS(ESI): (calc.) 400.52 (found) 401.2 (MH)+ | J, I, F (with 322), G |
| 530 | (S)-N-(4-aminobiphenyl-3-yl)-4-(3-(dimethylamino)pyrrolidin-1-yl)benzamide | $^1$H NMR (MeOD-d$_4$) δ (ppm): 7.91 (d, J = 8.8 Hz, 2 H), 7.56 (dd, J = 7.0, 1.4 Hz, 2 H), 7.46 (d, J = 2.0 Hz, 1 H), 7.37 (t, J = 7.0 Hz, 2 H), 7.36 (dd, J = 8.4, 2.0 Hz, 1 H), 7.24 (tt, J = 7.0, 1.4 Hz, 1 H), 6.97 (d, J = 8.4 Hz, 1 H), 6.65 (d, J = 9.0 Hz, 2 H), 3.65 (dd, J = 9.6, 7.2 Hz, 1 H), 3.57 (t, J = 8.2 Hz, 1 H), 3.39 (td, J = 10.0, 6.8 Hz, 1 H), 3.22 (t, J = 8.4 Hz, 1 H), 3.00 (quint, J = 8.8 Hz, 1 H), 2.38 (s, 6 H), 2.33 (m, 1 H), 2.15-1.90 (m, 1 H). LRMS(ESI): (calc.) 400.5 (found) 401.2 (MH)+ | J, I, F (with 322), G |
| 531 | N-(2-amino-5-thiophen-2-yl)phenyl)-4-benzylpiperazine-1-carboxamide | $^1$HNMR (MeOD-d$_4$) δ (ppm): 7.40-7.28 (m, 7H), 7.24 (dd, J = 5.1, 1.2 Hz, 1 H), 7.20 (dd, J = 3.5, 1.0 Hz, 1 H), 7.05-7.02 (m, 1 H), 6.85 (d, J = 8.2 Hz, 1 H), 3.62-3.54 (m, 6 H), 2.56-2.49 (m, 4 H). LRMS(ESI): (calc.) 392.2 (found) 393.4 (MH)+ | B, BB, FF |
| 532 | N-(4-aminobiphenyl-3-yl)-5-methoxypicolinamide | $^1$H NMR (DMSO-d$_6$) □ (ppm): 9.72 (s, 1 H), 8.82 (d, J = 1.6 Hz, 1 H), 8.26 (dd, J = 8.6, 2.2 Hz, 1 H), 7.55-7.50 (m, 3 H), 7.40-7.31 (m, 3 H), 7.23 (t, J = 7.4 Hz, 1 H), 6.93 (d, J = 8.8 Hz, 1 H), 6.85 (d, J = 8.4 Hz, 1 H), 5.12 (d, J = 11.4 Hz, 2 H), 3.92 (s, 3 H). LRMS(ESI) (calc.) 319.1 (found) 320.3 (MH)+ | F, G |
| 533 | N-(4-aminobiphenyl-3-yl)-5-(morpholinomethyl)thiophene-2-carboxamide | $^1$H NMR (MeOD-d$_4$) δ (ppm): 7.77 (d, J = 3.3 Hz, 1 H), 7.56-7.54 (m, 2 H), 7.46 (d, J = 2.2 Hz, 1 H), 7.39-7.34 (m, 3 H), 7.25-7.21 (m, 1 H), 7.05 (d, J = 3.4 Hz, 6.96 (d, J = 8.4 Hz, 1 H), 3.76 (s, 2 H), 3.70 (t, J = 4.5 Hz, 4 H), 2.56-2.50 (m, 4 H). LRMS: (calc) 393.2 (found) 394.4 (MH)+ | F, Z, G |
| 535 | (R)-N-(4-aminobiphenyl-3-yl)-4-(3-dimethylamino)pyrrolidin-1-yl)benzamide | $^1$H NMR (MeOD-d$_4$) δ (ppm): 7.91 (d, J = 8.8 Hz, 2 H), 7.56 (dd, J = 8.2, 1.2 Hz, 2 H), 7.46 (d, J = 2.1 Hz, 1 H), 7.37 (t, J = 7.4 Hz, 2 H), 7.36 (dd, J = 8.2, 2.1 Hz, 1 H), 7.24 (tt, J = 7.4, 1.2 Hz, 1 H), 6.97 (d, J = 8.2 Hz, 1 H), 6.67 (d, J = 9.2 Hz, 2 H), 3.72-3.65 (m, 1 H), 3.65-3.55 (m, 1 H), 3.45-3.25 (m, 3 H), 2.55-2.45 (m, 6 H), 2.45-2.34 (m, 1 H), 2.05-1.95 (m, 1 H). LRMS: (calc): 400.2 (found) 401.3 (MH)+ | J, I, F (with 322), G |
| 536 | (R)-N-(4-aminobiphenyl- | $^1$H NMR (MeOD-d$_4$) δ (ppm): 7.89 (d, J = 8.8 Hz, 2 H), 7.56 | J, T, I, F (with 322), |

TABLE 22-continued

Characterization and preparative sequence of compounds synthesized

| | | | |
|---|---|---|---|
| | 3-yl)-4-(3-ethylamino)pyrrolidin-1-yl)benzamide | (dd, J = 7.2 1.2 Hz, 2 H), 7.46 (d, J = 2.2 Hz, 1 H), 7.36 (t, J = 7.8 Hz, 2 H), 7.36 (dd, J = 8.2, 2.2 Hz, 1 H), 7.24 (t, J = 7.3 Hz, 1 H), 6.97 (d, J = 8.4 Hz, 1 H), 6.65 (d, J = 8.8 Hz, 2 H), 3.65 (dd, J = 9.8, 6.4 Hz, 1 H), 3.60-3.50 (m, 2 H), 3.39 (q, J = 7.4 Hz, 1 H), 3.20 (dd, J = 9.7, 6.0 Hz, 1 H), 2.80-2.68 (m, 2 H), 2.30 (sext, J = 5.8 Hz, 1 H), 1.95 (sext, J = 5.7 Hz, 1 H), 1.17 (t, J = 5.3 Hz, 3 H). LRMS: (calc.) 400.2 (found) 401.3 (MH)+ | G, R |
| 537 | 2-dimethylamino)ethyl 4-(4-amino-4'-cyano-3'-fluorobiphenyl-3-ylcarbamoly)phenylcarbamate | $^1$H NMR (DMSO-$d_6$) δ (ppm): 10.02 (s, 1 H), 9.62 (s, 1 H), 7.95 (d, J = 8.8 Hz, 2 H), 7.89-7.86 (m, 1 H), 7.73 (dd, J = 11.6, 1.6 Hz, 1 H), 7.67 (d, J = 2.0 Hz, 1 H), 7.63 (dd, J = 8.4, 2.0 Hz, 1 H), 7.60-7.58 (m, 2 H), 7.51 (dd, J = 8.4, 2.4 Hz, 1 H), 6.87 (d J = 8.4 Hz, 1 H), 5.46 (s, 2 H), 4.19 (t, J = 5.6 Hz, 2 H), 2.51 (t, J = 1.6 Hz, 2 H, overlapped DMSO-$d_6$), 2.18 (s, 6 H). LRMS: (calc.) 461.2 (found) 462.2 (MH)+ | C, F (with 335), B, G |
| 538 | N-(4-aminobiphenyl-3-yl)-4-(hydroxymethyl)benzamide | $^1$H NMR (MeOD-$d_4$) δ (ppm): 8.03 (d, J = 8.4 Hz, 2 H), 7.64-7.51 (m, 5 H), 7.47-7.37 (m, 3 H), 7.32-7.24 (m, 1 H), 7.01 (d, J = 8.2 Hz, 1 H), 4.74 (s, 2 H LRMS: (calc.) 318.1 (found) 319.4 (MH)+ | GG, P, F (with 322), G |
| 539 | N-(4-amino-4'-fluorobiphenyl-3-yl)-1-benzyl-6-oxo-1,6-dihydropyridine-3-carboxamide | $^1$H NMR (MeOD-$d_4$) δ (ppm): 8.57 (d, J = 2.0 Hz, 1 H), 8.12 (dd, J = 9.6, 2.3 Hz, 1 H), 7.60-7.53 (m, 2 H), 7.44-7.32 (m, 7H), 7.18-7.09 (m, 2 H), 6.96 (d, J = 8.4 Hz, 1 H), 6.64 (d, J = 9.4 Hz, 1 H), 5.29 (s, 2 H). LRMS: (calc.) 413.1 (found) 414.4 (MH)+ | F, G |
| 540 | N-(2-amino-5-(pyridin-4-yl)phenyl)-4-((4-(oyridin-3-yl)pyrimidin-2-ylamino)methyl)benzamide | $^1$HNMR (DMSO-$d_6$) δ (ppm): 9.66 (bs, 1 H), 9.23 (bs, 1 H), 8.66 (bs, 1 H), 8.48 (d, J = 6.0 Hz, 2 H), 8.39 (d, J = 5.2 Hz, 2 H), 8.00 (t, J = 6.0 Hz, 1 H), 7.93 (d, J = 8.0 Hz, 2 H), 7.65 (bs, 1 H), 7.55 (d, J = 6.0 Hz, 2 H), 7.50-7.46 (m, 4 H), 7.25 (d, J = 5.2 Hz, 1 H), 6.85 (d, J = 8.4 Hz, 1 H), 5.32 (d, J = 8.8 Hz, 2 H), 4.64 (d, J = 5.6 Hz, 2 H). LRMS(ESI): (calc.) 473.2 (found) 474.2 (MH)+ | F (with 390), G |
| 541 | pyridin-3-ylmethyl 4-(2-amino-5-(pyridin-4-yl)phenylcarbamoyl)benzylcarbamate | $^1$H NMR (DMSO-$d_6$) δ (ppm): 9.72 (s, 1 H), 8.57 (s, 1 H), 8.51 (dd, J = 1.6, 4.8 HZ, 1 H), 8.49 (dd, J = 1.6, 4.8 Hz, 2 H), 7.98-7.95 (m, 1 H), 7.94 (d, J = 8.4 Hz, 2 H), 7.77 (bd, J = 8.0 Hz, 1 H), 7.65 (d, J = 2.0 Hz, 1 H), 7.56 (dd, J = 1.6, 4.4 Hz, 2 H), 7.49 (dd, J = 2.4, 8.4 Hz, 1 H), 7.41-7.37 (m, 1 H), 7.36 (d, J = 8.4 Hz, 2 H), 6.87 (d, J = 8.4 Hz, 1 H), 5.35 (bs, 2 H), 5.08 (bs, 2 H), 4.26 (d, J = 6.0 Hz, 2 H). LRMS: (calc.) 453.2 (found) 454.2 (MH)+ | F (with 390), G |
| 542 | (S)-methyl 8-(1-(4-(2-amino-5-(thiophen-2-yl)phenylcarbamoyl)phenyl)pyrrolidin- | $^1$H NMR (DMSO-$d_6$) δ (ppm): 9.42 (s, 1 H), 8.11 (d, J = 6.4 Hz, 1 H), 7.87 (d, J = 8.8 Hz, 2 H), 7.45 (d, J = 2.2 Hz, 1 H), 7.34 (d, J = 5.1 Hz, 1 H), 7.27 to 7.22 (m, 2 H), 7.04 to 7.02 (m, 1 H), 6.79 | F, I, F (with 4), G |

TABLE 22-continued

Characterization and preparative sequence of compounds synthesized

| | | | |
|---|---|---|---|
| | 3-ylamino)-8-oxoctanoate | (d, J = 8.4 Hz, 1 H), 6.57 (d, J = 8.8 Hz, 2 H), 5.06 (s, 2 H), 4.38 to 4.37 (m, 1 H), 3.56 (s, 3 H), 3.42 to 3.27 (m, 2 H), 3.13 to 3.10 (m, 1 H), 2.26 (t, J = 7.4 Hz, 2 H), 2.19-2.15 (m, 1 H), 2.05 (t, J = 7.2 Hz, 2 H), 1.89-1.88 (m, 1 H), 1.48-1.47 (m, 4 H), 1.23-1.22 (m, 5 H). LRMS(ESI): (calc.) 548.3 (found) 549.3 (MH)+ | |
| 543 | N-(4-aminobiphenyl-3-yl)-6-(piperidin-4-yloxy)benzofuran-2-carboxamide | $^1$H NMR (MeOD-d$_4$) δ (ppm): 8.45 (s, 1 H), 7.64 (d, J = 8.8 Hz, 1 H), 7.57-7.54 (m, 4 H), 7.37 (t, J = 7.0 Hz, 3 H), 7.29 (s, 1 H), 7.24 (t, J = 7.2 Hz, 1 H), 7.05 (dd, J = 8.6, 2.0 Hz, 1 H), 6.98 (d, J = 8.2 Hz, 1 H), 4.79-4.77 (m, 1 H), 3.44-3.37 (m, 2 H), 3.25-3.19 (m, 2 H), 2.23-2.17 (m, 2 H), 2.09-2.03 (m, 2 H). LRMS: (calc. 427.2 (found) 428.5 (MH)+ | HH, P F (with 322), G |
| 544 | N-(4-aminobiphenyl-3-yl)-tetrahydro-1H-carbazole-6-carboxamide | $^1$H NMR (MeOD-d$_4$) δ (ppm): 8.18 (s, 1 H), 7.79-7.72 (m, 1 H), 7.64-7.58 (m, 2 H), 7.55 (s, 1 H), 7.44-7.34 (m, 4 H), 7.31-7.23 (m, 1 H), 7.06-7.00 (m, 1 H), 2.84-2.77 (m, 4 H), 2.02-1.89 (m, 4 H). LRMS: (calc.) 381.2 (found) 382.5 (MH)+ | F, G |
| 552 | (E)-N-(2-amino-5-(pyridin-4-yl)phenyl-11-(4-methylpiperazin-1-yl)dibenzo[b,f][1,4]oxazepine-8-carboxamide | $^1$H NMR (MeOD-d$_4$) δ (ppm): 8.39 (d, J = 6.0 Hz, 2 H), 7.75 (d, J = 2.4 Hz, 1 H), 7.63-7.19 (m, 10H), 6.92 (d, J = 8.4 Hz, 1 H), 3.53 (br s, 4 H), 2.51 (br s, 4 H), 2.30 (s, 3 H). LRMS: (calc.) 504.2 (found 505.3 (MH)+ | P, F (with 390), G |
| 553 | N-(4-amino-4'-fluorobiphenyl-3-yl)-6-piperidin-4-yloxy)benzofuran-2-carboxamide | $^1$H NMR (MeOD-d$_4$) δ (ppm): 8.54 (br s, 1 H), 7.62 (d, J = 8.6 Hz, 1 H), 7.55-7.50 (m, 4 H), 7.32 (dd, J = 8.4, 2.4 Hz, 1 H), 7.27 (d, J = 1.5 Hz, 1 H), 7.12-7.01 (m, 3 H), 6.96 (d, J = 8.4 Hz, 1 H), 4.77-4.74 (m, 1 H), 3.43-3.46 (m, 2 H), 3.24-3.28 (m, 2 H), 2.22-2.15 (m, 2 H), 2.09-2.01 (m, 2 H). LRMS(ESI): (calc.) 445.2 (found) 446.5 (MH)+ | HH, P, F (with 402), G |
| 554 | N-(4-aminobiphenyl-3-yl)imidazol[1,2-a]pyridine-2-carboxamide | $^1$H NMR (MeOD-d$_4$) δ (ppm): 8.55 (d, J = 6.7 Hz, 1 H), 8.46 (s, 1 H), 7.79 (s, 1 H), 7.68 (d, J = 9.4 Hz, 1 H), 7.61 (d, J = 7.8 Hz, 2 H), 7.49-7.37 (m, 4 H), 7.32-7.25 (m, 1 H), 7.08-6.99 (m, 2 H). LRMS: calc. 328.1, found 329.4. | F, G |
| 555 | N-(2-amino-5-(pyridin-4-yl)phenyl)miidazo[1,2-a]pyridine-2-carboxamide | $^1$H NMR (DMSO-d$_6$) δ (ppm): 9.84 (s, 1 H), 8.67 (d, J = 6.8 Hz, 1 H), 8.57 (s, 3 H), 7.95 (s, 1 H), 7.71 (d, J = 9.0 Hz, 1 H), 7.63 (d, J = 5.3 Hz, 2 H), 7.52 (d, J = 8.2 Hz, 1 H), 7.43 (t, J = 8.2 Hz, 1 H), 7.07 (t, J = 6.7 Hz, 1 H), 6.96 (d, J = 8.2 Hz, 1 H), 5.39 (s, 2 H). LRMS: calc. 329.1, found 330.4. | F, G |
| 556 | N-(4-aminobiphenyl-3-yl)imidazo[2,1-b]thiazole-6-carboxamide | $^1$H NMR (DMSO-d$_6$) δ (ppm): 9.61 (s, 1 H), 8.38 (s, 1 H), 8.04 (d, J = 4.5 hz, 1 H), 7.80 (d, J = 2.0 Hz, 1 H), 7.62-7.57 (m, 2 H), 7.49-7.41 (m, 3 H), 7.35-7.26 (m, 2 H), 6.92 (d, J = 8.7 Hz, 1 H), 5.10 (s, 2 H). LRMS: calc. 334.1, found 335.4. | F, G |

TABLE 22-continued

Characterization and preparative sequence of compounds synthesized

| | | | |
|---|---|---|---|
| 557 | N-(2-amino-5-(pyridin-4-yl)phenyl)imidazo[2,1-b]thiazole-6-carbozamide | $^1$H NMR (DMSO-d$_6$) δ (ppm): 9.63 (s, 1 H), 8.55 (s, 2 H), 8.39 (s, 1 H), 8.06-8.00 (m, 1 H), 7.94-7.88 (m, 1 H), 7.64-7.57 (m, 2 H), 7.53-7.44 (m, 2 H), 6.94 (d, J = 5.0 Hz, 1 H), 5.37 (s, 2 H). LRMS: calc. 335.1, found 336.4. | F, G |
| 558 | N-(4-aminobiphenyl-3-yl)pyrazol[1,5-a]pyridine-2-carboxamide | $^1$H NMR (MeOD-d$_4$) δ (ppm): 8.72-8.67 (m, 1 H), 7.78 (dt, J = 9.0, 1.2 Hz, 1 H), 7.70 (d, J = 2.2 Hz, 1 H), 7.62 (d, J = 1.2 Hz, 1 H), 7.60 (d, J = 1.2 Hz, 1 H), 7.44-7.39 (m, 3 H), 7.35-7.25 (m, 2 H), 7.18 (d, J = 0.8 Hz, 1 H), 7.09-7.01 (m, 2 H). LRMS: calc. 328.1, found 329.5. | F, G |
| 559 | N-(4-amino-4'-fluorobiphenyl-3-yl)pyrazolo[1,5-a]pyridine-2-carboxamide | $^1$H NMR (DMSO-d$_6$) δ (ppm): 9.81 (s, 1 H), 8.80 (dd, J = 7.0, 1.0 Hz, 1 H), 7.90-7.85 (m, 1 H), 7.70 (d, J = 2, 2 Hz, 1 H), 7.66-7.59 (m, 2 H), 7.40-7.23 (m, 4 H), 7.17 (d, J = .06 Hz, 1 H), 7.14-7.09 (m, 1 H), 6.92 (d, J = 8.4 Hz, 1 H), 5.15 (s, 2 H).LRMS: calc. 346.2, found 347.5. | F, G |
| 560 | N-(4-amino-4'-fluorobiphenyl-3-yl)pyrazolo[1,5-a]pyridine-2-carboxamide | $^1$H NMR (DMSO-d$_6$) δ (ppm): 9.81 (s, 1 H), 8.80 (dd, J = 7.0, 1.0 Hz, 1 H), 7090-7.85 (m, 1 H), 7.70 9d, J = 2, 2 Hz, 1 H), 7.66-7.59 (m, 2 H), 7.40-7.23 (m, 4 H), 7.17 (d, J = 0.6 Hz, 1 H), 7.14-7.09 (m, 1 H), 6.92 (d, J = 8.4 Hz, 1 H), 5.15 (s, 2 H). LRMS: calc. 346.1, found 347.5. | F, G |
| 561 | N-(2-amino-5-(pyridin-4-yl)phenyl)pyrazolo[1,5-a]pyridine-2-carboxamide | $^1$H NMR (DMSO-d$_6$) δ (ppm): 9.84 (s, 1 H), 8.80 (dd, J = 7.0, 0.8 Hz, 1 H), 8.56 (dd, J = 4.7, 1.6 Hz, 2 H), 7.90-7.85 (m, 2 H), 7.66-7.60 (m, 2 H), 7.54 (dd, J = 8.4, 2.2 Hz, 1 H), 7.40-7.35 (m, 1 H), 7.18 (s, 1 H), 7.15-7.10 (m, 1 H), 6.95 (d, J = 8.4 Hz, 1 H), 5.42 (s, 2 H). LRMS: calc. 329.1, found 330.4.. | F, G |
| 562 | N-(4-aminobiphenyl-3-yl)imidazo[1,2-a]pyrimidine-2-carboxamide | $^1$H NMR (DMSO-d$_6$) δ (ppm): 9.95 (br s, 1 H), 9.80 (dd, J = 6.8, 2.2 Hz, 1 H), 8.80-8.74 (m, 2 H), 7.63-7.59 (m, 2 H), 7.56 (d, J = 2.2 HZ, 1 H), 7.46-7.38 (m, 3 H), 7.34 (dd, 7.0, 4.3 Hz, 1 H), 7.31-26 (m, 1 H), 6.91 (d, J = 8.4 Hz, 1 H), 5.28 (s, 2 H). LRMS: calc. 329.1, found 330.4.. | F, G |
| 563 | N-(4-aminobiphenyl-3-yl)-5-(2-morpholinoethoxy)benzofuran-2-carbozamide | $^1$H NMR (CD$_3$OD) δ (ppm): 7.58-7.54 (m, 5 H), 7.41-7.36 (m, 3 H), 7.28-7.22 (m, 2 H), 7.13 (dd, J = 9.0, 2.6 Hz, 1 H), 6.99 (d, J = 8.4 Hz, 1 H), 4.20 (t, J = 5.5 Hz, 2 H), 3.73 (t, J = 4.7 Hz, 4 H), 2.85 (t, J = 5.5 Hz, 2 H), 2.63 (t, J = 4.7 Hz, 4 H).. LRMS: calc. 457.2, found 458.5. | Q, S, P, N (with 322), G |
| 564 | N-(4-amino-4'-fluorobiphenyl-3-yl)-5-(2-morpholinoethoxy)benzofuran-2-carboxamide | $^1$H NMR (CD$_3$OD) δ (ppm): 7.59-7.51 (m, 5 H), 7.35 (dd, J = 8.4, 2.2 Hz, 1 H), 7.28 (d, J = 2.3 Hz, 1 H), 7.15-7.09 (m, 3 H), 6.98 (d, J = 8.2 Hz, 1 H), 4.20 (t, J = 5.4 Hz, 2 H), 3.73 (t, J = 4.7 Hz, 4 H), 2.85 (t, J = 5.5 Hz, 2 H), 2.63 (t, J = 4.5 Hz, 4 H). LRMS: calc. 475.2, | Q, S, P, N (with 402), G |

TABLE 22-continued

Characterization and preparative sequence of compounds synthesized

| | | | |
|---|---|---|---|
| | | found 476.3. Do not fit with the structure | |
| 565 | N-(4-aminobiphenyl-3-yl)-5-(2-(piperidin-1-yl)ethoxy)benzofuran-2-carboxamide | ¹H NMR (CD₃OD) δ (ppm): 7.57-7.53 (m, 5 H), 7.40-7.35 (m, 3 H), 7.27-7.22 (m, 2 H), 7.12 (dd, J = 9.0, 2.5 Hz, 1 H), 6.98 (d, J = 8.4 Hz, 1 H), 4.18 (t, J = 5.5 Hz, 2 H), 2.82 (t, J = 5.5 Hz, 2 H), 2.85 (br s, 4 H), 1.65 (q, J = 5.7 Hz, 4 H), 1.51-1.49 (m, 2 H). LRMS: calc. 455.2, found 456.4 | Q, S, P, N (with 322), G |
| 566 | N-(4-amino-4'-fluorobiphenyl-3-yl)-5-(2-piperidin-1-yl)ethoxy)benzofuran-2-carboxamide | ¹H NMR (DMSOd₆) δ (ppm): 9.92 (s, 1 H), 7.62 (s, 1 H), 7.58-7.54 (m, 3 H), 7.48 (d, J = 1.5 Hz, 1 H), 7.31-7.28 (m, 2 H), 7.18 (t, J = 8.8 Hz, 2 H), 7.06 (dd, J = 9.0, 2.4 Hz, 1 H), 6.84 (d, J = 8.4 Hz, 1 H), 5.15 (s, 2 H), 4.09 (t, J = 5.9 Hz, 2 H), 2.66 (t, J = 6.0 Hz, 2 H), 2.43 (m, 4 H), 1.50-1.45 (m, 4 H), 1.38-1.36 (m, 2 H). LRMS: calc. 473.2, found 474.3 | Q, S, P, N (with 402), G |
| 567 | N-(4-aminobiphenyl-3-yl)-5-methoxy-7-(morphonlinomethyl)benzofuran-2-carboxamide | ¹H NMR (CD₃OD) δ (ppm): 7.60-7.55 (m, 4 H), 7.41-7.35 (m, 3 H), 7.27-7.22 (m, 1 H), 7.19 (d, J = 2.5 Hz, 1 H), 7.11 (d, J = 2.5 Hz, 1 H), 6.99 (d, J = 8.4 Hz, 1 H), 3.92 (s, 2 H), 3.86 (s, 3 H), 3.72 (t, J = 4.5 Hz, 4 H), 2.60-2.58 (m, 4 H). LRMS: calc. 457.2, found 458.5 | Q, S, P, N (with 322), G |
| 568 | N-(4-amino-4'-fluorobiphenyl-3-yl)-5-methoxy-7-(morpholinomethyl)benzofuran-2-carboxamide | ¹H NMR (CD₃OD) δ (ppm): 7.59-7.55 (m, 4 H), 7.36 (dd, J = 8.4, 1.7 Hz, 1 H), 7.19 (d, J = 2.2 Hz, 1 H), 7.14-7.09 (m, 3 H), 6.98 (d, J = 8.4 Hz, 1 H), 3.92 (s, 2 H), 3.86 (s, 3 H), 3.72 (t, J = 4.5 Hz, 4 H), 2.59-2.58 (m, 4 H). LRMS: calc. 475.5, found 476.6 | Q, S, P, N (with 402) G |
| 569 | N-(4-aminobiphenyl-3-yl)-7-methoxy-5-(morpholinomethyl)benzofuran-2-carboxamide | ¹H NMR (DMSOd₆) δ (ppm): 9.91 (s, 1 H), 7.69 (s, 1 H), 7.56-7.52 (m, 3 H), 7.41-7.33 (m, 3 H), 7.28-7.21 (m, 2 H), 7.04 (s, 1 H), 6.87 (d, J = 8.4 Hz, 1 H), 5.16 (s, 2 H), 3.98 (s, 3 H), 3.60-3.54 (m, 6 H), 2.39 (br s, 4 H). LRMS: calc. 457.2, found 458.6 | Q, S, P, N (with 322), G |
| 570 | N-(4-amino-4'-fluorobiphenyl-3-yl)-7-methoxy-5-(morpholinomethyl)benzofuran-2-carboxamide | ¹H NMR (DMSOd₆) δ (ppm): 9.89 (s, 1 H), 7.68 (s, 1 H), 7.57 (dd, J = 8.8, 5.5 Hz, 2 H), 7.49 (d, J = 2.1 Hz, 1 H), 7.31 (dd, J = 8.2, 2.0 Hz, 1 H), 7.27 (s, 1 H), 7.21 (t, J = 8.8 Hz, 2 H), 7.03 (s, 1 H), 6.86 (d, J = 8.2 Hz, 2 H), 3.97 (s, 3 H), 3.59 (t, J = 3.9 Hz, 4 H), 3.55 (s, 2 H), 2.40-2.36 (m, 4 H). LRMS: calc. 475.5, found 476.6 | Q, S, P, N (with 402), G |
| 571 | N-(2-amino-5-(pyridin-4-yl)phenyl)-4-((6,7,8,9,10,11-hexahydro-5 H-cycloocta[b]indol-5-yl)methyl)benzamide | ¹H NMR (DMSOd₆) δ (ppm): 9.58 (s, 1 H), 8.48 (d, J = 6.3 Hz, 2 H), 7.62-7.44 (m, 7H), 7.24-7.21 (m, 3 H), 6.84 (d, J = 8.4 Hz, 1 H), 6.71 (d, J = 8.2 Hz, 2 H), 5.31 (s, 2 H), 3.19 (q, J = 8.7 Hz, 2 H), 2.95-2.91 (m, 1 H), 2.67-2.61 (m, 1 H), 2.48-2.44 (m, 1 H), 2.24-2.20 (m, 1 H), 2.08-2.06 (m, 1 H), 1.78-1.27 (m, 5 H), 0.77-0.73 (m, 2 H). LRMS: (calc.) 500.6 (found) 501.5 (MH)+ | D (with NaH), P, F (with 390), G, |
| 572 | N-(4-aminobiphenyl-3-yl)-5-(4- | ¹H NMR (DMSOd₆) δ (ppm): 10.05 (s, 1 H), 8.22 (d, J = 1.2 Hz, 1 H), 7.96 (s, 4 H), 7.89- | Q, P, N (with 322), B, G |

TABLE 22-continued

Characterization and preparative sequence of compounds synthesized

| | | | |
|---|---|---|---|
| | cyanophenyl)benzofuran-2-carboxamide | 7.81 (m, 3 H), 7.57-7.53 (m, 3 H), 7.41-7.34 (m, 3 H), 7.26-7.22 (m, 1 H), 6.88 (d, J = 8.4 Hz, 1 H), 5.20 (s, 2 H). LRMS: (calc.) 429.2 (found) 430.5 (MH)+ | |
| 573 | N-(2-amino-5-(pyridin-2-yl)phenyl)-4-methoxybenzamide | $^1$H NMR (400 MHz, DMSO-d$_6$) δ (ppm): 9.65 (s, 1 H), 8.52 (m, 1 H), 8.01 (d, J = 5.8, 2 H), 7.92 (m, 1 H), 7.73 (m, 3 H), 7.18 (m, 1 H), 7.13 (d, J = 5.7 Hz, 2 H), 6.81 (d, J = 5.2 Hz, 1 H), 5.23 (s, 1 H), 3.83 (s, 3 H). MS (m/z): 320.2 (M + H). | K, G |
| 574 | 2-(dimethylaminno)ethyl 4-(2-amino-5-(pyridin-2-yl)phenylcarbamoyl)phenylcarbamate | $^1$H NMR (400 MHz, DMSO-d$_6$) δ (ppm): 10.01 (s, 1 H), 9.62 (s, 1 H), 8.52 (m, 1 H), 7.95 (m, 3 H), 7.76 (m, 3 H), 7.58 (d, J = 8.2 Hz, 2 H), 7.18 (m, 1 H), 6.84 (d, J = 8.1 Hz, 1 H), 5.23 (s, 2 H), 4.19 (t, J = 5.2 Hz, 2 H), 2.51 (t, J = 5.1 Hz, 2 H), 2.18 (s, 6 H). MS (m/z): 420.2 (M + H). | X, E, F, G |
| 575 | 2-(dimethylamino)ethyl 4-(2-amino-5-(pryidin-2-yl)phenylcarbamoyl)phenylcarbamate | $^1$H NMR (400 MHz, DMSO-d$_6$) δ (ppm): 9.47 (s, 1 H), 8.51 (d, J = 3.6 Hz, 1 H), 7.94 (d, J = 2.2 Hz, 1 H), 7.90 (d, J = 8.8 Hz, 2 H), 7.76 (m, 2 H), 7.70 (m, 1 H), 7.18 (m, 1 H), 6.82 (d, J = 8.1 Hz, 1 H), 6.54 (d, J = 8.1 Hz, 2 H), 5.21 (s, 2 H), 3.62 (m, 1 H), 3.48 (m, 3 H), 3.30 (m, 2 H), 3.05 (m, 1 H), 2.11 (m, 1 H), 1.80 (m, 1 H). MS (m/z): 374.1 (M + H). | J, T, I, F, R G |
| 576 | N-(4-aminobiphenyl-3-yl)-4-(3-hydroxyazetidin-1-yl)benzamide | $^1$H NMR (400 MHz, DMSO-d$_6$) δ (ppm): 9.47 (s, 1 H), 7.87 (d, J = 8.8 Hz, 2 H), 7.55 (dd, J = 8.4, 1.2 Hz, 2 H), 7.49 (d, J = 2.0 Hz, 1 H), 7.39 (tt, J = 7.8, 1.8 Hz, 2 H), 7.30 (dd, J = 8.2, 2.2 Hz, 1 H), 7.24 (tt, J = 7.4, 1.1 Hz, 1 H), 6.86 (d, J = 8.4 Hz, 1 H), 6.47 (d, J = 8.8 Hz, 2 H), 5.71 (d, J = 6.0 Hz, 1 H), 5.03 (bs, 2 H), 4.61 (sext, J = 5.3 Hz, 1 H), 4.15 (t, J = 7.6 Hz, 2 H), 3.61 (dd, J = 8.4, 4.8 Hz, 2 H). MS (m/z): 360.2 (M + H). | J, V, I, F, O, G |
| 577 | N-(4-aminobiphenyl)-3-yl)-4-(2,3-dihydroxypropylamino)benzamide | $^1$H NMR (400 MHz, DMSO-d$_6$) δ (ppm): 9.36 (s, 1 H), 7.78 (d, J = 8.4 Hz, 2 H), 7.55 (dd, J = 8.4, 0.8 Hz, 2 H), 7.50 (d, J = 2.0 Hz, 1 H), 7.39 (t, J = 7.8 Hz, 2 H), 7.29 (dd, J = 8.4, 2.0 Hz, 1 H), 7.24 (tt, J = 7.4, 1.1 Hz, 1 H), 6.85 (d, J = 8.4 Hz, 1 H), 6.65 (d, J = 8.8 Hz, 2 H), 6.19 (t, J = 5.8 Hz, 1 H), 5.05 (bs, 2 H), 4.48 (d, J = 5.2 Hz, 1 H), 4.65 (t, J = 5.8 Hz, 1 H), 3.65 (sext, J= 5.5 Hz, 1 H), 3.39 (m, 2 H), 3.24 (m, 1 H), 2.99 (m, 1 H). MS (m/z): 378.5 (M + H). | J, V, I, F, O, G |
| 578 | N-(4-amino-4'-fluorobiphenyl-3-yl)-4-(2,3-dihydroxypropylamino)benzamide | $^1$H NMR (400 MHz, DMSO-d$_6$) δ (ppm): 9.36 (s, 1 H), 7.78 (d, J = 8.0 Hz, 2 H), 7.57 (t, J = 6.6 Hz, 2 H), 7.47 (s, 1 H), 7.23 (m, 3 H), 6.84 (d, J = 8.4 Hz, 1 H), 6.65 (d, J = 8.4 2 H), 6.20 (t, J = 5.4 Hz, 1 H), 5.03 (bs, 2 H), 4.85 (d, J = 4.4 Hz, 1 H), 4.66 (t, J = 5.2 Hz, 1 H), 3.65 (q, J = 4.4 Hz, 1 H), 3.39 (m, 2 H), 3.24 (m, 1 H), 2.98 (m, 1 H). MS (m/z): 396.1 (M + H). | J, V, I, F, O, G |
| 579 | N-(4-amino-4'- | $^1$H NMR(400 MHz, DMSO-d$_6$) δ (ppm): 9.46 (s, 1 H), 7.78 (d, J = | J, V, I, F, O, G |

TABLE 22-continued

Characterization and preparative sequence of compounds synthesized

| | | | |
|---|---|---|---|
| | fluorobiphenyl-3-yl)-4-(3-hydroxyazetidin-1-yl) benzamine | 8.4 Hz, 2 H), 7.57 (dd, J = 8.2, 5.4 Hz, 2 H), 7.47 (bs, 1 H), 7.27 (d, J = Hz, 1 H), 7.21 (t, J = 8.8 Hz, 2 H), 6.85 (d, J = 8.4 Hz, 1 H), 6.47 (d, J = 8.4 Hz, 2 H), 5.71 (d, J = 6.8 Hz, 1 H), 5.04 (s, 2 H), 4.61 (sext, J = 5.5 Hz, 1 H), 4.15 (t, J = 7.0 Hz, 2 H), 3.61 (dd, J = 7.8 Hz, 2 H). MS (m/z): 378.1 (M + H). | |
| 580 | (S)-N-(4-amino-4'-fluorobiphenyl-3-yl)-4-(3-hydroxypyrrolidin-1-yl)benzamide | $^1$H NMR (400 MHz, DMSO-d$_6$) δ (ppm): 9.42 (s, 1 H), 7.88 (d, J = 8.8 Hz, 2 H), 7.58 (dd, J = 8.6, 5.4 Hz, 2 H), 7.48 (d, J = 1.6 Hz, 1 H), 7.27 (dd, J = 8.4 Hz, 1 H), 7.21 (t, J = 8.8 Hz, 2 H), 6.85 (d, J = 8.4 Hz, 1 H), 6.57 (d, J = 8.4 Hz, 2 H), 5.03 (bs, 2 H), 5.02 (s, 1 H), 4.43 (bs, 1 H), 3.47 (dd, J = 10.6, 4.6 Hz, 1 H), 3.37 (m, 2 H), 3.17 (d, J = 10.4 Hz, 1 H), 2.06 (m, 1 H), 1.93 (m, 1 H). MS (m/z): 392.2 (M + H). | J, I, F, G |
| 581 | (N-(2-amino-5-(pyridin-2-yl)phenyl)-4-(morpholinomethyl) benzamide | $^1$H NMR (400 MHz, DMSO-d$_6$) δ (ppm): 9.74 (s, 1 H), 8.54 (d, J = 4.8 Hz, 1 H), 7.98 (d, J = 8.4 Hz, 2 H), 7.97 (s, 1 H), 7.76 3 H), 7.45 (d, J = 8.0 Hz, 2 H), 7.19 (m, 1 H), 6.85 (d, J = 8.4 Hz, 1 H), 5.28 (s, 2 H), 3.59 (t, J = 4.4 Hz, 4 H), 3.55 (s, 2 H), 2.38 (bs, 4 H). MS (m/z): 389.5 (M +H). | F, G |
| 582 | N-(2-amino-5(pyridin-2-yl)phenyl)-4-(4-methylpiperazin-1-yl)benzamide | $^1$H NMR (400 MHz, DMSO-d$_6$) δ (ppm): 9.55 (s, 1 H), 8.54 (dt, J = 4.8, 1.4 Hz, 1 H), 7.95 (d, J = 2.0 Hz, 1 H), 7.91 (d, J = 8.8 Hz, 2 H), 7.75 (m, 3 H), 7.18 (m, 1 H), 7.01 (d, J = 9.2 Hz, 2 H), 6.85 (d, J = 8.4 Hz, 1 H), 5.22 (s, 2 H), 3.28 (t, J = 5.0 Hz, 4 H), 2.45 (t, J = 5.0 Hz, 4 H), 2.23 (s, 3 H). MS (m/z): 388.1 (M + H). | F, G |
| 583 | N-(2-amino-5-(pyridin-2-yl)phenyl)4-4 (4-aminopiperidin-1-yl)benzamide | $^1$H NMR(400 MHz, DMSO-d$_6$) δ (ppm): 9.51 (s, 1 H), 8.54 (dt, J = 4.5, 1.3 Hz, 1 H), 7.95 (d, J = 2.0 Hz, 1 H), 7.88 (d, J = 8.8 Hz, 2 H), 7.68 (m, 2 H), 7.73 (dd, J = 8.4, 2.0 Hz, 1 H), 7.18 (m, 1 H), 6.99 (d, J = 9.2 Hz, 2 H), 6.85 (d, J = 8.4 Hz, 1 H), 5.21 (s, 2 H), 3.82 (d, J = 13.2 Hz, 2 H), 2.86 (td, J = 12.2, 2.4 Hz, 2 H), 2.77 (m, 1 H), 1.77 (dd, J = 12.8, 3.2 Hz, 2 H), 1.27 (m, 2 H). MS (m/z): 388.1 (M + H). | J, T, I, F, R, G |
| 584 | (S)-N-(2-amino-5-(pyridin-2-yl)phenyl)-4-(3-hydroxypyrrlidin-1-yl)benzamide | $^1$H NMR (400 MHz, DMSO-d$_6$) δ (ppm): 9.46 (s, 1 H), 8.54 (dt, J = 4.5, 1.3 Hz, 1 H), 7.95 (d, J = 2.0 Hz, 1 H), 7.89 (d, J = 8.8 Hz, 2 H), 7.77 (m, 2 H), 7.72 (dd, J = 8.4, 2.4 Hz, 1 H), 7.18 (ddd, J = 6.1, 4.7, 2.3 Hz, 1 H), 6.85 (d, J = 8.4 Hz, 1 H), 6.57 (d, J = 8.8 Hz, 2 H), 5.20 (bs, 2 H), 5.03 (d, J = 3.6 Hz, 1 H), 4.43 (bs, 1 H), 3.47 (dd, J = 10.4, 4.8 Hz, 1 H), 3.39 (m, 2 H), 3.17 (d, J = 10.4 Hz, 1 H), 2.06 (m, 1 H), 1.93 (m, 1 H). MS (m/z): 375.1 (M + H). | J, I, F, G |

ASSAY EXAMPLES

Assay Example 1

Inhibition of Histone Deacetylase Enzymatic (HDAC-1) Activity

The following protocol was used to assay the compounds of the invention. In the assay, the buffer used was 25 mM HEPES, pH 8.0, 137 mM NaCl, 2.7 mM KCl, 1 mM $MgCl_2$ and the substrate was Boc-Lys(Ac)-AMC in a 50 mM stock solution in DMSO. The enzyme stock solution was 4.08 µg/mL in buffer.

The compounds were pre-incubated (2 µl in DMSO diluted to 13 µl in buffer for transfer to assay plate) with enzyme (20 µl of 4.08 µg/ml) for 10 minutes at room temperature (35 µl pre-incubation volume). The mixture was pre-incubated for 5 minutes at room temperature. The reaction was started by bringing the temperature to 37° C. and adding 15 µl substrate. Total reaction volume was 50 µl. The reaction was stopped after 20 minutes by addition of 50 µl developer, prepared as directed by Biomol (Fluor-de-Lys developer, Cat. # KI-105). A plate was incubated in the dark for 10 minutes at room temperature before reading ($\lambda_{Ex}$=360 nm, $\lambda_{Em}$=470 nm, Cut-off filter at 435 nm).

Table 21 below displays comparative data for the compounds of the invention demonstrating the increased HDAC-1 inhibitory activity resulting from incorporating a planar substituent.

Assay Example 2

MTT Assay

Compounds at various concentrations were added to human colon cancer HCT116 cells plated in 96-well plates. Cells were incubated for 72 hours at 37° C. in 5% $CO_2$ incubator. MTT (3-[4,5-dimethylthiazol-2-yl]-2,5 diphenyl tetrazolium bromide, Sigma) was added at a final concentration of 0.5 mg/ml and incubated with the cells for 4 hours before an equal volume of solubilization buffer (50% N,N-dimethylformamide, 20% SDS, pH 4.7) was added onto cultured cells. After overnight incubation, solubilized dye was quantified by colorimetric reading at 570 nM using a reference at 630 nM. OD values were converted to cell numbers according to a standard growth curve of the relevant cell line. The concentration which reduces cell numbers to 50% of those of DMSO-treated cells is determined as MTT $IC_{50}$.

$p21^{WAF1/Cip1}$ Assay.

HCT116 cells were stably transfected with reporter plasmids encoding the p21 promoter-driven luciferase. Cells were treated with indicated concentration of HDAC inhibitors for 16 hours before cells were harvested and luciferase activity analyzed. The effective concentration (EC) of MS-275 was designated as 1 µM. The ability of HDAC inhibitor was compared with that of MS-275 (T. Suzuki, et. al J. Med. Chem., 1999, 3001-3003). Lower EC of a given compound indicates that this compound is more potent than MS-275 to induce p21 expression.

TABLE 21

| Ex | Cpd | Structure | HDAC-1 (µM) | MTT HCT116 (µM) | Scheme | Log D (pH 7.4) |
|---|---|---|---|---|---|---|
| 1a | 9 | 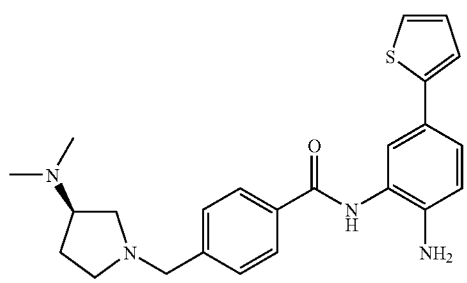 [SMILES: CN(C)[C@@H]1CCN(Cc2ccc(C(=O)Nc3cc(-c4cccs4)ccc3N)cc2)C1] | a | a | 1 | 2.11 |
| 1b | 10 | 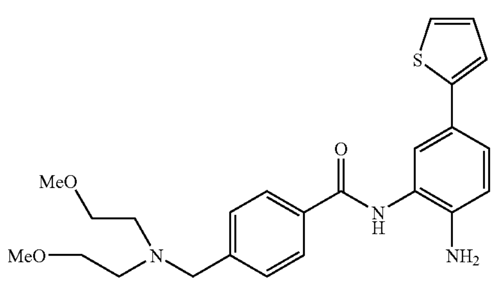 [SMILES: COCCN(CCOC)Cc1ccc(C(=O)Nc2cc(-c3cccs3)ccc2N)cc1] | a | a | 1 | 3.10 |

TABLE 21-continued

| Ex | Cpd | Structure | HDAC-1 (μM) | MTT HCT116 (μM) | Scheme | Log D (pH 7.4) |
|---|---|---|---|---|---|---|
| 1c | 11 | 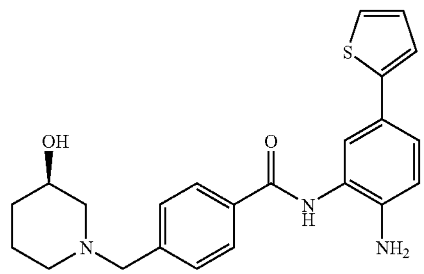 [SMILES: Nc1ccc(-c2cccs2)cc1NC(=O)c1ccc(CN2CCC[C@@H](O)C2)cc1] | a | a | 1 | 3.03 |
| 1d | 12 | 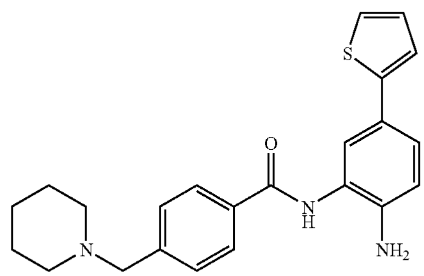 [SMILES: Nc1ccc(-c2cccs2)cc1NC(=O)c1ccc(CN2CCCCC2)cc1] | a | b | 1 | 3.86 |
| 1e | 13 | 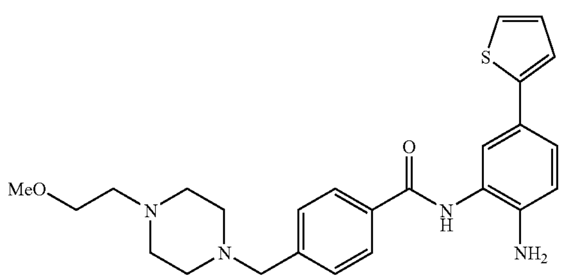 [SMILES: COCCN1CCN(Cc2ccc(C(=O)Nc3cc(-c4cccs4)ccc3N)cc2)CC1] | a | a | 1 | 2.22 |
| 1f | 14 | 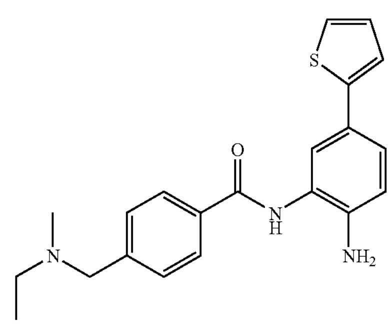 [SMILES: CCN(C)Cc1ccc(C(=O)Nc2cc(-c3cccs3)ccc2N)cc1] | a | a | 1 | 3.20 |
| 1g | 15 | 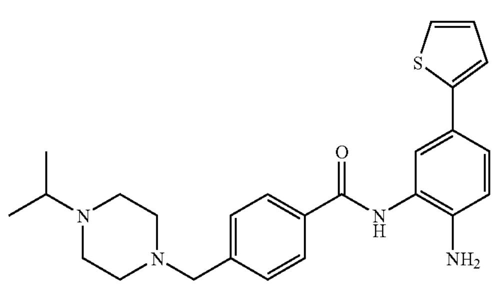 [SMILES: CC(C)N1CCN(Cc2ccc(C(=O)Nc3cc(-c4cccs4)ccc3N)cc2)CC1] | a | a | 1 | 2.15 |

TABLE 21-continued

| Ex | Cpd | Structure | HDAC-1 (μM) | MTT HCT116 (μM) | Scheme | Log D (pH 7.4) |
|---|---|---|---|---|---|---|
| 1h | 16 | 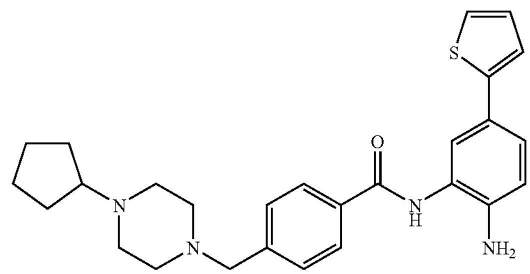 [SMILES: Nc1ccc(-c2cccs2)cc1NC(=O)c1ccc(CN2CCN(C3CCCC3)CC2)cc1] | a | a | 1 | 3.30 |
| 1j | 18 | 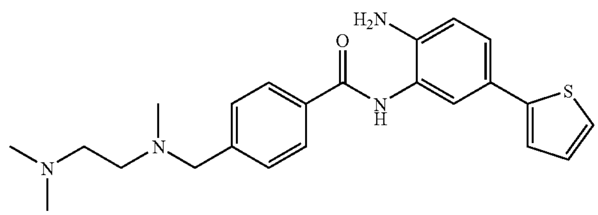 [SMILES: CN(C)CCN(C)Cc1ccc(C(=O)Nc2cc(-c3cccs3)ccc2N)cc1] | a | a | 1 | 1.64 |
| 6b | 77 | 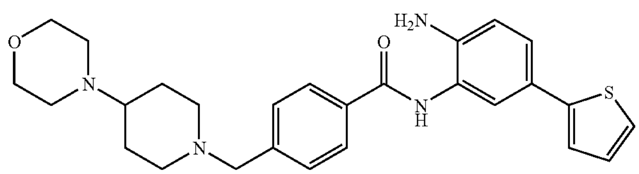 [SMILES: Nc1ccc(-c2cccs2)cc1NC(=O)c1ccc(CN2CCC(N3CCOCC3)CC2)cc1] | a | a | 6 | 2.59 |
| 6c | 78 | 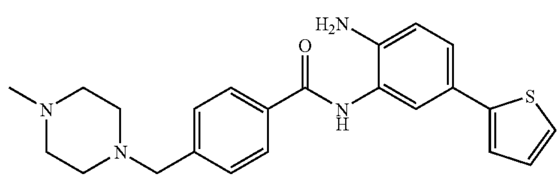 [SMILES: CN1CCN(Cc2ccc(C(=O)Nc3cc(-c4cccs4)ccc3N)cc2)CC1] | a | a | 6 | 2.29 |
| 6d | 79 | 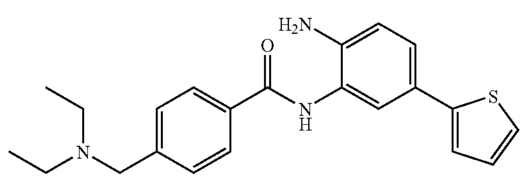 [SMILES: CCN(CC)Cc1ccc(C(=O)Nc2cc(-c3cccs3)ccc2N)cc1] | a | a | 6 | 3.19 |
| 6e | 80 | 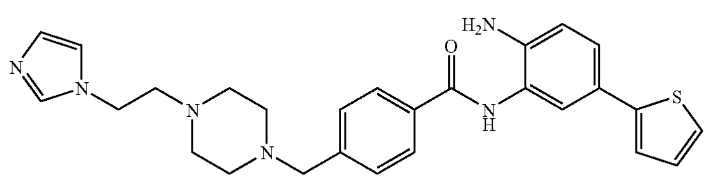 [SMILES: Nc1ccc(-c2cccs2)cc1NC(=O)c1ccc(CN2CCN(CCn3ccnc3)CC2)cc1] | a | a | 6 | 1.54 |
| 6f | 81 | 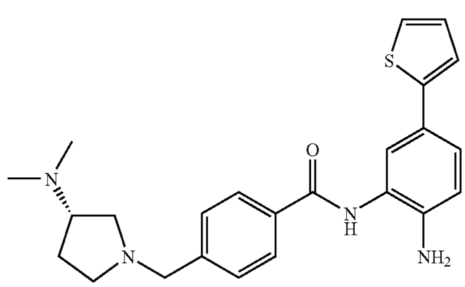 [SMILES: CN(C)[C@H]1CCN(Cc2ccc(C(=O)Nc3cc(-c4cccs4)ccc3N)cc2)C1] | a | a | 6 | 2.11 |

TABLE 21-continued

| Ex | Cpd | Structure | HDAC-1 (μM) | MTT HCT116 (μM) | Scheme | Log D (pH 7.4) |
|---|---|---|---|---|---|---|
| 6g | 82 | 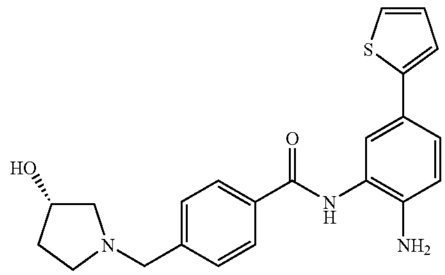 [SMILES: Nc1ccc(-c2cccs2)cc1NC(=O)c1ccc(CN2CC[C@H](O)C2)cc1] | a | a | 6 | 2.60 |
| 6h | 83 | 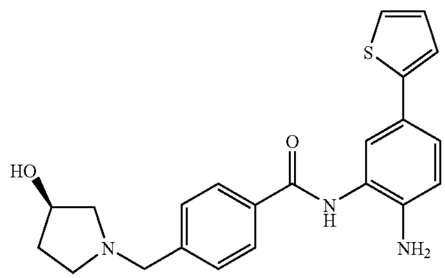 [SMILES: Nc1ccc(-c2cccs2)cc1NC(=O)c1ccc(CN2CC[C@@H](O)C2)cc1] | a | b | 6 | 2.60 |
| 6i | 84 | 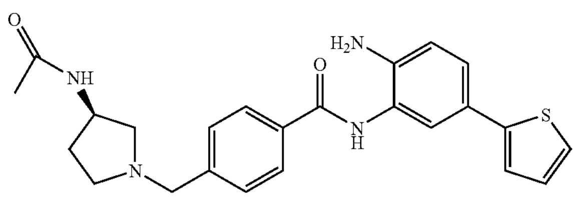 [SMILES: CC(=O)N[C@@H]1CCN(Cc2ccc(C(=O)Nc3cc(-c4cccs4)ccc3N)cc2)C1] | a | a | 6 | 2.15 |
| 6j | 85 | 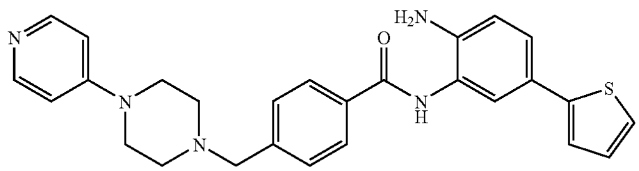 [SMILES: Nc1ccc(-c2cccs2)cc1NC(=O)c1ccc(CN2CCN(c3ccncc3)CC2)cc1] | a | a | 6 | 3.32 |
| 6k | 86 | 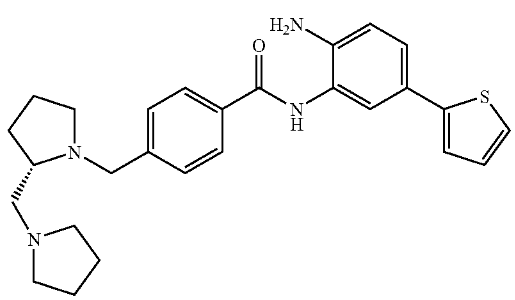 [SMILES: Nc1ccc(-c2cccs2)cc1NC(=O)c1ccc(CN2CCC[C@H]2CN2CCCC2)cc1] | a | a | 6 | 0.86 |
| 6l | 87 | 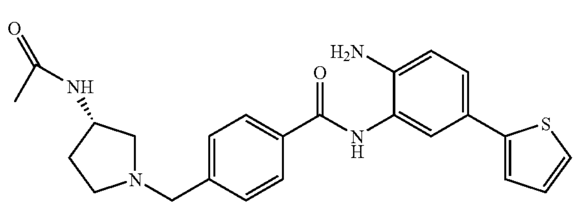 [SMILES: CC(=O)N[C@H]1CCN(Cc2ccc(C(=O)Nc3cc(-c4cccs4)ccc3N)cc2)C1] | a | a | 6 | 2.15 |

TABLE 21-continued

| Ex | Cpd | Structure | HDAC-1 (μM) | MTT HCT116 (μM) | Scheme | Log D (pH 7.4) |
|---|---|---|---|---|---|---|
| 6n | 89 | 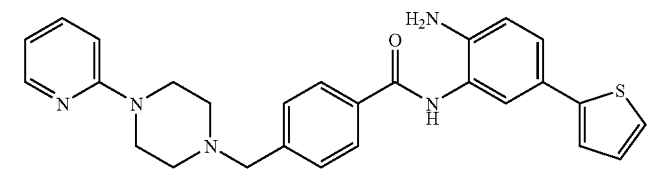 [SMILES: Nc1ccc(-c2cccs2)cc1NC(=O)c1ccc(CN2CCN(c3ccccn3)CC2)cc1] | a | a | 6 | 3.38 |
| 6o | 90 | 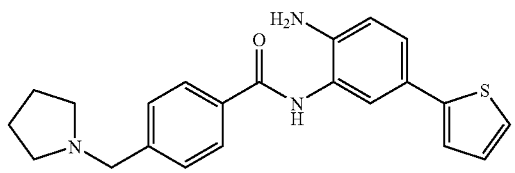 [SMILES: Nc1ccc(-c2cccs2)cc1NC(=O)c1ccc(CN2CCCC2)cc1] | a | a | 6 | 3.15 |
| 6p | 91 | 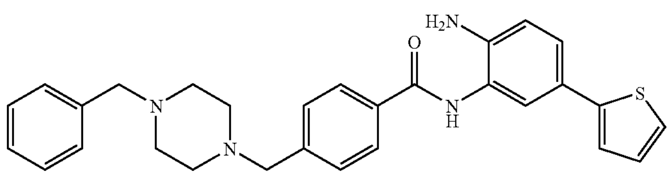 [SMILES: Nc1ccc(-c2cccs2)cc1NC(=O)c1ccc(CN2CCN(Cc3ccccc3)CC2)cc1] | a | a | 6 | 4.01 |
| 8a | 101 | 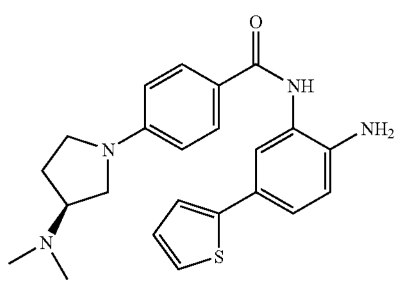 [SMILES: CN(C)[C@H]1CCN(c2ccc(C(=O)Nc3cc(-c4cccs4)ccc3N)cc2)C1] | a | a | 8 | 1.94 |
| 8b | 102 | 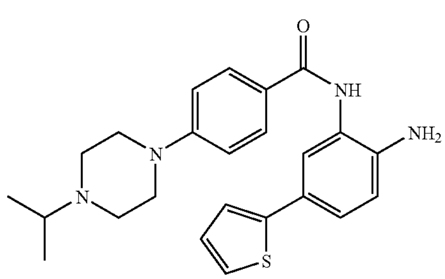 [SMILES: CC(C)N1CCN(c2ccc(C(=O)Nc3cc(-c4cccs4)ccc3N)cc2)CC1] | a | a | 8 | 1.52 |
| 8c | 103 | 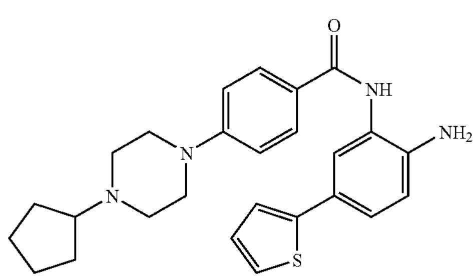 [SMILES: Nc1ccc(-c2cccs2)cc1NC(=O)c1ccc(N2CCN(C3CCCC3)CC2)cc1] | a | a | 8 | 2.68 |

TABLE 21-continued

| Ex | Cpd | Structure | HDAC-1 (μM) | MTT HCT116 (μM) | Scheme | Log D (pH 7.4) |
|---|---|---|---|---|---|---|
| 8d | 104 | 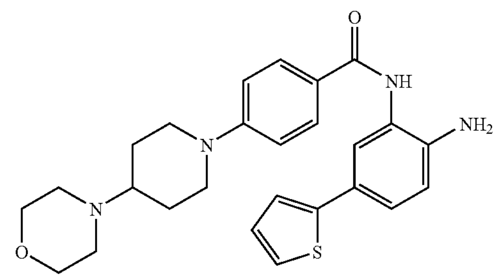 [SMILES: Nc1ccc(-c2cccs2)cc1NC(=O)c1ccc(N2CCC(N3CCOCC3)CC2)cc1] | a | a | 8 | 2.51 |
| 8e | 105 | 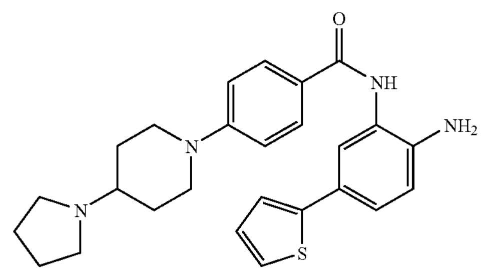 [SMILES: Nc1ccc(-c2cccs2)cc1NC(=O)c1ccc(N2CCC(N3CCCC3)CC2)cc1] | a | a | 8 | 1.60 |
| 8f | 106 | 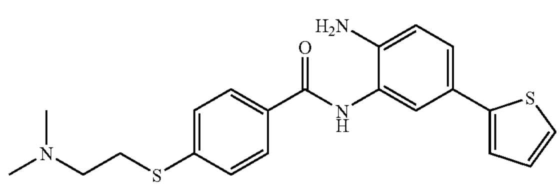 [SMILES: CN(C)CCSc1ccc(C(=O)Nc2cc(-c3cccs3)ccc2N)cc1] | a | b | 8 | 2.85 |
| 8g | 107 | 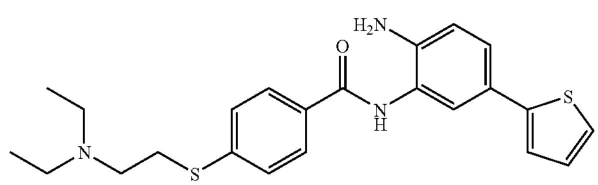 [SMILES: CCN(CC)CCSc1ccc(C(=O)Nc2cc(-c3cccs3)ccc2N)cc1] | a | | 8 | 2.58 |
| 8h | 108 | 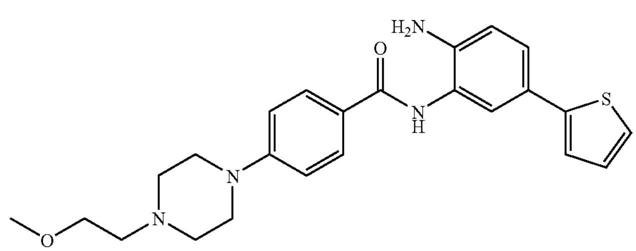 [SMILES: COCCN1CCN(c2ccc(C(=O)Nc3cc(-c4cccs4)ccc3N)cc2)CC1] | a | a | 8 | 1.78 |
| 25a | 221 | 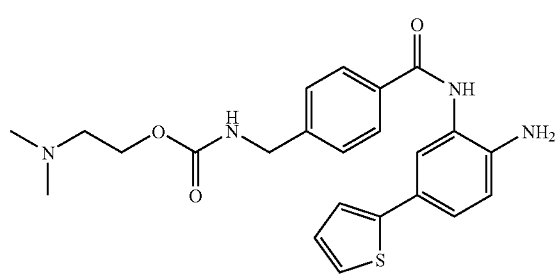 [SMILES: CN(C)CCOC(=O)NCc1ccc(C(=O)Nc2cc(-c3cccs3)ccc2N)cc1] | a | a | 25 | 1.85 |

TABLE 21-continued

| Ex | Cpd | Structure | HDAC-1 (μM) | MTT HCT116 (μM) | Scheme | Log D (pH 7.4) |
|---|---|---|---|---|---|---|
| 25b | 222 | 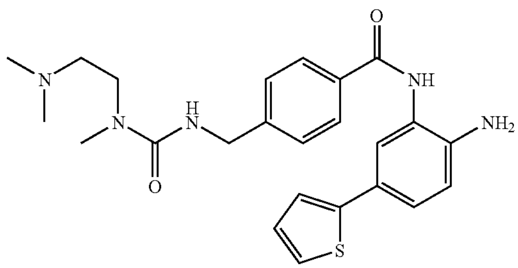 [SMILES: CN(C)CCN(C)C(=O)NCc1ccc(C(=O)Nc2cc(-c3cccs3)ccc2N)cc1] | a | a | 25 | 1.05 |
| 27a | 242 | 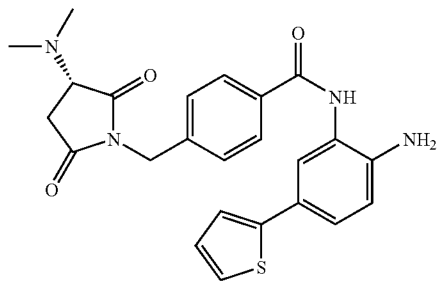 [SMILES: CN(C)[C@H]1CC(=O)N(Cc2ccc(C(=O)Nc3cc(-c4cccs4)ccc3N)cc2)C1=O] | a | b | 27 | 1.81 |
| 28a | 249 | 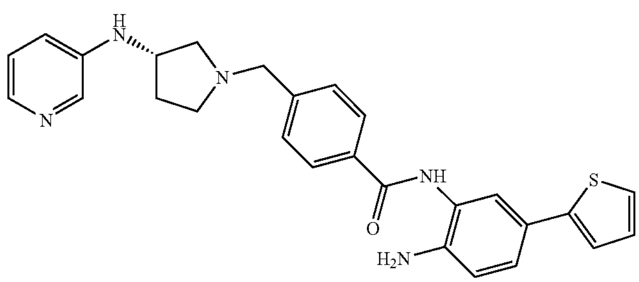 [SMILES: Nc1ccc(-c2cccs2)cc1NC(=O)c1ccc(CN2CC[C@H](Nc3cccnc3)C2)cc1] | a | a | 28 | 3.27 |
| 35 | 316 | 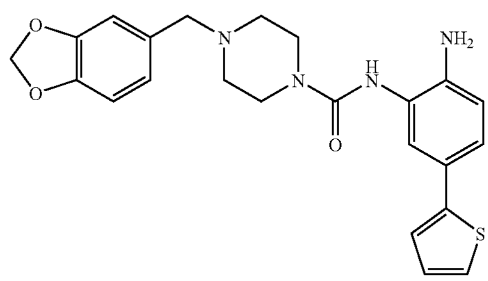 [SMILES: Nc1ccc(-c2cccs2)cc1NC(=O)N1CCN(Cc2ccc3c(c2)OCO3)CC1] | a | | 36 | 2.32 |
| 36 | 320 | 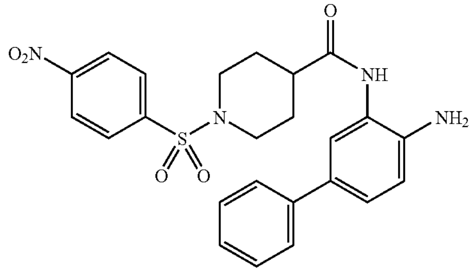 [SMILES: Nc1ccc(-c2ccccc2)cc1NC(=O)C1CCN(S(=O)(=O)c2ccc([N+](=O)[O-])cc2)CC1] | a | | 37 | 3.21 |

Unless specified otherwise, in all the tables in this specification, a<1 µM; 1 µM≤b<5 µM

TABLE 22

| Cpd number | HDAC IC50 |
| --- | --- |
| 441 | D |
| 284 | A |
| 61 | B |
| 147 | C |
| 148 | C |
| 173 | C |
| 283 | A |
| 62 | B |
| 150 | C |
| 161 | B |
| 65 | B |
| 174 | B |
| 56 | B |
| 57 | C |
| 149 | D |
| 132 | A |
| 172 | D |
| 140 | C |
| 184 | B |
| 19 | B |
| 19 | B |
| 19 | A |
| 19 | A |
| 171 | B |
| 193 | D |
| 194 | D |
| 170 | A |
| 43 | C |
| 44 | C |
| 42 | C |
| 47 | C |
| 12 | B |
| 64 | B |
| 64 | B |
| 17 | B |
| 17 | B |
| 9 | A |
| 9 | A |
| 101 | B |
| 101 | B |
| 49 | B |
| 49 | A |
| 49 | B |
| 201 | D |
| 127 | B |
| 209 | C |
| 210 | C |
| 14 | C |
| 14 | B |
| 15 | B |
| 13 | B |
| 13 | B |
| 16 | B |
| 124 | B |
| 125 | C |
| 11 | B |
| 11 | B |
| 23 | C |
| 66 | B |
| 25 | C |
| 24 | B |
| 108 | B |
| 108 | A |
| 106 | C |
| 21 | B |
| 20 | A |
| 103 | B |
| 105 | A |
| 105 | A |
| 22 | B |
| 10 | B |
| 102 | B |
| 104 | B |
| 104 | A |

TABLE 22-continued

| Cpd number | HDAC IC50 |
| --- | --- |
| 50 | B |
| 50 | B |
| 63 | C |
| 107 | B |
| 205 | C |
| 76 | B |
| 221 | B |
| 126 | B |
| 126 | B |
| 77 | B |
| 18 | B |
| 166 | B |
| 78 | B |
| 78 | D |
| 79 | B |
| 80 | B |
| 488 | C |
| 488 | D |
| 299 | B |
| 300 | C |
| 521 | A |
| 81 | A |
| 81 | B |
| 82 | B |
| 222 | A |
| 26 | B |
| 84 | B |
| 83 | B |
| 27 | B |
| 85 | A |
| 85 | B |
| 85 | A |
| 86 | B |
| 86 | A |
| 67 | C |
| 87 | A |
| 87 | A |
| 436 | A |
| 436 | B |
| 436 | B |
| 436 | A |
| 474 | B |
| 232 | B |
| 230 | A |
| 176 | A |
| 177 | A |
| 179 | A |
| 242 | A |
| 28 | C |
| 88 | A |
| 89 | B |
| 90 | A |
| 29 | C |
| 249 | A |
| 249 | A |
| 231 | A |
| 68 | C |
| 30 | D |
| 31 | C |
| 33 | D |
| 216 | B |
| 32 | D |
| 69 | C |
| 51 | A |
| 51 | B |
| 91 | B |
| 92 | A |
| 226 | B |
| 227 | B |
| 178 | A |
| 265 | D |
| 233 | B |
| 175 | A |
| 271 | A |
| 271 | A |
| 235 | A |
| 234 | A |
| 260 | D |

TABLE 22-continued

| Cpd number | HDAC IC50 |
|---|---|
| 261 | D |
| 262 | D |
| 70 | C |
| 71 | C |
| 285 | A |
| 286 | C |
| 287 | C |
| 301 | B |
| 302 | A |
| 510 | D |
| 253 | B |
| 58 | C |
| 109 | A |
| 288 | B |
| 288 | B |
| 288 | D |
| 303 | C |
| 289 | B |
| 289 | C |
| 72 | B |
| 305 | C |
| 290 | C |
| 308 | C |
| 304 | C |
| 110 | A |
| 338 | A |
| 307 | D |
| 291 | C |
| 339 | A |
| 340 | A |
| 340 | B |
| 341 | A |
| 278 | C |
| 96 | B |
| 96 | C |
| 306 | D |
| 292 | A |
| 292 | B |
| 279 | B |
| 380 | C |
| 431 | A |
| 381 | C |
| 293 | B |
| 293 | D |
| 475 | C |
| 379 | B |
| 518 | B |
| 327 | B |
| 327 | B |
| 327 | B |
| 327 | A |
| 327 | A |
| 327 | B |
| 327 | A |
| 327 | A |
| 327 | B |
| 327 | A |
| 327 | A |
| 309 | B |
| 294 | A |
| 520 | C |
| 295 | B |
| 296 | A |
| 310 | A |
| 320 | C |
| 519 | A |
| 519 | B |
| 316 | C |
| 328 | B |
| 328 | A |
| 372 | A |
| 389 | B |
| 342 | B |
| 343 | B |
| 477 | B |
| 337 | B |

TABLE 22-continued

| Cpd number | HDAC IC50 |
|---|---|
| 345 | B |
| 346 | C |
| 517 | B |
| 348 | B |
| 350 | A |
| 351 | C |
| 352 | B |
| 353 | D |
| 354 | D |
| 516 | A |
| 342 | B |
| 355 | B |
| 356 | C |
| 357 | A |
| 341 | A |
| 347 | B |
| 515 | C |
| 506 | C |
| 427 | C |
| 514 | C |
| 507 | B |
| 358 | B |
| 359 | C |
| 360 | C |
| 361 | C |
| 362 | D |
| 349 | C |
| 508 | B |
| 363 | B |
| 364 | C |
| 513 | B |
| 365 | C |
| 366 | C |
| 367 | C |
| 373 | C |
| 368 | D |
| 522 | C |
| 369 | D |
| 523 | D |
| 512 | B |
| 422 | B |
| 370 | B |
| 371 | B |
| 447 | D |
| 487 | A |
| 487 | A |
| 487 | B |
| 481 | B |
| 481 | A |
| 481 | B |
| 537 | D |
| 509 | C |
| 330 | A |
| 330 | B |
| 330 | B |
| 330 | A |
| 330 | D |
| 503 | C |
| 504 | C |
| 505 | D |
| 412 | B |
| 374 | C |
| 375 | B |
| 376 | C |
| 501 | D |
| 336 | B |
| 502 | C |
| 377 | B |
| 378 | B |
| 466 | C |
| 500 | D |
| 511 | A |
| 467 | D |
| 468 | B |
| 468 | A |
| 497 | A |
| 496 | B |
| 329 | A |

TABLE 22-continued

| Cpd number | HDAC IC50 |
|---|---|
| 388 | C |
| 387 | A |
| 385 | C |
| 469 | B |
| 392 | C |
| 383 | C |
| 486 | A |
| 382 | A |
| 386 | C |
| 495 | C |
| 493 | B |
| 384 | C |
| 470 | C |
| 398 | B |
| 499 | C |
| 530 | C |
| 531 | C |
| 480 | B |
| 492 | B |
| 471 | C |
| 472 | B |
| 529 | B |
| 529 | A |
| 485 | B |
| 485 | A |
| 484 | B |
| 479 | C |
| 479 | A |
| 524 | C |
| 525 | A |
| 491 | A |
| 498 | A |
| 483 | A |
| 528 | B |
| 527 | B |
| 526 | B |
| 494 | C |
| 482 | B |
| 406 | B |
| 490 | A |
| 489 | B |
| 408 | A |
| 478 | B |
| 476 | B |
| 464 | C |
| 465 | B |
| 541 | B |
| 539 | D |
| 540 | A |
| 552 | B |
| 551 | B |
| 444 | B |
| 532 | A |
| 533 | C |
| 460 | B |
| 535 | A |
| 536 | A |
| 538 | B |
| 416 | A |
| 473 | B |
| 542 | A |
| 491 | A |
| 463 | C |
| 544 | C |
| 563 | A |
| 553 | A |
| 576 | A |
| 577 | A |
| 563 | C |
| 564 | C |
| 565 | C |
| 554 | C |
| 578 | B |
| 579 | A |
| 566 | A |
| 580 | A |
| 555 | B |
| 556 | B |

TABLE 22-continued

| Cpd number | HDAC IC50 |
|---|---|
| 573 | C |
| 574 | B |
| 567 | D |
| 568 | D |
| 581 | C |
| 557 | A |
| 560 | A |
| 575 | B |
| 582 | B |
| 569 | A |
| 583 | B |
| 584 | B |
| 558 | A |
| 570 | A |
| 559 | C |
| 561 | C |
| 571 | C |
| 572 | C |

Unless specified otherwise, in all the tables in this specification, $0.001 \leq A \leq 0.025$ µM, $0.025 < B \leq 0.100$ uM, $0.100 < C \leq 1$ uM; $1 < D \leq 10$ uM for HDAC1 and/or HDAC2;

Compounds of the invention on average possess increased bioavailability, increased solubility and/or lower Log D values than previously disclosed compounds, such as those of WO 05/030705. Consequently these new chemical entities are more soluble, less protein bound, and, ultimately, are expected to possess better pharmacological properties.

We claim:

1. A compound of Formula $I_O$:

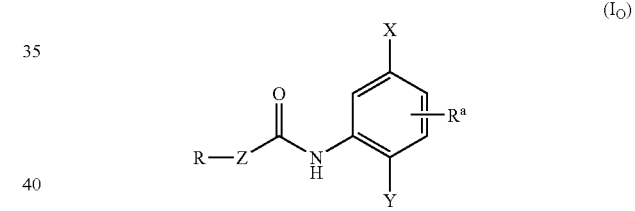

or a pharmaceutically acceptable salt or complex thereof, or a racemic or scalemic mixture, diastereomer, or enantiomer thereof, wherein X is optionally substituted phenyl;

Y is $NH_2$;

$R^a$ is H or halogen;

Z is phenyl optionally substituted with one or more groups independently selected from $C_1$-$C_7$alkyl, hydroxy, $C_1$-$C_7$alkoxy, halo, CN and amino; and R is $-(CR^{32}R^{33})_s-N(R^{30})(R^{31})$, $-Y^{31}-X^{30}$, $-O$-heterocyclyl, $-O-C_2$-$C_4$alkyl-$N(R^{30})(R^{31})$, or $-(CH_2)_s-N(R^{30})(R^{31})$;

wherein s is an integer from 0 to 6;

$R^{32}$ and $R^{33}$ are each independently selected from the group consisting of hydrogen, halo, hydroxyl, $-C_0$-$C_3$alkyl-aryl, $-C_0$-$C_3$alkyl-heteroaryl, $-C_0$-$C_3$alkyl-heterocyclyl, $-C_0$-$C_3$alkyl-cycloalkyl and $C_1$-$C_4$alkyl;

$R^{30}$ and $R^{31}$ are each independently selected from the group consisting of hydrogen, cyano, oxo, hydroxyl, $-C_1$-$C_8$alkyl, $C_1$-$C_8$heteroalkyl, $C_1$-$C_8$alkenyl, carboxamido, $C_1$-$C_3$alkyl-carboxamido-, carboxamido-$C_1$-$C_3$alkyl-, amidino, $C_2$-$C_8$hydroxyalkyl-, $C_1$-$C_3$alkylaryl-, aryl-$C_1$-$C_3$alkyl-, $C_1$-$C_3$alkylheteroaryl-, heteroaryl-$C_1$-$C_3$alkyl-, $C_1$-$C_3$alkylheterocyclyl-, heterocyclyl-$C_1$-$C_3$alkyl, $C_1$-$C_3$alkylcycloalkyl-, cycloalkyl-$C_1$-$C_3$alkyl-, $C_2$-$C_8$alkoxy, $C_2$-$C_8$alkoxy-$C_1$-$C_4$alkyl-, $C_1$-$C_8$alkoxycarbonyl-, aryloxycarbonyl, aryl-$C_1$-$C_3$alkoxycarbonyl-, heteroaryloxycarbonyl, heteroaryl-$C_1$-$C_3$alkoxycarbonyl-, $C_1$-$C_8$acyl, $C_0$-$C_8$alkyl-carbonyl-, aryl-$C_0$-$C_8$alkyl-carbonyl-, heteroaryl-$C_0$-$C_8$alkyl-carbonyl-, cycloalkyl-$C_0$-$C_8$alkyl-carbonyl-, $C_0$-$C_8$alkyl-NH-carbonyl-, aryl-$C_0$-$C_8$alkyl-NH-carbonyl-, heteroaryl-$C_0$-$C_8$alkyl-NH-carbonyl-, cycloalkyl-$C_0$-$C_8$alkyl-NH-carbonyl-, $C_0$-$C_8$alkyl-O-carbonyl-, aryl-$C_0$-$C_8$alkyl-O-carbonyl-, heteroaryl-$C_0$-$C_8$alkyl-O-carbonyl-, cycloalkyl-$C_0$-$C_8$alkyl-O-carbonyl-, $C_1$-$C_8$alkylsulfonyl-, arylalkylsulfonyl-, arylsulfonyl-, heteroarylalkylsulfonyl-, heteroarylsulfonyl-, $C_1$-$C_8$alkyl-NH-sulfonyl-, arylalkyl-NH-sulfonyl-, aryl-NH-sulfonyl-, heteroarylalkyl-NH-sulfonyl-, heteroaryl-NH-sulfonyl-, aroyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl- and a protecting group, wherein each of the foregoing is further optionally substituted with one more moieties selected from halo, cyano, oxo, carboxy, formyl, nitro, amino, amidino and guanidino; or $R^{30}$ and $R^{31}$ taken together with the N to which they are attached form a heterocyclyl or heteroaryl, each of which is optionally substituted with from 1 to 3 substituents selected from the group consisting of halo, cyano, carboxy, formyl, nitro, amino, amidino, guanidino, a protecting group, and ($X^{30}$—$Y^{31}$—), wherein said optional substituent is not spiro-fused to said heterocyclyl or heteroaryl, and wherein said heterocyclyl is optionally bridged with a methylene, ethylene or propylene bridge;

$X^{30}$ is selected from the group consisting of $C_1$-$C_8$alkyl-, $C_2$-$C_8$alkenyl-, $C_2$-$C_8$alkynyl-, $C_0$-$C_3$alkyl-$C_2$-$C_8$alkenyl-$C_0$-$C_3$alkyl-, $C_0$-$C_3$alkyl-$C_2$-$C_8$alkynyl-$C_0$-$C_3$alkyl-, $C_0$-$C_3$alkyl-O—$C_1$-$C_3$alkyl-, HO—$C_1$-$C_3$alkyl-, $C_0$-$C_4$alkyl-N($R^{30}$)—$C_0$-$C_3$alkyl-, N($R^{30}$)($R^{31}$)—$C_0$-$C_3$alkyl-, N($R^{30}$)($R^{31}$)—$C_0$-$C_3$alkenyl-, N($R^{30}$)($R^{31}$)—$C_0$-$C_3$alkynyl-, (N($R^{30}$)($R^{31}$))$_2$—C═N—, $C_0$-$C_3$alkyl-S(O)$_{0-2}$—$C_0$-$C_3$alkyl-, $CF_3$—$C_0$-$C_3$alkyl-, $C_1$-$C_8$heteroalkyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl- and N($R^{30}$)($R^{31}$)-heterocyclyl-$C_1$-$C_3$alkyl-, wherein the aryl, cycloalkyl, heteroaryl and heterocycyl are optionally substituted with from 1 to 3 substituents from halo, cyano, oxo, carboxy, formyl, nitro, amino, amidino and guanidino; and $Y^{31}$ is selected from the group consisting of a direct bond, —N($R^{30}$)—, —C(O)—, —O—C(O)—, —C(O)—O—, —N($R^{30}$)—C(O)—, —C(O)—N($R^{30}$)—, —N($R^{30}$)—C(S)—, —C(S)—N($R^{30}$)—, —N($R^{30}$)—C(O)—N($R^{31}$)—, —N($R^{30}$)—C(N$R^{30}$)—N($R^{31}$)—, —N($R^{30}$)—C(N$R^{31}$)—, —C(N$R^{31}$)—N($R^{30}$), —N($R^{30}$)—C(S)—N($R^{31}$)—, —N($R^{30}$)—C(O)—O—, —O—C(O)—N($R^{31}$)—, —N($R^{30}$)—C(S)—O—, —O—C(S)—N($R^{31}$)—, —S(O)$_{0-2}$—, —SO$_2$N($R^{31}$)—, —N($R^{31}$)—SO$_2$— and —N($R^{30}$)—SO$_2$N($R^{31}$)—;

provided that $Y^{31}$ and $X^{30}$ are not linked to form —O—O— or —O—N—.

2. A compound having formula III

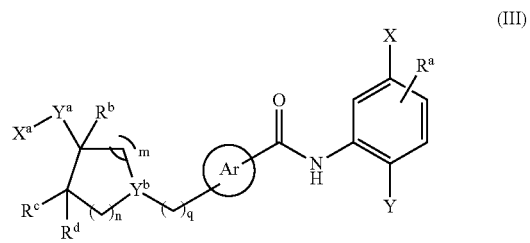

(III)

or a pharmaceutically acceptable salt or complex thereof, or a racemic or scalemic mixture, diastereomer, or enantiomer thereof, wherein X is optionally substituted phenyl or optionally substituted thienyl;

Ar is optionally substituted phenyl;

$R^a$ is H or halo;

$R^b$, $R^c$ and $R^d$ are each independently hydrogen, $C_1$-$C_8$ alkyl, aryl, heteroaryl, cycloalkyl, heterocyclyl or halo; or $R^b$ and $R^c$ together with the atoms to which they are bonded, optionally form a 5- or 6-membered cycloalkyl or heteroalkyl having 1 or 2 annular heteroatoms; each of which is optionally substituted with from 1 to 3 substituents;

Y is —NH$_2$;

$Y^b$ is —N— or —CH—;

$Y^a$ is direct bond, —O—, —N($R^{34}$)—, —C(O)—, —OC(O)—, —C(O)O—, —N($R^{34}$)—C(O)—, —C(O)—N($R^{34}$)—, —N($R^{34}$) —C(S)—, —C(S)—N($R^{34}$)—, —N($R^{34}$)—C(O)—N($R^{35}$)—, —N($R^{34}$)—C(N$R^{34}$)—N($R^{35}$)—, —N($R^{34}$)—C(N$R^{35}$)—, —C(N$R^{35}$)—N($R^{34}$)—, —N($R^{34}$)—C(S)—N($R^{35}$)—, —N($R^{34}$)—C(O)—O—, —O—C(O)—N($R^{34}$)—, —N($R^{34}$)—C(S)O—, —O—C(S)—N($R^{35}$)—, —S(O)$_{0-2}$—, —SO$_2$N($R^{35}$)—, —N($R^{35}$)—SO$_2$—, N($R^{34}$)—S(O)$_2$—N($R^{35}$)—, —O—$C_1$-$C_3$alkyl-, —N($R^{34}$)—$C_1$-$C_3$alkyl-, —C(O)—$C_1$-$C_3$alkyl- or —O—C(O)—$C_1$-$C_3$alkyl-;

$X^a$ is $C_1$-$C_8$alkyl-, $C_1$-$C_8$alkenyl-, $C_1$-$C_8$alkynyl-, $C_0$-$C_3$alkyl-$C_1$-$C_8$alkenyl-$C_0$-$C_3$alkyl-, $C_0$-$C_3$alkyl-$C_1$-$C_8$alkynyl-$C_0$-$C_3$alkyl-, $C_1$-$C_3$alkyl-O—$C_1$-$C_3$alkyl-, HO—$C_1$-$C_3$alkyl-, $C_1$-$C_4$alkyl-N($R^{34}$)—$C_0$-$C_3$alkyl-, N($R^{34}$)($R^{35}$)—$C_0$-$C_3$alkyl-, $C_1$-$C_3$alkyl-S(O)$_{0-2}$—$C_1$-$C_3$alkyl-, $CF_3$—$C_0$-$C_3$alkyl-, $CF_2$H—$C_0$-$C_3$alkyl-, $C_1$-$C_8$heteroalkyl-, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, aryl-$C_0$-$C_2$alkyl-heterocyclyl-$C_0$-$C_2$alkyl-, heteroaryl-$C_0$-$C_2$alkyl-heterocyclyl-$C_0$-$C_2$alkyl-, N($R^{34}$)($R^{35}$)-heterocyclyl-$C_0$-$C_3$alkyl-, heteroaryl-$C_0$-$C_3$alkyl-heterocyclyl- or $C_1$-$C_4$alkyl-CH(N($R^{34}$)($R^{35}$))—C(O)—N($R^{34}$)-aryl-, wherein the aryl, cycloalkyl, heteroaryl and heterocycyl are optionally substituted with from 1 to 3 independently selected substituents;

or $X^a$—$Y^a$— is selected from the group consisting of H—, halo-, HO—, HS—, HC(O)—, HOC(O)—, $C_1$-$C_4$alkyl-, $H_2$N—, ($R^{34}$)($R^{35}$)N—, $C_1$-$C_4$alkyl-NH—, ($C_1$-$C_4$alkyl)$_2$-N—, HC(O)N($R^{34}$)—, ($R^{34}$)($R^{35}$)N—S(O)$_2$—N($R^{36}$)—, ($R^{34}$)($R^{35}$)N—C(O)—, $H_2$N—C(O)—, HC(S)N($R^{34}$)—, ($R^{34}$)($R^{35}$)N—C(S)—, $H_2$N—C(S)—, ($R^{34}$)($R^{35}$)N—C(O)—O—, ($R^{34}$)($R^{35}$)N—C(S)—O—, ($R^{34}$)($R^{35}$)N—C(O)—N($R^{36}$)—, $(C_1-C_3\text{alkylN})_2-C=N-$, $(R^{34})(R^{35})N-C(NR^{37})-N(R^{36})-$, $(R^{34})(R^{35})N-C(NR^{36})-$, cycloalkyl-$C_0$-$C_2$alkyl-$C(NR^{36})-$, heterocyclyl-$C_0$-$C_2$alkyl-$C(NR^{36})-$, aryl-$C_0$-$C_2$alkyl-$C(NR^{36})-$, heteroaryl-$C_0$-$C_2$alkyl-$C(NR^{36})-$, $C_0$-$C_3$alkyl-$C(NR^{36})-$, $C_1$-$C_4$alkyl-$S(O)_2-N(R^{36})-$, $CF_3-C_0$-$C_4$alkyl-$S(O)_2-N(R^{36})$, $CF_3-C_0$-$C_4$alkyl-$C(O)-N(R^{36})-$, aryl-$C_0$-$C_4$alkyl-$S(O)_2-N(R^{36})-$, heteroaryl-$C_0$-$C_4$alkyl-$S(O)_2-N(R^{36})-$, cycloalkyl-$C_0$-$C_4$alkyl-$S(O)_2-N(R^{36})-$, heterocyclyl-$C_0$-$C_4$alkyl-$S(O)_2-N(R^{36})-$, $C_1$-$C_4$alkyl-$O-C(O)-NH-$, $C_1$-$C_4$alkyl-$O-C(O)-N(H)-C_1$-$C_4$alkyl-, $C_1$-$C_4$alkyl-$N(H)-C(O)-N(H)-$, $C_1$-$C_4$alkyl-$NH-C(O)-O-$, $C_1$-$C_4$alkyl-$C(O)-N(H)-$, $C_1$-$C_4$alkyl-$O-C(S)-N(H)-$, $C_1$-$C_4$alkyl-$N(H)-C(S)-N(H)-$, $C_1$-$C_4$alkyl-$N(H)-C(S)-O-$, $C_1$-$C_4$alkyl-$C(S)-N(H)-$, Me-$C(O)-O-$, Me-$C(O)-N(H)-$, aryl-$C_0$-$C_4$alkyl-$O-C(O)-N(H)-$, aryl-$C_0$-$C_4$alkyl-$O-C(O)-N(C_1$-$C_4$alkyl)-, aryl-$C_0$-$C_4$alkyl-$C(O)-N(H)-$, heteroaryl-$C_0$-$C_4$alkyl-$O-C(O)-N(H)-$, heteroaryl-$C_0$-$C_4$alkyl-$O-C(O)-N(C_1$-$C_4$alkyl)-, heteroaryl-$C_0$-$C_4$alkyl-$C(O)-N(H)-$, aryl-$C_0$-$C_4$alkyl-$N(H)-C(O)-O-$, heteroaryl-$C_0$-$C_4$alkyl-$N(H)-C(O)-O-$, heterocyclyl-$C_0$-$C_4$alkyl-$O-C(O)-N(H)-$, heterocyclyl-$C_0$-$C_4$alkyl-$O-C(O)-N(C_1$-$C_4$alkyl)-, heterocyclyl-$C_0$-$C_4$alkyl-$C(O)-N(H)-$, cycloalkyl-$C_0$-$C_4$alkyl-$O-C(O)-N(H)-$, cycloalkyl-$C_0$-$C_4$alkyl-$O-C(O)-N(C_1$-$C_4$alkyl)-, cycloalkyl-$C_0$-$C_4$alkyl-$C(O)-N(H)-$, heterocyclyl-$C_0$-$C_4$alkyl-$N(H)-C(O)-O-$, cycloalkyl-$C_0$-$C_4$alkyl-$N(H)-C(O)-O-$, heterocyclyl-$C_0$-$C_4$alkyl-$C(O)-N(H)-$, aryl-$C_0$-$C_4$alkyl-$N(H)-C(O)-N(H)-$, aryl-$C_0$-$C_4$alkyl-$N(H)-$, aryl-$C_0$-$C_4$alkyl-$O-$, aryl-$C_0$-$C_4$alkyl-$S(O)_{0-2}-$, heteroaryl-$C_0$-$C_4$alkyl-$N(H)-C(O)-N(H)-$, heteroaryl-$C_0$-$C_4$alkyl-$N(H)-$, heteroaryl-$C_0$-$C_4$alkyl-$O-$, heteroaryl-$C_0$-$C_4$alkyl-$S(O)_{0-2}-$, heterocyclyl-$C_0$-$C_4$alkyl-$N(H)-C(O)-N(H)-$, heterocyclyl-$C_0$-$C_4$alkyl-$N(H)-$, heterocyclyl-$C_0$-$C_4$alkyl-$O-$, heterocyclyl-$C_0$-$C_4$alkyl-$S(O)_{0-2}-$, cycloalkyl-$C_0$-$C_4$alkyl-$N(H)-C(O)-N(H)-$, cycloalkyl-$C_0$-$C_4$alkyl-$N(H)-$, cycloalkyl-$C_0$-$C_4$alkyl-$O-$, cycloalkyl-$C_0$-$C_4$alkyl-$S(O)_{0-2}$, aryl-$C_0$-$C_4$alkyl-$C(S)-N(H)-$, heteroaryl-$C_0$-$C_4$alkyl-$C(S)-N(H)-$, aryl-$C_0$-$C_4$alkyl-$O-C(S)-N(H)-$, heteroaryl-$C_0$-$C_4$alkyl-$O-C(S)-N(H)-$, aryl-$C_0$-$C_4$alkyl-$N(H)-C(S)-O-$, heteroaryl-$C_0$-$C_4$alkyl-$N(H)-C(S)-O-$, heterocyclyl-$C_0$-$C_4$alkyl-$C(S)-N(H)-$, cycloalkyl-$C_0$-$C_4$alkyl-$C(S)-N(H)-$, heterocyclyl-$C_0$-$C_4$alkyl-$O-C(S)-N(H)-$, cycloalkyl-$C_0$-$C_4$alkyl-$O-C(S)-N(H)-$, heterocyclyl-$C_0$-$C_4$alkyl-$N(H)-C(S)-O-$, cycloalkyl-$C_0$-$C_4$alkyl-$N(H)-C(S)-O-$, heterocyclyl-$C_0$-$C_4$alkyl-$C(S)-N(H)-$, aryl-$C_0$-$C_4$alkyl-$N(H)-C(S)-NH-$, heteroaryl-$C_0$-$C_4$alkyl-$N(H)-C(S)-N(H)-$, heterocyclyl-$C_0$-$C_4$alkyl-$N(H)-C(S)-N(H)-$, cycloalkyl-$C_0$-$C_4$alkyl-$N(H)-C(S)-N(H)-$, $C_1$-$C_4$alkyl-$O-C_1$-$C_4$alkyl-$C(O)-N(H)-$, $C_1$-$C_4$alkyl-$O-C_2$-$C_4$alkyl-$O-C(O)-N(H)-$, $C_1$-$C_4$alkyl-$O-C_2$-$C_4$alkyl-$N(H)-C(O)-N(H)-$, $C_1$-$C_4$alkyl-$O-C_2$-$C_4$alkyl-$N(H)-$, $C_1$-$C_4$alkyl-$O-C_2$-$C_4$alkyl-$O-$, $C_1$-$C_4$alkyl-$O-C_2$-$C_4$alkyl-$N(H)-C(O)-O-$, HO-$C_1$-$C_4$alkyl-$C(O)-N(H)-$, HO-$C_1$-$C_4$alkyl-$N(H)-$, HO-$C_1$-$C_4$alkyl-$N(R^3)-$, HO-$C_1$-$C_4$alkyl-$O-$, HO-$C_1$-$C_4$alkyl-$S(O)_{0-2}-$, HO-$C_2$-$C_4$alkyl-$O-C(O)-N(H)-$, HO-$C_2$-$C_4$alkyl-$N(H)-C(O)-N(H)-$, HO-$C_2$-$C_4$alkyl-$N(H)-C(O)-O-$, $C_1$-$C_4$alkyl-$O-C_1$-$C_4$alkyl-$C(S)-N(H)-$, $C_1$-$C_4$alkyl-$O-C_2$-$C_4$alkyl-$O-C(S)-N(H)-$, $C_1$-$C_4$alkyl-$O-C_2$-$C_4$alkyl-$N(H)C(S)-N(H)-$, $C_1$-$C_4$alkyl-$O-C_2$-$C_4$alkyl-$N(H)-C(S)-O-$, HO-$C_2$-$C_4$alkyl-$O-C(S)-N(H)-$, HO-$C_2$-$C_4$alkyl-$N(H)-C(S)-N(H)-$, HO-$C_2$-$C_4$alkyl-$N(H)-C(S)-O-$, $(C_1$-$C_4$alkyl$)_2N-C_1$-$C_4$alkyl-$C(O)-N(H)-$, $(C_0$-$C_4$alkyl)-$O-C_1$-$C_4$alkyl-$C(O)-N(H)-$, $(C_0$-$C_4$alkyl)-$O-C_1$-$C_4$alkyl-$C(S)-N(H)-$, $(C_0$-$C_4$alkyl)-$O-C_1$-$C_4$alkyl-$C(O)-O-$, $(C_0$-$C_4$alkyl)-$O-C_2$-$C_4$alkyl-$N(H)-C(O)-N(H)-$, $(C_0$-$C_4$alkyl)-$O-C_2$-$C_4$alkyl-$O-C(O)-N(H)-$, $(C_0$-$C_4$alkyl)-$O-C_2$-$C_4$alkyl-$N(H)-C(NH)-N(H)-$, $(C_0$-$C_4$alkyl)-$O-C_2$-$C_4$alkyl-$N(H)-C(O)-$, $(C_1$-$C_4$alkyl$)_2N-C_2$-$C_4$alkyl-$O-C(O)-N(H)-$, $(C_1$-$C_4$alkyl$)_2N-C_2$-$C_4$alkyl-$N(H)-$, $(C_1$-$C_4$alkyl$)_2N-C_2$-$C_4$alkyl-$O-$, $(C_1$-$C_4$alkyl$)_2N-C_2$-$C_4$alkyl-$S(O)_{0-2}-$, $(C_1$-$C_4$alkyl$)_2N-C_2$-$C_4$alkyl-$N(H)-C(O)-N(H)-$, $(C_1$-$C_4$alkyl$)_2N-C_2$-$C_4$alkyl-$N(H)-C(O)-O-$, $(C_1$-$C_4$alkyl$)_2N-C_1$-$C_4$alkyl-$C(S)-N(H)-$, $(C_1$-$C_4$alkyl$)_2N-C_2$-$C_4$alkyl-$N(H)-C(S)-N(H)-$, $(C_1$-$C_4$alkyl$)_2N-C_2$-$C_4$alkyl-$N(H)-C(S)-O-$, $(C_1$-$C_4$alkyl)-$O-C(O)C_1$-$C_8$alkyl-$C(O)-(H)-$, HO-$C(O)C_1$-$C_8$alkyl-$C(O)-N(H)-$, HO-$NH-C(O)C_1$-$C_8$alkyl-$C(O)-N(H)-$, $CF_2H-C_0$-$C_4$alkyl-$C(O)-N(H)-$, $CF_3-C_0$-$C_4$alkyl-$C(O)-N(H)-$, $CF_3-C_0$-$C_4$alkyl-$N(H)-$, $CF_3-C_0$-$C_4$alkyl-$N(R^3)-$, $CF_3-C_0$-$C_4$alkyl-$O-$, $CF_3-C_0$-$C_4$alkyl-$S(O)_{0-2}-$, $CF_3-C_0$-$C_4$alkyl-$O-C(O)-N(H)-$, $CF_3-C_0$-$C_4$alkyl-$N(H)C(O)-N(H)-$, $CF_3-C_0$-$C_4$alkyl-$N(H)-C(O)-O-$, $CF_3-C_0$-$C_4$alkyl-$O-C(S)-N(H)-$, $CF_3-C_0$-$C_4$alkyl-$N(H)-C(S)-N(H)-$, $CF_3-C_0$-$C_4$alkyl-$N(H)-C(S)-O-$, $CF_3-C_0$-$C_4$alkyl-$C(S)-N(H)-$, $CF_2H-C_0$-$C_4$alkyl-$N(H)-$, $CF_2H-C_0$-$C_4$alkyl-$O-$, $CF_2H-C_0$-$C_4$alkyl-$S(O)_{0-2}-$, $CF_2H-C_0$-$C_4$alkyl-$O-C(O)-N(H)-$, $CF_2H-C_0$-$C_4$alkyl-$N(H)C(O)-N(H)-$, $CF_2H-C_0$-$C_4$alkyl-$N(H)-C(O)-O-$, $CF_2H-C_0$-$C_4$alkyl-$O-C(S)-N(H)-$, $CF_2H-C_0$-$C_4$alkyl-$N(H)-C(S)-N(H)-$, $CF_2H-C_0$-$C_4$alkyl-$N(H)-C(S)-O-$, $CF_2H-C_0$-$C_4$alkyl-$C(S)-N(H)-$, $(H)(R^{34})N-C_1$-$C_3$alkyl-, $(H)(R^{34})N-C_1$-$C_3$alkyl-, HO-$C_1$-$C_3$alkyl-, $(H)(R^{34})N-S(O)_2-N(R^{35})-$, $(H)(R^{35})N-S(O)_2-$, $(H)(R^{34})N-C(S)-O-$, $(H)(R^{34})N-C(O)-O-$, $(H)(R^{34})N-C(S)-N(R^{35})-$, $(H)(R^{34})N-C(NR^{35})-$, $(H)(R^{34})N-C(NR^{34})-N(R^{38})-$, $(H)(R^{34})N-C(O)-N(R^{35})-$, HO-$C(O)-C_1$-$C_3$alkyl-, $C_1$-$C_4$alkyl-$S(O)_2-NH-$ and $((R^{34})(R^{35})N)_2-C=N-$;

m and n are independently 0, 1, 2 or 3;

q is 0, 1 or 2;

$R^{34}$, $R^{35}$, $R^{36}$ and $R^{37}$ are each independently selected from the group consisting of hydrogen, cyano, oxo, hydroxyl, $-C_1$-$C_8$alkyl, $C_1$-$C_8$heteroalkyl, $C_1$-$C_8$alkenyl, carboxamido, $C_1$-$C_3$alkyl-carboxamido-, carboxamido-$C_1$-$C_3$alkyl-, amidino, $C_2$-$C_8$hydroxyalkyl, $C_1$-$C_3$alkylaryl-, aryl-$C_1$-$C_3$alkyl-, $C_1$-$C_3$alkylheteroaryl-, heteroaryl-$C_1$-$C_3$alkyl-, $C_1$-$C_3$alkylheterocyclyl-, heterocyclyl-$C_1$-$C_3$alkyl-, $C_1$-$C_3$alkylcycloalkyl-, cycloalkyl-$C_1$-$C_3$alkyl-, $C_2$-$C_8$alkoxy-, $C_2$-$C_8$alkoxy-$C_1$-$C_4$alkyl-, $C_1$-$C_8$alkoxycarbonyl-, aryloxycarbonyl-, aryl-$C_1$-$C_3$alkoxycarbonyl-, heteroaryloxycarbonyl-, heteroaryl-$C_1$-$C_3$alkoxycarbonyl-, $C_1$-$C_8$acyl, $C_0$-$C_8$alkylcarbonyl-, aryl-$C_0$-$C_8$alkyl-carbonyl-, heteroaryl-$C_0$-$C_8$alkyl-carbonyl-, cycloalkyl-$C_0$-$C_8$alkyl-carbonyl-, $C_0$-$C_8$alkyl-N(H)-carbonyl-, aryl-$C_0$-$C_8$alkyl-N(H)-carbonyl-, heteroaryl-$C_0$-$C_8$alkyl-N(H)-carbonyl-, cycloalkyl-$C_0$-$C_8$alkyl-N(H)-carbonyl-, $C_0$-$C_8$alkyl-O- carbonyl-, aryl-$C_0$-$C_8$alkyl-O-carbonyl-, heteroaryl-$C_0$-$C_8$alkyl-O-carbonyl-, cycloalkyl-$C_0$-$C_8$alkyl-O-carbonyl-, $C_1$-$C_8$ alkylsulfonyl-, arylalkylsulfonyl-, arylsulfonyl-, heteroarylalkylsulfonyl-, heteroarylsulfonyl-, $C_1$-$C_8$alkyl-N(H)-sulfonyl-, arylalkyl-N(H)-sulfonyl-, aryl-N(H)-sulfonyl-, heteroarylalkyl-N(H)-sulfonyl-, heteroaryl-N(H)-sulfonyl, aroyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$ alkyl-, heteroaryl-$C_1$-$C_3$ alkyl-, and a protecting group, wherein each of the foregoing is further optionally substituted with one more moieties; or $R^{34}$ and $R^{35}$ taken together with the N to which they are attached form a heterocyclyl or heteroaryl, each of which is optionally substituted with from 1 to 3 substituents, wherein the heterocyclyl is optionally bridged with a methylene, ethylene or propylene bridge, provided that 1) when $Y^b$ is N, then m is not 0 if $Y^a$ is bound to the ring comprising Y, via a N, S or O in $Y^a$, or 2) when m and n are both 0 then $Y^b$ is —CH—.

3. The compound of claim 1, wherein —Z—R is

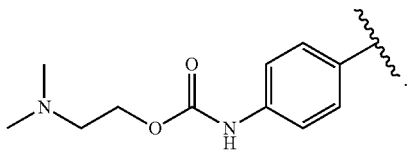 [SMILES: *c1ccc(NC(=O)OCCN(C)C)cc1]

4. A compound that is
N-(4,4'-diaminobiphenyl-3-yl)-4-(pyridin-3-yl)benzamide,
N-(4-amino-4'-fluorobiphenyl-3-yl)-4-(pyridin-3-yl)benzamide,
N-(4-aminobiphenyl-3-yl)-4-(morpholinomethyl)benzamide,
N-(4-aminobiphenyl-3-yl)-4-(pyridin-3-yl)benzamide,
N-(4-amino-4'-hydroxybiphenyl-3-yl)-4-(morpholinomethyl)benzamide,
(R)—N-(4-aminobiphenyl-3-yl)-4-((3-(dimethylamino)pyrrolidin-1-yl)methyl)benzamide,
(R)—N-(4-amino-4'-hydroxybiphenyl-3-yl)-4-((3-(dimethylamino)pyrrolidin-1-yl)methyl)benzamide,
N-(4-amino-4'-chlorobiphenyl-3-yl)-4-(morpholinomethyl)benzamide,
2-(dimethylamino)ethyl 4-(4-amino-4'-chloro-3'-fluorobiphenyl-3-ylcarbamoyl)phenylcarbamate,
2-(dimethylamino)ethyl 4-(4-amino-3'-fluorobiphenyl-3-ylcarbamoyl)phenylcarbamate,
2-(dimethylamino)ethyl 4-(4-amino-3',4'-dichlorobiphenyl-3-ylcarbamoyl)phenylcarbamate,
4-(4-amino-3',4'-dichlorobiphenyl-3-ylcarbamoyl)phenyl acetate,
2-(dimethylamino)ethyl 4-(4-amino-3',4'-difluorobiphenyl-3-ylcarbamoyl)phenylcarbamate,
4-(4-amino-3',4'-difluorobiphenyl-3-ylcarbamoyl)phenyl acetate,
2-(dimethylamino)ethyl 4-(4-aminobiphenyl-3-ylcarbamoyl)phenylcarbamate,
(S)—N-(4-aminobiphenyl-3-yl)-4-(3-aminopyrrolidin-1-yl)benzamide,
2-morpholinoethyl 4-(4-aminobiphenyl-3-ylcarbamoyl)phenylcarbamate,
2-(dimethylamino)ethyl 4-(4-amino-3'-(trifluoromethoxy)biphenyl-3-ylcarbamoyl)phenylcarbamate,
2-(dimethylamino)ethyl 4-(4-amino-4'-(trifluoromethoxy)biphenyl-3-ylcarbamoyl)phenylcarbamate,
2-(dimethylamino)ethyl 4-(4-amino-3'-fluoro-4'-methoxybiphenyl-3-ylcarbamoyl)phenylcarbamate,
2-(dimethylamino)ethyl 4-(4-amino-4'-fluorobiphenyl-3-ylcarbamoyl)phenylcarbamate,
2-(dimethylamino)ethyl 4-(4-amino-4'-chlorobiphenyl-3-ylcarbamoyl)phenylcarbamate,
2-(dimethylamino)ethyl 4-(4-amino-3'-fluoro-4'-hydroxybiphenyl-3-ylcarbamoyl)phenylcarbamate,
2-(dimethylamino)ethyl 4-(4-amino-2',4'-difluorobiphenyl-3-ylcarbamoyl)phenylcarbamate,
2-(dimethylamino)ethyl 4-(4-amino-4'-(trifluoromethyl)biphenyl-3-ylcarbamoyl)phenylcarbamate,
2-(dimethylamino)ethyl 4-(4-amino-2'-fluorobiphenyl-3-ylcarbamoyl)phenylcarbamate,
2-(dimethylamino)ethyl 4-(4-amino-4'-hydroxybiphenyl-3-ylcarbamoyl)phenylcarbamate,
2-(dimethylamino)ethyl 4-(4-amino-3',4',5'-trifluorobiphenyl-3-ylcarbamoyl)phenylcarbamate,
2-(dimethylamino)ethyl 4-(4-amino-4'-(dimethylamino)biphenyl-3-ylcarbamoyl)phenylcarbamate,
2-(dimethylamino)ethyl 4-(4-amino-4'-(methylthio)biphenyl-3-ylcarbamoyl)phenylcarbamate,
2-(dimethylamino)ethyl 4-(4-amino-4'-cyanobiphenyl-3-ylcarbamoyl)phenylcarbamate,
2-(dimethylamino)ethyl 4-(4-amino-2'-fluoro-4'-methoxybiphenyl-3-ylcarbamoyl)phenylcarbamate,
2-(dimethylamino)ethyl 4-(4-amino-3'-fluoro-4'-methylbiphenyl-3-ylcarbamoyl)phenylcarbamate,
2-(dimethylamino)ethyl 4-(4-amino-2',4',5'-trifluorobiphenyl-3-ylcarbamoyl)phenylcarbamate,
2-(dimethylamino)ethyl 4-(4-amino-4'-(methylsulfinyl)biphenyl-3-ylcarbamoyl)phenylcarbamate,
2-(dimethylamino)ethyl 4-(4-amino-2'-fluoro-4'-(trifluoromethyl)biphenyl-3-ylcarbamoyl)phenylcarbamate,
2-(dimethylamino)ethyl 4-(4-amino-4'-(methylsulfonyl)biphenyl-3-ylcarbamoyl)phenylcarbamate,
2-(dimethylamino)ethyl 4-(4,4'-diaminobiphenyl-3-ylcarbamoyl)phenylcarbamate,
2-(dimethylamino)ethyl 4-(4-amino-4'-ethoxybiphenyl-3-ylcarbamoyl)phenylcarbamate,
(S)-4-(3-acetamidopyrrolidin-1-yl)-N-(4-aminobiphenyl-3-yl)benzamide,
(S)-4-(3-acetamidopyrrolidin-1-yl)-N-(4-amino-4'-fluorobiphenyl-3-yl)benzamide,
2-(dimethylamino)ethyl 4-(4-amino-4'-cyano-3'-fluorobiphenyl-3-ylcarbamoyl)phenylcarbamate,
(S)—N-(4-amino-4'-fluorobiphenyl-3-yl)-4-(3-aminopyrrolidin-1-yl)benzamide,
(S)—N-(4-aminobiphenyl-3-yl)-4-(3-(bis(dimethylamino)methyleneamino)pyrrolidin-1-yl)benzamide,
(S)—N-(4-amino-4'-fluorobiphenyl-3-yl)-4-(3-(bis(dimethylamino)methyleneamino)pyrrolidin-1-yl)benzamide,
N-(4-amino-3',4'-difluorobiphenyl-3-yl)-4-(1,3-dioxoisoindolin-2-yl)benzamide,
N-(4-aminobiphenyl-3-yl)-3-(pyridin-3-yl)benzamide,
(S)—N-(4-aminobiphenyl-3-yl)-4-(3-(methylsulfonamido)pyrrolidin-1-yl)benzamide,
N-(4-aminobiphenyl-3-yl)-4-(4-methylpiperazin-1-yl)benzamide,
N-(4-aminobiphenyl-3-yl)-4-(pyrrolidin-1-yl)benzamide,
(R)—N-(4-aminobiphenyl-3-yl)-4-(3-aminopyrrolidin-1-yl)benzamide,
(S)—N-(4-aminobiphenyl-3-yl)-4-(3-(2,2,2-trifluoroacetamido)pyrrolidin-1-yl)benzamide, N-(4-aminobiphenyl-3-yl)-4-(4-methylpiperazin-1-ylsulfonyl)benzamide, (S)—N-(4-aminobiphenyl-3-yl)-4-(3-(dimethylamino)pyrrolidin-1-yl)benzamide, (R)—N-(4-aminobiphenyl-3-yl)-4-(3-hydroxypyrrolidin-1-yl)benzamide, (S)-methyl 1-(4-(4-aminobiphenyl-3-ylcarbamoyl)phenyl)pyrrolidin-3-ylcarbamate, N-(4-aminobiphenyl-3-yl)-4-(4-ethylpiperazin-1-yl)benzamide, N-(4-aminobiphenyl-3-yl)-4-(4-aminopiperidin-1-yl)benzamide, N-(4-aminobiphenyl-3-yl)-4-(3-oxopiperazin-1-yl)benzamide, (S)—N-(4-aminobiphenyl-3-yl)-4-(3-hydroxypyrrolidin-1-yl)benzamide, (S)—N-(4-aminobiphenyl-3-yl)-4-(3-(ethylamino)pyrrolidin-1-yl)benzamide, N-(4-aminobiphenyl-3-yl)-4-(1H-imidazol-1-yl)benzamide, (R)—N-(4-amino-4'-fluorobiphenyl-3-yl)-4-(3-aminopyrrolidin-1-yl)benzamide, 1-(4-(4-aminobiphenyl-3-ylcarbamoyl)phenyl)piperidine-4-carboxamide, (S)—N-(4-aminobiphenyl-3-yl)-4-(3-fluoropyrrolidin-1-yl)benzamide, N-(4-aminobiphenyl-3-yl)-4-(3,3-difluoropyrrolidin-1-yl)benzamide, (R)—N-(4-amino-4'-fluorobiphenyl-3-yl)-4-(3-(2-methoxyacetamido)pyrrolidin-1-yl)benzamide, (R)—N-(4-amino-4'-fluorobiphenyl-3-yl)-4-(3-(methylsulfonamido)pyrrolidin-1-yl)benzamide, (S)—N-(4-aminobiphenyl-3-yl)-4-(3-(2-methoxyacetamido)pyrrolidin-1-yl)benzamide, (S)—N-(4-aminobiphenyl-3-yl)-4-(3-(2-(dimethylamino)acetamido)pyrrolidin-1-yl)benzamide, (R)-4-(3-acetamidopyrrolidin-1-yl)-N-(4-amino-4'-fluorobiphenyl-3-yl)benzamide, (R)-methyl 1-(4-(4-amino-4'-fluorobiphenyl-3-ylcarbamoyl)phenyl)pyrrolidin-3-ylcarbamate, N-(4-aminobiphenyl-3-yl)-4-(piperazin-1-yl)benzamide, (S)—N-(4-aminobiphenyl-3-yl)-4-(3-(2-hydroxyethylamino)pyrrolidin-1-yl)benzamide, (S)—N-(4-aminobiphenyl-3-yl)-4-(3-(2,2,2-trifluoroethylamino)pyrrolidin-1-yl)benzamide, (R)—N-(4-aminobiphenyl-3-yl)-4-(3-(dimethylamino)pyrrolidin-1-yl)benzamide, (R)—N-(4-aminobiphenyl-3-yl)-4-(3-(ethylamino)pyrrolidin-1-yl)benzamide, N-(4-aminobiphenyl-3-yl)-4-(hydroxymethyl)benzamide, (R)—N-(4-aminobiphenyl-3-yl)-4-(3-methoxypyrrolidin-1-yl)benzamide, N-(4-aminobiphenyl-3-yl)-4-(3-hydroxyazetidin-1-yl)benzamide, N-(4-amino-4'-fluorobiphenyl-3-yl)-4-(3-hydroxyazetidin-1-yl)benzamide, (S)—N-(4-amino-4'-fluorobiphenyl-3-yl)-4-(3-hydroxypyrrolidin-1-yl)benzamide, or a pharmaceutically acceptable salt thereof.

5. A compound that is

N-(4-aminobiphenyl-3-yl)-4-(morpholinomethyl)benzamide;

2-(dimethylamino)ethyl 4-(4-amino-3',4'-difluorobiphenyl-3-ylcarbamoyl)phenylcarbamate;

2-(dimethylamino)ethyl 4-(4-amino-3'-fluoro-4'-methoxybiphenyl-3-ylcarbamoyl)phenylcarbamate;

2-(dimethylamino)ethyl 4-(4-amino-4'-fluorobiphenyl-3-ylcarbamoyl)phenylcarbamate;

2-(dimethylamino)ethyl 4-(4-amino-2',4'-difluorobiphenyl-3-ylcarbamoyl)phenylcarbamate;

(S)—N-(4-aminobiphenyl-3-yl)-4-(3-hydroxypyrrolidin-1-yl)benzamide;

(R)—N-(4-amino-4'-fluorobiphenyl-3-yl)-4-(3-(2-methoxyacetamido)pyrrolidin-1-yl)benzamide;

N-(4-amino-4'-fluorobiphenyl-3-yl)-4-(3-hydroxyazetidin-1-yl)benzamide;

(S)—N-(4-amino-4'-fluorobiphenyl-3-yl)-4-(3-hydroxypyrrolidin-1-yl)benzamide;

or a pharmaceutically acceptable salt thereof.

6. The compound of claim 2, wherein X is optionally substituted with one, two or three substituents independently selected from the group consisting of halo, oxo, hydroxy, $C_1$-$C_3$-hydrocarbyl, methoxy, HalCH$_2$—O—, Hal$_2$CH—O—, Hal$_3$C—O— (preferably F$_3$C—O—), NH$_2$—, —N($C_1$-$C_3$alkyl)$_2$, —CN, —S(O)$_{0-2}$—$C_1$-$C_4$alkyl, —CF$_3$, and mono-, di-, or tri-halo substituted alkyl, or, when there are two optional substituents bonded to adjacent atoms of the phenyl, thienyl, or pyridyl they, together with the atoms to which they are bonded, optionally form a 5- or 6-membered cycloalkyl or heteroalkyl having 1, 2, or 3 annular heteroatoms.

7. The compound of claim 2, wherein Ar is optionally substituted with one or two substituents independently selected from the group consisting of halo, nitro, hydroxy, $C_1$-$C_3$-hydrocarbyl, methoxy, HalCH$_2$—O—, Hal$_2$CH—O—, Hal$_3$C—O— (preferably F$_3$C—O—), and mono-, di-, or tri-halo substituted alkyl.

8. The compound of claim 2, wherein $X^a$—$Y^a$— is selected from the group consisting of CH$_3$—SO$_2$—, CF$_3$—C(O)—NH—, CH$_3$—C(O)—NH—, ((CH$_3$)$_2$N)$_2$—C=N—, (CH$_3$)$_2$N—, CH$_3$—O—CH$_2$—C(O)—NH—, (CH$_3$)$_2$N—CH$_2$—C(O)—NH—, CH$_3$CH$_2$—N(CH$_3$)—, CF$_3$CH$_2$—NH—, H—, HO—, CH$_3$—O—C(O)—NH—, H$_2$N—, CH$_3$CH$_2$—NH—, H$_2$N—C(O)—, phenyl-CH$_2$—O—C(O)—N(CH$_2$CH$_3$)—, CH$_3$CH$_2$—NH—, F, CH$_3$—O—CH$_2$—C(O)—NH—, heterocyclyl-heterocyclyl, heterocyclyl-heteroaryl, aryl-NH—, heteroaryl-NH—, (CH$_3$)$_2$N—CH$_2$—C(O)—NH— and HO—CH$_2$CH$_2$—NH—.

9. The compound of claim 2 of the formula:
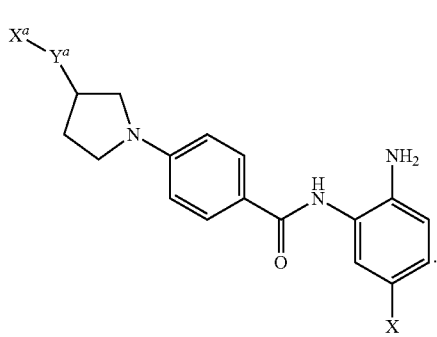
10. The compound of claim 2 of the formula:
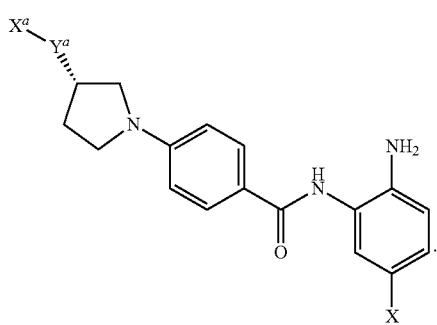
11. The compound of claim 2 of the formula:
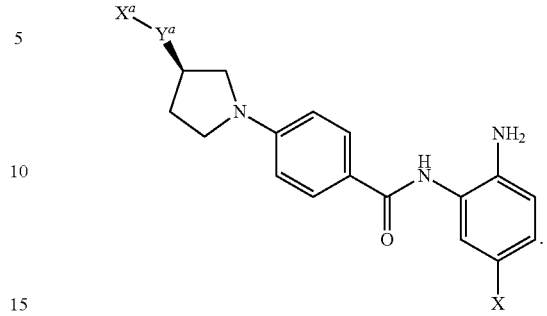
12. The compound of claim 1 of the formula:
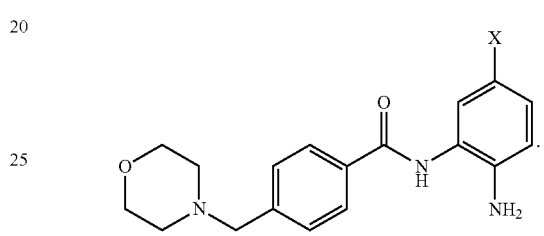
13. A composition comprising a compound according to any one of claims 1, 2, or 4-3, and a pharmaceutically acceptable carrier, excipient, or diluent.
* * * * *